(12) United States Patent
Han et al.

(10) Patent No.: US 9,371,539 B2
(45) Date of Patent: Jun. 21, 2016

(54) DNA ENCODING RING ZINC-FINGER PROTEIN AND THE USE OF THE DNA IN VECTORS AND BACTERIA AND IN PLANTS

(75) Inventors: Kyung-Hwan Han, Okemos, MI (US); Jae-Heung Ko, Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 56 days.

(21) Appl. No.: 13/180,953

(22) Filed: Jul. 12, 2011

(65) Prior Publication Data

US 2012/0011615 A1     Jan. 12, 2012

Related U.S. Application Data

(63) Continuation of application No. 11/484,947, filed on Jul. 12, 2006, now Pat. No. 7,977,535.

(51) Int. Cl.
    *C12N 15/82*     (2006.01)
    *C07K 14/415*     (2006.01)

(52) U.S. Cl.
    CPC .......... *C12N 15/8273* (2013.01); *C07K 14/415* (2013.01)

(58) Field of Classification Search
    None
    See application file for complete search history.

(56) References Cited

U.S. PATENT DOCUMENTS

| | | | |
|---|---|---|---|
| 7,196,245 B2 * | 3/2007 | Jiang et al. | 800/278 |
| 7,977,535 B2 | 7/2011 | Han et al. | |
| 2003/0082724 A1 * | 5/2003 | Flinn | C12N 15/8263 435/69.1 |
| 2004/0031072 A1 | 2/2004 | La Rosa | |
| 2006/0107345 A1 | 5/2006 | Alexandrov et al. | |
| 2007/0044171 A1 | 2/2007 | Kovalic et al. | |
| 2015/0225737 A1 | 8/2015 | Han et al. | |

FOREIGN PATENT DOCUMENTS

| | | | |
|---|---|---|---|
| NO | WO-2004/076638 A2 | 9/2004 | |
| WO | WO-2004031349 A2 | 4/2004 | |
| WO | WO2013/056000 | * | 4/2013 |

OTHER PUBLICATIONS

Borden K.L. et al. The RING finger domain: a recent example of a sequence-structure family. Curr Opin Struct Biol. Jun. 1996;6(3):395-401. Review.*
Whisstock J.C. et al. Prediction of protein function from protein sequence and structure. Q Rev Biophys. Aug. 2003;36(3):307-40. Review.*
Hill M.A. et al. Functional analysis of conserved histidines in ADP-glucose pyrophosphorylase from *Escherichia coli*. Biochem . Biophys Res Commun. Mar. 17, 1998;244(2):573-7.*
Rhoads D.M. et al. Regulation of the cyanide-resistant alternative oxidase of plant mitochondria. Identification of the cysteine residue involved in alpha-keto acid stimulation and intersubunit disulfide bond formation. J Biol Chem. Nov. 13, 1998;273(46):30750-6.*
Zhang et al., Curr Opin Plant Biol 6:430-40 (2003).*
Seq Id No. 1 aligned with Seq Id No:144_2015.*
Whisstock & Lesk, Q Rev Biophys. 36(3):307-40, (2003).*
Borden & Freemont, Curr Opin Struct Biol, 6(3):395-401 (1996).*
Zeng et al., J Plant Biochem Biotechnol 24(1):56-64 (2013).*
"Canadian Application Serial No. 2658391, Office Action mailed Nov. 22, 2012", 4 pgs.
"European Application Serial No. 07810352.0, Examination Notification Art. 94(3) mailed Mar. 11, 2013", 5 pgs.
"Database UniProt", "SubName: Full=Putative RING zinc finger protein; SubName: Full=T23015.13;", XP002591597, retrieved from EBI accession No. LINIPROT:Q9S109 Database accession No. Q9S109, (2000), 5 pgs.
"European Application Serial No. 07810352.0, Examination Notification Art. 94(3) mailed Oct. 18, 2013", 8 pgs.
"European Application Serial No. 13181042.6, Extended European Search Report mailed Oct. 18, 2013", 10 pgs.
Borden, K. L. B., et al., "The RING finger domain: a recent example of a sequence-structure family", Current Opinion in Structural Biology, 6(3), (1996), 395-401.
Ko, J-H, et al., "Upregulation of an Arabidopsis tolerance through increased abscisic acid 355 RING-H2 Gene, *XERICO*, confers drought biosynthesis", *Plant Journal*, 47(3), (2006), 343-355.
Sahin-Cevik, M., et al., "Isolation and characterization of a novel RING-H2 finger gene induced in response to cold and drought in the interfertile Citrus relative *Poncirus trifoliata*", Physiologia Plantarum,126(1), (2006), 153-161.
"Canadian Application Serial No. 2,658,391, Response filed May 21, 2013 to Office Action mailed Nov, 22. 2012", 7 pgs.
"European Application Serial No. 07810352.0, Response filed Jun. 21, 2013 to Examination Notification Art. 94(3) mailed Mar. 11, 2013".
"Canadian Application Serial No, 2,658,391, Office Action mailed Dec. 10, 2013"; 4 pgs.
"Indian Application Serial No. 731/CHENP/2009, First Examiner Report mailed Dec. 19, 2013", 2 pgs.
"European Application Serial No. 07810352.0, Response filed Feb. 13, 2014 to Examination Notification Art. 94(3) mailed Oct. 18, 2013", 13 pgs.
"European Application Serial No. 13181042.6, Response filed May 7, 2014 to Extended European Search Report mailed Oct. 18, 2013", 24 pgs.
"Indian Application Serial No. 731/CHENP/2009, Response filed May 30, 2014 to First Examiner Report mailed Dec. 19, 2013", 37 pgs.

(Continued)

*Primary Examiner* — Cynthia Collins
*Assistant Examiner* — Russell Boggs
(74) *Attorney, Agent, or Firm* — Schwegman Lundberg & Woessner, P.A.

(57) ABSTRACT

The present inventions relate to compositions and methods for providing stress tolerant transgenic plants comprising a RING domain zinc-finger motif transcription factor protein. More particularly, the invention relates to compositions and methods comprising a RING-H2 domain transcription factor protein for providing drought and salt tolerant plants, in particular comprising a recombinant XERICO gene and protein.

17 Claims, 96 Drawing Sheets

(56) References Cited

OTHER PUBLICATIONS

Matzke, Antonius J.M., et al., "Position effects and epigenetic silencing of plant transgenes", *Current Opinion in Plant Biology*, 1(2), (2009), 142-148.
"Australian Application Serial No. 2007272993, Response filed Oct. 26, 2011", 17 pgs.
"Australian Application Serial No. 2007272993, Response filed Nov. 11, 2011", 7 pgs.
"Canadian Application Serial No. 2,658,391, Amendment filed Apr. 14, 2009", 5 pgs.
"Canadian Application Serial No. 2,658,391, Office Action mailed Jan. 9, 2015", 5 pgs.
"Canadian Application Serial No. 2,658,391, Office Action mailed Oct. 6, 2010", 5 pgs.
"Canadian Application Serial No. 2,658,391, Response filed Jun. 10, 2014", 18 pgs.
"Canadian Application Serial No. 2,658,391, Voluntary Amendment filed Jul. 18, 2014", 9 pgs.
"European Application Serial No. 07810352.0, Response filed Jul. 11, 2013", 18 pgs.
"European Application Serial No. 07810352.0, Summons to Attend Oral Proceedings mailed Jul. 9, 2015", 8 pgs.
"European Application Serial No. 13181042.6, Examination Notification Art. 94(3) mailed Jul. 1, 2015", 9 pgs.
"Indian Application Serial No. 731/CHENP/2009, Response filed Dec. 16, 2014", 19 pgs.
"Indian Application Serial No. 731/CHENP/2009, Second Examiner Report mailed Nov. 13, 2014", 2 pgs.
"Putative RING zinc Finger protein-like protein, *Thellungiella halophila*", Genbank Accession No. Q8S2S3, (2002), 4 pgs.
"RING H-2 finger protein, *Poncirus trifoliata*", Genbank Accession No: Q30D22, [Online]. Retrieved from the Internet: <URL: https://www.lens.org/lens/patent/AU_2007_272993_B2/fulltext>, (2005), 4 pgs.
Harb, Amal, et al., "Molecular and Physiological Analysis of Drought Stress in Arabidopsis Reveals Early Responses Leading to Acclimation in Plant Growth", Plant Physiology 154(3), (2010), 1254-1271.
Verslues, Paul, et al., "Methods and concepts in quantifying resistance to drought, salt and freezing, abiotic stresses that affect plant water status", The Plant Journal 45(4), (2006), 523-539.
"SubName: Full =Putati ve uncharacteri zed protein AT4g27030; SubName: Full=Putative uncharacterized protein F10M23.370", Database UniProt, (May 1, 2000).
"U.S. Appl. No. 11/484,947, Examiner Interview Summary mailed Feb. 8, 2011", 3 pgs.
"U.S. Appl. No. 11/484,947, Final Office Action mailed Jan. 19, 2011", 6 pgs.
"U.S. Appl. No. 11/484,947, Final Office Action mailed Jun. 1, 2009", 11 pgs.
"U.S. Appl. No. 11/484,947, Non Final Office Action mailed May 26, 2010", 8 pgs.
"U.S. Appl. No. 11/484,947, Non Final Office Action mailed Aug. 6, 2008", 14 pgs.
"U.S. Appl. No. 11/484,947, Notice of Allowance mailed Mar. 2, 2011", 5 pgs.
"U.S. Appl. No. 11/484,947, Notice of Non Compliant Amendment mailed Jan. 15, 2009", 4 pgs.
"U.S. Appl. No. 11/484,947, Notice of Non Compliant Amendment mailed Jan. 21, 2010", 8 pgs.
"U.S. Appl. No. 11/484,947, Preliminary Amendment filed Apr. 26, 2007", 3 pgs.
"U.S. Appl. No. 11/484,947, Preliminary Amendment filed Dec. 6, 2006", 4 pgs.
"U.S. Appl. No. 11/484,947, Response filed Feb. 11, 2009 to Notice of Non Compliant Amendment mailed Jan. 15, 2009", 9 pgs.
"U.S. Appl. No. 11/484,947, Response filed Feb. 14, 2011 to Final Office Action mailed Jan. 19, 2011", 8 pgs.
"U.S. Appl. No. 11/484,947, Response Filed Feb. 16, 2010 to Notice of Non Compliant Amendment mailed Jan. 21, 2010", 16 pgs.
"U.S. Appl. No. 11/484,947, Response filed Apr. 3, 2008 to Restriction Requirement mailed Mar. 5, 2008", 3 pgs.
"U.S. Appl. No. 11/484,947, Response filed Aug. 24, 2010 to Non Final Office Action mailed May 26, 2010", 9 pgs.
"U.S. Appl. No. 11/484,947, Response filed Nov. 2, 2009 to Final Office Action mailed Jun. 1, 2009", 16 pgs.
"U.S. Appl. No. 11/484,947, Response filed Nov. 6, 2008 to Non Final Office Action mailed Aug. 6, 2008", 15 pgs.
"U.S. Appl. No. 11/484,947, Restriction Requirement mailed Mar. 5, 2008", 9 pgs.
"Australian Application Serial No. 2007272993, Examiners First Report mailed Oct. 27, 2010", 4 pgs.
"Australian Application Serial No. 2007272993, Response filed Oct. 28, 2011 to Examiners First Report mailed Oct. 27, 10", 17 pgs.
"European Application Serial No. 07810352.0, Extended European Search Report mailed Aug. 4, 2010", 10 pgs.
, "European Application Serial No. 07810352.0, Office Action mailed Jun. 9, 2009", 3 pgs.
"European Application Serial No. 07810352.0, Office Action mailed Aug. 22, 2011", 4 pgs.
"European Application Serial No. 07810352.0, Office Action mailed Aug. 23, 2010", 1 pg.
"European Application Serial No. 07810352.0, Response filed Mar. 2, 2011 to Office Action mailed Aug. 23, 2010", 10 pgs.
"European Application Serial No. 07810352.0, Response filed Jun. 25, 2009 to Office Action mailed Jun. 9, 2009", 1 pg.
"European Application Serial No. 07810352.0, Response filed Nov. 29, 2011 to Office Action mailed Aug. 22, 2011", 8 pgs.
"International Application Serial No. PCT/US2007/015823, International Preliminary Report on Patentability mailed Jan. 13, 2009", 6 pgs.
"International Application Serial No. PCT/US2007/015823, International Search Report mailed Sep. 29, 2008", 4 pgs.
"International Application Serial No. PCT/US2007/015823, Written Opinion mailed Sep. 29, 2008", 5 pgs.
"SubName:Full=Putative RING zinc finger protein; SubName: Full=T23015.13.", retrieved EBI accession No. UNIPROT:Q9S109 Database accession No. Q9SI09, Database UniProt [Online].
Jiang, C., et al., "GenBank Accession EAI06997, Sequence 375 from U.S. Pat. No. 7,196,245", (Apr. 11, 2007).
Ko, et al., "Ectopic expression of MYB46 identifies transcriptional regulatory genes involve din secondary wall biosynthesis in Arabidopsis.", The Plant Journal, Aug. 6. (Epub ahead of print).
Ko, J., et al., "Upregulation ofan Arabidopsis RING-H2 gene, XERICO, confers drought tolerance through increased abscisic acid biosynthesis.", Plant J. Aug. 2006;47(3):. Epub, (Jun. 22, 2006), 343-55.
Matzke, Marjori A., et al., "How and Why Do Plants Inactivate Homologous (Trans)genes?", Plant Physiol. 107, (1995), 679-685.
Pobjecky, N., et al., "Expression of the beta-glucuronidase gene under the control of the CaMV 35s promoter in Schizosaccharomyces pombe.", Mol Gen Genet. Jan. 1990;220(2):314-6.
Yamada, K., et al., "GenBank Accession AF339689,Arabidopsis thaliana putative RING zinc finger protein (At2g04240) mRNA, complete cds.", (Sep. 18, 2002).
"European Application Serial No. 13181042.6, Response filed Oct. 29, 2015 to Examination Notification Art. 94(3) mailed Jul. 1, 2015", 22 pgs.

\* cited by examiner (a)

(b)

(c)

(a)

WT        *35::XERICO*

SEQ ID NO:1
GenBank Accession AF339689 Arabidopsis thaliana putative RING zinc finger protein
(At2g04240) mRNA, complete cds gi|12642857; "putative RING zinc finger protein"
MGLSSLPGPSE<u>GMLCVILVNTALSISIVKGIV</u>RSFLGIVGI<u>SLSPSSSSPSSVTVSSEN
SSTSES</u>FDFRVCQPESYLEEFRNRTPTLRFESLCRCKKQADN<u>ECSVCLSKFQGDSE
INKLKCGHLFHKTCLEKWIDYWNITCPLCRTPL</u>VVVPEDHQLSSNVW SEQ ID NO:2
GenBank Accession NM_126459
Arabidopsis thaliana putative RING zinc finger protein (At2g04240)
Trimmed here to match full-length protein SEQ ID NO:01
atgggtctatcaagtcttcctggtccatcagaaggaatgttatgtgtgatattagttaatacagcattatcgatctccattgtcaaagg
cattgtaagatcattccttggcatagtaggaatcagtctctcgccgtcttcatcctcgccttcttcggtgacggtatcttcagagaattc
atcaacttcagagtcatttgatttccgggtctgccaaccagagagttaccttgaggagttcaggaaccggactccgacactgaggt
ttgagagcttgtgcaggtgcaagaaacaggcagacaatgagtgttctgtgtgtttgtcgaaattccaaggggattcagagatcaac
aagctcaagtgcggccatttgtttcacaaaacatgcttggagaaatggatagactattggaacatcacttgcccattgtgtaggact
cctcttgttgttgtgccagaagaccatcagctttcttctaatgtttgg SEQ ID NO:3
RING domain amino acid seq from identified with NCBI BLAST
E[C]SV[C]LSKFQGDSEINKLK[C]G[H]L[F][H]KT[C]LEKWIDYWNIT[C]PL[C]RTPL SEQ ID NO:4
RING domain nucleic acid seq
gagtgttctgtgtgtttgtcgaaattccaaggggattcagagatcaacaagctcaagtgcggccatttgtttcacaaaacatgcttg
gagaaatggatagactattggaacatcacttgcccattgtgtaggactcctctt SEQ ID NO:5
'cross-brace' motif of RING domain amino acid seq as identified by NCBI BLAST
C-X2-C-X(9-39)-C-X(1-3)- H-X(2-3)-(N/C/H)-X2-C-X(4-48)C-X2-C SEQ ID NO:6
motif of At2g04240 RING domain
[C]XX[C]XXXXXXXXXXXXXXX[C]X[H]XX[H]XX[C]XXXXXXXXXXXX[C]XX[C]

SEQ ID NO:7
motif of At2g04240 RING domain
[C]XX[C]XXXXXXXXXXXXXXX[C]X[H]XX[H]XX[C]XXXXXXXXXXXX[C]XX[C]

SEQ ID NO:8
Low complexity region
SLSPSSSSPSSVTVSSENSSTSES

SEQ ID NO:9
Transmembrane region
GMLCVILVNTALSISIVKGIV

FIG. 10 cont'd

SEQ ID NO:10
GenBank Accession AF326867    751 bp    mRNA    linear    PLN 18-SEP-2002
DEFINITION Arabidopsis thaliana putative RING zinc finger protein (At2g04240) mRNA, complete cds.
aaaaccaactctctctacacactttttcagattccatcatcacttgttcttttcacacccaataaaaacttgcatctttcttctaaattgttg
atgatcgcttctcatatttgaccctagagacaacatcatttctaccgacaaagatttgatatcgaatccaacaagtgaaagatgggtc
tatcaagtcttcctggtccatcagaaggaatgttatgtgtgatattagttaatacagcattatcgatctccattgtcaaaggcattgtaa
gatcattccttggcatagtaggaatcagtctctcgccgtcttcatcctcgccttcttcggtgacggtatcttcagagaattcatcaactt
cagagtcatttgatttccgggtctgccaaccagagagttaccttgaggagttcaggaaccggactccgacactgaggtttgagag
cttgtgcaggtgcaagaaacaggcagacaatgagtgttctgtgtgtttgtcgaaattccaaggggattcagagatcaacaagctc
aagtgcggccatttgtttcacaaaacatgcttggagaaatggatagactattggaacatcacttgcccattgtgtaggactcctcttg
ttgttgtgccagaagaccatcagctttcttctaatgtttggtgactgcttttcactgtataggttttttgtttgagtgtgtttgttgtgtacag
ctacttttactatgaattaggttgcatcgcggttgatt SEQ ID NO:11
Amplified sequence
tttg/gatccgacaacatcatttctaccgacaaagatttgatatcgaatccaacaagtgaaagatgggtctatcaagtcttcctggtc
catcagaaggaatgttatgtgtgatattagttaatacagcattatcgatctccattgtcaaaggcattgtaagatcattccttggcatag
taggaatcagtctctcgccgtcttcatcctcgccttcttcggtgacggtatcttcagagaattcatcaacttcagagtcatttgatttcc
gggtctgccaaccagagagttaccttgaggagttcaggaaccggactccgacactgaggtttgagagcttgtgcaggtgcaag
aaacaggcagacaatgagtgttctgtgtgtttgtcgaaattccaaggggattcagagatcaacaagctcaagtgcggccatttgttt
cacaaaacatgcttggagaaatggatagactattggaacatcacttgcccattgtgtaggactcctcttgttgttgtgccagaagac
catcagctttcttctaatgtttggtgactgcttttcactgtataggttttttgtttgagtgtgtttgttgtgtacat/ctagaggg SEQ ID NO:12
Restricted Amplified sequence
gatccgacaacatcatttctaccgacaaagatttgatatcgaatccaacaagtgaaagatgggtctatcaagtcttcctggtccatc
agaaggaatgttatgtgtgatattagttaatacagcattatcgatctccattgtcaaaggcattgtaagatcattccttggcatagtag
gaatcagtctctcgccgtcttcatcctcgccttcttcggtgacggtatcttcagagaattcatcaacttcagagtcatttgatttccggg
tctgccaaccagagagttaccttgaggagttcaggaaccggactccgacactgaggtttgagagcttgtgcaggtgcaagaaac
aggcagacaatgagtgttctgtgtgtttgtcgaaattccaaggggattcagagatcaacaagctcaagtgcggccatttgtttcaca
aaacatgcttggagaaatggatagactattggaacatcacttgcccattgtgtaggactcctcttgttgttgtgccagaagaccatc
agctttcttctaatgtttggtgactgcttttcactgtataggttttttgtttgagtgtgtttgttgtgtaca*T*

SEQ ID NO:13
Restricted Amplified sequence of RING nucleic acids
gacaacatcatttctaccgacaaagatttgatatcgaatccaacaagtgaaagatgggtctatcaagtcttcctggtccatcagaag
gaatgttatgtgtgatattagttaatacagcattatcgatctccattgtcaaaggcattgtaagatcattccttggcatagtaggaatca
gtctctcgccgtcttcatcctcgccttcttcggtgacggtatcttcagagaattcatcaacttcagagtcatttgatttccgggtctgcc
aaccagagagttaccttgaggagttcaggaaccggactccgacactgaggtttgagagcttgtgcaggtgcaagaaacaggca
gacaatgagtgttctgtgtgtttgtcgaaattccaaggggattcagagatcaacaagctcaagtgcggccatttgtttcacaaaaca
tgcttggagaaatggatagactattggaacatcacttgcccattgtgtaggactcctcttgttgttgtgccagaagaccatcagcttt
cttctaatgtttggtgactgcttttcactgtataggttttttgtttgagtgtgtttgttgtgtaca

SEQ ID NO:14

FIG. 10 cont'd

UNIPROT:Q8S2S3_THEHA; *Thellungiella halophila* (Salt cress)
UniProt/TrEMBL|Q8S2S3|Q8S2S3_THEHA Putative RING zinc finger protein-like protein
MGLSSLPGPSEGMLCVILVNTALSISIFKGIVRSVLHVLGIRLSQSSSSPSSVTASSEI
PASEPFDFRVSHPESFLEEFRNKTPTLRYESLCRCKKHEDNECSVCLSKFEEDSEIN
KLKCGHLFHKTCLEKWIDYWNITCPLCRTPLVVVAAAEDQKQLSSNVW SEQ ID NO:15
*Thellungiella halophila* (Salt cress) RING domain
ECSVCLSKFEEDSEINKLKCGHLFHKTCLEKWIDYWNITCPLCRTPL SEQ ID NO:16
*Thellungiella halophila* (Salt cress) AF499720
UniProt/TrEMBL|Q8S2S3|Q8S2S3_THEHA
gagtgctcggtttgcttgtcgaaatttgaagaggattcagagattaacaagctgaaatgtggacacttgtttcacaaaacgtgcttg
gagaaatggatagactattggaacatcacttgcccactgtgtaggactcctctt SEQ ID NO:17
*Thellungiella halophila* (Salt cress) AF499720
UniProt/TrEMBL|Q8S2S3|Q8S2S3_THEHA
atgggtctatcaagccttcctggtccatcagaaggaatgctatgcgtgatattagtcaacacagcattatcaatctccatcttcaaag
gcattgtcagatcagtccttcacgtattaggaatccgtctctctcagtcttcgtcttccccttcttcagtaactgcatcttcagagatcc
cagcttcagagccatttgatttccgtgtctcccacccggagagtttcctcgaggagtttaggaacaagactccaactctgaggtac
gagagcttgtgcaggtgcaagaaacacgaggacaacgagtgctcggtttgcttgtcgaaatttgaagaggattcagagattaac
aagctgaaatgtggacacttgtttcacaaaacgtgcttggagaaatggatagactattggaacatcacttgcccactgtgtaggact
cctcttgttgttgtggcagcagcagaagaccagaagcagctttcttctaatgtttgg SEQ ID NO:18
Brassica napus (rape)
oilseed_rape|CD834580 similar to UP|Q6I656 (Q6I656) RING
ECSVCLSKFEEDSEINKAKCGHLFHKTCLEKWIDYWNITCPLCRTPL SEQ ID NO:19
Brassica napus (rape)
seed_rape|CD834580 similar to UP|Q6I656 (Q6I656) RING
KMGLSSLPGPSEGMLCVILVNTALSISIFKGILRSVLQLIGIRLSPSSAAAAAASSEN
QTSDSFDFRVCQPESFLEEFRNRTPTVKFESLCKCKKQADNECSVCLSKFEEDSEI
NKAKCGHLFHKTCLEKWIDYWNITCPLCRTPLVVVAADDQLVSIMFG SEQ ID NO:20
Brassica napus (rape)
seed_rape|CD834580 similar to UP|Q6I656 (Q6I656) RING
gagtgttctgtatgcctgtcgaaattcgaagaggattcagagatcaacaaggctaaatgtggccatttgtttcacaaaacatgcttg
gagaaatggatagactactggaacatcacttgcccactctgtaggactcctctt

SEQ ID NO:21

FIG. 10 cont'd

Brassica napus (rape)
seed_rape|CD834580 similar to UP|Q6I656 (Q6I656) RING
atgggtctatcaagccttcctggtccatcagaaggaatgctatgcgtgatattagttaacacagcattgtcaatctccatcttcaaag
gcattctcaggtcagtgcttcagctaataggaatccgcctctctccttcttcagcagcagcagcagctgcatcttcagagaatcaaa
cttcagattcttttgatttccgggtctgccagcctgagagtttccttgaggaattcaggaacaggacccccacagtgaagtttgaga
gcttgtgcaagtgcaagaaacaggcggacaacgagtgttctgtatgcctgtcgaaattcgaagaggattcagagatcaacaagg
ctaaatgtggccatttgtttcacaaaacatgcttggagaaatggatagactactggaacatcacttgcccactctgtaggactcctct
tgttgttgtcgcagcagacgaccagctggtttctataatgtttggtgaggac SEQ ID NO:22
gi|54306636|gb|AAV33472.1| Q5ULY2_FRAAN zinc finger family protein [Fragaria x ananassa][Fragment]
SEDTLKTLRTFELHLSSSGSYIEEIRSRIPAVRFDSVCNLKTEHDCSVCLSEFQPESE
INHLTCGHVFHQDCLEKWLNYWNITCPLCRTPFQGLI SEQ ID NO:23
gi|54306636|gb|AAV33472.1| Q5ULY2_FRAAN zinc finger family protein [Fragaria x ananassa]
http://www.expasy.org/sprot/userman.html - ID_line
DCSVCLSEFQPESEINHLTCGHVFHQDCLEKWLNYWNITCPLCRTP SEQ ID NO:24
gi|54306636|gb|AAV33472.1| Q5ULY2_FRAAN zinc finger family protein [Fragaria x ananassa]
gactgctctgtttgcctgagtgagttccaaccagaatccgagataaaccacttgacttgtggccatgttttccatcaagattgcttgg
agaagtggttgaactactggaacattacatgccctctttgtaggactcctt SEQ ID NO:25
gi|54306636|gb|AAV33472.1| Q5ULY2_FRAAN zinc finger family protein [Fragaria x ananassa]
atcagaggatacattgaagaccctcagaacattcgagctccatctttcttcctcaggcagttacattgaggagatcaggagccgca
tcccagccgttcggtttgatagcgtgtgtaacctcaagacggagcacgactgctctgtttgcctgagtgagttccaaccagaatcc
gagataaaccacttgacttgtggccatgttttccatcaagattgcttggagaagtggttgaactactggaacattacatgccctcttg
taggactcctttccaaggactcatc SEQ ID NO:26
ACCESSION DQ158860 gi|76446335|gb|ABA42952.1| RING-H2 finger protein [Poncirus trifoliata]
MGLASMPSASEGMLCLILMNTAMPISIVKGIFRSILKVVGFQLAESSSTPYSYFAS
PQVVSAEPYDVNLSPPLSYVEEFRNQNPAIKYETLLHCEDAEHDCSVCLTEFEPQ
SDINNLSCGHLFHKVCLEKWLDYLNVTCPLCRTPLIPEFEDDPSCFW SEQ ID NO:27
ACCESSION DQ158860 gi|76446335|gb|ABA42952.1| RING-H2 finger protein [Poncirus trifoliata]
DCSVCLTEFEPQSDINNLSCGHLFHKVCLEKWLDYLNVTCPLCRTPL

FIG. 10 cont'd

SEQ ID NO:28
ACCESSION DQ158860 gi|76446335|gb|ABA42952.1| RING-H2 finger protein [Poncirus trifoliata]
gactgttctgtgtgtttgaccgagtttgagcctcaatctgatataaataacttgtcttgtggacatttgtttcataaagtgt
gcttggagaagtggctggactatttgaatg tcacgtgcccgctttgcaggacacctcta SEQ ID NO:29
ACCESSION DQ158860 gi|76446335|gb|ABA42952.1| RING-H2 finger protein [Poncirus trifoliata]
cagtcacaagattttgcttgatttctgattcagtatctcaaatttagtacaaaattgggtatctgtaaatttaaaattttaattcgaaaacat
gggcctcgctagtatgccgtccgcatcagaaggaatgctatgcttgattctaatgaacactgctatgccaatctcaatcgtcaaag
gcatattcagatcaatcctcaaggttgtcggtttccagcttgctgaatcatcatcgacaccgtattcatatttcgcttcacctcaagttg
tctccgcagagccatatgatgtaaatttaagtcctccccttagctatgttgaggagttccgaaaccagaaccctgcaatcaagtatg
aaacattgctccattgtgaagatgcagagcatgactgttctgtgtgtttgaccgagtttgagcctcaatctgatataaataacttgtctt
gtggacatttgtttcataaagtgtgcttggagaagtggctggactatttgaatgtcacgtgcccgctttgcaggacacctctaattcct
gagttcgaagatgatccctcttgtttctggtgagagtgttttatgagtttgtctagttgtggagacttccatgtacagcatgtagtgtac
aggtatttactaatgcatcggctggagtgtagtgttgttacacgccttctgtgtgtgagttaaatctcgagtccttttgaaggcttgttg
agaaaaccagaattctgttgtaaatattgtgaggtttctggttgttttatggcatataatctgacttttgatcttcagctttctttaaagttc
atattagtgactttggtttccatctttctttaatgagttgtatgtgactgaatatggagaagttgatgaggctttctagtttccatgctaga
attgctcaaaaagaagtttgaattttacttgagtttaccaaacaagcatttgacaaaaaaaaaaaaaaaaaaaaaaaaaa SEQ ID NO:30
gi|49532976|dbj|BAD26589.1| RING zinc finger protein [Citrullus lanatus]
D|C|SX|C|LTQFEPASEINHLSXG|H|LF|H|TE|C|LEKXLDYWNIT|C|PL|C|RTPL SEQ ID NO:31
gi|49532976|dbj|BAD26589.1| RING zinc finger protein [Citrullus lanatus]
XGSXWXYLEMXRNRYPRXRFDKLQGSEXREHDCSXCLTQFEPASEINHLSXGHL
FHTECLEKXLDYWNITCPLCRTPLMXEEEKSXFW SEQ ID NO:32
gi|49532976|dbj|BAD26589.1| RING zinc finger protein [Citrullus lanatus]
gactgctcggnctgtttaactcaatttgaacctgcatctgagataaatcacttatcttgnggtcatcttttcacacagaatgcttgga
gaagnggctagattactggaacatcacatgtcctctttgcagaactcctctaat SEQ ID NO:33
gi|49532976|dbj|BAD26589.1| RING zinc finger protein [Citrullus lanatus]
ttntggctccncttggagntacctcgagatgnttcgaaaccgatatccaaggganccgatttgataaattacagggctcagaatgn
cgngaacatgactgctcggnctgtttaactcaatttgaacctgcatctgagataaatcacttatcttgnggtcatcttttcacacaga
atgcttggagaagnggctagattactggaacatcacatgtcctctttgcagaactcctctaatgnccgaagaagagaaatcgngc
ttttggtgagcgtagaatctagttnggggaaactcatgtacagcatactcttaaagataattgtgaaagcgtttcctacctttggcac
gtatgacatttgaagnttgatgngtctgacaggncttagaggccaaagnnttgncactgtaaatacatgtttatgaagnnctatgc
ntttggcttgtgcctttagctttgagttaangcactgttactncactttctttgtacatggaattggctgagtatgcacaaagntattcaa
attctgtttgttt

FIG. 10 cont'd

SEQ ID NO:34
ACCESSION AY221983 Hevea brasiliensis putative C3HC4-type RING zinc finger protein (RGZF1) mRNA, complete cds. gi|37901055|gb|AAP46154.1| putative C3HC4-type RING zinc finger protein [Hevea brasiliensis]
MCLSNLPASSE<u>GVICVVVMNTALSISIFKGIVRSVLHIVDNRLAPF</u><u>SSSSSSS</u><u>ILFPDY</u>
<u>SDTESFEFPLHSSDDCVRELRSRRPAKRFDAVSSCKQPQHDCPVCLIQFKPDSEIN</u>
<u>CLSCGHVFHKACLEKWLDYRKVTCPLCKSPVMPEEEDTSSSW</u>

SEQ ID NO:35
EM_PL:AY221983 AY221983.1 Hevea brasiliensis putative C3HC4-type RING zinc finger protein (RGZF1) mRNA, complete cds. Length = 580
tcttcccttctacttccacaactgtcaattgatctaagaaaatgtgtctctcaaatcttccagcctcatctgaaggagtaatctgtgtgg
ttgtgatgaacactgccttatcaatctccattttcaaagggatagtccggtcggtccttcacattgttgacaaccgcttagcacccttc
tcctcatcatcatcttcaatcctctttccagattacagtgacaccgaatcatttgaatttcctttacattcatcagacgattgcgttaggg
agctccgaagcaggaggcctgcaaaacgatttgatgcagtgtctagctgtaaacagcctcaacatgactgcccagtttgcttgatt
caattcaagccagactcggagataaaattgcttatcctgtggccatgttttcataaggcgtgcttggagaagtggttggattatcgga
aagttacttgtccgctttgcaagtctcctgtgatgcctgaagaagaggatacatctagctcttggtaagcatataccagaagtttgct
cgncttagtaaatgttcacgtgcagcgtgttgagtccacttggtgttc SEQ ID NO:36
ACCESSION AY221983 Hevea brasiliensis putative C3HC4-type RING zinc finger protein (RGZF1) mRNA, complete cds
D[C]PV[C]LIQFKPDSEIN[C]LS[C]G[H]VF[H]KA[C]LEKWLDYRKVT[C]PL[C]KSPV SEQ ID NO:37
ACCESSION AY221983 Hevea brasiliensis putative C3HC4-type RING zinc finger protein (RGZF1) mRNA, complete cds
gactgcccagtttgcttgattcaattcaagccagactcggagataaaattgcttatcctgtggccatgttttcataaggcgtgcttgga
gaagtggttggattatcggaaagttacttgtccgctttgcaagtctcctgtga SEQ ID NO:38
ACCESSION AY221983 Hevea brasiliensis putative C3HC4-type RING zinc finger protein (RGZF1) mRNA, complete cds
atgtgtctctcaaatcttccagcctcatctgaaggagtaatctgtgtggttgtgatgaacactgccttatcaatctccattttcaaaggg
atagtccggtcggtccttcacattgttgacaaccgcttagcacccttctcctcatcatcatcttcaatcctctttccagattacagtgac
accgaatcatttgaatttcctttacattcatcagacgattgcgttagggagctccgaagcaggaggcctgcaaaacgatttgatgca
gtgtctagctgtaaacagcctcaacatgactgcccagtttgcttgattcaattcaagccagactcggagataaaattgcttatcctgtg
gccatgttttcataaggcgtgcttggagaagtggttggattatcggaaagttacttgtccgctttgcaagtctcctgtgatgcctgaa
gaagaggatacatctagctcttggt aagcatataccagaagtttgctcgncttag SEQ ID NO:39
*Vitis vinifera*
grape|TC48889 similar to UP|Q6I656 (Q6I656) RING zinc finger protein
DCAVCLTRFEPDSEINHLPCGHFFSQGLLGEVAGLLEHHLPSVQDSL

SEQ ID NO:40

FIG. 10 cont'd

*Vitis vinifera*
grape|TC48889 similar to UP|Q6I656 (Q6I656) RING zinc finger protein
MGLSSLPAPSEG<u>VLCVLLVNTALSISIFKGIVR</u>AILHVIGIHLSATPS<u>SSSDSPEPTSEP
FEFRRNPSETCMEEFRSRNPAIRFDTVCSCKRPEHD</u><u>CAVCLTRFEPDSEINHLPCG
HFFSQGLLGEVAGLLEHHLPSVQDSL</u>NAGRGNILLLVSNIWENDKLRKYSNITVQ
LMYRCFT SEQ ID NO:41
*Vitis vinifera*
grape|TC48889 similar to UP|Q6I656 (Q6I656) RING zinc finger protein
gactgtgcggtttgcttgactcgatttgaaccagactctgagataaatcacctgccttgtggccatttttttcacaaggtttgcttgga
gaagtggctggactattggaacatcacctgccctctgtgcaggactcccctt SEQ ID NO:42
*Vitis vinifera*
grape|TC48889 similar to UP|Q6I656 (Q6I656) RING zinc finger protein
atgggactatcgagtctcccagccccatctgaaggagtactgtgtgtgcttctggtgaacacagctctctccatctccatcttcaag
ggcatagtccgggccatcctccatgtcattggaattcacctctccgcaaccccatcctcctccgactcccctgaacccacctcaga
gcccttgagtttaggcggaacccatctgagacctgcatggaggaattcaggagcaggaacccagcaatcaggtttgacacagt
gtgctcctgcaagcgccctgaacatgactgtgcggtttgcttgactcgatttgaaccagactctgagataaatcacctgccttgtgg
ccatttttttcacaaggtttgcttggagaagtggctggactattggaacatcacctgccctctgtgcaggactcccttaatgccgga
agaggaaacatcttgcttttggtaagcaatatctgggagaatgacaagttgaggaaatattcaaatatcactgtacagcttatgtata
ggtgttttacatg SEQ ID NO:43
*Vitis vinifera*
grape|TC48889 similar to UP|Q6I656 (Q6I656) RING zinc finger protein (Fragment),
partial (39%)    Length = 863  >TC48889 TC16981 TC28970
acttctgctgtcaattccacatcattgggatcccatgaatttctatgctgctgctgcttcttctccttcctgatcactccaacgcccccat
catcttctcaagctcaaccctatcagaccctccttctccgcaaatctaaatcccaaaactccaatttggagcagcatgggactatcg
agtctcccagccccatctgaaggagtactgtgtgtgcttctggtgaacacagctctctccatctccatcttcaagggcatagtccgg
gccatcctccatgtcattggaattcacctctccgcaaccccatcctcctccgactcccctgaacccacctcagagcccttgagttt
aggcggaacccatctgagacctgcatggaggaattcaggagcaggaacccagcaatcaggtttgacacagtgtgctcctgcaa
gcgccctgaacatgactgtgcggtttgcttgactcgatttgaaccagactctgagataaatcacctgccttgtggccatttttttcac
aaggtttgcttggagaagtggctggactattggaacatcacctgccctctgtgcaggactcccttaatgccggaagaggaaacat
cttgcttttggtaagcaatatctgggagaatgacaagttgaggaaatattcaaatatcactgtacagcttatgtataggtgttttacatg
aatacatcagctaggtgtatctttattcatatgttagttatatgctccagttttatgcctttatgtgaagaatctatatgatatcagggtca
catatcccatgtctatatatgtatatatatatattgtacatgttgtgaggtttctgatgttttggcac SEQ ID NO:44
M.truncatula
EM_PL:CT030180 CT030180.3 M.truncatula DNA sequence from clone MTH2-177C12
on chromosome 3
DCSVCLTQFEPESEINYCI SCGHVFHKVCLEKWLDYWNITCPLCRSPL

SEQ ID NO:45

FIG. 10 cont'd

M.truncatula
MGLSSLPAQSEGVLCIILVNTAMSISIFKGIIRTILHIVGIIASPSSSPSQDYIPQNIPES
YEIHLSPSDDFVEEFRSRTPTLRFDSVCNSCKEPEHDCSVCLTQFEPESEINYCISC
GHVFHKVCLEKWLDYWNITCPLCRSPLIPEDDASCLW SEQ ID NO:46
M.truncatula
gattgctcagtgtgtctcactcaatttgaacctgaatcagagataaactattgcatatcatgtggccatgttttcataaagtgtgtttgg
agaagtggttggattattggaacattacatgtccactt SEQ ID NO:47
M.truncatula
atgggcctatcaagtcttccagcacaatctgaaggagtgttatgcatcattctagtaaacactgccatgtcaatatccatattcaaag
gcattataaggactatcctgcacattgttggtatcattgcttcaccatcttcctctccttcccaagactacattcctcaaaacatacctg
agtcatatgaaatccatctaagtccttcagatgatttcgttgaagagttcagaagcagaacaccaacacttaggtttgatagtgtgtg
taatagctgcaaagaacctgaacatgattgctcagtgtgtctcactcaatttgaacctgaatcagagataaactattgcatatcatgt
ggccatgttttcataaagtgtgtttggagaagtggttggattattggaacattacatgtccact
tgtaggagtcctttaattcctgaagatgatgcatcttgcttatgg SEQ ID NO:48
*Cotton (Gossypium)*
cotton|TC39148 similar to UP|Q6Z8T9 (Q6Z8T9) Zinc finger protein family-like
MGLSGLPAPSEGVLCVFQSILHIVGIASSSPSSDSVENPSESFEFTPTTCDSYMEEFR
NRTPAMRFDAICSCKQPEYECSVCLTRFEPESEVNRLTCGHLFHKVCLEKWLDY
QKVTCPDCRTPLLHEQEASCIW SEQ ID NO:49
*Cotton (Gossypium)*
cotton|TC39148 similar to UP|Q6Z8T9 (Q6Z8T9) Zinc finger protein family-like RING domain
E[C]SV[C]LTRFEPESEVNRLT[C]G[H]LF[H]KV[C]LEKWLDYQKVT[C]PD[C]RTPL SEQ ID NO:50
*Cotton (Gossypium)*
cotton|TC39148 similar to UP|Q6Z8T9 (Q6Z8T9) Zinc finger protein family-like RING domain
gaatgttcggtttgcctaactcgatttgagccggaatcggaggttaatcgcttgacctgcggccatctctttcacaaggtgtgcttgg
aaaagtggttggattatcagaaggttacatgcccggattccggacgcctctgct SEQ ID NO:51
*Cotton (Gossypium)*
cotton|TC39148 similar to UP|Q6Z8T9 (Q6Z8T9) Zinc finger protein family-like
TC39148 TC11181 TC15434 TC2359 TC25267 TC6891
atgggtctctcaggtctcccagcaccatcagaaggagtgctatgtgtattccaatcaatccttcacattgtcggtattgcgtcttcatc
gccatcctcggattctgtcgaaaatccctcggaatcattcgaattcaccccctacaacttgtgatagttacatggaagagttccggaa
tagaaccccagcgatgaggtttgatgctatatgtagctgcaagcaacctgagtatgaatgttcggtttgcctaactcgatttgagcc

FIG. 10 cont'd ggaatcggaggttaatcgcttgacctgcggccatctctttcacaaggtgtgcttggaaaagtggttggattatcagaaggttacatg
cccggattgccggacgcctctgctgcatgaacaagaggcttcctgcatttggtg SEQ ID NO:52
Pinus taeda (loblolly pine)
>pine|TC61230 weakly similar to UP|Q6Z8T9 (Q6Z8T9) Zinc finger protein
VCAVCLSRMEEEDEMRELCNCFHVFHRNCLEKW LHQRQTTCPL SEQ ID NO:53
Pinus taeda (loblolly pine)
>pine|TC61230 weakly similar to UP|Q6Z8T9 (Q6Z8T9) Zinc finger protein
MGFLVIPSLLLHAAVLVACIKNAITWALQLVGLAEILEPETSAAFSRQETDCNPSA
QDEIIREWLLPVTTFGEFVQRFQGGVADDDVCAVCLSRMEEEDEMRELCNCFHV
FHRNCLEKWLHQRQTTCPLCRCCLLPEPEMEKADTMAPQSNQSWLVDSISFLFS
QDLAGHTL SEQ ID NO:54
Pinus taeda (loblolly pine)
>pine|TC61230 weakly similar to UP|Q6Z8T9 (Q6Z8T9) Zinc finger protein
gtgtgtgctgtgtgtttgagcaggatggaggaggaagatgagatgagagaattgtgtaattgctttcatgtatttcacaggaattgtt
tggagaagtggctccatcaacgtcagacgacgtgccctctc SEQ ID NO:55
Pinus taeda (loblolly pine)
>pine|TC61230 weakly similar to UP|Q6Z8T9 (Q6Z8T9) Zinc finger protein)
atggggttcctcgtcattcctagcctgctgctgcacgccgcagttttggtagcgtgcataaagaacgccatcacgtgggctctcca
gcttgttgggttggccgagattttggaacccgagacctccgccgccttttcacggcaagaaaccgactgtaatccatccgcgcag
gacgaaataatacgagaatggctgctgcccgttactacgtttggcgagtttgtgcaaagatttcaggggggagttgcagacgatg
atgtgtgtgctgtgtgtttgagcaggatggaggaggaagatgagatgagagaattgtgtaattgctttcatgtatttcacaggaattg
tttggagaagtggctccatcaacgtcagacgacgtgccctctctgcagatgctgtctcctgccggaaccggaaatggaaaaggc
agatacgatggcccctcagagtaaccagtcatggcttgtggacagtatctcgttttattttctcaagatttagcaggtcacaccttgt
a SEQ ID NO:56
Pinus taeda (loblolly pine)
>pine|TC61230 weakly similar to UP|Q6Z8T9 (Q6Z8T9) Zinc finger protein
>TC61230 TC25214 TC32068 TC50872
gctccctctcattgttgctaatgattcctttccgcttcccctcctcttccgtccattcgtatgggtagattcttgctcacctgagccgttc
aaattctggtgcttaggattccttttctgcctttccgtgcgagagtcgtttcagacaacagcgggggatggtgttcggtcgtggggc
tttcaggctggctggatcccatctgggtcgttttcaattccatctgattttataccccacaaactggatttgacctttcaatccctcaggc
ttgactgtgtcttcttctgttctctatttattcatctcccagaccgttcttcacagcattggaggtccagggttcgactctcttccttcgct
cctcatggggttcctcgtcattcctagcctgctgctgcacgccgcagttttggtagcgtgcataaagaacgccatcacgtgggctc
tccagcttgttgggttggccgagattttggaacccgagacctccgccgccttttcacggcaagaaaccgactgtaatccatccgc
gcaggacgaaataatacgagaatggctgctgcccgttactacgtttggcgagtttgtgcaaagatttcaggggggagttgcagac
gatgatgtgtgtgctgtgtgtttgagcaggatggaggaggaagatgagatgagagaattgtgtaattgctttcatgtatttcacagg
aattgtttggagaagtggctccatcaacgtcagacgacgtgccctctctgcagatgctgtctcctgccggaaccggaaatggaaa

FIG. 10 cont'd aggcagatacgatggcccctcagagtaaccagtcatggcttgtggacagtatctcgtttttattttctcaagatttagcaggtcacac
cttgtaacgtgtggaggagaattgaatcatttgcttgcgttgcagctatgggttggagtaaaaaactaacaccnntaggatatcttct
tgactgtaatgttacgggctttnnatgtaacgttaccgnt SEQ ID NO:57
Pinus taeda (loblolly pine)
pine|TC67818 weakly similar to UP|Q5ULY2 (Q5ULY2) Zinc finger family protein
ECAVCLCKFEEGVEIRQLPCCHLFHRSCLDKWLDHQQITCPL SEQ ID NO:58
Pinus taeda (loblolly pine)
pine|TC67818 weakly similar to UP|Q5ULY2 (Q5ULY2) Zinc finger family protein
MGLSSFPTTVSEGVLPILIVNTALSFAIIKDILRSFLQIVGLTTGNEPDFNDPSWPYP
SENSPATSTDHSEVQFVAEEIRQSLPIKKFQSCSDGSVGSDNTHVECAVCLCKFEE
GVEIRQLPCCHLFHRSCLDKWLDHQQITCPLCRSCLISEEAAKNIRLREQELTDEL
VFWCSSFQDAAYHPTWIES SEQ ID NO:59
Pinus taeda (loblolly pine)
pine|TC67818 weakly similar to UP|Q5ULY2 (Q5ULY2) Zinc finger family protein
gagtgtgcagtctgcttatgcaaatttgaagaaggggttgagattagacagctgccttgctgccaccttttcacagatcttgtcttga
taaatggctggaccatcagcagatcacatgtcccttg SEQ ID NO:60
Pinus taeda (loblolly pine)
pine|TC67818 weakly similar to UP|Q5ULY2 (Q5ULY2) Zinc finger family protein
atgggtctctcaagctttccaccaccgtctctgaaggagtcctgccaattctgattgtgaatactgctctgtcgtttgccattatcaa
ggacatcctgaggtcttttcttcagatcgtaggccttaccacaggcaatgaacctgactttaacgatccatcatggccttacccatct
gagaatagccctgcaaccagtactgaccattccgaggtgcagttcgttgcagaggaaataaggcagagcctacccatcaaaaa
gttccaatcttgtagtgatgggtctgttggtagtgacaatacccatgttgagtgtgcagtctgcttatgcaaatttgaagaaggggtt
gagattagacagctgccttgctgccaccttttcacagatcttgtcttgataaatggctggaccatcagcagatcacatgtcccttgt
gtagatcatgtctgatatcagaagaagcagccaagaatatcaggctcagggaacaggagcttacagatgaattggtattctggtg
ttcatccttccaagatgcggcttatcatcctacatggattgaaagtta SEQ ID NO:61
Pinus taeda (loblolly pine)
pine|TC67818 weakly similar to UP|Q5ULY2 (Q5ULY2) Zinc finger family protein
>TC67818 TC54746
aaggtgttcattttctcacatctttctttgttcatgcagatcttgttcgttgtgccttctgtgactgaaaattctcatgggtctctcaagctt
tcccaccaccgtctctgaaggagtcctgccaattctgattgtgaatactgctctgtcgtttgccattatcaaggacatcctgaggtctt
ttcttcagatcgtaggccttaccacaggcaatgaacctgactttaacgatccatcatggccttacccatctgagaatagccctgcaa
ccagtactgaccattccgaggtgcagttcgttgcagaggaaataaggcagagcctacccatcaaaaagttccaatcttgtagtgat
gggtctgttggtagtgacaatacccatgttgagtgtgcagtctgcttatgcaaatttgaagaaggggttgagattagacagctgcct
tgctgccaccttttcacagatcttgtcttgataaatggctggaccatcagcagatcacatgtcccttgtgtagatcatgtctgatatca
gaagaagcagccaagaatatcaggctcagggaacaggagcttacagatgaattggtattctggtgttcatccttccaagatgcgg
cttatcatcctacatggattgaaagttagaatttcttggatcctggtttgatggattcttcgacacttgaaccagtcatctggggtctata

FIG. 10 cont'd attggagattctgtaatttttttttttgtaaataatctttaggaaagttgcttgtttctacaggatgctttgttgtttctcctgttgaaagcaat
cctgttttctgaagattatgtagtcaatacttcttctgtatatagcaggaaagcctatatgtagagaagacctagaacttagaatctgtt
cttttcagtacttgaggttttctagggtggcctgagaaggtctggaatgatctgtgtgggatctgagatctaccgatcagccaagaa
aaaggaaaaaaaatcgtgtgccctgtctgttagtggatggcatacacaccattacaaaaactttgttttgaagatatcattttgcagtc
cccatgggattggctgagcagtgaagtcgggtgatttccgctctgccatctatggctgttttgtggggatgtctgtaataactttgtat
tactctctatttgaacatggaatttgattttttgatgagttaggcaaagaa SEQ ID NO:62
Nicotiana tabacum (common tobacco) tobacco|BP130278
ECPVCPGSISTMMKNRLVSVAHVFHKLCXEKWIKNWNVTCPHL SEQ ID NO:63
Nicotiana tabacum (common tobacco) tobacco|BP130278
gaatgcccggtatgccctggcagtatttcaaccatgatgtagaaatagaaccgcctcgtcagtgtggcccatgtttttcataagctc
tgtntcgagaaatggatcaagaattggaatgtcacctgtcctcatctg SEQ ID NO:64
Nicotiana tabacum (common tobacco) tobacco|BP130278
LKSPGTRLNVVGSPSGSYMEDFRSRTPAVSLFNVYIITLRQECPVCPGSISTMMKN
RLVSVAHVFHKLCXEKWIKNWNVTCP SEQ ID NO:65
Nicotiana tabacum (common tobacco) tobacco|BP130278
ggttgaacacagccatatctatctctgttgtcaaggagatantttggtctattcttcatgtgatnggcatccacttggcatcttcggaa
gaatattctgattgaagtcccctgggacccgtttgaatgtcgtggggagcccctcgggttcatatatggaggacttccgaagccga
actcctgcagtatcgttatgattcaatgtgtacatctgaatcaccctgcgacaagaatgcccggtatgccctggcagtatttcaacc
atgatgtagaaatagaaccgcctcgtcagtgtggcccatgtttttcataagctctgtntcgagaaatggatcaagaattggaatgtc
acctgtcctcatctgtcaggaagttacattatgcctcaagaa SEQ ID NO:66
Nicotiana tabacum (common tobacco) tobacco|BP130278
ttcttgaggcataatgtaacttcctgacagatgaggacaggtgacattccaattcttgatccatttctcganacagagcttatgaaaa
acatgggccacactgacgaggcggttctatttctacatcatggttgaaatactgccagggcataccgggcattcttgtcgcagggt
gattcagatgtacacattgaatcataacgatactgcaggagttcggcttcggaagtcctccatatatgaacccgaggggctcccca
cgacattcaaacgggtcccaggggacttcaatcagaatattcttccgaagatgccaagtggatgccnatcacatgaagaataga
ccaaaantatctccttgacaacagagatagatatggctgtgttcaacc SEQ ID NO:67
spruce|TC4946 weakly similar to UP|Q6I656 (Q6I656) RING zinc finger protein
<u>NTALSFAIIKDILRSFLQIVGLTTGTEPDFIDPSWPYPPENTPAVSTGHSEAQFIAEEI
RQSLPIKRFQSFTDGFVGSDNSHV</u>ECAVCLSKFEEGVEIRQLTCCHLFHRPCLDW
LDHQQITCPLCRSCLISEEAAKNIRLREQELTDESVFWCSSFQEAAYHHTWIES SEQ ID NO:68
spruce|TC4946 weakly similar to UP|Q6I656 (Q6I656) RING zinc finger protein

FIG. 10 cont'd

ECAVCLSKFEEGVEIRQLTCCHLFHRPCLDKWLDHQQITCPLCRSCL

SEQ ID NO:69
spruce|TC4946 weakly similar to UP|Q6I656 (Q6I656) RING zinc finger protein (Fragment), partial (57%)
aatactgctctgtcttttgccattatcaaggacatcctgaggtcttttcttcagattgtaggccttaccacaggcactgaacctgatttta
tcgacccatcatggccttacccacctgaaaatacccctgcagtcagtactggccattccgaagcgcagttcattgcagaggaaat
caggcagagcctacccatcaaaaggttccaatcttttactgatgggtttgttggtagtgacaatagccatgttgagtgtgcagtctgt
ttatccaaatttgaggaaggggttgagatcagacagctgacttgctgccaccttttcacagaccttgccttgataaatggctggac
catcagcagatcacctgtcccttgtgtagatcatgtctgatatccgaagaagcagccaagaatatcaggctcagggaacaggag
cttacagatgaatcggtattttggtgttcatccttccaagaagctgcttatcatcatacatggattgaaagtta SEQ ID NO:70
*Triphysaria*
yellow owl's clover [Hrusa 2001], yellowbeak owl's-clover annual herb
MFCIYAESHLGTLTFIFYTCIWIPFFQTTLTILRHFTCFIYQTKNINLGSNVREVDLR
VSHFRDLESKSKNKGEGIIDNEENEELCSICLMVFEEKDSVNKLPRCRHTFHTEC
LKKWLDRCQITCPLCRSLV SEQ ID NO:71
*Triphysaria*
yellow owl's clover [Hrusa 2001], yellowbeak owl's-clover
annual herb 53%
CSICLMVFEEKDSVNKLPRCRHTFHTECLKKWLDRCQITCPLCRS SEQ ID NO:72
*Triphysaria*
yellow owl's clover [Hrusa 2001], yellowbeak owl's-clover annual herb
tgttttgcatatatgcagaatcccatttaggcacattaaccttcatcttctacacatgcatatggatcccattttccaaacaactctaac
aattctcagacacttcacctgtttatttatcaaaccaaaaacatcaacttaggatctaatgttcgcgaggtggatcttcgggtctcac
attttcgtgatttggaaagcaaaagcaaaaacaaaggagagggcattatagataatgaagaaaacgaagaactctgctcgatttg
cttgatggtattcgaggaaaaagattcagtgaacaaactgccaagatgcaggcacacatttcacaccgagtgcctgaaaaaatg
gcttgatagatgccaaattacctgcccattgtgtcggtctttggtgtag SEQ ID NO:73
*Lotus japonicus*
BP045442 Lotus corniculatus var. japonicus pods
ECSVCLTKFEPESEINCLPCGHLFHKACLEKWLDYWNITCPLCRTPL SEQ ID NO:74
*Lotus japonicus*
l_japonicus|BP045442
BP045442 Lotus corniculatus var. japonicus pods
LRFESVCSSCKQQPEHECSVCLTKFEPESEINCLPCGHLFHKACLEKWLDYWNIT
CPLCRTPLMPEDDASCFW

FIG. 10 cont'd

SEQ ID NO:75
*Lotus japonicus* l_japonicus|BP045442 Lotus corniculatus var. japonicus pods
gagtgttcagtgtgtctcactaaatttgaaccagaatcagagataaactgtttaccttgtggccatctcttccataaagcatgcttgga
gaaatggttggactattggaacattacgtgcccactttgcaggactcccta SEQ ID NO:76
*Lotus japonicus* l_japonicus|BP045442 Lotus corniculatus var. japonicus pods
cttaggtttgagagtgtgtgtagcagttgcaaacaacaacctgaacatgagtgttcagtgtgtctcactaaatttgaaccagaatca
gagataaactgtttaccttgtggccatctcttccataaagcatgcttggagaaatggttggactattggaacattacgtgcccactttg
caggactcccttaatgcctgaagatgatgcatcttgcttttgg SEQ ID NO:77
*Lotus japonicus* l_japonicus|BP045442 Lotus corniculatus var. japonicus pods
aacatgaaatcctctcacttgaatcccacgtgtatgctacaatgtctacttaccagaatcaaacacaactaaccaaccagaaattat
atccaccaggtacagagaaactaagaacaaaaccctctacaagctctacatcataaagagcaaaaggttaaattgactctataag
tcagctccatgagaacatcaaaattgtcacaaatatgtacaccctacactgtacattaaactctcttattctatttagcatgatcactca
ttgcttaccaaaagcaagatgcatcatcttcaggcattaagggagtcctgcaaagtgggcacgtaatgttccaatagtccaaccatt
tctccaagcatgctttatggaagagatggccacaaggtaaacagtttatctctgattctggttcaaatttagtgagacacactgaaca
ctcatgttcaggttgttgtttgcaactgctacacacactctcaaacctaag SEQ ID NO:78
Helianthus annuus (common sunflower) sunflower|BU672034
KICLVEFKPDAEINHLSCGHVFHTCCLEKWLKYWNITCPL SEQ ID NO:79
Helianthus annuus (common sunflower) sunflower|BU672034
KICLVEFKPDAEINHLSCGHVFHTCCLEKWLKYWNITCPLCRNHMMGGNQVEE
NMCPM SEQ ID NO:80
Helianthus annuus (common sunflower) sunflower|BU672034
ttcgagcggccgcccgggcaggtcaagaataaaaaatttgtttggttgagtttaaaccggagcggagattaatcacctttcttgtg
gacatgtgttccatacatgttgccttgagaaatggttgaagtattggaacattacttgtcctcttt SEQ ID NO:81
Helianthus annuus (common sunflower) sunflower|BU672034
actcagctatgctccagcgttgggcatcaaaagagggtcgacctgcaggcgttccaaaatactagtgattagcgtggtcgcggc
cgaggtacactaacacattatctcacccttaacacatgatgagctaaccactcacattgggcacatgttttcttccacttgattaccac
ccatcatatggttcctacaaagaggacaagtaatgttccaatacttcaaccatttctcaaggcaacatgtatggaacacatgtccac
aagaaaggtgattaatctccgcatccggtttaaactcaaccaaacaaattttttattcttgacctgcccgggcggccgctcgaa SEQ ID NO:82
*Wheat (Triticum aestivum)* wheat|TC233399 similar to UP|Q6Z8T9 (Q6Z8T9) Zinc
finger protein family-like
MGI<u>SSMP</u>APKESLLIYLLYHAVVSIAALAGLLRAALVFLGLPAPPSLLAGEDADG
ADQLTAATPAGPSLAERFRSRFRPARFGRRRGAAASATP<u>DCRVCLVRFEADAVV</u>

FIG. 10 cont'd

NRLPCGHLFHRACLETWLDYDHATCPLCRSRLLPXXGFGGDESWSCAGPTLTG
WI

SEQ ID NO:83
*Wheat (Triticum aestivum)* wheat|TC233399 similar to UP|Q6Z8T9 (Q6Z8T9) Zinc finger protein family-like, RING domain
DCRVCLVRFEADAVVNRLPCGHLFHRACLETWLDYDHATCPLCRSRL SEQ ID NO:84
*Wheat (Triticum aestivum)*
wheat|TC233399 similar to UP|Q6Z8T9 (Q6Z8T9) Zinc finger protein family-like
gactgccgcgtctgcctggtgcggttcgaggccgacgccgtggtgaaccgcctcccctgcggccacctcttccaccgcgcctg
cctcgagacctggctggactacgaccacgccacctgcccgctctgccgctcccgcctt SEQ ID NO:85
*Wheat (Triticum aestivum)*
wheat|TC233399 similar to UP|Q6Z8T9 (Q6Z8T9) Zinc finger protein family-like
atgggcatctccagcatgccggcgcccaaggagagcctcctgatctacctgctctaccacgccgtcgtctcgatcgccgccctg
gcgggcctcctccgcgccgcgctcgtcttcctcggcctccccgcgccgccctcgctgctggccggcgaggacgccgacggc
gccgaccagctcacggcggccaccccggcgggcccagctggcggagcggttcaggagcaggttccgccccgcgcggtt
cggccggagaaggggcgcggcggcgtcggcgacacccgactgccgcgtctgcctggtgcggttcgaggccgacgccgtg
gtgaaccgcctcccctgcggccacctcttccaccgcgcctgcctcgagacctggctggactacgaccacgccacctgcccgct
ctgccgctcccgccttcttccggncgncggcttcggcggcgacgagtcgtggtcgtgcgccgggcccaccctgacgggctgg
attta SEQ ID NO:86
Potato|TC120988 (Q8S2S3) Putative RING zinc finger protein-like protein
MGLSQYPTPADA<u>GVLGVILVNTAISISIIKEILRSILRVIGIRIASWEDYSVEGPLDSL
ECRGSPPES</u>YMEEFRNRTPAFCYDSLCISNHPEQECSVCLTKFEPDAGVNSLSCGH
VFHKLCLEKWLRYWHVTCPLCRNYLMSQQERMIRVRCEIKRFTVPLHPFDDVII
YSLVVYRPSMWMLDL SEQ ID NO:87
Potato|TC120988 (Q8S2S3) Putative RING zinc finger protein-like protein, RING domain
ECSVCLTKFEPDAGVNSLSCGHVFHKLCLEKWLRYWHVTCPLCRNYL SEQ ID NO:88
Potato|TC120988 (Q8S2S3) Putative RING zinc finger protein-like protein, RING domain
gaatgctctgtgtgcctgacaaaattcgagcctgatgcaggggtaaacagtctctcatgcggtcacgttttccataagctgtgtcta
gagaagtggctcaggtattggcatgtaacttgtcctctttgcagaaattacttg SEQ ID NO:89
Potato|TC120988 (Q8S2S3) Putative RING zinc finger protein-like protein

FIG. 10 cont'd atgggcctctcacaatatccaactccagcagatgcaggagtacttggtgtgattctagtaaacacagccatatccatctccattatc
aaggagatactccgatcgatccttcgtgtgattggcatccgtatcgcatcatgggaagactattctgttgaaggacccttggactca
cttgaatgccgtggaagcccaccagagtcatacatggaggagttcagaaaccgaacacctgcattttgttatgactcgctatgtat
ctctaaccaccctgaacaagaatgctctgtgtgcctgacaaaattcgagcctgatgcaggggtaaacagtctctcatgcggtcac
gttttccataagctgtgtctagagaagtggctcaggtattggcatgtaacttgtcctctttgcagaaattacttgatgtctcaacaaga
gaggatgatacgtgtccgatgtgagattaaacgttttacggtgccacttcatccatttgatgatgttatcatttacagcttagtagtgta
caggccgagtatgtggatgcttgatctttg SEQ ID NO:90
*Capsicum annuum* pepper|CA525749
ECSVCLTKFEPDAGVNSLSCGHVFHKLCLEKWLTYWHVTCPLCRNHL SEQ ID NO:91
*Capsicum annuum* pepper|CA525749
gaatgccgtggaagcccaccagagtcatacatggaggagttcagaagccgaacacctgcatttcgttatgactcgctatgcatct
ctaaccacccttcatgtggtcatgttttccataagctgtgtctagagaagtggctcacgtattggcatgtaacttgtcctctttgcaga
aatcacttg SEQ ID NO:92
*Capsicum annuum* pepper|CA525749
MGLSQYPTPADA<u>GVLGVILVNTAISISIVKEILRSILRL</u>IGIRIASWEDYSIEGSSDSL
ECRG<u>SPPES</u>YMEEFRSRTPAFRYDSLCISNHPEQECSVCLTKFEPDAGVNSLSCGH
VFHKLCLEKWLTYWHVTCPLCRNHLMPQQEQDDT SEQ ID NO:93
*Capsicum annuum* pepper|CA525749
atgggcctctcacaatatccaactccagcagatgcaggagtactaggtgtgattctagtaaacacagccatatccatatccattgtc
aaggagatactacgatcgattcttcgcctgataggcatccgtatcgcatcatgggaagactattctattgaaggctcctcagactca
cttgaatgccgtggaagcccaccagagtcatacatggaggagttcagaagccgaacacctgcatttcgttatgactcgctatgca
tctctaaccaccctgaacaagaatgttctgtgtgcctaacaaaatttgagcctgatgcaggggtaaacagtctcgaacaagaatgtt
ctgtgtgcctaacaaaatttgagcctgatgcaggggtaaacagtctctcatgtggtcatgttttccataagctgtgtctagagaagtg
gctcacgtattggcatgtaacttgtcctctttgcagaaatcacttgatgcctcaacaagaacaggacgatacgtg SEQ ID NO:94
*Capsicum annuum* pepper|CA525749
gtccctcttacaaaaataaaaataaagtactacagaaaattgctacaaaaaagtctcaagttttcatattattagatccggtatattg
agctcttccagaaggttttgaagaaagaatcatcatttcaacactaggttccgatccgttatgggcctctcacaatatccaactccag
cagatgcaggagtactaggtgtgattctagtaaacacagccatatccatatccattgtcaaggagatactacgatcgattcttcgcc
tgataggcatccgtatcgcatcatgggaagactattctattgaaggctcctcagactcacttgaatgccgtggaagcccaccaga
gtcatacatggaggagttcagaagccgaacacctgcatttcgttatgactcgctatgcatctctaaccaccctgaacaagaatgttc
tgtgtgcctaacaaaatttgagcctgatgcaggggtaaacagtctctcatgtggtcatgttttccataagctgtgtctagagaagtgg
ctcacgtattggcatgtaacttgtcctctttgcagaaatcacttgatgcctcaacaagaacaggacgatacgtg SEQ ID NO:95
Soybean (*Glycine max*) Soybean|TC230215 probable RING zinc finger protein

FIG. 10 cont'd

MGLSSLPAPSEGVLCVLLVNTALSISIFKGIVRTILQIVGIRVSSLSPSPDISRNPPEP
LEFNLSPSEGFIEEFRSRTPTLRFGSMCGSKQPQHECCCVCLTKFEPESEINCLSCG
HIFHKVCMEKWLDYWNITCPLCRTSLMPEDDASCFW

SEQ ID NO:96
Soybean (*Glycine max*) Soybean|TC230215 probable RING zinc finger protein
ECCCVCLTKFEPESEINCLSCGHIFHKVCMEKWLDYWNITCPLCRTSL SEQ ID NO:97
Soybean (*Glycine max*) Soybean|TC230215 probable RING zinc finger protein
gaatgttgttgtgtgtgtctcacaaagtttgaaccagaatctgagataaactgtttatcatgtggccatattttcacaaagtgtgcatg
gagaagtggttggactattggaacattacatgcccactttgcaggacttccttg SEQ ID NO:98
Soybean (*Glycine max*) Soybean|TC230215 probable RING zinc finger protein
atgggcctgtcaagtctcccagcaccatctgaaggagtgttatgtgtgcttcttgtaaacactgccttgtctatatccatattcaaagg
cattgttaggacaattctacaaattgtcggtatccgcgtttcgtcgttgtctccttcaccagacatctcccgaaacccacctgagcca
ttagaattcaacctcagcccctcggagggtttcattgaagagttcagaagcaggacaccaacacttaggtttggcagcatgtgtgg
cagtaaacaacctcaacatgaatgttgttgtgtgtgtctcacaaagtttgaaccagaatctgagataaactgtttatcatgtggccata
ttttcacaaagtgtgcatggagaagtggttggactattggaacattacatgcccactttgcaggacttccttgatgcctgaagatga
tgcatcttgcttttggta SEQ ID NO:99
Soybean (*Glycine max*)
TC217409 (Q8S2S3) Putative RING zinc finger protein-like protein
MGLSSLPAPSEGVLCVLLVNTVLSISIFKGIVRTILHIVGIHLSSSSSTSPSSPDPSLT
APESFEFHLSPSESYIEEFRSRTPTLRFDSVCCCKQPEHDCSVCLTQFEPESEINRLS
CGHLFHKVCLEKWLDYWNITCPLCRTPLMPEDDTPCFQ SEQ ID NO:100
Soybean (*Glycine max*)
TC217409 (Q8S2S3) Putative RING zinc finger protein-like protein, RING domain
DCSVCLTQFEPESEINRLSCGHLFHKVCLEKWLDYWNITCPLCRTPL SEQ ID NO:101
Soybean (*Glycine max*)
TC217409 (Q8S2S3) Putative RING zinc finger protein-like protein, RING domain
gactgctctgtatgcctcactcagtttgaaccggaatcggagataaaccgcttatcgtgcggccatctcttccacaaagtgtgctta
gagaagtggctggactactggaacattacatgccctctttgcaggactcccttgat SEQ ID NO:102
Soybean (*Glycine max*)
TC217409 (Q8S2S3) Putative RING zinc finger protein-like protein
atgggcctttcaagtctcccagcaccatctgaaggagtattatgtgtccttctggtgaacactgtattgtcaatttcaatattcaaagg
cattgttaggacaatcctacacattgttggcatccatctttcatcatcatcctccacttcaccctcttcaccagatccctcgctaaccgc
acctgagtcatttgaattccatcttagtccctctgagagttacattgaagagttcagaagccggacgccaacacttcggttcgacag

FIG. 10 cont'd tgtgtgctgctgtaaacaacctgagcatgactgctctgtatgcctcactcagtttgaaccggaatcggagataaaccgcttatcgtg
cggccatctcttccacaaagtgtgcttagagaagtggctggactactggaacattacatgccctctttgcaggactcccttgatgcc
tgaagatgacacaccttgctttcagta SEQ ID NO:103
Lettuce (Lactuca sativa) Lettuce|TC9685 putative RING zinc finger protein-like protein
MGLSPYSNPSDAGVLCVILVNTAMSISIMKEIVCSILHVVGLRVASSPSSSNQGSP
EASERRGSPSETYMEEFRSRTPSLRYISLRRPTKQECSVCLTEFKPDSEINKLSCGH
VFHKSCLEKWLKCWNITCPLCRNHMMISKEMEENNTCPM SEQ ID NO:104
Lettuce (Lactuca sativa) Lettuce|TC9685 putative RING zinc finger protein-like protein
ECSVCLTEFKPDSEINKLSCGHVFHKSCLEKWLKCWNITCPLCRNHM SEQ ID NO:105
Lettuce (Lactuca sativa) Lettuce|TC9685 putative RING zinc finger protein-like protein
gaatgctccgtttgcttaacggagtttaaaccagattcagagataaataagctttcgtgtgggcatgttttcataaatcctgccttga
aaaatggctaaaatgctggaacattacttgccctctctgtagaaaccacatgat SEQ ID NO:106
Lettuce (Lactuca sativa) Lettuce|TC9685 putative RING zinc finger protein-like protein
atggggctctcgccatactcaaacccatcggatgcaggagtgttgtgcgtaattctggttaacacagctatgtcgatatcaatcatg
aaggaaatagtttgttcgattcttcatgtggtggggttacgtgtagcgtcatcaccgtcatcatccaatcaaggctcgccggaagct
tctgagcgccggggaagtccgtcggagacgtacatggaggagttcagaagccggacgccgtcgctccgttacatctccctccg
tcgtcccaccaaacaagaatgctccgtttgcttaacggagtttaaaccagattcagagataaataagctttcgtgtgggcatgtttt
cataaatcctgccttgaaaaatggctaaaatgctggaacattacttgccctctctgtagaaaccacatgatgatttctaaagaaatgg
aagaaaacaacacttgcccgatgtg SEQ ID NO:107
Tomato (Lycopersicon esculentum)
Tomato|TC157346 (Q8S2S3) Putative RING zinc finger protein-like protein
MGLSQYPTPADAGVLGVILVNTAISISIIKEILRSILRVIGIRIASWEDYSIEGPLDSL
ECRGSPPESYMEEFRSRTPAFRYDSLRISNHPEQECSVCLTKFEPDAGVNSLSCGH
VFHKLCLEKWLRYWHVTCPLCRNYLMPQQEEDDTCPM SEQ ID NO:108
Tomato (Lycopersicon esculentum)
Tomato|TC157346 (Q8S2S3) Putative RING zinc finger protein-like protein
ECSVCLTKFEPDAGVNSLSCGHVFHKLCLEKWLRYWHVTCPLCRNYL SEQ ID NO:109
Tomato (Lycopersicon esculentum)
Tomato|TC157346 (Q8S2S3) Putative RING zinc finger protein-like protein
gaatgctctgtgtgcctgacaaaatttgagcctgatgcaggggtaaacagcctctcatgtggtcatgttttccataagctgtgtctag
agaagtggctcaggtattggcatgtaacttgtcctctttgtagaaattacttg

FIG. 10 cont'd

SEQ ID NO:110
Tomato (Lycopersicon esculentum)
Tomato|TC157346 (Q8S2S3) Putative RING zinc finger protein-like protein
atgggcctctcacaatatccaactccagcagatgcaggagtactcggtgtaattctagtaaacacagccatatccatctccattatc
aaggagatactccgttcgatccttcgtgtgattggcatccgtatcgcatcatgggaagactattctattgaaggacccttggactca
cttgaatgccgtggaagcccaccagaatcatacatggaggagttcagaagccgaacgcctgcatttcgttatgactcgctacgta
tctctaaccaccctgaacaagaatgctctgtgtgcctgacaaaatttgagcctgatgcaggggtaaacagcctctcatgtggtcat
gttttccataagctgtgtctagagaagtggctcaggtattggcatgtaacttgtcctctttgtagaaattacttgatgcctcaacaaga
agaggacgatacatgtccaatgtg SEQ ID NO:111
Sorghum bicolor sorghum|TC110812 similar to UP|BAD10011 (BAD10011) Zinc finger protein family-like
DCRVCLVRFEPESVVNRLPCGHLFHRACLETWLDYDHATCPLCR SEQ ID NO:112
Sorghum bicolor sorghum|TC110812 similar to UP|BAD10011 (BAD10011) Zinc finger protein family-like
gactgccgcgtgtgcctggtgcggttcgagccggagtcggtggtcaaccggctcccctgcggccacctcttccaccgcgcatg
cctcgagacctggctcgactacgacc acgccacctgcccgctctgccgccaccgcctcct SEQ ID NO:113
Sorghum bicolor
sorghum|TC110812 similar to UP|BAD10011 (BAD10011) Zinc finger protein family-like,
MGISSMPAPKDSLLGFVLYNAAASVAILSGLVRAALLFLGVAAAPSSSPWEAPEE
ERRQQQQGAVRVTPVGPTLADRFRSRFRPSRFGRRRGCGGSGDCRVCLVRFEPE
SVVNRLPCGHLFHRACLETWLDYDHATCPLCRHRLLPPAA SEQ ID NO:114
Sorghum bicolor sorghum|TC110812 similar to UP|BAD10011 (BAD10011) Zinc finger protein family-like,
atgggcatctcgagcatgccggcgcccaaggacagcctgctggggttcgtgctgtacaacgcggcggcgtccgtcgcgatcct
gtcgggtctggtgcgcgccgcgctgctcttcctgggcgtggcggcggcgccgtcgtcgtccccgtgggaagcgccggagga
ggagcggcggcagcagcagcaggggggcggtgagggtcacgcccgtggggcccaccctcgcggaccggttccggagcag
gttccgtccgtcgcgcttcgggcggcgccgcggctgcggcggttcggggggactgccgcgtgtgcctggtgcggttcgagccg
gagtcggtggtcaaccggctcccctgcggccacctcttccaccgcgcatgcctcgagacctggctcgactacgaccacgccac
ctgcccgctctgccgccaccgcctcctgccccccgccgca SEQ ID NO:115
Zea mays maize|TC302897 similar to UP|Q6Z8T9_ORYSA (Q6Z8T9) Zinc finger protein family-like
DCRVCLVRFETESVVQRLPCGHLFHRACLETWIDYDHATCPLCR

SEQ ID NO:116

FIG. 10 cont'd

Zea mays maize|TC302897 similar to UP|Q6Z8T9_ORYSA (Q6Z8T9) Zinc finger protein family-like
gcggggactgccgcgtgtgcctggtgcggttcgagacggagtcggtggtgcagcggctcccctgcggccacctcttccaccg cgcatgcctcgagacctgg atcgactacgaccacgccacctgcccgctgtgccgccaccgcctcct SEQ ID NO:117
Zea mays maize|TC302897 similar to UP|Q6Z8T9_ORYSA (Q6Z8T9) Zinc finger protein family-like
MGISSMPAPEDSLLGFVLYNTAASVAILAGLVRAALLFLGLAAAAEDEEPRQQA
EAVTVTAVGPSLADRFRSRFRPSRYGRRRGGDCRVCLVRFETESVVQRLPCGHL
FHRACLETWIDYDHATCPLCRHRLLPPAAAADEVAPDCLISALGIESRRSTLHLA
AAVSLYRFFFSFPFCSGEREDRTEIEGRKWWQQSCSPFVSKKKNYILYTDLSKTQ
NCLWACAGVDAKTTILL SEQ ID NO:118
Zea mays maize|TC302897 similar to UP|Q6Z8T9_ORYSA (Q6Z8T9) Zinc finger protein family-like
gggcatctcgagcatgccggcgcccgaggacagcctgctggggttcgtgctgtacaacacggcggcgtcggtggcgatcctg gcggggctggtgcgcgccgcgctgctgttcctgggcctggcggcggcggcggaggacgaggagccgcggcagcaggcg gaggccgtgacggtcacggccgtggggcccagcctcgcggaccggttccggagcaggttccggccgtcgcgctacgggcg gcgccggggcggggactgccgcgtgtgcctggtgcggttcgagacggagtcggtggtgcagcggctcccctgcggccacct cttccaccgcgcatgcctcgagacctggatcgactacgaccacgccacctgcccgctgtgccgccaccgcctcctgccccccg ccgctgccgccgacgaggtgccccggattgcctgattagcgccctaggaattgagagtaggcgtagcactctgcacctcgcag cagcagtgtctctgtacaggttttttttttcttttcctttttgttcg SEQ ID NO:119
*Oryza sativa* Q6Z8T9_ORYSA Zinc finger protein family-like
MGISSMPAPKDSVVAYLLYNTAVSIAILADMVRAALVFLGLPVPPSAWED
GDDQLAAIAAAAAAAAAAAGGPSLADRFRSRFRPARFGRRRGGGAGAADC
RVCLARFEPESVVNRLPCGHLFHRACLEKWLDYDHATCPLCRHRLLPATT
ESPSPSPATATPHFARI SEQ ID NO:120
*Oryza sativa* Q6Z8T9_ORYSA Zinc finger protein family-like
DCRVCLARFEPESVVNRLPCGHLFHRACLEKWLDYDHATCPLCRHRL SEQ ID NO:121
*Oryza sativa* Q6Z8T9_ORYSA Zinc finger protein family-like
gactgccgcgtctgcctcgcgcggttcgagccggagtcggtggtgaaccgcctccctgcggccacctcttccaccgcgcctg cctcgagaagtggctcgactacgaccacgccacctgcccgctctgccgccaccgcctcc SEQ ID NO:122
*Oryza sativa* Q6Z8T9_ORYSA Zinc finger protein family-like ACCESSION
AK065316 Gramene TREMBL Q6Z8T9; EMBL AP004762; GenBank BAD10011
gtaccatctcccgtgtcctcctcccacctcgctcccccgtaaaacccgaaattacaatcaggtcctcggcggacgccaccccccaa atctgaaaccctcgccgccgccgccgcgcgatccccccggaattccatcggatcggccccgcctctccggcgagatg

FIG. 10 cont'd ggcatctcgagcatgccggcgcccaaggacagcgtggtggcgtacctgctgtacaacacggcggtgtcgatcgccatcctgg
cggacatggtgcgggcggcgctggtgttcctcggcctccccgtgccgccctcggcgtgggaggacggcgacgaccagctgg
cggcgatcgcggcggccgccgcggccgcggccgcggcggcggggggcccgagcctggcggacaggttccggagcaggt
tcaggccggcgaggttcgggcggcggcgaggcgggggcgcgggcgcggccgactgccgcgtctgcctcgcgcggttcga
gccggagtcggtggtgaaccgcctccctgcggccacctcttccaccgcgcctgcctcgagaagtggctcgactacgaccac
gccacctgcccgctctgccgccaccgcctcctccccgccaccaccgagtcccctcgccgtcgccggcgacggcgacccc
catttcgcccggatttagagagatctccccccttcaatccgccactggg SEQ ID NO:123
*Oryza sativa* Q6Z8T9_ORYSA Zinc finger protein family-like ACCESSION
AK065316 Gramene TREMBL Q6Z8T9; EMBL AP004762; GenBank BAD10011
atgggcatctcgagcatgccggcgcccaaggacagcgtggtggcgtacctgctgtacaacacggcggtgtcgatcgccatcct
ggcggacatggtgcgggcggcgctggtgttcctcggcctccccgtgccgccctcggcgtgggaggacggcgacgaccagct
ggcggcgatcgcggcggccgccgcggccgcggccgcggcggcggggggcccgagcctggcggacaggttccggagca
ggttcaggccggcgaggttcgggcggcggcgaggcgggggcgcgggcgcggccgactgccgcgtctgcctcgcgcggtt
cgagccggagtcggtggtgaaccgcctccctgcggccacctcttccaccgcgcctgcctcgagaagtggctcgactacgac
cacgccacctgcccgctctgccgccaccgcctcctccccgccaccaccgagtcccctcgccgtcgccggcgacggatttag
agagatctccccccttcaatccggcgacccccatttcgcccggattt SEQ ID NO:124
Zea mays maize|TC287578 similar to UP|Q6Z8T9_ORYSA (Q6Z8T9) Zinc finger
protein family-like,
DCSVCLAGFEAEAVVNRLPCGHLFHRACLETWLRYERATCPL SEQ ID NO:125
Zea mays maize|TC287578 similar to UP|Q6Z8T9_ORYSA (Q6Z8T9) Zinc finger
protein family-like,
DCSVCLAGFEAEAVVNRLPCGHLFHRACLETWLRYERATCPLCRAHVPLPADET
PVLRYPELE SEQ ID NO:126
Zea mays maize|TC287578 similar to UP|Q6Z8T9_ORYSA (Q6Z8T9) Zinc finger
protein family-like,
gactgcagcgtgtgcctggccgggttcgaggcggaggccgtggtgaaccggctcccctgcggccacctcttccaccgcgcct
gcctcgagacctggctccggtacgagcgcgccacgtgcccgctctgccgcg SEQ ID NO:127
Zea mays maize|TC287578 similar to UP|Q6Z8T9_ORYSA (Q6Z8T9) Zinc finger
protein family-like,
cggccgcgggcgacgacgactgcagcgtgtgcctggccgggttcgaggcggaggccgtggtgaaccggctcccctgcggc
cacctcttccaccgcgcctgcctcgagacctggctccggtacgagcgcgccacgtgcccgctctgccgcgcccacgtgcccct
ccccgccgacgagacgccggtgctccgctacccggagctcgagtga SEQ ID NO:128
Zea mays
maize|TC287578 similar to UP|Q6Z8T9_ORYSA (Q6Z8T9) Zinc finger protein

FIG. 10 cont'd family-like, partial (29%)
acgacgactgcagcgtgtgcctggccgggttcgaggcggaggccgtggtgaaccggctcccctgcggccacctcttccaccg
cgcctgcctcgagacctggctccggtacgagcgcgccacgtgcccgctctgccgcgcccacgtgcccctccccgccgacga
gacgccggtgctccgctacccggagctcgagtgatccgggcctcggccgtcgcgcgcctcggctgtgtgctgcaagctccgt
gtggccttccgtgtgcgcgtagcaaaggaaaaaaaggagtataggagcggtagtagtagagttgctgttgctttcccttctcgttt
tgtgttttgcggttgcccccatgctcttgttgtttccgcgctgtcgctgtagcgtgtaaatactccggttcgcccttggcagcagaga
gtagtagagtgctcccgtggctgggccgatggtgtagcacctttacgagctcagctcgtgtgtgtacatttgcatgctttcaattcc
aatttcccgaga SEQ ID NO:129
barley|TC132854 similar to UP|Q6Z8T9 (Q6Z8T9) Zinc finger protein family-like,
MGISSMPAPKESLLIYLLYHAVVSIAALAGLLRAALAFLGLPTPPSLLAGEDADG
GDQLTAATPAGPSLAERFRSRFRPARFGRRRGAAAAPDCRVCLVRFEADAVVNR
LPCGHMFHRACLETWLDYDHATCPLCRSRLLPAVAAAADESSRSPPAPSLTAW
M SEQ ID NO:130
barley|TC132854 similar to UP|Q6Z8T9 (Q6Z8T9) Zinc finger protein family-like,
DCRVCLVRFEADAVVNRLPCGHMFHRACLETWLDYDHATCPLCRSRL SEQ ID NO:131
barley|TC132854 similar to UP|Q6Z8T9 (Q6Z8T9) Zinc finger protein family-like,
gactgccgcgtgtgcctggtgcggttcgaggcggacgccgtggtgaaccgcctcccctgcggccacatgttccaccgcgcctg
cctcgagacctggctcgactacgaccacgccacctgcccgctctgccgctcccgcctc SEQ ID NO:132
barley|TC132854 similar to UP|Q6Z8T9 (Q6Z8T9) Zinc finger protein family-like,
atgggcatctccagcatgccggcgcccaaggagagcctcctgatctacctgctctaccacgcggtcgtctcgatcgccgccctg
gcggggctcctccgcgccgcgctcgccttcctcggcctgcccacgccgccgtcgctgctggccggggaggacgcggatggc
ggcgaccagctcacggcggccacccccggccggccccagcctggccgagaggttcaggagcaggttccgcccggcgcgctt
tggccggaggcggggcgcggcggcggcgcctgactgccgcgtgtgcctggtgcggttcgaggcggacgccgtggtgaacc
gcctcccctgcggccacatgttccaccgcgcctgcctcgagacctggctcgactacgaccacgccacctgcccgctctgccgc
tcccgcctcctcccggcggtagccgctgccgccgacgagtcgtcgcggtcgccgccggcccccagcctgacggcgtggatgt
a SEQ ID NO:133
barley|TC132854 similar to UP|Q6Z8T9 (Q6Z8T9) Zinc finger protein family-like,
TC132854 TC111269 TC47687 TC79328 TC89677
cggcacgaggcaccaccatagaagctcagagcaggcagcccctgaaagaaggcgaaaattgcagacgggtccagggatcg
atccccaacaccggccgccgcgatgggcatctccagcatgccggcgcccaaggagagcctcctgatctacctgctctaccacg
cggtcgtctcgatcgccgccctggcggggctcctccgcgccgcgctcgccttcctcggcctgcccacgccgccgtcgctgctg
gccggggaggacgcggatggcggcgaccagctcacggcggccacccccggccggccccagcctggccgagaggttcagg
agcaggttccgcccggcgcgctttggccggaggcggggcgcggcggcggcgcctgactgccgcgtgtgcctggtgcggttc
gaggcggacgccgtggtgaaccgcctcccctgcggccacatgttccaccgcgcctgcctcgagacctggctcgactacgacc
acgccacctgcccgctctgccgctcccgcctcctcccggcggtagccgctgccgccgacgagtcgtcgcggtcgccgccggc
ccccagcctgacggcgtggatgtagagacgagacaagagaagagagattcgccccgtcgcccccggctacgtgctagctcc

FIG. 10 cont'd gtgtgtggcctctccgtgtgcgcgtaggaatttaggtcgatcctagcaaagcagagagggtgctcgttccccttcgcatccctccc
tcctttttttttttgatttcgttttctgtaggcctcgtgccgtcgctgtgccgtgtacatattttcagcagagagcgctcctacgggtgta
gcgctttgtgtgatgagagatttgcgtgcagcccttggcctttttttttacgagaaacggaaaattgatgcgaagaggattgtgtgtt
cttgcttgccctctttcttggatggctgcccctaacccgtctctccagatatttatgaagaaagttactctgctgatttccctt SEQ ID NO:134
Sorghum bicolor sorghum|TC104925 homologue to UP|Q84PD9 (Q84PD9) Ring zinc finger protein-like protein
ECCICLSAYDDGAELRELPCGHHFHCTCIDKWLHINATCPLCK SEQ ID NO:135
Sorghum bicolor sorghum|TC104925 homologue to UP|Q84PD9 (Q84PD9) Ring zinc finger protein-like protein
gagtgttgtatttgcctatcggcttatgatgatggtgcagagttgcgcgaactcccctgtgggcaccatttccactgcacctgcatc
gacaagtggcttcacatcaatgcaacatgcccctgtgcaagtacaacattc SEQ ID NO:136
Sorghum bicolor sorghum|TC104925 homologue to UP|Q84PD9 (Q84PD9) Ring zinc finger protein-like protein
MPLRTWVAGYALQCVVHMVCVAIEYRMRHGQGGGAGAAPTDEERGSDGSSSS
SDDDDREFDRHGRRTDYASIAKHLESANTMFSFIWWIIGFYWISAGGEEVIRDAP
QLYWLCIVFLAFDVFFVVFCVALACIIGIAVCCCLPCIIAILYAVSDQEGASEDDIR
QIPRYKFRRTDEPEKQDVDPMGPFGGIMTECGTNQPIEKVLAAEDAECCICLSAY
DDGAELRELPCGHHFHCTCIDKWLHINATCPLCKYNIRKSSSSSGSEEV SEQ ID NO:137
Sorghum bicolor sorghum|TC104925 homologue to UP|Q84PD9 (Q84PD9) Ring zinc finger protein-like protein, partial (97%)
atgccgctccggacctgggtcgccggctacgccctgcagtgcgtcgtacacatggtctgcgtcgcaatcgagtaccggatgcg
ccacggccagggcggcggcgccggcgccgcgcccactgacgaggaaaggggcagcgacggatcgtcctcgtccagcgac
gacgatgacagggagttcgatcgccatggtcgccgcaccgattacgccagtattgcaaagcacttggagtctgctaatacaatgt
tctccttcatatggtggataattggatttattggatatctgctgggggtgaagaggttatccgggatgcacctcaactttactggcttt
gcatagtctttctggcatttgatgtgttttttgttgtattctgcgttgctctggcttgtatcattggtattgctgtctgttgttgccttccttgta
tcatagcaattctctatgcagtatctgaccaggaaggagcatctgaagatgacattcgtcaaatcccaagatacaaatttcggcgg
accgacgagcctgaaaagcaagatgttgaccccatgggtccttttggtggaataatgacagagtgcggcaccaatcaacctattg
agaaagtgcttgcagctgaggatgcagagtgttgtatttgcctatcggcttatgatgatggtgcagagttgcgcgaactcccctgt
gggcaccatttccactgcacctgcatcgacaagtggcttcacatcaatgcaacatgcccctgtgcaagtacaacattcggaaaa
gcagcagtagcagtggaagtgaagaagtttg SEQ ID NO:138
*Oryza sativa* (japonica cultivar-group) Q84MU8_ORYSA ACCESSION AAP12944 putative ring-H2 zinc finger protein
DCAVCITELAAGESARVLPRCGHGFHVECVDMWLRSNSTCPLCRCAVI

SEQ ID NO:139

FIG. 10 cont'd

*Oryza sativa* (japonica cultivar-group) Q84MU8_ORYSA ACCESSION AAP12944
putative ring-H2 zinc finger protein
gactgcgccgtctgcatcacggagctcgccgccggggagtccgcccgcgtgctgccgcggtgcggccacgggttccacgtc
gagtgcgtcgacatgtggctccggtcaaactccacctgcccgctctgccgctgcgccgtcat SEQ ID NO:140
*Oryza sativa* (japonica cultivar-group) Q84MU8_ORYSA
ACCESSION AAP12944 putative ring-H2 zinc finger protein [Oryza sativa (japonica cultivar-group)]
MAVTGTSVAAAATML<u>AAAAA</u>IFITFVVCFYLFLCAKRYRGAAPTIGGDSGGGGR
GRARFVFGGPGDGGCGGGRGLDEAAIAALPTKVVAAAAEGGDGGDPAADCAV
CITELAAGESARVLPRCGHGFHVECVDMWLRSNSTCPLCRCAVIDEALPPPPAVR
PPEADAESPNFPTNVLFFGSQDAVRTGGAAAATPPPPPPSSHHQQQPAFPPQPSAG
PIAGVAAVVEAARIAALRRLLGCGGATPPPPPAPAQGDRDVEMGLPGGESSASRP
ATKPQPGS SEQ ID NO:141
*Oryza sativa* (japonica cultivar-group) Q84MU8_ORYSA
ACCESSION AAP12944 putative ring-H2 zinc finger protein [Oryza sativa (japonica cultivar-group)].
atggcggtgacggggacgtcggtggcggccgcggcgacgatgctggcggcggcggcggcgatcttcatcacgttcgtcgtgt
gcttctacctcttcctctgcgccaagaggtaccgcggcgccgcgcccacgatcggcggcgacagcggtggggagggaggg
gacgcgcgcggttcgtgttcggggggccccggggacggcgggtgcggaggcgggagggggcttgacgaggcggccatcgc
ggcgctgccgacgaaggtggtggcggcggcggccgagggggcgacggcggcgaccccgcggcggactgcgccgtctg
catcacggagctcgccgccggggagtccgcccgcgtgctgccgcggtgcggccacgggttccacgtcgagtgcgtcgacat
gtggctccggtcaaactccacctgcccgctctgccgctgcgccgtcatcgacgaggcgctgccgccgccgccgccgtgcgc
ccgccggaggctgacgcggagtcgcccaacttccccaccaacgtgctcttcttcggctcccaggacgccgtcaggacaggcg
gcgccgccgcggcaacgccgccgccgccgcctccgtcgtccatcatcagcagcaaccggccttcccgccgcagccgtcgg
cgggacccatcgccggagtcgccgccgtggtggaagcggcgaggatagcggccctgcggcggctgctgggctgcggcgg
cgcgactccccgccccccgccggcgccggcgcagggcgaccgcgacgtggagatgggcctccccggcggcgagagcag
cgcgtcgcggccggcgacgaagccgcagccaggttcttga SEQ ID NO:142
*Zea mays*
ring-H2 zinc finger protein [Q8W1C6_MAIZE] AAL59234
gi|18092342|gb|AAL59234.1|AF448416_14[18092342]
E<span style="border:1px solid">C</span>AV<span style="border:1px solid">C</span>LSEVGAGEKVRTLPK<span style="border:1px solid">C</span><span style="border:1px solid">H</span>GF<span style="border:1px solid">H</span>VE<span style="border:1px solid">C</span>IDMWF<span style="border:1px solid">H</span>SHDT<span style="border:1px solid">C</span>PL<span style="border:1px solid">C</span>RAPV SEQ ID NO:143
*Zea mays*
ring-H2 zinc finger protein [Q8W1C6_MAIZE] AAL59234
gi|18092342|gb|AAL59234.1|AF448416_14[18092342]
gagtgcgcggtgtgcctgtccgaggtgggcgccggcgagaaggtgcggacgctgcccaagtgctcccacgggttccacgtg
gagtgcatcgacatgtggttccattcccacgacacgtgccccctctgccgcgccccgt

SEQ ID NO:144

FIG. 10 cont'd

*Zea mays*
ring-H2 zinc finger protein [Q8W1C6_MAIZE] AAL59234
gi|18092342|gb|AAL59234.1|AF448416_14[18092342]
MFPAPGSSGQQQLAISNGVLLAAVIFLFMVVVFVFLLYLYAKRYLGANPLL<u>APSS
PSSRFLFVAASPLPQRGLPASVLQSLPVTVYGSPGGKDKDALECAVCLSEVGAGE
KVRTLPKCSHGFHVECIDMWFHSHDTCPLCRAPVGDLDALPREEPSGAPLELPVF
PTNVLFWGTHDEVTNAGL</u>VAPPRAAPSASSSASGRRKENLVIDIPTRAVATTTTT
PPPANSPLPASRMPGSADEMRSPVSARLRSLRRLLSRGKQAMVGTSSSYSPRDIE
QGLAGGE<u>AAAAA</u>TAR PPKTPKTPPSAHAH SEQ ID NO:145
Zea mays ring-H2 zinc finger protein [Q8W1C6_MAIZE] AAL59234
gi|18092342|gb|AAL59234.1|AF448416_14[18092342]
atgttccggccccgggtagctcggggcagcagcagctggccatcagcaacggggtgctcctcgccgccgtcatcttcctcttc
atggtcgtcgtcttcgtcttcctcctctacctctacgccaagcgctacctgggcgcgaacccgctgctggcgccgtcgtcgccgtc
ctcgcggttcctcttcgttgccgcgtccccgctcccgcagcgcggcctgcccgcctccgtcctgcaatccctccccgtcaccgtc
tacggctcccccggcggcaaggacaaggacgcgctggagtgcgcggtgtgcctgtccgaggtgggcgccggcgagaaggt
gcggacgctgcccaagtgctcccacgggttccacgtggagtgcatcgacatgtggttccattcccacgacacgtgccccctctg
ccgcgcccccgtgggcgacctcgacgcgctgccgcggaggagccctccggcgcgccgctggagttgcccgtgttccccac
caacgtcctgttctggggcacccacgacgaggtcaccaacgccgggctcgtcgcgccgccgcgcgccgccccgtcggccag
ctcctcggcctccgggcgcaggaaggagaacctggtcatcgacatcccgacgcgggccgtggccacgaccacgaccacgc
cgccgcccgccaactccccgctgccggccagccggatgcccgggagcgccgacgagatgcggtccccggtgtccgccagg
ctgcggtcgctgcgccggctgctgagcagaggaaagcaggccatggtcggcacctcctcctcctacagcccgcgcgacatcg SEQ ID NO:146
Q5GAQ1_MAIZE Zea mays ring-H2 zinc finger protein
>tr|Q5GAQ1|Q5GAQ1_MAIZE Ring-H2 zinc finger protein - Zea mays (Maize).
MLAAVAAVFLTLVLCFYVFLCAKRYRGEAPPHAVAAAGGGGVRAWLRVVFGV
GGGAGAHVGGGTEWCYDGGLDDKSMAKLPRREVGRGDEAADCAVCITELAPG
ETARVLPRCGHAFHVDCVDMWLRSHSTCPLCRCPAVDDPPVPPAVPTPEADPES
PNFPTNVLFFGSQDEVSTGRSQSQQHTAPQEACAGLRRLIGCGGAPPPTQPCDCE
QRRCRREEEDDDDDAGGDIEMGLAAGAGTGESSASRPVKPPQPGS SEQ ID NO:147
Q5GAQ1_MAIZE Zea mays ring-H2 zinc finger protein
D<span style="border:1px solid">C</span>AV<span style="border:1px solid">C</span>ITELAPGETARVLPR<span style="border:1px solid">C</span>G<span style="border:1px solid">H</span>AF<span style="border:1px solid">H</span>VD<span style="border:1px solid">C</span>VDMWLRSHST<span style="border:1px solid">C</span>PL<span style="border:1px solid">C</span>R<span style="border:1px solid">C</span>PAVD SEQ ID NO:148
Q5GAQ1_MAIZE Zea mays ring-H2 zinc finger protein
gactgcgccgtgtgcatcacggagctggcgccgggggagacggcgcgcgtgctgccgcggtgcgggcacgccttccacgt
ggactgcgtcgacatgtggctccgctcccactccacctgcccgctctgccggtgccccgccgtggac SEQ ID NO:149
Q5GAQ1_MAIZE Zea mays ring-H2 zinc finger protein
Sequence 777 BP; 91 A; 283 C; 306 G; 97 T; 0 other; 1460925569 CRC32;

FIG. 10 cont'd atgctggcggccgtggcggcggtcttcctgaccctggtgctctgcttctacgtcttcctctgcgccaagcggtaccgcggcgag
gcgccgccgcacgcggtggccgccgccggcggcggcggcgtcagggcgtggctgcgcgtcgtgttcggcgtcgggggag
gcgcaggcgcgcacgtcggcggcggcacggagtggtgctacgacggcgggctcgacgacaagtcgatggcgaagctgcc
ccggcgggaggtgggcaggggcgacgaggcggcggactgcgccgtgtgcatcacggagctggcgccgggggagacggc
gcgcgtgctgccgcggtgcgggcacgccttccacgtggactgcgtcgacatgtggctccgctcccactccacctgcccgctct
gccggtgccccgccgtggacgacccgcccgtcccgcccgccgtgcccacgcccgaggccgaccggagtcccccaacttc
cccaccaacgtcctcttcttcggctcccaggacgaggtcagcaccggccgctcgcagtcgcagcaacacacggcgccgcagg
aggcgtgcgccgggctgcggaggctgatcgggtgtggcggcgcgccgccgcccacgcagccttgcgactgcgagcagcgt
cgctgtcgtcgggaggaggaggacgacgacgacgacgcgggcggggacatcgagatgggcctcgccgccggcgcc
ggcaccggcgagagcagcgcgtcgcggccggtgaagccgccgcagcccggttcgtga SEQ ID NO:150
ACCESSION XP_470885 putative ring-H2 zinc finger protein [Oryza sativa (japonica cultivar-group)].
MAVTGTSVAAAATMLAAAAAIFITFVVCFYLFLCAKRYRGAAPTIGGDSGGGGR
GRARFVFGGPGDGGCGGGRGLDEAAIAALPTKVVAAAAEGGDGGDPAADCAV
CITELAAGESARVLPRCGHGFHVECVDMWLRSNSTCPLCRCAVIDEALPPPPAVR
PPEADAESPNFPTNVLFFGSQDAVRTGGAAAATPPPPPPSSHHQQQPAFPPQPSAG
PIAGVAAVVEAARIAALRRLLGCGGATPPPPPAPAQGDRDVEGLPGGESSASRPA
TKPQPGS SEQ ID NO:151
ACCESSION XP_470885 putative ring-H2 zinc finger protein [Oryza sativa (japonica cultivar-group)].
DCAVCITELAAGESARVLPRCGHGFHVECVDMWLRSNSTCPLCRCAVI SEQ ID NO:152
ACCESSION XP_470885 putative ring-H2 zinc finger protein [Oryza sativa (japonica cultivar-group)].
gact gcgccgtctg catcacggag ctcgccgccg gggagtccgc ccgcgtgctgccgcggtgcg gccacgggtt
ccacgtcgag tgcgtcgaca tgtggctccg gtcaaactccacctgcccgc tctgccgctg cgccgtcatc g SEQ ID NO:153
ACCESSION XP_470885 putative ring-H2 zinc finger protein [Oryza sativa (japonica cultivar-group)]
atggcggtgacggggacgtcggtggcggccgcggcgacgatgctggcggcggcggcggcgatcttcatcacgttcgtcgtgt
gcttctacctcttcctctgcgccaagaggtaccgcggcgccgcgcccacgatcggcggcgacagcggtgggggagggaggg
gacgcgcgcggttcgtgttcggggggccccggggacggcgggtgcggaggcgggaggggcttgacgaggcggccatclg
cggcgctgccgacgaaggtggtggcggcggcggccgaggggggcgacggcggcgaccccgcggcggactgcgccgtct
gcatcacggagctcgccgccggggagtccgcccgcgtgctgccgcggtgcggccacgggttccacgtcgagtgcgtcgaca
tgtggctccggtcaaactccacctgcccgctctgccgctgcgccgtcatcgacgaggcgctgccgccgccgccgccgtgcg
cccgccggaggctgacgcggagtcgcccaacttcccaccaacgtgctcttcttcggctcccaggacgccgtcaggacaggc
ggcgccgccgcggcaacgccgccgccgccgcctccgtcgtcccatcatcagcagcaaccggcctccgccgcagccgtcg
gcgggacccatcgccggagtcgccgccgtggtggaagcggcgaggatagcggccctgcggcggctgctgggctgcggcg
gcgcgactccccgccccgccggcgccggcgcagggcgaccgcgacgtggagatgggcctccccggcggcgagagca
gcgcgtcgcggccggcgacgaagccgcagccaggttcttga

FIG. 10 cont'd

SEQ ID NO:154
poplar|TC21770 similar to UP|Q6I656 (Q6I656) RING zinc finger protein
MGLSSLPAPSEGVLCVLLVNTALSISIVKGIVRSILHVVGIRLSPSASLPSSDNAED
TRESFEFRLSPPENYIEEFRSRMPSIRFNTVCSCKQPEHDCSVCLTQFEPESEINSLS
CGHIFHKMCLEKWLDYWNITCPLCRTPLLPEEDASCFW SEQ ID NO:155
poplar|TC21770 similar to UP|Q6I656 (Q6I656) RING zinc finger protein
DCSVCLTQFEPESEINSLSCGHIFHKMCLEKWLDYWNITCPLCRTPL SEQ ID NO:156
poplar|TC21770 similar to UP|Q6I656 (Q6I656) RING zinc finger protein
gactgctcggtttgcttgacccaatttgagccagaatcggagataaatagcctgtcatgtggccatatctttcataaaatgtgcttgg
agaagtggttggactattggaacattacatgccctctttgcaggactcctttgct SEQ ID NO:157
poplar|TC21770 similar to UP|Q6I656 (Q6I656) RING zinc finger protein
TC21770 TC16228
atgggtctatcaagtctgccagctccatctgaaggagtgctatgtgtgcttttagtaaacactgccttgtcaatttccattgtcaaagg
gatagtccgttcaatccttcacgttgttggcatccgtttgtcaccatctgcttcactccatcgtcagataatgctgaagacaccaga
gagtcgtttgaatttcgtttaagtcccccagagaattacattgaggagttccgaagcaggatgccatcaatccgattcaacacggtg
tgcagctgtaaacagcctgaacatgactgctcggtttgcttgacccaatttgagccagaatcggagataaatagcctgtcatgtgg
ccatatctttcataaaatgtgcttggagaagtggttggactattggaacattacatgccctctttgcaggactcctttgctgcctgaag
aggatgcatcttgcttttggtg SEQ ID NO:158
poplar|TC21770 similar to UP|Q6I656 (Q6I656) RING zinc finger protein
TC21770 TC16228
gggcagccatcttcatctccatcttctatgaaacaatcccatatgacatgtataaaagttttgataatcccatgaatatgtcatgtttcta
ggctgctagcatgttcttgatgcttatatatttctttgcatagagaccaagacaggaacttcaaagcttccctagtgtcactgttgtcg
gctccttttacaggattttgctattcatcacttcatcatagtcaaaaacctgtttatatgccccaagatcaagcaaagaaggaaacat
ccggttttctccatttgcttcaactgtgatttatacaagcatccccccattggcttccataacttccatttgagcacactgtgaatcaag
aatctcttgttagcttgagctttgcggaatcactgcaaaaaaaaaaccaagtcccacgaaacttcaatgggtctatcaagtctgcca
gctccatctgaaggagtgctatgtgtgcttttagtaaacactgccttgtcaatttccattgtcaaagggatagtccgttcaatccttcac
gttgttggcatccgtttgtcaccatctgcttcactccatcgtcagataatgctgaagacaccagagagtcgtttgaatttcgtttaag
tcccccagagaattacattgaggagttccgaagcaggatgccatcaatccgattcaacacggtgtgcagctgtaaacagcctga
acatgactgctcggtttgcttgacccaatttgagccagaatcggagataaatagcctgtcatgtggccatatctttcataaaatgtgc
ttggagaagtggttggactattggaacattacatgccctctttgcaggactcctttgctgcctgaagaggatgcatcttgcttttggtg
agcgcatactaccatgtatgctttgtcagaggaattctccttgtacagcgtgtacatgtatttacgtgagtgcatcgggcagggcat
agtggtgtatactttgtgcttgagatcaagcatgatgtgctgatgggtccttgagagaccaaaaatttattgtacatattgtgaagaa
gtgatgtttaacctatctatcttgctttgatctccaccttttcttttttccttgatctttgcacacgttttactcttcttaacagaccagaag
gatggaatctaatgtatgggcaagctaaactagaataaaaaaaattcctccatgtttac

SEQ ID NO:159

FIG. 10 cont'd poplar|TC23157 *weakly similar to* UP|Q8S2S3 (Q8S2S3) Putative RING zinc finger protein-like protein
MFIKYLNLISAHLRWAFNFLCYYPFSFQEHELFAVTAIGEELNTVINEAPAECAVC
LSDVQEGEEIRELRCGHIFHRACLYRWLDFRQSTCPLCRGSLAPRRTLILDQHRTE
VLTFKFCSFTSTDERDXMVATMNQVFKILVPRQEKAQRSNYLLPPPSEYHGMFV
NELLLMQTSQA SEQ ID NO:160
poplar|TC23157 *weakly similar to* UP|Q8S2S3 (Q8S2S3) Putative RING zinc finger protein-like protein
E[C]AV[C]LSDVQEGEEIRELR[C]G[H]IF[H]RA[C]LYRWLDFRQST[C]PL[C]RGSL SEQ ID NO:161
poplar|TC23157 *weakly similar to* UP|Q8S2S3 (Q8S2S3) Putative RING zinc finger protein-like protein
gaatgtgctgtgtgtctaagtgacgttcaagaaggcgaagaaatcagagagctgagatgtgggcatatctttcatagagcatgctt
atacagatggcttgacttccggcaatcgacttgcccactttgccgaggaagtcttgctccccggagaacatt SEQ ID NO:162
poplar|TC23157 *weakly similar to* UP|Q8S2S3 (Q8S2S3) Putative RING zinc finger protein-like protein
atgtgctgtgtgtctaagtgacgttcaagaaggcgaagaaatcagagagctgagatgtgggcatatctttcatagagcatgcttat
acagatggcttgacttccggcaatcgacttgcccactttgccgaggaagtcttatgttcatcaaatacttaaatctcattagtgcccat
ctcagatgggcatttaatttcttgtgttactatccgttcagcttccaagaacacgaattgtttgctgtgactgcaattggtgaagaacta
aacacggtgatcaatgaagctcctgcggaatgtgctgtgtgtctaagtgacgttcaagaaggcgaagaaatcagagagctgaga
tgtgggcatatctttcatagagcatgcttatacagatggcttgacttccggcaatcgacttgcccactttgccgaggaagtcttgctc
cccggagaacattgatccttgatcagcaccgaacagaagtattgacgttcaagttctgttctttcacatccaccgatgaacgtgatx
acatgg SEQ ID NO:163
poplar|TC23157 *weakly similar to* UP|Q8S2S3 (Q8S2S3) Putative RING zinc finger protein-like protein TC23157 TC5134
atgttcatcaaatacttaaatctcattagtgcccatctcagatgggcatttaatttcttgtgttactatccgttcagcttccaagaacacg
aattgtttgctgtgactgcaattggtgaagaactaaacacggtgatcaatgaagctcctgcggaatgtgctgtgtgtctaagtgacg
ttcaagaaggcgaagaaatcagagagctgagatgtgggcatatctttcatagagcatgcttatacagatggcttgacttccggcaa
tcgacttgcccactttgccgaggaagtcttgctccccggagaacattgatccttgatcagcaccgaacagaagtattgacgttcaa
gttctgttctttcacatccaccgatgaacgtgatxacatggtggctacgatgaatcaagtcttcaagattttagtacctcgtcaggag
aaagcacaacggagtaactaccttctccccctccttcagaatatcatggcatgttcgttaacgagttgctattgatgcaaacttctc
aagcatga SEQ ID NO:164
poplar|TC23157 *weakly similar to* UP|Q8S2S3 (Q8S2S3) Putative RING zinc finger protein-like protein TC23157 TC5134
ctccttgttcatctctcccaactcctttctagctcattttgttttgcgacaaaattaacctctaaactcaaccaatcatgttcatcaaat
acttaaatctcattagtgcccatctcagatgggcatttaatttcttgtgttactatccgttcagcttccaagaacacgaattgtttgctgt
gactgcaattggtgaagaactaaacacggtgatcaatgaagctcctgcggaatgtgctgtgtgtctaagtgacgttcaagaaggc

FIG. 10 cont'd gaagaaatcagagagctgagatgtgggcatatctttcatagagcatgcttatacagatggcttgacttccggcaatcgacttgccc
actttgccgaggaagtcttgctccccggagaacattgatccttgatcagcaccgaacagaagtattgacgttcaagttctgttctttc
acatccaccgatgaacgtgatacatggtggctacgatgaatcaagtcttcaagattttagtacctcgtcaggagaaagcacaacg
gagtaactaccttctccccctccttcagaatatcatggcatgttcgttaacgagttgctattgatgcaaacttctcaagcatgaagtg
atcgttaattcctgagcatgtgacagactaattaagctgaaggttcattgttagaatataacgttttttttttccttcctatattgcatcatct
gctaatttacctgaaagggtgaagccatctccctctcggaatctctaataacagtcctgcaatgccatgcatgttgtctcttagccat
gcttgtaataaacttgatgtttggtaagtgttgttttagtt SEQ ID NO:165
medicago|TC96403 similar to UP|Q5ULY2 (Q5ULY2) Zinc finger family protein
DCSVCLTQFEPESEINYCISCGHVFHKVCLEKWLDYWNITCPLCRSPL SEQ ID NO:166
medicago|TC96403 similar to UP|Q5ULY2 (Q5ULY2) Zinc finger family protein
MGLSSLPAQSEGVLCIILVNTAMSISIFKGIIRTILHIVGIIASPSSSPSQDYIPQNIPES
YEIHLSPSDDFVEEFRSRTPTLRFDSVCNSCKEPEHDCSVCLTQFEPESEINYCISC
GHVFHKVCLEKWLDYWNITCPLCRSPLIPEDDASCLW SEQ ID NO:167
medicago|TC96403 similar to UP|Q5ULY2 (Q5ULY2) Zinc finger family protein
gattgctcagtgtgtctcactcaatttgaacctgaatcagagataaactattgcatatcatgtggccatgttttcataaagtgtgtttgg
agaagtggttggattattggaacattacatgtccactt SEQ ID NO:168
medicago|TC96403 similar to UP|Q5ULY2 (Q5ULY2) Zinc finger family protein
(Fragment), partial (47%)
atgggcctatcaagtcttccagcacaatctgaaggagtgttatgcatcattctagtaaacactgccatgtcaatatccatattcaaag
gcattataaggactatcctgcacattgttggtatcattgcttcaccatcttcctctccttcccaagactacattcctcaaaacatacctg
agtcatatgaaatccatctaagtccttcagatgatttcgttgaagagttcagaagcagaacaccaacacttaggtttgatagtgtgtg
taatagctgcaaagaacctgaacatgattgctcagtgtgtctcactcaatttgaacctgaatcagagataaactattgcatatcatgt
ggccatgttttcataaagtgtgtttggagaagtggttggattattggaacattacatgtccactttgtaggagtcctttaattcctgaa
gatgatgcatcttgcttatggta SEQ ID NO:169
medicago|TC96403 similar to UP|Q5ULY2 (Q5ULY2) Zinc finger family protein
(Fragment), partial (47%) TC96403 TC10161 TC26671 TC33538 TC54790 TC62999
TC88889
gcaccaggagaaaaacacaatatcaaaaactcacttcttgtaacaaaaacaacctcttcacaaattgttcttgttgacccacatcac
aaatcctcaaatcctttatctgtaaactattaacaagatcaaaatagtttccattgataaattctgcttcaaaatacacattgcatcataa
agtgtatcacaaatttgttcatcaaaatgggcctatcaagtcttccagcacaatctgaaggagtgttatgcatcattctagtaaacact
gccatgtcaatatccatattcaaaggcattataaggactatcctgcacattgttggtatcattgcttcaccatcttcctctccttcccaa
gactacattcctcaaaacatacctgagtcatatgaaatccatctaagtccttcagatgatttcgttgaagagttcagaagcagaaca
ccaacacttaggtttgatagtgtgtgtaatagctgcaaagaacctgaacatgattgctcagtgtgtctcactcaatttgaacctgaat
cagagataaactattgcatatcatgtggccatgttttcataaagtgtgtttggagaagtggttggattattggaacattacatgtccac
tttgtaggagtcctttaattcctgaagatgatgcatcttgcttatggtaagagcaatgattgaagcatgcacaaaatatctaatggaga
ggttacttcatgtacagtatatagtgtgtacaaatatccctgtgacagttttgatgtacctatctatgtatctgacttttctnttagtcttct

FIG. 10 cont'd tagtgcttttgccttttatgatgtagagttagtggagggttttgtttaccttgttttttttcctttttctgtatcatatgtttgccacatatgagat
tagggatata SEQ ID NO:170
Saccharum officinarum s_officinarum|BQ532997
DCRVCLVRFEPESVVNRLPCGHLFHRACLETWLDYDHATCPL SEQ ID NO:171
Saccharum officinarum s_officinarum|BQ532997
gactgccgcgtgtgcctggtgcggttcgagccggagtcggtggtgaaccggctcccctgcggtcacctcttccaccgcgcctg
cctcgagacctggctcgactacgaccacgccacctgcccgctc SEQ ID NO:172
*Saccharum officinarum* s_officinarum|BQ532997
GAGGGGXDCRVCLVRFEPESVVNRLPCGHLFHRACLETWLDYDHATCPLCRHR
LLPPAADDELSKTIAAPRLVRF SEQ ID NO:173
*Saccharum officinarum* s_officinarum|BQ532997
ggcgcgggaggggggaggtnccgactgccgcgtgtgcctggtgcggttcgagccggagtcggtggtgaaccggctcccctgc
ggtcacctcttccaccgcgcctgcctcgagacctggctcgactacgaccacgccacctgcccgctctgtcgccaccgcctcctc
cctcccgccgcagac gacgagctctcaaagaccatcgcggcgccccgcctcgtccggttc SEQ ID NO:174
*Saccharum officinarum* s_officinarum|BQ532997
LEAF4_15_D03 pSL Saccharum officinarum cDNA 5', mRNA sequence
agccaacagtgttttcagccggcttaaacgagccaaagcctgtacacagacactgctgcgaggtgcagagtgctcctacgcct
acatcatcagagcactccgccagtatttacagtacagcaccaaacacgagcaaccaagacgagagagagagagatgaacaaaaa
cgaagaaaaggaaaggtactagtcctaatcgagagctaatcaggtaattggagcctcttaattcctaagcaggactggagtttgg
agatccgtctgtctctagaaccggacgaggcggggcgccgcgatggtctttgagagctcgtcgtctgcggcgggagggagga
ggcggtggcgacagagcgggcaggtggcgtggtcgtagtcgagccaggtctcgaggcaggcgcggtggaagaggtgacc
gcaggggagccggttcaccaccgactccggctcgaaccgcaccaggcacacgcggcagtcggnacctcccccctcccgcgc
c SEQ ID NO:175
*Saccharum officinarum* s_officinarum|BQ532997 LEAF4_15_D03 BQ532997
agccaacagtgttttcagccggcttaaacgagccaaagcctgtacacagacactgctgcgaggtgcagagtgctcctacgcct
acatcatcagagcactccgccagtatttacagtacagcaccaaacacgagcaaccaagacgagagagagagagatgaacaaaaa
cgaagaaaaggaaaggtactagtcctaatcgagagctaatcaggtaattggagcctcttaattcctaagcaggactggagtttgg
agatccgtctgtctctagaaccggacgaggcggggcgccgcgatggtctttgagagctcgtcgtctgcggcgggagggagga
ggcggtggcgacagagcgggcaggtggcgtggtcgtagtcgagccaggtctcgaggcaggcgcggtggaagaggtgacc
gcaggggagccggttcaccaccgactccggctcgaaccgcaccaggcacacgcggcagtcggnacctcccccctcccgcgc
c

SEQ ID NO:176

FIG. 10 cont'd

*Saccharum officinarum* >s_officinarum|TC49498 similar to UP|Q6Z8T9 (Q6Z8T9) Zinc finger protein family-like
DCSVCLSGFVAKAVVNR LPCGHLFHRACLETWLRYERATCPLCRANVPL SEQ ID NO:177
*Saccharum officinarum* >s_officinarum|TC49498 similar to UP|Q6Z8T9 (Q6Z8T9) Zinc finger protein family-like
gactgcagcgtgtgcctgtccgggttcgtggcgaaggccgtggtgaaccgcctcccctgcggccacctcttccaccgcgcctg
cctcgagacctggctccggtacgagcgcgccacgtgcccgctctgccgcgccaacgtgcccctccc SEQ ID NO:178
*Saccharum officinarum* >s_officinarum|TC49498 similar to UP|Q6Z8T9 (Q6Z8T9) Zinc finger protein family-like, partial (51%)
MGISSMPEPRDSLLWYLVYNTVISITALAGLVRKALVFLDLQAPALPVGGDDAA
GGRLVASGPGLRLCLADRFLRAFRPALYGVLVSTSTTCSAADADGDDCSVCLSG
FVAKAVVNRLPCGHLFHRACLETWLRYERATCPLCRANVPLPPEETPVLRYPEFE SEQ ID NO:179
*Saccharum officinarum* >s_officinarum|TC49498 similar to UP|Q6Z8T9 (Q6Z8T9) Zinc finger protein family-like, partial (51%)
ggggatctcgagcatgccggagccacgggacagcctgctgtggtacctggtgtacaacacggtgatctcgatcacggcgctg
gcggggctggtgcgcaaggcgctggtgttcctggacctccaggccccgcgctgccagtcggcggggacgacgccgccgg
gggccgcctcgtggcgtcggggcccggcctgcgcctgtgcctggcggaccggttcctgagggcgttccggccggcgctgta
cggggtgctggtgtcgacgtcgacgacgtgcagcgcggcggacgcggacggcgacgactgcagcgtgtgcctgtccgggtt
cgtggcgaaggccgtggtgaaccgcctcccctgcggccacctcttccaccgcgcctgcctcgagacctggctccggtacgag
cgcgccacgtgcccgctctgccgcgccaacgtgcccctcccgcccgaagagacgcccgtgctccgctacccggagttcgagt
g SEQ ID NO:180
EM_PL:CT030180 CT030180.3 M.truncatula DNA sequence from clone MTH2-177C12 on chromosome 3
DCSVCLTQFEPESEINYCISCGHVFHKVCLEKWLDYWNITCPL SEQ ID NO:181
EM_PL:CT030180 CT030180.3 M.truncatula DNA sequence from clone MTH2-177C12 on chromosome 3
MGLSSLPAQSEGVLCIILVNTAMSISIFKGIIRTILHIVGIIASPSSSPSQDYIPQNIPE
SYEIHLSPSDDFVEEFRSRTPTLRFDSVCNSCKEPEHDCSVCLTQFEPESEINYCISC
GHVFHKVCLEKWLDYWNITCPLCRSPLIPEDDASCLW SEQ ID NO:182
EM_PL:CT030180 CT030180.3 M.truncatula DNA sequence from clone MTH2-177C12 on chromosome 3
gattgctcagtgtgtctcactcaatttgaacctgaatcagagataaactattgcatatcatgtggccatgttttcataaagtgtgtttgg
agaagtggttggattattggaacattacatgtccactttgtaggagtcccttta

FIG. 10 cont'd

SEQ ID NO:183
EM_PL:CT030180 CT030180.3 M.truncatula DNA sequence from clone MTH2-177C12 on chromosome 3
atgggcctatcaagtcttccagcacaatctgaaggagtgttatgcatcattctagtaaacactgccatgtcaatatccatattcaaag
gcattataaggactatcctgcacattgttggtatcattgcttcaccatcttcctctccttcccaagactacattcctcaaaacatacctg
agtcatatgaaatccatctaagtccttcagatgatttcgttgaagagttcagaagcagaacaccaacacttaggtttgatagtgtgtg
taatagctgcaaagaacctgaacatgattgctcagtgtgtctcactcaatttgaacctgaatcagagataaactattgcatatcatgt
ggccatgttttcataaagtgtgtttggagaagtggttggattattggaacattacatgtccactttgtaggagtcctttaattcctgaa
gatgatgcatcttgcttatgg SEQ ID NO:184
AF499727 *Cucumis melo* Q84KA9_CUCME RING/C3HC4/PHD zinc finger-like protein
CAVCLNEFEDDETLRLIPKCDHVFHPECIDAWLASHSTCPVCRAN
ECAVCLNEFEDDETLRLIPKCDHVFHPECIDAWLASHSTCPVCRAN SEQ ID NO:185
AF499727 *Cucumis melo* Q84KA9_CUCME RING/C3HC4/PHD zinc finger-like protein
gaatgcgctgtttgtttgaatgaatttgaagatgatgaaacgctgcgtttaatccctaaatgtgatcatgtgtttcaccctgaatgtatt
gatgcttggttggcttctcactct acttgccctgtttgt SEQ ID NO:186
AF499727 *Cucumis melo* Q84KA9_CUCME RING/C3HC4/PHD zinc finger-like protein
MPSLTAPHGLPLFLFLLLFLFSSVSAQFQPAPDPRSDPYQYRLSGSMAVIIVILIAA
LFFMAFFSVYIRHCNDSPSNTVRPITAAAGRSRRATRGLDPAVIETFPTLIYSDVKE
HKIGKSALECAVCLNEFEDDETLRLIPKCDHVFHPECIDAWLASHSTCPVCRANL
SPQPTDSVHRADDSNAVVNSDTDGGDIEAQSNDVVSETTAPPTVQIQTESELSTT
TSNKALNRTRTRGSRSNRLRWLFPRSHSTGHSLVQPGEDTERFTLRLPVEIRKQV
VNRKLHRATSMVVLARQSSSMRGYRFGSGEGSSRGKYYRRLERLDRTSKSDRW
VLSMTPPFFTRMSSMKTPRGGSNRAEPGSGRELGQGNTAVDSSRLPV SEQ ID NO:187
AF499727 *Cucumis melo* Q84KA9_CUCME RING/C3HC4/PHD zinc finger-like protein
atgccctctctcaccgcccccatggccttcccctcttcctcttcctcctcctcttcctcttctcctccgtctccgcccagttccagccc
gccccgaccccagatcagaccttaccagtaccgcctcagcggttccatggccgtcatcatcgtcatcctcatcgccgctctctt
cttcatggctttcttctccgtctacatccgtcactgcaacgattcaccatccaacaccgtccgccctatcaccgccgccgcggcc
gctcccgtcgcgcaacccgcggtctcgatccggcggtaattgaaacgtttccgactctgatttactccgatgtgaaagagcataa
aattggtaaaagtgccctagaatgcgctgtttgtttgaatgaatttgaagatgatgaaacgctgcgtttaatccctaaatgtgatcatg
tgtttcaccctgaatgtattgatgcttggttggcttctcactctacttgccctgtttgtcgagctaatttgtctccccaacccactgactc
cgtccaccgagctgacgattccaacgctgtcgttaactccgataccgacggaggtgatattgaagctcagtccaacgacgttgttt
cagagacgacggctccacctacggttcagatacaaacggaatcagagctcagtacgacgacaagtaacaaggcgttgaatcg
gacacgtacacggggatcccgatccaatagattgcggtggctatttccccggtctcactcgaccggccactccttggttcagcct
ggggaagacactgagcggtttactctccggttgccagtggagataaggaaacaagtggtgaaccggaagctgcaccgggcga
ctagtatggtggttctggcgaggcagagcagttcgatgaggggataccgatttggttcaggtgaagggagtagtcgagggaagt
attaccggaggcttgagcggttggacagaacatcgaagtcggaccggtgggtgttgtcaatgacaccgccgtttttacgcgtat

FIG. 10 cont'd gtcgtcgatgaagactccgcgtggagggagtaaccgtgctgaacccggttcgggccgagaacttggacaggggaataccgcg
gtcgattcaagtaggcttccggtctga SEQ ID NO:188
AF417491 *Medicago sativa* alfalfa Q2HTN3_MEDTR Zinc finger, RING-type; RINGv
ECAVCLMEFEDTETLRLIPKCDHVFHPECIDEWLSSHTTCPVCRANL SEQ ID NO:189
AF417491 *Medicago sativa* alfalfa Q2HTN3_MEDTR Zinc finger, RING-type; RINGv
MKKDPTNLFILFGILLLSITKTQSQATNDNPTNPNFNQEFNPSFAIIIVILVAALFLM
GFFSIYIRRCSDSPSSNNLLLPITNGRRAVARGLDPSVIETFPILEYSEVKIHKIGKD
VLECAVCLMEFEDTETLRLIPKCDHVFHPECIDEWLSSHTTCPVCRANLVPQPGD
SVHGVPESQQQDVEAQNDAVQLPTESDSVLLAPEVISLNKTLNRNRTRGSQSNRP
RRFPRSHSTGHSLIQPGENTDRFTLKLPNKVRKQIMSRQLQRARSLITLPRESSSRH
GYRTGGEGSNRGKSLRRLDLSFKSDRWIFNRAPSFLARALSFRSPKPKVNNSDDD
EGTSSAAAPIMPSSAVDSARPQI SEQ ID NO:190
*Medicago* sativa alfalfa Q2HTN3_MEDTR Zinc finger, RING-type; RINGv
gagtgtgccgtttgtttaatggaattcgaagatactgaaacgctgcgtttgattccaaagtgtgatcatgttttcaccctgagtgtatt
gacgagtggttatcttctcacacaacgtgtcccgtt tgtcgcgcgaatctc SEQ ID NO:191
*Medicago* sativa alfalfa Q2HTN3_MEDTR Zinc finger, RING-type; RINGv
atgaagaaagatccaaccaatttattcatcctctttggaatccttcttctctcaatcacaaaaacccaatcccaagctactaacgataa
ccccacaaatccaaatttcaaccaagaatttaaccctt ccttcgctataatcatagtcatttta gtagctgctcttttctcatgggcttt
ttctccatctacatccgtcgctgctccgattcaccttcctccaacaacctccttctccccatcaccaacggccgtagagcggtggcg
cgtggactcgatccatcagtaatcgaaactttcccgattcttgaatactccgaagtcaagatccataagatcggaaaagatgttctt
gagtgtgccgtttgtttaatggaattcgaagatactgaaacgctgcgtttgattccaaagtgtgatcatgttttcaccctgagtgtatt
gacgagtggttatcttctcacacaacgtgtcccgtttgtcgcgcgaatctcgttccacaacctggtgactcagttcacggcgttcct
gagtcacagcaacaagacgttgaagctcaaaacgacgcggttcaattaccgacggaatctgactcagtattacttgctccagaag
tgatttcgttgaataaaacactgaaccggaaccgtacgcgtggatctcaatcaaaccggccgcgtcgttttccacggtctcactcg
accggacattcttt aatccaacc gggtgaaaa cacggaccggttcactttgaaactgcctaataaggttaggaaacagataatga
gccggcaattgcaacgagcgagaagtttgattacgttaccaagagaaagtagctcaagacatggctaccgaaccggaggtgaa
ggaagtaatagaggaaaaagtttgaggcggttggacctgagttttaaatcagaccggtggatatttaatagagcaccgtcgtttta
gcaagggcattgtcgtttaggtctccaaagccaaaagtcaataatagcgatgatgatgaaggaacttcttctgcagctgctcctatc
atgccatcctctgctgttgactctgcacgccctcagatttga SEQ ID NO:192
AF417491 *Medicago sativa* alfalfa Q8H740_MEDSA RING-H2 protein (RH2-1) gene
DCAVCLSKFEQNDLLRLLPLCCHAFHTECIDAWLASNQTCPLCRS SEQ ID NO:193
AF417491 *Medicago sativa* alfalfa Q8H740_MEDSA RING-H2 protein (RH2-1) gene
gactgcgccgtttgcttatcaaagttcgagcaaaacgatctcctccgtcttcttcctctctgctgtcacgcatttcacaccgaatgcat
tgacgcgtggttagcttcaaatcaaacctgtccgtta

FIG. 10 cont'd

SEQ ID NO:194
AF417491 *Medicago sativa* alfalfa Q8H740_MEDSA RING-H2 protein (RH2-1) gene
MGNTNSSHNLLITVTVFAVTVTVFFILYFILRRRRFSPSSSSTVRVSPVTPTSSTSSS
VVDSLPIFTFSSIKRRSSTVVSGDCAVCLSKFEQNDLLRLLPLCCHAFHTECIDAW
LASNQTCPLCRSSVFVSESEIMKIFRSSSTSSGNNSFRLEIGNISHRREATATDNNN
NNNNVAGETDRRTYSVGAFDYFVDEEAEIPVGNTNRRIFSGEKDDAAVLSVEVE
TPVDSQASLIGEGNWLKDYVDGLTRVMSFRGSGSSRRNDVVAGVGDFDVEANG
NGFGEEISEMFRWISGV SEQ ID NO:195
AF417491 *Medicago sativa* alfalfa Q8H740_MEDSA RING-H2 protein (RH2-1) gene
atgggaaacacaaattcctcacacaaccttctcataaccgtaaccgttttcgccgttaccgtcaccgttttcttcattctctacttcatc
ctccgtcgtcgtcgtttctctccgtcatcctcctccactgttagagtttctccggtgacgcctacttcatcaacctcatcttccgtcgttg
attctcttccgattttcactttctcctccatcaaacgccgttcctccaccgtcgtctccggcgactgcgccgtttgcttatcaaagttcg
agcaaaacgatctcctccgtcttcttcctctctgctgtcacgcatttcacaccgaatgcattgacgcgtggttagcttcaaatcaaac
ctgtccgttatgtcgatcatcggtattcgtatcggaatcggagattatgaagattttccgttcatcatccacttcttccggtaacaacag
cttccgtttagagataggtaacatcagccaccgccgtgaagcaaccgcaactgacaataacaataacaataacaatgtcgccgg
agaaactgaccggaggacatactccgtcggcgcgttcgattatttcgtcgacgaggaagctgagattccggttggaaacactaat
cggagaatattttccggtgaaaaggacgatgcggcggtgctttcggtggaggtggagactccggtggattctcaggcgagtttg
atcggtgaaggtaactggttgaaggattacgttgatggtttaacaagagtgatgtcgtttcgaggttctggaagtagtagaagaaa
cgacgtcgtagctggtgttggagattttgatgttgaagctaatggtaatggatttggtgaagagattagtgagatgtttaggtggattt
caggggtttaaatgggaatat SEQ ID NO:196
*Oryza sativa* (japonica cultivar-group) Q8H5Z8_ORYSA AP003019
ECAVCLDEFAAGDVLAHLPCGHRFHWACALPWLEAGAAPRSCPFCRAAVDTPP SEQ ID NO:197
*Oryza sativa* (japonica cultivar-group) Q8H5Z8_ORYSA AP003019
gagtgcgccgtgtgcctggacgagttcgccgccggcgacgtcctggcccatctcccctgcggccaccgcttccactgggcctg
cgcgctcccctggctcgaggccggcgccgcccctcgctcctgcccattctgccgcgccgccgtcga SEQ ID NO:198
*Oryza sativa* (japonica cultivar-group) Q8H5Z8_ORYSA AP003019
MEERYSYHPLLLLLHLLPQMAADHAAFPALARFLARKRTRTAIAMVIMAAMLP
GVECARRRRLRQGGGAGADAAAAGGGTRRSSFCVHAAGHGGGQTCGGAAAN
HSGKQRSSVMELIHGWSLDSNAREAKERLDQKLRSQRESVIKRHHSTGSIKLNRG
ATGGGGGGGRSTATAAMGVQREVYSRKGVMRRLMRWSRLRWDAAEQAECAV
CLDEFAAGDVLAHLPCGHRFHWACALPWLEAGAAPRSCPFCRAAVDTPPPPPPP
ACSS SEQ ID NO:199
*Oryza sativa* (japonica cultivar-group) Q8H5Z8_ORYSA AP003019

FIG. 10 cont'd atggaggagcgctactcgtaccacccgctgcttctcctcctccaccttctcccacaaatggccgccgaccatgctgctttccccgc
cctcgctagatttcttgcccgcaagcgcactcgcactgcgattgcgatggtgatcatggcggcgatgctgcccggggtggagtg
cgcgcggcggcggcggctccggcagggaggggagctggggcggatgcggcggcggctggcggaggtacgaggcggt
cgtcgttctgcgtgcacgcggccgggcatggtggtggtcagacatgtggcggcgccgccgcgaatcattccggcaagcagag
gagtagtgtgatggagctcatccatgggtggtcgctggacagcaatgcccgggaggcgaaggagcggctggaccagaagct
gaggagccagagggaatccgtcatcaagaggcatcacagcacgggaagcatcaagctgaacagaggcgccaccggcggc
ggcggagggggcgggagatcgacggcgacggcggcgatggggggtgcagagggaggtgtactcgaggaaaggggtgatg
cggcggctgatgcggtggagccggctgcggtgggacgcggcggagcaggcggagtgcgccgtgtgcctggacgagttcgc
cgccggcgacgtcctggcccatctccctgcggccaccgcttccactgggcctgcgcgctccctggctcgaggccggcgcc
gccctcgctcctgcccattctgccgcgccgccgtcgacacgccgccgccgccgccgccggcgtgctcgtcctag SEQ ID NO:200
*Beta vulgaris* Beet TC1535similar to UP|Q8H5Z8 (Q8H5Z8) RING-H2 zinc finger protein-like, partial (19%)
EECAVCLDEFKVGENLVNLPCAHRFHSRCLVPWLHTNAQCPCCRTSI SEQ ID NO:201
*Beta vulgaris* Beet TC1535similar to UP|Q8H5Z8 (Q8H5Z8) RING-H2 zinc finger protein-like, partial (19%)
tgtgcagtttgtttggatgaatttaaggtgggtgaaaatctggtgaatttaccttgtgctcattgtagatttcattccaggtgtttggtgc
cttggcttcacaccaatgcccaatgcccttgctgcaggacctccatc SEQ ID NO:202
*Beta vulgaris* Beet TC1535 similar to UP|Q8H5Z8 (Q8H5Z8) RING-H2 zinc finger protein-like, partial (19%)
MAGMLPGVEAARRRRFHQSSGTNGNGASPSSRRSSFSLFSPNSSTSFLSHSANRT
YHDDEKLGQLARQAKERLHEKLRAQTKSLIRNNSDLSEERVNGRSRVNTRYELK
TEVFGSKKNGGAKRLIGWAKLGWKSGEQEECAVCLDEFKVGENLVNLPCAHRF
HSRCLVPWLHTNAQCPCCRTSIFS SEQ ID NO:203
*Beta vulgaris* beet|TC2159 weakly similar to PIR|T47938|T47938 RING finger protein - Arabidopsis thaliana
ESCAVCLHEYESDDEVRRMRNCRHMFHRCCVDRWIDHDRKTCPLCRKPL SEQ ID NO:204
*Beta vulgaris* beet|TC2159 weakly similar to PIR|T47938|T47938 RING finger protein - Arabidopsis thaliana
gagagctgcgcggtgtgcctgcacgagtacgagagcgacgacgaggtgcggaggatgagaaactgccgccacatgttccac
cggtgctgcgtggaccgatggatcgaccacgatcgaaagacgtgcccgttgtgtaggaagccgctg SEQ ID NO:205
*Beta vulgaris* beet|TC2159 weakly similar to PIR|T47938|T47938 RING finger protein - Arabidopsis thaliana
MGFPAGYTEVLLPKLFLTALSLLGFLRKSVLSLLRLLGLASLIEPASPLEHDHPEP
GPALSESSAAALIREMLPAVTYAEAIAAGPDEPGPAESCAVCLHEYESDDEVRRM

FIG. 10 cont'd

RNCRHMFHRCCVDRWIDHDRKTCPLCRKPLVPHELQEDFNEKLWAASGIPDFYS
EYSPITNFL

SEQ ID NO:206
*Beta vulgaris* beet|TC2159 weakly similar to PIR|T47938|T47938 RING finger protein - Arabidopsis thaliana
atggggtttccagcaggatacacggaggtgctcctccccaaactattcctgacagctctctccctcctcggcttcctccgcaagtc
cgtcctctccctcctccgcctcctcggcctcgcctccttaatcgagcccgctcccccctcgagcacgaccatcccgagcccgg
cccggccctctcggaatcctccgcagcagccctcatccgggagatgctccccgccgtcacctacgccgaggcaatcgccgcc
gggcccgacgagcccggcccggcggagagctgcgcggtgtgcctgcacgagtacgagagcgacgacgaggtgcggagg
atgagaaactgccgccacatgttccaccggtgctgcgtggaccgatggatcgaccacgatcgaaagacgtgcccgttgtgtag
gaagccgctggtgccgcatgagttgcaggaggatttcaatgagaagctttgggctgcttctgggatacctgattttattctgaatat
tctcctataactaatttctta SEQ ID NO:207
*Beta vulgaris* beet|TC2159 weakly similar to PIR|T47938|T47938 RING finger protein - Arabidopsis thaliana
MGFPAGYTEVLLPKLFLTALSLLGFLRKSVLSLLRLLGLASLIEPASPLEHDHPEP
GPALSESSAAALIREMLPAVTYAEAIAAGPDEPGPAESCAVCLHEYESDDEVRRM
RNCRHMFHRCCVDRWIDHDRKTCPLCRKPLVPHELQEDFNEKLWAASWDT SEQ ID NO:208
*Beta vulgaris* beet|TC2159 weakly similar to PIR|T47938|T47938 RING finger protein - Arabidopsis thaliana
atggggtttccagcaggatacacggaggtgctcctccccaaactattcctgacagctctctccctcctcggcttcctccgcaagtc
cgtcctctccctcctccgcctcctcggcctcgcctccttaatcgagcccgctcccccctcgagcacgaccatcccgagcccgg
cccggccctctcggaatcctccgcagcagccctcatccgggagatgctccccgccgtcacctacgccgaggcaatcgccgcc
gggcccgacgagcccggcccggcggagagctgcgcggtgtgcctgcacgagtacgagagcgacgacgaggxtgcggag
gatgagaaactgccgccacatgttccaccggtgctgcgtggaccgatggatcgaccacgatcgaaagacgtgcccgttgtg SEQ ID NO:209
*Beta vulgaris* beet|TC2159 weakly similar to PIR|T47938|T47938 RING finger protein - Arabidopsis thaliana
tcaggtatcccaxgaagcagcccaaagcttctcattgaaatcctcctgcaactcatgcggcaccagcggcttcctacacaacgg
gcacgtctttcgatcgtggtcgatccatcggtccacgcagcaccggtggaacatgtggcggcagtttctcatcctccgcaxcctc
gtcgtcgctctcgtactcgtgcaggcacaccgcgcagctctccgccgggccgggctcgtcgggcccggcggcgattgcctcg
gcgtaggtgacggcggggagcatctcccggatgagggctgctgcggaggattccgagagggccgggccgggctcgggatg
gtcgtgctcgagggggggaggcgggctcgattaaggaggcgaggccgaggaggcggaggagggagaggacggacttgcg
gaggaagccgaggagggagagagctgtcaggaatagtttggggaggagcacctccgtgtatcctgctggaaacccat SEQ ID NO:210
*Beta vulgaris* beet|TC2159 weakly similar to PIR|T47938|T47938 RING finger protein - Arabidopsis thaliana
ataccttaactaacttagctcgaaaagatctcggattcaagacctaattttaagttcaaaaactacctaaaaattccgacctaataag
ttagccaatagaaagaaagaaaaactgctatttactcattttttttttcttcttcttgaaaactataagaaattagttataggagaatattc
agaataaaaatcaggtatcccagaagcagcccaaagcttctcattgaaatcctcctgcaactcatgcggcaccagcggcttccta

FIG. 10 cont'd cacaacgggcacgtctttcgatcgtggtcgatccatcggtccacgcagcaccggtggaacatgtggcggcagtttctcatcctcc
gcacctcgtcgtcgctctcgtactcgtgcaggcacaccgcgcagctctccgccgggccgggctcgtcgggcccggcggcgat
tgcctcggcgtaggtgacggcggggagcatctcccggatgagggctgctgcggaggattccgagagggccgggccgggct
cgggatggtcgtgctcgagggggggaggcgggctcgattaaggaggcgaggccgaggaggcggaggagggagaggacgg
acttgcggaggaagccgaggagggagagagctgtcaggaatagtttggggaggagcacctccgtgtatcctgctggaaaccc
cattttttagattttggagggagggattgttttggttgtcttgtagatgtgtgtgtttttattttctttttccaaggggggatagagattagag
agataggag SEQ ID NO:211
Ice Plant (Mesembryanthemum crystallinum) >ice_plant|BM300187
ECCVCLCKFGEEEEVSELSCKHFFHKKCLDKWFDNHHSTCPLCRS SEQ ID NO:212
Ice Plant (Mesembryanthemum crystallinum) >ice_plant|BM300187
gagtgctgtgtttgtttgtgtaaatttggggaagaagaagaggtgagtgaattgtcttgtaagcatttcttccacaagaagtgcttgg
ataagtggtttgataaccatcacagtacttgcccactttgcagatcc SEQ ID NO:213
Ice Plant (Mesembryanthemum crystallinum) >ice_plant|BM300187
GLSNFPSAAEGVLPVLVMNTVMSVAILKNLLKSFLELMGAAAWISSNFEEDPTSV
TGAEFYPPNSSSRRRNMRGIRITQFKYLCVRERKSKSTNFALGGAGGRTAVECCV
CLCKFGEEEEVSELSCKHFFHKKCLDKWFDNHHSTCPLCRSIH SEQ ID NO:214
Ice Plant (Mesembryanthemum crystallinum) >ice_plant|BM300187
ggattgtcaaattttcctagtgcagctgaaggtgtgctaccagttctagtgatgaacacagtaatgtcagtagcaatattgaagaact
tgttgaagtcattcttggaattgatgggagcagctgcttggatttcaagcaatttgaagaagacccaacatcagtaacaggagctg
aattttacccaccaaacagttcctctaggaggaggaacatgagggggattagaatcacacagttcaagtatttgtgtgttagagag
agaaaatcaaaatctaccaattttgcccttggaggtgcaggaggaagaacagcagtggagtgctgtgtttgtttgtgtaaatttggg
gaagaagaagaggtgagtgaattgtcttgtaagcatttcttccacaagaagtgcttggataagtggtttgataaccatcacagtactt
gcccactttgcagatccatccattgatcatttcatgcctaaatatcttacaaaatttccatctgagggttcagatttcaggctacaaatt
agggttttatcttcttttgggaccttttggtggttggggaagatgagtacactttttttttttttttttttcctttctttctttttgtgatactgtc
ttttgaggagtctttcatctcctttttttttttttagttttttattt SEQ ID NO:215
Medicago truncatula >medicago|TC110906 weakly similar to UP|Q6Z8T9 (Q6Z8T9)
Zinc finger protein family-like
DCSVCLSEFEEGEKVRRLKCKHTFHKDCLDKWLQDYFATCPLCR SEQ ID NO:216
Medicago truncatula >medicago|TC110906 weakly similar to UP|Q6Z8T9 (Q6Z8T9)
Zinc finger protein family-like
gattgtagcgtgtgcttatcagaattcgaagaaggagagaaggttcggggttgaaatgcaaacacacatttcataaggattgtttg
gataaatggttgcaagattatttgctacatgtccactttgtagggaacaagtt

SEQ ID NO:217

FIG. 10 cont'd

Medicago truncatula >medicago|TC110906 weakly similar to UP|Q6Z8T9 (Q6Z8T9)
Zinc finger protein family-like
MTVDISNVFQKLCNKIAILLIFVLVELIIFIWKLTSDTQSITTRQYIKFIEEKNPTIRY
NKKLNSHGDCSVCLSEFEEGEKVRRLKCKHTFHKDCLDKWLQDYFATCPLCRE
QVLPDNVVLKHRQQRNQQSNIEGNDENLPYVLFLLRGGNNSHLRR SEQ ID NO:218
Medicago truncatula >medicago|TC110906 weakly similar to UP|Q6Z8T9 (Q6Z8T9)
Zinc finger protein family-like
atgacagttgatatctccaacgtcttccaaaaactttgcaacaaaattgcaatcttactaatattcgtgttagtagaacttatcatcttca
tttggaaactaacatcagatacacaatcaatcacaactcgccaatacataaaattcatcgaagaaaagaaccctactattcgttaca
acaaaaagttgaattcacacggggattgtagcgtgtgcttatcagaattcgaagaaggagagaaggttcggaggttgaaatgca
aacacacatttcataaggattgtttggataaatggttgcaagattattttgctacatgtccactttgtagggaacaagttttaccagata
atgttgtgttaaaacatcgtcagcaacgaaatcaacagagtaatattgaggggaatgatgaaaatcttccctatgtgttgttcttgtta
cgtggtggtaataacagtcacttgcgtagatag SEQ ID NO:219
embAB182936[Citrullus lanatus]Citrullus lanatus mRNA for
RING zinc finger protein, partial cds. 537 bp trembl|AB182936s ptrembl|Q6I656
DCSXCLTQFEPASEINHLSXGHLFHTECLEKXLDYWNITCPLCRTPL SEQ ID NO:220
embAB182936[Citrullus lanatus]Citrullus lanatus mRNA for
RING zinc finger protein, partial cds. 537 bp trembl|AB182936s ptrembl|Q6I656
XGSXWXYLEMXRNRYPRXRFDKLQGSEXREHDCSXCLTQFEPASEINHLSXGHL
FHTECLEKXLDYWNITCPLCRTPLMXEEEKSXFW SEQ ID NO:221
embAB182936[Citrullus lanatus]Citrullus lanatus mRNA for
RING zinc finger protein, partial cds. 537 bp trembl|AB182936s ptrembl|Q6I656
gactgctcggnctgtttaactcaattt gaacctgcatctgagataaatcacttatcttgnggtcatcttttcacacagaatgcttg
gagaagnggctagattactggaacatcacatgtcctctttgcagaactcctcta SEQ ID NO:222
embAB182936[Citrullus lanatus]Citrullus lanatus mRNA for
RING zinc finger protein, partial cds. 537 bp trembl|AB182936s ptrembl|Q6I656
tttntggctccncttggagntacctcgagatgnttcgaaaccgatatccaaggannccgatttgataaattacagggctcagaatgn
cgngaacatgactgctcggnctgtttaactcaatttgaacctgcatctgagataaatcacttatcttgnggtcatcttttcacacaga
atgcttggagaagnggctagattactggaacatcacatgtcctctttgcagaactcctctaatgnccgaagaagagaaatcgngc
ttttggtgagcgtagaatctagttnggggaaactcatgtacagcatactcttaaagataattgtgaaagcgtttcctacctttggcac
gtatgacatttgaagnttgatgngtctgacaggncttagaggccaaagnnttgncactgtaaatacatgtttatgaagnnctatgc
ntttggcttgtgcctttagctttgagttaangcactgttactncactttctttgtacatggaattggctgagtatgcacaaagntattcaa
attctgtttgttt

SEQ ID NO:223

FIG. 10 cont'd embAY702979[Capsicum annuum]Capsicum annuum clone YAC
YCA22D8 genomic sequence. 103975 bp
CIVCMEGFQRGHVDGHGIKVPCGHVFHANCLTKWLSICNSCPLCRFKFI SEQ ID NO:224
embAY702979[Capsicum annuum]Capsicum annuum clone YAC
YCA22D8 genomic sequence. 103975 bp
ctttgtatagtatgtatggaaggttttcaaagaggtcatgttgatggtcatggcataaaagtcccttgtggtcatgtttttcatgcaaatt
gtcttaccaaatggctctccatttgtaattcttgtcctctt tgc cgttttaaattcatc SEQ ID NO:225
embAY702979[Capsicum annuum]Capsicum annuum clone YAC
YCA22D8 genomic sequence. 103975 bp
aaaccaaattcatggtatttgggttgttgtccaaccctcacccacgtagtgtagcacaaggtttgaattttttttcatctatatatattca
actatatatctaatcaaccatcacaaattacatattttcattctacatggataaagatttcgatctagatttagcattaacggtgatcgga
atttcaggcggtgacacgactgagccatcgcggtgttcaacgcgttacgatgatcacgatgagagtagtcaagttcaattattgcc
tatggttaattgtgaaaatgggctttgtatagtatgtatggaaggttttcaaagaggtcatgttgatggtcatggcataaaagtcccctt
gtggtcatgtttttcatgcaaattgtcttaccaaatggctctccatttgtaattcttgtcctctttgccgttttaaattcatcggaaacagtc
tctctacctttacgagataggagtaaggt SEQ ID NO:226
Allium cepa onion|CF452180
DCAVCLSEFSQDDKLRLLPICGHAFHINCIETWLLFYSTCPLCRGAL SEQ ID NO:227
Allium cepa onion|CF452180
gattgtgcagtttgcttatccgagttctctcaagatgataagcttcgtcttcttccaatatgtggtcatgcatttcatatcaattgtataga
aacttggcttcttttctattccacgtgccctctatgtagaggagctctcta SEQ ID NO:228
Allium cepa onion|CF452180
IVFRTSKMMLKTAFFSSKSYRVLSQIGKDSLPLQTSQSPPAQPSSNTTRISPAVLFII
IILAVIFFISGLLHLLVRFLIRKNPSSSSPQSNGHNQENSNSDALQRQLQQLFHLHD
SGLDQAFIDALPVFLYKEIVGSKEPFDCAVCLSEFSQDDKLRLLPICGHAFHINCIE
TWLLFYSTCPLCRGALYVQGRPS SEQ ID NO:229
Allium cepa onion|CF452180
ggtgacctatagaacagtttgtactaaaaagcaggctggtaccggtccggaattcccgggattcaaatttcaatattgatgaacgc
ccatcttctcagttgagctggaaacatttgatttaagagctcaaccatcttcacaaatcatcagttttaatcaaacaaagtttgattttg
agctgtattgagctcttctacagtagaaagtttgaattttagcctcctcatgctttcaaatgaattgttttcgtacgagcaagatgatgt
taaaaacagcctttttctcgtcaaaatcatatcgggttttatcccaaatcggaaaggattcacttccattgcaaacatctcagtctcca
ccggctcaaccttcatcaaatactaccagaataagtccagctgtgctttcatcatcataattctagcagtaatattttttatatctggttt
acttcatcttttggttagatttctaataagaaagaatccatcttcgtcctctccacaatccaatggccacaatcaagaaaactcaaattc
tgatgcgttacaaagacaacttcaacaattgtttcatctccacgattctggactcgatcaagctttcattgatgccttacccgtgtttct
ctataaagagattgtcgggtcgaaagagccctttgattgtgcagtttgcttatccgagttctctcaagatgataagcttcgtcttcttcc

FIG. 10 cont'd aatatgtggtcatgcatttcatatcaattgtatagaaacttggcttcttttctattccacgtgccctctatgtagaggagctctctatgttc
aagggcgtcccagttgaaatccaatgtacgagtttgatgaagagatgggactggaaggagggcgatttggaaatacggagact
gggaagagattggtgtgagaagagaatattc SEQ ID NO:230
Cucumis melo (Muskmelon) Q84KA9_CUCME
ECAVCLNEFEDDETLRLIPKCDHVFHPECIDAWLAS-HSTCPVCRANL SEQ ID NO:231
Cucumis melo (Muskmelon) Q84KA9_CUCME
gaatgcgctgtttgtttgaatgaatttgaagatg atgaaacgctgcgtttaatccctaaatgtgatcatgtgtttcaccctg
aatgtattgatgcttggttggcttctcactctacttgccctgtttgt cgagctaatttgtctccccaa SEQ ID NO:232
Cucumis melo (Muskmelon) Q84KA9_CUCME
MPSLTAPHGLPLFLFLLLFLFSSVSAQFQPAPDPRSDPYQYRLSGSMAVIIVILIAA
LFFMAFFSVYIRHCNDSPSNTVRPITAAAGRSRRATRGLDPAVIETFPTLIYSDVKE
HKIGKSALECAVCLNEFEDDETLRLIPKCDHVFHPECIDAWLASHSTCPVCRANL
SPQPTDSVHRADDSNAVVNSDTDGGDIEAQSNDVVSETTAPPTVQIQTESELSTT
TSNKALNRTRTRGSRSNRLRWLFPRSHSTGHSLVQPGEDTERFTLRLPVEIRKQV
VNRKLHRATSMVVLARQSSSMRGYRFGSGEGSSRGKYYRRLERLDRTSKSDRW
VLSMTPPFFTRMSSMKTPRGGSNRAEPGSGRELGQGNTAVDSSRLPV SEQ ID NO:233
Cucumis melo (Muskmelon) Q84KA9_CUCME
atgccctctctcaccgcccccatggccttcccctcttcctcttcctcctcctcttcctcttctcctccgtctccgcccagttccagccc
gcccccgaccccagatcagacccttaccagtaccgcctcagcggttccatggccgtcatcatcgtcatcctcatcgccgctctctt
cttcatggctttcttctccgtctacatccgtcactgcaacgattcaccatccaacaccgtccgccctatcaccgccgccgccggcc
gctcccgtcgcgcaaccgcggtctcgatccggcggtaattgaaacgtttccgactctgatttactccgatgtgaaagagcataa
aattggtaaaagtgccctagaatgcgctgtttgtttgaatgaatttgaagatgatgaaacgctgcgtttaatccctaaatgtgatcatg
tgtttcaccctgaatgtattgatgcttggttggcttctcactctacttgccctgtttgtcgagctaatttgtctccccaacccactgactc
cgtccaccgagctgacgattccaacgctgtcgttaactccgataccgacggaggtgatattgaagctcagtccaacgacgttgttt
cagagacgacggctccacctacggttcagatacaaacggaatcagagctcagtacgacgacaagtaacaaggcgttgaatcg
gacacgtacacggggatcccgatccaatagattgcggtggctatttccccggtctcactcgaccggccactccttggttcagcct
ggggaagacactgagcggtttactctccggttgccagtggagataaggaaacaagtggtgaaccggaagctgcaccgggcga
ctagtatggtggttctggcgaggcagagcagttcgatgaggggataccgatttggttcaggtgaagggagtagtcgagggaagt
attaccggaggcttgagcggttggacagaacatcgaagtcggaccggtgggtgttgtcaatgacaccgccgttttttacgcgtat
gtcgtcgatgaagactccgcgtggagggagtaaccgtgctgaacccggttcgggccgagaacttggacaggggaataccgcg
gtcgattcaagtaggcttccggtctga SEQ ID NO:234
Cucumis melo AF499727 Cucumis melo BAC clone PIT92-60K17, complete sequence.
AAO45753.1 "GI:28558782"
ECAVCLNEFEDDETLRLIPKCDHVFHPECIDAWLAS-HSTCPV

SEQ ID NO:235

FIG. 10 cont'd

Cucumis melo AF499727 Cucumis melo BAC clone PIT92-60K17, complete sequence.
AAO45753.1 "GI:28558782"
gaatgcgctgtttgtttgaatgaatttgaagatg atgaaacgctgcgtttaatccctaaatgtgatcatgtgtttcaccctg
aatgtattgatgcttggttggcttctcactctacttgccctgtttgt cgagctaatttgtctccccaa SEQ ID NO:236
Cucumis melo AF499727 BAC clone PIT92-60K17, complete sequence. AAO45753.1
"GI:28558782"
MPSLTAPHGLPLFLFLLLFLFSSVSAQFQPAPDPRSDPYQYRLSGSMAVIIVILIAA
LFFMAFFSVYIRHCNDSPSNTVRPITAAAGRSRRATRGLDPAVIETFPTLIYSDVKE
HKIGKSALECAVCLNEFEDDETLRLIPKCDHVFHPECIDAWLASHSTCPVCRANL
SPQPTDSVHRADDSNAVVNSDTDGGDIEAQSNDVVSETTAPPTVQIQTESELSTT
TSNKALNRTRTRGSRSNRLRWLFPRSHSTGHSLVQPGEDTERFTLRLPVEIRKQV
VNRKLHRATSMVVLARQSSSMRGYRFGSGEGSSRGKYYRRLERLDRTSKSDRW
VLSMTPPFFTRMSSMKTPRGGSNRAEPGSGRELGQGNTAVDSSRLPV SEQ ID NO:237
Cucumis melo AF499727 Cucumis melo BAC clone PIT92-60K17, complete sequence.
AAO45753.1 "GI:28558782"
atgccctctctcaccgcccccatggccttccctcttcctcttcctcctcctcttcctcttctcctccgtctccgcccagttccagccc
gcccccgacccagatcagaccttaccagtaccgcctcagcggttccatggccgtcatcatcgtcatcctcatcgccgctctctt
cttcatggctttcttctccgtctacatccgtcactgcaacgattcaccatccaacaccgtccgccctatcaccgccgccggcc
gctcccgtcgcgcaacccgcggtctcgatccggcggtaattgaaacgtttccgactctgatttactccgatgtgaaagagcataa
aattggtaaaagtgccctagaatgcgctgtttgtttgaatgaatttgaagatgatgaaacgctgcgtttaatccctaaatgtgatcatg
tgtttcaccctgaatgtattgatgcttggttggcttctcactctacttgccctgtttgtcgagctaatttgtctccccaacccactgactc
cgtccaccgagctgacgattccaacgctgtcgttaactccgataccgacggaggtgatattgaagctcagtccaacgacgttgttt
cagagacgacggctccacctacggttcagatacaaacggaatcagagctcagtacgacgacaagtaacaaggcgttgaatcg
gacacgtacacggggatcccgatccaatagattgcggtggctatttccccggtctcactcgaccggccactccttggttcagcct
ggggaagacactgagcggtttactctccggttgccagtggagataaggaaacaagtggtgaaccggaagctgcaccgggcga
ctagtatggtggttctggcgaggcagagcagttcgatgaggggataccgatttggttcaggtgaagggagtagtcgagggaagt
attaccggaggcttgagcggttggacagaacatcgaagtcggaccggtgggtgttgtcaatgacaccgccgttttttacgcgtat
gtcgtcgatgaagactccgcgtggagggagtaaccgtgctgaacccggttcgggccgagaacttggacaggggaataccgcg
gtcgattcaagtaggcttccggtc SEQ ID NO:238
Capsicum annuum pepper|CA525749
ECSVCLTKFEPDAGVNSLSCGHVFHKLCLEKWLTYWHVTCPL SEQ ID NO:239
Capsicum annuum pepper|CA525749
RKNHHFNTRFRSVMGLSQYPTPADAGVLGVILVNTAISISIVKEILRSILRLIGIRIA
SWEDYSIEGSSDSLECRGSPPESYMEEFRSRTPAFRYDSLCISNHPEQECSVCLTKF
EPDAGVNSLSCGHVFHKLCLEKWLTYWHVTCPLCRNHLMPQQEQDDT SEQ ID NO:240
Capsicum annuum pepper|CA525749 transmembrane

FIG. 10 cont'd

GVLGVILVNTAISISIVKEILRSILRLIGIRIA

SEQ ID NO:241
Capsicum annuum pepper|CA525749
GAATGTTCTGTGTGCCTAACAAAATTTGAGCCTGATGCAGGGGTAAACAGTC
TCTCATGTGGTCATGTTTTCCATAAGCTGTGTCTAGAGAAGTGGCTCACGTAT
TGGCATGTAACTTGTCCTCTT SEQ ID NO:242
Capsicum annuum pepper|CA525749
agaaagaatcatcatttcaacactaggttccgatccgttatgggcctctcacaatatccaactccagcagatgcaggagtactagg
tgtgattctagtaaacacagccatatccatatccattgtcaaggagatactacgatcgattcttcgcctgataggcatccgtatcgca
tcatgggaagactattctatactacgatcgattcttcgcctgataggcatccgtatcgcatcatgggaagactattctattgaaggct
cctcagactcacttgaatgccgtggaagcccaccagagtcatacatggaggagttcagaagccgaacacctgcatttcgttatga
ctcgctatgcatctctaaccaccctgaacaagaatgttctgtgtgcctaacaaaatttgagcctgatgcaggggtaaacagtctctc
atgtggtcatgttttccataagctgtgtctagagaagtggctcacgtattggcatgtaacttgtcctctttgcagaaatcacttgatgcc
tcaacaagaacaggacgatacgtg SEQ ID NO:243
Capsicum annuum pepper|CA525749
>embl|CA525749|CA525749 KS12061A09 KS12 Capsicum annuum cDNA, mRNA
sequence
gtccctcttacaaaaataaaaataaagtactacagaaaattgctacaaaaaagtctcaagttttcatattattagatccggtatattg
agctcttccagaaggttttgaagaaagaatcatcatttcaacactaggttccgatccgttatgggcctctcacaatatccaactccag
cagatgcaggagtactaggtgtgattctagtaaacacagccatatccatatccattgtcaaggagatactacgatcgattcttcgcc
tgataggcatccgtatcgcatcatgggaagactattctattgaaggctcctcagactcacttgaatgccgtggaagcccaccaga
gtcatacatggaggagttcagaagccgaacacctgcatttcgttatgactcgctatgcatctctaaccaccctgaacaagaatgttc
tgtgtgcctaacaaaatttgagcctgatgcaggggtaaacagtctctcatgtggtcatgttttccataagctgtgtctagagaagtgg
ctcacgtattggcatgtaacttgtcctctttgcagaaatcacttgatgcctcaacaagaacaggacgatacgtg SEQ ID NO:244
GenBank ACCESSION  AY780430
Populus alba x Populus tremula RING-H2 subgroup RHE protein (RHE1) mRNA,
complete cds.
MDPDSRDPPIEYREGYALSGKIMLSAILILFFVIIVMVLLHLYARWYLTRARQRQV
RRVRNRRTHLVFYVDSPQNPNNVTSHVTRGLEETVKNSLPVFVYPRKTHQDSIE
CAVCLSEFEENERGRVLPKCNHSFHTECIDMWFHSHSTCPLCRSPVEPVAENPVP
EGSNFGISEAGSGLCTSCQHEEDHLGSASTSSFNGGRKPVGLIGVTIDVPRRNGNF
EDESNTESPSASHSFRSPMSRMLSFKRMLSRERRGTVSPTVANSVSCGGGSGTTE
FDIEQGRDESMPQQTRC SEQ ID NO:245
GenBank ACCESSION  AY780430
Populus alba x Populus tremula RING-H2 subgroup RHE protein (RHE1) mRNA,
complete cds.
ECAVCLSEFEENERGRVLPKCNHSFHTECIDMWFH SHSTCPLCRSPV

FIG. 10 cont'd

SEQ ID NO:246
GenBank ACCESSION AY780430
Populus alba x Populus tremula RING-H2 subgroup RHE protein (RHE1) mRNA, complete cds.
gagtgtgcggtttgtttatccgaattcgaagagaacgaaaggggtcgggtcttgcccaagtgtaaccacagtttccacaccgagt
gcatcgatatgtggtttcattctcactccacttgccctctttgtcgctctccggttg SEQ ID NO:247
GenBank ACCESSION AY780430
Populus alba x Populus tremula RING-H2 subgroup RHE protein (RHE1) mRNA, complete cds.
tgctaaaccaaacccattatccttctctttctcttaagcacacaagaatcaaaattggtccatttattcaagaaatggacccagactcg
agagatccaccaattgaatacagagaaggctatgcattaagtggcaagataatgcttagtgctattcttattctcttctttgttatcatt
gtaatggttcttctccaccttacgctcgttggtacctcactcgtgcacgccagcgccaagtccgccgtgtccgcaaccgccgtac
ccatcttgtcttctacgtcgactcccccaaaaccccaacaatgtcacctctcatgtcacgcgtggccttgaagagactgtcaaaa
attctcttcctgttttgtatatccaagaaaaacccaccaagattcgattgagtgtgcggtttgtttatccgaattcgaagagaacgaa
aggggtcgggtcttgcccaagtgtaaccacagtttccacaccgagtgcatcgatatgtggtttcattctcactccacttgccctcttt
gtcgctctccggttgagccggtggcggaaaaccccgttccagaaggttcaaatttcgggatttcagaagcaggttcgggtctgtg
tacctcgtgccagcacgaggaggatcatttgggatcggcttctacgtcgtcgtttaatggtggaaggaaacctgttgggcttattg
gtgtgaccatagacgtgccaaggagaaatgggaatttcgaggacgagtcaaataccgagtcaccatcagcgagtcactcctta
gatcgccaatgagtcggatgttgtcgtttaagaggatgctaagtagggaaagaagaggtactgtgtctccaaccgtggctaactc
agtgagctgcggtggtgggtcagggacgaccgagtttgatattgagcaagggagggatgagtcgatgcctcagcaaactcggt
gttaaaataagaggtggcaattcttgacccggttag SEQ ID NO:248
>tr|Q8H222|Q8H222_9ROSI Putative RING protein - Populus alba x Populus tremula.
AY129244
MEFEKYFTQGWKSVSSAASDSENPSGCFDCNICFDFAHEPVVTLCGHLYCWPCI
YKWLHVQSASLASDEHPQCPVCKADISHTTMVPLYGRGQGSTEAEGKTPYRGMI
IPPRPSACGAQGVVSNTSNTGQRLPYRNPYRNHNYNANPYGSFEEASPSPLLNLG
DPAMTGLQQPAVGMFREMVYARVFGPFPNSYHLMGTGSPRLRRHELMADKSL
NRISIFLFCCFLLCLIVF SEQ ID NO:249
>tr|Q8H222|Q8H222_9ROSI Putative RING protein - Populus alba x Populus tremula.
AY129244
DCNICFDFAHEPVVTLCGHLYCWPCIYKWLHVQSASLASDEHPQCPVCKADI SEQ ID NO:250
>tr|Q8H222|Q8H222_9ROSI Putative RING protein - Populus alba x Populus tremula.
AY129244
gactgtaatatctgttttgactttgcacatgagccagtagtcaccctctgtggccacctctactgctggccctgcatctacaagtggc
tccacgtccagagcgcctcgcttgcctccgatgagcacccgcaatgcccagtttgcaaggctgatata

SEQ ID NO:251

FIG. 10 cont'd

GenBank Accession AY129244
Populus x canescens putative RING protein (RING) mRNA, complete cds
gi|22795036|gb|AY129244.1|[22795036]
acgcggggggtcccttcgtggaaatctctgtgtctctgttatctgcaaaatctccattaaagcttcctcgaatcctcttattttaatc
aagccaaagaacactctgttattttgcctttaactttccttcagagttaaagaagaacgtgggaatccatggaatttgagaaatatttt
acccagggatggaaatcagtttcaagtgcggcatctgactcggaaaatcccagtggttgtttcgactgtaatatctgttttgactttg
cacatgagccagtagtcaccctctgtggccacctctactgctggccctgcatctacaagtggctccacgtccagagcgcctcgct
tgcctccgatgagcaccgcaatgcccagtttgcaaggctgatatatctcacaccaccatggttcccctgtatggccgtggccaa
ggctcaaccgaagctgaaggcaagacaccatacaggggcatgatcattcctcctagaccatcagcttgtggtgctcaaggtgtg
gtgtcaaacacatctaataccggccagcggcttccatatcgtaatccttaccggaaccataactataatgctaatccatacggcagt
ttcgaagaggcttccccatcacccttgcttaatcttggagaccctgcaatgaccggtttgcagcaaccagctgttgggatgttcaga
gagatggtgtatgcgagggttttcgggcccttccaaactcgtatcacttaatgggtactggtagccctaggctgagaaggcatga
gctgatggcagacaagtcattgaatagaatctccattttctcttttgttgctttctttatgcctcattgtattttgaaatatagaactaggt
tagtctccattgttcacctcgatagttagtttgtaaagggcaatggatccgagtttatgaaatatccatggatcacttatatttatatat
atgatttgatcttcatattttgctggaaaaaaaaa SEQ ID NO:252
Arabidopsis thaliana (Mouse-ear cress) >tr|Q9XF92|Q9XF92_ARATH BRH1 RING
finger protein (Putative RING finger protein)
NCAVCLYEFEGEQEIRWLRNCRHI FHRSCLDRWMDHDQKTCPLCRTPF SEQ ID NO:253
Arabidopsis thaliana (Mouse-ear cress) >tr|Q9XF92|Q9XF92_ARATH BRH1 RING
finger protein (Putative RING finger protein)
aactgcgccgtttgtctatacgaa ttcgaaggagaacaagagatccggtggctgagaaattgcagacatatatttcaccggagc
tgtcttgaccgttggatggatcatgatcagaagacgtgtccactttgtagaacaccgttt SEQ ID NO:254
Arabidopsis thaliana (Mouse-ear cress) >tr|Q9XF92|Q9XF92_ARATH BRH1 RING
finger protein (Putative RING finger protein)
MGFPVGYTEVFLPKLFVQTLSILGFIRTIVFSIFRFLGLSDFLEMDQTWPDYTSYPT
RIPETRSPFSALLIREILPVIKFEELTNSGEDLPENCAVCLYEFEGEQEIRWLRNCRH
IFHRSCLDRWMDHDQKTCPLCRTPFVPDEMQEEFNQRLWAASGVHDFHCPVTE
LL SEQ ID NO:255
Arabidopsis thaliana (Mouse-ear cress) >tr|Q9XF92|Q9XF92_ARATH BRH1 RING
finger protein (Putative RING finger protein)
atgggctttcccgtaggttacacagagggttttcttaccgaagcttttcgtacaaacgctttcgattctcggattcatcagaaccatcgt
cttctctatcttccgcttcttgggtctctcagattttctcgaaatggatcaaacctggcccgattacacatcgtacccgacccgaatac
ccgaaacccgctcacctttctccgcactcctaattagagagatcctaccggttatcaaattcgaagagttaacgaattccggcgaa
gatctaccggaaaactgcgccgtttgtctatacgaattcgaaggagaacaagagatccggtggctgagaaattgcagacatatat
ttcaccggagctgtcttgaccgttggatggatcatgatcagaagacgtgtccactttgtagaacaccgtttgttccagatgagatgc
aagaagagttaatcaacggctatgggctgcttctggtgttcatgattttcactgtcccgtgaccgaattattatag

SEQ ID NO:256

FIG. 10 cont'd

Arabidopsis thaliana (Mouse-ear cress) >tr|Q9XF92|Q9XF92_ARATH BRH1 RING finger protein (Putative RING finger protein)
aactgcgccgtttgtctatacgaattcgaaggagaacaagagatccggtggctgagaaattgcagacatatatttcaccggagct
gtcttgaccgttggatggatcatgatcagaagacgtgtccactttgtagaacaccgtttgt SEQ ID NO:257
>tr|Q9XF92|Q9XF92_ARATH BRH1 RING finger protein (Putative RING finger protein) - Arabidopsis thaliana (Mouse-ear cress).
taaaaaccctagctttctccatgggctttcccgtaggttacacagaggttttcttaccgaagcttttcgtacaaacgctttcgattctcg
gattcatcagaaccatcgtcttctctatcttccgcttcttgggtctctcagattttctcgaaatggatcaaacctggcccgattacacat
cgtacccgacccgaatacccgaaacccgctcaccttctccgcactcctaattagagagatcctaccggttatcaaattcgaagag
ttaacgaattccggcgaagatctaccggaaaactgcgccgtttgtctatacgaattcgaaggagaacaagagatccggtggctg
agaaattgcagacatatatttcaccggagctgtcttgaccgttggatggatcatgatcagaagacgtgtccactttgtagaacaccg
tttgttccagatgagatgcaagaagagtttaatcaacggctatgggctgcttctggtgttcatgattttcactgtcccgtgaccgaatt
attatagaagaagccacgcttttctatctttttctgtgtcccttatgttctttttttgttttgactttcaccccctctactttttgatgttgctttttca
ccctcttactgacatttagacttgccacgcttttatgtgtgtatatactccttacatatgaatgagagatgagcaataaatattaccga
gacaggaaa SEQ ID NO:258
RHA2A_ARATH Q9ZT50 RING-H2 zinc finger protein RHA2a RING-type; atypical
DCVVCLSKLKEGEEVRKLECRHVFHKKCLEGWLHQFNFTCPLCRSALV SEQ ID NO:259
RHA2A_ARATH Q9ZT50 RING-H2 zinc finger protein RHA2a RING-type; atypical
MGLQGQLSDVSSDSIPLMLLSLLAVFINHLRSFLLRLTSKSNPNLPVDDVSIASGL
ANIIVLADQLSLNRLFSYRCGDGGGGGSDCVVCLSKLKEGEEVRKLECRHVFHK
CLEGWLHQFNFTCPLCRSALVSDDCVSKTQRSVGRDLISCFSLH SEQ ID NO:260
RHA2A_ARATH Q9ZT50 RING-H2 zinc finger protein RHA2a RING-type; atypical
tgtgttgtgtgtttgtcgaagttaaaggaaggtgaagaggtgaggaagctggaatgtcgacacgtgttccacaagaagtgtttgga
aggatggcttcatcaattcaatttcacttgtcctctttgtagatctgctttggttt SEQ ID NO:261
>embl|AX506870|AX506870 Sequence 1565 from Patent WO0216655.
atggggctacaaggtcagctaagtgacgtctcttccgattcaatccctcttatgctcctctctctcctcgccgtcttcatcaaccatct
ccgatctttcctcctccgtctcacctctaaatcaaatcctaatctccccgtagacgatgtctctatagcatcgggactagccaacata
atcgttctcgccgatcagcttagtttgaatcggttattctcgtaccggtgcggtgacggaggtggtggcggctccgattgtgttgtgt
gtttgtcgaagttaaaggaaggtgaagaggtgaggaagctggaatgtcgacacgtgttccacaagaagtgtttggaaggatggc
ttcatcaattcaatttcacttgtcctctttgtagatctgctttggtttccgatgattgcgtctctaaaacgcagcgtagcgttgggaggg
atttgatctcgtgtttctctctccactga SEQ ID NO:262
RHA2A_ARATH Q9ZT50 RING-H2 zinc finger protein RHA2a
gaagaagaagaaagatggggctacaaggtcagctaagtgacgtctcttccgattcaatccctcttatgctcctctctctcctcgcc
gtcttcatcaaccatctccgatctttcctcctccgtctcacctctaaatcaaatcctaatctccccgtagacgatgtctctatagcatcg

FIG. 10 cont'd ggactagccaacataatcgttctcgccgatcagcttagtttgaatcggttattctcgtaccggtgcggtgacggaggtggtggcgg
ctccgattgtgttgtgtgtttgtcgaagttaaaggaaggtgaagaggtgaggaagctggaatgtcgacacgtgttccacaagaagt
gtttggaaggatggcttcatcaattcaatttcacttgtcctctttgtagatctgctttggtttccgatgattgcgtctctaaaacgcagcg
tagcgttgggagggatttgatctcgtgtttctctctccactgagtaaaagatcggaagatgaagaagatccgatggtatctgagag
atctacggtggctggctggttcggtttgaccacgcgcgtgcgccccttcttttctcggatttttttgaggtctctttcttctgtgagag
gagaaccttttgtttgtttggtttttttttttactttttcgatttggaatatgtaaattttgaatatacaaattttcaccgtttgt atctttgttg
ttccttgctgttgagtatat ataaatggagaagatatcaattccagtataaaaaaaaaaaaaaaaaaaaaaa SEQ ID NO:263
*Arabidopsis Thaliana* RING-H2 zinc finger protein RHA2B_ARATH Q9ZU51
CIVCLSKLKTGEEVRKLDCRHVFHKQCLEGWLQHLNFNCPLCRSPLL SEQ ID NO:264
*Arabidopsis Thaliana* RING-H2 zinc finger protein RHA2B_ARATH Q9ZU51
tgcatcgtgtgtctgtctaaa ctcaagaccggagaagaagtgaggaagctagattgcagacacgtcttccataagcagtgt
ttggaaggctggcttcaacatctcaacttcaattgcccgctctgtagatctccattgcta SEQ ID NO:265
*Arabidopsis Thaliana* RING-H2 zinc finger protein RHA2B_ARATH Q9ZU51
MGLQGQLSDVSSDSIPLMLLALLATFFRHVRSLLLFPSSAPVVVVTSNLSVLADQ
LNLNRLFSYRYSDNAASDCIVCLSKLKTGEEVRKLDCRHVFHKQCLEGWLQHLN
FNCPLCRSPLLPHHHQGHGSDASISAFPLRSTSTASSH SEQ ID NO:266
*Arabidopsis Thaliana* RING-H2 zinc finger protein RHA2B_ARATH Q9ZU51
atgggactacaaggtcagctctccgacgtgtcatcagattcgatcccactgatgctactggctctcctcgcaacttcttcagacac
gtccggtctcttctcctcttcccttcttctgccccgttgttgttgttacttcaaacctcagcgtcctcgccgaccagctcaacctaaat
cgcctcttctcgtaccgctactccgacaacgcagcctctgactgcatcgtgtgtctgtctaaactcaagaccggagaagaagtga
ggaagctgattgcagacacgtcttccataagcagtgtttggaaggctggcttcaacatctcaacttcaattgcccgctctgtagatc
tccattgctacctcatcatcatcagggacatggcagtgatgcgtcgatctcagccttccctcttcgctctacctctactgcatcatctc
attga SEQ ID NO:267
ATL3J_ARATH Q9LY41 RING-H2 finger protein ATL3J/ RHX1a/ ATL4
DCAVCLSKFEPEDQLRLLPLCCHAFH ADCIDIWLVSNQTCPLCRSPL SEQ ID NO:268
ATL3J_ARATH Q9LY41 RING-H2 finger protein ATL3J/ RHX1a/ ATL4
MESLINPSHGGGNYDSHSSSLDSLKPSVLVIILILLMTLLISVSICFLLRCLNRCSHR
SVLPLSSSSSVATVTSDSRRFSGHRVSPETERSSVLDSLPIFKFSSVTRRSSSMNSG
DCAVCLSKFEPEDQLRLLPLCCHAFHADCIDIWLVSNQTCPLCRSPLFASESDLM
KSLAVVGSNNGGGENSFRLEIGSISRRRQTPIPESVEQHRTYSIGSFDYIVDDVDSE
ISESNFNRGKQEDATTTTATATAVTTNPTSFEASLAADIGNDGSRSWLKDYVDRL
SRGISSRAMSFRSSGRFFTGSSRRSEELTVMDLEANHAGEEISELFRWLSGV

SEQ ID NO:269

FIG. 10 cont'd

ATL3J_ARATH Q9LY41 RING-H2 finger protein ATL3J/ RHX1a/ATL4
TRANSMEM (Potential)
VLVIILILLM TLLISVSICF L SEQ ID NO:270
ATL3J_ARATH Q9LY41 RING-H2 finger protein ATL3J/ RHX1a/ATL4
atggaatctctcatcaatcccagccatggcggaggaaactacgattctcactcttcttctctcgatagtctcaaaccaagcgtacta
gtcatcattctcattctcctcatgactcttctcatctccgtttccatttgcttcctcctccgctgtctcaatcgctgtagccaccgctccgt
tctccctctttcatcttcctcttccgtcgcaaccgtaacttccgattcccgacgattctctggacatcgagtctctcccgaaacagaac
ggtcctccgtgcttgattcgcttccgattttcaaattctcctccgtcactcgccgatctagctccatgaattccggagattgcgccgttt
gtttgtcgaaattcgaaccggaggatcagctccgtcttcttcctctctgttgtcacgcttttcacgccgattgtatcgatatctggctag
tctctaaccagacttgtcctctctgtcgctctcctctcttcgcttcagaatctgatctcatgaagtctctcgccgtcgtcggctcaaaca
acggcggaggagaaaacagcttccgtctcgaaatcggatccatcagccgtcgtcgtcaaacaccgattccagaatccgttgagc
agcatcgaacttactcaatcggttcgttcgattacatagtagacgacgtagattcagaaatctcagagtcaaatttcaaccgtggaa
aacaggaagacgcgactacaacaactgccacagcaacggcggttacgactaatccgacgtcgtttgaagctagtttagcggcg
gatataggtaacgatggttctagaagctggctcaaggattacgttgacagactctcacgaggtatatcgtcgcgtgcaatgtcgttt
agaagctctggtagattttttactgggagtagtcgtcggagtgaggaattgacggtgatggatttagaagcgaatcatgccggag
aagagataagtgagcttttccggtggctctcaggggtgtga SEQ ID NO:271
*Arabidopsis Thaliana* ATL2N_ARATH O22255 RING-H2 finger protein
CSVCLSEFEEEDEGRLLPKCGHSFHVDCIDTWFRSRSTCPLCRECSVCLSEFEEED
EGRLLPKCGHSFHVDCIDTWFRS-RSTCPLCRAPV SEQ ID NO:272
*Arabidopsis Thaliana* ATL2N_ARATH O22255 RING-H2 finger protein
MGIGEESTKPIWGSVSHTSSGYALNGKIMLSSVIVLFVAVIMILCFHSYARWLFRR
HNRRIRRRIRSHLRTLSASPRDQALDQAVLDKIPIFVYSSKNPPPPEEKEECSVCLS
EFEEEDEGRLLPKCGHSFHVDCIDTWFRSRSTCPLCRAPVQPPFQVIETG<u>SSSSSSP</u>
LTFPTEGCEREPIDLAGIIVDISREVEFEGSNPGLPIENGSKFPGSRVLSLKRLWSI SEQ ID NO:273
*Arabidopsis Thaliana* ATL2N_ARATH O22255 TRANSMEM (Potential)
IMLSSVIVLFVAVIMILCFH S SEQ ID NO:274
*Arabidopsis Thaliana* ATL2N_ARATH O22255 RING-H2 finger protein
atgggaatcggtgaagaaagcacaaagcctatttgggggagcgtgagccacacgtcttcaggctacgctctcaacggcaaaat
catgctctcctccgtgatcgttctattcgtcgccgttattatgatcctctgcttccacagctacgccgttggttattccgtcgtcacaa
ccgtcgcattcgccgccgtattcgttctcacctccgcactctctccgcctcaccccgagaccaagctctcgaccaggctgttctcg
acaagattccgatcttcgtttactcctccaagaatccaccaccaccagaagagaaggaggagtgctccgtctgcttgtcggagttc
gaggaagaagacgaaggccgtcttcttcctaaatgtggccactcttttcacgtcgactgcatcgatacttggttccgttccagatcc
acttgcccgctttgcagagctccggttcaaccccgtttcaggtcattgaaaccggttcttcttcttcttcttcgccgttgacatttccg
acggagggttgcgagagagaaccgattgacctcgccggtatcattgtggatatttccagagaagttgaatttgaaggctcaaatc
cgggtctacccatcgaaaacggatcaaagtttccgggtagtcgggttttgtctttaaaaaggctatggagcatctga

FIG. 10 cont'd

SEQ ID NO:275
Arabidopsis thaliana RIE1 (RING-FINGER PROTEIN FOR EMBRYOGENESIS);
ubiquitin-protein ligase/ zinc ion binding AT2G01735 (RIE1) mRNA, complete cds
gi|42570265|ref|NM_179593.2|[42570265] NM_179593 tr|Q8GUU2|Q8GUU2_ARATH
RES protein
MSSYSSDSTAARDQHAPLLRPRHDGSFSSSSSSARPTALAVLLGRITGHRAPSML
VRETAARALEERRIDWGYSKPVVAADILWNAALVLASAVMLVGTVEERPNEPIR
VWICVYGLQCLFHVVLVWSEYWRRNSTRRARDLESYDHEDYNIEYDYEQDSDD
NSTTYSFVKRCESINTVISFIWWIIGFYWVVEGGDKLLGEAPNLYWLSVIFLAIDV
FFAVFCVVLACLVGIALCCCLPCIIALLYAVAGTEGVSEAELGVLPLYKFKAFHS
NEKNITGPGKMVPIPINGLCLATERTLLAEDADCCICLSSYEDGAELHALPCNHHF
HSTCIVKWLKMRATCPLCKYNILKGTTDQS SEQ ID NO:276
Arabidopsis thaliana RIE1 (RING-FINGER PROTEIN FOR EMBRYOGENESIS);
ubiquitin-protein ligase/ zinc ion binding AT2G01735 (RIE1) mRNA, complete cds
gi|42570265|ref|NM_179593.2|[42570265] NM_179593
Q8GUU2_ARATH AT2G01735
DCCICLSSYEDGAELHALPCNHHFHSTCIVKWLKMRATCPLCKYNIL SEQ ID NO:277
Arabidopsis thaliana RIE1 (RING-FINGER PROTEIN FOR EMBRYOGENESIS);
ubiquitin-protein ligase/ zinc ion binding AT2G01735 (RIE1) mRNA, complete cds
gi|42570265|ref|NM_179593.2|[42570265] NM_179593
Q8GUU2_ARATH AT2G01735
gattgttgcatatgtctgagttcatatgaggatggcgcagagcttcatgctcttccttgtaaccaccattttcattcgacttgtattgtga
aatggcttaagatgagagcaacatgccctctttgcaaatacaacattctt SEQ ID NO:278
Arabidopsis thaliana RIE1 (RING-FINGER PROTEIN FOR EMBRYOGENESIS);
ubiquitin-protein ligase/ zinc ion binding AT2G01735 (RIE1) mRNA, complete cds
gi|42570265|ref|NM_179593.2|[42570265] NM_179593
Q8GUU2_ARATH AT2G01735
gaagaatctcaattctcttcgttactaatgtcatcgtattcttcagattccacggcggcgcgtgatcaacatgcgcctctactccgtcc
acgacacgacggctctttttcttcttcttcttcatcagccagacctacagctctcgccgttctattaggacggatcaccggccaccga
gcaccgtcgatgctggttagagaaacagcggcgcgtgctctcgaggagagacgaatcgattggggttactcgaagcctgtagtt
gctgctgatatactatggaacgctgctttagttcttgcgtcagcggttatgcttgtcggtaccgttgaagaaagacctaatgaaccg
attagggtttggatctgtgtgtatgggttacagtgtttgttccatgtggttttggtttggtctgagtattggagaagaaactcaactcgta
gagctagggatttggagtcttatgatcatgaagattacaacattgagtatgattatgaacaagacagtgatgacaattcaacaactta
cagttttgtgaagagatgtgagtcgataaacacagtgatatcattcatatggtggataattggattctactgggttgttgaaggtggt
gataagcttttaggagaagctcctaatcttactggttatcggtgattttcctggcgattgacgtcttctttgctgtttctgtgttgttttg
gcttgccttgttggaatagctctttgttgctgtcttccttgcataattgctcttctttatgccgttgctggaacggaaggtgtatcggagg
cggagctcggtgttcttcccttgtacaaatttaaggctttccatagcaatgagaagaacattactggacctggtaaaatggttcctat
accgatcaatggcttatgcttagcaactgaaagaacactgcttgctgaggatgcggattgttgcatatgtctgagttcatatgagga
tggcgcagagcttcatgctcttccttgtaaccaccattttcattcgacttgtattgtgaaatggcttaagatgagagcaacatgccctc
tttgcaaatacaacattcttaaaggaaccactgatcaatcttgaagacaaaactcaaccaaccagagggaataagattctgcacat

FIG. 10 cont'd atagaaacagattccatttcctcaattaaaaagcttctgtatatatttatttacataactatcaaagtcatgtgtcttttgttaaaagcatcc
attttaaatgtaaaagatcacacttttacaaatgcccttttctatatttgcccatatttgagaatacagctgatgctcatagtcatagctca
aatcataagaaagttcacgaacagttcacttcattgccacactgtttgctgcaatccgcatcacttactgctgttacaagcccccttct
ctgcatatcaagaagcaaatccgaagcagcggccatgtttccctccttttcataagctctaatcaagagatcaaaaacagccgaat
caggacttattccgctattcaacatttcatcgaaaacttgtcttgcctcaaccatcaaaccccttgctagctagcccgtaaatcaatgta
gtataggctaacaaatcaagcaaaagaccttcctgaaccattctggttttttaacttaaacgcatccaccaaattcccttgcttacaca
aaccagctatccaagaagtgtacatgaacttatctggaacaagtccagcctctgagattttactaaacaatctctcaacttctataaa
gtctccttctttgcacaaagcatcaataagcacagtgtacataacatcattagctttctctatacagaaataaactatagcttcatgaa
agcctctctcaattaatttgtggtacatgttaaccgcagccttcatgcgtccggatttaaaatatgcattcatcattgtagtaaaaatca
ccatatcaggaactaaat cacttttctc catatcttct acaatctcag ttgcctcctt tagtttacca ttaccacaaa
ggcctgatat ga SEQ ID NO:279
COP1_ARATH P43254 At2g32950
"COP1, an Arabidopsis regulatory gene, encodes a protein with both a
zinc-binding motif and a G-beta homologous domain";
atggaagagatttcgacggatccggttgttccagcggtgaaacctgacccgagaacatcttcagttggtgaaggtgctaatcgtc
atgaaaatgacgacggaggaagcggcggttctgagattggagcaccggatctggataaagacttgctttgtccgatttgtatgca
gattattaaagatgctttcctcacggcttgtggtcatagtttctgctatatgtgtatcatcacacatcttaggaacaagagtgattgtcc
ctgttgtagccaacacctcaccaataatcagctttaccctaatttcttgctcgataagctattgaagaaaacttcagctcggcatgtgt
caaaaactgcatcgcccttggatcagtttcgggaagcactacaaaggggttgtgatgtgtcaattaaggaggttgataatcttctga
cacttcttgcggaaaggaagagaaaaatggaacaggaagaagctgagaggaacatgcagatacttttggacttttgcattgtcta
aggaagcaaaaagttgatgaactaaatgaggtgcaaactgatctccagtatattaaagaagatataaatgccgttgagagacata
gaatagatttataccgagctagggacagatattctgtaaagttgcggatgctcggagatgatccaagcacaagaaatgcatggcc
acatgagaagaaccagattggtttcaactccaattctctcagcataagaggaggaaattttgtaggcaattatcaaaacaaaaagg
tagaggggaaggcacaaggaagctctcatgggctaccaaagaaggatgcgctgagtgggtcagattcgcaaagtttgaatcag
tcaactgtctcaattgctagaaagaaacggattcatgctcagttcaatgatttacaagaatgttacctccaaaagcggcgtcagttg
gcagaccaaccaaatagtaaacaagaaaatgataagagtgtagtacggagggaaggctatagcaacggccttgcagattttcaa
tctgtgttgactaccttcactcgctacagtcgtctaagagttatagcagaaatccggcatggggatatatttcattcagccaacattgt
atcaagcatagagtttgatcgtgatgatgagctgtttgccactgctggtgtttctagatgtataaaggttttttgacttctcttcgtttgtaa
atgaaccagcagatatgcagtgtccgattgtggagatgtcaactcggtctaaacttagttgcttgagttggaataagcatgaaaaa
aatcacatagcaagcagtgattatgaaggaatagtaacagtgtgggatgtaactactaggcagagtcggatggagtatgaagag
cacgaaaaacgtgcctggagtgttgacttttcacgaacagaaccatcaatgcttgtatctggtagtgacgactgcaaggttaaagtt
tggtgcacgaggcaggaagcaagtgtgattaatattgatatgaaagcaaacatatgttgtgtcaagtacaatcctggctcaagcaa
ctacattgcggtcggatcagctgatcatcacatccattattacgatctaagaaacataagccaaccacttcatgtcttcagtggaca
caagaaagcagtttcctatgttaaattttttgtccaacaacgagctcgcttctgcgtccacagatagcacactacgcttatgggatgtc
aaagacaacttgccagttcgaacattcagaggacatactaacgagaagaactttgtgggtctcacagtgaacagcgagtatctcg
cctgtggaagcgagacaaacgaagtatatgtatatcacaaggaaatcacgagacccgtgacatcgcacagatttggatcgccag
acatggacgatgcagaggaagaggcaggttcctactttattagtgcggtttgctggaagagtgatagtcccacgatgttgactgc
gaatagtcaaggaaccatcaaagttctggtactcgctgcgtga SEQ ID NO:280
COP1_ARATH P43254 At2g32950
MEEISTDPVVPAVKPDPRTSSVGEGANRHENDDGGSGGSEIGAPDLDKDLL<u>CPIC
MQIIKDAFLTACGHSFCYMCIITHLRNKSDCPCCSQHLTNNQLYPNFLLDKLLKK
TSARHVSKTASPLDQFREALQRGCDVSIKEVDNLLTLLAERKRKMEQEEAERNM

FIG. 10 cont'd

QILLDFLHCLRKQKVDELNEVQTDLQYIKEDINAVERHRIDLYRARDRYSVKLR
MLGDDPSTRNAWPHEKNQIGFNSNSLSIRGGNFVGNYQNKKVEGKAQGSSHGL
PKKDALSGSDSQSLNQSTVSMARKKRIHAQFNDLQECYLQKRRQLADQPNSKQE
NDKSVVRREGYSNGLADFQSVLTTFTRYSRLRVIAEIRHGDIFHSANIVSSIEFDR
DDELFATAGVSRCIKVFDFSSVVNEPADMQCPIVEMSTRSKLSCLSWNKHEKNHI
ASSDYEGIVTVWDVTTRQSLMEYEEHEKRAWSVDFSRTEPSMLVSGSDDCKVK
VWCTRQEASVINIDMKANICCVKYNPGSSNYIAVGSADHHIHYYDLRNISQPLHV
FSGHKKAVSYVKFLSNNELASASTDSTLRLWDVKDNLPVRTFRGHTNEKNFVGL
TVNSEYLACGSETNEVYVYHKEITRPVTSHRFGSPDMDDAEEEAGSYFISAVCW
KSDSPTMLTANSQGTIKVLVLAA

SEQ ID NO:281
At2g32950
CPICMQIIKDAFLTACGHSFCYMCIITHLRNKSDCPCCS

SEQ ID NO:282
>embl|AX506870|AX506870 Sequence 1565 from Patent WO0216655 100% identity to
ACCESSION NM_101378 Arabidopsis thaliana RHA2A; protein binding / ubiquitin-
protein ligase/ zinc ion binding AT1G15100 (RHA2A) mRNA, complete cds
MGLQGQLSDVSSDSIPLMLLSLLAVFINHLRSFLLRLTSKSNPNLPVDDVSIASGL
ANIIVLADQLSLNRLFSYRCGDGGGGGSDCVVCLSKLKEGEEVRKLECRHVFHK
KCLEGWLHQFNFTCPLCRSALVSDDCVSKTQRSVGRDLISCFSLHDCVVCLSKLK
EGEEVRKLECRHVFHKKCLEGWLHQFNFTCPLCRSALV SEQ ID NO:283
>embl|AX506870|AX506870 Sequence 1565 from Patent WO0216655.
100% identity to ACCESSION NM_101378 Arabidopsis thaliana RHA2A; protein
binding / ubiquitin-protein ligase/ zinc ion binding AT1G15100 (RHA2A) mRNA,
complete cds.
DCVVCLSKLKEGEEVRKLECRHVFHKKCLEGWLHQFNFTCPLCRSAL SEQ ID NO:284
>embl|AX506870|AX506870 Sequence 1565 from Patent WO0216655.
100% identity to ACCESSION NM_101378 Arabidopsis thaliana RHA2A; protein
binding / ubiquitin-protein ligase/ zinc ion binding AT1G15100 (RHA2A) mRNA,
complete cds.
gattgtgttgtgtgtttgtcgaagttaaaggaaggtgaagaggtgaggaagctggaatgtcgacacgtgttccacaagaagtgttt
ggaaggatggcttcatcaattcaatttcacttgtcctctttgtagatctgctttg SEQ ID NO:285
>embl|AX506870|AX506870 Sequence 1565 from Patent WO0216655.
100% identity to ACCESSION NM_101378 Arabidopsis thaliana RHA2A; protein
binding / ubiquitin-protein ligase/ zinc ion binding AT1G15100 (RHA2A) mRNA,
complete cds.
atggggctacaaggtcagctaagtgacgtctcttccgattcaatccctcttatgctcctctctctcctcgccgtcttcatcaaccatct
ccgatctttcctcctccgtctcacctctaaatcaaatcctaatctccccgtagacgatgtctctatagcatcgggactagccaacata

FIG. 10 cont'd atcgttctcgccgatcagcttagtttgaatcggttattctcgtaccggtgcggtgacggaggtggtggcggctccgattgtgttgtgt
gtttgtcgaagttaaaggaaggtgaagaggtgaggaagctggaatgtcgacacgtgttccacaagaagtgtttggaaggatggc
ttcatcaattcaatttcacttgtcctctttgtagatctgctttggtttccgatgattgcgtctctaaaacgcagcgtagcgttgggaggg
atttgatctcgtgtttctctctccactga SEQ ID NO:286
>embl|AX506870|AX506870 Sequence 1565 from Patent WO0216655.
100% identity to ACCESSION NM_101378 Arabidopsis thaliana RHA2A; protein
binding / ubiquitin-protein ligase/ zinc ion binding AT1G15100 (RHA2A) mRNA,
complete cds.
DCVVCLSKLKEGEEVRKLECRHVFHKKCLEGWLHQFNFTCPLCRSAL SEQ ID NO:287
>embl|AX506870|AX506870 Sequence 1565 from Patent WO0216655.
100% identity to ACCESSION NM_101378 Arabidopsis thaliana RHA2A; protein
binding / ubiquitin-protein ligase/ zinc ion binding AT1G15100 (RHA2A) mRNA,
complete cds.
gattgtgttgtgtgtttgtcgaagttaaaggaaggtgaagaggtgaggaagctggaatgtcgacacgtgttccacaagaagtgttt
ggaaggatggcttcatcaattc aatttcacttgtcctctttgtagatctgctttg SEQ ID NO:288
*Cotton (Gossypium)*
cotton|TC38514 (Q6XNP9) Putative C3HC4-type RING zinc finger protein 62%
MGLSSLPSPSEGVLCILLVNTALSISIVKGIIRSILHVVGVHLPPPSSDYTENLSESFD
FHLNTPESYIEEFRSRTPTIHFGAVLCSCKRPQHDCQVCLTQFEPKSEINHLSCGHL
FHKVCLEKWLDYWNITCPLCRTPLLPEEEASCFW SEQ ID NO:289
*Cotton (Gossypium)*
cotton|TC38514 (Q6XNP9) Putative C3HC4-type RING zinc finger protein 76%
DCQVCLTQFEPKSEINHLSCGHLFHKVCLEKWLDYWNITCPLCRTPL SEQ ID NO:290
*Cotton (Gossypium)*
cotton|TC38514 (Q6XNP9) Putative C3HC4-type RING zinc finger protein NS
gactgtcaggtttgtctgactcagtttgagccaaaatccgagattaaccacttgtcgtgtggccatctctttcacaaggtgtgt
ttggaaaaatggttggattattggaatattacatgccctctttgcaggactcccttg SEQ ID NO:291
*Cotton (Gossypium)*
cotton|TC38514 (Q6XNP9) Putative C3HC4-type RING zinc finger protein
gggtctctcaagtcttccatctccatcagaaggagtgttatgtatactcttggtaaacacagctttatctatatctatagttaaaggcat
aatccgatcgatccttcacgttgtcggtgtccatctcccaccaccatcatcggattacactgaaaatctctcggaatcattcgatttcc
accttaatactcctgaaagttacatcgaggaattccggagtaggaccccaacaattcatttcggtgctgtttatgtagctgcaaacg
gcctcagcacgactgtcaggtttgtctgactcagtttgagccaaaatccgagattaaccacttgtcgtgtggccatctctttcacaag

FIG. 10 cont'd gtgtgtttggaaaaatggttggattattggaatattacatgccctctttgcaggactcccttgttgcctgaagaagaagcttcttgctttt
ggta SEQ ID NO:292
*Lotus japonicus*
L.japonicus|TC18128 (Q8S2S3) Putative RING zinc finger protein-like protein
60%
MGLSSLPAPSEGVLCVLLVNTVMSISIFKGIVRTILHIVGIHLSSPDASQNPPESFEV
HLSPSES SEQ ID NO:293
*Lotus japonicus*
L.japonicus|TC18128 (Q8S2S3) Putative RING zinc finger protein-like protein 76%
Atgggtctctcaagtctcccagcaccatctgaaggagtgttatgtgtgcttcttgtgaacactgtgatgtccatttccatattcaaag
gcattgtcagaacaattctacacattgttggtatccatctttcttcaccagatgcctcccaaaacccacctgaatcatttgaagtccat
ctcagcccctctgagagtt SEQ ID NO:294
*Potato (Solanum tuberosum)*
Potato|TC128001 (Q8S2S3) Putative RING zinc finger protein-like protein 55%
MGLSQYPTPADAGVLCVILVNTAISISIVKEMVRSILHVIGIHIASWDDYSIEGSLE
SFECRRSPSESYMEEFRSHTPAIRYDSICISNHAEKECSVCLTDFEPDAEINHLSCG
HVFHKHCLEKWLKYWNVTCPLCRNYMMSQEGEEDTCPM SEQ ID NO:295
*Potato (Solanum tuberosum)*
Potato|TC128001 (Q8S2S3) Putative RING zinc finger protein-like protein 72%
ECSVCLTDFEPDAEINHLSCGHVFHKHCLEKWLKYWNVTCPLCR SEQ ID NO:296
*Potato (Solanum tuberosum)*
Potato|TC128001 (Q8S2S3) Putative RING zinc finger protein-like protein NS
gagtgctccgtctgcctgacggattttgagcctgatgcagagataaaccatctctcatgtggccatgttttccacaagcattgtttag
agaagtggctcaagtactggaatgtaacttgtccactttgcaggaattac SEQ ID NO:297
*Potato (Solanum tuberosum)*
Potato|TC128001 (Q8S2S3) Putative RING zinc finger protein-like protein NS
gggcctctcacagtatccaactccagcagatgcaggagtgctctgtgttattctagtgaacacagccatatccatctccattgtcaa
ggagatggtccgatcgatccttcatgtgattggcatccatattgcatcatgggacgattattccattgaaggctccttggagtcgttt
gaatgtcgcagaagcccatcagagtcatatatggaggaattcagaagccatacccctgcaattcgttatgattcaatctgtatctct
aaccatgctgagaaagagtgctccgtctgcctgacggattttgagcctgatgcagagataaaccatctctcatgtggccatgttttc
cacaagcattgtttagagaagtggctcaagtactggaatgtaacttgtccactttgcaggaattacatgatgtctcaagaaggcgaa
gaagatacttgtcctatgtg

SEQ ID NO:298

FIG. 10 cont'd

Tomato (Lycopersicon esculentum)
Tomato|TC157728 (Q8S2S3) Putative RING zinc finger protein-like protein 54%
MGLSQYPTPADAGVLCVILVNTAISISIVKEMVRSILHVIGIHIASWDDYSIEGSLD
SFECRRSPSESYMEEFRSHTPAIRYDSICISNHAEKECSVCLTDFEPDAQINHLSCG
HVFHKHCLEKWLKYWNVTCPLCRNYMMSQEGEEDTCPM SEQ ID NO:299
Tomato (Lycopersicon esculentum)
Tomato|TC157728 (Q8S2S3) Putative RING zinc finger protein-like protein 70%
ECSVCLTDFEPDAQINHLSCGHVFHKHCLEKWLKYWNVTCPLCRNY SEQ ID NO:300
Tomato (Lycopersicon esculentum)
Tomato|TC157728 (Q8S2S3) Putative RING zinc finger protein-like protein NS
gagtgctcagtctgcctgacggattttgagcctgacgcacagataaaccatctctcatgtggccatgttttccacaagcattgctta
gagaagtggctcaagtactggaatgtaacttgtccactttgcaggaattac SEQ ID NO:301
Tomato (Lycopersicon esculentum)
Tomato|TC157728 (Q8S2S3) Putative RING zinc finger protein-like protein NS
Gggactctcacagtatccaactccagcagatgcaggagtgctctgtgttattctagtgaacacagccatatccatctccattgtcaa
ggagatggtccgatcgatccttcatgtgattggcatccacattgcatcatgggacgattattccatcgaaggctccttggactcgttt
gaatgtcgcagaagcccatcagagtcatatatggaggaattcagaagccatacccctgcaattcgttatgattccatctgtatctct
aaccacgctgagaaagagtgctcagtctgcctgacggattttgagcctgacgcacagataaaccatctctcatgtggccatgtttt
ccacaagcattgcttagagaagtggctcaagtactggaatgtaacttgtccactttgcaggaattacatgatgtctcaagaaggcg
aagaagatacttgtcctatgtg SEQ ID NO:302
*Soybean (Glycine max)*
Soybean|TC230215 probable RING zinc finger protein [imported] - Arabidopsis thaliana
MGLSSLPAPSEGVLCVLLVNTALSISIFKGIVRTILQIVGIRVSSLSPSPDISRNPPEP
L
EFNLSPSEGFIEEFRSRTPTLRFGSMCGSKQPQHECCCVCLTKFEPESEINCLSCGH
IFH
KVCMEKWLDYWNITCPLCRTSLMPEDDASCFW SEQ ID NO:303
*Soybean (Glycine max)*
Soybean|TC230215 probable RING zinc finger protein [imported] - Arabidopsis thaliana
ECCCVCLTKFEPESEINCLSCGHIFHKVCMEKWLDYWNITCPLCRTS SEQ ID NO:304
*Soybean (Glycine max)*
Soybean|TC230215 probable RING zinc finger protein [imported] - Arabidopsis thaliana
gagtgctcagtctgcctgacggattttgagcctgacgcacagataaaccatctctcatgtggccatgttttccacaagcattgctta
gagaagtggctcaagtactggaatgtaacttgtccactttgcaggaattac

FIG. 10 cont'd

SEQ ID NO:305
*Soybean (Glycine max)*
Soybean|TC230215 probable RING zinc finger protein [imported] - Arabidopsis thaliana
gggcctgtcaagtctcccagcaccatctgaaggagtgttatgtgtgcttcttgtaaacactgccttgtctatatccatattcaaaggc
attgttaggacaattctacaaattgtcggtatccgcgtttcgtcgttgtctccttcaccagacatctcccgaaacccacctgagccatt
agaattcaacctcagcccctcggagggtttcattgaagagttcagaagcaggacaccaacacttaggtttggcagcatgtgtggc
agtaaacaacctcaacatgaatgttgttgtgtgtgtctcacaaagtttgaaccagaatctgagataaactgtttatcatgtggccatat
ttttcacaaagtgtgcatggagaagtggttggactattggaacattacatgcccactttgcaggacttc
cttgatgcctgaagatgatgcatcttgcttttggta SEQ ID NO:365
Brassica napus cultivar="Tapidor", EM: DU101305 JBnY037E11F
ECSVCLSNFEEDSEINKLKCGHLFHKTCLEKWIDYWNITCPLCRTPL SEQ ID NO:366
Brassica napus cultivar="Tapidor", EM: DU101305 JBnY037E11F
KMGLSSLPGPSEGMLCVILVNTALSISIFKGILRSVLQLIGIRLCPSSAAAAAAASS
ENQTSETFDFRVCQPESFLEEFRNRTPTVKFESLCKCKKQADNECSVCLSNFEEDS
EINKLKCGHLFHKTCLEKWIDYWNITCPLCRTPLVVVAADDQLVSSNVW SEQ ID NO:367
Brassica napus cultivar="Tapidor", EM: DU101305 JBnY037E11F
BAC library JBnY Brassica napus genomic clone
acatctctct gagaagaaca aagatctgat cggcttccga gaattacata ccttttgaaa catccaaaag agttgaaaga
tgggtctatc aagccttcct ggtccatcag aaggaatgct atgcgtgata ttagttaaca cagcattgtc aatctccatc
ttcaaaggca ttctcaggtc agtgcttcag ctaataggaa tccgtctctg tccttcttca gcagcagcag cagcagctgc
atcttcagag aatcaaactt cagagacttt tgatttccgg gtctgccagc ctgagagttt ccttgaggaa ttcaggaaca
ggaccccccac agtgaagttt gagagcttgt gcaagtgcaa gaaacaggcg gacaacgagt gttctgtatg cctgtcgaat
ttcgaagagg attcagagat caacaagcta aaatgtggcc atttgtttca caaaacatgc ttggagaaat ggatagacta
ctggaacatc acttgcccac tctgtaggac tcctcttgtt gttgtcgcag cagacgacca gctggtttcc tctaatgttt
ggtgactact ttctttgta tagagttttc ctgggggttg ggtgtgtctg ttgttgtgta cagctactac tacttttac
tctgaaatta ggctgcgtca cggttgattc tttatcagat tcagaccgga gatgggagta ttctgttgtg catatttttgt
gagctgttta tgtatgtagt agacccatgt gtaatggaag ctcttgtttg aacatagtct tgatgaatct atctatgtgt
gtattaagag ctcaggcttt gtcccaaaaa aaaaaaaca SEQ ID NO:368
CD834580 Brassica napus (rape) cultivar="jet neuf", At2g04240
ECSVCLSKFEEDSEINKAKCGHLFHKTCLEKWIDYWNITCPLCRTPL SEQ ID NO:369
CD834580 Brassica napus (rape) cultivar="jet neuf", At2g04240
KMGLSSLPGPSEGMLCVILVNTALSISIFKGILRSVLQLIGIRLSPSSAAAAAAS
SENQTSDSFDFRVCQPESFLEEFRNRTPTVKFESLCKCKKQADNECSVCLSKFEED
SEINKAKCGHLFHKTCLEKWIDYWNITCPLCRTPLVVVAADDQLVSIMFG

FIG. 10 cont'd

SEQ ID NO:370
CD834580 Brassica napus (rape) cultivar="jet neuf", At2g04240
gatccatctctcacttctcagattcccatcactattttcaacagaaactcaaaactttataataaagattcaatctttcgtttaattggtga
tcatcgcctctcatacttgtctccagatcacatctctctgagaagaacaaagatctgatcggcttccgagaattacatattgtttgaaa
catccaaaagagttgaaagatgggtctatcaagccttcctggtccatcagaaggaatgctatgcgtgatattagttaacacagcatt
gtcaatctccatcttcaaaggcattctcaggtcagtgcttcagctaataggaatccgcctctctccttcttcagcagcagcagcagct
gcatcttcagagaatcaaacttcagattcttttgatttccgggtctgccagcctgagagtttccttgaggaattcaggaacaggacc
cccacagtgaagtttgagagcttgtgcaagtgcaagaaacaggcggacaacgagtgttctgtatgcctgtcgaaattcgaagag
gattcagagatcaacaaggctaaatgtggccatttgtttcacaaaacatgcttggagaaatggatagactactggaacatcacttg
cccactctgtaggactcctcttgttgttgtcgcagcagacgaccagctggtttctataatgtttggtga SEQ ID NO:371
AM059482 Brassica oleracea var. alboglabra (Chinese kale)
ECSVCLSKFEEDSEINKLKCGHLFHKTCLEKWIDYWNITCPLCRTPLVV SEQ ID NO:372
AM059482 Brassica oleracea var. alboglabra (Chinese kale)
KMGLSSLPGPSEGMLCVILVNTALSISIFKGILRSVLQLIGIRLSPSSAAAAAASSEN
QTSDSFDFRVCQPESFLEEFRNRTPTVKFESLCKCKKQADNECSVCLSKFEEDSEI
NKLKCGHL FHKTCLEKWIDYWNITCPLCRTPLVV SEQ ID NO:373
AM059482 Brassica oleracea var. alboglabra (Chinese kale)
tcccatcactattttcaacagaaactcaaaactttataataaagattcaatctttcgtttaattggtgatcatcgcctctcatacttgtctc
cagatcacatctctctgagaagaacaaagatctgatcggcttccgagaattacatattgtttgaaacatccaaaagagttgaaagat
gggtctatcaagccttcctggtccatcagaaggaatgctatgcgtgatattagttaacacagcattgtcaatctccatcttcaaaggc
attctcaggtcagtgcttcagctaataggaatccgcctctctccttcttcagcagcagcagcagctgcatcttcagagaatcaaactt
cagattcttttgatttccgggtctgccagcctgagagtttccttgaggaattcaggaacaggacccccacagtgaagtttgagagct
tgtgcaagtgcaagaaacaggcggacaacgagtgttctgtatgcctgtcgaaattcgaagaggattcagagatcaacaagctaa
aatgtggccatttgtttcacaaaacatgcttggagaaatggatagactactggaacatcacttgcccactctgtaggactcctcttgt
tgttgtcgcagca SEQ ID NO:374
Chinese cabbage root library Brassica rapa subsp. pekinensis partial cDNA
KMGLSSLPGPSEGMLCIILVNAALSISMFKGIVRSVLHLVGIRLSPSSVASSEIQLR
DFRFPDLPA SEQ ID NO:375
Chinese cabbage root library Brassica rapa subsp. pekinensis partial cDNA
cccacgcgtccgcacttttcagattctccgaaacaccacacactaccttcaccagaggaaaacacacncaaagggtattaagg
aaaattatatctttcaatcagtgaccatcatcgcctttcatactttgactccagatcacatcccttgagaagaacaaagatataaaga
caaattacatatagttcgaaacatctaaagagttgaaagatgggtctatcgagtcttcctggtccatcagaaggaatgctatgcatta
tattagtcaacgcagcattatcaatctccatgttcaaaggcattgtcagatcagtgcttcacctagtaggaatccgtctctctccttctt
cagtagcatcttcagagattcaacttcgagactttcgatttccggatctgccagcctgagagtttcttgagaatcaggacagactcc
acgctaagtcgagagttgtgcaaaacagag

FIG. 11

SEQ ID NO: 376
35S promoter sequence:
aacatggtggagcacgacactctcgtctactccaagaatatcaaagatacagtctcagaagaccaaagggctattgagactttca
acaaagggtaatatcgggaaacctcctcggattccattgcccagctatctgtcacttcatcaaaaggacagtagaaaaggaaggt
ggcacctacaaatgccatcattgcgataaaggaaaggctatcgttcaagatgcctctgccgacagtggtcccaaagatggaccc
ccacccacgaggagcatcgtggaaaaagaagacgttccaaccacgtcttcaaagcaagtggattgatgtgatatctccactgac
gtaagggatgacgcacaatcccactatccttcgca agacccttcctctatataaggaagttcatttcatttggaga SEQ ID NO: 377
B-Box motif
C-X2-H-X7-C-X7-C-X2-C-H-X2-H SEQ ID NO: 378
AtUBC8; Arabidopsis thaliana CIP8 (COP1-INTERACTING PROTEIN 8); protein
binding / zinc ion binding NM_125891
MSDAPSSSPDATASHWCYHCNKRVVVETLDDFVVCCECNKGFVESIQPTPAAYS
SPAPPQPLSPDLNVEDSSIGSHFLQMLRLLAHAPSQRSPPRHLDVLSYEDDFFRLE
LNSRNEIDDDEDEDEDDGDEEEEDEEENLTVNDEEDEEDDLRRRNRFPLTTTQSR
TGRNRILDWAEILMGIEDNSIEFRMESDRYAGNPADYIDDAAGYEALLQNLAEG
DGGGGGGRRGAPPAAKSAIEALETFEVSSSEGEMVMVCAVCKDGMVMGETGK
KLPCGHCYHGDCIVPWLGTRNSCPVCRFQLETDDAEYEEERKKRTSTVSDSAAA
SSSSSTSRY SEQ ID NO: 379
AtUBC8; Arabidopsis thaliana CIP8 (COP1-INTERACTING PROTEIN 8); protein
binding / zinc ion binding NM_125891
    1 acagagagac cttttctttt tattttctcc atcctcttaa tcggcttatc ggatccgaat
   61 ccggacccga aagcctgaaa acccgacgat taattgcacg atgtccgatg ctccgtcgtc
  121 ttccccggat gccacggcgt cgcactggtg ctatcactgc aacaaacgcg tcgtcgttga
  181 aaccttagat gactttgtcg tgtgctgcga atgtaacaaa ggtttcgtcg agtcaattca
  241 accgactccc gccgcttatt catcgccggc gccaccgcag ccactttccc cagatctgaa
  301 tgtagaagac tccagtattg gctcgcattt cctccagatg ctccgcttgt tagcccacgc
  361 gccttctcag cgttcaccac cacgacacct tgatgtttta tcttacgaag atgatttctt
  421 caggttggag ctcaatagta gaaacgaaat cgacgatgac gaagacgaag atgaagatga
  481 tggagatgaa gaagaagagg atgaggaaga gaatttaacc gtcaacgacg aagaagacga
  541 agaagatgat ctgaggagga gaaatcgttt tcctctcacg acgacgcagt cgagaaccgg
  601 aagaaacaga attctcgatt gggctgagat tttgatggga atcgaagaca attcgattga
  661 gttccgtatg gaatcagatc gatacgcagg aaatccggct gattacatag acgatgcagc
  721 cggatacgaa gctttgctac agaatttagc agaaggagat ggtggtggtg gcggaggaag
  781 gagaggcgca ccaccggctg cgaaatcggc aatagaggca ttggagactt tcgaggttag
  841 ttcttcggag ggagagatgg ttatggtttg tgctgtgtgt aaagatggaa tggtgatggg
  901 agaaactggt aagaagttac cgtgtggaca ttgttaccac ggagattgta ttgtgccatg
  961 gttaggaaca aggaactctt gtcctgtctg tagattccag cttgagactg atgatgctga
 1021 atatgaggaa gagaggaaaa aaagaacttc taccgtgtca gattctgctg ctgcttcttc
 1081 ttcttcttca acttctcgtt actgaagtgg aggaaatgcc cccatttgtt gttactttg
 1141 ttgttactct ttctctttag attaatcttt gcttagtctc tcaacactat ttggttggtt

FIG. 11 cont'd

SEQ ID NO: 376
35S promoter sequence:
aacatggtggagcacgacactctcgtctactccaagaatatcaaagatacagtctcagaagaccaaagggctattgagactttca
acaaagggtaatatcgggaaacctcctcggattccattgcccagctatctgtcacttcatcaaaaggacagtagaaaaggaaggt
ggcacctacaaatgccatcattgcgataaaggaaaggctatcgttcaagatgcctctgccgacagtggtcccaaagatggaccc
ccacccacgaggagcatcgtggaaaaagaagacgttccaaccacgtcttcaaagcaagtggattgatgtgatatctccactgac
gtaagggatgacgcacaatcccactatccttcgca agacccttcctctatataaggaagttcatttcatttggaga SEQ ID NO: 377
B-Box motif
C-X2-H-X7-C-X7-C-X2-C-H-X2-H SEQ ID NO: 378
AtUBC8; Arabidopsis thaliana CIP8 (COP1-INTERACTING PROTEIN 8); protein
binding / zinc ion binding NM_125891
MSDAPSSSPDATASHWCYHCNKRVVVETLDDFVVCCECNKGFVESIQPTPAAYS
SPAPPQPLSPDLNVEDSSIGSHFLQMLRLLAHAPSQRSPPRHLDVLSYEDDFFRLE
LNSRNEIDDDEDEDEDDGDEEEEDEEENLTVNDEEDEEDDLRRRNRFPLTTTQSR
TGRNRILDWAEILMGIEDNSIEFRMESDRYAGNPADYIDDAAGYEALLQNLAEG
DGGGGGGRRGAPPAAKSAIEALETFEVSSSEGEMVMVCAVCKDGMVMGETGK
KLPCGHCYHGDCIVPWLGTRNSCPVCRFQLETDDAEYEEERKKRTSTVSDSAAA
SSSSSTSRY SEQ ID NO: 379
AtUBC8; Arabidopsis thaliana CIP8 (COP1-INTERACTING PROTEIN 8); protein
binding / zinc ion binding NM_125891
    1 acagagagac cttttctttt tatttctcc atcctcttaa tcggcttatc ggatccgaat
   61 ccggacccga aagcctgaaa acccgacgat taattgcacg atgtccgatg ctccgtcgtc
  121 ttccccggat gccacggcgt cgcactggtg ctatcactgc aacaaacgcg tcgtcgttga
  181 aaccttagat gactttgtcg tgtgctgcga atgtaacaaa ggtttcgtcg agtcaattca
  241 accgactccc gccgcttatt catcgccggc gccaccgcag ccactttccc cagatctgaa
  301 tgtagaagac tccagtattg gctcgcattt cctccagatg ctccgcttgt tagcccacgc
  361 gccttctcag cgttcaccac cacgacacct tgatgtttta tcttacgaag atgatttctt
  421 caggttggag ctcaatagta gaaacgaaat cgacgatgac gaagacgaag atgaagatga
  481 tggagatgaa gaagaagagg atgaggaaga gaatttaacc gtcaacgacg aagaagacga
  541 agaagatgat ctgaggagga gaaatcgttt tcctctcacg acgacgcagt cgagaaccgg
  601 aagaaacaga attctcgatt gggctgagat tttgatggga atcgaagaca attcgattga
  661 gttccgtatg gaatcagatc gatacgcagg aaatccggct gattacatag acgatgcagc
  721 cggatacgaa gctttgctac agaatttagc agaaggagat ggtggtggtg gcggaggaag
  781 gagaggcgca ccaccggctg cgaaatcggc aatagaggca ttggagactt tcgaggttag
  841 ttcttcggag ggagagatgg ttatggtttg tgctgtgtgt aaagatggaa tggtgatggg
  901 agaaactggt aagaagttac cgtgtggaca ttgttaccac ggagattgta ttgtgccatg
  961 gttaggaaca aggaactctt gtcctgtctg tagattccag cttgagactg atgatgctga
 1021 atatgaggaa gagaggaaaa aaagaacttc taccgtgtca gattctgctg ctgcttcttc
 1081 ttcttcttca acttctcgtt actgaagtgg aggaaatgcc cccatttgtt gttacttttg
 1141 ttgttactct ttctctttag attaatcttt gcttagtctc tcaacactat ttggttggtt

FIG. 11 cont'd

```
1201 gcatgttgca tcaaagaagc gagaaaacag agaacaaaaa aaaaaaatcc ggctccaaaa
1261 agacaattgt tatttgtaag tgtgttgtat ctttggccta aacaatccca tagtggtttc
1321 tttgattctc agttgttcat aaagtttgcc gaaacaaaaa ggttcctggg tttaggagaa
1381 acggttacag gacttcgtga gccttcccga agtacctgtt tatgaacggg gactgcacag
1441 agaccaacaa acttatatca gattttggca ataatattca gagttccatt gacaaactaa
1501 gttggatttg ttttgtacct tctcaattcc tgcagtgtgg ggtgtgtctg gtgaa
```

SEQ ID NO: 380
AtTLP9; phosphoric diester hydrolase/ transcription factor At3g06380; NM_111513
MTFRSLLQEMRSRPHRVVHAAASTANSSDPFSWSELPEELLREILIRVETVDGGD
WPSRRNVVACAGVCRSWRILTKEIVAVPEFSSKLTFPISLKQSGPRDSLVQCFIKR
NRNTQSYHLYLGLTTSLTDNGKFLLAASKLKRATCTDYIISLRSDDISKRSNAYLG
RMRSNFLGTKFTVFDGSQTGAAKMQKSRSSNFIKVSPRVPQGSYPIAHISYELNV
LGSRGPRRMRCIMDTIPMSIVESRGVVASTSISSFSSRSSPVFRSHSKPLRSNSASCS
DSGNNLGDPPLVLSNKAPRWHEQLRCWCLNFHGRVTVASVKNFQLVAVSDCEA
GQTSERIILQFGKVGKDMFTMDYGYPISAFQAFAICLSSFETRIACE SEQ ID NO: 381
AtTLP9; phosphoric diester hydrolase/ transcription factor At3g06380; NM_111513
```
   1 atccttatcc tatcagcgaa taatagaaga aaaagtacaa attctctaat aaagcggtaa
  61 aagcgtttaa gaagatgaag aagaaaaagg aaacgcctcc aaatcaccat tatttgtccga
 121 atcttcttcg cgtctctcac caacaccact tctcctacct tcttcttcac accaaatgat
 181 tctctcgtat aatattcatc aaacccagat catgttttca tcatcaatca tctcttaaac
 241 tcctctatag atctccaccgc atgacgttcc gaagtttact ccaggaaatg cggtctaggc
 301 cacaccgtgt agttcacgcc gccgcctcaa ccgctaatag ttcagaccct ttcagctggt
 361 cggagctccc ggaggagctg cttagagaaa tcctgattag ggttgagact gttgacggcg
 421 gcgattggcc gtcgcggcga aacgtggtgg cttgtgccgg cgtttgtcgt agctggagga
 481 ttctcaccaa ggagattgta gctgttcctg aattctcctc taaattgact ttccctatct
 541 ccctcaagca gtctggtcca agagattctc tagttcaatg ctttataaaa cgtaatcgaa
 601 atactcaatc gtatcatctc tatctcggat taactacctc tttgacggat aacgggaagt
 661 ttcttcttgc tgcttctaag ctgaagcgcg caacttgcac tgattacatc atctctttgc
 721 gttcagacga tatctcaaag agaagcaacg cgtatcttgg gagaatgaga tcgaacttcc
 781 ttggaacaaa attcacggtc tttgatggta gtcagaccgg agcagcgaag atgcagaaga
 841 gccgctcttc taatttcatc aaagtttcac ctagagttcc tcagggaagt taccccatcg
 901 ctcacatttc atacgagtta aacgtcttag gctctcgggg accgagaaga atgcgttgca
 961 tcatggatac aataccatg agcatcgtgg agtcgcgagg agtagtagct tcaacatcca
1021 taagctcttt ttccagtcgg tcatcaccag tctttaggtc tcactcaaaa ccattgcgca
1081 gtaatagtgc atcatgtagc gactcaggca acaacctggg agatccacca ttggtgctga
1141 gcaacaaagc tccacggtgg catgagcagt tacgttgctg gtgcttaaat ttccatggtc
1201 gagtcacagt ggcttcggtt aagaactttc agcttgtggc agttagtgac tgtgaagcag
1261 ggcagacatc tgagaggatc atactccagt ttgggaaagt tgggaaggac atgtttacca
1321 tggattatgg atatccgatt tctgcgtttc aagcgtttgc tatctgcctg agcagttttg
1381 aaaccagaat tgcctgtgaa taatgaagag actaaccta aatcacctcc gtgtgctcgt
1441 tgttgtggtc tgtagatggt gtagtacttg tccaaaatct caggaacgtt aatagctttc
1501 tctggattct ttctgacaat tcaaatctat ctgttgtatt tatttgtctt tcatgcaaag
1561 aagcgtacca gaaataggct acgattacgt tttttt

FIG. 11 cont'd

SEQ ID NO: 382
AtNCED3; (9-cis-epoxycarotenoid dioxygenase; At3g14440 Iuchi et al., 2001
9-cis-epoxycarotenoid dioxygenase [Arabidopsis thaliana] AY056255
MASFTATAAVSGRWLGGNHTQPPLSSSQSSDLSYCSSLPMASRV
TRKLNVSSALHTPPALHFPKQSSNSPAIVVKPKAKESNTKQMNLFQRAAAAALD
AAEGFLVSHEKLHPLPKTADPSVQIAGNFAPVNEQPVRRNLPVVGKLPDSIKGVY
VRNGANPLHEPVTGHHFFDGDGMVHAVKFEHGSASYACRFTQTNRFVQERQLG
RPVFPKAIGELHGHTGIARLMLFYARAAAGIVDPAHGTGVANAGLVYFNGRLLA
MSEDDLPYQVQITPNGDLKTVGRFDFDGQLESTMIAHPKVDPESGELFALSYDV
VSKPYLKYFRFSPDGTKSPDVEIQLDQPTMMHDFAITENFVVVPDQQVVFKLPE
MILGGSPVVYDKNKVARFGILDKYAEDSSNIKWIDAPDCFCFHLWNAWEEPETD
EVVVIGSCMTPPDSIFNESDENLKSVLSEIRLNLKTGESTRRPIISNEDQQVNLEAG
MVNRNMLGRKTKFAYLALAEPWPKVSGFAKVDLTTGEVKKHLYGDNRYGGEP
LFLPGEGGEEDEGYILCFVHDEKTWKSELQIVNAVSLEVEATVKLPSRVPYGFHG
TFIGADDLAKQVV"

SEQ ID NO: 383
*AtNCED3;* (9-cis-epoxycarotenoid dioxygenase; At3g14440 Iuchi *et al.*, 2001
9-cis-epoxycarotenoid dioxygenase [Arabidopsis thaliana] AY056255
1 aaaccaactc tctcttctct cttctctcct ctcttctaca agaagaaaaa aaacagagcc
   61 tttacacatc tcaaaatcga acttacttta accaccaaat actgattgaa cacacttgaa
  121 aaatggcttc tttcacggca acggctgcgg tttctgggag atggcttggt ggcaatcata
  181 ctcagccgcc attatcgtct tctcaaagct ccgacttgag ttattgtagc tccttaccta
  241 tggccagtcg tgtcacacgt aagctcaatg tttcatctgc gcttcacact cctccagctc
  301 ttcatttccc taagcaatca tcaaactctc ccgccattgt tgttaagccc aaagccaaag
  361 aatccaacac taaacagatg aatttgttcc agagagcggc ggcggcagcg ttggacgcgg
  421 cggagggttt ccttgtcagc cacgagaagc tacacccgct tcctaaaacg gctgatccta
  481 gtgttcagat cgccggaaat tttgctccgg tgaatgaaca gcccgtccgg cgtaatcttc
  541 cggtggtcgg aaaacttccc gattccatca aaggagtgta tgtgcgcaac ggagctaacc
  601 cacttcacga gccggtgaca ggtcaccact tcttcgacgg agacggtatg gttcacgccg
  661 tcaaattcga acacggttca gctagctacg cttgccggtt tactcagact aaccggtttg
  721 ttcaggaacg tcaattgggt cgaccggttt tccccaaagc catcggtgag cttcacggcc
  781 acaccggtat tgcccgactc atgctattct acgccagagc tgcagccggt atagtcgacc
  841 cggcacacgg aaccggtgta gctaacgccg gtttggtcta tttcaatggc cggttattgg
  901 ctatgtcgga ggatgattta cctaccaag ttcagatcac tcccaatgga gatttaaaaa
  961 ccgttggtcg gttcgatttt gatggacaat tagaatccac aatgattgcc cacccgaaag
 1021 tcgacccgga atccggtgaa ctcttcgctt taagctacga cgtcgtttca aagccttacc
 1081 taaaatactt ccgattctca ccggacggaa ctaaatcacc ggacgtcgag attcagcttg
 1141 atcagccaac gatgatgcac gatttcgcga ttacagaaa cttcgtcgtc gtacctgacc
 1201 agcaagtcgt tttcaagctg ccggagatga tcctcggtgg gtctccggtg gtttacgaca
 1261 agaacaaggt cgcaagattc gggattttag acaaatacgc cgaagattca tcgaacatta
 1321 agtggattga tgctccagat tgcttctgct tccatctctg gaacgcttgg gaagagccag
 1381 aaacagatga agtcgtcgtg atagggtcct gtatgactcc accagactca attttcaacg
 1441 agtctgacga gaatctcaag agtgtcctgt ctgaaatccg cctgaatctc aaaaccggtg
 1501 aatcaactcg ccgtccgatc atctccaacg aagatcaaca agtcaacctc gaagcaggga

FIG. 11 cont'd

```
1561 tggtcaacag aaacatgctc ggccgtaaaa ccaaattcgc ttacttggct ttagccgagc
1621 cgtggcctaa agtctcagga ttcgctaaag ttgatctcac tactggagaa gttaagaaac
1681 atctttacgg cgataaccgt tacggaggag agcctctgtt tctccccgga gaaggaggag
1741 aggaagacga aggatacatc ctctgtttcg ttcacgacga gaagacatgg aaatcggagt
1801 tacagatagt taacgccgtt agcttagagg ttgaagcaac ggttaaactt ccgtcaaggg
1861 ttccgtacgg atttcacggt acattcatcg gagccgatga tttggcgaag caggtcgtgt
1921 gagttcttat gtgtaaatac gcacaaaata catatacgtg atgaagaagc ttctagaagg
1981 aaaagagaga gcgagattta ccagtgggat gctctgcata tacgtccccg gaatctgctc
2041 ctctgttttt ttttttttg ctctgtttct tgtttgttgt ttcttttggg gtgcggtttg
2101 ctagttccct ttttttgggg gtcaatctag aaatctgaaa gattttgagg gaccagcttg
2161 tagcttttgg gctgtagggt agcctagccg ttcgagctca gctggtttct gttattcttt
2221 cacttattgt tcatcgtaat gagaagtata taaaatatta aacaacaaag atatgtttgt
2281 atatgtgcat gaattaagga acattttttt ttccgaaaaa aaaaaaaaaa a
```

SEQ ID NO: 384
Pinus taeda (loblolly pine) similar to Arabidopsis thaliana sequence At3g14440
*AtNCED3;* (9-cis-epoxycarotenoid dioxygenase;

```
   1 acgatttcga caagcagctc aactcgtcca tgatagcgca cccgaagatc gatcccgaga
  61 ccaaggagtt cttcgctctg agctacgata tcatcaagaa gccttatctc aagtacttca
 121 tggtccgccc cgatggaact aagagccccg atgtcacaat ttcgctgaag gagcctacaa
 181 tgatgcatga tttcgccata acaaagaatt atgtcgtcgt tcctgatcag caagttgttt
 241 tccggctcca agaaatgatc agaggcggtt ctccagttat tcacaacaaa gaaaaagtcc
 301 cgcgcttcgg gcttctgccc aaatatgctt ctgacgagag tgagctgaaa tggatcgagg
 361 tcccggattg cttctgcttt catctcnnnn ncgnnnnnnn nanaagagaa gacgnnnntg
 421 tcgtcatcgg ctcctgtatg accccgccgg acgccatttt caacgaatct gacagcgcgc
 481 tgcggagtgt tctgtcggaa attcggctca atctcaaaac cggcttgtcc accagacgcg
 541 agannacgcc ga
```

SEQ ID NO: 385
*RD29a/COR78/LTI78;* At5g52310; Yamaguchi-Shinozaki and Shinozaki, 1993
responsive to desiccation stress29a/COLD REGULATED 78/ low temperature78
MDQTEEPPLNTHQQHPEEVEHHENGATKMFRKVKARAKKFKNSLTKHGQSNEH
EQDHDLVEEDDDDDELEPEVIDAPGVTGKPRETNVPASEEIIPPGTKVFPVVSSDY
TKPTESVPVQEASYGHDAPAHSVRTTFTSDKEEKRDVPIHHPLSELSDREESRETH
HESLNTPVSLLSGTEDVTSTFAPSGDDEYLDGQRKVNVETPITLEEESAVSDYLSG
VSNYQSKVTDPTKEETGGVPEIAESFGNMEVTDESPDQKPGQFERDLSTRSKEFK
EFDQDFDSVLGKDSPAKFPGESGVVFPVGFGDESGAELEKDFPTRSHDFDMKTET
GMDTNSPSRSHEFDLKTESGNDKNSPMGFGSESGAELEKEFDQKNDSGRNEYSP
ESDGGLGAPLGGNFPVRSHELDLKNESDIDKDVPTGFDGEPDFLAKGRPGYGEA
SEEDKFPARSDDVEVETELGRDPKTETLDQFSPELSHPKERDEFKESRDDFEETRD
EKTEEPKQSTYTEKFASMLGYSGEIPVGDQTQVAGTVDEKLTPVNEKDQETESA
VTTKLPISGGGSGVEEQRGEDKSVSGRDYVAEKLTTEEEDKAFSDMVAEKLQIG
GEEEKKETTTKEVEKISTEKAASEEGEAVEEEVKGGGGMVGRIKGWFGGGATDE
VKPESPHSVEEAPKSSGWFGGGATEEVKPKSPHSVEESPQSLGSTVVPVQKEL

SEQ ID NO: 386

FIG. 11 cont'd

*RD29a/COR78/LTI78*; At5g52310; Yamaguchi-Shinozaki and Shinozaki, 1993
responsive to desiccation stress29a/COLD REGULATED 78/ low temperature78

```
   1 acaaatatgc aaactagaaa acaatcatca ggaataaagg gtttgattac ttctattgga
  61 aagaaaaaaa tctttggaaa atggatcaaa cagaggaacc accactcaac acacaccagc
 121 agcacccaga agaagttgaa catcatgaga atggtgcgac taagatgttt aggaaagtaa
 181 aggctagagc taagaagttc aagaacagtc tcactaaaca tggacaaagc aatgagcatg
 241 agcaagatca tgatttggtt gaagaagatg atgatgatga cgagctagaa cctgaagtga
 301 tcgatgcacc aggcgtaaca ggtaaaccta gagaaactaa tgttccagca tcggaggaaa
 361 ttattccacc agggacaaag gtgtttcctg tcgtgtcttc cgattacacc aaacccactg
 421 aatctgtacc agtacaagag gcctcttacg gacacgatgc accggctcat tctgtaagga
 481 cgacgtttac atcggacaag gaagagaaaa gagatgtacc gattcatcat cctctgtccg
 541 aattgtcaga cagagaagag agtagagaga ctcatcatga gtcattgaac actccggtct
 601 ctctgctttc tggaacagag gatgtaacga gtacgtttgc tccaagtggt gatgatgaat
 661 atcttgatgg tcaacggaag gtcaacgtcg agacccgat aacgttggag gaagagtcgg
 721 ctgtttcaga ctatcttagt ggtgtatcta attatcagtc caaagttact gatcccacca
 781 aagaagaaac tggaggagta ccggagattg ctgagtcttt tggtaatatg gaagtgactg
 841 atgagtctcc tgatcagaag ccaggacaat ttgaaagaga cttgtcgacg agaagcaaag
 901 aattcaaaga gtttgatcag gactttgact ctgttctcgg taaggattcg ccggcgaaat
 961 ttccaggtga atcaggagtt gtttttccgg tgggctttgg tgacgagtca ggagctgagc
1021 tggaaaaaga ttttccgacg agaagtcatg attttgatat gaagactgaa actggaatgg
1081 acacgaattc tccatcaaga agccatgaat ttgatctgaa gactgaatct ggaaacgaca
1141 agaattctcc gatgggcttt ggtagtgaat caggagctga gctggaaaaa gaatttgatc
1201 agaagaacga ttctggaaga aacgagtatt cgccggaatc tgacggcggt ttaggagctc
1261 cgttgggagg aaattttccg gtgagaagtc atgagttgga tctgaagaac gaatctgata
1321 tcgacaagga tgtgccgacg ggatttgacg gagaaccaga ttttctggcg aagggaagac
1381 ctggatacgg tgaggcatca gaagaggata aatttccggc gagaagtgat gatgtggaag
1441 tagagactga gctgggaaga gacccaaaga cggagactct tgatcaattc tcaccggaac
1501 tttctcatcc taaagaaaga gatgagttta aggagtccag agatgatttt gaggagacga
1561 gagatgagaa aacagaggag ccaaaacaga gcacttacac agagaagttt gcttcaatgc
1621 taggttactc cggagaaatt ccggtgggag atcaaactca gtggcggga actgttgatg
1681 agaagttgac tccggtcaat gagaaggatc aagaaacaga gtctgccgtg acgacgaagt
1741 tacctatctc cggaggtgga agtggagtag aggagcaacg aggggaagat aaaagtgtgt
1801 cgggtagaga ttatgtggcg gagaaactga caactgaaga agaagacaaa gccttttctg
1861 atatggttgc cgagaaactt cagattggag gagaagaaga gaagaaggaa acgacgacaa
1921 aggaagtgga agatctct accgagaagg cagcatcgga ggagggtgag gcggtggaag
1981 aggaagtgaa aggaggagga ggaatggttg ggaggattaa aggatggttc ggtggtggtg
2041 cgactgatga ggtgaagcca gaatcgccac attctgttga agaggctcca aaatcatctg
2101 gctggtttgg tggtggtgcg acggaggagg tgaagccaaa atcgcctcat tccgttgaag
2161 agtctccaca atcacttggc tccactgttg ttccggtgca gaaggagctt taagaatatg
2221 agaactgaga ttttcaagtt tcactttgga tgtttatgtg tgttttgttt gacgtctttg
2281 atgtattatg gtataattcc ttgttttgtgt gaaaaaagga catttggtta ataaattgtt
2341 cggcttttgga ttaagaagtt cctccatacc agctactagg tctaaagtgg gtaaaatcat
2401 tggatttatt cccttcaaag ttcttagaat tattcacagg attttacatt atgagctagt
2461 agtgtgactt gttgaggtgt tgtctctatc gttaaagttc
```

SEQ ID NO: 387

FIG. 11 cont'd

ARABIDOPSIS SERINE/THREONINE KINASE 1 ASK1 (Arabidopsis Skp1-like 1)
NM_100969 Arabidopsis thaliana ASK1 (ARABIDOPSIS SERINE/THREONINE
KINASE 1); ATP binding / kinase/ protein kinase/ protein serine/threonine kinase/
protein-ty> AT1G10940 (ASK1) transcript variant AT1G10940.1
MDKYELVKDIGAGNFGVARLMKVKNSKELVAMKYIERGPKIDENVAREIINHRS
LRHPNIIRFKEVVLTPTHLAIAMEYAAGGELFERICSAGRFSEDEARYFFQQLISGV
SYCHAMQICHRDLKLENTLLDGSPAPRLKICDFGYSKSSLLHSRPKSTVGTPAYIA
PEVLSRREYDGKMADVWSCGVTLYVMLVGAYPFEDQEDPKNFRKTIQKIMAVQ
YKIPDYVHISQDCKNLLSRIFVANSLKRITIAEIKKHSWFLKNLPRELTETAQAAYF
KKENPTFSLQTVEEIMKIVADAKTPPPVSRSIGGFGWGGNGDADGKEEDAEDVE
EEEEEVEEEEDDEDEYDKTVKEVHASGEVRIS SEQ ID NO: 388
NM_100969 Arabidopsis thaliana ASK1 (ARABIDOPSIS SERINE/THREONINE
KINASE 1); ATP binding / kinase/ protein kinase/ protein serine/threonine kinase/
protein-ty> AT1G10940 (ASK1) transcript variant AT1G10940.1

```
   1 ggagtttgtt taggcagggg agattcttct tcattctcat cattatttct ctattaattt
  61 caccccaaaa aagaaaaaag aaaaattcca acaagaaaaa aaaaagaaaa agaaagttga
 121 ttcttcgctt aggcttgaaa tctctccaat ccaaatctca aattaacctt ccatcgtcat
 181 ctctttccct tttttttcc cactttcttt gcgaatcgcg agatctcgga atcgcatcct
 241 tgattttggg atactgtttt tttttttttt aatcttgttt cattttcacg tgaaattctt
 301 agctgctaga actggacttg aatttcaacg agaattttgg agatttttt tttgtttggg
 361 tttttccttt ctgttttgtg tgtttggaat tagggttgtc gagcgagaat ggacaagtac
 421 gagctggtga agacataggt gctgggaat tttggagttg ccaggctcat gaaggtcaaa
 481 aactctaagg aacttgttgc catgaagtac atcgagcgtg gtcctaagat tgatgagaat
 541 gtggcaagag agatcattaa tcacagatca cttcgccatc cgaatataat ccggttcaag
 601 gaggtggtgt tgactccaac ccatcttgcc attgccatgg aatatgctgc tggtggtgaa
 661 ctattcgagc gtatatgcag tgctggaaga tttagtgagg atgaggcgag atatttcttc
 721 cagcagctta tatcaggtgt tagctattgc catgctatgc aaatatgcca tagagatctg
 781 aagctcgaga atacgctctt ggatggaagt cctgctccac gtctgaaaat ctgtgatttt
 841 ggttattcca agtcctctct gctgcactct aggcccaaat caacagttgg aactccagca
 901 tatattgcac ctgaggtcct ttctcgaaga gaatatgatg gcaagatggc tgatgtatgg
 961 tcttgtggtg tgactcttta tgtcatgctg gttggagcat acccatttga agaccaggaa
1021 gacccccaaga acttcaggaa aacaatacaa aaaataatgg ctgtccagta caagatcccg
1081 gactacgtcc atatctcaca ggattgtaaa aatctccttt cccgtatatt tgtcgccaat
1141 tcactcaaga ggatcaccat tgcagaaatc aagaaacatt catggttcct aaagaatttg
1201 ccaagggaac tcacagagac agctcaagct gcatatttca agaaagagaa cccaaccttc
1261 tcccttcaga ccgttgaaga gatcatgaag atagtggctg acgccaaaac accgcctcct
1321 gtttcccgat ccatcggagg ttttggctgg ggaggaaatg gggatgcaga tggaaaagag
1381 gaagatgcag aagacgtgga ggaggaagag gaggaggtgg aagaagagga agacgatgag
1441 gatgaatacg ataagactgt aaaggaagta cacgcaagtg gagaagtgag aataagttga
1501 tattttggtt tttggtctgt gtaagaaaga agtcgtcgtt ggtttgttga aactgaaaag
1561 tctctgttct cgtgtttgcc tttacaatgc tttggctaag gttttggttc tggttttgga
1621 gatttgtaaa atttgcagta taagatgaac aaacagagag gttgatgatg agaatgagtc
1681 ctttgctacg catggtacta tgaacattgt gacctccaat aaatatttt gtaaattaga
1741 ttttattttc cg
```

FIG. 11 cont'd

SEQ ID NO: 389
NM_001035944
Arabidopsis thaliana ASK1 (ARABIDOPSIS SERINE/THREONINE KINASE 1); ATP binding / kinase/ protein kinase/ protein serine/threonine kinase/ protein-ty> AT1G10940 (ASK1) transcript variant AT1G10940.2 mRNA, complete cds.
MDKYELVKDIGAGNFGVARLMKVKNSKELVAMKYIERGPKIDENVAREIINHRS
LRHPNIIRFKEVVLTPTHLAIAMEYAAGGELFERICSAGRFSEDEARYFFQQLISGV
SYCHAMQICHRDLKLENTLLDGSPAPRLKICDFGYSKSSLLHSRPKSTVGTPAYIA
PEVLSRREYDGKMADVWSCGVTLYVMLVGAYPFEDQEDPKNFRKTIQKIMAVQ
YKIPDYVHISQDCKNLLSRIFVANSLKRITIAEIKKHSWFLKNLPRELTETAQAAYF
KKENPTFSLQTVEEIMKIVADAKTPPPVSRSIGGFGWGGNGDADGKEEDAEDVE
EEEEEVEEEEDDEDEYDKTVKEVHASGEVRISMASKRILKELKDLQKDPPTSCSA
GPVAEDMFHWQATIMGPAESPYSGGVFLVTIHFPPDYPFKPPKVAFRTKVFHPNI
NSNGSICLDILKEQWSPALTISKVLLSICSLLTDPNPDDPLVPEIAHMYKTDRAKY
EATARNWTQKYAMG"

SEQ ID NO: 390
NM_001035944
Arabidopsis thaliana ASK1 (ARABIDOPSIS SERINE/THREONINE KINASE 1);
ATP binding / kinase/ protein kinase/ protein serine/threonine/kinase/ protein-ty>
AT1G10940 (ASK1) transcript variant AT1G10940.2
mRNA, complete cds.
1 ggagtttgtt taggcagggg agattcttct tcattctcat cattatttct ctattaattt
61 caccccaaaa aagaaaaaag aaaaattcca acaagaaaaa aaaaagaaaa agaaagttga
121 ttcttcgctt aggcttgaaa tctctccaat ccaaatctca aattaacctt ccatcgtcat
181 ctctttccct ttttttttcc cactttcttt gcgaatcgcg agatctcgga atcgcatcct
241 tgattttggg atactgtttt ttttttttt aatcttgttt cattttcacg tgaaattctt
301 agctgctaga actggacttg aatttcaacg agaattttgg agatttttt tttgtttggg
361 ttttcccttt ctgttttgtg tgtttggaat tagggttgtc gagcgagaat ggacaagtac
421 gagctggtga agacatagg tgctgggaat tttggagttg ccaggctcat gaaggtcaaa
481 aactctaagg aacttgttgc catgaagtac atcgagcgtg gtcctaagat tgatgagaat
541 gtggcaagag agatcattaa tcacagatca cttcgccatc cgaatataat ccggttcaag
601 gaggtggtgt tgactccaac ccatcttgcc attgccatgg aatatgctgc tggtggtgaa
661 ctattcgagc gtatatgcag tgctggaaga tttagtgagg atgaggcgag atatttcttc
721 cagcagctta tatcaggtgt tagctattgc catgctatgc aaatatgcca tagagatctg
781 aagctcgaga atacgctctt ggatggaagt cctgctccac gtctgaaaat ctgtgatttt
841 ggttattcca gtcctctct gctgcactct aggcccaaat caacagttgg aactccagca
901 tatattgcac ctgaggtcct ttctcgaaga gaatatgatg gcaagatggc tgatgtatgg
961 tcttgtggtg tgactctta tgtcatgctg gttggagcat acccatttga agaccaggaa
1021 gaccccaaga acttcaggaa aacaatacaa aaaataatgg ctgtccagta caagatcccg
1081 gactacgtcc atatctcaca ggattgtaaa aatctcctt cccgtatatt tgtcgccaat
1141 tcactcaaga ggatcaccat tgcagaaatc aagaaacatt catggttcct aaagaatttg
1201 ccaagggaac tcacagagac agctcaagct gcatatttca agaaagagaa cccaaccttc
1261 tcccttcaga ccgttgaaga gatcatgaag atagtggctg acgccaaaac accgcctcct
1321 gtttcccgat ccatcggagg ttttggctgg ggaggaaatg gggatgcaga tggaaaagag

FIG. 11 cont'd 1381 gaagatgcag aagacgtgga ggaggaagag gaggaggtgg aagaagagga agacgatgag
1441 gatgaatacg ataagactgt aaaggaagta cacgcaagtg gagaagtgag aataagttga
1501 tattttggtt tttggtctgt gtaagaaaga agtcgtcgtt ggtttgttga aactgaaaag
1561 tctctgttct cgtgtttgcc tttacaatgc tttggctaag gttttggttc tggttttgga
1621 gatttgtaaa atttgcagta taagatgaac aaacagagag gttgatgatg agaatgagtc
1681 ctttgctacg catggtacta tgaacattgt gacctccaat aaatattttt gtaaattaga
1741 ttttattttc cgaaaagatt catgtatttg att SEQ ID NO: 391
GenBank Accession NM_111513; locus_tag="AT3G06380"Arabidopsis thaliana phosphoric diester hydrolase/ transcription factor AT3G06380 mRNA, complete cds, F-box family protein / tubby family protein
MTFRSLLQEMRSRPHRVVHAAASTANSSDPFSWSELPEELLREILIRVETVDGGD
WPSRRNVVACAGVCRSWRILTKEIVAVPEFSSKLTFPISLKQSGPRDSLVQCFIKR
NRNTQSYHLYLGLTTSLTDNGKFLLAASKLKRATCTDYIISLRSDDISKRSNAYLG
RMRSNFLGTKFTVFDGSQTGAAKMQKSRSSNFIKVSPRVPQGSYPIAHISYELNV
LGSRGPRRMRCIMDTIPMSIVESRGVVASTSISSFSSRSSPVFRSHSKPLRSNSASCS
DSGNNLGDPPLVLSNKAPRWHEQLRCWCLNFHGRVTVASVKNFQLVAVSDCEA
GQTSERIILQFGKVGKDMFTMDYGYPISAFQAFAICLSSFETRIACE SEQ ID NO: 392
GenBank Accession NM_111513; *Arabidopsis thaliana* phosphoric diester hydrolase/ transcription factor AT3G06380 mRNA, complete cds/locus_tag="AT3G06380" "F-box family protein / tubby family protein,
1 atccttatcc tatcagcgaa taatagaaga aaaagtacaa attctctaat aaagcggtaa
61 aagcgtttaa gaagatgaag aagaaaaagg aaacgcctcc aaatcaccat tattgtccga
121 atcttcttcg cgtctctcac caacaccact tctcctacct tcttcttcac accaaatgat
181 tctctcgtat aatattcatc aaacccagat catgttttca tcatcaatca tctcttaaac
241 tcctctatag atctcaccgc atgacgttcc gaagtttact ccaggaaatg cggtctaggc
301 cacaccgtgt agttcacgcc gccgcctcaa ccgctaatag ttcagaccct ttcagctggt
361 cggagctccc ggaggagctg cttagagaaa tcctgattag ggttgagact gttgacggcg
421 gcgattggcc gtcgcggcga aacgtggtgg cttgtgccgg cgtttgtcgt agctggagga
481 ttctcaccaa ggagattgta gctgttcctg aattctcctc taaattgact ttccctatct
541 ccctcaagca gtctggtcca agagattctc tagttcaatg ctttataaaa cgtaatcgaa
601 atactcaatc gtatcatctc tatctcggat taactacctc tttgacggat aacgggaagt
661 ttcttcttgc tgcttctaag ctgaagcgcg caacttgcac tgattacatc atctctttgc
721 gttcagacga tatctcaaag agaagcaacg cgtatcttgg gagaatgaga tcgaacttcc
781 ttggaacaaa attcacggtc tttgatggta gtcagaccgg agcagcgaag atgcagaaga
841 gccgctcttc taatttcatc aaagtttcac ctagagttcc tcagggaagt taccccatcg
901 ctcacatttc atacgagtta aacgtcttag gctctcgggg accgagaaga atgcgttgca
961 tcatggatac aataccctatg agcatcgtgg agtcgcgagg agtagtagct tcaacatcca
1021 taagctcttt ttccagtcgg tcatcaccag tctttaggtc tcactcaaaa ccattgcgca
1081 gtaatagtgc atcatgtagc gactcaggca acaacctggg agatccacca ttggtgctga
1141 gcaacaaagc tccacggtgg catgagcagt tacgttgctg gtgcttaaat tccatggtc
1201 gagtcacagt ggcttcggtt aagaactttc agcttgtggc agttagtgac tgtgaagcag
1261 ggcagacatc tgagaggatc atactccagt ttgggaaagt tgggaaggac atgtttacca

FIG. 11 cont'd 1321 tggattatgg atatccgatt tctgcgtttc aagcgtttgc tatctgcctg agcagttttg
1381 aaaccagaat tgcctgtgaa taatgaagag actaaccta aatcaccctcc gtgtgctcgt
1441 tgttgtggtc tgtagatggt gtagtacttg tccaaaatct caggaacgtt aatagctttc
1501 tctggattct ttctgacaat tcaaatctat ctgttgtatt tatttgtctt tcatgcaaag
1561 aagcgtacca gaaataggct acgattacgt tttttt SEQ ID NO: 393
AT1G10940; Arabidopsis thaliana Ser/Thr kinase (At1g10940) mRNA, complete cds.
MDKYELVKDIGAGNFGVARLMKVKNSKELVAMKYIERGPKIDENVAREIINHRS
LRHPNIIRFKEVVLTPTHLAIAMEYAAGGELFERICSAGRFSEDEARYFFQQLISGV
SYCHAMQICHRDLKLENTLLDGSPAPRLKICDFGYSKSSLLHSRPKSTVGTPAYIA
PEVLSRREYDGKMADVWSCGVTLYVMLVGAYPFEDQEDPKNFRKTIQKIMAVQ
YKIPDYVHISQDCKNLLSRIFVANSLKRITIAEIKKHSWFLKNLPRELTETAQAAYF
KKENPTFSLQTVEEIMKIVADAKTPPPVSRSIGGFGWGGNGDADGKEEDAEDVE
EEEEEVEEEEDDEDEYDKTVKEVHASGEVRIS SEQ ID NO: 394
AT1G10940; Arabidopsis thaliana Ser/Thr kinase (At1g10940) mRNA, complete cds.
1 gagtttgttt aggcagggga gattcttctt cattctcatc attatttctc tattaatttc
61 accccaaaaa agaaaaaaga aaaattccaa caagaaaaaa aaaagaaaaa gaaagttgat
121 tcttcgctta ggcttgaaat ctctccaatc caaatctcaa attaaccttc catcgtcatc
181 tctttcccctt tttttttccc actttctttg cgaatcgcga gatctcggaa tcgcatcctt
241 gattttggga tactgttttt tttttttta atcttgtttc attttcacgt gaaattctta
301 gctgctagaa ctggacttga atttcaacga gaattttgga gatttttttt ttgtttgggt
361 ttttccttc tgttttgtgt gtttggaatt agggttgtcg agcgagaatg gacaagtacg
421 agctggtgaa agacataggt gctgggaatt ttggagttgc caggctcatg aaggtcaaaa
481 actctaagga acttgttgcc atgaagtaca tcgagcgtgg tcctaagatt gatgagaatg
541 tggcaagaga gatcattaat cacagatcac ttcgccatcc gaatataatc cggttcaagg
601 aggtggtgtt gactccaacc catcttgcca ttgccatgga atatgctgct ggtggtgaac
661 tattcgagcg tatatgcagt gctggaagat ttagtgagga tgaggcgaga tatttcttcc
721 agcagcttat atcaggtgtt agctattgcc atgctatgca aatatgccat agagatctga
781 agctcgagaa tacgctcttg gatggaagtc ctgctccacg tctgaaaatc tgtgattttg
841 gttattccaa gtcctctctg ctgcactcta ggcccaaatc aacagttgga actccagcat
901 atattgcacc tgaggtcctt tctcgaagag aatatgatgg caagatggct gatgtatggt
961 cttgtggtgt gactctttat gtcatgctgg ttggagcata cccatttgaa gaccaggaag
1021 accccaagaa cttcaggaaa acaatacaaa aaataatggc tgtccagtac aagatcccgg
1081 actacgtcca tatctcacag gattgtaaaa atctcctttc ccgtatattt gtcgccaatt
1141 cactcaagag gatcaccatt gcagaaatca gaaacattc atggttccta aagaatttgc
1201 caagggaact cacagagaca gctcaagctg catatttcaa gaaagagaac ccaaccttct
1261 cccttcagac cgttgaagag atcatgaaga tagtggctga cgccaaaaca ccgcctcctg
1321 tttcccgatc catcggaggt tttggctggg gaggaaatgg ggatgcagat ggaaaagagg
1381 aagatgcaga agacgtggag gaggaagagg aggaggtgga agaagaggaa gacgatgagg
1441 atgaatacga taagactgta aaggaagtac acgcaagtgg agaagtgaga ataagttgat
1501 attttggttt tggtctgtg taagaaagaa gtcgtcgttg gtttgttgaa actgaaaagt
1561 ctctgttctc gtgtttgcct ttacaatgct ttggctaagg ttttggttct ggttttggag
1621 atttgtaaaa tttgcagtat aagatgaaca aacagagagg ttgatgatga gaatgagtcc

FIG. 11 cont'd 1681 tttgctacgc atggtactat gaacattgtg acctccaata aatattttg taaattagat
1741 tttattttc SEQ ID NO: 395
GenBank Accession AF325009
Arabidopsis thaliana AT5g41700 (AT5g41700/MBK23_24) mRNA, complete cds.
"ubiquitin-conjugating enzyme"/gene="AT5g41700/MBK23_24"
MASKRILKELKDLQKDPPTSCSAGPVAEDMFHWQATIMGPAESPYSGGVFLVTI
HFPPDYPFKPPKVAFRTKVFHPNINSNGSICLDILKEQWSPALTISKVLLSICSLLTD
PNPDDPLVPEIAHMYKTDRAKYEATARNWTQKYAMG SEQ ID NO: 396
GenBank Accession AF325009
Arabidopsis thaliana AT5g41700 (AT5g41700/MBK23_24) mRNA, complete cds.
"ubiquitin-conjugating enzyme"/gene="AT5g41700/MBK23_24"
    1 caatcatctg caggagtgaa tcgcaaaacc aaatttggag gattctttct gagggggtttc
   61 tcagtgagaa aatggcttcg aaacggatct tgaaggagct gaaggatctc cagaaagacc
  121 ctccaacctc ctgcagtgca ggtccagttg ctgaagacat gtttcattgg caagctacaa
  181 ttatgggtcc tgcagagagt ccgtattcag gcggtgtgtt tctcgttacc attcacttcc
  241 ctccggacta tccattcaaa ccaccaaagg ttgcatttag gacgaaggtg tttcaccta
  301 atatcaacag caacggaagc atttgccttg acattttgaa agaacaatgg agccctgccc
  361 tcaccatttc caaggtgttg ctctcgatat gttcgctgtt aacagatcca aatccagatg
  421 acccttggt accagagatt gcacacatgt acaaaaccga cagagccaaa tacgaggcta
  481 ctgcaagaaa ctggactcag aagtatgcca tgggctaaac aaagattcgt atgcttcagc
  541 acctgtttat gttttcatgt ctgtttcttt cttcttcttg ttaaactt aataaaaatg
  601 tctaaaatat caactttttc gtctgtacta tatgtttta tgggttttat tatcatcatc
  661 tttatct SEQ ID NO: 397
ribulose-bisphosphate carboxylase (RBCS) At1g67090
transcript variant 1 NM_202369.1
MASSMLSSATMVASPAQATMVAPFNGLKSSAAFPATRKANNDITSITSNGGRVN
CMQVWPPIGKKKFETLSYLPDLTDSELAKEVDYLIRNKWIPCVEFELEHGFVYRE
HGNSPGYYDGRYWTMWKLPLFGCTDSAQVLKEVEECKKEYPNAFIRIIGFDNTR
QVQCISFIAYKPPSFTG SEQ ID NO: 398
ribulose-bisphosphate carboxylase (RBCS) At1g67090
transcript variant 1 NM_202369.1
    1 tcagtcacac aaagagtaaa gaagaacaat ggcttcctct atgctctctt ccgctactat
   61 ggttgcctct ccggctcagg ccactatggt cgctccttc aacggactta gtcctccgc
  121 tgccttccca gccacccgca aggctaacaa cgacattact tccatcacaa gcaacggcgg
  181 aagagttaac tgcatgcagg tgtggcctcc gattggaaag aagaagtttg agactctctc
  241 ttaccttcct gaccttaccg attccgaatt ggctaaggaa gttgactacc ttatccgcaa
  301 caagtggatt ccttgtgttg aattcgacac ggatttgtgt accgtgagca cggtaactca

FIG. 11 cont'd

```
361 cccggatact atgatggacg gtactggaca atgtggaagc ttcccttgtt cggttgcacc
421 gactccgctc aagtgttgaa ggaagtggaa gagtgcaaga aggagtaccc caatgccttc
481 attaggatca tcggattcga caacacccgt caagtccagt gcatcagttt cattgcctac
541 aagccaccaa gcttcaccgg ttaatttccc tttgcttttg tgtaaacctc aaaactttat
601 cccccatctt tgattttatc ccttgttttt ctgctttttt cttctttctt gggttttaat
661 ttccggactt aacgtttgtt ttccggtttg cgagacatat tctatcggat tctcaactgt
721 ctgatgaaat aaatatgtaa tgttctataa gtctttcaat ttgatatgca tatcaacaaa
781 aagaaaatag gacaatgcgg ctacaaatat gaaatttaca agtttaagaa ccatgagtcg
841 ctaaagaaat cattaagaaa attagtttca c
```

SEQ ID NO: 399
ribulose-bisphosphate carboxylase (RBCS) At1g67090
transcript variant 2 NM_105379.2
MASSMLSSATMVASPAQATMVAPFNGLKSSAAFPATRKANNDITSITSNGGRVN
CMQVWPPIGKKKFETLSYLPDLTDSELAKEVDYLIRNKWIPCVEFDTDLCTVSTV
THPDTMMDGTGQCGSFPCSVAPTPLKC SEQ ID NO: 400
ribulose-bisphosphate carboxylase (RBCS) At1g67090
transcript variant 2 NM_105379.2

```
  1 tcagtcacac aaagagtaaa gaagaacaat ggcttcctct atgctctctt ccgctactat
 61 ggttgcctct ccggctcagg ccactatggt cgctcctttc aacggactta agtcctccgc
121 tgccttccca gccacccgca aggctaacaa cgacattact tccatcacaa gcaacggcgg
181 aagagttaac tgcatgcagg tgtggcctcc gattggaaag aagaagtttg agactctctc
241 ttaccttcct gaccttaccg attccgaatt ggctaaggaa gttgactacc ttatccgcaa
301 caagtggatt ccttgtgttg aattcgagtt ggagcacgga tttgtgtacc gtgagcacgg
361 taactcaccc ggatactatg atggacggta ctggacaatg tggaagcttc ccttgttcgg
421 ttgcaccgac tccgctcaag tgttgaagga agtggaagag tgcaagaagg agtaccccaa
481 tgccttcatt aggatcatcg gattcgacaa cacccgtcaa gtccagtgca tcagtttcat
541 tgcctacaag ccaccaagct tcaccggtta atttcccttt gcttttgtgt aaacctcaaa
601 actttatccc ccatctttga ttttatccct tgttttttctg cttttttctt cttctttggg
661 ttttaatttc cggacttaac gtttgttttc cggtttgcga gacatattct atcggattct
721 caactgtctg atgaaataaa tatgtaatgt tctataagtc tttcaatttg atatgcatat
781 caacaaaaag aaaataggac aatgcggcta caaatatgaa atttacaagt ttaagaacca
841 tgagtcgcta aagaaatcat taagaaaatt agtttcac
```

SEQ ID NO: 401
AY052401; Q940X7 RING-box protein 1a (RBX1a-At) (At-Rbx1;1) (RBX1-2) Locus
Tag: AT5G20570; Synonyms: F7C8.160, F7C8_160, HRT1, ROC1
MATLDSDVTMIPAGEASSSVAASSSNKKAKRFEIKKWSAVALWAWDIVVDNCA
ICRNHIMDLCIECQANQASATSEECTVAWGVCNHAFHFHCISRWLKTRQVCPLD
NSE WEFQKYGH

SEQ ID NO: 402
AY052401; Q940X7

FIG. 11 cont'd

RING-box protein 1a (RBX1a-At) (At-Rbx1;1) (RBX1-2) Locus Tag: AT5G20570;
Synonyms: F7C8.160, F7C8_160, HRT1, ROC1
1 atggcgactc tagactccga cgttaccatg attcctgccg agaagccctc cagcagcgta
61 gccgcgtcgt cttccaacaa gaaagctaag cgattcgaaa ttaagaagtg gagcgccgtt
121 gctctctggg cttgggatat cgttgttgac aactgtgcga tctgcagaaa ccacatcatg
181 gatctttgta tcgagtgtca ggctaatcag gccagtgcca caagtgaaga gtgcactgta
241 gcttgggggg tttgcaatca cgccttccac tttcactgca tcagcagatg gctaaagact
301 cgtcaagttt gtccattgga taacagtgag tgggagtttc agaaatatgg tcactaa SEQ ID NO: 403
Q9M2B0 Putative RING-box protein 1b (RBX1b-At) (At-Rbx1;2) (RBX1-1)
NM_114151 AT3G42830
MASLNSDVIM GESSSISVPS SSSKNSKRFE LKKWSAVALW AWDIVVDNCA 50
ICRNHIMDLC IECLANQASA TSEECTVAWG VCNHAFHFHC ISRWLKTRQV 100
CPLDVCEWEF QKYGH SEQ ID NO: 404
Putative RING-box protein 1b (RBX1b-At) (At-Rbx1;2) (RBX1-1) NM_114151
AT3G42830
1 atggcttctc tcaactccga cgttatcatg ggtgaatcct cctccatctc cgtaccttca
61 tcttcgtcca agaactcgaa acgatttgaa ttaaagaagt ggagtgctgt cgctctctgg
121 gcttgggata tcgttgttga taactgcgca atttgtagga atcacatcat ggatctctgt
181 attgaatgtc tagctaatca agctagtgcc actagtgagg aatgcactgt tgcttggggg
241 gtttgcaacc acgcctttca cttccactgt atcagcgagt ggctcaaaac tcgtcaagtg
301 tgtccactag atgtctgcga gtgggaattc agaaatatg gtcactaa SEQ ID NO: 405
EL5 E3 ubiquitin ligase EL5 AB045120
Oryza sativa (japonica cultivar-group)
MVRGVEQGGPAMDESSSSSSPSPVSAPAGQAAMTAGGIATVAAVLIVFAALTLA
FVLLQCYCDERRRAVTTTSTSGRGRRPRPRRRSGSGGDGGTGGGVDPEVLRSLP
VTVYSRSTAAAAKEEEEEDDDGVECAVCLAELEDGEEARFLPRCGHGFHAECV
DMWLGSHSTCPLCRLTVVVPPPPLPPVPPEPPASYTVSLPASVLLGLSDHGAGAV
TMTAEGRSTLVIEIPESAASTTPRDAAARSSPSLARLRSLRRLWSFGRQGAAGSTS
SCSCATGGDNDDGDVEHGVSVTVAIRAVEAATPARPPEAEAGARTAAAHVRN SEQ ID NO: 406
EL5 E3 ubiquitin ligase EL5 AB045120
Oryza sativa (japonica cultivar-group)
1 gtcgattatt atggtgcggg gtgtcgagca gggcggcccc gccatggacg agtcttcgtc
61 gtcgtcgtcg ccgtcgccgg tgtccgcgcc tgcagggcag gcagccatga cggccggcgg
121 catcgccacc gtggcggccg tgctcatcgt cttcgcggcg ctcacgctcg ccttcgtcct
181 gctccagtgc tactgcgacg agcggcgcgc cgccgtgacg acgacgtcga cgagcgggcg
241 cgggcggcgg ccgcggccgc ggcggcgctc tgggagcggc ggggacggtg gaacgggagg

FIG. 11 cont'd

```
 301 aggggtcgac ccggaggtgc tccggtcgct gccggtcacg gtgtacagcc gcagcacggc
 361 ggcggcggcg gcgaaggagg aggaggagga ggacgacgac ggcgtcgagt gcgcggtgtg
 421 cctcgcggag ctcgaggacg gcgaggaggc caggttcctc ccccggtgcg gccacggctt
 481 ccacgccgag tgcgtcgaca tgtggctcgg ctcccactcc acctgcccgc tctgccgcct
 541 caccgtcgtc gtgccgccgc cgcctcttcc tcccgtcccg ccggagccgc cggcgagcta
 601 caccgtgagc ctcccggcga gcgtcctgct cggcctgtcc gaccatggcg ccggcgcggt
 661 gaccatgaca gcggagggcc gcagcacgct ggtgatcgag atccccgaat ccgcggcttc
 721 gacgaccccg cgcgacgcgg cggcgaggtc gtcgccgagc ttggcgcggc tgaggtcact
 781 gagaaggctc tggagcttcg ggcggcaagg ggcggcgggg tcgacgtcgt catgctcctg
 841 cgccaccgga ggagacaacg acgacggcga cgtcgagcac ggtgtcagcg tcaccgtcgc
 901 catccgcgcc gtggaggcgg caacgccggc acggccaccg gaggccgagg ccggtgcaag
 961 aaccgccgcc gcgcatgtcc ggaattgacg gcggcgaggt cgtcaagtat tataaggcga
1021 tctccctgta catatcggta gaaccgaact ggaatcgcca ttaattccta cgattttaga
1081 aaatatcaat ttcattttta agattagaaa catttaagta gaaattattt gttcatcagt
1141 caagtagcaa agagaaatgt atggatggca gtgagaagca tccctctccg tatgttccaa
1201 aaaaaaaaaa aaaaaa
```

SEQ ID NO: 407
Arabidopsis thaliana RMA1 mRNA AB008518
MALDQSFEDAALLGELYGEGAFCFKSKKPEPITVSVPSDDTDDS
NFDCNICLDSVQEPVVTLCGHLFCWPCIHKWLDVQSFSTSDEYQRHRQCPVCKS
KVSHSTLVPLYGRGRCTTQEEGKNSVPKRPVGPVYRLEMPNSPYASTDLRLSQR
VHFNSPQEGYYPVSGVMSSNSLSYSAVLDPVMVMVGEMVATRLFGTRVMDRF
AYPDTYNLAGTSGPRMRRRIMQADKSLGRIFFFFMCCVVLCLLLF SEQ ID NO: 408
Arabidopsis thaliana RMA1 mRNA AB008518
```
  1 ctctcgtcga aagcaaaaca gtctcctttc tctatcttct gctcatatca gccattgaca
 61 cagttgcttt gggtttccct caaacggcgc cgattgtctg gattttgacc actgatggcc
121 ttagatcaat cttttgaaga tgctgcttta cttggagaac tctatggaga aggtgcattt
181 tgtttcaaga gcaagaaacc tgaacccatt acagtctcgg ttccttctga tgatactgat
241 gattcgaatt ttgactgcaa tatttgctta gactcggtgc aagaacctgt tgtgactctc
301 tgtggtcacc tcttttgctg gccttgtatt cacaaatggc ttgatgtaca gagcttctca
361 acaagtgatg aataccaaag acatagacag tgtcctgttt gtaaatctaa agtttctcat
421 tctactttgg ttcctttgta tggtagaggc cgttgtacta ctcaggagga aggtaaaaac
481 agtgtgccta aaagacccgt aggaccggtt tatcggcttg aaatgccgaa ttcacttat
541 gcaagtactg atctgcggtt atcacaacgg ttcatttca atagcccaca ggaaggttac
601 tacccctgtct caggggtgat gagctcgaac agtttatcat actctgctgt tttggatccg
661 gtgatggtga tggttggaga aatggtagct acgaggttgt ttggaacacg agtgatggat
721 agatttgcgt atccggacac ttacaatctc gcagggacta gcgggccgag gatgagaagg
781 cggataatgc aggcagataa atcgctggga agaatcttct tcttctttat gtgttgtgtt
841 gttctgtgtc ttctcttgtt ttaggttttc atagctagct tggttctgct actgttcagt
901 ttcttcaggt gtaaggaaaa catagtcaaa gaaatgtaca tttgtgttgg aaacaaatca
961 aagttgctta atgttgaggg
```

SEQ ID NO: 409

FIG. 11 cont'd

Arabidopsis thaliana ABI5 (ABA INSENSITIVE 5) NM_129185 AT2G36270
MVTRETKLTSEREVESSMAQARHNGGGGGENHPFTSLGRQSSIYSLTLDEFQHA
LCENGKNFGSMNMDEFLVSIWNAEENNNNQQQAAAAAGSHSVPANHNGFNNN
NNNGGEGGVGVFSGGSRGNEDANNKRGIANESSLPRQGSLTLPAPLCRKTVDEV
WSEIHRGGGSGNGGDSNGRSSSSNGQNNAQNGGETAARQPTFGEMTLEDFLVK
AGVVREHPTNPKPNPNPNQNQNPSSVIPAAAQQQLYGVFQGTGDPSFPGQAMGV
GDPSGYAKRTGGGGYQQAPPVQAGVCYGGGVGFGAGGQQMGMVGPLSPVSSD
GLGHGQVDNIGGQYGVDMGGLRGRKRVVDGPVEKVVERRQRRMIKNRESAAR
SRARKQAYTVELEAELNQLKEENAQLKHALAELERKRKQQYFESLKSRAQPKLP
KSNGRLRTLMRNPSCPL"

SEQ ID NO: 410
Arabidopsis thaliana ABI5 (ABA INSENSITIVE 5) NM_129185 AT2G36270
     1 atctctctct ttctcaaaac ctttcagtca aaattctccg gcggcttta aactatgtga
    61 aggaggagaa cctccataac aagaagcgga ttctctcagt tttccggcgg cggaggaaca
   121 caaagccacc ggttttaga cacacagatt tcattttcag ttgttaaatg gtaactagag
   181 aaacgaagtt gacgtcagag cgagaagtag agtcgtccat ggcgcaagcg agacataatg
   241 gaggaggtgg tggtgagaat catccgttta cttctttggg aagacaatcc tctatctact
   301 cattgaccct tgacgagttc aacatgctt tatgtgagaa cggcaagaac tttgggtcca
   361 tgaacatgga cgagttctt gtctctattt ggaacgcaga ggagaataat aacaatcaac
   421 aacaagcagc agcagctgca ggttcacatt ctgttccggc taatcacaat ggtttcaaca
   481 acaacaataa caatggaggc gagggtggtg ttggtgtctt tagtggtggt tctagaggca
   541 acgaagatgc taacaataag agagggatag cgaacgagtc tagtcttcct cgacaaggct
   601 ctttgacact tccagctccg ctttgtagga agactgttga tgaggtttgg tctgagatac
   661 atagaggtgg tggtagcggt aatggaggag acagcaatgg acgtagtagt agtagtaatg
   721 gacagaacaa tgctcagaac ggcggtgaga ctgcggctag acaaccgact tttggagaga
   781 tgacacttga ggatttcttg gtgaaggctg gtgtggttag agaacatccc actaatccta
   841 aacctaatcc aaacccgaac caaaaccaaa acccgtctag tgtaataccc gcagctgcac
   901 agcaacagct ttatggtgtg tttcaaggaa ccggtgatcc ttcattcccg ggtcaagcta
   961 tgggtgtggg tgacccatca ggttatgcta aaaggacagg aggaggaggg tatcagcagg
  1021 cgccaccagt tcaggcaggt gtttgctatg gaggtggcgt tgggtttgga gcgggtggac
  1081 agcaaatggg aatggttgga ccgttaagcc cggtgtcttc agatggatta ggacatggac
  1141 aagtggataa cataggaggt cagtatggag tagatatggg agggctaagg ggaaggaaaa
  1201 gagtagtgga tggtccagtg gagaaagtag tggagagaag acagaggagg atgatcaaga
  1261 accgcgagtc tgctgctaga tctagagcaa gaaaacaagc atatacagtg gaattggaag
  1321 ctgaacttaa ccagttgaaa gaagagaatg cgcagctaaa acatgcattg gcggagttgg
  1381 agaggaagag gaagcaacag tattttgaga gtttgaagtc aagggcacaa ccgaaattgc
  1441 cgaaatcgaa cgggagattc ggacattga tgaggaaccc gagttgtcca ctctaaacaa
  1501 acaataggaa gatggagaag aagtcggaga cagaacgagg gaaaaactga tgattttcta
  1561 cgttgttgtt ttgtctttga ggaatgaggt tatagaatct ttatactttg atgttttctg
  1621 tgttggtagg aggaacacca tctgatctgc ttactagtg ttccctgtga acaaagaaag
  1681 tgattctgtg tttc SEQ ID NO: 411
Arabidopsis thaliana ABI3 (ABA INSENSITIVE 3) NM_113376 AT3G24650
MKSLHVAANAGDLAEDCGILGGDADDTVLMDGIDEVGREIWLDD

FIG. 11 cont'd

HGGDNNHVHGHQDDDLIVHHDPSIFYGDLPTLPDFPCMSSSSSSSTSPAPVNAIVS
SASSSSAASSSTSSAASWAILRSDGEDPTPNQNQYASGNCDDSSGALQSTASMEIP
LDSSQGFGCGEGGGDCIDMMETFGYMDLLDSNEFFDTSAIFSQDDDTQNPNLMD
QTLERQEDQVVVPMMENNSGGDMQMMNSSLEQDDDLAAVFLEWLKNNKETV
SAEDLRKVKIKKATIESAARRLGGGKEAMKQLLKLILEWVQTNHLQRRRTTTTT
TNLSYQQSFQQDPFQNPNPNNNNLIPPSDQTCFSPSTWVPPPPQQQAFVSDPGFG
YMPAPNYPPQPEFLPLLESPPSWPPPPQSGPMPHQQFPMPPTSQYNQFGDPTGFN
GYNMNPYQYPYVPAGQMRDQRLLRLCSSATKEARKKRMARQRRFLSHHHRHN
NNNNNNNNNQQNQTQIGETCAAVAPQLNPVATTATGGTWMYWPNVPAVPPQL
PPVMETQLPTMDRAGSASAMPRQQVVPDRRQGWKPEKNLRFLLQKVLKQSDV
GNLGRIVLPKKEAETHLPELEARDGISLAMEDIGTSRVWNMRYRFWPNNKSRMY
LLENTGDFVKTNGLQEGDFIVIYSDVKCGKYLIRGVKVRQPSGQKPEAPPSSAAT
KRQNKSQRNINNNSPSANVVVASPTSQTVK"

SEQ ID NO: 412
Arabidopsis thaliana ABI3 (ABA INSENSITIVE 3) NM_113376 AT3G24650
```
   1 gttggagtaa acccaaacgg ttttagatta cttattagct gttcatcagt tcttcctctc
  61 taaaagagta aaacctaaac atctctctct gttctattag aaccaaagac caatctttgt
 121 gaacaaaaca catctcgtat acttcagatc tagactcgaa aattttagac ctctttacaa
 181 ttggtctttg ttcatctgaa gttggagaaa atagttagct taggtcggat cttttcatat
 241 gctttggatc ctccttcgtc tcttttgtat aattttaacc ttatcaagag ttcttttttga
 301 atctcaaaag attatatagt agtatagaag gtttatatgt atatgtatag ccagatagtt
 361 tatgttgttt aaagattcga tgatagccaa gttgggttaa ctttcttttt ccttgcctcc
 421 ttactcacat acaaacccta tctgtccgta caaaatacta aaaaccctaa cttttctctc
 481 tccaccaatc tagtttattg tttcatttcc acttcaacga tgaaaagctt gcatgtggcg
 541 gccaacgccg gagatctggc tgaggattgt ggaatactcg gtgggagacg tgatgatact
 601 gttttgatgg atggaattga tgaagttggt agagagatct ggttagatga ccatggagga
 661 gataataatc atgttcatgg tcatcaagat gatgattttga ttgttcatca tgacccttca
 721 atcttctatg gagatctccc aacgcttcct gatttcccat gcatgtcgtc ttcatcatcg
 781 tcttcaacat ctccagctcc tgtcaacgca atcgtctcct cagcctcttc ttcttcggca
 841 gcttcttcct ccacttcctc agctgcttct tgggctatat tgagatcaga tggagaagat
 901 ccgactccaa accaaaacca atacgcatca ggaaactgtg acgactcttc tggtgcattg
 961 caatccacag cttccatgga gattccatta gacagcagtc aaggttttgg ttgcggcgaa
1021 ggcggtggtg attgcattga tatgatggag actttcgggt acatggatct acttgatagc
1081 aacgagttct ttgacacctc agctatattt agccaagacg acgacacgca aaaccctaac
1141 ttgatggacc aaacccttga gacaagaa gaccaggtcg ttgttccgat gatggagaat
1201 aacagtggtg gagacatgca aatgatgaat tcttccttgg aacaggacga tgatctcgct
1261 gctgtgtttt tggagtggct aaagaacaac aaggagactg tgtcggctga ggatttgagg
1321 aaagtaaaga taaagaaagc tacgattgaa tcagcggcaa gaagactagg cggtggtaaa
1381 gaagcgatga gcagcttttt aaagctgatt cttgaatggg tccaaactaa tcacttacaa
1441 agaagacgca ccaccaccac caccaccaac ctctcttatc aacaatcatt ccaacaagat
1501 ccatttcaaa accctaaccc taataacaac aacctaatcc caccgtccga ccaaacctgt
1561 ttctcacctt caacatgggt tcctccacca ccacaacaac aagcttttgt ctcggacccg
1621 ggttttggat acatgcctgc tccaaactat ccgccacagc cagagttcct tcctttactt
1681 gaatctccac cgtcatggcc accaccacca cagtctggtc ccatgccaca tcaacaattc
1741 cccatgccgc caacctcgca gtataatcaa tttggagatc caacaggttt caatggatac
```

FIG. 11 cont'd

```
1801 aacatgaatc cgtaccaata tccttatgtt cctgcaggac aaatgagaga tcagagatta
1861 ctccgtttgt gttcctcagc aactaaagag gcaagaaaga aacggatggc gagacagagg
1921 aggttcttgt ctcatcacca cagacataac aacaacaaca acaacaacaa caataatcag
1981 cagaaccaaa cccaaatcgg agaaacctgt gccgcggtgg ctccacaact taaccccgtg
2041 gccacaaccg ccacgggagg gacctggatg tattggccta atgtcccggc agtgccgcct
2101 caattaccgc cagtgatgga gactcagtta cctaccatgg accgagctgg ctcagcttct
2161 gctatgccac gtcagcaggt ggtaccagat cgccggcagg gatggaaacc agaaaagaat
2221 ttgcggtttc tcttgcagaa agtcttgaag caaagcgacg tgggtaacct cggaaggatc
2281 gttttgccaa aaaaagaagc tgagacacac ttgccggagc tagaggcaag agacggcatc
2341 tctctggcca tggaagacat cggaacctct cgtgtttgga acatgcgcta caggttttgg
2401 cctaacaaca aaagcaggat gtatctcctc gagaacaccg gcgattttgt gaaaaccaat
2461 gggctccaag aaggtgattt catagtcata tactccgacg tcaaatgtgg caaatatttg
2521 atacgagggg ttaaagtaag acaaccgagc ggacaaaagc cggaggcccc accgtcgtca
2581 gcagctacga agagacaaaa caagtcgcaa aggaacataa acaataactc tccgtcggcg
2641 aatgtggtgg tcgcttcacc aacttctcaa actgttaaat gaaaaacaga gacaaaaaga
2701 aacaatataa atattattat gtaccaaata agaaagaggg caaaaggaaa aaatggcagc
2761 gtacccgagt gtgccacttc tcgtgcatgc atgggatctt gaagacaaat ggagggtcat
2821 gattaaagct gtttggtcgg ggtccgggtt tttactccat tttttgcttt ttcttgtcga
2881 gtcggttctt ttataactct ttactctttt taccttcagg atattgtaga gatgattaat
2941 tctggaaatg gtgtttgtgt tatat
```

SEQ ID NO: 413
Transcription factor AtMYC2 (R-homologous Arabidopsis protein 1) (RAP-1) (Basic
helix-loop-helix protein 6) (bHLH6) (AtbHLH006) (rd22BP1)
gi|34222779|sp|Q39204|RAP1_ARATH[34222779]
MTDYRLQPTM NLWTTDDNAS MMEAFMSSSD ISTLWPPAST TTTTATTETT
PTPAMEIPAQ AGFNQETLQQ RLQALIEGTH EGWTYAIFWQ PSYDFSGASV
LGWGDGYYKG EEDKANPRRR SSSPPFSTPA DQEYRKKVLR ELNSLISGGV
APSDDAVDEE VTDTEWFFLV SMTQSFACGA GLAGKAFATG NAVWVSGSDQ
LSGSGCERAK QGGVFGMHTI ACIPSANGVV EVGSTEPIRQ SSDLINKVRI
LFNFDGGAGD LSGLNWNLDP DQGENDPSMW INDPIGTPGS NEPGNGAPSS
SSQLFSKSIQ FENGSSSTIT ENPNLDPTPS PVHSQTQNPK FNNTFSRELN
FSTSSSTLVK PRSGEILNFG DEGKRSSGNP DPSSYSGQTQ FENKRKRSMV
LNEDKVLSFG DKTAGESDHS DLEASVVKEV AVEKRPKKRG RKPANGREEP
LNHVEAERQR REKLNQRFYA LRAVVPNVSK MDKASLLGDA IAYINELKSK
VVKTESEKLQ IKNQLEEVKL ELAGRKASAS GGDMSSSCSS IKPVGMEIEV
KIIGWDAMIR VESSKRNHPA ARLMSALMDL ELEVNHASMS VVNDLMIQQA
TVKMGFRIYT QEQLRASLIS KIG SEQ ID NO: 414
Transcription factor AtMYC2 (R-homologous Arabidopsis protein 1) (RAP-1) (Basic
helix-loop-helix protein 6) (bHLH6) (AtbHLH006) (rd22BP1)
```
  1 actttctcct atctctctct ctctcattaa aaacgtgttt ttttttaccg gtcaccggtt
 61 tatggaatga ctgattaccg gctacaacca acgatgaatc tttggaccac cgtcgtcaac
121 gcttctatga tggaagcttt catgagctct tccgatatct caactttatg gcctccggcg
181 tcgacgacaa ccacgacggc gacgactgaa acaactccga cgccggcgat ggagattccg
```

FIG. 11 cont'd

```
 241 gcacaggcgg gatttaatca agagactctt cagcaacgtt tacaagcttt gattgaagga
 301 acacacgaag gttggaccta cgctatattc tggcaaccgt cgtatgattt ctccggcgcc
 361 tccgtgctcg gatggggaga tggttattac aaaggtgaag aagataaagc aaacccgaga
 421 cggagatcga gttcgccgcc gttttctact ccggcggatc aggagtacag gaaaaaagtg
 481 ttgagagagc ttaactcgtt gatctccggt ggtgttgctc cgtcggatga cgctgttgat
 541 gaggaggtga cggatacgga atggtttttc ttggtttcga tgacgcagag cttcgcttgc
 601 ggtgcgggat tagctggtaa agcgtttgca acgggtaacg cggtttgggt ttccgggtca
 661 gatcaattat ccgggtcggg ttgtgaacgg gctaagcaag gaggagtgtt tgggatgcat
 721 actattgcgt gtattccttc ggcgaacgga gttgtggaag tcgggtcaac ggagccgatc
 781 cgacagagtt cggacccttat taacaaggtt cgaattcttt tcaatttcga cggcggagct
 841 ggagatttat cgggtcttaa ttggaatctt gacccggatc aaggtgagaa cgacccgtct
 901 atgtggatta atgacccgat tggaacacct ggatctaacg aaccgggtaa cggagctcca
 961 agttctagct cccagctttt ttcaaagtct attcagtttg agaacggtag ctcaagcaca
1021 ataaccgaaa acccgaatct ggatccgact ccgagtccgg ttcattctca gacccagaat
1081 ccgaaattca ataacacttt ctcccgagaa cttaattttt cgacgtcaag ttctacttta
1141 gtgaaaccaa gatccggcga gatattaaac ttcggcgatg aaggtaaacg aagctccgga
1201 aacccggatc caagttctta ttcgggtcaa acacaattcg aaaacaaaag aaagaggtcg
1261 atggttttga acgaagataa agttctatca ttcggagata aaaccgccgg agaatcagat
1321 cactccgatc tagaagcttc cgtcgtgaaa gaagtagcag tagagaaacg tccaaagaaa
1381 cgaggaagaa agccagcaaa cggtagagaa gagccactaa accacgtcga agcagagaga
1441 caaagacgcg agaaactaaa ccaaagattc tacgcgttac gagcggttgt accaaacgtt
1501 tcaaaaatgg ataaagcttc gttactcggt gacgcaatcg cttacatcaa cgagcttaaa
1561 tccaaagtag tcaaaacaga gtcagagaaa ctccaaatca agaaccagct cgaggaagtg
1621 aaactcgagc tcgccggaag aaaagcgagt gctagtggag gagatatgtc gtcttcgtgt
1681 tcttcgatta aaccggtggg gatggagatt gaagtgaaga taattggttg ggacgcaatg
1741 attagagttg aatctagtaa gaggaatcat ccggcggcga ggttgatgtc ggcgttgatg
1801 gatttggagt tggaagtgaa tcacgcgagt atgtcggtgg ttaacgattt gatgattcaa
1861 caagcgacgg tgaagatggg ttttaggatc tatacgcaag aacagctcag agcaagtttg
1921 atttcaaaaa tcggttaaaa gggtgtgttt tgggaagttt agaaagttat ggggtcaaat
1981 cataattaat tcgttttagt ggcttcagta attttgtaga ttttagtttt gtaagaaaaa
2041 aatcttaaaa tagagcgaca agtttcttct tttgctctat gtttgagtct gtatcgtttt
2101 attgttgtat ctcctcaatg agtaaacttg tatatattga tatgagcccg ggggaaaagg
2161 aatcagtttt tggtggaagt aattgatccg atctaggaaa aatgggagga ggtgatcatg
2221 gacatggagc agaaggaggc gatttcagag ccaaagtctg gagtatgact ggtgggccct
2281 aactgtaggc ccaaacattg gcgtcggaac accgccattg ctatgttcgg ccgttttcct
2341 tgtgtgcatc cccatcgcca agctatctgc taagcttgag caaaggccac acatgccagt
2401 acgcccaatt ccttcacaga tctggtgcaa gaactttgga accaaggacg attacgaaaa
2461 agagcattaa aagttttttt cttggtttgg agagaaccct ttaattggtc ttcttatttg
2521 cagacaatgt gagcataaaa aaagcgcaac tagctttgtc tatggatttc agagtactgt
2581 gaacataata atatgtcttt ttccttgcca tgtagaacaa caccatggaa tctttccaaa
2641 ttaagaaatt tcatgttttt ttccatatta aaaaaa
```

SEQ ID NO: 415
Arabidopsis thaliana Atmyb2 gene D14712
MEDYERINSNSPTHEEDSDVRKGPWTEEEDAILVNFVSIHGDARWNHIARSSGLK
RTGKSCRLRWLNYLRPDVRRGNITLEEQFMILKLHSLWGNRWSKIAQYLPGRTD

FIG. 11 cont'd

NEIKNYWRTRVQKQAKHLRCDVNSNLFKETMRNVWMPRLVERINAQSLPTTCE
QVESMITDPSQPVNEPSPVEPGFVQFSQNHHQQFVPATELSATSSNSPAETFSDVR
GGVVNGSGYDPSGQTGFGEFNDWGCVGGDNMWTDEESFWFLQDQFCPDTTSY
SYN"

SEQ ID NO: 416
Arabidopsis thaliana Atmyb2 gene D14712
```
   1 tcccaacgta cgataaaatt ttgtttgata aaactcacaa aagtttagta tatttctgta
  61 aatatatgca tagaagtcat agtgattgac agaggaaaga cgtctctttg actactcttc
 121 aatcgaaaac aaaatgtgct aaaatttcaa aagcaaagtc cctaaactcg cctaactcca
 181 tttctcattt gactttgcct taaatgtcaa tagtcctatg ttatttagct acattcaaaa
 241 ttgggaatta agaattattt tagactccat atacttagaa acgaatccgt attggaaact
 301 aatttccatt tagtaatagt atttaagtat tattatgctt accgagtagc atgtagtagt
 361 ttcttaatgt tagctaattt caaagcaaac gcgaatatta aatcgtgatt gcacacaaca
 421 tgaagtgatt aataaatcat taatttcgcc catagtaatc actaaccaga gtaatttga
 481 acaagactaa ggatgtacaa taacttacgt ctgcgatact gtgtgggaat aaatatagaa
 541 actttatgaa atagaactct cttaccaaag aaagaaaaag caagagtgcg tgttactata
 601 catctgaaca ggtcaaaggg tcaaaccttta gtattttaaa attacacaaa caattgacca
 661 aatggagagc taattatgtt tagcataatt tactatatag ttgcaaaatt ccactttaga
 721 aacaggataa aaaaataaaa attgaacata acacttatgc cgtgttccag tcactcttca
 781 acattctact cattttcaaa tatccttttt ataaaatact acttttaaaa ttatttgatt
 841 cttatgttcc ttcactatat atatataaat atcgcacatt gctttaatca cttcaaatct
 901 aatccacaaa accattcaca ccatctcatc ttctttctct ctatctcttt tcctttcctc
 961 atttaaagtt tctttataag aaatggaaga ttacgagcga ataaactcaa actctccaac
1021 acatgaagaa gattctgatg tacggaaagg tccatggacc gaggaagaag atgcaatcct
1081 agtcaacttc gtctctattc atggcgatgc tcgttggaac cacatcgctc gttcctctgg
1141 tatcatcaaa acatcaatct ctaaatatac atatacacaa aggctttata tatagataaa
1201 cttatatata ttttactcat atatgtgcag ggctaaagcg aactggtaag agttgtagat
1261 taagatggct taattactta cgtccagatg ttagaagagg caacatcact ctcgaagaac
1321 aatttatgat cctcaaactc cattctcttt ggggcaatag gtacacacta tatatctcaa
1381 atgttaatat tttgctattc tatatgttac tagttaagta tgttattaat atatgtcttt
1441 tttttcaatt gaatatataa ggtggtcgaa gattgcgcaa tatctaccgg gaagaacaga
1501 taatgaaata aagaattatt ggagaactcg agtccaaaag caagccaaac acctaagatg
1561 cgatgttaac agtaatcttt tcaaggagac tatgagaaat gtttggatgc cgagattagt
1621 ggaacgaatc aacgcccaat cattacccac cacgtgtgaa caagtggagt caatgatcac
1681 cgacccaagt caaccagtta acgaaccgag tccggtcgag ccgggtttcg ttcaattcag
1741 ccagaatcat catcagcaat tcgtaccggc tacggaattg tcagcaacgt cttcgaattc
1801 tccggctgag acgttttcgg acgttcgagg tggggtggtg aacgggtcag gttatgatcc
1861 gtcgggtcaa acgggtttcg gagagttcaa cgattggggc tgtgttggtg gggacaacat
1921 gtggactgac gaggagagtt tttggttctt gcaggaccag ttctgccccg atacgacatc
1981 gtattcgtat aattaaggaa atatacgatt actatacgta acgaggaatt caattgcgtc
2041 acgtttggtg taatattcat tcgtgcgtga tgccaatttt agatacggcc ttggtatacg
2101 aatctttgac ttaattatta tctttctttt tcctctcttg ttttaaaccc ctgattaaat
2161 taagatttga tcatcagacg aggatatttg tgattcactg atttgtgata ttgatatatg
2221 tgaattattt gatataacgt tttaaaaacc aacaaaaaaa aaaaatcatt ccaaggaaaa
2281 gttcttaatt ttgatactcg aaaagagcgt agactgactc gaatcagttc atattttctt
```

FIG. 11 cont'd 2341 tggttcgttt tatttacgac aaaattcact aacaaaaatt aaaaaacgac aaaacgaaaa
2401 tatgactaaa tttatttttt tgtcagttaa ccactgatta taggttgaaa ttgtcacaac
2461 acatgattta tcttgataga aatttagtag tccagaatgc tgcatggttg atcctaagaa
2521 a SEQ ID NO: 417
ACCESSION NM_116873 Arabidopsis thaliana ACS11; 1-aminocyclopropane-1-carboxylate synthase 11 (ACC synthase 11) (S-adenosyl-L-methionine methylthioadenosine-lyase 11) AT4G08040 (ACS11) mRNA, complete cds.
MLSSKVVGDSHGQDSSYFLGWQEYEKNPFHESFNTSGIVQMGLAENQLSFDLIE
KWLEEHPEVLGLKKNDESVFRQLALFQDYHGLPAFKDAMAKFMGKIRENKVKF
DTNKMVLTAGSTSANETLMFCLANPGDAFLIPAPYYPGFDRDLKWRTGVEIVPIH
CVSSNGYKITEDALEDAYERALKHNLNVKGVLITNPSNPLGTSTTREELDLLLTFT
STKKIHMVSDEIYSGTVFDSPEFTSVLEVAKDKNMGLDGKIHVVYSLSKDLGLPG
FRVGLIYSNNEKVVSAATKMSSFGLISSQTQHLLANLLSDERFTTNYLEENKKRL
RERKDRLVSGLKEAGISCLKSNAGLFCWVDLRHLLKSNTFEAEHSLWTKIVCEV
GLNISPGSSCHCDEPGWFRVCFANMSDQTMEVAMDRVKGFVDNNNGGKQKRT
MWDTRRRSLINKWVSKLSSVTCESER SEQ ID NO: 418
ACCESSION NM_116873 Arabidopsis thaliana ACS11; 1-aminocyclopropane-1-carboxylate synthase/ catalytic/ transferase, transferring nitrogenous groups AT4G08040 (ACS11) mRNA, complete cds.
    1 atgttgtcaa gcaaagttgt tggcgactct catggacaag actcatccta cttccttgga
   61 tggcaagaat acgagaagaa tccttccac gagtcgttta acactagtgg gattgttcaa
  121 atgggtcttg ctgaaaacca gctttctttt gacctaatag agaaatggct tgaagagcat
  181 ccagaagtct tggggtttgaa gaaaaatgat gagtcggtgt ttagacaatt agctctgttc
  241 caagattacc atggcttgcc agctttcaag gatgccatgg cgaagttcat ggggaaaatc
  301 agagagaaca aagtgaaatt cgatacgaac aagatggttc ttacagctgg atcaacctcg
  361 gctaacgaga ctctaatgtt ctgtcttgct aatccaggag atgcctttct tatccctgca
  421 ccttattatc cagggtttga tagagatctc aaatggagga caggagtaga gattgttcct
  481 atccattgcg taagctcaaa tgggtacaag ataaccgagg atgcattaga agatgcctac
  541 gaacgagctc tcaaacataa cctaaatgtt aaaggagttc tcataaccaa cccttcaaac
  601 ccacttggaa cctctaccac ccgtgaagag cttgatcttc ttctgacctt cacatcaacc
  661 aagaaaatcc atatggttag cgatgagatc tactcgggaa cggttttcga ctctcctgag
  721 ttcaccagcg ttctagaagt ggctaaggac aagaacatgg gtttagatgg taaaatccat
  781 gttgtttaca gcttgtccaa agatctaggc ctccccggat ttcgtgttgg cttgatttac
  841 tcaaacaatg agaaagtggt gtcagccgcg actaaaatgt cgagttttgg actcatttct
  901 tcccaaactc aacatttgct agccaatttg ctgtctgatg aaagattcac gaccaactat
  961 ttggaagaga acaagaagag gctgagagag agaaaggata ggctggtttc gggtctaaag
 1021 gaagcgggta tcagttgttt gaagagtaac gcaggttttgt tctgttgggt tgacttaaga
 1081 cacctcttga aatccaacac ttttgaggcc gagcattctt tatggacaaa gattgtgtgt
 1141 gaagttggtc ttaacatctc tccaggctca tcgtgtcatt gcgatgaacc tggttggttt
 1201 agagtttgtt tcgcgaatat gtcggaccaa acgatggagg ttgctatgga ccgtgttaaa
 1261 ggttttgttg acaacaataa tggtggtaaa caaaagagaa ccatgtggga tacaaggaga
 1321 agatctctta tcaacaaatg ggtctccaag ctttcctctg ttacttgtga atcagaacgt

FIG. 11 cont'd 1381 tga

SEQ ID NO: 419
NM_119801 Arabidopsis thaliana ROT3 (ROTUNDIFOLIA 3); oxygen binding / steroid hydroxylase AT4G36380 (ROT3) mRNA, complete cds
MQPPASAGLFRSPENLPWPYNYMDYLVAGFLVLTAGILLRPWLWLRLRNSKTK
DGDEEEDNEEKKKGMIPNGSLGWPVIGETLNFIACGYSSRPVTFMDKRKSLYGK
VFKTNIIGTPIIISTDAEVNKVVLQNHGNTFVPAYPKSITELLGENSILSINGPHQKR
LHTLIGAFLRSPHLKDRITRDIEASVVLTLASWAQLPLVHVQDEIKKMTFEILVKV
LMSTSPGEDMNILKLEFEEFIKGLICIPIKFPGTRLYKSLKAKERLIKMVKKVVEER
QVAMTTTSPANDVVDVLLRDGGDSEKQSQPSDFVSGKIVEMMIPGEETMPTAM
TLAVKFLSDNPVALAKLVEENMEMKRRKLELGEEYKWTDYMSLSFTQNVINET
LRMANIINGVWRKALKDVEIKGYLIPKGWCVLASFISVHMDEDIYDNPYQFDPW
RWDRINGSANSSICFTPFGGGQRLCPGLELSKLEISIFLHHLVTRYSWTAEEDEIVS
FPTVKMKRRLPIR VATVDDSASPISLEDH SEQ ID NO: 420
NM_119801 Arabidopsis thaliana ROT3 (ROTUNDIFOLIA 3); oxygen binding / steroid hydroxylase AT4G36380 (ROT3) mRNA, complete cds
```
   1 attgagaaaa cccttttaaa attctctatc gatctcatca caaattttgc tatatccaca
  61 attcatgtgc ttaggcatat agttattccc aagaaaccgg tttaactgtt tacgtatgca
 121 acctccggca agcgcaggac ttttccggtc gccggaaaat ctcccttggc cttataatta
 181 catggattat ttggtcgctg gtttcttggt tttgacggcc ggaatacttc tccgtccatg
 241 gctctggtta cgtctacgaa actcgaaaac gaaagatgga gatgaagaag aagataatga
 301 ggagaagaag aagggaatga ttccaaacgg aagcttaggc tggccggtga tcggagaaac
 361 cctaaacttc atcgcttgtg gttattcttc tcggcctgtt accttcatgg acaaacgaaa
 421 gtctttatac gggaaagtgt tcaaaacgaa cataataggg acaccaatca taatatcaac
 481 cgatgcagag gtgaataaag tggtgctcca aaaccatggg aacacatttg tccctgcata
 541 ccctaaatca attacggaac tacttggaga aaactctatt ctcagcatca atggacctca
 601 tcaaaaaagg cttcacacgc tcattggcgc gttcctcaga tctcctcacc tcaaagaccg
 661 gatcactcga gacattgagg cctcggttgt tctcactttg gcgtcttggg ctcaacttcc
 721 attggttcat gttcaggatg agatcaaaaa gatgacgttt gagatattag taaaagtgtt
 781 gatgagcaca tctcctggtg aagatatgaa cattctcaaa cttgagttcg aagaattcat
 841 caaaggtttg atttgtatcc caatcaaatt ccctggcact agactctaca atccttaaa
 901 ggcgaaagag aggttaataa agatggtaaa aaaggttgtg gaggagagac aagtggcgat
 961 gacaacgacg tctccggcaa atgacgtggt ggacgtactt ctaagagacg gtggtgattc
1021 agagaagcaa tctcaaccgt cagatttcgt cagcggaaag atcgtagaga tgatgatacc
1081 cggagaggaa acaatgccaa cggcgatgac cttggctgtc aaattcttaa gtgacaaccc
1141 cgtcgctcta gccaaactcg tggaggagaa tatggagatg aagaggcgta aattggaatt
1201 gggagaagaa tacaagtgga ccgattatat gtctctctct tttactcaaa atgtgataaa
1261 cgaaacgctt agaatggcta acattattaa cggggtgtgg aggaaagctc tcaaggatgt
1321 agaaattaaa ggttacttaa taccgaaagg atggtgtgta ttggcatcat tcatatcggt
1381 tcacatggat gaagacattt atgataatcc ctatcaattc gatccgtgga gatgggacag
1441 aattaatgga tcggcaaaca gcagtatttg cttcacaccc tttggtggtg ggcaaaggct
1501 atgtcctggt ttagagctgt cgaagctcga aatatccatc tttcttcacc accttgtaac
1561 ccggtacagt tggacggctg aggaagacga gatagtgtca tttccgactg tgaagatgaa
```

FIG. 11 cont'd 1621 gcggaggctc ccgatccgag tggctactgt agatgatagt gcttctccga tctcacttga
1681 agatcattaa tagatcattt caaagaacaa aactgtttgt gcaaagagga agcagagaag
1741 taaacaaatg atcttattaa caaatagtag agaagagaag caaacaagat tggtgggtaa
1801 gacagaaaga gccatacgta cagctagtga tggctcaaag atgagagatt ctaattataa
1861 tttttttgt ttgtcatgtc aaattataag cgttggttag gttgtccctt tctcttttat
1921 ttatcgtacc aaacgcaagt tgagatatga ttccatatat atggatgata gatatgtata
1981 ttaatatata ccttcttct SEQ ID NO: 421
ACCESSION BT010564 brassinolide (BL) 26-hydroxylase Arabidopsis thaliana
At2g26710 gene, complete cds.
MEEESSSWFIPKVLVLSVILSLVIVKGMSLLWWRPRKIEEHFSKQGIRGPPYHFFIG
NVKELVGMMLKASSHPMPFSHNILPRVLSFYHHWRKIYGATFLVWFGPTFRLTV
ADPDLIREIFSKSEFYEKNEAHPLVKQLEGDGLLSLKGEKWAHHRKIISPTFHMEN
LKLLVPVVLKSVTDMVDKWSDKLSENGEVEVDVYEWFQILTEDVISRTAFGSSY
EDGRAVFRLQAQQMLLCAEAFQKVFIPGYRFFPTRGNLKSWKLDKEIRKSLLKLI
ERRRQNAIDGEGEECKEPAAKDLLGLMIQAKNVTVQDIVEECKSFFFAGKQTTSN
LLTWTTILLSMHPEWQAKARDEVLRVCGSRDVPTKDHVVKLKTLSMILNESLRL
YPPIVATIRRAKSDVKLGGYKIPCGTELLIPIIAVHHDQAIWGNDVNEFNPARFAD
GVPRAAKHPVGFIPFGLGVRTCIGQNLAILQAKLTLAVMIQRFTFHLAPTYQHAP
TVLMLLYPQHGAPITFRRLTNHED SEQ ID NO: 422
ACCESSION BT010564 brassinolide (BL) 26-hydroxylase Arabidopsis thaliana
At2g26710 gene, complete cds.
1 atggaggaag aaagtagcag ctggttcatt ccaaaggttc ttgttctgtc tgtaatctta
61 agtcttgtaa tagtgaaggg tatgtctctg ttatggtgga gaccaagaaa gattgaagaa
121 catttctcta acaaggaat tcgaggtcct ccttatcatt tcttcatcgg aaatgttaaa
181 gaacttgttg gaatgatgct taaagcttct tctcatccta tgccttctc tcacaatatt
241 cttcctagag ttctctcttt ttaccatcac tggagaaaaa tctacggtgc tacatttctg
301 gtttggttcg gtccaacttt ccggttaacg gtagccgatc ctgatttgat cagagagatc
361 ttctctaagt ctgagttcta cgagaagaat gaagctcacc ctttggttaa acaacttgaa
421 ggcgatggac tacttagtct caaaggtgaa aaatgggctc atcatcgaaa aatcattagc
481 cctacttttc atatggagaa tcttaagttg cttgtaccag ttgtgttgaa gagtgtgact
541 gatatggtgg ataaatggtc cgataagtta tcagaaaacg gtgaagttga ggtagatgtc
601 tatgagtggt ttcagatttt gactgaagat gttattagta gaacagcttt tggaagtagc
661 tatgaagatg gtcgagcagt ttttcgactt caagctcaac aaatgcttct ttgtgctgaa
721 gcttttcaaa aagtcttcat tcctggctat agattttttc cgacaagagg gaatttgaag
781 tcttggaagt tagacaagga gataaggaag tcgttgttga agctgataga gcggcggaga
841 caaaacgcta tagatggaga aggggaagaa tgtaaggagc cggcggcgaa ggatttgttg
901 ggattaatga ttcaggcaaa gaatgtgacg gttcaggaca ttgtggagga gtgtaaaagc
961 ttttcttcg ccgggaaaca gacaacttct aatctgctga cgtggacgac catcttgcta
1021 tccatgcacc cggagtggca ggccaaagca cgtgatgagg tcctcagggt ctgcggctca
1081 cgtgatgtcc ctaccaagga ccatgtcgtt aagcttaaaa cgttgagtat gatcttgaac
1141 gagtctttaa ggttgtatcc accaatagta gctacgattc gacgcgctaa atcggatgtg
1201 aagctaggag ggtacaaaat cccatgtggc acggagcttc taatcccaat catagcggtc

FIG. 11 cont'd

```
1261 catcatgacc aagccatttg gggtaatgac gtgaacgaat tcaatccagc tcggtttgcg
1321 gatggagtgc cgcgtgctgc caaacacccc gttggattca taccgtttgg cctcggagtt
1381 cgtacatgca ttggtcagaa tcttgctata cttcaggcca aattgacact cgctgtaatg
1441 atccaacgct tcacctttca cttggctcct acttatcagc atgcacctac cgtccttatg
1501 ttgctttatc ctcaacatgg tgcaccaatc accttccgga gattgaccaa tcatgaggat
1561 tga
```

SEQ ID NO: 423
ACCESSION NM_101424 Arabidopsis thaliana GA4 (GA REQUIRING 4); gibberellin 3-beta-dioxygenase AT1G15550 (GA4) mRNA, complete cds
MPAMLTDVFRGHPIHLPHSHIPDFTSLRELPDSYKWTPKDDLLFSAAPSPPATGEN
IPLIDLDHPDATNQIGHACRTWGAFQISNHGVPLGLLQDIEFLTGSLFGLPVQRKL
KSARSETGVSGYGVARIASFFNKQMWSEGFTITGSPLNDFRKLWPQHHLNYCDI
VEEYEEHMKKLASKLMWLALNSLGVSEEDIEWASLSSDLNWAQAALQLNHYPV
CPEPDRAMGLAAHTDSTLLTILYQNNTAGLQVFRDDLGWVTVPPFPGSLVVNVG
DLFHILSNGLFKSVLHRARVNQTRARLSVAFLWGPQSDIKISPVPKLVSPVESPLY
QSVTWKEYLRTKATHFNKALSMIRNHREE"

SEQ ID NO: 424
ACCESSION NM_101424
Arabidopsis thaliana GA4 (GA REQUIRING 4); gibberellin 3-beta-dioxygenase
AT1G15550 (GA4) mRNA, complete cds.

```
   1 atcaccaaac accacacttc tcataagaaa aaaaacacaa acatctatca aatttacaaa
  61 gttttaaaac taattaaaaa agagcaagat gcctgctatg ttaacagatg tgtttagagg
 121 ccatcccatt cacctccac actctcacat acctgacttc acatctctcc gggagctccc
 181 ggattcttac aagtggaccc ctaaagacga tctcctcttc tccgctgctc cttctcctcc
 241 ggccaccggt gaaaacatcc ctctcatcga cctcgaccac ccggacgcga ctaaccaaat
 301 cggtcatgca tgtagaactt ggggtgcctt ccaaatctca aaccacggcg tgcctttggg
 361 acttctccaa gacattgagt ttctcaccgg tagtctcttc gggctacctg tccaacgcaa
 421 gcttaagtct gctcggtcgg agacaggtgt gtccggctac ggcgtcgctc gtatcgcatc
 481 tttcttcaat aagcaaatgt ggtccgaagg tttcaccatc actggctcgc ctctcaacga
 541 tttccgtaaa ctttggcccc aacatcacct caactactgc gatatcgttg aagagtacga
 601 ggaacatatg aaaaagttgg catcgaaatt gatgtggtta gcactaaatt cacttggggt
 661 cagcgaagaa gacattgaat gggccagtct cagttcagat ttaaactggg cccaagctgc
 721 tctccagcta aatcactacc cggtttgtcc tgaaccggac cgagccatgg gtctagcagc
 781 tcataccgac tccaccctcc taaccattct gtaccagaac aataccgccg gtctacaagt
 841 atttcgcgat gatcttggtt gggtcaccgt gccaccgttt cctggctcgc tcgtggttaa
 901 cgttggtgac ctcttccaca tcctatccaa tggattgttt aaaagcgtgt tgcaccgcgc
 961 tcgggttaac caaaccagag cccggttatc tgtagcattc cttgggggtc cgcaatctga
1021 tatcaagata tcacctgtac cgaagctggt tagtcccgtt gaatcgcctc tataccaatc
1081 ggtgacatgg aaagagtatc ttcgaacaaa agcaactcac ttcaacaaag ctctttcaat
1141 gattagaaat cacagagaag aatgattaga taataatagt tgtgatctac tagttagttt
1201 gattaataaa ttgttgtaaa tgatttcagc aatatgattt gtttgtcctc aatcat
```

SEQ ID NO: 425

FIG. 11 cont'd

ACCESSION AB122149 Arabidopsis thaliana CYP707A1 mRNA for cytochrome P450 monooxygenase, complete cds.
MDISALFLTLFAGSLFLYFLRCLISQRRFGSSKLPLPPGTMGWPYVGETFQLYSQD
PNVFFQSKQKRYGSVFKTHVLGCPCVMISSPEAAKFVLVTKSHLFKPTFPASKER
MLGKQAIFFHQGDYHAKLRKLVLRAFMPESIRNMVPDIESIAQDSLRSWEGTMIN
TYQEMKTYTFNVALLSIFGKDEVLYREDLKRCYYILEKGYNSMPVNLPGTLFHK
SMKARKELSQILARILSERRQNGSSHNDLLGSFMGDKEELTDEQIADNIIGVIFAA
RDTTASVMSWILKYLAENPNVLEAVTEEQMAIRKDKEEGESLTWGDTKKMPLT
SRVIQETLRVASILSFTFREAVEDVEYEGYLIPKGWKVLPLFRNIHHSADIFSNPGK
FDPSRFEVAPKPNTFMPFGNGTHSCPGNELAKLEMSIMIHHLTTKYSWSIVGASD
GIQYGPFALPQNGLPIVLARKPEIEV SEQ ID NO: 426
ACCESSION AB122149 Arabidopsis thaliana CYP707A1 mRNA for cytochrome P450 monooxygenase, complete cds.
```
   1 attacattaa aactccaaaa aattcatttt tgttttcttt tagagttcac aagttcttcg
  61 ttgttcagct actcccactg tcataacacg aagtgggttt ttttctgatc aaagaacaaa
 121 aacaaaaatg gatatctccg ccttgtttct cactctcttc gccggaagtc tcttcctttta
 181 ctttctccgg tgtctaatct ctcagcgccg ctttggatct tccaaactcc cactccctcc
 241 gggaacaatg ggttggcctt acgtcggaga aactttccag ctttactctc aagaccctaa
 301 tgtctttttc caatcaaaac agaaaaggta tggatcggtg tttaagactc atgtattggg
 361 atgtccatgt gtgatgatct cgagtccaga ggctgctaag ttcgtgctgg tgacgaaatc
 421 tcatctcttt aaaccaactt ttccggcgag taaagagagg atgttgggga aacaagccat
 481 cttcttccac cagggtgatt atcacgctaa actcaggaag cttgttcttc gtgcttttat
 541 gcctgaatct atcagaaaca tggttcctga tattgaatcc atcgctcaag actctctccg
 601 aagttgggag ggaacaatga tcaacactta ccaagaaatg aaaacataca ccttcaacgt
 661 tgcgttgcta tcgatcttcg gaaaagacga ggttttatac agagaagatc taaaacgatg
 721 ctactacatt ctcgagaaag gttacaattc gatgccagtg aatctccctg gaacactttt
 781 ccacaaatca atgaaagctc ggaaggaact ctcacagatc ctcgctagaa tcttatcaga
 841 gagaagacag aacggttcct cacacaacga tcttctcgga tcattcatgg agacaaaga
 901 agagctaacc gacgaacaga tcgccgacaa cataatcgga gtaatcttcg ccgctagaga
 961 cacgacggcg agtgtgatgt cgtggatcct caagtaccta gccgagaatc caacgttct
1021 agaagccgtt actgaagaac aaatggcaat aaggaaagac aaagaagaag gagagtctct
1081 aacttgggga gatacaaaga agatgccatt aacttcaaga gttattcaag aaacattaag
1141 agtcgcttca atcttatctt tcacattcag agaagctgtc gaagatgtcg aatacgaagg
1201 atatttgata cctaaaggat ggaaagtgtt accctatc agaaacattc atcatagtgc
1261 tgatattttt tctaatccgg ggaaatttga tccatcaaga ttcgaggtgg ctccaaaacc
1321 caatacgttc atgccatttg gcaatggaac ccactcgtgt cctggaaatg aattagccaa
1381 gcttgagatg tctattatga ttcatcatct caccaccaag tacagttggt caattgttgg
1441 agcgagcgac gggattcagt atgggccatt cgcgcttccc caaaacggac tgcccattgt
1501 gctggcccgg aagccggaga tcgaagtgta gaatgacaga attgccttta gcttttctat
1561 atttggaaag aggagactag agaagaagaa taaataattc tttctttctt tatcaagaaa
1621 aaaagataga gatggaggaa aacaggttca agattttggt agaaaaatat tccccaaatg
1681 ggatcaagga gaaaacacca agtgtacaaa aacttcaatt ttatttttct tgactttctt
1741 tagttttttt tttttgagtt tttaattta atttaagatg ggaaaagcta gtaattgaat
1801 ttaaaaaaac aggggaaaat gttagtacaa gtctctcatg tattttttt ttgttttcc
```

FIG. 11 cont'd 1861 tgaaaaanatc ttatggttat gttataacta tttcctcctg gattgagact tcccttgttt
1921 tttgaataaa tttttttgt tataaaaaaa aaaaaaaaaa aaaaaaaaaa aaaaaaaaaa
1981 aaaaaaaaa SEQ ID NO: 427
ACCESSION  NM_128466  Arabidopsis thaliana CYP707A2; heme binding / iron ion binding / monooxygenase/ oxygen binding AT2G29090 (CYP707A2) mRNA, complete cds. (ABA 8'-hydroxylase; At2g29090
MQISSSSSSNFFSSLYADEPALITLTIVVVVVVLLFKWWLHWKEQRLRLPPGSMG
LPYIGETLRLYTENPNSFFATRQNKYGDIFKTHILGCPCVMISSPEAARMVLVSKA
HLFKPTYPPSKERMIGPEALFFHQGPYHSTLKRLVQSSFMPSALRPTVSHIELLVL
QTLSSWTSQKSINTLEYMKRYAFDVAIMSAFGDKEEPTTIDVIKLLYQRLERGYN
SMPLDLPGTLFHKSMKARIELSEELRKVIEKRRENGREEGGLLGVLLGAKDQKR
NGLSDSQIADNIIGVIFAATDTTASVLTWLLKYLHDHPNLLQEVSREQFSIRQKIK
KENRRISWEDTRKMPLTTRVIQETLRAASVLSFTFREAVQDVEYDGYLIPKGWK
VLPLFRRIHHSSEFFPDPEKFDPSRFEVAPKPYTYMPFGNGVHSCPGSELAKLEML
ILLHHLTTSFRWEVIGDEEGIQYGPFPVPKKGLPIRVTPI SEQ ID NO: 428
ACCESSION  NM_128466  Arabidopsis thaliana CYP707A2; heme binding / iron ion binding / monooxygenase/ oxygen binding AT2G29090 (CYP707A2) mRNA, complete cds.  (ABA 8'-hydroxylase; At2g29090
    1 atgcaaatct catcttcatc gtcttcaaat ttcttctctt ctctttatgc tgatgaaccg
   61 gcactaatca cattaacaat tgttgtagta gtagtagtgt tactatttaa atggtggttg
  121 cactggaaag agcaaagact acggctacct cctggctcca tggggttgcc ttacatcgga
  181 gagacactcc gcctctacac agaaaatccc aattccttct tcgccactcg ccaaaacaag
  241 tacggggata tattcaagac gcacatatta ggatgtccat gtgtgatgat aagtagtcca
  301 gaggcggctc gaatggtgtt agtgagcaaa gctcacttgt tcaagccaac ttatcctcca
  361 agcaaagagc gtatgattgg accagaggct cttttcttcc accaaggtcc ataccattct
  421 accttaagc ggctggtcca gtcttctttc atgccttctg ctctcagacc aaccgtctct
  481 cacatcgagc tccttgtcct ccaaaccctt tcctcttgga cgtcccaaaa gtccatcaac
  541 accctcgaat acatgaaacg atatgcattc gatgtggcga tcatgtcagc gttcggggac
  601 aaagaggagc ccactacgat tgatgttatt aagcttctct atcaacgtct cgaaaggggt
  661 tacaactcca tgcctctcga cctaccgggc acattttc ataagtccat gaaggcaaga
  721 atagaattaa gcgaggaact aaggaaagta atagaagaa gaagagaa tgggagagaa
  781 gaaggaggac tattgggagt acttctggga gcaaaggatc aaaaacgcaa cggcttaagt
  841 gattcacaga ttgctgacaa catcatcggt gttatattcg ccgccaccga caccaccgct
  901 tctgtcttaa cttggcttct caagtactta cacgaccacc caatctcct ccaagaagtc
  961 tccagggagc aattcagcat tcgacagaaa ataaaaaag aaaaccgaag aatctcatgg
 1021 gaagatacaa gaaaaatgcc actgaccact agggtgatac aagagacact aagagcagca
 1081 agtgtactgt cctttacatt tagagaagca gtacaagacg tcgaatatga tggctacttg
 1141 atcccaaagg gttggaaggt tcttcctctt ttccggcgaa tccatcactc ctccgaattc
 1201 ttccccgatc ctgaaaaatt cgatccttct agattcgagg tggcaccaaa accttacacg
 1261 tacatgccat tcggaaatgg agtgcactca tgtccaggaa gtgagctggc taaacttgag
 1321 atgcttatcc tccttcacca cctcactact tccttcagat gggaagtgat tggagatgaa
 1381 gaaggtatac agtatggtcc tttccctgta cccaagaagg gtttaccaat aagagtaacc

FIG. 11 cont'd 1441 ccgatttaa

SEQ ID NO: 429
ACCESSION AB122150 Arabidopsis thaliana CYP707A3 mRNA for cytochrome P450 monooxygenase, complete cds.
MDFSGLFLTLSAAALFLCLLRFIAGVRRSSSTKLPLPPGTMGYPYVGETFQLYSQ
DPNVFFAAKQRRYGSVFKTHVLGCPCVMISSPEAAKFVLVTKSHLFKPTFPASKE
RMLGKQAIFFHQGDYHSKLRKLVLRAFMPDAIRNMVPHIESIAQESLNSWDGTQ
LNTYQEMKTYTFNVALISILGKDEVYYREDLKRCYYILEKGYNSMPINLPGTLFH
KAMKARKELAQILANILSKRRQNPSSHTDLLGSFMEDKAGLTDEQIADNIIGVIFA
ARDTTASVLTWILKYLADNPTVLEAVTEEQMAIRKDKKEGESLTWEDTKKMPLT
YRVIQETLRAATILSFTFREAVEDVEYEGYLIPKGWKVLPLFRNIHHNADIFSDPG
KFDPSRFEVAPKPNTFMPFGSGIHSCPGNELAKLEISVLIHHLTTKYRWSIVGPSD
GIQYGPFALPQNGLPIALERKP SEQ ID NO: 430
ACCESSION AB122150 Arabidopsis thaliana CYP707A3 mRNA for cytochrome P450 monooxygenase, complete cds
    1 caaaaaccaa tccattagag agagaactca caaaacatac ttcgaattcc cattgtttaa
   61 aagacgaaga taatggattt ctccggtttg tttctcactc tctccgcggc ggctctgttt
  121 ctctgtttac tccgatttat cgccggagtc cgccgtagct cctccacgaa actccctctt
  181 cctccgggaa caatgggtta tccttacgtc ggcgaaacat tccaactta ctcacaagac
  241 cctaatgtgt tctttgcagc aaaaacagaga agatacggat cggtgttcaa gactcatgta
  301 ttgggatgtc catgtgtgat gatctcgagc cctgaagcag cgaaattcgt attggttaca
  361 aagtctcatt tgttttaaacc gacttttccg gccagtaaag agaggatgct tgaaaacaa
  421 gccatcttct tccatcaagg agattatcat ccaaactta gaaagcttgt tttaagagct
  481 ttcatgcctg atgcaatcag aaacatggtc cctcacattg aatcaattgc tcaagaatca
  541 ctcaattctt gggatggaac tcaactcaac acttaccagg aaatgaaaac atacacttc
  601 aatgttgcgt taatctcaat actcggcaaa gacgaagttt attaccgaga agatctaaaa
  661 cgatgctact acattctaga gaaaggttac aattcgatgc cgattaatct tccaggaaca
  721 ttattccaca aagccatgaa agctcgcaag gagctagctc aaatcctcgc taacatctta
  781 tccaaaagaa gacaaaaccc atcatcacac acagatctcc tcggatcatt catggaagac
  841 aaagcaggat taaccgacga acaaatcgcc gataacatca tcggagtaat cttcgccgca
  901 agagacacga cggcgagtgt tctgacgtgg atcctcaagt acttagctga taatccaact
  961 gttctagaag ctgtcactga agagcaaatg gcaataagga aagataaaaa agaaggagag
 1021 agtctcactt gggaagatac aaagaagatg ccattaactt atagagtaat ccaagagaca
 1081 ttaagagctg ctacaatctt atctttcaca tttagagaag ctgtcgaaga tgtcgaatac
 1141 gaaggatatt tgataccaaa gggatggaaa gtactgccac tattcagaaa tattcatcac
 1201 aatgctgata tattttcgga tccgggggaaa ttcgatccgt cgagattcga agttgcgccg
 1261 aaaccgaata cattcatgcc ttttggtagt gggattcatt cttgtccagg caatgagtta
 1321 gctaaacttg aaatctctgt tctaatccat catctcacca ctaagtacag atggtcaatc
 1381 gtagggccta gcgatggaat tcagtatggg ccgttcgctc ttcctcagaa tggattgcct
 1441 attgccttgg aacgaaaacc atagatgaat tacgagaata ccatttacct ttcttaaatt
 1501 agaaagtgag gaattttttt tcttatttaa gaggaaaatc taattctttt ttataataga
 1561 aatgaaaaga aagtagaaga aaaaaatccc aagtgggacc ccccaagtgt atataagttt
 1621 tagtttataa aatgtagaga attaaatttt cggagaaaaa agagaattag ttatataaat

FIG. 11 cont'd

```
1681 gttccatgtg tatgtaactt ggttcatgcc tctatatctt tatttttgta attttctcaa
1741 attgtaaatt cctttattac gaatgtaatg actgatggaa tgctcataga gaatttcaga
1801 aaaaaaaaaa aaaa
```

SEQ ID NO: 431
ACCESSION NM_112814 Arabidopsis thaliana CYP707A4; heme binding / iron ion binding / monooxygenase/ oxygen binding AT3G19270 (CYP707A4) mRNA, complete cds MAEIWFLVVPILILCLLLVRVIVSKKKKNSRGKLPPGSMGWPYLGETLQLYSQNP
NVFFTSKQKRYGEIFKTRILGYPCVMLASPEAARFVLVTHAHMFKPTYPRSKEKL
IGPSALFFHQGDYHSHIRKLVQSSFYPETIRKLIPDIEHIALSSLQSWANMPIVSTYQ
EMKKFAFDVGILAIFGHLESSYKEILKHNYNIVDKGYNSFPMSLPGTSYHKALMA
RKQLKTIVSEIICERREKRALQTDFLGHLLNFKNEKGRVLTQEQIADNIIGVLFAA
QDTTASCLTWILKYLHDDQKLLEAVKAEQKAIYEENSREKKPLTWRQTRNMPLT
HKVIVESLRMASIISFTFREAVVDVEYKGYLIPKGWKVMPLFRNIHHNPKYFSNP
EVFDPSRFEVNPKPNTFMPFGSGVHACPGNELAKLQILIFLHHLVSNFRWEVKGG
EKGIQYSPFPIPQNGLPATFRRHSL SEQ ID NO: 432
ACCESSION NM_112814 Arabidopsis thaliana CYP707A4; heme binding / iron ion binding / monooxygenase/ oxygen binding AT3G19270 (CYP707A4) mRNA, complete cds

```
   1 gtatgttttt gttccctatt atatcttcta gcttctttct tcctcttctt ccttaaaaat
  61 tcatcctcca aaacattcta tcatcaacga aacatttcat attaaattaa ataataatcg
 121 atggctgaaa tttggttctt ggttgtacca atcctcatct tatgcttgct tttggtaaga
 181 gtgattgttt caaagaagaa aaagaacagt agaggtaagc ttcctcctgg ttccatggga
 241 tggccttact taggagagac tctacaactc tattcacaaa accccaatgt tttcttcacc
 301 tccaagcaaa agagatatgg agagatattc aaaacccgaa tcctcggcta tccatgcgtg
 361 atgttggcta gccctgaggc tgcgaggttt gtacttgtga ctcatgccca tatgttcaaa
 421 ccaacttatc cgagaagcaa agagaagctg ataggaccct ctgcactctt tttccaccaa
 481 ggagattatc attcccatat aaggaaactt gttcaatcct ctttctaccc tgaaaccatc
 541 cgtaaactca tccctgatat cgagcacatt gcccttttct ccttacaatc ttgggccaat
 601 atgccgattg tctccaccta ccaggagatg aagaagttcg cctttgatgt gggtattcta
 661 gccatatttg gacatttgga gagttcttac aaagagatct tgaaacataa ctacaatatt
 721 gtggacaaag gctacaactc tttccccatg agtctccccg gaacatctta tcacaaagct
 781 ctcatggcga gaaagcagct aaagacgata gtaagcgaga ttatatgcga aagaagagag
 841 aaaagggcct tgcaaacgga cttcttggt catctactca acttcaagaa cgaaaaaggt
 901 cgtgtgctaa cccaagaaca gattgcagac aacatcatcg gagtcctttt cgccgcacag
 961 gacacgcacg ctagttgctt aacttggatt cttaagtact tacatgatga tcagaaactt
1021 ctagaagctg ttaaggctga gcaaaaggct atatatgaag aaaacagtag agagaagaaa
1081 cctttaacat ggagacaaac gaggaatatg ccactgacac ataaggttat agttgaaagc
1141 ttgaggatgg caagcatcat atccttcaca ttcagagaag cagtggttga tgttaatat
1201 aagggatatt tgatacctaa gggatggaaa gtgatgccac tgtttcggaa tattcatcac
1261 aatccgaaat attttcaaaa ccctgaggtt ttcgacccca ctagattcga ggtaaatccg
1321 aagccgaata cattcatgcc ttttggaagt ggagttcatg cttgtcccgg gaacgaactc
1381 gccaagttac aaattcttat atttctccac catttagttt ccaatttccg atgggaagtg
```

FIG. 11 cont'd

```
1441 aagggaggag agaaaggaat acagtacagt ccatttccaa tacctcaaaa cggtcttccc
1501 gctacatttc gtcgacattc tctttagttc cttaaaccrt tgtagtaatc tttgttgtag
1561 ttagccaaat ctaatccaaa ttcgatataa aaaatccect ttctattttt ttttaaaatc
1621 attgttgtag tcttgagggg gtttaacatg taacaactat gatgaagtaa aatgtcgatt
1681 ccggt
```

SEQ ID NO: 433
E3 ubiquitin-protein ligase CBL (Signal transduction protein CBL) (Proto-oncogene c-CBL) (Casitas B-lineage lymphoma proto-oncogene) (RING finger protein 55)
>embl|X57110|HSCCBL Human mRNA for c-cbl proto-oncogene
MAGNVKKSSGAGGGTGSGGSGSGGLIGLMKDAFQPHHHHHHHLSPHPPGTVDK
KMVEKCWKLMDKVVRLCQNPKLALKNSPPYILDLLPDTYQHLRTILSRYEGKM
ETLGENEYFRVFMENLMKKTKQTISLFKEGKERMYEENSQPRRNLTKLSLIFSML
AELKGIFPSGLFQGDTFRITKADAAEFWRKAFGEKTIVPWKSFRQALHEVHPISSG
LEAMALKSTIDLTCNDYISVFEFDIFTRLFQPWSSLLRNWNSLAVTHPGYMAFLT
YDEVKARLQKFIHKPGSYIFRLSCTRLGQWAIGYVTADGNILQTIPHNKPLFQALI
DGFREGFYLFPDGRNQNPDLTGLCEPTPQDHIKVTQEQYELYCEMGSTFQLCKIC
AENDKDVKIEPCGHLMCTSCLTSWQESEGQGCPFCRCEIKGTEPIVVDPFDPRGS
GSLLRQGAEGAPSPNYDDDDDERADDTLFMMKELAGAKVERPPSPFSMAPQAS
LPPVPPRLDLLPQRVCVPSSASALGTASKAASGSLHKDKPLPVPPTLRDLPPPPPP
DRPYSVGAESRPQRRPLPCTPGDCPSRDKLPPVPSSRLGDSWLPRPIPKVPVSAPS
SSDPWTGRELTNRHSLPFSLPSQMEPRPDVPRLGSTFSLDTSMSMNSSPLVGPECD
HPKIKPSSSANAIYSLAARLPVPKLPPGEQCEGEEDTEYMTPSSRPLRPLDTSQSSR
ACDCDQQIDSCTYEAMYNIQSQAPSITESSTFGEGNLAAAHANTGPEESENEDDG
YDVPKPPVPAVLARRTLSDISNASSSFGWLSLDGDPTTNVTEGSQVPERPPKPFPR
RINSERKAGSCQQGSPAASAATASPQLSSEIENLMSQGYSYQDIQKALVIAQNNI
EMAKNILREFVSISSPAHVAT SEQ ID NO: 434
E3 ubiquitin-protein ligase CBL (Signal transduction protein CBL) (Proto-oncogene c-CBL) (Casitas B-lineage lymphoma proto-oncogene) (RING finger protein 55)
>embl|X57110|HSCCBL Human mRNA for c-cbl proto-oncogene
gaattccgggcccggatagccggcggcggcggcggcggcggcggcggccgggagaggcccctccttcacgcc
ctgcttctctccctcgctcgcagtcgagccgagccggcggacccgcctgggctccgaccctgcccaggccatggccggcaac
gtgaagaagagctctggggccggggggcggcacgggctccgggggctcggggttcgggtggcctgattgggctcatgaagga
cgccttccagccgcaccaccaccaccaccaccacctcagcccccacccgccggggacggtggacaagaagatggtggaga
agtgctggaagctcatggacaaggtggtgcggttgtgtcagaacccaaagctggcgctaaagaatagcccaccttatatcttaga
cctgctaccagatacctaccagcatctccgtactatcttgtcaagatatgaggggaagatggagacacttggagaaaatgagtatt
ttagggtgtttatggagaatttgatgaagaaaactaagcaaaccataagcctcttcaaggagggaaaagaaagaatgtatgagga
gaattctcagcctaggcgaaacctaaccaaactgtccctcatcttcagccacatgctggcagaactaaaaggaatctttccaag
tggactctttcaggagacacatttcggattactaaagcagatgctgcggaattttggagaaaagcttttggggaaaagacaatag
tcccttggaagagctttcgacaggctctacatgaagtgcatcccatcagttctgggctggaggccatggctctgaaatccactatt
gatctgacctgcaatgattatatttcggttttgaatttgacatctttacccgactcttcagccctggtcctcttgctcaggaattggaa
cagccttgctgtaactcatcctggctacatggctttttgacgtatgacgaagtgaaagctcggctccagaaattcattcacaaacct
ggcagttatatcttccggctgagctgtactcgtctgggtcagtgggctattgggtatgttactgctgatgggaacattctccagaca
atccctcacaataaacctctcttccaagcactgattgatggcttcagggaaggcttctatttgtttcctgatggacgaaatcagaatc
ctgatctgactggcttatgtgaaccaactccccaagaccatatcaaagtgacccaggaacaatatgaattatactgtgagatgggc
```

FIG. 11 cont'd tccacattccaactatgtaaaatatgtgctgaaaatgataaggatgtaaagattgagccctgtggacacctcatgtgcacatcctgt
cttacatcctggcaggaatcagaaggtcagggctgtcctttctgccgatgtgaaattaaaggtactgaacccatcgtggtagatcc
gtttgatcctagagggagtggcagcctgttgaggcaaggagcagagggagctccctccccaaattatgatgatgatgatgatga
acgagctgatgatactctcttcatgatgaaggaattggctggtgccaaggtggaacggccgccttctccattctccatggccccac
aagcttcccttcccccggtgccaccacgacttgaccttctgccgcagcgagtatgtgttccctcaagtgcttctgctcttggaactg
cttctaaggctgcttctggctcccttcataaagacaaaccattgccagtacctcccacacttcgagatcttccaccaccaccgcctc
cagaccggccatattctgttggagcagaatcccgacctcaaagacgccccttgccttgtacaccaggcgactgtccctccagag
acaaactgcccctgtcccctctagccgccttggagactcatggctgccccggccaatccccaaagtaccagtatctgccccaa
gttccagtgatccctggacaggaagagaattaaccaaccggcactcacttccatttcattgccctcacaaatggagcccagacc
agatgtgcctaggctcggaagcacgttcagtctggatacctccatgagtatgaatagcagcccattagtaggtccagagtgtgac
cacccaaaatcaaaccttcctcatctgccaatgccatttattctctggctgccagacctcttcctgtgccaaaactgccacctggg
gagcaatgtgagggtgaagaggacacagagtacatgactccctcttccaggcctctacggcctttggatacatcccagagttcac
gagcatgtgattgcgaccagcagattgatagctgtacgtatgaagcaatgtataatattcagtcccaggcgccatctatcaccgag
agcagcacctttggtgaagggaatttggccgcagcccatgccaacactggtcccgaggagtcagaaaatgaggatgatgggta
tgatgtcccaaagccacctgtgccggccgtgctggcccgccgaactctctcagatatctctaatgccagctcctcctttggctggtt
gtctctggatggtgatcctacaacaaatgtcactgaaggttcccaagttcccgagaggcctccaaaaccattcccgcggagaatc
aactctgaacggaaagctggcagctgtcagcaaggtagtggtcctgccgcctctgctgccaccgcctcacctcagctctccagt
gagatcgagaacctcatgagtcaggggtactcctaccaggacatccagaaagctttggtcattgcccagaacaacatcgagatg
gccaaaaacatcctccgggaatttgtttccatttcttctcctgcccatgtagctacctagcacaccatctccctgctgcaggtttaga
ggaccagtgagttgggagttattactcaagtggcacctagaagggcaggagttcctttggtgacttcacagtgaagtcttgccctc
tctgtgggatatcacatcagtggttccaagatttcaaagtggtgaaatgaaaatggagcagctagtatgtttattattttatgggtctt
gagtgcatttgaaggtg SEQ ID NO: 435
Arabidopsis thaliana ADH1 (ALCOHOL DEHYDROGENASE 1) AT1G77120.1
MSTTGQIIRCKAAVAWEAGKPLVIEEVEVAPPQKHEVRIKILFTSLCHTDVYFWE
AKGQTPLFPRIFGHEAGGIVESVGEGVTDLQPGDHVLPIFTGECGECRHCHSEESN
MCDLLRINTERGGMIHDGESRFSINGKPIYHFLGTSTFSEYTVVHSGQVAKINPDA
PLDKVCIVSCGLSTGLGATLNVAKPKKGQSVAIFGLGAVGLGAAEGARIAGASRI
IGVDFNSKRFDQAKEFGVTECVNPKDHDKPIQQVIAEMTDGGVDRSVECTGSVQ
AMIQAFECVHDGWGVAVLVGVPSKDDAFKTHPMNFLNERTLKGTFFGNYKPKT
DIPGVVEKYMNKELELEKFITHTVPFSEINKAFDYMLKGESIRCIITMGA SEQ ID NO: 436
Arabidopsis thaliana ADH1 (ALCOHOL DEHYDROGENASE 1) AT1G77120.1
1 tacatcacaa tcacacaaaa ctaacaaaag atcaaaagca agttcttcac tgttgataat
61 gtctaccacc ggacagatta ttcgatgcaa agctgctgtg gcatgggaag ccggaaagcc
121 actggtgatc gaggaagtgg aggttgctcc accgcagaaa cacgaagttc gtatcaagat
181 tctcttcact tctctctgtc acaccgatgt ttacttctgg gaagctaagg gacaaacacc
241 gttgtttcca cgtatcttcg gccatgaagc tggagggatt gttgagagtg ttggagaagg
301 agtgactgat cttcagccag gagatcatgt gttgccgatc tttaccggag aatgtggtga
361 gtgtcgtcat tgccactcgg aggaatcaaa catgtgtgat cttctcagga tcaacaccga
421 gcgaggaggg atgattcacg atggtgaatc aagattctcc attaatggca aaccaattta
481 ccatttcctt gggacttcca cgttcagtga gtacacagtg gttcactctg gtcaggttgc
541 taagatcaat ccggatgctc ctcttgacaa ggtctgtatt gtcagttgtg gtttgtctac
601 tgggttagga gcaactttga atgtggctaa acccaagaaa ggtcaaagtg ttgccatttt

FIG. 11 cont'd

```
 661 tggtcttggt gctgttggtt taggcgctgc agaaggtgct agaatcgctg gtgcttctag
 721 gatcatcggt gttgatttta actctaaaag attcgaccaa gctaaggaat tcggtgtgac
 781 cgagtgtgtg aacccgaaag accatgacaa gccaattcaa caggtgatcg ctgagatgac
 841 ggatggtggg gtggacagga gtgtggaatg caccggaagc gttcaggcca tgattcaagc
 901 atttgaatgt gtccacgatg gctggggtgt tgcagtgctg gtgggtgtgc caagcaaaga
 961 cgatgccttc aagactcatc cgatgaattt cttgaatgag aggactctta agggtacttt
1021 cttcgggaac tacaaaccca aaactgacat tcccggggtt gtggaaaagt acatgaacaa
1081 ggagctggag cttgagaaat tcatcactca cacagtgcca ttctcggaaa tcaacaaggc
1141 ctttgattac atgctgaagg gagagagtat tcgttgcatc atcaccatgg gtgcttgaag
1201 ccattctctc gcagatgatg ttcactttgt gttttacttc ctttatgcat tcacagcaat
1261 aaaagaaaga aatctccatc gcttttggtt ttcttctctg tcttaagtta gtcgttttcg
1321 tgtctaatct attacttatc attgtaatag actcttcttc tattgagatt tgaatataaa
1381 ctaaaacaca ttccatttt
```

FIG. 12

SEQ ID NO: 437
forward primer; 5'- TTTGGATCCGACAACATCATTTCTACCGACA-3'

SEQ ID NO: 438
reverse primer; 5'- CCCTCTAGATAGCTGTACACAACAAACACACTC-3'

SEQ ID NO: 439
*XERICO* forward primer; 5'- TTGGAACATCACTTGCCCAT-3'

SEQ ID NO: 440
*XERICO* reverse primer; 5'-TGTGTTCAAACAAGAGCTCCA-3'

SEQ ID NO: 441
*AtNCED3* forward primer; 5'-AATCATACTCAGCCGCCATT-3'

SEQ ID NO: 442
*AtNCED3* reverse primer; 5'-TTTAGTTCCGTCCGGTGAGAA-3'

SEQ ID NO: 443
*AtCYP707A2* forward primer; 5'-TGCAAATCTCATCTTCATCGT-3'

SEQ ID NO: 444
*AtCYP707A2* reverse primer; 5'-TGTCGAATGCTGAATTGCTC-3'

SEQ ID NO: 445
*RD29a* forward primer; 5'-GTGGAGAAGATCTCTACCGAGAAGG-3'

SEQ ID NO: 446
*RD29a* reverse primer; 5'-CATCAAAGACGTCAAACAAAACACA-3'

SEQ ID NO: 447
*Actin 8* forward; 5'-ATGAAGATTAAGGTCGTGGCA-3'

SEQ ID NO: 448
*Actin 8* reverse 5'- TCCGAGTTTGAAGAGGCTAC-3'

SEQ ID NO: 449
truncated *XERICO* cDNA without transmembrane domain
forward 5'- GGGGGAATTCGAGTCATTTGATTTCCGGGT-3'

SEQ ID NO: 450
truncated *XERICO* cDNA without transmembrane domain
reverse 5'- GGGGCTGCAGTCACCAAACATTAGAAGAAAGC -3'

SEQ ID NO: 451

FIG. 12 cont'd

*XERICO* probe for Northern blots
ttggaacatcacttgcccattgtgtaggactcctcttgttgttgtgccagaagaccatcagctttcttctaatgtttggtgactgcttttc
actgtataggtttttgtttgagtgtgtttgttgtgtacagctacttttactatgaattaggttgcatcgcggttgattctcgagcagattta
aaccggggatgggataatctgatgtacatatatatatatacccatgtgtatggagctcttgtttgaacaca SEQ ID NO: 452
AtNCED3
aatcata ctcagccgcc attatcgtct
 201 tctcaaagct ccgacttgag ttattgtagc tccttaccta tggccagtcg
 251 tgtcacacgt aagctcaatg tttcatctgc gcttcacact cctccagctc
 301 ttcatttccc taagcaatca tcaaactctc ccgccattgt tgttaagccc
 351 aaagccaaag aatccaacac taaacagatg aatttgttcc agagagcggc
 401 ggcggcagcg ttggacgcgg cggagggttt ccttgtcagc cacgagaagc
 451 tacaccgct tcctaaaacg gctgatccta gtgttcagat cgccggaaat
 501 tttgctccgg tgaatgaaca gcccgtccgg cgtaatcttc cggtggtcgg
 551 aaaacttccc gattccatca aaggagtgta tgtgcgcaac ggagctaacc
 601 cacttcacga gccggtgaca ggtcaccact tcttcgacgg agacggtatg
 651 gttcacgccg tcaaattcga acacggttca gctagctacg cttgccggtt
 701 tactcagact aaccggtttg ttcaggaacg tcaattgggt cgaccggttt
 751 tccccaaagc catcggtgag cttcacggcc acaccggtat tgcccgactc
 801 atgctattct acgccagagc tgcagccggt atagtcgacc cggcacacgg
 851 aaccggtgta gctaacgccg gtttggtcta tttcaatggc cggttattgg
 901 ctatgtcgga ggatgattta ccttaccaag ttcagatcac tcccaatgga
 951 gatttaaaaa ccgttggtcg gttcgatttt gatggacaat tagaatccac
1001 aatgattgcc cacccgaaag tcgacccgga atccggtgaa ctcttcgctt
1051 taagctacga cgtcgtttca aagccttacc taaaatactt ccgattctca
1101 ccggacggaa ctaaa SEQ ID NO: 453
AtCYP707A2
tgcaaatct catcttcatc gtcttcaaat ttcttctctt ctctttatgc
  51 tgatgaaccg gcactaatca cattaacaat tgttgtagta gtagtagtgt
 101 tactatttaa atggtggttg cactggaaag agcaaagact acggctacct
 151 cctggctcca tggggttgcc ttacatcgga gagacactcc gcctctacac
 201 agaaaatccc aattccttct tcgccactcg ccaaaacaag tacggggata
 251 tattcaagac gcacatatta ggatgtccat gtgtgatgat aagtagtcca
 301 gaggcggctc gaatggtgtt agtgagcaaa gctcacttgt tcaagccaac
 351 ttatcctcca agcaaagagc gtatgattgg accagaggct cttttcttcc
 401 accaaggtcc ataccattct acccttaagc ggctggtcca gtcttctttc
 451 atgccttctg ctctcagacc aaccgtctct cacatcgagc tccttgtcct
 501 ccaaacccctt tcctcttgga cgtcccaaaa gtccatcaac accctcgaat
 551 acatgaaacg atatgcattc gatgtggcga tcatgtcagc gttcggggac
 601 aaagaggagc ccactacgat tgatgttatt aagcttctct atcaacgtct
 651 cgaaaggggt tacaactcca tgcctctcga cctaccgggc acacttttc
 701 ataagtccat gaaggcaaga atagaattaa gcgaggaact aaggaaagta
 751 atagagaaga gaagagagaa tgggagagaa gaaggaggac tattgggagt

FIG. 12 cont'd

```
801 acttctggga gcaaaggatc aaaaacgcaa cggcttaagt gattcacaga
851 ttgctgacaa catcatcggt gttatattcg ccgccaccga caccaccgct
901 tctgtcttaa cttggcttct caagtactta cacgaccacc ccaatctcct
951 ccaagaagtc tccagggagc aattcagcat tcgaca
```

SEQ ID NO: 454
RD29a
gtgga gaagatctct accgagaagg
```
1951 cagcatcgga ggagggtgag gcggtggaag aggaagtgaa aggaggagga
2001 ggaatggttg ggaggattaa aggatggttc ggtggtggtg cgactgatga
2051 ggtgaagcca gaatcgccac attctgttga agaggctcca aaatcatctg
2101 gctggtttgg tggtggtgcg acggaggagg tgaagccaaa atcgcctcat
2151 tccgttgaag agtctccaca atcacttggc tccactgttg ttccggtgca
2201 gaaggagctt taagaatatg agaactgaga ttttcaagtt tcactttgga
2251 tgtttatgtg tgttttgttt gacgtctttg atg
```

SEQ ID NO: 455
Actin 8
atg
```
1151 aagattaagg tcgtggcacc acccgagagg aagtacagtg tctggattgg
1201 tggttctatc cttgcttccc tcagcacttt ccagcagatg tggatctcta
1251 aggcagagta tgatgaagca ggtccaggca ttgtccacag aaaatgcttc
1301 taaactaaag agacatcgtt tccatgacgg gatcacattt ctttctattt
1351 ctccaatttg tttgtttcaa attttttttcc cctttgtcat ttgtgcacta
1401 tgtgagaaac tttccggtta cagcgtttgg agagatgtct aaggaggagc
1451 aggtttgaaa acccgctctc gctcttacct gaggcactaa tccgcgtttc
1501 aaactcagct tcattctcta ttcttgtcca tttgtttgtt tgtttgtagc
1551 ctcttcaaac tcgga
```

DNA ENCODING RING ZINC-FINGER PROTEIN AND THE USE OF THE DNA IN VECTORS AND BACTERIA AND IN PLANTS

BENEFIT OF PRIORITY

This Application is a Continuation of U.S. patent application Ser. No. 11/484,947, filed Jul. 12, 2006, now U.S. Pat. No. 7,977,535, which application is incorporated by reference herein its entirety.

This invention was made with government support under 2004-34158-15188 awarded by the United States Department of Agriculture. The government has certain rights in this invention.

FIELD OF THE INVENTION

The present inventions relate to compositions and methods for providing stress tolerant transgenic plants comprising a RING domain zinc-finger motif transcription factor protein. More particularly, the invention relates to compositions and methods comprising a RING-H2 domain transcription factor protein for providing drought and salt tolerant plants, in particular comprising a recombinant XERICO gene and protein.

BACKGROUND OF THE INVENTION

Drought is one of the major limiting factors for plant productivity and spatial distribution. The annual loss in yield of major cereal crops due to drought is estimated to exceed ten billion dollars globally. Furthermore, desertification, defined as "Land degradation in arid, semi-arid and dry sub-humid areas," is happening in about 70% of the total drylands (3.6 billion hectares) of the world and has become a very distinctive global issue with major environmental consequences. It affects about 25% of the total land area of the world and about 17% of the world population. Development of drought-tolerant plant species represents a promising strategy to tackle these problems. Conventional crop improvement for enhanced drought tolerance has been ineffective, mainly due to limited germplasm resources and incompatibility in crosses between distantly related plant species. Recent advances in plant gene discovery and genetic transformation paved the road to generate stress-tolerant crops using transgenic approaches.

Despite the enormous economic and environmental significance, identification and characterization of plant genes that confer drought tolerance remains a challenge.

SUMMARY OF THE INVENTION

The present inventions relate to compositions and methods for providing stress tolerant transgenic plants comprising a RING domain zinc-finger motif transcription factor protein. More particularly, the invention relates to compositions and methods comprising a RING-H2 domain transcription factor protein for providing drought and salt tolerant plants, in particular comprising a recombinant XERICO gene and protein.

The present invention is not limited to any particular plant gene sequence encoding a polypeptide comprising a RING-H2 zinc-finger motif transcription domain having effects on environmental tolerance. In some embodiments, the invention provides an expression vector construct comprising a nucleic acid encoding a polypeptide at least 32% identical to SEQ ID NO:01, operably linked to a heterologous promoter, wherein said nucleic acid encodes a polypeptide comprising a RING-112 zinc-finger motif transcription domain, a low complexity region, and a transmembrane domain, for increasing tolerance to abiotic stress in a plant. In other embodiments, said polypeptide is at least 56% identical to SEQ ID NO:01. In some embodiments, the present invention provides polypeptide sequences at least 32%, 35%, 36%, 38%, 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:01. In some embodiments, the present invention provides polypeptide fragments. In some embodiments, the present invention provides full-length polypeptides. In other embodiments, said RING-H2 zinc-finger motif transcription domain comprises SEQ ID NO:06 or SEQ ID NO:07.

In other embodiments, said RING-H2 zinc-finger motif transcription domain has at least a 40% amino acid sequence identity to SEQ ID NO:03. In some embodiments, the present invention provides RING-H2 zinc-finger motif transcription domain polypeptide sequences at least 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:03. The present invention is not limited to any particular low complexity region. Indeed, a variety of low complexity regions are contemplated. In other embodiments, said low complexity region is selected from one or more of the group SEQ ID NOs:456-477. In other embodiments, said transmembrane region is selected from the group consisting of SEQ ID NOs:478-492. In other embodiments, said polypeptide binds to a COP1-INTERACTING PROTEIN 8 SEQ ID NO:378 or a TUBBY-like protein 9 SEQ ID NO:380. In other embodiments, said abiotic stress is one or more of drought tolerance and salt tolerance. In other embodiments, said heterologous promoter is a eukaryotic promoter. In other embodiments, said heterologous promoter is a plant promoter. In other embodiments, said heterologous promoter is active in a plant. The expression vector construct, wherein said heterologous promoter is a yeast promoter, active in yeast. In other embodiments, said vector is a eukaryotic vector. In other embodiments, said eukaryotic vector is a plant vector. In other embodiments, said plant vector is a T-DNA vector. In other embodiments, said expression vector is a prokaryotic vector. In other embodiments, said plant is selected from the group consisting of Aizoaceae (iceplant family), Amaranthaceae (amaranth family), including Chenopodiaceae and Chenopodioideae, further including beet, goosefoot, quinoa, and spinach, Alliaceae, further comprising *Allium* sp., including onions (*Allium cepa*), chives (*A. schoenoprasum*), garlic (*A. sativum*) and leeks (*A. porrum*), Asteraceae or Compositae (daisy and sunflower family), Brassicaceae or Cruciferae (mustard family and cabbage family) including *Brassica oleracea* such as cabbage, broccoli, cauliflower, brussels sprouts, collards, kale, further, *Brassica rapa* such as Bok choy (chinensis group), Chinese kale, Chinese cabbage (pekinensis group), rutabaga, seakale, Turnip (rapa group), radish, kohl rabi, rapini (ruvo group), flowering cabbage (parachinensis group) and *Brassica napus* (rape) rapeseed (such as oilseed rape, canola and others), mustard, horseradish, wasabi, watercress *Arabidopsis thaliana*, and *Thellungiella* Halophila, Cucurbitaceae (cucumber family) including melon, cucumber, calabash, squash, and luffa, Euphorbiaceae (spurge family) including manioc, castor bean, and the Para rubber tree, ornamental plants, such as poinsettia (*Euphorbia pulcherrima*), Fabaceae or Leguminosae (pea family) including legumes and pulses, such as beans, peas, peanuts, soybeans, lentils, lupins, clover, alfalfa, *Lotus corniculatus* var. *japonicus* (Bird's-foot Trefoil, Birdsfoot Trefoil, Birdfoot Trefoil, or Bird's Foot Trefoil) *cassia*, and soybean, ornamental trees and shrubs such as Laburnum, *Robinia, Gleditsia, Acacia, Mimosa,* and *Delonix*, Malvaceae (mallow family) including *Gossypium* sp. such as cotton, Pinaceae (pine family) including conifers such as cedars, firs, hemlocks, larches, pines and spruces, Poaceae or Gramineae (grass family), Rosaceae (rose family), Solanaceae (nightshade family), Salicaceae (willow family), Scrophulariaceae, wherein Scrophulariaceae further comprises Orobanchaceae and Plantaginaceae, and Vitaceae (grape family). In some embodiments, the invention provides a transgenic plant comprising a heterologous nucleic acid molecule encoding a polypeptide that is at least 32% identical to SEQ ID NO:01, wherein said polypeptide comprises a RING-H2 zinc-finger motif transcription domain, a low complexity region, and a transmembrane domain, for increasing tolerance to abiotic stress in a plant. In other embodiments, said polypeptide is at least 56% identical to SEQ ID NO:01. In some embodiments, the present invention provides polypeptide sequences at least 32%, 35%, 36%, 38%, 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:01. In some embodiments, the present invention provides polypeptide fragments. In some embodiments, the present invention provides full-length polypeptides. In other embodiments, said heterologous nucleic acid molecule is contained within the expression vector. In other embodiments, said RING-H2 zinc-finger motif transcription domain comprises SEQ ID NO:06 or SEQ ID NO:07. In other embodiments, said RING-H2 zinc-finger motif transcription domain has at least 40% amino acid sequence identity to SEQ ID NO:03. In some embodiments, the present invention provides RING-H2 zinc-finger motif transcription domain polypeptide sequences at least 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:03. In other embodiments, said low complexity region is selected from one or more of the group SEQ ID NOs:376-397. In other embodiments, said transmembrane region is selected from the group consisting of SEQ ID NOs:478-492. In other embodiments, said polypeptide binds to a COP1-INTERACTING PROTEIN 8 SEQ ID NO:378 or a TUBBY-like protein 9 SEQ ID NO:380. In other embodiments, said polypeptide alters expression of COP1-INTERACTING PROTEIN 8 SEQ ID NO: 378 or a TUBBY-like protein 9 SEQ ID NO:0:380. In other embodiments, said polypeptide alters function of COP1-INTERACTING PROTEIN 8 SEQ ID NO:378 or a TUBBY-like protein 9 SEQ ID NO:380. In other embodiments, said abiotic stress is one or more of drought tolerance and salt tolerance. In other embodiments, said plant is selected from the group consisting of Aizoaceae, Amaranthaceae, Alliaceae, Asteraceae, Brassicaceae, Cucurbitaceae, Euphorbiaceae, Fabaceae, Malvaceae, Pinaceae, Poaceae, Rosaceae, Solanaceae, Salicaceae, Scrophulariaceae, and Vitaceae. In other embodiments, said plant is selected from the group consisting of a crop plant, an herb plant, a turfgrass plant, an ornamental plant and a tree. In other embodiments, said plant is selected from the group consisting of *Arabidopsis* sp., *Capsicum* sp., *Citrullus* sp., *Fragaria* sp., *Glycine* sp., *Gossypium* sp., *Helianthus* sp., *Hevea* sp., *Hordeum* sp., *Lactuca* sp., *Lycopersicon* sp., *Lotus* sp. *Oryza* sp., *Pinus* sp., *Picea* sp., *Ponciru* sp., *Solanum* sp., *Sorghum* sp., *Thellungiella* sp., *Triphysaria* sp., *Triticum* sp., *Vaccinium* sp., and *Zea* species. The transgenic plant, wherein said crop plant is one or more of *Arabidopsis* sp., *Capsicum* sp., *Citrullus* sp., *Fragaria* sp., *Glycine* sp., *Gossypium* sp., *Helianthus* sp., *Hevea* sp., *Hordeum* sp., *Lactuca* sp., *Lycopersicon* sp., *Medicago* sp., *Oryza* sp., *Ponciru* sp., *Solanum* sp., *Sorghum* sp., *Thellungiella* sp., *Trifolium* sp., *Triticum* sp., *Vaccinium* sp., and *Zea* species. In other embodiments, said herb plant is a *Triphysaria* species. In other embodiments, said ornamental plant is a *Lotus* sp. or a *Helianthus* species. In other embodiments, said grass plant is one or more of a bromegrass, clover, alfalfa, timothy, orchard grass, bahiagrass, Bermudagrass, centipedegrass, St. Augustine grass, zoysiagrass, carpetgrass, centipedegrass, buffalograss, hurricanegrass, tall fescue and seashore *paspalum*. In other embodiments, said tree is one or more of a *Hevea* sp., *Picea* sp., *Pinus* sp., and *Populus* species. In a preferred embodiment said tree is a poplar or a hybrid poplar. In other embodiments, said transgenic plant is a seed. In other embodiments, said transgenic plant is a tiller. In other embodiments, said transgenic plant is a plant cell. In some embodiments, the invention provides a vector, comprising a first nucleic acid sequence encoding a nucleic acid product that interferes with the expression of a second nucleic acid sequence encoding a polypeptide at least 32% identical to SEQ ID NO:01, wherein said polypeptide comprises a RING-H2 zinc-finger motif transcription domain, a low complexity region, and a transmembrane domain, for increasing tolerance to abiotic stress in a plant. In other embodiments, said polypeptide is at least 56% identical to SEQ ID NO:01. In some embodiments, the present invention provides polypeptide sequences at least 32%, 35%, 36%, 38%, 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:01. In some embodiments, the present invention provides polypeptide fragments. In some embodiments, the present invention provides full-length polypeptides. In other embodiments, said RING-H2 zinc-finger motif transcription domain comprises SEQ ID NO:06 or SEQ ID NO:07. In other embodiments, said nucleic acid product that interferes is an antisense sequence. In other embodiments, said nucleic acid product that interferes is a dsRNA that mediates RNA interference.

In some embodiments, the invention provides a method for altering the phenotype of a plant, comprising: a) providing; i) an expression vector construct comprising a nucleic acid sequence encoding a polypeptide at least 32% identical to SEQ ID NO:01, wherein said polypeptide comprises a RING-H2 zinc-finger motif transcription domain, operably linked to a heterologous promoter, and ii) plant tissue; and b) transfecting the plant tissue with the vector so that the phenotype of a plant derived from said plant tissue is altered. In other embodiments, said polypeptide is at least 56% identical to SEQ ID NO:01. In some embodiments, the present invention provides polypeptide sequences at least 32%, 35%, 36%, 38%, 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:01. In some embodiments, the present invention provides polypeptide fragments. In some embodiments, the present invention provides full-length polypeptides. In other embodiments, said RING-1-12 zinc-finger motif transcription domain comprises SEQ ID NO:06 or SEQ ID NO:07. In other embodiments, said RING-H2 zinc-finger motif transcription domain having at least a 40% amino acid sequence identity to SEQ ID NO:03. In some embodiments, the present invention provides RING-H2 zinc-finger motif transcription domain polypeptide sequences at least 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:03. In other embodiments, said low complexity region is selected from one or more of the group SEQ ID NOs:456-477. In other embodiments, said transmembrane region is selected from the group consisting of SEQ ID NOs:478-492.

In other embodiments, said polypeptide binds to a COP1-INTERACTING PROTEIN 8 SEQ ID NO:289 or a TUBBY-like protein 9 SEQ ID NO:291. In other embodiments, said altered phenotype is altered environmental tolerance. In other embodiments, said altered environmental tolerance is altered abiotic stress. In other embodiments, said altered abiotic stress is selected from the group consisting of water tolerance and salt tolerance. In other embodiments, said plant tissue comprises one or more of calli and primordial meristem. In other embodiments, said plant is selected from the group consisting of Aizoaceae, Amaranthaceae, Alliaceae, Asteraceae, Brassicaceae, Cucurbitaceae, Euphorbiaceae, Fabaceae, Malvaceae, Pinaceae, Poaceae, Rosaceae, Solanaceae, Salicaceae, Scrophulariaceae, and Vitaceae. In other embodiments, said plant is selected from the group consisting of a crop plant, an herb plant, a turfgrass plant, an ornamental plant and a tree. In other embodiments, said plant is selected from the group consisting of *Arabidopsis* sp., *Capsicum* sp., *Citrullus* sp., *Fragaria* sp., *Glycine* sp., *Gossypium* sp., *Helianthus* sp., *Hevea* sp., *Hordeum* sp., *Lactuca* sp., *Lycopersicon* sp., *Lotus* sp. *Oryza* sp., *Pinus* sp., *Picea* sp., *Ponciru* sp., *Solanum* sp., *Sorghum* sp., *Thellungiella* sp., *Triphysaria* sp., *Triticum* sp., *Vaccinium* sp., and *Zea* species. In other embodiments, said altered phenotype comprises altering the gene expression of one or more of a 9-cis-epoxycarotenoid dioxygenase (SEQ ID NO:383), abscisic acid 8'-hydroxylase (SEQ ID NO:428), RD29a/COR78/LTI78 (SEQ ID NO:386), brassinolide (BL) 26-hydroxylase (SEQ ID NO:422); gibberellin 3-beta-dioxygenase (SEQ ID NO:424), CYP707A1 (SEQ ID NO:426), CYP707A2 (SEQ ID NO:428), CYP707A3 (SEQ ID NO:430), and CYP707A4 (SEQ ID NO:432).

In some embodiments, the invention provides a method for altering the phenotype of a plant, comprising: a) providing; i) an expression vector construct comprising a nucleic acid sequence encoding a polypeptide at least 32% identical to SEQ ID NO:01 wherein said polypeptide comprises a RING-H2 zinc-finger motif transcription domain, for increasing tolerance to abiotic stress in a plant; and ii) plant tissue; and b) transfecting the plant tissue with the vector so that the phenotype of a plant derived from said plant tissue is altered. In other embodiments, said polypeptide is at least 56% identical to SEQ ID NO:01. In some embodiments, the present invention provides polypeptide sequences at least 32%, 35%, 36%, 38%, 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:01. In some embodiments, the present invention provides polypeptide fragments. In some embodiments, the present invention provides full-length polypeptides. In other embodiments, said RING-H2 zinc-finger motif transcription domain comprises SEQ ID NO:06 or SEQ ID NO:07. In other embodiments, said altered phenotype is altered environmental tolerance. In other embodiments, said altered environmental tolerance is altered abiotic stress. In other embodiments, said altered abiotic stress is selected from the group consisting of water tolerance and salt tolerance. In other embodiments, said plant tissue comprises one or more of calli and primordial meristem. In other embodiments, said RING-H2 zinc-finger motif transcription domain having at least a 40% amino acid sequence identity to SEQ ID NO:03. In some embodiments, the present invention provides RING-H2 zinc-finger motif transcription domain polypeptide sequences at least 40%, 41%, 45%, 50%, 51%, 55%, 56%, 58%, 60%, 65%, 70%, 75%, 80%, 81%, 85%, 86%, 89%, 90%, 95%, 98%, 99% (or more) identical to any of SEQ ID NO:03. In other embodiments, said low complexity region is selected from one or more of the group SEQ ID NOs:456-477. In other embodiments, said transmembrane region is selected from the group consisting of SEQ ID NOs: 478-492. In other embodiments, said polypeptide binds to a COP1-INTERACTING PROTEIN 8 SEQ ID NO:289 or a TUBBY-like protein 9 SEQ ID NO:291 In other embodiments, said plant is selected from the group consisting of Aizoaceae, Amaranthaceae, Alliaceae, Asteraceae, Brassicaceae, Cucurbitaceae, Euphorbiaceae, Fabaceae, Malvaceae, Pinaceae, Poaceae, Rosaceae, Solanaceae, Salicaceae, Scrophulariaceae, and Vitaceae. In other embodiments, said plant is selected from the group consisting of a crop plant, an herb plant, a turfgrass plant, an ornamental plant and a tree. In other embodiments, said plant is selected from the group consisting of *Arabidopsis* sp., *Capsicum* sp., *Citrullus* sp., *Fragaria* sp., *Glycine* sp., *Gossypium* sp., *Helianthus* sp., *Hevea* sp., *Hordeum* sp., *Lactuca* sp., *Lycopersicon* sp., *Lotus* sp. *Oryza* sp., *Pinus* sp., *Picea* sp., *Ponciru* sp., *Solanum* sp., *Sorghum* sp., *Thellungiella* sp., *Triphysaria* sp., *Triticum* sp., *Vaccinium* sp., and *Zea* species. In other embodiments, said altered phenotype comprises altering the gene expression of one or more of a 9-cis-epoxycarotenoid dioxygenase (SEQ ID NO:383), abscisic acid 8'-hydroxylase (SEQ ID NO:428), RD29a/COR78/LTI78 (SEQ ID NO:386), brassinolide (BL) 26-hydroxylase (SEQ ID NO:422); gibberellin 3-beta-dioxygenase (SEQ ID NO:424), CYP707A1 (SEQ ID NO:426), CYP707A2 (SEQ ID NO:428), CYP707A3 (SEQ ID NO:430), and CYP707A4 (SEQ ID NO:432).

DESCRIPTION OF THE FIGURES

FIG. 10 shows full-length and partial nucleic acid sequences and amino acid sequences encoding plant RING zinc finger proteins, putative RING zinc finger proteins, RING-like proteins, and RING motifs (SEQ ID NOs:1-375).

FIG. 11 shows a 35S promoter sequence SEQ ID NO:376, a B-Box motif SEQ ID NO:377, genes and their encoded products that are regulated and/or associated with upregulation of RING zinc finger proteins in plants (SEQ ID NOs: 378-436).

FIG. 12 shows primers and probes of the present invention (SEQ ID NOs:437-455).

DEFINITIONS

Figure 1:
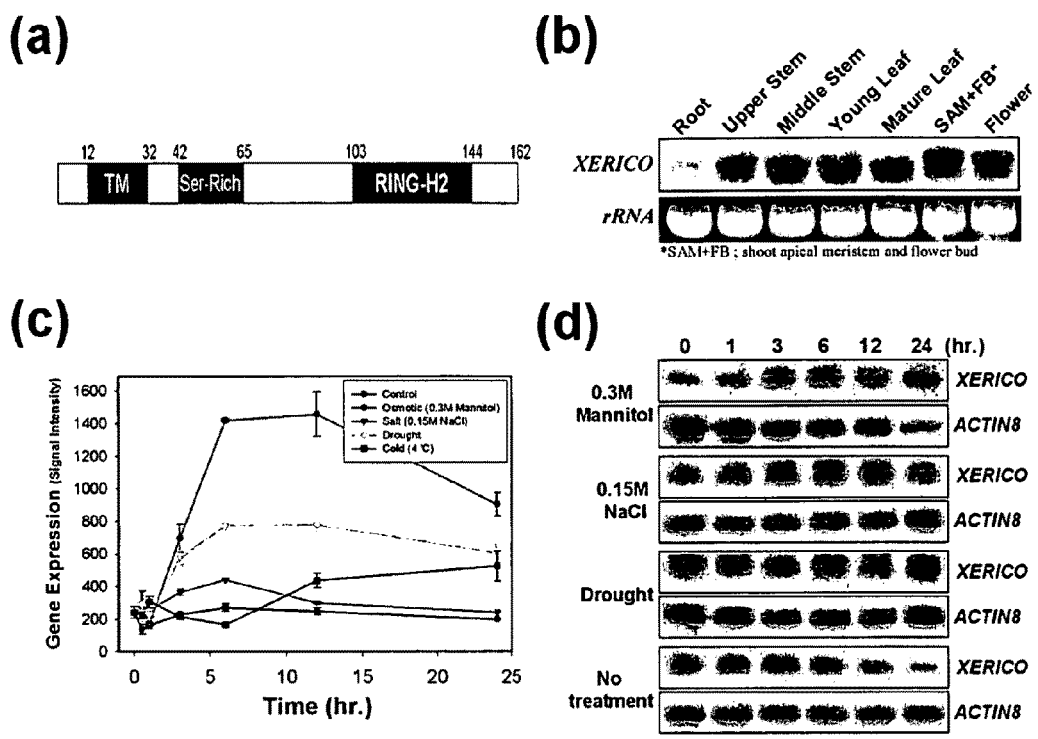
FIG. 1 demonstrates that XERICO (SEQ ID NO:02) encodes a novel RING-H2 type zinc finger protein. (a) Structure of XERICO (SEQ ID NO:01) protein showing a transmembrane (TM) domain (SEQ ID NO:09), a low complexity serine rich domain (Ser-Rich) (SEQ ID NO:08), and a RING-H2 domain (SEQ ID NO:03). (b) Tissue specific expression of XERICO in *Arabidopsis*. RNA gel blot analysis was performed using 10 μg of total RNA from the specified tissues and hybridized with [$^{32}$P]-labeled gene specific probe. Ethidium bromide stained rRNA serves as a RNA loading control. (c) Analysis of time course expression of XERICO in response to various abiotic stresses using the publicly available gene expression profiles from AtGenExpress as published on the AtGenExpress website. Experimental data were obtained from 18-day old wild-type *Arabidopsis* seedlings subjected to various abiotic stress treatments. The error bars indicate the mean±S.E. (d) Northern blot analysis to validate the microarray results presented in (c). Treatments of abiotic stresses (indicated on left side) were performed on plants for up to 24 hours. RNA gel blot analysis was performed using 10 μg of total RNA and hybridized with [$^{32}$P]-labeled gene specific probe. Actin 8 probing serves as a RNA loading control (SEQ ID NO:455).

To facilitate an understanding of the present invention, a number of terms and phrases are defined below:

The use of the article "a" or "an" is intended to include one or more.

The term "host cell" refers to any cell capable of replicating and/or transcribing and/or translating a heterologous gene. Thus, a "host cell" refers to any eukaryotic or prokaryotic cell (e.g., plant cells, algal cells such as *C. reinhardtii*, bacterial cells such as yeast cells, *E. coli*, insect cells, etc.), whether located in vitro or in vivo. For example, a host cell may be located in a transgenic plant, or located in a plant part or part of a plant tissue or in cell culture. The terms "eukaryotic" and "eukaryote" are used in it broadest sense. It includes, but is not limited to, any organisms containing membrane bound nuclei and membrane bound organelles. Examples of eukaryotes include but are not limited to plants, yeast, animals, alga, diatoms, and fungi. The terms "prokaryote" and "prokaryotic" are used in it broadest sense. It includes, but is not limited to, any organisms without a distinct nucleus. Examples of prokaryotes include but are not limited to bacteria, blue-green algae, archaebacteria, actinomycetes and mycoplasma. In some embodiments, a host cell is any microorganism. As used herein the term "microorganism" refers to microscopic organisms and taxonomically related macroscopic organisms within the categories of yeast, algae, bacteria, and fungi (including lichens).

As used herein, terms defined in the singular are intended to include those terms defined in the plural and vice versa.

As used herein, the terms "Really Interesting New Gene" "RING" and "RING-finger" refer to nucleic acids that code for an proteins comprising any of a specialized type of Zinc (Zn) finger of 40 to 60 amino acid residues that binds at least two atoms of zinc further defined by a "RING zinc-finger motif transcription domain" specifically comprising a "cross-brace" motif C-X2-C-X(9-39)-C-X(1-3)-H-X(2-3)-(N/C/H)-X2-C-X(4-48)C-X2-C (SEQ ID NO:05). A RING finger domain consists of either a RING-H2 type domain comprising a C3H2C3-type domain (see, for e.g., SEQ ID NO:06 or 07) or a RING-HC type domain comprising a C3HC4-type domain based upon a cysteine/histidine pattern in relation to whether a H or C occupies the 5th position of the domain motif. A further subset of RINGS comprises a B-Box motif that refers to a C-X2-H-X7-C-X7-C-X2-C-H-X2-H; see, for e.g., SEQ ID NO:377 (see, for e.g., Saurin et al. (1996) June; 21(6):208-14 and Kipreos and Pagano (2000) Genome Biol. 1(5):REVIEWS3002. Epub 2000 Nov. 10; herein incorporated by reference) and/or an "F-box" motif and "motif in cyclin F" comprising approximately 50 amino acids that functions as a site of protein-protein interaction (see, for e.g., Kipreos and Pagano (2000) Genome Biol. 1(5):REVIEWS3002, Epub 2000 Nov. 10; herein incorporated by reference). F-box proteins comprise a wide range of secondary motifs including zinc fingers, cyclin domains, leucine zippers, ring fingers, tetratricopeptide (TPR) repeats, and proline-rich regions.

As used herein, the term "XERICO" refers to *Arabidopsis thaliana* gene AT2G04240 and a protein encoded by AT2G04240. As used herein for the present invention the coding region of AT2G04240 comprises an expressed RING-H2 zinc-finger motif transcription domain, also referred to as a C3H2C3-type and/or a cd00162 type RING.

As used herein, the term "zinc-finger" and "ZFP" refers to nucleic acid coding for and the translated protein thereof wherein the protein in predicted to comprise a putative finger-shaped fold created by the binding of specific amino acids in the protein to at least one zinc atom. Zinc-finger proteins regulate the expression of genes as well as functioning in nucleic acid recognition, reverse transcription, virus assembly and protein-protein interactions.

The term "SCF complex" "Skp-Cullin-F-box" refers to a group of proteins comprising "Skp1," "Cdc53/Cul1," "Roc1/Rbx1/Hrt1" and "F-box" proteins comprising a class of ubiquitin ligase, i.e. "ubiquitin-protein isopeptide ligase (E3)" proteins required for the degradation of key regulatory proteins involved in one or more of cell cycle progression, development, and signal transduction.

The terms, "ABA," and "abscisic acid" refer to molecules that induce "ABA-responsive proteins" comprising "abscisic acid responsive elements" and "ABA responsive elements" that refer to DNA regions of in the promoter region that bind to ABA of genes that respond to ABA mediated environmental stress.

The term "abiotic stress" refers to a nonliving environmental factors such as drought, salt, cold, excessive heat, high winds, etc., that can have harmful effects upon plants. For the purposes of the present invention, examples of abiotic stress specifically include drought and salt factors.

The terms "altered environmental tolerance" and "altering environmental tolerance" refer to any changes in a plant's ability to tolerate an environmental abiotic stress. The terms "altered abiotic stress" and "altering abiotic stress" refer to any changes in abiotic tolerance such as an increased tolerance to an abiotic stress, such as "dry conditions" or "drought" and "high saline" or "salt." The terms "altered drought and/or salt tolerance" and "altering drought and/or salt tolerance" refer to any changes in drought and/or salt tolerance and changes in environmental factors such as low-potassium conditions/treatments.

As used herein, the term "hypersensitivity" refers to altered reactivity to an abiotic stress, for example, hypersensitivity to an environmental factor may be a pathological sensitivity such as reduced growth or death in response to salt or water deprivation such as demonstrated herein to salt/osmotic stress during early seedling growth.

For the purposes of the present invention, an "increasing" or "increased" tolerance refers to an increase over a control, such as a wild-type control or an nontransformed control plant or nontransformed plant part, such as when comparing a transgenic plant or leaf from a transgenic plant of the present invention to a closely related nontransformed wild-type plant or a leaf from a nontransformed wild-type plant. Examples include increasing expression of XERICO, increasing ABA content of plants under drought conditions, increasing the capability of a plant to continue growing under environmental conditions such as extreme dryness and higher salt exposure, such as using water comprising a higher than usual salinity, see, EXAMPLES.

The term "transgenic" when used in reference to a plant or leaf or fruit or seed for example a "transgenic plant," "transgenic leaf," "transgenic fruit," "transgenic seed," or a "transgenic host cell" refers to a plant or leaf or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells. In one embodiment, transgenic seedlings of the present invention may express XERICO at increased levels over wild-type seedlings (FIG. 2a).

The terms "transgenic" when used in reference to a plant or leaf or fruit or seed or plant part for example a "transgenic plant," "transgenic leaf," "transgenic fruit," "transgenic seed," and a "transgenic host cell" refer to a plant or leaf or fruit or seed or part or cell that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells. The term "portion" when used in reference to a protein (as in "a portion of a given protein") refers to fragments of that protein. The fragments may range in size from four amino acid residues to the entire amino sequence minus one amino acid.

The term "transgene" refers to a foreign gene that is placed into an organism or host cell by the process of transfection. The term "foreign gene" or heterologous gene refers to any nucleic acid (e.g., gene sequence) that is introduced into the genome of an organism or tissue of an organism or a host cell by experimental manipulations, such as those described herein, and may include gene sequences found in that organism so long as the introduced gene does not reside in the same location, as does the naturally occurring gene.

The terms "transformants" and "transformed cells" include the primary transformed cell and cultures derived from that cell without regard to the number of transfers. Resulting progeny may not be precisely identical in DNA content, due to deliberate or inadvertent mutations. Mutant progeny that have the same functionality as screened for in the originally transformed cell are included in the definition of transformants. The term "*Agrobacterium*" refers to a soil-borne, Gram-negative, rod-shaped phytopathogenic bacterium that causes crown gall. *Agrobacterium* is a representative genus of a soil-borne, Gram-negative, rod-shaped phytopathogenic bacterium family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. *Agrobacterium tumefaciens* causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell.

The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain GV3101, LBA4301, C58, A208, etc.) are referred to as "nopaline-type" Agrobacteria; *Agrobacterium* strains which cause production of octopine (e.g., strain LBA4404, Ach5, B6, etc.) are referred to as "octopine-type" Agrobacteria; and *Agrobacterium* strains which cause production of agropine (e.g., strain EHA105, EHA101, A281, etc.) are referred to as "agropine-type" Agrobacteria.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, and so on). Thus, nucleotide sequences of the present invention can be engineered in order to introduce or alter a XERICO coding sequence for a variety of reasons, including but not limited to initiating the production of environmental stress tolerance; alterations that modify the cloning, processing and/or expression of the gene product (such alterations include inserting new restriction sites and changing codon preference), as well as varying the protein function activity (such changes include but are not limited to differing binding kinetics to nucleic acid and/or protein or protein complexes or nucleic acid/protein complexes, differing binding inhibitor affinities or effectiveness, differing reaction kinetics, varying subcellular localization, and varying protein processing and/or stability).

The term "fusion" when used in reference to a polypeptide refers to a chimeric protein containing a protein of interest joined to an exogenous protein fragment (the fusion partner). The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms. The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

As used herein, the term "plant" is used in it broadest sense. It includes, but is not limited to, any species of grass (e.g. turf grass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like. The term includes, but is not limited to any species of plant used as a feed for animals or birds, or fish, or reptiles, or marine animals. In some embodiments of the present invention transgenic plants are crop plants. The terms "crop" and "crop plant" is used herein its broadest sense. The term includes, but is not limited to, any species of plant or alga edible by humans or used as a feed for animals or fish or marine animals, or consumed by humans, or used by humans (natural pesticides), or viewed by humans (flowers) or any plant or alga used in industry or commerce or education. Indeed, a variety of crop plants are contemplated, including but not limited to soybean, barley, sorghum, rice, corn, wheat, tomato, potato, pepper, onions, brassica sp., melons, cotton, turf grass, sunflower, herbs and trees.

For the purposes of the present invention, family assignment of a plant is based upon a combination of sequence identity, phylogeny and gene organization (as described herein).

As used herein, the term plant cell "compartments or organelles" is used in its broadest sense. As used herein, the term includes but is not limited to, the endoplasmic reticulum, Golgi apparatus, trans Golgi network, plastids, sarcoplasmic reticulum, glyoxysomes, mitochondrial, chloroplast, thylakoid membranes and nuclear membranes, and the like.

As used herein, the term "trait" in reference to a plant refers to an observable and/measurable characteristics of an organism, such as drought tolerance in a plant or microbe.

As used herein, the term "agronomic trait" and "economically significant trait" refers to any selected trait that increases the commercial value of a plant part, for example a preferred yield, a oil content, protein content, seed protein content, seed size, seed color, seed coat thickness, seed sugar content, seed free amino acid content, seed germination rate, seed texture, seed fiber content, food-grade quality, hilum color, seed yield, color of a plant part, drought resistance, water resistance, cold weather resistance, hot weather resistance, and growth in a particular hardiness zone.

The terms "leaf" and "leaves" refer to a usually flat, green structure of a plant where photosynthesis and transpiration take place and that grow attached to a stem or branch.

The terms "cotyledon," "true leaf," and "seed leaf" refers to any one of the first leaves to appear after germination (there may be one, such as a monocotyledon, two, such a dicotyledoen or more) and the foliar portion of the embryo as found in the seed. The term "hypocotyl" refers to a part of the stem of an embryo or young seedling below the cotyledons.

As used herein, "stoma" and "stomata" refers to an orifice in the epidermis of a leaf communicating with internal air cavities and a pore in the wall of a plant epidermis surrounded by special guard-cells.

As used herein, "aerial" and "aerial parts of *Arabidopsis* plants" refers to any plant part that is above water in aquatic plants or any part of a terrestrial plant part found above ground level.

The terms "radicle" and "radicles" refer to "rootlets emerging from the sides and base of the stem and the end of a plant embryo which gives rise to the first root. A radicle may also comprise a "rhizoid" which refers to a cellular outgrowth of a plant that usually aids in anchoring to the surface and increasing surface area to acquire water or nutrients.

The terms "calli" and "callus" refer to a tough, often hairy, swelling at the base or insertion of the lemma. The term "lemma" refers to the lower of the two bracts enclosing the flower in the spikelet of grasses. The term "bract" refers to a leaf from the axil of which a flower arises. The term "axil" refers to the angle between a branch or leaf and the stem from which it grows. The term "inflorescence" refers to a flowering part of a plant.

The term "meristem" refers to undifferentiated tissue from which new cells are formed, e.g., the tips of roots or stems; the growing tip.

The term "meristem cloning" refers to artificial propagation of a plant using cells taken from the meristem of a parent plant and yielding genetically identical offspring.

The term "stem" refers to a main ascending axis of a plant.

The term "tiller" refers to a portion of a plant where a lateral stem (or shoot), usually erect, develops from the central crown, often used for propagation of grass plants. Also refers to the branch or shoot that originates at a basal node.

The term "variety" refers to a biological classification for an intraspecific group or population, that can be distinguished from the rest of the species by any characteristic (for example morphological, physiological, cytological, etc.). A variety may originate in the wild but can also be produced through selected breeding (for example, see, cultivar).

The terms "cultivar," "cultivated variety," and "cv" refer to a group of cultivated plants distinguished by any characteristic (for example morphological, physiological, cytological, etc.) that when reproduced sexually or asexually, retain their distinguishing features to produce a cultivated variety.

The term "seed" refers to a ripened ovule, consisting of the embryo and a casing.

The term "propagation" refers to the process of producing new plants, either by vegetative means involving the rooting or grafting of pieces of a plant, or by sowing seeds. The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. For example, the division of a clump, rooting of proliferations, or cutting of mature crowns can produce a new plant.

The terms "tissue culture" and "micropropagation" refer to a form of asexual propagation undertaken in specialized laboratories, in which clones of plants are produced from small cell clusters from very small plant parts (e.g. buds, nodes, leaf segments, root segments, etc.), grown aseptically (free from any microorganism) in a container where the environment and nutrition can be controlled.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full-length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. The term "a nucleotide comprising at least a portion of a gene" may comprise fragments of the gene or the entire gene. The term "cDNA" refers to a nucleotide copy of the "messenger RNA" or "mRNA" for a gene. In some embodiments, cDNA is derived from the mRNA. In some embodiments, cDNA is derived from genomic sequences. In some embodiments, cDNA is derived from EST sequences. In some embodiments, cDNA is derived from assembling portions of coding regions extracted from a variety of BACs, contigs, Scaffolds and the like.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The terms "allele" and "alleles" refer to each version of a gene for a same locus that has more than one sequence. For example, there are multiple alleles for eye color at the same locus. The terms "recessive," "recessive gene," and "recessive phenotype" refer to an allele that has a phenotype when two alleles for a certain locus are the same as in "homozygous" or as in "homozygote" and then partially or fully loses that phenotype when paired with a more dominant allele as when two alleles for a certain locus are different as in "heterozygous" or in "heterozygote." The terms "dominant," "dominant allele," and "dominant phenotype" refer to an allele that has an effect to suppress the expression of the other allele in a heterozygous (having one dominant allele and one recessive allele) condition.

The term "heterologous" when used in reference to a gene or nucleic acid refers to a gene that has been manipulated in some way. For example, a heterologous gene includes a gene from one species introduced into another species. A heterologous gene also includes a gene native to an organism that has been altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The terms "nucleic acid sequence," "nucleotide sequence of interest" or "nucleic acid sequence of interest" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.).

The term "structural" when used in reference to a gene or to a nucleotide or nucleic acid sequence refers to a gene and/or A nucleotide or nucleic acid sequence whose ultimate expression product is a protein (such as an enzyme or a structural protein), an rRNA, an sRNA, a tRNA, and the like.

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "polynucleotide" refers to refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term "an oligonucleotide (or polypeptide) having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region of the gene if needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc., or a combination of both endogenous and exogenous control elements.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "EST" and "expressed sequence tag" refer to a unique stretch of DNA within a coding region of a gene; approximately 200 to 600 base pairs in length. The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "protein," "polypeptide," "peptide," "encoded product," "amino acid sequence," are used interchangeably to refer to compounds comprising amino acids joined via peptide bonds and a "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence. The term "X" may represent any amino acid.

The terms "homolog," "homologue," "homologous," and "homology" when used in reference to amino acid sequence or nucleic acid sequence or a protein or a polypeptide refers to a degree of sequence identity to a given sequence, or to a degree of similarity between conserved regions, or to a degree of similarity between three-dimensional structures or to a degree of similarity between the active site, or to a degree of similarity between the mechanism of action, or to a degree of similarity between functions. In some embodiments, a homologue has a greater than 30% sequence identity to a given sequence. In some embodiments, a homologue has a greater than 40% sequence identity to a given sequence. In some embodiments, a homologue has a greater than 60% sequence identity to a given sequence. In some embodiments, a homologue has a greater than 70% sequence identity to a given sequence. In some embodiments, a homologue has a greater than 90% sequence identity to a given sequence. In some embodiments, a homologue has a greater than 95% sequence identity to a given sequence. In some embodiments, homology is determined by comparing internal conserved sequences to a given sequence. In some embodiments, homology is determined by comparing designated conserved functional and/or structural regions, for example a RING domain, a low complexity region or a transmembrane region. In some embodiments, homology is determined by comparing designated conserved "motif" regions, such as a RING-H2 zinc finger domain motif. In some embodiments, means of determining homology are described in the Examples.

The term "homology" when used in relation to nucleic acids or proteins refers to a degree of identity. There may be partial homology or complete homology. The following terms are used to describe the sequence relationships between two or more polynucleotides and between two or more polypeptides: "identity," "percentage identity," "identical," "reference sequence," "sequence identity," "percentage of sequence identity," and "substantial identity." "Sequence identity" refers to a measure of relatedness between two or more nucleic acids or proteins, and is described as a given as a percentage "of homology" with reference to the total comparison length. A "reference sequence" is a defined sequence used as a basis for a sequence comparison; a reference sequence may be a subset of a larger sequence, for example, the sequence that forms an active site of a protein or a segment of a full-length cDNA sequence or may comprise a complete gene sequence. Since two polynucleotides or polypeptides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of in internal region of a polypeptide. In one embodiment, a comparison window is at least 77 amino acids long. In another embodiment, a comparison window is at least 84 amino acids long. In another embodiment, conserved regions of proteins are comparison windows. In a further embodiment, an amino acid sequence for a conserved transmembrane domain is 24 amino acids. Calculations of identity-may be performed by algorithms contained within computer programs such as the ClustalX algorithm (Thompson, et al. Nucleic Acids Res. 24, 4876-4882 (1997)); herein incorporated by reference); MEGA2 (version 2.1) (Kumar, et al. Bioinformatics 17, 1244-1245 (2001); herein incorporated by reference); "GAP" (Genetics Computer Group, Madison, Wis.), "ALIGN" (DNAStar, Madison, Wis.), BLAST (National Center for Biotechnology Information; NCBI as described at ncbi.nlm.nih.g-ov/BLAST/blast_help.shtml) and MultAlin (Multiple sequence alignment) program (Corpet, Nucl. Acids Res., 16 (22), 10881-10890 (1988); herein incorporated by reference, at prodes.toulouse.inra.fr/multalin/multalin.html), all of which are herein incorporated by reference) and as described in EXAMPLE IX.

For comparisons of nucleic acids, 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2:482 (1981)) by the homology alignment algorithm of Needleman and Wunsch (Needleman and Wunsch, J. Mol. Biol. 48:443 (1970); herein incorporated by reference), by the search for similarity method of Pearson and Lipman (Pearson and Lipman, Proc. Natl. Acad. Sci. (U.S.A.) 85:2444 (1988); herein incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis.; herein incorporated by reference), or by inspection, and the best alignment (i.e., resulting in the highest percentage of homology over the comparison window) generated by the various methods is selected.

The term "sequence identity" means that two polynucleotide or two polypeptide sequences are identical (i.e., on a nucleotide-by-nucleotide basis or amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) or amino acid, in which often conserved amino acids are taken into account, occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment (see, for e.g. SEQ ID NOs:03 and 04) of the full-length sequences of the compositions claimed in the present invention (see, for e.g. SEQ ID NOs:01 and 02).

The term "ortholog" refers to a gene in different species that evolved from a common ancestral gene by speciation. In some embodiments, orthologs retain the same function. The term "paralog" refers to genes related by duplication within a genome. In some embodiments, paralogs evolve new functions. In further embodiments, a new function of a paralog is related to the original function.

The term "partially homologous nucleic acid sequence" refers to a sequence that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely complementary to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial-degree of identity (e.g., less than about 30% identity); in the absence of non-specific binding the probe will not hybridize to the second non-identical target.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. Melting temperature $T_m$ is the midpoint of the temperature range over which nucleic acids are denatured (e.g. DNA:DNA, DNA:RNA and RNA:RNA, etc.). Methods for calculating the $T_r$, of nucleic acids are well known in the art (see, for e.g., Sambrook, et al. Molecular Cloning: A Laboratory Manual, 2.sup.nd ed., Cold Spring Harbor Laboratory Press, New York (1989) pp. 9.50-51, 11.48-49 and 11.2-11.3; herein incorporated by reference).

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml:05 g Ficoll (Type 400, Pharmacia):05 g BSA (Fraction V; Sigma)) and 100 µg g/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

As used herein, the term "polymerase chain reaction" and "PCR" refers to the method of K. B. Mullis (U.S. Pat. Nos. 4,683,195 4,683,202, and 4,965,188; herein incorporated by reference), which describe a method for increasing the concentration of a segment of a target sequence in a mixture of genomic DNA without cloning or purification. This process for amplifying the target sequence consists of introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences. Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (see, for e.g., Kacian et al. Proc. Natl. Acad. Sci. USA, 69:3038-3042 (1972); herein incorporated by reference). Other nucleic acids will not be replicated by this amplification enzyme. Similarly, in the case of T7 RNA polymerase, this amplification enzyme has a stringent specificity for its own promoters (see, for e.g., Chamberlin et al. (1970) Nature, 228:227; herein incorporated by reference). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989); herein incorporated by reference). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989); herein incorporated by reference).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "vector" refers to nucleic acid molecules that transfer DNA segment(s). Transfer can be into a cell, cell to cell, et cetera. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. The term "expression vector" when used in reference to a construct refers to an expression vector construct comprising, for example, a heterologous DNA encoding a gene of interest and the various regulatory elements that facilitate the production of the particular protein of interest in the target cells. In certain embodiments of the present invention, a nucleic acid sequence of the present invention within an expression vector is operatively linked to an appropriate expression control sequence(s) (promoter) to direct mRNA synthesis.

The terms "in operable combination," "in operable order," and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, and the like.

Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

The terms "promoter element," "promoter," or "promoter sequence" refer to a DNA sequence that is located at the 5' end (i.e. precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene and/or A reporter gene expressing a reporter molecule, to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

The term "cell type specific" as applied to a promoter refers to a promoter that is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody that is specific for the polypeptide product encoded by the nucleotide sequence of interest whose expression is controlled by the promoter. A labeled (e.g., peroxidase conjugated) secondary antibody that is specific for the primary antibody is allowed to bind to the sectioned tissue and specific binding detected (e.g., with avidin/biotin) by microscopy.

Promoters may be "constitutive" or "inducible." The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to Cauliflower Mosaic Virus (CaMV SD; see e.g., U.S. Pat. No. 5,352,605, incorporated herein by reference), mannopine synthase, octopine synthase (ocs), superpromoter (see e.g., WO 95/14098; herein incorporated by reference), and ubi3 promoters (see e.g., Garbarino and Belknap, Plant Mol. Biol. 24:119-127 (1994); herein incorporated by reference). Such promoters have been used successfully to direct the expression of heterologous nucleic acid sequences in transformed plant tissue.

In contrast, an "inducible" promoter is one that is capable of directing a level of transcription of an operably linked nucleic acid sequence in the presence of a stimulus (e.g., heat shock, chemicals, light, etc.) that is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, and the like.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, therein making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. Molecular Cloning: A Laboratory Manual, 2.sup.nd ed., Cold Spring Harbor Laboratory Press, New York (1989) pp. 16.7-16.8; herein incorporated by reference). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "stable transfection" and "stably transfected" refer to the introduction and integration of foreign DNA into the genome of the transfected cell. The term "stable transfectant" refers to a cell that has stably integrated foreign DNA into the genomic DNA.

The terms "transient transfection" and "transiently transfected" refer to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb in Virol., 52:456 (1973); herein incorporated by reference, has been modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding, "bombardment, and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807; herein incorporated by reference), and are commercially available (e.g. the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al. Mol. Cell. Biol. 7:725 (1987) and U.S. Pat. Nos. 6,074,859; 5,976, 796; 5,674,713; and 5,618,682; all of which are herein incorporated by reference in their entirety), green fluorescent protein (e.g., GenBank Accession Number U43284; GFP variants commercially available from CLONTECH Laboratories, Palo Alto, Calif.; herein incorporated by reference), chloramphenicol acetyltransferase, β-galactosidase (lacZ gene), alkaline phosphatase, and horse radish peroxidase. An example of using β-glucuronidase (GUS) as a reporter gene and using GFP as a reporter marker for expression studies of an *Arabidopsis* gene encoding a RING domain protein is provided in Lee et al. ((2001) Genes Dev. April 1; 15(7):912-24; herein incorporated by reference).

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew (2001) has reported (Curr. Opin. Cell Biol. 13(2):244-248) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The terms "hpRNA" and "hairpin RNA" refer to self-complementary RNA that forms hairpin loops and functions to silence genes (e.g. Wesley et al. (2001) The Plant Journal 27(6):581-590; herein incorporated by reference). The term "ihpRNA" refers to intron-spliced hpRNA that functions to silence genes.

The term "target RNA molecule" refers to an RNA molecule to which at least one strand of the short double-stranded region of a siRNA is homologous or complementary. Typically, when such homology or complementary is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The terms "posttranscriptional gene silencing" and "PTGS" refers to silencing of gene expression in plants after transcription, and appears to involve the specific degradation of mRNAs synthesized from gene repeats. The term "cosuppression" refers to silencing of endogenous genes by heterologous genes that share sequence identity with endogenous genes.

The term "coexpression" refers to the expression of a foreign gene that has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The term "overexpression" generally refers to the production of a gene product in transgenic organisms that exceeds levels of production in normal or non-transformed organisms.

The terms "overexpression" and "overexpressing" and grammatical equivalents, are specifically used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook, et al. Molecular Cloning: A Laboratory Manual, 2.sup.nd ed., Cold Spring Harbor Laboratory Press, New York (1989) pp. 9.31-9.58; herein incorporated by reference).

The term "Northern blot analysis," "Northern blot," and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al. (1989) supra, pp 7.39-7.52; herein incorporated by reference).

The term "isolated" when used in relation to a nucleic acid or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the terms "purified" and "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is therein increased in the sample.

The term "accession" when used herein associated with sequences of genes and proteins refers to a gene or group of similar genes or proteins from these genes or proteins received from a single source at a single time. The term "accession number" when used herein refers to a unique identifier for protein and gene sequences and is assigned when an accession is entered into a database (for example GenBank at NCBI, European Molecular Biology Laboratory (EMBL) and the like.

The term "sample" is used in its broadest sense. In one sense it can refer to a plant cell or tissue, such as a leaf. In another sense, it is meant to include a specimen or culture obtained from any source, as well as biological and environmental samples. Biological samples may be obtained from plants or animals and encompass fluids, solids, tissues, and gases. Environmental samples include environmental material such as surface matter, soil, water, salt, and industrial samples. These examples are not to be construed as limiting the sample types applicable to the present invention.

GENERAL DESCRIPTION OF THE INVENTION

The present inventions relate to compositions and methods for providing stress tolerant transgenic plants comprising a RING domain zinc-finger motif transcription factor protein. More particularly, the invention relates to compositions and methods comprising a RING-H2 domain transcription factor protein for providing drought and salt tolerant plants, in particular comprising a recombinant XERICO gene (see, for e.g., SEQ ID NO:02) and XERICO protein (see, for e.g., SEQ ID NO:01).

The present invention relates to genes, proteins and methods comprising RING-H2 zinc finger proteins. In a preferred embodiment, the present invention relates to altering environmental stress tolerance in plants and microorganisms using XERICO RING-H2 zinc finger domain proteins (AT2G04240; SEQ ID NO:01). Thus, the presently claimed invention provides compositions comprising XERICO genes, XERICO coding sequences, and XERICO polypeptides, and in particular to expression vectors encoding XERICO (AT2G04240; see, for e.g., SEQ ID NO:02) and related genes in the AT2G04240 RING-H2 zinc finger domain family (AT2G04240-like), see, for e.g., SEQ ID NOs:17, 21, 35, 42, 55, 157 and their encoded AT2G04240-like polypeptides SEQ ID NOs: 14, 19, 34, 40, 53, 154, respectively, in addition to those shown in FIG. 10 and described in Table 2.

The present invention also provides methods for using XERICO genes, and XERICO polypeptides; such methods include but are not limited to use of these genes to produce transgenic plants, to produce XERICO protein, to increase levels of XERICO protein, to increase ABA levels, to alter environmental stress tolerance, to alter environmental stress phenotypes, and for controlled production of drought and or salt tolerance. It is not meant to limit the present invention to alterations in XERICO expression. In some embodiments, XERICO alters one or more of the following: ABA levels, open stomata, AtTLP9; SEQ ID NO:381; expression and/or activity, and AtUBC8; SEQ ID NO:379, expression and/or activity. In some embodiments, XERICO polypeptides are overexpressed in transgenic plants, transgenic tissue, transgenic leaves, transgenic seeds, and transgenic host cells. It may be desirable to integrate the nucleic acid sequence of interest to the plant genome. Introduction of the nucleic acid sequence of interest into the plant cell genome may be achieved by, for example, heterologous recombination using *Agrobacterium*-derived sequences, such as described herein and in the EXAMPLES.

Alternatively, the responsiveness of a plant or plant cell to a stress condition can be modulated by use of a suppressor construct containing dominant negative mutation for any of the stress-regulated sequences described herein. Expression of a suppressor construct containing a dominant mutant mutation generates a mutant transcript that, when coexpressed with the wild-type transcript inhibits the action of the wild-type transcript. Methods for the design and use of dominant negative constructs are well known (see, for e.g., in Herskowitz, (1987) Nature 329:219-222; Lagna and Hemmati-Brivanlou, (1998) Curr. Topics Devel. Biol. 36:75-98; all of which are herein incorporated by reference).

The present invention also provides methods for inhibiting XERICO (AT2G04240) genes, and XERICO polypeptides; such methods include but are not limited to use of these genes in antisense constructs to produce transgenic plants, to inhibit XERICO protein, to decrease XERICO protein, to decrease levels of endogenous XERICO protein, to decrease ABA levels, to alter environmental stress tolerance, to alter environmental stress phenotypes, and for controlled production of drought and or salt tolerance. In some embodiments, XERICO (AT2G04240) polypeptides are underexpressed in transgenic plants, transgenic tissue, transgenic leaves, transgenic seeds, and transgenic host cells. Introduction of the nucleic acid sequence of interest into the plant cell genome may be achieved by, for example, heterologous recombination using *Agrobacterium*-derived sequences.

Thus, the presently claimed invention provides compositions comprising XERICO related (AT2G04240-like/homologous) genes and coding sequences, and AT2G04240-like/homologous polypeptides, and in particular to expression vectors encoding AT2G04240-like/homologous, and related genes in the AT2G04240 family (AT2G04240-like/homologues) and their encoded polypeptides.

The present invention also provides methods for using XERICO related (AT2G04240-like/homologous) genes, and XERICO related (AT2G04240-like/homologous) polypeptides; such methods include but are not limited to use of these genes to produce transgenic plants, to alter environmental stress tolerance, to alter phenotypes, and for controlled drought production. It may be desirable to target the nucleic acid sequence of interest to a particular locus on the plant genome. In some embodiments, AT2G04240-like polypeptides are overexpressed in transgenic plants, transgenic tissue, transgenic leaves, transgenic seeds, transgenic host cells. In some embodiments, AT2G04240-like polypeptides are underexpressed in transgenic plants, transgenic tissue, transgenic leaves, transgenic seeds, transgenic host cells. Introduction of the nucleic acid sequence of interest into the plant cell genome may be achieved by, for example, heterologous recombination using *Agrobacterium*-derived sequences.

The present invention is not limited to any particular mechanism of action. Indeed, an understanding of the mechanism of action is not needed to practice the present invention. The following description describes pathways involved in regulating environmental stress, with an emphasis on controlling XERICO protein expression, production or controlling XERICO protein activity. Also described are methods for identifying genes involved in providing or controlling XERICO activity, and of XERICO mutants and related AT2G04240 genes discovered through use of these methods. Further, using the sequences of the present invention, additional AT2G04240 and AT2G04240-like genes and amino acid sequences are identified, isolated, and characterized for the methods of the present invention. This description also provides methods of identifying, isolated, characterizing and using these genes and their encoded proteins. In addition, the description provides specific, but not limiting, illustrative examples of embodiments of the present invention.

Methods of the invention can be performed with respect to identifying a pathway involving any of the XERICO stress-regulated polypeptides as encoded by a polynucleotide of SEQ ID NO:01, including for example, a stress-regulated transcription factor, an enzyme, including a kinase, a channel protein. Pathways in which the disclosed stress-regulated stress factors are involved can be identified, for example, ubiquitin ligase 3 pathways, by searching the Munich Information Center for Protein Sequences (MIPS) *Arabidopsis thaliana* database (MATDB).

The present invention also relates to methods of identifying a polynucleotide that modulates a XERICO stress response in a plant cell. Such a method can be performed, for example, by contacting an array of probes representative of a plant cell genome, such as an ATH1 Genechip array, and nucleic acid molecules expressed in plant cell exposed to a particular stress; such as osmotic stress and/or salt stress, detecting a nucleic acid molecule that is expressed at a level different from a level of expression in the absence of the stress; introducing the nucleic acid molecule that is expressed differently into a plant cell; and detecting a modulated response of the plant cell containing the introduced nucleic acid molecule to a stress, therein identifying a polynucleotide that modulates a stress response in a plant cell. The contacting is under conditions that allow for selective hybridization of a nucleic acid molecule with probe having sufficient complementarity, for example, under stringent hybridization conditions.

The present invention also relates to methods of using a polynucleotide portion of a plant stress-regulated gene, such as XERICO and AT2G04240-like genes, to confer a selective advantage on a plant cell. In one embodiment, such a method is performed by introducing a plant stress-regulated regulatory element into a plant cell, such as a RING-H2 domain, for example, those described herein, wherein, upon exposure of the plant cell to a stress condition to which the regulatory element is responsive, a nucleotide sequence operatively linked to the regulatory element is expressed, therein conferring a selective advantage to plant cell. The operatively linked nucleotide sequence can be, for example, a XERICO transcription factor, the expression of which induces the further expression of polynucleotides involved in a stress response, therein enhancing the response of a plant to the stress condition. In another embodiment, a coding sequence of a plant stress-regulated XERICO gene as disclosed herein is introduced into the cell, therein providing the plant with a selective advantage in response to a stress condition. In still another embodiment, the method results in the knock-out of a plant stress-regulated gene, such as XERICO, as disclosed herein, in a first population of plants, therein providing a selective advantage to a stress condition in a second population of plants.

The invention further relates to a method of identifying an agent that modulates the activity of a stress-regulated regulatory element of a plant. In a particular embodiment, methods are provided for identifying an agent that alters the activity of an abiotic stress responsive regulatory element comprising contacting the agent or a composition containing an agent to be tested with at least one abiotic stress responsive regulatory element, preferably an element associated with regulating, for e.g., SEQ ID NO:01 and/or SEQ ID NO:03 (see, also, for e.g. XERICO-like sequences in FIG. 10), and determining the effect of the agent on the ability of the regulatory sequence to regulate XERICO transcription. In further embodiments, the regulatory elements are associated with particular stresses or combination of stresses such as osmotic stress and saline stress.

In one embodiment, the regulatory element can be operatively linked to a heterologous polynucleotide encoding a reporter molecule, and an agent that modulates the activity of the stress-regulated regulatory element can be identified by detecting a change in expression of the reporter molecule due to contacting the regulatory element with the agent. Such a method can be performed in vitro in a plant cell-free system, or in a plant cell in culture or in a plant in situ. In another embodiment, the agent is contacted with a transgenic plant containing an introduced plant stress-regulated regulatory element, and an agent that modulates the activity of the regulatory element is identified by detecting a phenotypic change in the transgenic plant. The methods of the invention can be performed in the presence or absence of the stress condition to which the particularly regulatory element is responsive, in particular to osmotic stress and/or saline stress.

Another aspect provides a method for identifying an agent that alters abiotic stress responsive polynucleotide expression in a plant or plant cell comprising contacting a plant or plant cell with a test agent; subjecting the plant cell or plant cell to an abiotic stress or combination of stresses before, during or after contact with the agent to be tested; obtaining an expression profile of the plant or plant cell and comparing the expression profile of the plant or plant cell to an expression profile from a plant or plant cell not exposed to the abiotic stress or combination of stresses. In one embodiment, the expression profile comprises expression data for at least one nucleotide sequence comprising any of SEQ ID NO:02 (see, also, for e.g. FIGS. 10, 11 and 12). In additional embodiments, the expression profile comprises expression data for at least one, and preferably two or more sequences associated with a particular abiotic stress or combination of stresses such as osmotic stress and/or saline stress (see, also, Table 1).

Yet another aspect provides nucleotide probes useful for detecting an abiotic stress response in plants, the probes comprising a nucleotide sequence of at least 15, 25, 50 or 100 nucleotides that hybridizes under stringent, preferably highly stringent, conditions to at least one sequence comprising any of SEQ ID NO:02. Also provided are nucleotide probes comprising at least 15, 25, 50 or 100 nucleotides in length that hybridize under stringent, preferably highly stringent conditions, to at least one gene associated with a particular stress or combination of stresses, for example saline/salt stress and osmotic stress (SEQ ID NO:451).

A plant stress-regulated regulatory element, such as XERICO, can be operatively linked to a heterologous polynucleotide such that, upon expression from the regulatory element in the plant cell, confers a desirable phenotype on the plant cell. For example, the heterologous polynucleotide can encode an aptamer, which can bind to a stress-induced polypeptide, for example, a XERICO polypeptide. Aptamers are nucleic acid molecules that are selected based on their ability to bind to and inhibit the activity of a protein or metabolite. Aptamers can be obtained by the SELEX (Systematic Evolution of Ligands by Exponential Enrichment) method (see, for e.g., U.S. Pat. No. 5,270,163; herein incorporated by reference), wherein a candidate mixture of single stranded nucleic acids having regions of randomized sequence is contacted with a target, and those nucleic acids having a specific affinity to the target are partitioned from the remainder of the candidate mixture, and amplified to yield a ligand enriched mixture. After several iterations a nucleic acid molecule (aptamer) having optimal affinity for the target is obtained. For example, such a nucleic acid molecule can be operatively linked to a plant stress-regulated regulatory element, such as XERICO, and introduced into a plant. Where the aptamer is selected for binding to a polypeptide that normally is expressed from the regulatory element and is involved in an adaptive response of the plant to a stress, the recombinant molecule comprising the aptamer can be useful for inhibiting the activity of the stress-regulated polypeptide, therein decreasing the tolerance of the plant to the stress condition.

The present invention further relates to a method of modulating the activity of a biological pathway in a plant cell, wherein the pathway involves a stress-regulated XERICO polypeptide. As used herein, reference to a pathway that "involves" a stress-regulated polypeptide means that the polypeptide is required for normal function of the pathway. For example, plant stress-regulated XERICO polypeptides as disclosed herein include those acting as transcription factors or as protein binding elements or affecting ABA mediated stress responses, which are well known to be involved in signal transduction pathways. As such, a method of the invention provides a means to modulate biological pathways involving plant stress-regulated XERICO polypeptides, for example, by altering the expression of the XERICO polypeptides in response to a stress condition or in response to changes in ABA levels. Thus, a method of the invention can be performed, for example, by introducing a XERICO polynucleotide portion of a plant stress-regulated XERICO gene into the plant cell, therein modulating the activity of the biological pathway, see, FIG. 1.

I. RING Finger Proteins

RING finger proteins are involved in various biological processes, however the majority of them, including specifically At2g04240; SEQ ID NO:01 and 02, have not been reported to be associated with obvious phenotypic consequences on plant growth and development. In experiments conducted during the course of the present inventions, a RING-H2 type zinc-finger gene and protein, At2g04240; SEQ ID NO:02, was isolated and inserted (SEQ ID NO:13) into *Arabidopsis* plants. These transgenic plants showed a dramatic increase in cellular ABA levels and consequently demonstrated a phenotype of drought tolerance. Therefore for reference, At2g04240 was named XERICO, meaning 'drought tolerant' in Greek. Further experiments demonstrated that a XERICO protein interacts with AtTLP9 (SEQ ID NO:380 and/or 381) an ASK1-interacting F-box protein involved in ABA signaling pathway and (SEQ ID NO:387 and/or 388), implying a connection between XERICO and ABA homeostasis through a ubiquitin/proteasome pathway.

RING zinc-finger proteins have important regulatory roles in the development of a variety of organisms. One of these, encoded by the gene named XERICO; SEQ ID NO:02, encodes a small protein (162 amino acids; SEQ ID NO:01) with an N-terminal trans-membrane domain SEQ ID NO:09, an low complexity region SEQ ID NO:08, and a RING-H2 zinc-finger motif, SEQ ID NO:03, located at the C-terminus. In silico gene expression analysis showed that XERICO is induced by salt/osmotic stress. Compared to wild-type *Arabidopsis* plants, transgenic adult 35S::XERICO plants, over-expressing XERICO (35S::XERICO) showed a marked increase in their tolerance to drought stress. In contrast to adult 35S::XERICO plants, early seedling growth of transgenic 35S::XERICO plants exhibited hypersensitivity to salt/osmotic stress and exogenous abscisic acid (ABA) during germination and early seedling growth. When subjected to a drought treatment, transcriptional upregulation of a key ABA biosynthesis gene, AtNCED3; SEQ ID NO:382, and was much faster and stronger in 35S::XERICO plants compared to wild-type plants. Further, upregulation of XERICO substantially increased cellular ABA levels. Yeast two-hybrid screening indicated that XERICO interacts with an E2 ubiquitin conjugating enzyme (AtUBC8 SEQ ID NO:378 and/or 379) and ASK1-interacting F-box protein (AtTLP9; SEQ ID NO:387 and/or 388; see, for e.g., Lai et al. (2004) Plant Physiol. 134:1586-1597; herein incorporated by reference), which is involved in ABA signaling pathway. Affymetrix GeneChip Array analysis showed that the expressions of many of the genes involved in the biosynthesis of plant hormones (for, e.g., ethylene; brassinosteroid; and gibberellic acid) were significantly changed in the 35S::XERICO plants. These results imply that the homeostasis of various plant hormones might be altered in 35S::XERICO plants, possibly by over-accumulation of ABA.

A. RING Zinc-finger Protein Regulation of Tolerance to Abiotic Stress in Plants

Zinc-finger proteins are among the most abundant proteins in eukaryotes. Their zinc-binding motifs vary widely in structure as well as in function, ranging from DNA/RNA binding to protein-protein interactions and membrane association (see, for e.g., Laity et al. (2001) Curr. Opin. Struct. Biol. 11:9-46; herein incorporated by reference). The RING (Really Interesting New Gene) finger motif was defined as a novel zinc-finger domain (Freemont et al. (1991) Cell 64:483-484; herein incorporated by reference). RING zinc-finger motif, a small Cys/His rich (C3HC/HC3), is represented in two distinct variants RING-HC and RING-H2 (SEQ ID NO:05), depending on which amino acid (Cys or His) occupies the fifth position of the motif (see, for e.g., Freemont (2000) Curr. Biol. 10:R84-87; herein incorporated by reference). The RING finger domain has been found in the proteins involved in various signal transduction pathways and regulatory proteins such as breast cancer susceptibility factor BRCA1, transcriptional intermediary factor TIF1, proto-oncoproteins Cb1 and Bmi-1 (see, for e.g., Saurin et al. (1996) Trends Biochem. Sci. 21:208-214; Joazeiro et al. (1999) Science 286:309-312; Freemont (2000) Curr. Biol. 10:R84-87; all of which are herein incorporated by reference). Genes encoding RING finger proteins have been isolated from a variety of organisms including animals, plants, and viruses (see, for e.g., Freemont (1993) Ann. NY Acad. Sci. 684:174-192; Saurin et al. (1996) Trends Biochem. Sci. 21:208-214; Jensen et al. (1998) FEBS Lett. 436:283-287; all of which are herein incorporated by reference). In plants, several RING finger proteins have been identified and characterized, including photomorphogenic repressor COP1 (SEQ ID NO:378 and 379) (see, for e.g., Deng et al. (1992) Cell 71:791-801; Torii et al. (1998) EMBO J. 17:5577-5587; all of which are herein incorporated by reference), an early elicitor-responsive ATL2 (NM_112545; SEQ ID NO:493) (see, for e.g., Serrano and Guzman (2004) Genetics 167:919-929; herein incorporated by reference), RIE1 (SEQ ID NO:275 and 278) involved in seed development (see, for e.g., Xu and Li (2003) Plant Mol. Biol. 53:37-50; herein incorporated by reference), and BRH1 a brassinosteroid-responsive RING-H2 gene (SEQ ID NO:254 and 255) (see, for e.g., Molnár et al. (2002) Planta 215:127-133; herein incorporated by reference).

A RING motif is a protein-protein interaction domain (SEQ ID NO:05) which has been implicated in a range of diverse biological processes (see, for e.g., Borden and Freemont, 1996; Saurin et al. (1996) Trends Biochem. Sci. 21:208-214; all of which are herein incorporated by reference). Various RING fingers exhibit binding to E2 ubiquitin-conjugating enzymes. E3 ubiquitin-protein ligase activity is inherent to the RING domain of c-Cbl, suggesting a general function of RING domains (see, for e.g., Joazeiro et al. 1999 Science 286(5438):309-312; Joazeiro and Weissman (2000) Cell 102(5):549-52; Freemont, 2000; all of which are herein incorporated by reference). Several plant RING finger proteins have been shown to interact with components in ubiquitin-mediated protein degradation pathway; including a component of SCF complexes involved in ubiquitination (RBX1b; SEQ ID NOs:403 and 404; see, for e.g., Gray et al. (2002) Plant Cell 14:2137-2144; herein incorporated by reference), an elicitor-responsive ubiquitin ligase EL5 (SEQ ID NO:405 and 406) (see, for e.g., Takai et al. (2002)) Plant J. 30:447-455; herein incorporated by reference, a membrane-bound ubiquitin ligase RMA1 (SEQ ID NO:407 and 408) (see, for e.g., Matsuda et al. (1998) Plant Cell Physiol.

39:545-554; Matsuda et al. (2001) J. Cell Sci. 114:1949-1957; all of which are herein incorporated by reference, and a COP1-interacting protein CIP8 (SEQ ID NO:378 and 379) (Torii (1998) EMBO J. 17:5577-5587; herein incorporated by reference). Recently, targeted degradation of cellular proteins by ubiquitination/proteasome pathway has been recognized as an important mode of regulation for many cellular processes, especially in plant hormone action (see, for e.g., Hare et al. (2003) Curr. Opin. Plant Biol. 6:453-462; Vierstra (2003) Trends Plant Sci. 8:135-142; Dill et al. (2004) Plant Cell, 16:1392-1405; Gagne et al. (2004) Proc. Natl. Acad. Sci. USA, 101:6803-6808; Dharmasiri et al. (2005) Nature, 435:441-445; all of which are herein incorporated by reference).

Abscisic acid (ABA) is involved in a variety of plant development and stress responses such as dormancy and growth regulation, leaf senescence, and desiccation tolerance (for review, examples, Seo and Koshiba (2002) Trends Plant Sci. 7:41-48; Himmelbach et al. (2003) Curr. Opin. Plant Biol. 6:470-479; all of which are herein incorporated by reference). Endogenous ABA levels peak during seed maturation and dormancy onset, and regulate vegetative development in response to various environmental stresses such as drought and high-salinity conditions. Under drought stress conditions, the endogenous level of ABA increases and, through its complex signaling cascade, results in stomatal closure to prevent transpirational water loss (Blatt, (2000) Annual Review of Cell and Developmental Biology 16; 221-241. When water relations return to normal conditions for growth, the endogenous level of ABA decreases to reverse the process. Thus, understanding the regulation of endogenous level of ABA is crucial to develop plant improvement strategies for managing drought tolerance including increasing drought tolerance.

B. RING-H2 Zinc Finger Protein Genes, Coding Sequences and Polypeptides

1. *Arabidopsis* XERICO (AT2G04240) Genes

The present invention provides plant XERICO genes and proteins including their homologues, orthologs, paralogs, variants and mutants, all of which refer to XERICO and/or AT2G04240-like genes and proteins. In some embodiments, isolated nucleic acid sequences comprising XERICO (SEQ ID NO:02 and/or SEQ ID NO:13) encoding a XERICO polypeptide (SEQ ID NO:01) or XERICO homologue (AT2G04240-like) are provided, see, for nonlimiting examples, FIG. 10. These sequences include nucleotide sequences comprising AT2G04240 RING-H2 cDNA, as shown in FIG. 10; such as SEQ ID NO: 04, with and without genomic sequences. AT2G04240 and AT2G04240-like further comprise sequences encoding low complexity regions, including but not limited to a serine rich region (SEQ ID NO:08 and 456-477) domains including but not limited to (SEQ ID NO:09 and 478-492), (see, for e.g., Olof et al. (2000) Journal of Molecular Biology 300:1005-1016; herein incorporated by reference). In some embodiments of the present invention, isolated nucleic acid sequences comprising genes upregulating XERICO are provided, (see, Table 1). In some contemplated embodiments, mutations in upregulating genes that induce expression of the XERICO genes, result in altered abiotic stress tolerance ratios and abiotic stress tolerance phenotype. In some contemplated embodiments of the present invention, isolated nucleic acid sequences comprising genes downregulating XERICO are provided, (see, Table 1). In some contemplated embodiments, mutations in genes upregulating or genes down-regulating XERICO genes disrupt expression of the XERICO genes resulting in altered abiotic stress tolerance and altered abiotic stress tolerance phenotype.

2. Additional Brassicaceae AT2G04240 Genes

The present invention provides nucleic acid sequences comprising additional AT2G04240 RING-H2 zinc finger protein genes, such as GenBank Accession AF499720 (SEQ ID NO:17 as described in, for example, Wang et al. (2004) Plant Sci. 166 (3), 609-616; herein incorporated by reference). Some embodiments of the present invention provide polynucleotide sequences that are homologue to at least one of exemplary Brassicaceae SEQ ID NOs:02, 18, 22 and 373. In some embodiments, the Brassicaceae polynucleotides are at least 84%, 90%, 95% (or more) identical to any of exemplary SEQ ID NOs:02, 21, 367, 369, 373 and 375. Other embodiments of the present invention provide polynucleotide sequences encoding polypeptides that are homologous to at least one of exemplary SEQ ID NOs:01, 19, 366, 370, 372 and 374. For example, some embodiments of the present invention provide polynucleotide sequences that are at least 80%, 90%, 95% (or more) identical to any of exemplary SEQ ID NOs: 02, 21, 367, 369, 373 and 375.

3. Viridiplantae AT2G04240-like Genes

The present invention provides nucleic acid sequences comprising additional AT2G04240-like RING-H2 zinc finger protein plant genes. For example, some embodiments of the present invention provide polynucleotide sequences that are homologous to at least one of exemplary SEQ ID NOs:02, 25, 29, 35. In some embodiments, the polynucleotides are at least 30%, 40%, 50%, 60%, 70%, 80%, 90%, 95% (or more) identical to any of exemplary SEQ ID NOs: 233, 229, 124, 81, 162, 1, 35, 40, 29, 157, and 18. Other embodiments of the present invention provide polynucleotide sequences encoding polypeptides that are homologous to at least one of exemplary SEQ ID NOs: 228, 232, 121, 79, 159, 58, 26, 154 and 2. For example, some embodiments of the present invention provide polypeptides that are homologous to at least one of reference SEQ ID NO:01. In some embodiments, the polypeptides are at least 32%, 40%, 50%, 60%, 70%, 80%, 90%, 95% (or more) identical to any of exemplary SEQ ID NOs: 228, 232, 121, 79, 159, 58, 26, 154 and 3.

Other embodiments of the present invention provide sequences assembled through EST sequences that produce polypeptides at least 30% or more (e.g., 60%, 70%, 80%, 90%, 95%) identical to at least one of SEQ ID NOs:02 and 04. In other embodiments, the present invention provides nucleic acid sequences that hybridize under conditions ranging from low to high stringency to at least one of SEQ ID NOs:02 and 04, as long as the polynucleotide sequence capable of hybridizing to at least one of SEQ ID NOs:02 and 04 encodes a protein that retains a desired biological activity of a abiotic stress tolerance RING-H2 zinc finger domain protein; in some preferred embodiments, the hybridization conditions are high stringency. In preferred embodiments, hybridization conditions are based on the melting temperature ($T_m$) of the nucleic acid binding complex and confer a defined "stringency" as explained above (See e.g., Wahl et al. Meth. Enzymol., 152:399-407 (1987), incorporated herein by reference).

4. Alleles of XERICO (AT2G04240) and AT2G04240-like Genes

In other embodiments of the present invention, alleles of XERICO (AT2G04240) RING-H2 zinc finger domain genes, and in particular of AT2G04240-like genes, are provided. Any given gene may have none, one or many allelic forms. Common mutational changes that give rise to alleles are generally ascribed to deletions, additions, or insertions, or substitutions of nucleic acids. Each of these types of changes may occur alone, or in combination with the others, and at the rate of one or more times in a given sequence. Mutational changes in alleles also include rearrangements, insertions, deletions, additions, or substitutions in upstream regulatory regions.

In some embodiments, alleles result from a mutation, (i.e., a change in the nucleic acid sequence) and generally produce altered mRNAs or polypeptides whose structure or function may or may not be altered. In preferred embodiments, the invention provides alleles resulting from a mutation for producing altered mRNAs or polypeptides whose structure or function increase tolerance to abiotic stress.

In other embodiments of the present invention, the polynucleotide sequence encoding a XERICO and/or AT2G04240-like gene is extended utilizing the nucleotide sequences (e.g., SEQ ID NOs: 02) in various methods known in the art to detect upstream sequences such as promoters and regulatory elements. For example, it is contemplated that for XERICO, or related AT2G04240 RING-H2 zinc finger domains, the sequences upstream are identified from the *Arabidopsis* genomic database. For other AT2G04240-like genes for which a database is available, the sequences upstream of the identified AT2G04240-like genes can also be identified. For other AT2G04240-like genes for which a public genomic database is not available, or not complete, it is contemplated that polymerase chain reaction (PCR) finds use in the present invention.

In another embodiment, inverse PCR is used to amplify or extend sequences using divergent primers based on a known region (see, for e.g., Triglia et al. (1988) Nucleic Acids Res., 16:8186; herein incorporated by reference). In yet another embodiment of the present invention, capture PCR (see, for e.g., Lagerstrom et al. PCR Methods Applic., 1:111-19 (1991); herein incorporated by reference) is used. In still other embodiments, walking PCR is utilized. Walking PCR is a method for targeted gene walking that permits retrieval of unknown sequence (see, for e.g., Parker et al. Nucleic Acids Res., 19:3055-60 (1991); herein incorporated by reference). The PROMOTERFINDER kit (Clontech) uses PCR, nested primers and special libraries to "walk in" genomic DNA. This process avoids the need to screen libraries and is useful in finding intron/exon junctions. In yet other embodiments of the present invention, add TAIL PCR is used as a preferred method for obtaining flanking genomic regions, including regulatory regions (see, for e.g., Liu and Whittier, Genomics, February 10; 25(3):674-81 (1995); Liu et al. Plant J., September; 8(3):457-63 (1995); all of which are herein incorporated by reference). Preferred libraries for screening for full-length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

5. Variant XERICO Genes

In some embodiments, the present invention provides isolated variants of the disclosed nucleic acid sequences encoding XERICO and/or AT2G04240-like genes, and in particular of XERICO, or related AT2G04240-like RING-H2 zinc finger domains genes, and the polypeptides encoded therein; these variants include mutants, fragments, fusion proteins or functional equivalents of genes and gene protein products.

Thus, nucleotide sequences of the present invention are engineered in order to introduce or alter a XERICO coding sequence for a variety of reasons, including but not limited to initiating the production of abiotic stress tolerance; augmenting or increasing abiotic stress tolerance, alterations that modify the cloning, processing and/or expression of the gene product (such alterations include inserting new restriction sites and changing codon preference), as well as varying the protein function activity (such changes include but are not limited to differing binding kinetics to nucleic acid and/or protein or protein complexes or nucleic acid/protein complexes, differing binding inhibitor affinities or effectiveness, differing reaction kinetics, varying subcellular localization, and varying protein processing and/or stability).

a. Mutants. Some embodiments of the present invention provide nucleic acid sequences encoding mutant forms of XERICO proteins, (i.e., mutants), and the polypeptides encoded therein. In preferred embodiments, mutants result from mutation of the coding sequence, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence. Mutants of XERICO genes can be generated by any suitable method well known in the art, including but not limited to EMS (ethyl methanesulfonate) induced mutagenesis, site-directed mutagenesis, randomized "point" mutagenesis, and domain-swap mutagenesis in which portions of XERICO cDNA are "swapped" with the analogous portion of AT2G04240-like encoding cDNAs (Back and Chappell, (1996) PNAS 93: 6841-6845; herein incorporated by reference).

It is contemplated that is possible to modify the structure of a peptide having an activity (e.g., such as a RING-H2 zinc finger domain activity), for such purposes as increasing synthetic activity or altering the affinity of the XERICO protein for a binding partner or a kinetic activity. Such modified peptides are considered functional equivalents of peptides having an activity of a XERICO activity as defined herein. A modified peptide can be produced in which the nucleotide sequence encoding the polypeptide has been altered, such as by substitution, deletion, or addition. In some preferred embodiments of the present invention, the alteration increases or decreases the effectiveness of the XERICO gene product to exhibit a phenotype caused by altered abiotic stress tolerance production. In other words, construct "X" can be evaluated in order to determine whether it is a member of the genus of modified or variant XERICO genes of the present invention as defined functionally, rather than structurally. Accordingly, in some embodiments the present invention provides nucleic acids comprising a XERICO or AT2G04240-like sequence that complement the coding regions of any of SEQ ID NOs:02, as well as the polypeptides encoded by such nucleic acids.

Moreover, as described above, mutant forms of XERICO proteins are also contemplated as being equivalent to those peptides that are modified as set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide nucleic acids comprising sequences encoding variants of XERICO gene products disclosed herein containing conservative replacements, as well as the proteins encoded by such nucleic acids. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, 2nd ed, WH Freeman and Co., 1981; herein incorporated by reference). Whether a change in the amino acid sequence of a peptide results in a functional homologue can be readily determined by assessing the ability of the variant peptide to function in a fashion similar to the wild-type protein. Peptides having more than one replacement can readily be tested in the same manner.

More rarely, a mutant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.; herein incorporated by reference in its entirety). Accordingly, other embodiments of the present invention provide nucleic acids comprising sequences encoding variants of XERICO gene products disclosed herein containing non-conservative replacements where the biological activity of the encoded protein is retained, as well as the proteins encoded by such nucleic acids.

b. Directed Evolution. Variants of XERICO genes or AT2G04240-like coding sequences may be produced by methods such as directed evolution or other techniques for producing combinatorial libraries of variants. Thus, the present invention further contemplates a method of generating sets of nucleic acids that encode combinatorial mutants of the XERICO and AT2G04240-like proteins, as well as truncation mutants, and is especially useful for identifying potential variant sequences (i.e., homologues) that possess the biological activity of the encoded XERICO and AT2G04240-like proteins. In addition, screening such combinatorial libraries is used to generate, for example, novel encoded XERICO and AT2G04240-like gene product homologues that possess novel binding or other kinetic specificities or other biological activities. The invention further provides sets of nucleic acids generated as described above, where a set of nucleic acids encodes combinatorial mutants of XERICO and AT2G04240-like proteins, or truncation mutants, as well as sets of the encoded proteins. The invention further provides any subset of such nucleic acids or proteins, where the subsets comprise at least two nucleic acids or at least two proteins.

It is contemplated that XERICO and AT2G04240-like, and in particular RING-H2 zinc finger domain genes; genes and coding sequences (e.g., any one or more of SEQ ID NOs:04 and fragments and variants thereof) can be utilized as starting nucleic acids for directed evolution. These techniques can be utilized to develop encoded XERICO and AT2G04240-like product variants having desirable properties such as increased kinetic activity or altered binding affinity.

In some embodiments, artificial evolution is performed by random mutagenesis (e.g., by utilizing error-prone PCR to introduce random mutations into a given coding sequence). This method requires that the frequency of mutation be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (see, for e.g., Moore and Arnold (1996) Nat. Biotech., 14: 458-67; Leung et al. (1989) Technique, 1:11-15; Eckert and Kunkel (1991) PCR Methods Appl., 1:17-24; Caldwell and Joyce (1992) PCR Methods Appl., 2:28-33; and Zhao and Arnold (1997) Nuc. Acids. Res. 25:1307-08; all of which are herein incorporated by reference in its entirety).

After mutagenesis, the resulting clones are selected for desirable activity (e.g., screened for abolishing or restoring RING-H2 zinc finger domain activity in a constitutive mutant, in a wild type background where RING-H2 zinc finger domain activity is required, as described above and below). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or special PCR procedures (e.g., Smith (1994) Nature, 370: 324-25; U.S. Pat. Nos. 5,837,458; 5,830,721; 5,811,238; 5,733,731, all of which are herein incorporated by reference). Gene shuffling involves random fragmentation of several mutant DNAs followed by their reassembly by PCR into full-length molecules. Examples of various gene shuffling procedures include, but are not limited to, assembly following DNase treatment, the staggered extension process (STEP), and random priming in vitro recombination.

c. Homologues. In some embodiments, the present invention provides isolated variants of the disclosed nucleic acid sequence encoding AT2G04240-like genes, and in particular of XERICO and AT2G04240-like, or related RING-H2 zinc finger domains genes, and the polypeptides encoded therein; these variants include mutants, fragments, fusion proteins or functional equivalents genes and protein products.

Some homologues or variants of encoded XERICO and/or AT2G04240-like products are contemplated to have an intracellular half-life dramatically different than the corresponding wild-type protein. For example, the altered protein is rendered either more stable or less stable to proteolytic degradation or other cellular process that result in destruction of, or otherwise inactivate the encoded XERICO and/or AT2G04240-like product. Such homologues, and the genes that encode them, can be utilized to alter the activity of the encoded XERICO and/or AT2G04240-like products by modulating the half-life of the protein. For instance, a short half-life can give rise to more transient biological effect. Other homologues have characteristics that are either similar to wild-type XERICO and/or AT2G04240-like, or which differ in one or more respects from wild-type XERICO and/or AT2G04240-like.

In some embodiments of the present invention, the amino acid sequences for a population of XERICO and/or a AT2G04240-like gene product homologues are aligned, preferably to promote the highest homology possible. Such a population of variants can include, for example, XERICO gene homologues from one or more species, or XERICO gene homologues from the same species but which differ due to mutation. Amino acids that appear at each position of the aligned sequences are selected to create a degenerate set of combinatorial sequences.

In a preferred embodiment of the present invention, the combinatorial XERICO gene library is produced by way of a degenerate library of genes encoding a library of polypeptides that each include at least a portion of candidate encoded XERICO-protein sequences. For example, a mixture of synthetic oligonucleotides is enzymatically ligated into gene sequences such that the degenerate set of candidate XERICO sequences are expressible as individual polypeptides, or alternatively, as a set of larger fusion proteins (e.g., for phage display) containing the set of XERICO sequences therein.

There are many ways by which the library of potential XERICO homologues can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential XERICO sequences and AT2G04240-like sequences. The synthesis of degenerate oligonucleotides is well known in the art (see, e.g., Narang, (1983) Tetrahedron Lett. 39(1):3-22; Itakura et al. Recombinant DNA, in Walton (ed.), Proceedings of the 3rd Cleveland Symposium on Macromolecules, Elsevier, Amsterdam, pp 273-289 (1981); Itakura et al. (1984) Annu. Rev. Biochem. 53:323; Itakura et al. (1977) Science 198:1056; Ike et al. (1983) Nucl. Acid Res., 11:477; all of which are herein incorporated by reference in their entirety. Such techniques have been employed in the directed evolution of other proteins (See e.g., Scott et al (1990) Science, 249:386-390; Roberts et al. (1992) Proc. Natl. Acad. Sci. USA, 89:2429-2433; Devlin et al (1990) Science, 249:404-406; Cwirla et al (1990) Proc. Natl. Acad. Sci. USA, 87:6378-6382; in addition to U.S. Pat. Nos. 5,223,409, 5,198,346, and 5,096,815; all of which are herein incorporated by reference in their entirety).

Functional variants can be screened for by expressing the variant in an appropriate vector (described in more detail below) in a plant cell and analyzing the produced by the plant.

d. Truncation Mutants of XERICO and/or AT2G04240-like Orthologs

In addition, the present invention provides isolated nucleic acid sequences encoding fragments of encoded XERICO and/or AT2G04240-like ortholog products (i.e., truncation mutants), and the polypeptides encoded by such nucleic acid sequences. In preferred embodiments, the XERICO fragment is biologically active. An example of a truncation unit is described herein as a XERICO without a transmembrane domain (provided by SEQ ID NOs:358 and 359). In some embodiments of the present invention, when expression of a portion of a XERICO and/or a AT2G04240-like ortholog protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (see, for e.g., Ben-Bassat et al. (1987) J. Bacteriol., 169:751-757; herein incorporated by reference) and *Salmonella typhimurium* and its in vitro activity has been demonstrated on recombinant proteins (see, for e.g., Miller et al. (1987) Proc. Natl. Acad. Sci. USA, 84:2718-1722; herein incorporated by reference). Therefore, removal of an N-terminal methionine, if desired, can be achieved either in vivo by expressing such recombinant polypeptides in a host that produces MAP (e.g., *E. coli* or CM89 or *S. cerevisiae*), or in vitro by use of purified MAP.

II. Transgenic Plants, Seeds, and Plant Parts

Plants of the present invention are transformed with at least one heterologous gene encoding an AT2G04240 or AT2G04240-like related gene, or encoding a sequence designed to increase AT2G04240 or AT2G04240-like related gene expression, according to any procedure well known or developed in the art. In some embodiments, the heterologous gene may introduce AT2G04240 or AT2G04240-like gene expression and protein activity of the expressed protein. In some embodiments, expression of the heterologous gene may decrease endogenous AT2G04240 or AT2G04240-like expression. In some embodiments, the hererologous gene may replace endogenous hololgogues of AT2G04240 or AT2G04240-like gene expression. It is contemplated that these heterologous genes, or nucleic acid sequences of the present invention and of interest, are utilized to increase the level of the polypeptide encoded by heterologous genes, or to decrease the level of the protein encoded by endogenous genes. It is contemplated that these heterologous genes, or nucleic acid sequences of the present invention and of interest, are utilized augment and/or increase the level of the protein encoded by endogenous genes. It is also contemplated that these heterologous genes, or nucleic acid sequences of the present invention and of interest, are utilized to provide a polypeptide encoded by heterologous genes.

The methods of the present invention are not limited to any particular plant. Indeed, a variety of plants are contemplated, including but not limited to grains, citris, melons, fruits, vegetables, flowers, herbs, ornamentals, bushes, grasses and trees. A polynucleotide sequence of a stress-regulated gene as disclosed herein can be particularly useful for performing the methods of the invention on a variety of plants, including but not limited to, *Brassica* sp. (e.g., *B. napus, B. rapa, B. juncea* and *B. oleracea*, etc.), alfalfa (e.g., *Medicago sativa*, etc.), rice (e.g., *Oryza sativa*, etc.), rye (e.g., *Secale cereale*, etc.), sorghum (e.g., *Sorghum bicolor, Sorghum vulgare*, etc.), millet (e.g., pearl millet (*Pennisetum glaucum*), proso millet (*Panicum miliaceum*), foxtail millet (*Setaria italica*), finger millet (*Eleusine coracana*), etc.), sunflower (e.g., *Helianthus annuus*, etc.), safflower (e.g., *Carthamus tinctorius*, etc.), wheat (e.g., *Triticum aestivum*, etc.), soybean (e.g., *Glycine max*, etc.), corn (*Zea mays*, etc.), tobacco (e.g., *Nicotiana tabacum*, etc.), potato (e.g., *Solanum tuberosum*, etc.), peanuts (e.g., *rachis hypogaea*, etc.), cotton (e.g., *Gossypium barbadense, Gossypium hirsutum*, etc.), sweet potato (e.g., *Ipomoea batatus*, etc.), cassava (e.g., *Manihot esculenta*, etc.), coffee (e.g., *Cofea* spp., etc.), coconut (e.g., *Cocos nucifera*, etc.), pineapple (e.g., *Ananas comosus*, etc.), citrus trees (e.g., *Citrus* spp., etc.), cocoa (e.g., *Theobroma cacao*, etc.), tea (e.g., *Camellia sinensis*, etc.), banana (e.g., *Musa* spp., etc.), avocado (e.g., *Persea* ultilane, etc.), fig (e.g., *Ficus casica*, etc.), guava (e.g., *Psidium* guava, etc.), mango (e.g., *Mangifera indica*, etc.), olive (e.g., *Olea europaea*, etc.), papaya (e.g., *Carica papaya*, etc.), cashew (e.g., *Anacardium occidentale*, etc.), macadamia (e.g., *Macadamia integrifolia*, etc.), ahnond (e.g., *Prunus amygdalus*, etc.), sugar beets (e.g., *Beta vulgaris*, etc.), sugarcane (e.g., *Saccharum* spp., etc.), oats (e.g., *Aveneae* spp., such as *Avena sativa*), duckweed (e.g., *Lemna*, etc.), barley (e.g., *Hordeum vulgare*, etc.), tomatoes (e.g., *Lycopersicon esculentum*, etc.), lettuce (e.g., *Lactuca sativa*, etc.), green beans (e.g., *Phaseolus vulgaris*, etc.), lima beans (e.g., *Phaseolus limensis*, etc.), peas (e.g., *Lathyrus* spp., etc.), and members of the genus *Cucumis* such as cucumber (*C. sativus*, etc.), cantaloupe (*C. cantalupensis*, etc.), and musk melon (*C. melo*), etc.; ornamentals such as azalea (e.g., *Rhodondendron* spp., etc.), hydrangea (e.g., *Macrophylla hydrangea*, etc.), hibiscus (e.g., *Hibiscus rosasan-* ensis, etc.), roses (e.g., *Rosa* spp., etc.), tulips (e.g., *Tulipa* spp., etc.), daffodils (e.g., *Narcissus* spp., etc.), petunias (e.g., *Petunia hybrida*, etc.), carnation (e.g., *Dianthus caryophyllus*, etc.), poinsettia (e.g., *Euphorbia pulcherrima*, etc.), and chrysanthemum are also included. Additional ornamentals within the scope of the invention include impatiens, Begonia, Pelargonium, Viola, Cyclamen, Verbena, Vinca, Tagetes, Primula, Saint Paulia, Agertum, Amaranthus, Antihirrhinum, Aquilegia, Cineraria, Clover, Cosmo, Cowpea, Dahlia, *Datura, Delphinium, Gerbera, Gladiolus, Gloxinia, Hippeastrum, Mesembryanthemum, Salpiglossos, and Zinnia.*

Attempts were made to produce draught or salt tolerant poplar trees, for example, hybrid poplar (INRA 7171-B4, *Populus tremula* L.×*P. alba* L.) lines were transformed to overexpress a pine cytosolic glutamine synthetase (GS1) gene for enhancing tolerance to water stress when compared to nontransformed plants, (see, for e.g., el-Khatib et al., (2004) Tree Physiol. July; 24(7):729-36; herein incorporated by reference) and transgenic hybrid poplar trees were created (*Pupulus*×*Xiao zhannica*, cv. "balizhuang-yang") with a mtl-D gene for enhancing salt tolerance, (see, for e.g., Sun et al., (2002), Sheng Wu Gong Cheng Xue Bao. July; 18(4):481-5; herein incorporated by reference). In one preferred embodiment, trees may be employed in practicing the present invention, in particular including nonhybrid and hybrid trees such as Poplars, (*Populus* spp.), for example, *Populus*×*canescens, Populus alba*×*Populus tremula*, etc.; and Conifers, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga ultilane*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*).

In another preferred embodiment, leguminous plants may be used in the practice of the present invention including but not limited to beans, such as guar, locust bean, fenugreek, soybean, garden beans, cowpea, mung bean, lima bean, fava bean, lentils, chickpea, etc.; *Arachis*, e.g., peanuts, *Vicia*, e.g., crown vetch, hairy vetch, adzuki bean, mung bean, and chickpea, *Lupinus*, e.g., lupine, *trifolium, Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Preferred forage and turf grass for use in the methods of the invention include alfalfa, orchard grass, tall fescue, perennial ryegrass, creeping bent grass, and redtop. Other plants within the scope of the invention include *Acacia*, aneth, artichoke, arugula, blackberry, canola, cilantro, clementines, escarole, eucalyptus, fennel, grapefruit, honey dew, jicama, kiwifruit, lemon, lime, mushroom, nut, okra, orange, parsley, persimmon, plantain, pomegranate, poplar, radiata pine, radicchio, Southern pine, sweetgum, tangerine, triticale, vine, yams, apple, pear, quince, cherry, apricot, melon, hemp, buckwheat, grape, raspberry, chenopodium, blueberry, nectarine, peach, plum, strawberry, watermelon, eggplant, pepper, cauliflower, *Brassica*, e.g., broccoli, cabbage, ultilan sprouts, onion, carrot, leek, beet, broad bean, celery, radish, pumpkin, endive, gourd, garlic, snapbean, spinach, squash, turnip, ultilane, chicory, groundnut and zucchini.

A. Expression Cassettes

The methods of the present invention contemplate the use of at least one heterologous gene encoding a XERICO gene and/or AT2G04240-like gene, or encoding a sequence designed to decrease or increase, XERICO, or AT2G04240-like gene expression, as described previously (e.g., vectors encoding a nucleic acid encoding a polypeptide comprising SEQ ID No:01, or nucleic acids corresponding to SEQ ID NO: 02. Heterologous genes include but are not limited to naturally occurring coding sequences, as well variants encoding mutants, variants, truncated proteins, and fusion proteins, as described above. Heterologous genes may be used alone or in combination with a selected agronomic trait (such as yield, etc.). Heterologous genes intended for expression in plants are first assembled in expression cassettes comprising a promoter. Methods which are well known to or developed by those skilled in the art may be used to construct expression vectors containing a heterologous gene and appropriate transcriptional and translational control elements. These methods include in vitro recombinant DNA techniques, synthetic techniques, and in vivo genetic recombination. Exemplary techniques are widely described in the art (see e.g., Sambrook. et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.; herein incorporated by reference).

In general, these vectors comprise a nucleic acid sequence encoding a XERICO gene and/or AT2G04240-like gene, or encoding a sequence designed to decrease XERICO gene and/or AT2G04240-like gene expression, (as described above) operably linked to a promoter and other regulatory sequences (e.g., enhancers, polyadenylation signals, etc.) required for expression in a plant.

Promoters include but are not limited to constitutive promoters, tissue-, organ-, and developmentally-specific promoters, and inducible promoters. Examples of promoters include but are not limited to: constitutive promoter 35S of cauliflower mosaic virus; a wound-inducible promoter from tomato, leucine amino peptidase ("LAP," see, for e.g., Chao et al. Plant Physiol 120: 979-992 (1999); herein incorporated by reference); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (see, e.g. U.S. Pat. No. 5,187,267; herein incorporated by reference); a tetracycline-inducible promoter (see, e.g. U.S. Pat. No. 5,057,422; herein incorporated by reference); and seed-specific promoters, such as those for seed storage proteins (e.g., phaseolin, napin, oleosin, and a promoter for soybean beta conglycin (see, for e.g., Beachy et al. (1985) EMBO J. 4: 3047-3053; herein incorporated by reference). All references cited herein are incorporated in their entirety.

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (see, for examples, Odell et al. (1985) Nature 313:810; Rosenberg et al. (1987) Gene, 56:125; Guerineau et al. (1991) Mol. Gen. Genet. 262:141;

Proudfoot (1991) Cell 64:671); Sanfacon et al. (1991) Genes Dev., 5:141; Mogen et al. (1990) Plant Cell, 2:1261; Munroe et al. (1990) Gene 91:151; Ballas et al. (1989) Nucleic Acids Res. 17:7891; Joshi et al. (1987) Nucleic Acid Res., 15:9627, all of which are incorporated herein by reference in their entirety).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introduced into maize cells (see, for e.g., Callis et al. (1987) Genes Develop. 1: 1183; herein incorporated by reference). Intron sequences have been routinely incorporated into plant transformation vectors, typically within the non-translated leader.

In some embodiments of the present invention, the construct for expression of the nucleic acid sequence of interest also includes a regulator such as a nuclear localization signal (see, for e.g., Kalderon et al. (1984) Cell 39:499; Lassner et al. (1991) Plant Molecular Biology 17:229; all of which are herein incorporated by reference), a plant translational consensus sequence (see, for e.g., Joshi (1987) Nucleic Acids Research 15:6643; all of which are herein incorporated by reference), an intron (see, for e.g., Luehrsen and Walbot (1991) Mol. Gen. Genet. 225:81; all of which are herein incorporated by reference), and the like, operably linked to the nucleic acid sequence encoding a XERICO gene.

In preparing the construct comprising the nucleic acid sequence encoding a XERICO gene, or encoding a sequence designed to decrease XERICO gene expression, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (see, for e.g., Messing and Vierra, (1982) Gene 19: 259; Bevan et al. (1983) Nature 304:184; all of which are incorporated herein by reference), the bar gene which confers resistance to the herbicide phosphinothricin (see, for e.g., White et al. (1990) Nucl Acids Res. 18:1062; Spencer et al. (1990) Theor. Appl. Genet. 79:625; all of which are incorporated herein by reference), the hph gene which confers resistance to the antibiotic hygromycin (see, for e.g., Blochlinger and Diggelmann, (1984) Mol. Cell. Biol. 4:2929; herein incorporated by reference), and the dhfr gene, which confers resistance to methotrexate (see, for e.g., Bourouis et al. EMBO J., 2:1099 (1983); herein incorporated by reference).

In some preferred embodiments, the Ti (T-DNA) plasmid vector is adapted for use in an *Agrobacterium* mediated transfection process (see e.g., U.S. Pat. Nos. 5,981,839; 6,051,757; 5,981,840; 5,824,877; and 4,940,838; all of which are herein incorporated by reference in their entirety). Construction of recombinant Ti and Ri plasmids in general follows methods typically used with the more common vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or Ri-plasmid has been described in EPO No. 116,718 and PCT Application Nos. WO 84/02913, 02919 and 02920 all of which are herein incorporated by reference in their entirety). See, for further examples, Herrera-Estrella (1983) Nature 303:209-213; Fraley et al. (1983) Proc. Natl. Acad. Sci, USA 80:4803-4807; Horsch et al. (1984) Science 223:496-498; and DeBlock et al. (1984) EMBO J. 3:1681-1689, all of which are herein incorporated by reference).

The second system is called the "binary" system or "binary vector" in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

In other embodiments of the invention, the nucleic acid sequence of interest is targeted to a particular locus on the plant genome. Site-directed integration of the nucleic acid sequence of interest into the plant cell genome may be achieved by, for example, homologous recombination using *Agrobacterium*-derived sequences. Generally, plant cells are incubated with a strain of *Agrobacterium* which contains a targeting vector in which sequences that are homologous to a DNA sequence inside the target locus are flanked by *Agrobacterium* transfer-DNA (T-DNA) sequences, as previously described (see, e.g. U.S. Pat. No. 5,501,967; herein incorporated by reference). One of skill in the art knows that homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

*Agrobacterium tumefaciens* is a common soil bacterium that causes crown gall disease by transferring some of its DNA to the plant host. The transferred DNA (T-DNA) is stably integrated into the plant genome, where its expression leads to the synthesis of plant hormones and thus to the tumorous growth of the cells. In yet other embodiments, the nucleic acids such as those disclosed herein is utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted heterologous polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

B. Vectors for Expressing a XERICO and/or a AT2G04240-like Gene

The nucleic acid sequences of the present invention may be employed for producing polypeptides by recombinant techniques. Thus, for example, the XERICO nucleic acid sequence may be included in any one of a variety of expression vectors for expressing a polypeptide. In some embodiments of the present invention, vectors include, but are not limited to, chromosomal, nonchromosomal and synthetic DNA sequences (for example, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host plant or microbe.

In particular, some embodiments of the present invention provide recombinant constructs comprising one or more of the nucleic sequences as broadly described above (for example, SEQ ID NO:02). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In some embodiments of the present invention, a heterologous nucleic acid sequence of interest is introduced directly into a plant. One vector useful for direct gene transfer techniques in combination with selection by the herbicide Basta (or phosphinothricin) is a modified version of the plasmid pCIB246, with a CaMV 35S promoter in operational fusion to the E. coli GUS gene and the CaMV 35S transcriptional terminator (Intl. Publication No. WO 93/07278; herein incorporated by reference).

C. Generating Transgenic Plants: Transformation Techniques

Once a nucleic acid sequence encoding a XERICO gene is operatively linked to an appropriate promoter and inserted into a suitable vector for the particular transformation technique utilized (e.g., one of the vectors described above), the recombinant DNA described above can be introduced into the plant cell in a number of art-recognized ways. Those skilled in the art will appreciate that the choice of method might depend on the type of plant targeted for transformation. In some embodiments, the vector is maintained episomally. In other embodiments, the vector is integrated into the genome. A method of the invention can be performed by introducing a polynucleotide portion of a plant stress-regulated gene into the plant. A polynucleotide can be introduced into a cell by a variety of methods well known to those of ordinary skill in the art. For example, the polynucleotide can be introduced into a plant cell using a direct gene transfer method such as electroporation or microprojectile mediated transformation, or using *Agrobacterium* mediated transformation. Non-limiting examples of methods for the introduction of polynucleotides into plants are provided in greater detail herein.

In addition to direct transformation, in some embodiments, the vectors comprising a nucleic acid sequence encoding a XERICO gene are transferred using *Agrobacterium*-mediated transformation (see, for e.g., Hinchee et al. (1988) Biotechnology, 6:915; Ishida et al. (1996) Nature Biotechnology 14:745, all of which are herein incorporated by reference). *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention), can be introduced into appropriate plant cells, by means of the Ti plasmid of *Agrobacterium tumefaciens*. The Ti plasmid is transmitted to plant cells on infection by *Agrobacterium* and is stably integrated into the plant genome (Schell (1987) Science, 237: 1176; all of which are herein incorporated by reference). Species which are susceptible infection by *Agrobacterium* may be transformed in vitro.

In particular, methods for transformation techniques for overexpressing nucleic acids encoding RING type proteins (specifically nucleic acids from moss, *Physcomitrella patens* (Hedw.) B.S.G., are shown for soybean, rapeseed/canola, corn, and wheat in U.S. Patent Appln. Nos. 20040107463 and 20020102695; all of which are herein incorporated by reference. Further, numerous examples of plant stress-regulated genes, transformation methods and transgenic plants including genes for and plants expressing *Arabidopsis thaliana* RING transcription factors are described in U.S. Patent Appln. Nos. 20020023280; 20020160378; 20040009476; 20040078852; 20040019927; 20040019927; 20060021088; 20060041961; 20060041962; 20020059663; 20040045049; all of which are herein incorporated by reference, in addition to *Arabidopsis thaliana* DREB1A transcription factors for providing a transgenic plant having improved tolerance to environmental stresses such as dehydration, low temperature and salt, in U.S. Pat. No. 6,670,528; herein incorporated by reference.

Intl. Publications WO 2002/016655; WO 2004/092398; and WO 2004/061122; all of which are herein incorporated by reference. Examples of transgenic forage plants are described in U.S. Patent Appln. Pub. Nos. 20020019997A1; 20020023279A1; and U.S. Pat. No. 5,985,666; all of which are herein incorporated by reference. Additional plant transcription factors and methods of using these plant transcription factors for providing environmental stress tolerance in plants are shown in U.S. Patent Appln. Pub. No. 20050028234 (C-repeat/dehydration-responsive element-binding factor increases tolerance of the cell and the plant to chilling, oxidative stress, water-deficit, or salt); including RING domain stress tolerance genes in Intl. Publications WO 03/062455; WO 2004/090141; and U.S. Patent Appln. No. 20040091878; all of which are herein incorporated by reference.

Further examples of transformation techniques for providing transgenic berry plants are provided (see, for e.g., Oosumi et al. (2005) Planta Published online: 1 December: 1-12; Cao et al. (1998) Plant Cell Rep 18, 266-270; all of which are herein incorporated by reference) while nonlimiting exemplary transformation methods are provided for other crop plants including tobacco and lotus plants in Bellucci et al. (2000) Plant Cell Tiss Org Cult 62, 141-151; alfalfa Galili et al. (2000) Transgenic Res 9, 137-144 and Trieu et al. (2000) Plant Journal 22, 531-541; fescue Wang et al. (2000) Plant Cell Rep 20, 213-219; potato Chakraborty et al. (2000) Proc Natl Acad Sci USA 97, 3724-3729 and Maimann et al. (2000) Plant Journal 23, 747-758; tomato Van Roekel et al. (1993) Plant Cell Rep 12, 644-647; *Brassica* Guerche et al. (1990) Mol Gen Genet 221, 306-314; bean Jaaska (1997) Genetic Resources & Crop Evol 44, 557-574; sunflower Müller et al. (2001) Transgenic Res 10, 435-444; and herb Niu et al. (2000) Plant Cell Rep 19, 304-310; all of which are herein incorporated by reference.

Transgenic plants have been produced of a number of fruit species thus providing nonlimiting exemplary transformation methods, including but not limited to the following examples: kiwi-fruit (Uematsu et al. (1991) Plant Cell Reports 10, 286-290); papaya (Fitch et al. (1990) Plant Cell Reports 9, 189-194); citrus (Vardi et al. (1990) Plant Science 69, 199-206); apple (James et al. (1990) In: (Eds G. & Grierson, D.), Genetic Engineering of Crop Plants, Lycett, Butterworths, London, pp. 239-248); strawberry (Nehra et al. (1990) Plant Cell Reports 9, 10-13); grape (Mullins et al. (1990) Bio/Technology 8, 1041-1045); cranberry (Serres et al. (1992) J American Soc. for Horticultural Sci. 117:174-180; peach (Hammerslag (1988) J America Soc. for Horticultural Sci. 111, 164-166); plum (Mante et al. (1991) Bio/Technology 9, 853-857); and orange Spiegel-Roy et al. (1983) Zeitschrift fur Pflanzenphysiologie 109, 41-48; all of which are herein incorporated by reference.

In some embodiments, direct transformation in the plastid genome is used to introduce the vector into the plant cell (See e.g., U.S. Pat. Nos. 5,451,513; 5,545,817; 5,545,818; PCT application WO 95/16783, all of which are incorporated herein by reference). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (see, for e.g., Svab et al. (1990) PNAS, 87:8526; Staub and Maliga, (1992) Plant Cell, 4:39; all of which are herein incorporated by reference). The presence of cloning sites between these markers allowed creation of a plastid targeting vector introduction of foreign DNA molecules (see, for e.g., Staub and Maliga (1993) EMBO J., 12:601; herein incorporated by reference). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyltransferase (Svab and Maliga (1993) PNAS, 90:913; herein incorporated by reference). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAi encoded by the DNA molecule.

In other embodiments, vectors useful in the practice of the present invention are microinjected directly into plant cells by use of micropipettes to mechanically transfer the recombinant DNA (see, for e.g., Crossway (1985) Mol. Gen. Genet, 202:179; herein incorporated by reference). In still other embodiments, the vector is transferred into the plant cell by using polyethylene glycol (see, for e.g., Krens et al. (1982) Nature, 296:72; Crossway et al. (1986) BioTechniques, 4:320; all of which are herein incorporated by reference); fusion of protoplasts with other entities, either minicells, cells, lysosomes or other fusible lipid-surfaced bodies (see, for e.g., Fraley et al. (1982) Proc. Natl. Acad. Sci., USA, 79:1859; herein incorporated by reference); protoplast transformation (see, for e.g., EP 0 292 435; herein incorporated by reference); direct gene transfer (see, for e.g., Paszkowski et al. (1984) EMBO J., 3:2717); Hayashimoto et al. (1990) Plant Physiol. 93:857; all of which are herein incorporated by reference).

In still further embodiments, the vector may also be introduced into the plant cells by electroporation (see, for e.g., Fromm, et al. (1985) Pro. Natl Acad. Sci. USA 82:5824; Riggs et al. (1986) Proc. Natl. Acad. Sci. USA 83:5602; all of which are herein incorporated by reference). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, the vector is introduced through ballistic particle acceleration using devices (e.g., available from Agracetus, Inc., Madison, Wis. and Dupont, Inc., Wilmington, Del.). (See, e.g., U.S. Pat. No. 4,945,050; and McCabe et al. Biotechnology 6:923 (1988); all of which are herein incorporated by reference). See, for further examples, Weissinger et al. Annual Rev. Genet. 22:421 (1988); Sanford et al. Particulate Science and Technology, 5:27 (1987) (onion); Svab et al. Proc. Natl. Acad. Sci. USA, 87:8526 (1990) (tobacco chloroplast); Christou et al. Plant Physiol., 87:671 (1988) (soybean); McCabe et al. Bio/Technology 6:923 (1988) (soybean); Klein et al. Proc. Natl. Acad. Sci. USA, 85:4305 (1988) (maize); Klein et al. Bio/Technology, 6:559 (1988) (maize); Klein et al. Plant Physiol., 91:4404 (1988) (maize); Fromm et al. Bio/Technology, 8:833 (1990); and Gordon-Kamm et al. Plant Cell, 2:603 (1990) (maize); Koziel et al. Biotechnology, 11:194 (1993) (maize); Hill et al. Euphytica, 85:119 (1995) and Koziel et al. Annals of the New York Academy of Sciences 792:164 (1996); Shimamoto et al. Nature 338: 274 (1989) (rice); Christou et al. Biotechnology, 9:957 (1991) (rice); Datta et al. Bio/Technology 8:736 (1990)

(rice); European Application EP 0 332 581 (orchardgrass and other Poaceae); Vasil et al. Biotechnology, 11: 1553 (1993) (wheat); Weeks et al. Plant Physiol., 102: 1077 (1993) (wheat); Wan et al. Plant Physiol. 104: 37 (1994) (barley); Jahne et al. Theor. Appl. Genet. 89:525 (1994) (barley); Knudsen and Muller, Planta, 185:330 (1991) (barley); Umbeck et al. Bio/Technology 5: 263 (1987) (cotton); Casas et al. Proc. Natl. Acad. Sci. USA 90:11212 (1993) (sorghum); Somers et al. Bio/Technology 10:1589 (1992) (oat); Torbert et al. Plant Cell Reports, 14:635 (1995) (oat); Weeks et al. Plant Physiol., 102:1077 (1993) (wheat); Chang et al. WO 94/13822 (wheat) and Nehra et al. The Plant Journal, 5:285 (1994) (wheat); all of which are herein incorporated by reference in their entirety.

1. Marker-assisted Trait Selection and Plant Breeding

In one embodiment, the present invention provides a method for marker-assisted selection. Marker-assisted selection involves the selection of plants having desirable phenotypes based on the presence of particular nucleotide sequences "markers" or expressed produce, such as GUS or GFP. The use of markers allows plants to be selected early in development, often before the phenotype would normally be manifest. Because it allows for early selection, marker-assisted selection decreases the amount of time need for selection and thus allows more rapid genetic progress. Briefly, marker-assisted selection involves obtaining nucleic acid from a plant to be selected. The nucleic acid obtained is then probed with probes that selectively hybridize under stringent, preferably highly stringent, conditions to a nucleotide sequence or sequences associated with the desired phenotype. In one embodiment, the probes hybridize to any of the stress-responsive genes or regulatory regions disclosed herein, for example, any one of SEQ ID NOs:02, 04, 290, 292, 294, 297, 299, 301 and 360-363. The presence of any hybridization products formed is detected and plants are then selected on the presence or absence of the hybridization products.

An additional aspect provides a method for marker-assisted breeding to select plants having an altered resistance to abiotic stress comprising obtaining nucleic acid molecules from the plants to be selected; contacting the nucleic acid molecules with one or more probes that selectively hybridize under stringent, preferably highly stringent, conditions to a nucleic acid sequence selected from the group consisting of SEQ ID NOs:02, 04, 290, 292, 294, 297, 299, 301 and 360-363; detecting the hybridization of the one or more probes to the nucleic acid sequences wherein the presence of the hybridization indicates the presence of a gene associated with altered resistance to abiotic stress; and selecting plants on the basis of the presence or absence of such hybridization. Marker-assisted selection can also be accomplished using one or more probes which selectively hybridize under stringent, preferably highly stringent conditions, to a nucleotide sequence comprising a polynucleotide expressed in response associated with a particular stress, for example, a nucleotide sequence comprising any of SEQ ID NOs:02, 04, 290, 292, 294, 297, 299, 301 and 360-363. In each case marker-assisted selection can be accomplished using a probe or probes to a single sequence or multiple sequences or as fusion sequences. If multiple sequences are used they can be used simultaneously or sequentially.

2. Regeneration.

After selecting for transformed plant material that can express a heterologous XERICO gene encoding a XERICO protein, or AT2G04240-like gene encoding a AT2G04240-like protein or variant thereof, whole plants are regenerated. Plant regeneration from cultured protoplasts is described in Evans et al. Handbook of Plant Cell Cultures, Vol. 1: (MacMillan Publishing Co. New York, 1983); and Vasil I. R. (ed.), Cell Culture and Somatic Cell Genetics of Plants, Acad. Press, Orlando, Vol. I, 1984, and Vol. III, 1986; herein incorporated by reference. It is known that many plants can be regenerated from cultured cells or tissues, including but not limited to all major species of sugarcane, sugar beet, cotton, fruit and other trees, legumes and vegetables, and monocots (e.g., the plants described above). Means for regeneration vary from species to species of plants, but generally a suspension of transformed protoplasts containing copies of the heterologous gene is first provided. Callus tissue is formed and shoots may be induced from callus and subsequently rooted.

Alternatively, embryo formation can be induced from the protoplast suspension. These embryos germinate and form mature plants. The culture media will generally contain various amino acids and hormones, such as auxin and cytokinins. Shoots and roots normally develop simultaneously. Efficient regeneration will depend on the medium, on the genotype, and on the history of the culture. The reproducibility of regeneration depends on the control of these variables.

3. Generation of Transgenic Lines

Transgenic lines are established from transgenic plants by tissue culture propagation. The presence of nucleic acid sequences encoding an exogenous XERICO gene and/or AT2G04240-like gene or mutants or variants thereof may be transferred to related varieties by traditional plant breeding techniques. Examples of transgenic lines are described herein and in Examples. Transgenic lines are established from transgenic plants by tissue culture propagation. The presence of nucleic acid sequences encoding a heterologous gene or mutants or variants thereof may be transferred to related varieties by traditional plant breeding techniques.

Transgenic lines over-expressing XERICO or AT2G04240-like genes of drought resistant cultivars may be utilized for evaluation of drought resistant activity. These transgenic lines are then utilized for evaluation of abiotic stress tolerance and agronomic traits such as phenotype, color, pathogen resistance and other agronomic traits.

4. Evaluation of Abiotic Stress Tolerance

Figure 2:
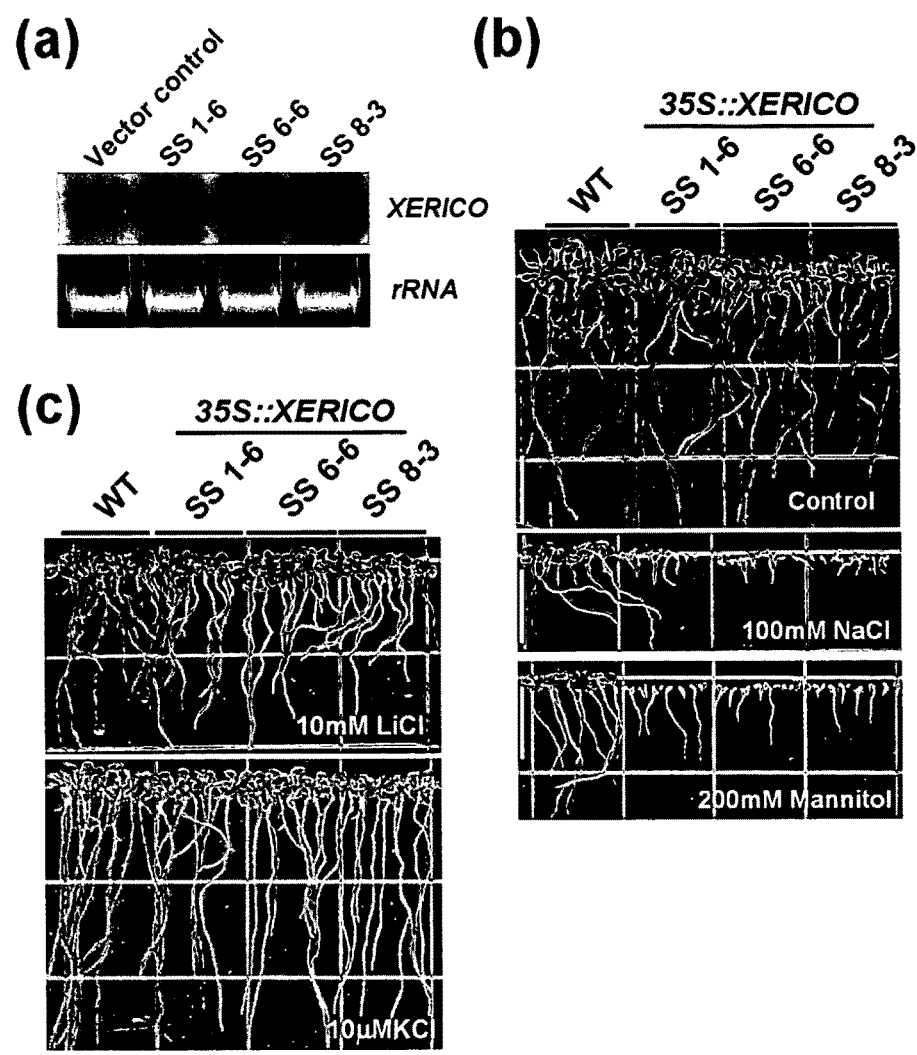
FIG. 2 demonstrates that upregulation of XERICO confers hypersensitivity to salt/osmotic stress during early seedling growth. (a) RNA gel blot analysis-showing upregulation of XERICO gene in three 35S::XERICO transgenic plants (labeled SS1-6, SS6-6 and SS8-3) compared to the vector control (wild-type) plants. Each lane was loaded with 10 μg of total RNA isolated from leaf tissue. The RNA blot was hybridized with [$^{32}$P]-labeled gene specific probe. Ethidium bromide stained rRNA was used as a RNA loading control. (b) Effects of NaCl and mannitol treatment on the early seedling growth of wild-type (WT) and 35S::XERICO plants. Photos were taken from seven-day old plants grown on MS nutrient media containing indicated chemicals. Scale bars represent 1 cm. Representative pictures of each treatment are shown. (c) Effects of low-potassium environment. Seedlings were grown for 7 days on MS nutrient media containing 10 mM LiCl (upper panel) and modified MS nutrient media containing 10 µM KCl (lower panel). Representative picture of each treatments were shown.

The transgenic plants and lines are tested for the effects of the transgene on abiotic stress tolerance phenotype. The parameters evaluated for abiotic stress tolerances are compared to those in control untransformed plants and lines. Parameters evaluated include rates of abiotic stress tolerance production, effects of drying, water deprivation, high or low salt, light, heat, cold; effects on altering steady-state ratios of abiotic stress tolerance and altering effects on abiotic stress tolerance production. Rates of abiotic stress tolerance production can be expressed as a unit of time, or in a particular tissue or as a developmental state; for example, abiotic stress tolerance production in *Arabidopsis* can be measured in leaves and in plant parts. These tests are conducted both in the greenhouse and in the field. The terms "altered abiotic stress tolerance" and "altering abiotic stress tolerance" refers to any changes in abiotic stress tolerance production. An example of such changes is shown in FIG. 2.

5. Monitoring a Population of Plants for Abiotic Stress Tolerance

A further aspect provides a method for monitoring a population of plants comprising providing at least one sentinel plant containing a recombinant polynucleotide comprising a stress responsive regulatory sequence selected from the group consisting of SEQ ID NO:02 with exemplary examples in Table 2 which is operatively linked to a nucleotide sequence encoding a detectable marker, for example a fluorescent protein. Additional aspects provide the use of various regulatory sequences including those associated with osmotic and/or salt stress (SEQ ID NO:02) with exemplary examples in Table 2 or fragments thereof wherein such fragments can alter transcription of an operatively linked nucleotide sequence in response to an abiotic stress.

It should be recognized that one or more polynucleotides, which are the same or different can be introduced into a plant, therein providing a means to obtain a genetically modified plant containing multiple copies of a single transgenic sequence, or containing two or more different transgenic sequences, either or both of which can be present in multiple copies. Such transgenic plants can be produced, for example, by simply selecting plants having multiple copies of a single type of transgenic sequence; by cotransfecting plant cells with two or more populations of different transgenic sequences and identifying those containing the two or more different transgenic sequences; or by crossbreeding transgenic plants, each of which contains one or more desired transgenic sequences, and identifying those progeny having the desired sequences.

EXPERIMENTAL

The following examples are provided in order to demonstrate and further Illustrate certain preferred embodiments and aspects of the present invention and are not to be construed as limiting the scope thereof.

In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade/Celsius).

Example I

Materials and Methods
Experimental Procedures
Plant Materials and Growth Conditions

*Arabidopsis thaliana*, ecotype Columbia (Col), was used as the wild-type plant for phenotypic assays for comparison to transgenic 35S::XERICO *Arabidopsis thaliana*, plants in these experiments. Unless noted otherwise, plants were grown under sterile conditions on MS nutrient agar media (1×MS basal medium (Sigma, stock number M5519) with 2% sucrose and 0.3% phytagel (Sigma) containing 2% sucrose or on soil in a growth chamber (16 h light/8 h dark) at 23° C., after stratification. For monitoring of hypocotyl elongation and root growth with response salt/osmotic stress, a minimum of 20 seeds were sowed on MS nutrient agar media containing specified treatments, following which the plates were held in the vertical position for 7 days. For testing the effects of ABA on germination and early seedling growth, seeds were grown horizontally. For abiotic stress treatments, wild-type seedlings were grown on MS nutrient agar media containing 2% sucrose for 10-days and then treated the stresses indicated in FIG. 1, for up to 24 hour without a treatment control. Samples were collected at the indicated time and frozen immediately in liquid $N_2$ and were stored at −80° C. until use. Experiments were performed in triplicates and repeated at least three times.
Generating Transgenic Plants Over-Expressing XERICO A full-length cDNA of XERICO (At2g04240; SEQ ID NO:02 and 12) was amplified by PCR using primers 5'-TTTGGATCCGACAACATCATTTCTACCGACA-3' (forward; SEQ ID NO:437) and 5'-CCCTCTAGATAGCTG- TACACAACAAACACACTC-3' (reverse; SEQ ID NO:438); designed to contain BamHI and XbaI site (restriction enzymes used for this invention were purchased from Roche Inc.), respectively. The resulting product (SEQ ID NO:11) was digested with BamHI and XbaI and inserted between a 35S promoter of the Cauliflower mosaic virus (CaMV; SEQ ID NO:376) and a nopaline synthase terminator in the pCB302-3 binary vector containing a bar gene encoding phosphinothricin acetyltransferase (PAT) inside the T-DNA for the selection of transformants (see, for e.g., Xiang et al. (1999) Plant Mol Biol. 40(4):711-7; herein incorporated by reference). The vector was introduced into *Agrobacterium tumefaciens* strain C58 (see, for e.g., Han et al. (1997) Transgenic Research 6: 415-420; herein incorporated by reference), then used to transform *Arabidopsis* ecotype Columbia by the floral-dip method as described by Clough and Bent (1998) Plant J. 16:735-743; herein incorporated by reference in its entirety. Eighteen of T3 progeny resulting from self-crosses that were homozygous were used for phenotypic characterizations.
RNA Extraction and Northern Blot Analysis Total RNA was extracted using the Trizol reagent method (Gibco-BRL, Gaithersburg, Md.). For northern blot analysis, 10 µg of total RNA from each sample was denatured and separated using a 1% agarose-formaldehyde gel. RNA was transferred onto a Hybond-N+ membrane (Stratagene, La Jolla, Calif.) by capillary action. Gene-specific probes were prepared by PCR and labeled with [$^{32}$P]-dCTP using a Prime-it II Random Primer Labeling kit (Stratagene, La Jolla, Calif.). Primers used in this analysis were following: XERICO (forward; SEQ ID NO:439, 5'-TTGGAACAT-CACTTGCCCAT-3 and reverse; SEQ ID NO:440, 5'-TGT-GTTCAAACAAGAGCTCCA-3'), AtNCED3 (forward, SEQ ID NO:441, 5'-AATCATACTCAGCCGCCATT-3' and reverse; SEQ ID NO:442, 5'-TTTAGTTCCGTCCGGT-GAGAA-3'), AtCYP707A2 (forward; SEQ ID NO:443, 5'-GCAAATCTCATCTTCATCGT-3' and reverse; SEQ ID NO:444, 5'-TGTCGAATGCTGAATTGCTC-3'), RD29a (forward; SEQ ID NO:445, 5'-GTGGAGAAGATCTCTAC-CGAGAAGG-3' and reverse; SEQ ID NO:446, 5'-CAT-CAAAGACGTCAAACAAAACACA-3'), and Actin 8 (forward; SEQ ID NO:447, 5'-ATGAAGATTAAGGTCGTGGCA-3' and reverse; SEQ ID NO:450, 5'-TCCGAGTTTGAAGAGGCTAC-3'). Hybridization was carried out using ULTRAhyb® according to the manufacturer's instructions (Ambion, Austin, Tex.), and a Kodak Biomax film (Sigma) was exposed to the blot. An Actin 8 gene (SEQ ID NO:457) or ethidium bromide-stained ribosomal RNA was used as a loading control.
Drought Stress Treatment and Measurements of ABA Content Drought stress was treated by the method of Qin and Zeevaart (1999) Proc. Natl. Acad. Sci. USA, 96:15354-15361; herein incorporated by reference. In brief, aerial parts of *Arabidopsis* plants were harvested from 14 day-old seedlings, and the fresh weight was reduced rapidly (<10 min) by 12-15%, using a hair dryer. The stressed samples were stored in a polyethylene bag in darkness at 23° C. for six hours. Samples were frozen immediately in liquid $N_2$ and were stored at −80° C. until use. Material used for ABA determinations was lyophilized followed by a dry weight was measure. The procedure for extraction, purification, and quantitation of ABA was as described (Cornish and Zeevaart, (1984) Plant Physiol. 76:1029-1035; herein incorporated by reference) with modifications. The lyophilized samples were extracted and homogenized in 80% (v/v) aqueous acetone with a Polytron homogenizer (Brinkmann Instruments, Westbury, N.Y.). Five mL of 1 M phosphate buffer (pH 8.0) was added to the extract. After removal of the acetone on a rotary evaporator, lipids were removed by partitioning the aqueous concentrate twice with hexanes. The pH of the aqueous phase was adjusted to 2.5 with 6 N HCl and extracted three times with ethyl acetate. The acidic fraction was collected and dried in a centrifugal vacuum concentrator (Jouan, Winchester, Va.) and subjected to reverse-phase HPLC (see, for e.g., Cornish and Zeevaart, (1984) Plant Physiol. 76:1029-1035; herein incorporated by reference in its entirety).

Drought Tolerance and Water Loss Analysis

Thirty-days-old wild-type and 35S::XERICO plants, grown in pots (10×10×10 cm), with approximately 10 leaves were kept in a growth room maintained without further watering to evaluate their drought tolerance. For water loss analysis, three fully expanded leaves from three wild-type and 35S::XERICO plants that had developed approximately 14 leaves were detached and left on a bench to dry. The leaves were weighed at certain times to determine the rate of water loss. Each experiment was done at least three times.

Measurement of Stomatal Aperture

Leaves were taken at 11:00 AM (Light turns on at 9:00 AM) from 4-week-old soil-grown wild-type plants and 35S::XERICO plants. Immediately after the harvest, a commercial nail polisher was applied to the lower epidermis. The prepared epidermal strips were observed under a Nikon Diaphot, inverse microscope. Pictures were taken with a Sony MAVICA digital camera and used for measurements of stomatal aperture. The apertures of the stomatal pores were measured by using 'the measure tool' of Adobe PhotoShop 5.5 (Adobe Systems Inc.), which calculates the distances between any two points.

Gene Expression Analysis Using Affymetrix Genechip™

Total RNA isolation: wild-type *Arabidopsis* plants and the 35S::XERICO *Arabidopsis* plants were grown for 20 days on soil under long-day conditions (16 h light/8 h dark). The plant samples (aerial parts) were pooled from several batches of plants to minimize a variation in gene expression patterns caused by a subtle change in environmental condition and harvested around 4:00 PM. These experiments were duplicated. Methods for the preparation of cRNA from mRNA, and the subsequent steps leading to hybridization and scanning of the ATH1 GeneChip Arrays, were performed as described (see, for e.g., Ko et al. (2004) Plant Physiol. 135:1069-1083; Ko and Han, (2004) Plant Mol. Biol. 55:433-453; all of which are herein incorporated by reference in their entirety). The average difference and expression call, for each of the duplicated samples, was computed using Microarray Suite (MAS) 5.0 (Affymetrix, Santa Clara, Calif.) with default parameters. The resulting hybridization intensity values (signal intensity) reflect the abundance of a given mRNA species relative to the total mRNA population were used to calculate the fold-changes of individual gene expressions between 35S::XERICO plants and wild-type plants. Expression data from this experiment was recorded. Technical references for *Arabidopsis* GeneChip® arrays include, for example, Hennig et al. (2003) Plant Mol Biol 53: 457-465; Liu et al. (2002) Bioinformatics 18: 1593-1599; Lockhart et al. (1996) Nat Biotechnol 14: 1675-1680; Menges et al. (2003) Plant Mol Biol 53: 423-442 and Redman et al. (2004) Plant J 38: 545-561; all of which are herein incorporated by reference in their entirety.

Yeast Two-Hybrid Screening

Two-hybrid screening was performed using the BD Matchmaker™ library construction and screening kit (Clonetech, Palo Alto, Calif.); pGADT7 was used as the base for a GAL4 activation domain (AD) vector and pGBKT7 was used for a GAL4 DNA-binding domain (DNA-BD) vector (pGADT7 and pGBKT7 were obtained from "BD Matchmaker Library Construction & Screening Kits" (Clontech, Palo Alto, Calif.)). The yeast strain AH109 (leu⁻, trp⁻, Ade⁻, his⁻) (obtained from "BD Matchmaker Library Construction & Screening Kits (Clontech, Palo Alto, Calif.)) with chromosomally integrated reporter genes lacZ and HIS under the control of the GAL1 promoter activated by the GAL4 transcription factor was used to host all constructs. Truncated XERICO cDNA without a transmembrane domain (SEQ ID NO: 451) was amplified by PCR using primers 5'-GGGG-GAATTCGAGTCATTTGATTTCCGGGT-3' (forward; SEQ ID NO:449) and 5'-GGGGCTGCAGTCACCAAACATTA-GAAGAAAGC-3' (reverse; SEQ ID NO:450) designed to contain EcoRI and PstI site, respectively. The amplified PCR product was digested with EcoRI and PstI, and subcloned into pGBKT7 as a fusion to the DNA binding domain of GAL4 and verified by sequencing. The pGBKT7/XERICO vector was used as a bait to screen an *Arabidopsis thaliana* cDNA library in pGADT7 as a fusion to the activation domain of GAL4. Transformation of AH109 was performed using the Matchmaker Library Protocol (Protocol No. PT3624-2; Version No. PR21638, Clontech, Palo Alto, Calif.; herein incorporated by reference in its entirety). Positive clones were isolated from high stringency screening on SD DO medium (−His, −Ade, −Leu, −Trp, Clontech, Palo Alto, Calif.) and sequenced. Yeast two-hybrid interactions were further confirmed in vivo by vector swap. For the swap, truncated XERICO was subcloned into pGADT7 as a GAL4 AD vector.

Example II

Transgenic Plants Over-Expressing XERICO Demonstrated Hypersensitivity to Salt and Osmotic Stress During Germination and Early Seedling Growth XERICO (At2g04240; SEQ ID NO:02) is a single copy gene in the *Arabidopsis* genome that encodes a small protein (162 amino acids; SEQ ID NO:01) with an N-terminal transmembrane domain (SEQ ID NO:09), a RING-H2 zinc-finger motif located at the C-terminus (SEQ ID NO:3), and a serine-rich domain in the middle (SEQ ID NO:08) (FIG. 1*a*). XERICO is expressed ubiquitously in the plant, but its transcript is accumulated more in the actively growing tissues (FIG. 1*b*). Using Affymetrix GeneChip array data available on the AtGenExpress website (AtGenExpress, web.uni-frankfurt.de/fb15/botanik/mcb/AFGN/atgenex.htm), transcriptional regulation of XERICO was examined at various aspects of plant growth and development, including during plant hormonal and environmental stress responses. The information obtained showed that salt and osmotic stress considerably induced the expression of XERICO, reaching the highest level (up to 5.8-fold increase compared to control) at 6 hours (FIG. 1*c*), which was validated by Northern blot analysis (FIG. 1*d*). These results showed that XERICO may function in salt/osmotic stress responses.

Example III

Figure 3:
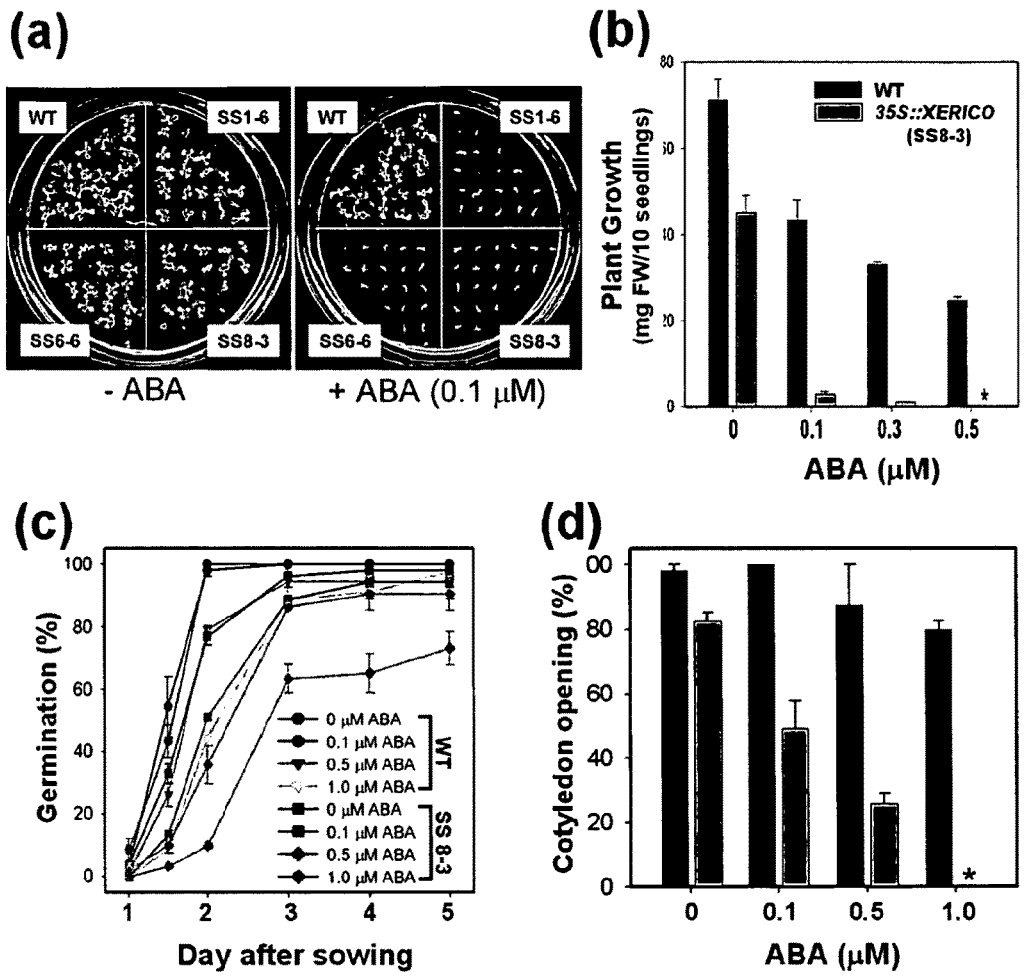
FIG. 3 demonstrates that abscisic acid (ABA) treatment inhibits germination and early seedling growth of 35S::XERICO plants. (a) Effects of ABA treatment on the early seedling growth of wild-type (WT) and three independent 35S::XERICO T3 homozygote lines. The plants were grown for 8-days on MS nutrient media with or without 0.1 µM ABA. Representative pictures of each treatment were shown. Scale bars indicate 1 cm. (b) Effects of ABA treatment on early seedling growth. Fresh weights of plants grown for 8-days on MS nutrient media containing different levels of ABA were measured. Asterisk indicates that no measurement was made due to germination failure. The error bars indicate the mean±SE from three independent experiments. (c) Effect of ABA treatment on seed germination. Seeds were plated on media containing various concentrations of ABA. Seedlings with fully emerged radicles (>1 mm) were counted. The error bars indicate the mean±SE of approximately 70 seeds from three independent experiments. (d) Differential sensitivity of seedling development to ABA between wild-type (black bar) and 35S::XERICO plants (SS8-3 line) (gray bar). The numbers shown in Y-axis are the percentages of 5-days-old seedlings with cotyledon openings over total number of seeds planted in the experiment (c).

Transgenic Plants Over-expressing XERICO Demonstrated Hypersensitivity to Salt and Osmotic Stress During Germination and Early Seedling Growth Transgenic *Arabidopsis* plants over-expressing the gene (35S::XERICO) were created during the course of the present inventions. See, EXAMPLE I for methods. Fifteen out of 18 over-expression transgenic lines showed similar phenotypes such as short hypocotyl, round-shaped rosette leaves, ABA hyper-sensitivities of early seedling growth. Of these 15 lines, three T3 homozygous lines (SS1-6, SS6-6 and SS8-3) were used for further phenotypic characterizations based on their XERICO expression levels (FIG. 2a). The early seedling growth of all of the tested 35S::XERICO plants was hypersensitive to both salt and osmotic stresses, compared to wild-type plants (FIG. 2b). To address whether the observed sensitivity of the 35S::XERICO plants is from a defect in potassium uptake for osmoregulation, effects of both LiCl treatment, an inhibitor of potassium uptake, and a low potassium environment were investigated. In the experiments conducted during the course of the present inventions, no significant differences in the seedling growth between wild-type plants and 35S::XERICO plants upon these treatments were observed (FIG. 3c). These results show that the sensitivity to salt/osmotic stress of the 35S::XERICO plants in early seedling growth is not likely due to a defect in potassium uptake.

Example VI

A 35S::XERICO Plant is Hypersensitive to ABA

Since the hypersensitivity to salt or osmotic stress was the most prominent phenotype of the three independent T3 homozygous lines of 35S::XERICO plants, the functional relationship of the gene with ABA, a plant stress hormone involved in salt and drought stress adaptation, was investigated. Even at the sub-micro molar concentration of exogenous ABA (0.1 μM), the growth of all three independent lines of 35S::XERICO plants were arrested immediately after germination compared to wild-type plants (FIG. 3a). Although 35S::XERICO plants germinated slightly later than wild-type even in the absence of exogenous ABA (FIG. 3c), germination was further delayed following ABA treatment. At 0.1 μM of ABA, 13% of 35S::XERICO plants were germinated 1.5 day after sowing, while 43% of wild-type seeds germinated. In the presence of 1.0 μM ABA, more than 20% of 35S::XERICO plants failed to germinate, even after the prolonged incubation (FIG. 3c). Germination was scored by the emergence of a radicle (>1 mm). The number of 'cotyledon opening' of seedlings at five days after sowing were counted and recorded. At 1 μM ABA, 35S::XERICO plants did not develop a cotyledon, while approximately 80% of wild-type plants had opened cotyledons (FIG. 3d). For evaluation of the loss-of-function phenotypes of this gene, antisense transgenic plants of XERICO were produced. Significant phenotypic changes in cotyledon openings in the antisense transgenic plants were observed.

Example V

Upregulation of XERICO Modulates the Expression of ABA-biosynthesis and ABA-responsive Genes 35S::XERICO plants appeared to have disturbance in ABA homeostasis, therefore transcriptional regulation of genes involved in the control of endogenous ABA level was investigated. AtNCED3 (9-cis-epoxycarotenoid dioxygenase; At3g14440; SEQ ID NO: 383) encodes a key enzyme in ABA biosynthesis (SEQ ID NO:382) (see, for e.g., Iuchi et al, (2001) Plant J. 27:325-333; herein incorporated by reference), while AtCYP707A2 (ABA 8'-hydroxylase; At2g29090; SEQ ID NO:427 and 428) was recently identified as a key enzyme in the oxidative catabolism of ABA (see, for e.g., Kushiro et al. (2004) EMBO J. 23:1647-1656; Saito et al. (2004) Plant Physiol. 134:1439-1449; all of which are herein incorporated by reference). Transcripts of AtNCED3 (SEQ ID NO:452) was clearly increased by ABA treatment in both wild-type and 35S::XERICO plants (FIG. 4a). However, in the 358::XERICO plants, the ABA induction of the AtNCED3 was much stronger than wild-type plants. The expression of AtNCED3 peaked at 6-hour after ABA treatment and then sustained up to 24-hour. However, the induction of AtNCED3 was decreased after the peak at 3-hour in wild-type plants. Accordingly, AtCYP707A2 (SEQ ID NO:428) induction kinetics was changed in both wild-type and 35S::XERICO plants, probably to control the endogenous ABA level. The expression of AtCYP707A2 was sustained up to 24-hour in the 35S::XERICO plants (FIG. 4a).

The expression of an ABA and desiccation-inducible gene (RD29a/COR78/LTI78; At5g52310; SEQ ID NO:386) (Yamaguchi-Shinozaki and Shinozaki, (1993) Mol. Gen. Genet. 236:331-340; herein incorporated by reference) as a positive control was investigated. The result showed that the induction of RD29a was strongly enhanced in the 358::XERICO plants compared to wild-type plants when treated with exogenous ABA (FIG. 4a). It was noted that RD29a gene expression was much stronger in 358::XERICO plants without ABA treatment.

Drought treatment, which induces endogenous ABA, showed a more clear distinction between wild-type and mutant plants. Transcriptional upregulation of AtNCED3 (SEQ ID NO:452) by drought treatment was much faster and stronger in 35S::XERICO plants than in wild-type plants (FIG. 4b). Substantial induction of AtCYP707A2 (SEQ ID NO:428) appeared one-hour after the drought treatment in the 35S::XERICO plants, implying more rapid synthesis and accumulation of endogenous ABA in the 358::XERICO plants (FIG. 4b). These results show that ABA may regulate the expression of ABA biosynthetic gene and the catabolic gene, with the upregulation of XERICO altering this regulation.

Figure 4:
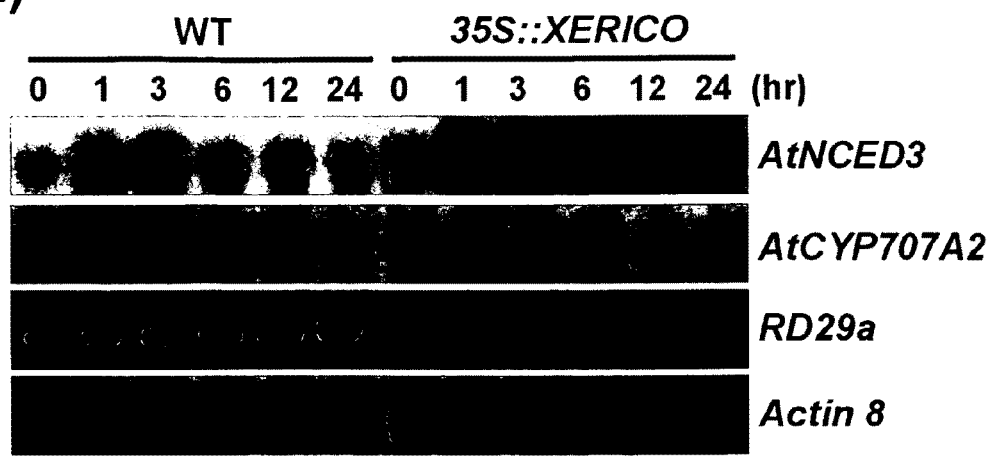
FIG. 4 demonstrates that upregulation of XERICO modulates the expression of ABA regulated genes. (a) RNA gel blot analysis showing a response to ABA. Wild-type (WT) and 35S::XERICO plants were grown on MS nutrient agar media for 10 days and then treated with 10 µM of ABA for up to 24 hour. Total RNA was isolated at the indicated times after treatment. Each lane was loaded with 10 µg total RNA. The RNA blot was hybridized with [$^{32}$P]-labeled gene specific probes for AtNCED3 (SEQ ID NO:452), AtCYP707A2 (SEQ ID NO:428) and RD29a (SEQ ID NO:386). Probing with Actin 8 (SEQ ID NO:455) was used as a RNA loading control. (b) RNA gel blot analysis in response to drought treatment. Wild-type (WT) and 35S::XERICO plants were grown on MS medium for 14 days and then dehydrated (see, EXAMPLE I).
Figure 4:

Upregulation of XERICO in *Arabidopsis* induced hypersensitivity to salt/osmotic stress and ABA treatments during germination and early seedling growth. It was contemplated that hypersensitivity to ABA may have come from altered ABA metabolism or signaling. ABA is known to affect the expression of many genes involved in ABA metabolism (see, for e.g., Seo and Koshiba (2002) Trends Plant Sci. 7:41-48; herein incorporated by reference) therefore the transcriptional regulation of genes involved in the processes of ABA metabolism and signaling was investigated. Indeed, the kinetics of ABA- and drought-mediated induction of a key ABA biosynthesis gene (AtNCED3) (see, for e.g., Iuchi et al, (2001) Plant J. 27:325-333; Tan et al. (2003) Plant J. 35:44-56; all of which are herein incorporated by reference) was much faster and stronger in the 35S::XERICO plants compared to wild-type plants (FIG. 4a). Moreover, the elevated expression of RD29a (SEQ ID NO:389) in the absence of ABA treatment and substantial induction of AtCYP707A2 (SEQ ID NO:428) one-hour after the drought treatment strongly suggests either a more rapid biosynthesis or higher level of endogenous ABA in the 35S::XERICO plants (FIG. 4).

Example VI

Upregulation of XERICO Increases Cellular ABA Content

Figure 5:
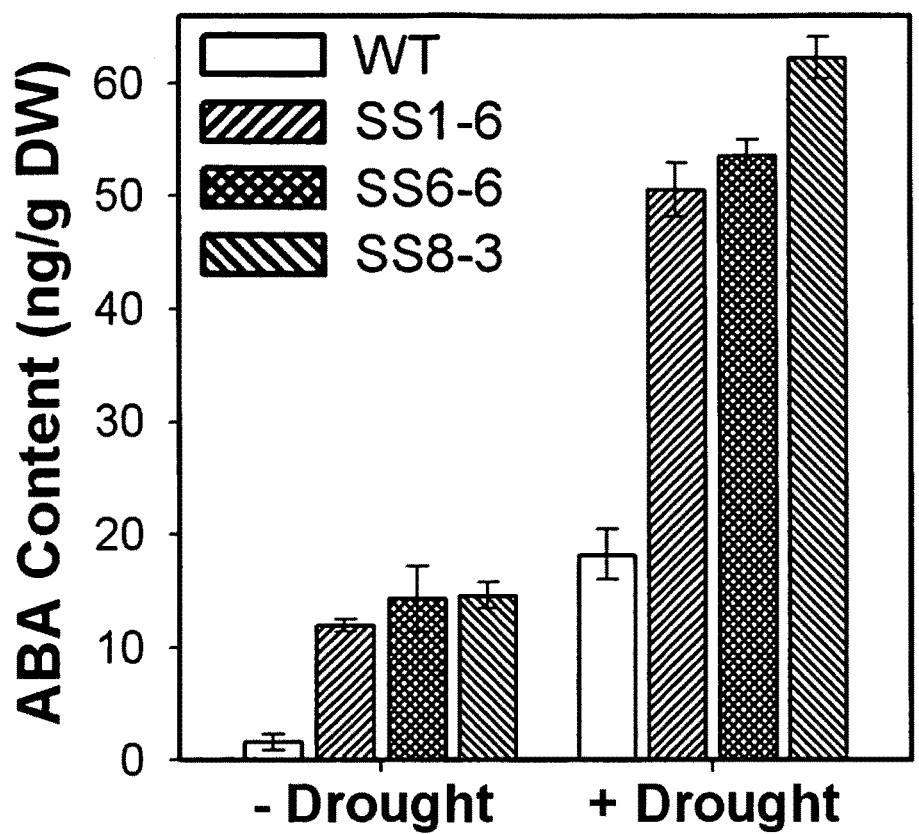
FIG. 5 demonstrates that upregulation of XERICO increases cellular ABA level. ABA contents were measured from wild-type (WT) and three independent 35S::XERICO T3 homozygote lines grown for 14-days and then subjected to drought treatment for 6 hour (see, EXAMPLE I). The error bars indicate the mean±S.D. from three independent experiments.

High level expression of ABA-biosynthetic and ABA-responsive genes in 35S::XERICO plants, in both the presence and absence of ABA and with drought treatment led to the prediction that 35S::XERICO transgenic plants should have elevated endogenous ABA. Therefore, endogenous ABA content with or without drought treatment by reverse-phase HPLC was measured. Results from three independent experiments showed that the levels of ABA in 35S::XERICO plants (SS1-6, SS6-6 and SS8-3) were more than 10-fold higher than in the wild-type plants when grown on soil for 14 days without drought treatment (FIG. 5). A six-hour drought treatment dramatically increased endogenous ABA content in the 35S::XERICO plants, which is up to 3-fold higher than the ABA increase of wild-type plants (FIG. 5). These results clearly demonstrated that upregulation of XERICO gene increases cellular ABA levels. Upregulation of XERICO gene also substantially increased ABA biosynthesis (FIG. 5). However, it should be noted that the expression of transcriptional regulators of ABA signaling (e.g., ABI5 (ABA insensitive ABI gene family, member 15) (SEQ ID NO:321 and 322) ABI3 (ABA insensitive ABI gene family, member 3) (SEQ ID NO:323 and 324), AtMYB2 (SEQ ID NO:326 and 327), and AtMYC (SEQ ID NO:324 and 325); see, for e.g., Finkelstein et al. (2002) Plant Cell, 14 Suppl, S15-45; herein incorporated by reference) were not changed in the 35S::XERICO plants (Table 1). Thus hypersensitivity of 35S::XERICO plants to ABA and salt/osmotic stress during germination and early seedling growth was associated with the increased level of endogenous ABA. However, no significant changes in the expression of XERICO upon ABA treatment (10 μM) up to 3-hours post-treatment were detected.

TABLE 1

Genes up or downregulated in the 35S::XERICO plants identified by Genechip analysis.

| Gene Name | Affy I.D[a] | AGI[b] | WT[c] (S.I.)[d] | MT[e] (S.I.) | Change[f] p-value | Change Call[g] | FC[h] (Log$_2$) |
|---|---|---|---|---|---|---|---|
| Up-regulated Genes | | | | | | | |
| ACC synthase (ACS11) | 255177_at | At4g08040 | 9.05 | 295.25 | 0.000028 | I | 5.0 |
| XERICO | 263325_at | At2g04240 | 845.2 | 16610.2 | 0.000020 | I | 4.1 |
| CYP707A2, ABA 8'-hydroxylase | 266778_at | At2g29090 | 47.2 | 192.95 | 0.000030 | I | 2.0 |
| actin-like protein | 249127_at | At5g43500 | 162.9 | 583.4 | 0.000049 | I | 1.8 |
| AtWRKY53 | 254231_at | At4g23810 | 85 | 251.4 | 0.000269 | I | 1.4 |
| Unknown protein | 251072_at | At5g01740 | 86.5 | 231.4 | 0.000020 | I | 1.4 |
| Expressed protein | 247882_at | At5g57785 | 1585.45 | 3949.1 | 0.000030 | I | 1.3 |
| Unknown protein | 262661_s_at | At1g14250 | 674.2 | 1602.4 | 0.000020 | I | 1.3 |
| Unknown protein | 245422_at | At4g17470 | 482.4 | 1204.3 | 0.000020 | I | 1.3 |
| Putative myrosinase-binding protein homolog | 265058_s_at | At1g52040 | 226 | 584.75 | 0.000020 | I | 1.1 |
| At14a | 256601_s_at | At3g28290 | 632.2 | 1457.3 | 0.000022 | I | 1.1 |
| Unknown protein | 265441_at | At2g20870 | 243.55 | 462.45 | 0.001344 | I | 1.1 |
| NADH-dependent glutamate synthase | 248267_at | At5g53460 | 644.5 | 1422.8 | 0.000020 | I | 1.1 |
| Vegetative Storage Protein Vsp1 | 245928_s_at | At5g24780 | 3451 | 7121.2 | 0.000020 | I | 1.1 |
| Expressed protein | 253737_at | At4g28703 | 58.95 | 158.8 | 0.000383 | I | 1.0 |
| CYP90C1, *rotundifolia* (rot3) | 246216_at | At4g36380 | 58.8 | 116.75 | 0.000482 | I | 1.0 |
| Putative myrosinase binding protein | 265053_at | At1g52000 | 424.6 | 645.9 | 0.000356 | I | 1.0 |
| GH3 like protein | 253908_at | At4g27260 | 218.75 | 386.8 | 0.000206 | I | 1.0 |
| Down-regulated Genes | | | | | | | |
| Expressed protein | 258370_at | At3g14395 | 64.65 | 4.6 | 0.999977 | D | −3.5 |
| putative monodehydroascorbate reductase | 258941_at | At3g09940 | 43.5 | 3.35 | 0.998911 | D | −3.2 |
| osmotin precursor | 254889_at | At4g11650 | 67.95 | 8.3 | 0.997941 | D | −3.2 |
| putative protein | 254692_at | At4g17860 | 112.1 | 11.1 | 0.999854 | D | −3.0 |
| nonspecific lipid-transfer protein-like | 247718_at | At5g59310 | 141.8 | 31.55 | 0.999894 | D | −2.9 |
| protein kinase, putative | 256359_at | At1g66460 | 41.05 | 7.7 | 0.997879 | D | −2.7 |
| putative DNA binding protein | 265263_at | At2g42940 | 92.9 | 16.8 | 0.998940 | D | −2.6 |
| unknown protein | 263836_at | At2g40330 | 89.05 | 19.85 | 0.999138 | D | −2.4 |
| putative protein | 250744_at | At5g05840 | 61.75 | 18.75 | 0.999355 | D | −2.1 |
| chlorophyll a/b binding protein | 265722_at | At2g40100 | 37.95 | 12.75 | 0.999980 | D | −1.7 |
| hypothetical protein | 265264_at | At2g42930 | 1750.25 | 488.85 | 0.999704 | D | −1.7 |
| Serine/threonine kinase-like | 254253_at | At4g23320 | 44.35 | 13.9 | 0.997859 | D | −1.7 |
| hypothetical protein | 251284_at | At3g61840 | 160.4 | 63.15 | 0.999938 | D | −1.5 |
| hypothetical protein | 257057_at | At3g15310 | 86.15 | 58.05 | 0.998664 | D | −1.4 |
| putative tyrosine aminotransferase | 263539_at | At2g24850 | 173.2 | 68.25 | 0.999926 | D | −1.4 |
| At-EXP11, expansin | 261226_at | At1g20190 | 1395.95 | 364.75 | 0.999955 | D | −1.3 |
| Peroxidase | 267053_s_at | At2g38390 | 100.45 | 50.3 | 0.999867 | D | −1.3 |
| unknown protein | 262832_s_at | At1g14870 | 345.75 | 250.25 | 0.999980 | D | −1.3 |
| putative protein | 246000_at | At5g20820 | 539.3 | 253.65 | 0.999259 | D | −1.3 |
| Putative ethylene response factor | 264083_at | At2g31230 | 135.25 | 52.6 | 0.999904 | D | −1.2 |
| Similar to transcriptional activator CBF1 | 255937_at | At1g12610 | 158.1 | 74.45 | 0.998141 | D | −1.2 |
| hypothetical protein | 261247_at | At1g20070 | 1536.25 | 791.75 | 0.999979 | D | −1.2 |
| CYP72B1, BL 26-hydroxylase | 267614_at | At2g26710 | 129 | 49.85 | 0.999050 | D | −1.1 |
| CYP94C1, cytochrome p450 | 266246_at | At2g27690 | 291.65 | 135.35 | 0.999970 | D | −1.1 |
| myb family transcription factor | 263549_at | At2g21650 | 98.4 | 45.7 | 0.999799 | D | −1.1 |
| putative lectin | 257206_at | At3g16530 | 236.25 | 113.25 | 0.999980 | D | −1.1 |
| unknown protein | 255479_at | At4g02380 | 547.35 | 274.85 | 0.999975 | D | −1.1 |
| extensin related | 253024_at | At4g38080 | 1098 | 451.45 | 0.999547 | D | −1.1 |
| Ferritin 1 precursor | 251109_at | At5g01600 | 761.7 | 297 | 0.999817 | D | −1.1 |
| RING zinc finger protein-like | 249306_at | At5g41400 | 265.5 | 134.35 | 0.999448 | D | −1.1 |
| Nonspecific lipid-transfer protein precursor | 247717_at | At5g59320 | 640.85 | 302.6 | 0.999979 | D | −1.1 |
| DC1.2 homologue-like protein | 247478_at | At5g62360 | 426.75 | 238.05 | 0.999963 | D | −1.1 |
| hypothetical protein | 245771_at | At1g30250 | 1016.25 | 495.15 | 0.999951 | D | −1.1 |
| unknown protein | 258100_at | At3g23550 | 99.75 | 55.35 | 0.999955 | D | −1.1 |
| Similar to auxin-induced protein 15A | 253103_at | At4g36110 | 316.5 | 141.4 | 0.998702 | D | −1.1 |
| CYP94B3, cytochrome p450 | 252368_at | At3g48520 | 179.9 | 91.65 | 0.999933 | D | −1.1 |
| putative protein DRT100 | 250277_at | At5g12940 | 194.8 | 72.35 | 0.999685 | D | −1.1 |
| apetala2 domain TINY like protein | 245445_at | At4g16750 | 344.1 | 107.2 | 0.999935 | D | −1.1 |

TABLE 1-continued

Genes up or downregulated in the 35S::XERICO plants identified by Genechip analysis.

| Gene Name | Affy I.D[a] | AGI[b] | WT[c] (S.I.)[d] | MT[e] (S.I.) | Change[f] p-value | Change Call[g] | FC[h] (Log$_2$) |
|---|---|---|---|---|---|---|---|
| hypothetical protein | 260744_at | At1g15010 | 531.15 | 284.05 | 0.999980 | D | −1.0 |
| phytocyanin | 266884_at | At2g44790 | 112.2 | 68.95 | 0.999181 | D | −1.0 |
| unknown protein | 265837_at | At2g14560 | 162 | 112.4 | 0.999980 | D | −1.0 |
| putative trypsin inhibitor | 260551_at | At2g43510 | 869.9 | 468.25 | 0.999980 | D | −1.0 |
| Putative expansin | 255822_at | At2g40610 | 202.8 | 101.9 | 0.999980 | D | −1.0 |
| calcium-binding protein-like | 249417_at | At5g39670 | 3318.4 | 1532.55 | 0.996443 | D | −1.0 |

[a]Identification number of Affymetrix *Arabidopsis* genechip (ATH1).
[b]*Arabidopsis* Gene Index number.
[c]WT, wild-type plants.
[d]S.I., Average Signal Intensity of both replicates.
[e]MT, 35S::XERICO plants (SS8-3 line).
[f]Change p-value for S.I. of MT over S.I. of WT was caculated from both replicates by Microarray Suite (MAS) 5.0 (Affymetrix, Santa Clara, CA). Values close to 0.0 indicate likelihood for an increase (I), wherease values close to 1.0 indicate likelihood for a decrease (D).
[g]Change calling caculated by MAS 5.0; I, increase, D, decrease.
[h]Fold changes were calculated from signal log ratio of MT over WT by MAS 5.0. Averaged fold change of both replicate experiments were shown.
Note:
whole Genechip data with detailed statistical analysis was recorded for these experiments.

Example VII

Upregulation of XERICO Confers Drought Tolerance in *Arabidopsis*

Figure 6:
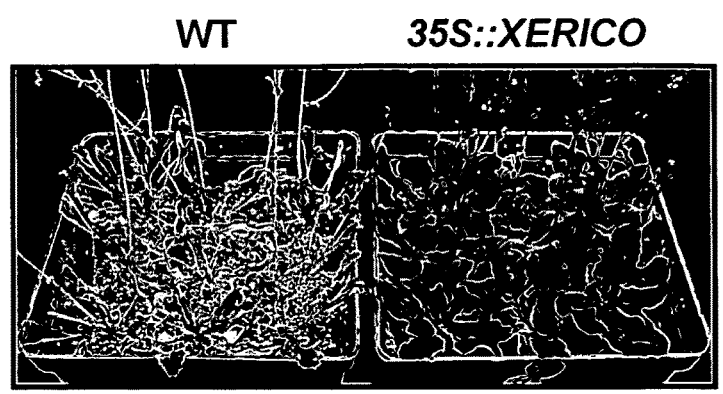
FIG. 6 demonstrates that over-expression of XERICO enhances drought tolerance in *Arabidopsis*. (a) Drought tolerance: Thirty-days-old soil grown wild-type and 35S::XERICO plants (SS8-3) were kept in a growth chamber without further watering. The photographs were taken 10 days after the last watering. A representative picture is shown. (b) Drought tolerance of 35S::XERICO plants (SS8-3) in a single pot with wild-type plants. The exemplary photographs were taken 8 days after the last watering. A representative picture is shown. (c) Differential transpirational water loss between wild-type and 35S::XERICO plants. Detached leaves from 25-day-old plants grown on soil were incubated on a bench and fresh weights were measured at the indicated time intervals. Water loss was calculated from the decrease of fresh weights compared to time-0. The error bars indicate the mean±SE from three independent experiments.
Figure 6:
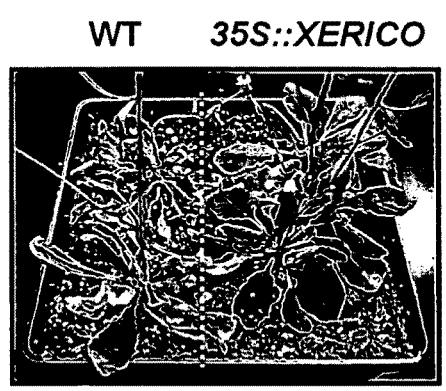
Figure 6:
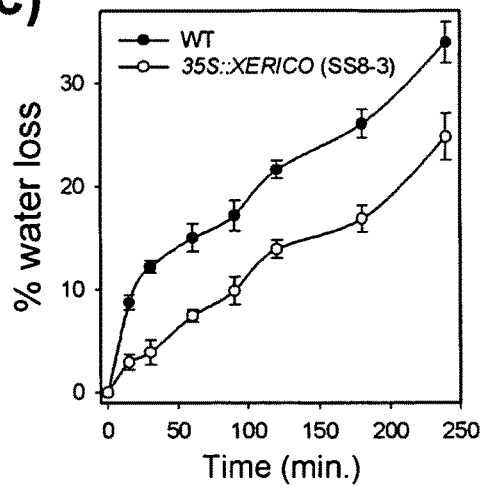
Figure 8:
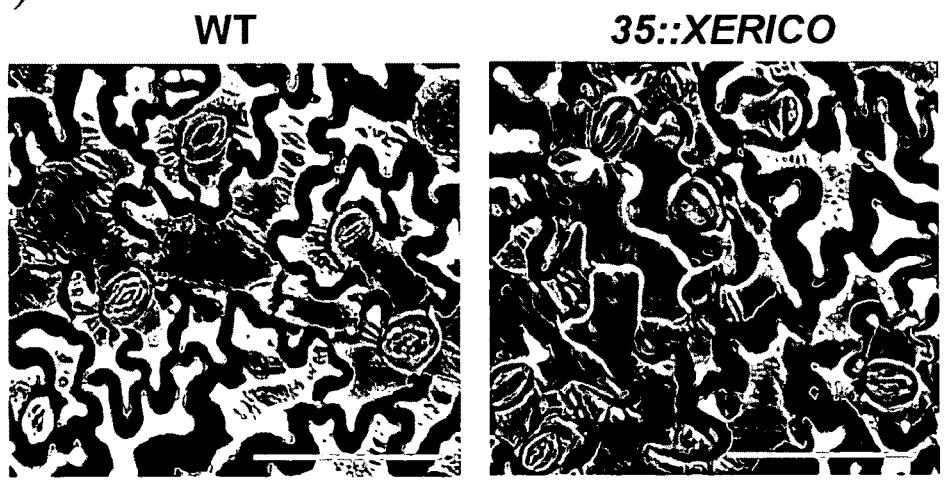
FIG. 8 demonstrates stomata openings in wild-type and closure in 35S::XERICO plants. (a) Pictures showing stomata openings in wild-type and closure in 35S::XERICO plants. Leaf samples were taken at 11:00 AM from 4-week-old soil-grown plants and applied immediately the commercial nail polisher on the lower epidermis. The prepared epidermal strips were observed under a Nikon Diaphot, inverse microscope. Pictures were taken with a Sony MAVICA digital camera. Representative pictures were shown. Scale bars, 100 µm. (b) Measurement of stomatal aperture of wild-type and 35S::XERICO plants. The apertures of the stomatal pores were measured by using 'the measure tool' of Adobe PhotoShop 5.5, which calculates the distance between any two points in the work area, from pictures taken above. Error bars represent standard errors (n=68).
Figure 8:
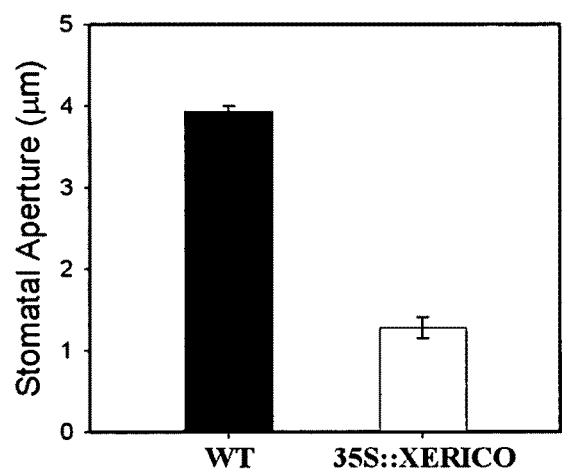
Figure 9:
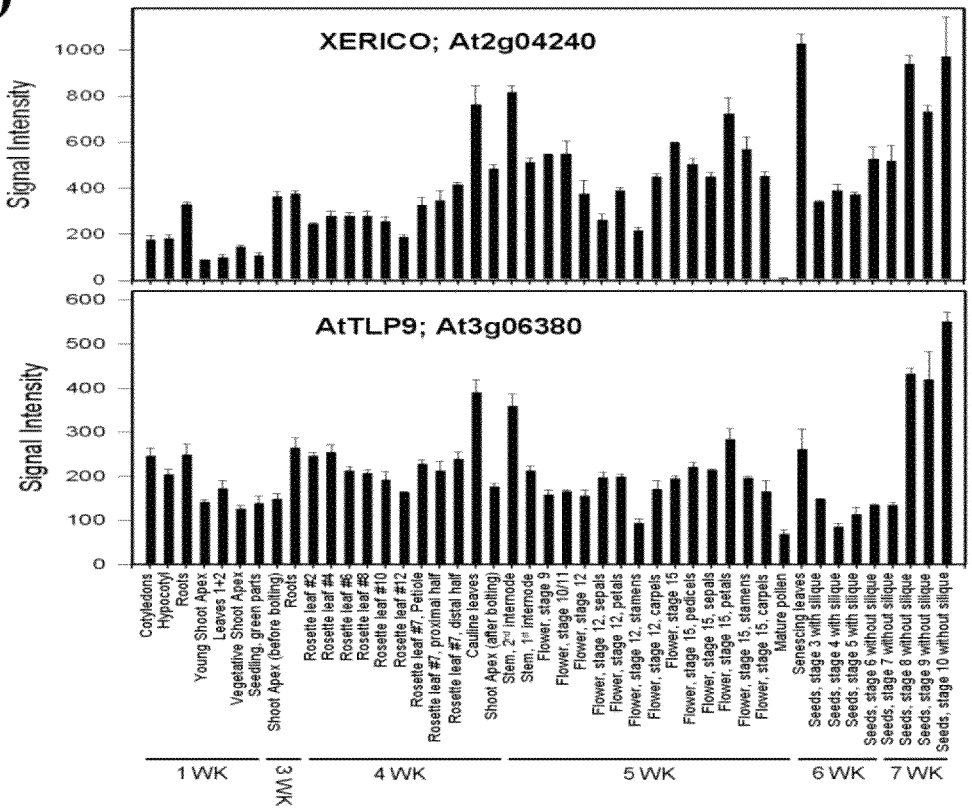
FIG. 9 demonstrates that transcriptional co-regulation of the XERICO (see, for e.g., SEQ ID NO:01) and AtTLP9 (see, for e.g., SEQ ID NO:381) (a) Plant development and organ-specific gene expression of XERICO and AtTLP9. Genechip data was collected from the AtGenExpress database available hosted by The *Arabidopsis* Functional Genomics Network (unifrankfurt.de/fb15/botanik/mcb/AFGN/atgenex.htm) and reconstructed for providing information for the present invention. (b) Correlation of gene expression by 'Gene Correlator' comparing 1122 genechip data of AtGenExpress. Left panel, XERICO and AtTLP9; Right panel, XERICO and RBCS (see, for e.g., SEQ ID NO:398) as a negative control. Each spot indicates individual genechip data. Red spot, both present (p-value <0.04); Green spot, both absent (p-value >0.06); Blue spot, X-axis gene present no Y-axis gene; Light blue spot, Y-axis gene present no Y-axis gene. Pearson's correlation coefficient ($r^2$) is given. Data were collected using the GENEVESTIGATOR website (Zimmermann et al. (2004) Plant Physiol. 136:2621-2632; herein incorporated by reference in its entirety).
Figure 9:
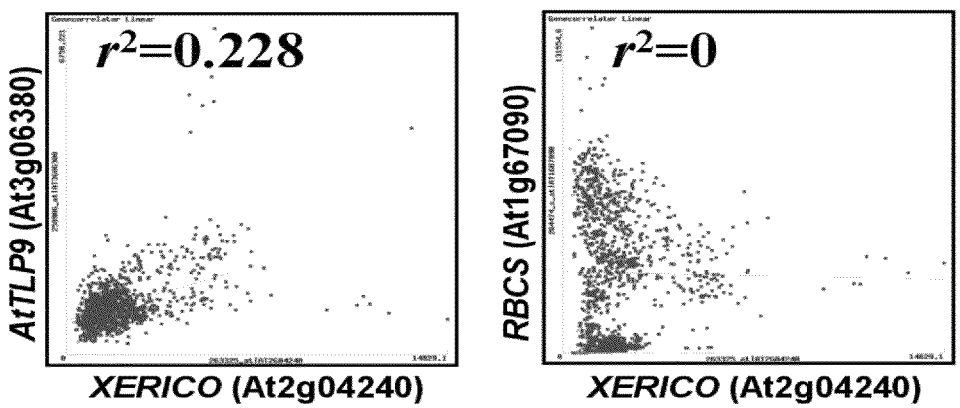

Increased ABA levels resulted in drought stress tolerance in *Nicotiana plumbaginifolia* (Qin and Zeevaart (2002) Plant Physiol. 128:544-551; herein incorporated by reference). Therefore, the effect of XERICO upregulation on drought stress tolerance by discontinued watering of 30-days-old wild-type and 35S::XERICO plants growing on soil in a 4-inch diameter pot were evaluated. Afterward, the plants were kept in a growth room maintained at low humidity. In contrast to early seedling growth, adult 35S::XERICO water stressed plants showed striking drought stress-tolerance when compared to wild-type plants. FIG. 6a shows representative picture of each treatments after 10 days without watering. These drought tolerance treatment experiments were repeated with wild-type and 35S::XERICO plants planted side by side in one pot (FIG. 6b). The results showed that enhanced drought-tolerance of 35S::XERICO plants was successfully reproduced. Water retention after 10 days without watering was slightly higher in the pots having 35S::XERICO plants than those of wild-type plants, implying that the enhanced drought tolerance of 35S::XERICO plants may come from decreased water loss by transpiration. Measurements of fresh weights of detached leaves over different time periods was provided as an indicator of transpirational water loss. The most rapid loss of water occurred during the first 30 min after detachment (FIG. 6c), which is consistent with the previous report by Qin and Zeevaart (2002) Plant Physiol. 128:544-551; herein incorporated by reference. The leaves from wild-type plants lost about 15% of their fresh weight in one hour, while leaves from 35S::XERICO plants had a much reduced water loss (about 7.5%) (FIG. 6c). These data indicate that an increase of cellular ABA levels resulted in the closure of stomata of 35S::XERICO plants leaves thus decreasing water loss by transpiration. This was confirmed by observation of stomata of wild-type and 35S::XERICO plants where the majority of the stomata of 35S::XERICO plants were closed during day time when those of wild-type plants were opened (FIG. 8).

The *Arabidopsis* genome contains a large number of genes encoding RING finger proteins (see, for e.g., Jensen et al. (1998) FEBS Lett. 436:283-287; Lechner et al. (2002) Gene, 290:63-71; all of which are herein incorporated by reference), which implies evolutionarily important roles for these proteins in *Arabidopsis* growth and development. Many RING-H12 proteins function as part of the E3 ubiquitin ligases (see, for e.g., Tyers and Jorgensen (2000) Curr. Opin. Genet. Dev. 10:54-6; Joazeiro and Weissman (2000) Cell 102:549-552; all of which are herein incorporated by reference). Ubiquitin-mediated protein degradation plays key regulatory roles during several plant growth and developmental events and has been implicated in plant hormone signaling (see, for e.g., Gray et al. (1999) Genes Dev. 13:1678-1691; Hare et al. (2003) Curr. Opin. Plant Biol. 6:453-462; Dill et al. (2004) Plant Cell, 16:1392-1405; Gagne et al. (2004) Proc. Natl. Acad. Sci. USA, 101:6803-6808; Dharmasiri et al. (2005) Nature, 435:441-445; all of which are herein incorporated by reference).

Example VIII

XERICO Interacts In Vivo with AtUBC8 and AtTLP9, Respectively, in Yeast

The RING domain is known to play a role in protein-protein interaction thus experiments for identifying binding partners were provided with a yeast two-hybrid screening. AtTLP9 (At3g06380; SEQ ID NO:381) is a member of *Arabidopsis* TUBBY-like protein having an N-terminal F-box domain, which interacts with ASK1 (Arabidopsis Skp1-like 1; SEQ ID NO:388) (see, for e.g., Lai et al. (2004) EMBO J. 23:1647-1656; herein incorporated by reference). ASK1, one of the 21 Skp proteins in *Arabidopsis*, is involved in both vegetative growth and reproductive development (see, for e.g., Yang et al. (1999) Proc. Natl. Acad. Sci. USA, 96:11416-11421; Zhao et al. (2003) Plant Physiol. 133:203-217; all of which are herein incorporated by reference). F-box protein is a component of SCF complexes, which acts as a factor for substrate recognition (see, for e.g., Bai et al. (1996) Cell 86:263-274; Pickart and Eddins (2004) Biochim. Biophys. Acta, 1695:55-72; all of which are herein incorporated by reference).

Knock-out mutants of AtTLP9 showed ABA-insensitive phenotypes whereas transgenic plants overexpressing AtTLP9 were hypersensitive to ABA, suggesting that AtTLP9 may participate in ABA signaling pathway (see, for e.g., Lai et al. (2004) EMBO J. 23:1647-1656: herein incorporated by reference). AtUBC8 is a member of *Arabidopsis* ubiquitin-conjugating enzyme, E2.

Figure 7:
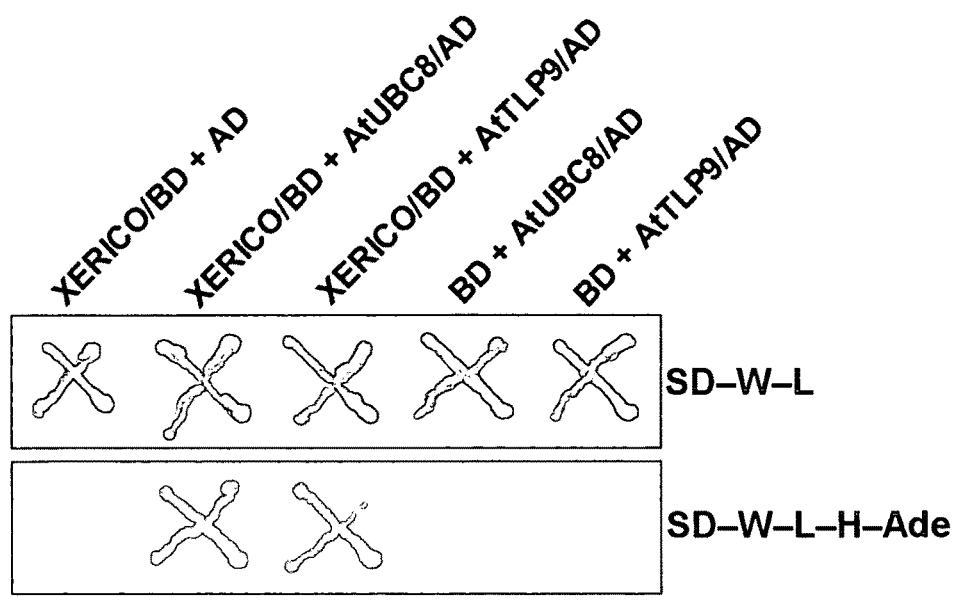
FIG. 7 demonstrates that XERICO interacts in vivo with AtUBC8 and AtTLP9 in yeast. Interactions of XERICO with AtUBC8 and AtTLP9 were shown by His (Histadine) and Ade (Adenine) auxotrophic growth of yeast. Yeast cells (AH109) transformed with the plasmid pairs, XERICO with AtUBC8 and XERICO with AtTLP9, were cultured on minimal synthetic (SD) dropout medium for nutritional selection (minimal SD base (providing a nitrogen base, a carbon source, and in some cases, ammonium sulfate) with a stock of "dropout" (DO) solution that contains a specific mixture of amino acids and nucleosides; Clontech Laboratories, Inc.), SD-W-L-[SD media without W, Trp, Tryptophan, and L, Leu, Leucine, His/Leu DO Supplement Clontech Laboratories, Inc., Catalog Number 8609-1]; SD-W-L-H-Ade, [SD media without W, L, H, His, Histidine and Ade, Adenine, Clontech Laboratories, Inc., Catalog Number 8619-1).

AtTLP9; SEQ ID NO:381 and AtUBC8; SEQ ID NO:379 were identified as potential interacting partners of XERICO in a yeast 2 hybrid system of the present invention. Their interactions in yeast were also confirmed in vivo under high-stringency conditions (FIG. 7). These demonstrations show that XERICO functions in ABA homeostasis on a post-translational level, probably through ubiquitin/proteasome-dependent substrate specific degradation by interacting with AtTLP9. Thus ubiquitin/proteasome pathway-mediated substrate-specific degradation is expected to play a role in XERICO function.

Example IX

GeneChip Analysis of 35S::XERICO Plants

To find further functional clues of XERICO, a whole-transcriptome profiling of wild-type and 35S::XERICO plants that were grown for 20 days on soil was performed. Aerial parts of the plants for sampling were used because no significant phenotypic changes in the root development was observed. Gene expression data were obtained from two independent experiments conducted with the *Arabidopsis* ATH1 Genome Array (Affymetrix, Santa Clara, Calif.).

Eighteen up-regulated and 44 down-regulated genes were shown in the 35S::XERICO plants compared to the wild-type plants using two-fold change threshold (Table 1). The plant hormone metabolism/response-related genes comprise a significant portion of the differentially expressed genes. For example, ABA 8'-hydroxylases such as one or more of abscisic acid 8'-hydroxylase (one example is SEQ ID NOs:339), was upregulated up to four-fold in the 35S::XERICO plants. The expression of ACS/I, SEQ ID NO:329, one of the ACC synthase known as a rate-limiting enzyme in ethylene biosynthesis, was drastically upregulated (up to 32-fold) in the 35S::XERICO plants. In addition, the expression of BL 26-hydroxylase SEQ ID NO:422, which inactivates brassinosteroid hormones (see, for e.g., Turk et al. (2003) Plant Physiol. 133:1643-1653; herein incorporated by reference), was downregulated, whereas BR biosynthesis enzyme ROT3 (CYP90C1; SEQ ID NO:331; see, for e.g., Kim et al. (2005) Plant J. 41:710-721; herein incorporated by reference) was upregulated in the 35S::XERICO plants. In addition, GA4 (gibberellin β-hydroxylase; SEQ ID NO:424), which converts inactive form of GA to an active form (see, for e.g., Martin et al. (1996) Planta, 200:159-166; herein incorporated by reference), was down in the 35S::XERICO plants. These results show that the homeostasis of various plant hormones was altered in 35S::XERICO plants, possibly by over-accumulation of ABA.

35S::XERICO plants produced substantially higher levels of ABA than the wild-type plants even without stress conditions GeneChip analysis shows that the expression of genes involved in ABA biosynthesis were not substantially altered. Thus increased level of endogenous ABA in the 35S::XERICO plants may be controlled at post-transcriptional level such as RNA processing or turnover (see, for e.g., Xiong et al. (2001) Dev. Cell, 1:771-781; herein incorporated by reference), or post-translational control. GENEVESTIGATOR analysis revealed that the transcription of XERICO and AtTLP9 are highly co-regulated in various conditions during plant growth and development (see, for e.g., Zimmermann et al. (2004) Plant Physiol 136:2621-2632; herein incorporated by reference) (FIG. 8). These observations further support the role of AtTLP9 as a functional partner of XERICO in planta.

GeneChip analysis for the present inventions showed that expression of many plant hormone biosynthesis genes (e.g., wherein plant hormones include ethylene, brassinosteroid, and gibberellic acid) were significantly changed in the 35S::XERICO plants compared to wild-type plants. See, Table 1. In addition to the well-characterized antagonistic relationships between ABA and gibberellic acid (GA), cytokinins, or auxins; recent studies have revealed various signaling interactions between ABA and one or more of ethylene, brassinosteroid, light, or sugars (for review, see, examples, Finkelstein and Gibson (2002) Curr. Opin. Plant Biol. 5:26-32; Fedoroff (2002) Sci STKE, RE10; Finkelstein et al. (2002) Plant Cell, 14 Suppl, S15-45; Gazzarrini and McCourt (2003) Ann. Bot. (Lond) 91, 605-612; and Rock and Sun (2005) Planta, 222, 98-106; all of which are herein incorporated by reference). Thus it is likely that cross-talks between ABA and other plant hormones are altered by ABA over-accumulation in the 35S::XERICO plants, resulting in the phenotypic alterations demonstrated by the 35S::XERICO plants.

In experiments conducted during the course of the present inventions, expression of XERICO was shown to be induced by salt/osmotic stress and overexpression of this gene increased cellular ABA levels. It is not clear how XERICO stimulates transcriptional regulation of the genes involved in ABA homeostasis. However, as shown herein, cellular ABA levels are altered by a gene encoding a RING finger protein that was not previously known to be involved in the ABA biosynthetic pathway. Future investigations will address whether XERICO can serve as a functional E3 ubiquitin ligase or whether XERICO is a target of AtTLP9 in a biochemical pathway, and further whether mechanisms for XERICO regulation of cellular ABA levels.

Example X

Identification of XERICO (AT2G04240) Homologues in Brassicaceae and At2g04240-like Genes in Other Plants Plant sequences comprising RING-H2 zinc finger domains, low complexity regions and transmembrane motifs were identified in a databank using The Basic Local Alignment Search Tool (BLAST) for finding regions of local similarity between reference sequences of XERICO mRNA (SEQ ID NO:02) or XERICO protein sequence (SEQ ID NO:01) or amino acid sequence of the XERICO RING-H2 domain (SEQ ID NO:03) or nucleic acid coding region for the XERICO RING-H2 domain (SEQ ID NO:04) at default settings, except for removing "Filter" or "Filter the sequence for low-complexity regions" or "masking of low-complexity" and the like, at the following websites maintained by GenBank at NCBI, European Molecular Biology Laboratory (EMBL), Expert Protein Analysis System (ExPASy) World Wide Web (WWW) proteomics server of the Swiss Institute of Bioinformatics (SIB) (SWISS-PROT), The Institute for Genomic Research (TIGR) Plant Gene indices, Gramene: A Resource for Comparative Grass Genomics, UK Crop Plant Bioinformatics Network (UK CropNet) and BrassicaDB BLAST Server maintained at the John Innes Centre. Further, the following WU BLAST 2.08 family of programs were used: blastp for comparing an amino acid query sequence against a protein sequence database, blastn for comparing a nucleotide query sequence against a nucleotide sequence database, and blastx for comparing a nucleotide query sequence translated in all reading frames against a protein sequence database. See, for e.g., States et al. (1993) METHODS: A Companion to Methods in Enzymology Vol. 3, No. 1, August, pp. 66-70, 1991; States et al. (1993) Nat. Genet. 3:266-72; States and Gish; and Altschul et al. (1990) Mol. Biol. 215:403-410; all of which are herein incorporated by reference in its entirety. Homologous nucleic acid sequences were translated using online DNA to RNA translation websites, in particular ExPASy translation, and compared to any of the most relevant of SEQ ID NO:01, SEQ ID NO:02, SEQ ID NO:03, or SEQ ID NO:04 for obtaining percentages of identity with results summarized in Table 2.

TABLE 2

Plant At2g04240 sequences, At2g04240-like sequences, and other types of RING finger sequences.

| Genus sp. H2 (C3H2C3) RING unless otherwise designated | SEQ ID NO: XX* | protein aa identity (%) | SEQ ID NO: XX | mRNA na identity (%) | SEQ ID NO: XX | RING domain aa identity (%) | SEQ ID NO: XX | RING mRNA na identity (%) |
|---|---|---|---|---|---|---|---|---|
| *Arabidopsis Thaliana* (thale cress/mouse-ear cress) Putative RING zinc finger protein At2g04240 PIR\|E84455 Q9SI09_ARATH arab\|TC264142 | SEQ ID NO: 01 | 100% | SEQ ID NO: 02 | 100% | SEQ ID NO: 03 | 100% | SEQ ID NO: 04 | 100% |
| *Thellungiella Halophila* (salt cress) Q8S2S3_THEHA | SEQ ID NO: 14 | 82% | SEQ ID NO: 17 | 86% | SEQ ID NO: 15 | 95% | SEQ ID NO: 16 | 91% |
| *Brassica napus* oilseed_rape\|CD834580 RING zinc finger protein similar to Q8S2S3; Q6I656_CITLA; and PIR\|E84455 | SEQ ID NO: 19 | 81% | SEQ ID NO: 21 | 84% partial sequence | SEQ ID NO: 18 | 93% | SEQ ID NO: 20 | 90% |
| *Lotus corniculatus* var. japonicus l_japonicus\|BP045442 BP045442 | SEQ ID NO: 74 | 84% partial sequence | SEQ ID NO: 77 | 84% partial sequence | SEQ ID NO: 73 | 82% | SEQ ID NO: 75 | 75% |
| *Glycine max* Soybean TC217409 (Q8S2S3_THEHA) Putative RING zinc finger protein-like protein | SEQ ID NO: 99 | 68% | SEQ ID NO: 102 | 66% | SEQ ID NO: 100 | 78% | SEQ ID NO: 101 | 70% |
| poplar\|TC21770 similar to UP\|Q6I656 (Q6I656) RING zinc finger protein | SEQ ID NO: 154 | 66% | SEQ ID NO: 157 | 80% | SEQ ID NO: 155 | 76% | SEQ ID NO: 156 | 70% |
| *Citrullus lanatus* (Watermelon) RING zinc finger protein [Fragment] gi\|49532976\|dbj\|BAD26589.1\| | SEQ ID NO: 31 | 70% | SEQ ID NO: 33 | 77% | SEQ ID NO: 30 | 70% | SEQ ID NO: 32 | 77% |
| *Helianthus annuus* sunflower\|BU672034 (common sunflower) | SEQ ID NO: 79 | 62% partial sequence | SEQ ID NO: 81 | 40% partial sequence | SEQ ID NO: 78 | 68% | SEQ ID NO: 80 | 49% |
| *Glycine max* Soybean\|TC230215 probable RING zinc finger protein | SEQ ID NO: 95 | 59% | SEQ ID NO: 98 | 66% | SEQ ID NO: 96 | 73% | SEQ ID NO: 97 | 81% |
| *Medicago truncatula* (barrel medic) medicago\|TC96403 similar to UP\|Q5ULY2 (Q5ULY2) Zinc finger family protein | SEQ ID NO: 166 | 58% | SEQ ID NO: 168 | 66% | SEQ ID NO: 165 | 70% | SEQ ID NO: 167 | 64% |
| *Poncirus trifoliata* (Hardy orange) RING-H2 finger protein | SEQ ID NO: 26 | 56% | SEQ ID NO: 29 | 63% | SEQ ID NO: 27 | 72% | SEQ ID NO: 28 | 79% |

TABLE 2-continued

Plant At2g04240 sequences, At2g04240-like sequences, and other types of RING finger sequences.

| Genus sp. H2 (C3H2C3) RING unless otherwise designated | SEQ ID NO: XX* | protein aa identity (%) | SEQ ID NO: XX | mRNA na identity (%) | SEQ ID NO: XX | RING domain aa identity (%) | SEQ ID NO: XX | RING mRNA na identity (%) |
|---|---|---|---|---|---|---|---|---|
| Lettuce\|TC9685 putative RING zinc finger protein-like protein | SEQ ID NO: 103 | 55% | SEQ ID NO: 106 | 76% | SEQ ID NO: 104 | 77% | SEQ ID NO: 105 | 76% |
| *Fragaria x ananassa* (hybrid strawberry) [Fragment] sptrembl\|Q5ULY2 trembl\|AY679613 | SEQ ID NO: 22 | 55% partial sequence | SEQ ID NO: 25 | 68% partial sequence | SEQ ID NO: 23 | 76% | SEQ ID NO: 24 | 82% |
| *Capsicum annuum* pepper\|CA525749 | SEQ ID NO: 92 | 52% | SEQ ID NO: 93 | 56% | SEQ ID NO: 90 | 65% | SEQ ID NO: 91 | 46% |
| cotton\|TC39148 similar to UP\|Q6Z8T9 (Q6Z8T9) Zinc finger protein family-like | SEQ ID NO: 48 | 51% | SEQ ID NO: 51 | 57% | SEQ ID NO: 49 | 70% | SEQ ID NO: 50 | 61% |
| *Hevea brasiliensis* (Para rubber tree) Putative C3HC4-type RING zinc finger protein [RGZF1] Q6XNP9_HEVBR | SEQ ID NO: 34 | 51% | SEQ ID NO: 35 | 60% | SEQ ID NO: 36 | 63% | SEQ ID NO: 37 | 65% |
| *Vitis vinifera* grape\|TC48889 similar to UP\|Q6I656 (Q6I656) RING zinc finger protein | SEQ ID NO: 40 | 51% | SEQ ID NO: 42 | 59% | SEQ ID NO: 39 | 55% | SEQ ID NO: 41 | 83% |
| Potato\|TC120988 (Q8S2S3) Putative RING zinc finger protein | SEQ ID NO: 86 | 50% | SEQ ID NO: 89 | 51% | SEQ ID NO: 87 | 65% | SEQ ID NO: 88 | 62% |
| *Saccharum officinarum* s_officinarum\|BQ 532997 | SEQ ID NO: 172 | 50% partial | SEQ ID NO: 173 | 45% | SEQ ID NO: 170 | 57% | SEQ ID NO: 171 | 31% |
| *Triphysaria* yellow owl's clover | SEQ ID NO: 70 | 50% | SEQ ID NO: 72 | 46% | SEQ ID NO: 71 | 53% | SEQ ID NO: XX | XX % |
| sorghum\|TC104925 homologue to UP\|Q84PD9 (Q84PD9) Ring zinc finger protein-like protein | SEQ ID NO: 136 | 50% partial | SEQ ID NO: 137 | 38% partial | SEQ ID NO: 134 | 50% | SEQ ID NO: 135 | 56% |
| *Lycopersicon esculentum* Tomato\|TC157346 (Q8S2S3) Putative RING zinc finger protein-like protein | SEQ ID NO: 107 | 49% | SEQ ID NO: 110 | 57% | SEQ ID NO: 108 | 65% | SEQ ID NO: 109 | 61% |
| spruce\|TC4946 weakly similar to UP\|Q6I656 (Q6I656) RING zinc finger protein (Fragment), partial (57%) | SEQ ID NO: 67 | 57% partial | SEQ ID NO: 69 | 45% | SEQ ID NO: 68 | 61% | SEQ ID NO: XX | XX % |

TABLE 2-continued

Plant At2g04240 sequences, At2g04240-like sequences, and other types of RING finger sequences.

| Genus sp. H2 (C3H2C3) RING unless otherwise designated | SEQ ID NO: XX* | protein aa identity (%) | SEQ ID NO: XX | mRNA na identity (%) | SEQ ID NO: XX | RING domain aa identity (%) | SEQ ID NO: XX | RING mRNA na identity (%) |
|---|---|---|---|---|---|---|---|---|
| *Oryza sativa* (japonica cultivar-group) Q6Z8T9_ORYSA Zinc finger protein family-like | SEQ ID NO: 119 | 36% partial | SEQ ID NO: 122 | 40% | SEQ ID NO: 120 | 61% | SEQ ID NO: 121 | 57% |
| *Zea mays* maize\|TC302897 similar to UP\|Q6Z8T9_ORYSA (Q6Z8T9) Zinc finger protein family-like, partial (71%) | SEQ ID NO: 177 | 71% partial | SEQ ID NO: 4 | 44% | SEQ ID NO: 5 | 59% | SEQ ID NO: 6 | 59% |
| *Saccharum officinarum* > s_officinarum\|TC49498 similar to UP\|Q6Z8T9 (Q6Z8T9) Zinc finger protein family-like, partial (51%) | SEQ ID NO: 178 | 33% | SEQ ID NO: 179 | 52% | SEQ ID NO: 176 | 59% | SEQ ID NO: 177 | 52% |
| sorghum\|TC110812 similar to UP\|BAD10011 (BAD10011) Zinc finger protein family-like, partial (74%) | SEQ ID NO: 113 | 39% | SEQ ID NO: 114 | 48% | SEQ ID NO: 111 | 59% | SEQ ID NO: 112 | 59% |
| poplar\|TC23157 weakly similar to Q8S2S3 Putative RING zinc finger protein-like protein | SEQ ID NO: 159 | 41% | SEQ ID NO: 162 | 51% | SEQ ID NO: 160 | 55% | SEQ ID NO: 161 | 59% |
| *Cucumis melo* Q84KA9_CUCME RING/C3HC4/PHD zinc finger-like protein | SEQ ID NO: 186 | 40% | SEQ ID NO: 187 | 30% | SEQ ID NO: 184 | 40% | SEQ ID NO: 185 | 51% |
| *Zea mays* maize\|TC287578 similar to UP\|Q6Z8T9_ORYSA (Q6Z8T9) Zinc finger protein family-like, partial (29%) | SEQ ID NO: 125 | 47% partial sequence | SEQ ID NO: 127 | 48% partial sequence | SEQ ID NO: 124 | 56% | SEQ ID NO: 126 | 54% |
| *Pinus taeda* pine\|TC67818 weakly similar to UP\|Q5ULY2 (Q5ULY2) Zinc finger family protein | SEQ ID NO: 58 | 43% | SEQ ID NO: 60 | 50% | SEQ ID NO: 57 | 59% | SEQ ID NO: 59 | 60% |
| *Cucumis melo* (Muskmelon) Q84KA9_CUCME | SEQ ID NO: 232 | 40% | SEQ ID NO: 233 | 30% | SEQ ID NO: 230 | 41% | SEQ ID NO: 231 | 53% |
| *Beta vulgaris* beet\|TC2159 | SEQ ID NO: 205 | 39% partial | SEQ ID NO: 7 | 45% partial | SEQ ID NO: 203 | 46% | SEQ ID NO: 204 | 56% |
| *Nicotiana tabacum* (common tobacco) tobacco\|BP130278 | SEQ ID NO: 64 | 38% partial | SEQ ID NO: 65 | 48% partial | SEQ ID NO: 62 | 43% | SEQ ID NO: 63 | 58% |
| *Mesembryanthemum crystallinum* ice_plant\|BM300187 | SEQ ID NO: 213 | 35% | SEQ ID NO: 214 | 45% | SEQ ID NO: 211 | 55% | SEQ ID NO: 212 | 60% |

TABLE 2-continued

Plant At2g04240 sequences, At2g04240-like sequences, and other types of RING finger sequences.

| Genus sp. H2 (C3H2C3) RING unless otherwise designated | SEQ ID NO: XX* | protein aa identity (%) | SEQ ID NO: XX | mRNA na identity (%) | SEQ ID NO: XX | RING domain aa identity (%) | SEQ ID NO: XX | RING mRNA na identity (%) |
|---|---|---|---|---|---|---|---|---|
| *Triticum aestivum* wheat|TC233399 similar to UP|Q6Z8T9 (Q6Z8T9) Zinc finger protein family-like | SEQ ID NO: 82 | 35% | SEQ ID NO: 85 | 50% | SEQ ID NO: 83 | 57% | SEQ ID NO: 84 | 56% |
| *Hordeum vulgare* barley|TC132854 similar to Q6Z8T9 Zinc finger protein family-like | SEQ ID NO: 129 | 35% | SEQ ID NO: 132 | 49% | SEQ ID NO: 130 | 55% | SEQ ID NO: 131 | 57% |
| *Allium cepa* onion|CF452180 | SEQ ID NO: 228 | 32% | SEQ ID NO: 229 | 34% | SEQ ID NO: 226 | 47% | SEQ ID NO: 227 | 54% |
| *Arabidopsis Thaliana* RING-H2 zinc finger protein RHA2a RING-type; Sequence 1565 from Patent WO0216655. Harper, et al. AT1G15100 | SEQ ID NO: 259 | 55% | SEQ ID NO: 261 | 50% | SEQ ID NO: 258 | 55% | SEQ ID NO: 260 | 64% |
| *Arabidopsis Thaliana* ATL2N_ARATH O22255 RING-H2 finger protein | SEQ ID NO: 272 | 52% | SEQ ID NO: 274 | 38% | SEQ ID NO: 271 | 52% | SEQ ID NO: XX | XX % |
| *Arabidopsis Thaliana* RING-H2 zinc finger protein RHA2B_ARATH Q9ZU51 | SEQ ID NO: 265 | 49% | SEQ ID NO: 266 | 48% | SEQ ID NO: 263 | 55% | SEQ ID NO: 264 | 57% |
| *Zea mays* ring-H2 zinc finger protein - znf Q8W1C6_MAIZE AAL59234 | SEQ ID NO: 145 | 43% | SEQ ID NO: 144 | 35% | SEQ ID NO: 142 | 43% | SEQ ID NO: 143 | 53% |
| *Arabidopsis Thaliana* RIE1 (RING-FINGER PROTEIN FOR EMBRYOGENESIS; RES protein) Xu and Li, 2003 AT2G01735 | SEQ ID NO: 275 | 43% | SEQ ID NO: 278 | 16% | SEQ ID NO: 276 | 43% | SEQ ID NO: 277 | 55% |
| *Zea mays* Ring-H2 zinc finger protein Q5GAQ1_MAIZE | SEQ ID NO: 146 | 38% | SEQ ID NO: 149 | 34% | SEQ ID NO: 147 | 38% | SEQ ID NO: 148 | 59% |
| *Populus alba* x *Populus tremula* RING-H2 subgroup RHE protein (RHE1) | SEQ ID NO: 244 | 37% | SEQ ID NO: 247 | 34% | SEQ ID NO: 245 | 45% | SEQ ID NO: 246 | 59% |
| *Oryza sativa* (japonica cultivar-group) putative ring-H2 zinc finger protein Q84MUS_ORYSA AAP12944 | SEQ ID NO: 142 | 36% | SEQ ID NO: 143 | 33% | SEQ ID NO: 140 | 40% | SEQ ID NO: 141 | 53% |
| *Oryza sativa* (japonica cultivar-group) putative ring-H2 zinc | SEQ ID NO: 150 | 36% | SEQ ID NO: 153 | 33% | SEQ ID NO: 151 | 40% | SEQ ID NO: 152 | 52% |

TABLE 2-continued

Plant At2g04240 sequences, At2g04240-like sequences, and other types of RING finger sequences.

| Genus sp. H2 (C3H2C3) RING unless otherwise designated | SEQ ID NO: XX* | protein aa identity (%) | SEQ ID NO: XX | mRNA na identity (%) | SEQ ID NO: XX | RING domain aa identity (%) | SEQ ID NO: XX | RING mRNA na identity (%) |
|---|---|---|---|---|---|---|---|---|
| finger protein XP_470885 *Oryza sativa* (japonica cultivar-group) Q8H5Z8_ORYSA AP003019 | SEQ ID NO: 198 | 35% | SEQ ID NO: 199 | 35% | SEQ ID NO: 196 | 39% | SEQ ID NO: XX | XX % |
| *Arabidopsis Thaliana* ATL3J_ARATH Q9LY41 RING-H2 finger protein ATL3J/ RHX1a/ ATL4 RING-H2 finger protein | SEQ ID NO: 268 | 32% | SEQ ID NO: 270 | 31% | SEQ ID NO: 267 | 47% | SEQ ID NO: XX | XX % |
| *Arabidopsis Thaliana* BRH1 RING-H2 brassinosteroid-responsive Molnár et al., 2002 Q9XF92_ARATH | SEQ ID NO: 254 | 29% | SEQ ID NO: 255 | 50% | SEQ ID NO: 252 | 54% | SEQ ID NO: 253 | 58% |
| *Arabidopsis Thaliana* COP1-C3HC4 HC RING Zn finger At2g32950 | SEQ ID NO: 282 | NS | SEQ ID NO: 279 | 18% | SEQ ID NO: 281 | NS | SEQ ID NO: XX | XX % |
| *Populus* x canescens putative RING protein AY129244 | SEQ ID NO: 248 | NS | SEQ ID NO: 251 | NS | SEQ ID NO: 249 | NS | SEQ ID NO: 250 | XX % |

*X as in SEQ ID NO: XX and XX % refers to information either not available or not provided.

TABLE 3

Low Complexity Motifs Including Serine Rich Regions and Transmembrane sequence motifs

| SEQ ID NO | Sequence |
|---|---|
| SEQ ID NO: 478 | GXX(C/G)XXXXNTAXXISIXK(G/E)IX |
| SEQ ID NO: 456 | SLSPSSSSPSSVTVSSENSSTSES |
| SEQ ID NO: 457 | AAAAAAAAAA |
| SEQ ID NO: 458 | APSSPSSRFLFVAASPLP |
| SEQ ID NO: 459 | ASSSPSSDS |
| SEQ ID NO: 460 | SSSTPYSYFAS |
| SEQ ID NO: 461 | SSLSPSP |
| SEQ ID NO: 462 | SPSASLPSS |
| SEQ ID NO: 463 | SPPES |
| SEQ ID NO: 464 | STSES |
| SEQ ID NO: 465 | SSPSS |
| SEQ ID NO: 466 | SSSAS |
| SEQ ID NO: 467 | SSVSA |
| SEQ ID NO: 468 | SSMP |
| SEQ ID NO: 469 | SPSS |
| SEQ ID NO: 470 | SPSN |
| SEQ ID NO: 471 | SPSD |
| SEQ ID NO: 472 | SSSG |
| SEQ ID NO: 473 | SSST |
| SEQ ID NO: 474 | SSSS |
| SEQ ID NO: 475 | SSSP |
| SEQ ID NO: 476 | SSSA |

TABLE 3-continued

Low Complexity Motifs Including Serine Rich Regions and Transmembrane sequence motifs

| SEQ ID NO | Sequence |
|---|---|
| SEQ ID NO: 477 | SSSN |
| SEQ ID NO: 479 | GXX(C/G)XXXXNTA(X)S(I/V)XI |
| SEQ ID NO: 480 | GMLCVILVNTALSISIVKGIV |
| SEQ ID NO: 481 | GMLCVILVNTALSISIFKGIL |
| SEQ ID NO: 482 | GMLCLILMNTAMPISIVKGIF |
| SEQ ID NO: 483 | GVICVVVMNTALSISIFKGIV |
| SEQ ID NO: 484 | GVLCVFQSILHIVGI |
| SEQ ID NO: 485 | NTALSXXXIXXXXSFLQIV |
| SEQ ID NO: 486 | GVLCIILVNTAMSISIFKGIX |
| SEQ ID NO: 487 | GVLGVILVNTAISISIIKEIL |
| SEQ ID NO: 488 | GVLGVILVNTAISISIVKEIL |
| SEQ ID NO: 489 | GVLCVILVNTAMSISIMKEIV |
| SEQ ID NO: 490 | DSVVAYLLYNTAVSIAILADMV |
| SEQ ID NO: 491 | GVLCIILVNTAMSISIFKGII |
| SEQ ID NO: 492 | SLLGFVLYNTAASVAILAGLV |

Identification of Transmembrane sequence motifs for Table 4, SEQ ID NO:478-480. TargetP website: Olof, et al., (2000) J of Molecular Biology 300: 1005-1016; herein incorporated by reference. cbs.dtu.dk/services/TargetP/ChloroP website: Nielsen, et al., (1997) Protein Engineering, 10:1-6, cbs.dtu.dk/services/TargetP/ChloroP All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

We claim:

1. An expression vector construct comprising a nucleic acid sequence encoding a polypeptide that has greater than 95% amino acid sequence identity to SEQ ID NO:144, wherein said nucleic acid sequence is operably linked to a heterologous promoter, and wherein said polypeptide comprises a domain with sequence SEQ ID NO:142.

2. The expression vector construct of claim 1, wherein said nucleic acid further encodes a low complexity region with a sequence selected from the group consisting of SEQ ID NOs: 456-476 and 477.

3. The expression vector construct of claim 1, wherein said nucleic acid also encodes a transmembrane domain with a sequence selected from the group consisting of SEQ ID NOs: 478-491 and 492.

4. The expression vector construct of claim 1, wherein said nucleic acid is operably linked to a terminator.

5. A transgenic plant comprising a heterologous nucleic acid sequence encoding a polypeptide that has greater than 95% amino acid sequence identity to SEQ ID NO:144, wherein said nucleic acid sequence is operably linked to a heterologous promoter, and wherein said polypeptide comprises a domain with sequence SEQ ID NO:142.

6. The transgenic plant of claim 5, wherein said heterologous nucleic acid sequence also encodes a low complexity region with a sequence selected from the group consisting of SEQ ID NOs:456-477.

7. The transgenic plant of claim 5, wherein said heterologous nucleic acid sequence also encodes a transmembrane domain with a sequence selected from the group consisting of SEQ ID NOs:478-492.

8. The transgenic plant of claim 5, wherein said heterologous nucleic acid sequence is contained within the expression vector of claim 3.

9. A plant part of a transgenic plant, wherein the plant part comprises a heterologous nucleic acid sequence encoding a polypeptide that has greater than 95% amino acid sequence identity to SEQ ID NO: 144, wherein said nucleic acid sequence is operably linked to a heterologous promoter, and wherein said polypeptide comprises a domain with sequence SEQ ID NO: 142.

10. A method for generating a transgenic plant, comprising
a) providing,
   i) an expression vector comprising a nucleic acid sequence encoding a polypeptide that has greater than 95% amino acid sequence identity to SEQ ID NO:144, wherein said nucleic acid sequence is operably linked to a heterologous promoter, and wherein said polypeptide comprises a domain with sequence SEQ ID NO:142, and
   ii) a plant tissue, and
b) transfecting said plant tissue with said vector to produce a transgenic plant.

11. The method of claim 10, further comprising c) exposing said transgenic plant to abiotic stress.

12. The method of claim 11, wherein said abiotic stress comprises drought.

13. A transgenic plant produced by the method of claim 10.

14. A method for generating a transgenic plant, comprising
a) providing,
   i) an expression vector comprising a heterologous nucleic acid sequence encoding a polypeptide that has greater than 95% amino acid sequence identity to SEQ ID NO: 144, wherein said nucleic acid sequence is operably linked to a heterologous promoter, and wherein said polypeptide comprises a domain with sequence SEQ ID NO:142, and
   ii) a plant tissue,
b) transfecting said plant tissue with said expression vector to produce the transgenic plant, and
c) exposing said transgenic plant to abiotic stress.

15. The method of claim 14, further comprising the step d) of breeding said transgenic plant for producing a transgenic plant.

16. The plant part of claim 9, which is a plant seed.

17. An expression cassette or expression vector comprising a heterologous promoter operably linked to a coding region comprising a nucleic acid segment encoding a transmembrane region with the sequence selected from any of SEQ ID NOs:9, 478-491, or 492.

\* \* \* \* \*

SEQUENCE LISTING

```
<160> NUMBER OF SEQ ID NOS: 493

<210> SEQ ID NO 1
<211> LENGTH: 162
<212> TYPE: PRT
<213> ORGANISM: Arabidopsis thaliana

<400> SEQUENCE: 1

Met Gly Leu Ser Ser Leu Pro Gly Pro Ser Glu Gly Met Leu Cys Val
1               5                   10                  15

Ile Leu Val Asn Thr Ala Leu Ser Ile Ser Ile Val Lys Gly Ile Val
            20                  25                  30

Arg Ser Phe Leu Gly Ile Val Gly Ile Ser Leu Ser Pro Ser Ser Ser
        35                  40                  45

Ser Pro Ser Ser Val Thr Val Ser Ser Glu Asn Ser Ser Thr Ser Glu
    50                  55                  60

Ser Phe Asp Phe Arg Val Cys Gln Pro Glu Ser Tyr Leu Glu Glu Phe
65                  70                  75                  80

Arg Asn Arg Thr Pro Thr Leu Arg Phe Glu Ser Leu Cys Arg Cys Lys
                85                  90                  95

Lys Gln Ala Asp Asn Glu Cys Ser Val Cys Leu Ser Lys Phe Gln Gly
            100                 105                 110

Asp Ser Glu Ile Asn Lys Leu Lys Cys Gly His Leu Phe His Lys Thr
        115                 120                 125

Cys Leu Glu Lys Trp Ile Asp Tyr Trp Asn Ile Thr Cys Pro Leu Cys
    130                 135                 140

Arg Thr Pro Leu Val Val Val Pro Glu Asp His Gln Leu Ser Ser Asn
145                 150                 155                 160

Val Trp
```

<210> SEQ ID NO 2
<211> LENGTH: 486
<212> TYPE: DNA
<213> ORGANISM: Arabidopsis thaliana

<400> SEQUENCE: 2

```
atgggtctat caagtcttcc tggtccatca gaaggaatgt tatgtgtgat attagttaat      60
acagcattat cgatctccat tgtcaaaggc attgtaagat cattccttgg catagtagga     120
atcagtctct cgccgtcttc atcctcgcct tcttcggtga cggtatcttc agagaattca     180
tcaacttcag agtcatttga tttccgggtc tgccaaccag agagttacct tgaggagttc     240
aggaaccgga ctccgacact gaggtttgag agcttgtgca ggtgcaagaa acaggcagac     300
aatgagtgtt ctgtgtgttt gtcgaaattc caagggggatt cagagatcaa caagctcaag     360
tgcggccatt tgtttcacaa acatgcttg gagaaatgga tagactattg gaacatcact     420
tgcccattgt gtaggactcc tcttgttgtt gtgccagaag accatcagct ttcttctaat     480
gtttgg                                                                486
```

<210> SEQ ID NO 3
<211> LENGTH: 47
<212> TYPE: PRT
<213> ORGANISM: Arabidopsis thaliana

<400> SEQUENCE: 3

```
Glu Cys Ser Val Cys Leu Ser Lys Phe Gln Gly Asp Ser Glu Ile Asn
1               5                   10                  15

Lys Leu Lys Cys Gly His Leu Phe His Lys Thr Cys Leu Glu Lys Trp
            20                  25                  30

Ile Asp Tyr Trp Asn Ile Thr Cys Pro Leu Cys Arg Thr Pro Leu
        35                  40                  45
```

<210> SEQ ID NO 4
<211> LENGTH: 141
<212> TYPE: DNA
<213> ORGANISM: Arabidopsis thaliana

<400> SEQUENCE: 4

```
gagtgttctg tgtgtttgtc gaaattccaa ggggattcag agatcaacaa gctcaagtgc      60
ggccatttgt ttcacaaaac atgcttggag aaatggatag actattggaa catcacttgc     120
ccattgtgta ggactcctct t                                                141
```

<210> SEQ ID NO 5
<211> LENGTH: 107
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(13)
<223> OTHER INFORMATION: Xaa can be any naturally occurring amino acid
<220> FEATURE:
<221> NAME/KEY: MISC_FEATURE
<222> LOCATION: (14)..(43)
<223> OTHER INFORMATION: Xaa can be any naturally occuring amino acid
       and may be present or absent.
<220> FEATURE:
<221> NAME/KEY: misc_feature

```
<222> LOCATION: (45)..(46)
<223> OTHER INFORMATION: Xaa can be any naturally occurring amino acid
<220> FEATURE:
<221> NAME/KEY: MISC_FEATURE
<222> LOCATION: (47)..(47)
<223> OTHER INFORMATION: Xaa can be any naturally occuring amino acid
      and may be present or absent.
<220> FEATURE:
<221> NAME/KEY: misc_feature
<222> LOCATION: (49)..(51)
<223> OTHER INFORMATION: Xaa can be any naturally occurring amino acid
<220> FEATURE:
<221> NAME/KEY: MISC_FEATURE
<222> LOCATION: (52)..(52)
<223> OTHER INFORMATION: Residue may be Asparagine, Cysteine, or
      Histidine.
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(59)
<223> OTHER INFORMATION: Xaa can be any naturally occurring amino acid
<220> FEATURE:
<221> NAME/KEY: MISC_FEATURE
<222> LOCATION: (60)..(103)
<223> OTHER INFORMATION: Xaa can be any naturally occuring amino acid
      and may be present or absent.
<220> FEATURE:
<221> NAME/KEY: misc_feature
<222> LOCATION: (105)..(106)
<223> OTHER INFORMATION: Xaa can be any naturally occurring amino acid

<400> SEQUENCE: 5

Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Cys Xaa Xaa Xaa His
        35                  40                  45

Xaa Xaa Xaa Xaa Xaa Xaa Cys Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Cys Xaa Xaa Cys
                100                 105

<210> SEQ ID NO 6
<211> LENGTH: 42
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(23)
```

```
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid

<400> SEQUENCE: 6

Cys Xaa Xaa Cys Xaa Xaa Xaa Xaa Xaa Xaa Xaa Xaa Xaa Xaa Xaa
1               5                   10                  15

Xaa Xaa Cys Xaa His Xaa Xaa His Xaa Xaa Cys Xaa Xaa Xaa Xaa
            20                  25                  30

Xaa Xaa Xaa Xaa Xaa Xaa Cys Xaa Xaa Cys
            35                  40

<210> SEQ ID NO 7
<211> LENGTH: 41
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (22)..(23)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid
<220> FEATURE:
<221> NAME/KEY: misc_feature
<222> LOCATION: (28)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid

<400> SEQUENCE: 7

Cys Xaa Xaa Cys Xaa Xaa Xaa Xaa Xaa Xaa Xaa Xaa Xaa Xaa Xaa
1               5                   10                  15

Xaa Xaa Cys Xaa His Xaa Xaa His Xaa Xaa Cys Xaa Xaa Xaa Xaa
            20                  25                  30

Xaa Xaa Xaa Xaa Xaa Cys Xaa Xaa Cys
            35                  40

<210> SEQ ID NO 8
<211> LENGTH: 24
<212> TYPE: PRT
<213> ORGANISM: Arabidopsis thaliana

<400> SEQUENCE: 8
```

Ser Leu Ser Pro Ser Ser Ser Pro Ser Ser Val Thr Val Ser Ser
1               5                   10                  15

Glu Asn Ser Ser Thr Ser Glu Ser
            20

<210> SEQ ID NO 9
<211> LENGTH: 21
<212> TYPE: PRT
<213> ORGANISM: Arabidopsis thaliana

<400> SEQUENCE: 9

Gly Met Leu Cys Val Ile Leu Val Asn Thr Ala Leu Ser Ile Ser Ile
1               5                   10                  15

Val Lys Gly Ile Val
            20

<210> SEQ ID NO 10
<211> LENGTH: 751
<212> TYPE: DNA
<213> ORGANISM: Arabidopsis thaliana

<400> SEQUENCE: 10
aaaaccaact ctctctacac acttttttcag attccatcat cacttgttct tttcacaccc      60
aataaaaact tgcatctttc ttctaaattg ttgatgatcg cttctcatat ttgaccctag     120
agacaacatc atttctaccg acaaagattt gatatcgaat ccaacaagtg aaagatgggt     180
ctatcaagtc ttcctggtcc atcagaagga atgttatgtg tgatattagt taatacagca     240
ttatcgatct ccattgtcaa aggcattgta agatcattcc ttggcatagt aggaatcagt     300
ctctcgccgt cttcatcctc gccttcttcg gtgacggtat cttcagagaa ttcatcaact     360
tcagagtcat tgatttccg ggtctgccaa ccagagagtt accttgagga gttcaggaac      420
cggactccga cactgaggtt tgagagcttg tgcaggtgca agaaacaggc agacaatgag     480
tgttctgtgt gtttgtcgaa attccaaggg gattcagaga tcaacaagct caagtgcggc     540
catttgtttc acaaaacatg cttggagaaa tggatagact attggaacat cacttgccca     600
ttgtgtagga ctcctcttgt tgttgtgcca gaagaccatc agctttcttc taatgtttgg     660
tgactgcttt tcactgtata ggttttttgt ttgagtgtgt ttgttgtgta cagctacttt     720
tactatgaat taggttgcat cgcggttgat t                                    751

<210> SEQ ID NO 11
<211> LENGTH: 609
<212> TYPE: DNA
<213> ORGANISM: Arabidopsis thaliana

<400> SEQUENCE: 11
tttggatccg acaacatcat ttctaccgac aaagatttga tatcgaatcc aacaagtgaa      60
agatgggtct atcaagtctt cctggtccat cagaaggaat gttatgtgtg atattagtta     120
atacagcatt atcgatctcc attgtcaaag gcattgtaag atcattcctt ggcatagtag     180
gaatcagtct ctcgccgtct tcatcctcgc cttcttcggt gacggtatct tcagagaatt     240
catcaacttc agagtcattt gatttccggg tctgccaacc agagagttac cttgaggagt     300
caggaaccg gactccgaca ctgaggtttg agagcttgtg caggtgcaag aaacaggcag      360
acaatgagtg ttctgtgtgt ttgtcgaaat tccaagggga ttcagagatc aacaagctca     420
agtgcggcca tttgtttcac aaaacatgct tggagaaatg gatagactat tggaacatca     480

```
cttgcccatt gtgtaggact cctcttgttg ttgtgccaga agaccatcag ctttcttcta    540
atgtttggtg actgcttttc actgtatagg ttttttgttt gagtgtgttt gttgtgtaca    600
tctagaggg                                                            609

<210> SEQ ID NO 12
<211> LENGTH: 597
<212> TYPE: DNA
<213> ORGANISM: Arabidopsis thaliana

<400> SEQUENCE: 12
gatccgacaa catcatttct accgacaaag atttgatatc gaatccaaca agtgaaagat     60
gggtctatca agtcttcctg gtccatcaga aggaatgtta tgtgtgatat tagttaatac    120
agcattatcg atctccattg tcaaaggcat tgtaagatca ttccttggca tagtaggaat    180
cagtctctcg ccgtcttcat cctcgccttc ttcggtgacg gtatcttcag agaattcatc    240
aacttcagag tcatttgatt ccgggtctgc ccaaccagag agttaccttg aggagttcag    300
gaaccggact ccgacactga ggtttgagag cttgtgcagg tgcaagaaac aggcagacaa    360
tgagtgttct gtgtgtttgt cgaaattcca aggggattca gagatcaaca agctcaagtg    420
cggccatttg tttcacaaaa catgcttgga gaaatggata gactattgga acatcacttg    480
cccattgtgt aggactcctc ttgttgttgt gccagaagac catcagcttt cttctaatgt    540
ttggtgactg cttttcactg tataggtttt tgtttgagt gtgtttgttg tgtacat       597

<210> SEQ ID NO 13
<211> LENGTH: 591
<212> TYPE: DNA
<213> ORGANISM: Arabidopsis thaliana

<400> SEQUENCE: 13
gacaacatca tttctaccga caaagatttg atatcgaatc caacaagtga agatgggtc     60 tatcaagtct tcctggtcca tcagaaggaa tgttatgtgt gatattagtt aatacagcat    120
tatcgatctc cattgtcaaa ggcattgtaa gatcattcct tggcatagta ggaatcagtc    180
tctcgccgtc ttcatcctcg ccttcttcgg tgacggtatc ttcagagaat tcatcaactt    240
cagagtcatt tgatttccgg gtctgccaac cagagagtta ccttgaggag ttcaggaacc    300
ggactccgac actgaggttt gagagcttgt gcaggtgcaa gaaacaggca gacaatgagt    360
gttctgtgtg tttgtcgaaa ttccaagggg attcagagat caacaagctc aagtgcggcc    420
atttgtttca caaacatgc ttggagaaat ggatagacta ttggaacatc acttgcccat    480
tgtgtaggac tcctcttgtt gttgtgccag aagaccatca gctttcttct aatgtttggt    540
gactgctttt cactgtatag gttttttgtt tgagtgtgtt tgttgtgtac a             591

<210> SEQ ID NO 14
<211> LENGTH: 164
<212> TYPE: PRT
<213> ORGANISM: Thellungiella halophila

<400> SEQUENCE: 14

Met Gly Leu Ser Ser Leu Pro Gly Pro Ser Glu Gly Met Leu Cys Val
1               5                   10                  15

Ile Leu Val Asn Thr Ala Leu Ser Ile Ser Ile Phe Lys Gly Ile Val
            20                  25                  30

Arg Ser Val Leu His Val Leu Gly Ile Arg Leu Ser Gln Ser Ser Ser
        35                  40                  45
```

```
Ser Pro Ser Ser Val Thr Ala Ser Ser Glu Ile Pro Ala Ser Glu Pro
    50                  55                  60

Phe Asp Phe Arg Val Ser His Pro Glu Ser Phe Leu Glu Glu Phe Arg
 65                  70                  75                  80

Asn Lys Thr Pro Thr Leu Arg Tyr Glu Ser Leu Cys Arg Cys Lys Lys
                 85                  90                  95

His Glu Asp Asn Glu Cys Ser Val Cys Leu Ser Lys Phe Glu Glu Asp
                100                 105                 110

Ser Glu Ile Asn Lys Leu Lys Cys Gly His Leu Phe His Lys Thr Cys
                115                 120                 125

Leu Glu Lys Trp Ile Asp Tyr Trp Asn Ile Thr Cys Pro Leu Cys Arg
            130                 135                 140

Thr Pro Leu Val Val Val Ala Ala Ala Glu Asp Gln Lys Gln Leu Ser
145                 150                 155                 160

Ser Asn Val Trp

<210> SEQ ID NO 15
<211> LENGTH: 47
<212> TYPE: PRT
<213> ORGANISM: Thellungiella halophila

<400> SEQUENCE: 15

Glu Cys Ser Val Cys Leu Ser Lys Phe Glu Glu Asp Ser Glu Ile Asn
1               5                  10                  15

Lys Leu Lys Cys Gly His Leu Phe His Lys Thr Cys Leu Glu Lys Trp
             20                  25                  30

Ile Asp Tyr Trp Asn Ile Thr Cys Pro Leu Cys Arg Thr Pro Leu
         35                  40                  45

<210> SEQ ID NO 16
<211> LENGTH: 141
<212> TYPE: DNA
<213> ORGANISM: Thellungiella halophila

<400> SEQUENCE: 16
gagtgctcgg tttgcttgtc gaaatttgaa gaggattcag agattaacaa gctgaaatgt      60
ggacacttgt ttcacaaaac gtgcttggag aaatggatag actattggaa catcacttgc     120
ccactgtgta ggactcctct t                                               141

<210> SEQ ID NO 17
<211> LENGTH: 492
<212> TYPE: DNA
<213> ORGANISM: Thellungiella halophila

<400> SEQUENCE: 17
atgggtctat caagccttcc tggtccatca gaaggaatgc tatgcgtgat attagtcaac      60
acagcattat caatctccat cttcaaaggc attgtcagat cagtccttca cgtattagga     120
atccgtctct ctcagtcttc gtcttcccct tcttcagtaa ctgcatcttc agagatccca     180
gcttcagagc catttgattt ccgtgtctcc cacccggaga gtttcctcga ggagtttagg     240
aacaagactc caactctgag gtacgagagc ttgtgcaggt gcaagaaaca cgaggacaac     300
gagtgctcgg tttgcttgtc gaaatttgaa gaggattcag agattaacaa gctgaaatgt     360
ggacacttgt ttcacaaaac gtgcttggag aaatggatag actattggaa catcacttgc     420
ccactgtgta ggactcctct tgttgttgtg gcagcagcag aagaccagaa gcagctttct     480
tctaatgttt gg                                                         492
```

<210> SEQ ID NO 18
<211> LENGTH: 47
<212> TYPE: PRT
<213> ORGANISM: Brassica napus

<400> SEQUENCE: 18

```
Glu Cys Ser Val Cys Leu Ser Lys Phe Glu Glu Asp Ser Glu Ile Asn
1               5                   10                  15

Lys Ala Lys Cys Gly His Leu Phe His Lys Thr Cys Leu Glu Lys Trp
            20                  25                  30

Ile Asp Tyr Trp Asn Ile Thr Cys Pro Leu Cys Arg Thr Pro Leu
        35                  40                  45
```

<210> SEQ ID NO 19
<211> LENGTH: 161
<212> TYPE: PRT
<213> ORGANISM: Brassica napus

<400> SEQUENCE: 19

```
Lys Met Gly Leu Ser Ser Leu Pro Gly Pro Ser Glu Gly Met Leu Cys
1               5                   10                  15

Val Ile Leu Val Asn Thr Ala Leu Ser Ile Ser Ile Phe Lys Gly Ile
            20                  25                  30

Leu Arg Ser Val Leu Gln Leu Ile Gly Ile Arg Leu Ser Pro Ser Ser
        35                  40                  45

Ala Ala Ala Ala Ala Ala Ser Ser Glu Asn Gln Thr Ser Asp Ser Phe
    50                  55                  60

Asp Phe Arg Val Cys Gln Pro Glu Ser Phe Leu Glu Glu Phe Arg Asn
65                  70                  75                  80

Arg Thr Pro Thr Val Lys Phe Glu Ser Leu Cys Lys Cys Lys Lys Gln
                85                  90                  95

Ala Asp Asn Glu Cys Ser Val Cys Leu Ser Lys Phe Glu Glu Asp Ser
            100                 105                 110

Glu Ile Asn Lys Ala Lys Cys Gly His Leu Phe His Lys Thr Cys Leu
        115                 120                 125

Glu Lys Trp Ile Asp Tyr Trp Asn Ile Thr Cys Pro Leu Cys Arg Thr
    130                 135                 140

Pro Leu Val Val Val Ala Ala Asp Asp Gln Leu Val Ser Ile Met Phe
145                 150                 155                 160

Gly
```

<210> SEQ ID NO 20
<211> LENGTH: 141
<212> TYPE: DNA
<213> ORGANISM: Brassica napus

<400> SEQUENCE: 20

```
gagtgttctg tatgcctgtc gaaattcgaa gaggattcag agatcaacaa ggctaaatgt    60
ggccatttgt ttcacaaaac atgcttggag aaatggatag actactggaa catcacttgc   120
ccactctgta ggactcctct t                                              141
```

<210> SEQ ID NO 21
<211> LENGTH: 486
<212> TYPE: DNA
<213> ORGANISM: Brassica napus

<400> SEQUENCE: 21

```
atgggtctat caagccttcc tggtccatca gaaggaatgc tatgcgtgat attagttaac    60
acagcattgt caatctccat cttcaaaggc attctcaggt cagtgcttca gctaatagga   120
atccgcctct ctccttcttc agcagcagca gcagctgcat cttcagagaa tcaaacttca   180
gattcttttg atttccgggt ctgccagcct gagagtttcc ttgaggaatt caggaacagg   240
accccacag tgaagtttga gagcttgtgc aagtgcaaga acaggcgga caacgagtgt     300
tctgtatgcc tgtcgaaatt cgaagaggat tcagagatca caaggctaa atgtggccat    360
ttgtttcaca aaacatgctt ggagaaatgg atagactact ggaacatcac ttgcccactc   420
tgtaggactc ctcttgttgt tgtcgcagca gacgaccagc tggtttctat aatgtttggt   480
gaggac                                                              486
```

```
<210> SEQ ID NO 22
<211> LENGTH: 95
<212> TYPE: PRT
<213> ORGANISM: Fragaria x ananassa

<400> SEQUENCE: 22
```

Ser Glu Asp Thr Leu Lys Thr Leu Arg Thr Phe Glu Leu His Leu Ser
1               5                   10                  15

Ser Ser Gly Ser Tyr Ile Glu Glu Ile Arg Ser Arg Ile Pro Ala Val
            20                  25                  30

Arg Phe Asp Ser Val Cys Asn Leu Lys Thr Glu His Asp Cys Ser Val
        35                  40                  45

Cys Leu Ser Glu Phe Gln Pro Glu Ser Glu Ile Asn His Leu Thr Cys
    50                  55                  60

Gly His Val Phe His Gln Asp Cys Leu Glu Lys Trp Leu Asn Tyr Trp
65                  70                  75                  80

Asn Ile Thr Cys Pro Leu Cys Arg Thr Pro Phe Gln Gly Leu Ile
                85                  90                  95

```
<210> SEQ ID NO 23
<211> LENGTH: 46
<212> TYPE: PRT
<213> ORGANISM: Fragaria x ananassa

<400> SEQUENCE: 23
```

Asp Cys Ser Val Cys Leu Ser Glu Phe Gln Pro Glu Ser Glu Ile Asn
1               5                   10                  15

His Leu Thr Cys Gly His Val Phe His Gln Asp Cys Leu Glu Lys Trp
            20                  25                  30

Leu Asn Tyr Trp Asn Ile Thr Cys Pro Leu Cys Arg Thr Pro
        35                  40                  45

```
<210> SEQ ID NO 24
<211> LENGTH: 139
<212> TYPE: DNA
<213> ORGANISM: Fragaria x ananassa

<400> SEQUENCE: 24
gactgctctg tttgcctgag tgagttccaa ccagaatccg agataaacca cttgacttgt    60
ggccatgttt tccatcaaga tgcttggag aagtggttga actactggaa cattacatgc   120
cctctttgta ggactcctt                                               139
```

```
<210> SEQ ID NO 25
<211> LENGTH: 286
```

```
<212> TYPE: DNA
<213> ORGANISM: Fragaria x ananassa

<400> SEQUENCE: 25
atcagaggat acattgaaga ccctcagaac attcgagctc catctttctt cctcaggcag    60
ttacattgag gagatcagga gccgcatccc agccgttcgg tttgatagcg tgtgtaacct   120
caagacggag cacgactgct ctgtttgcct gagtgagttc caaccagaat ccgagataaa   180
ccacttgact tgtggccatg ttttccatca agattgcttg gagaagtggt tgaactactg   240
gaacattaca tgccctcttt gtaggactcc tttccaagga ctcatc                  286

<210> SEQ ID NO 26
<211> LENGTH: 158
<212> TYPE: PRT
<213> ORGANISM: Poncirus trifoliata

<400> SEQUENCE: 26

Met Gly Leu Ala Ser Met Pro Ser Ala Ser Glu Gly Met Leu Cys Leu
1               5                  10                  15

Ile Leu Met Asn Thr Ala Met Pro Ile Ser Ile Val Lys Gly Ile Phe
            20                  25                  30

Arg Ser Ile Leu Lys Val Val Gly Phe Gln Leu Ala Glu Ser Ser Ser
        35                  40                  45

Thr Pro Tyr Ser Tyr Phe Ala Ser Pro Gln Val Val Ser Ala Glu Pro
    50                  55                  60

Tyr Asp Val Asn Leu Ser Pro Pro Leu Ser Tyr Val Glu Glu Phe Arg
65                  70                  75                  80

Asn Gln Asn Pro Ala Ile Lys Tyr Glu Thr Leu Leu His Cys Glu Asp
                85                  90                  95

Ala Glu His Asp Cys Ser Val Cys Leu Thr Glu Phe Glu Pro Gln Ser
            100                 105                 110

Asp Ile Asn Asn Leu Ser Cys Gly His Leu Phe His Lys Val Cys Leu
        115                 120                 125

Glu Lys Trp Leu Asp Tyr Leu Asn Val Thr Cys Pro Leu Cys Arg Thr
    130                 135                 140

Pro Leu Ile Pro Glu Phe Glu Asp Asp Pro Ser Cys Phe Trp
145                 150                 155

<210> SEQ ID NO 27
<211> LENGTH: 47
<212> TYPE: PRT
<213> ORGANISM: Poncirus trifoliata

<400> SEQUENCE: 27

Asp Cys Ser Val Cys Leu Thr Glu Phe Glu Pro Gln Ser Asp Ile Asn
1               5                  10                  15

Asn Leu Ser Cys Gly His Leu Phe His Lys Val Cys Leu Glu Lys Trp
            20                  25                  30

Leu Asp Tyr Leu Asn Val Thr Cys Pro Leu Cys Arg Thr Pro Leu
        35                  40                  45

<210> SEQ ID NO 28
<211> LENGTH: 141
<212> TYPE: DNA
<213> ORGANISM: Poncirus trifoliata

<400> SEQUENCE: 28
gactgttctg tgtgtttgac cgagtttgag cctcaatctg atataaataa cttgtcttgt    60
```

```
ggacatttgt tcataaagt gtgcttggag aagtggctgg actatttgaa tgtcacgtgc    120
ccgctttgca ggacacctct a                                             141
```

<210> SEQ ID NO 29
<211> LENGTH: 981
<212> TYPE: DNA
<213> ORGANISM: Poncirus trifoliata

<400> SEQUENCE: 29

```
cagtcacaag attttgcttg atttctgatt cagtatctca aatttagtac aaaattgggt    60
atctgtaaat ttaaaatttt aattcgaaaa catgggcctc gctagtatgc cgtccgcatc   120
agaaggaatg ctatgcttga ttctaatgaa cactgctatg ccaatctcaa tcgtcaaagg   180
catattcaga tcaatcctca aggttgtcgg tttccagctt gctgaatcat catcgacacc   240
gtattcatat ttcgcttcac ctcaagttgt ctccgcagag ccatatgatg taaatttaag   300
tcctcccctt agctatgttg aggagttccg aaaccagaac cctgcaatca agtatgaaac   360
attgctccat tgtgaagatg cagagcatga ctgttctgtg tgtttgaccg agtttgagcc   420
tcaatctgat ataaataact tgtcttgtgg acatttgttt cataaagtgt gcttggagaa   480
gtggctggac tatttgaatg tcacgtgccc gctttgcagg acacctctaa ttcctgagtt   540
cgaagatgat ccctcttgtt tctggtgaga gtgttttatg agtttgtcta gttgtggaga   600
cttccatgta cagcatgtag tgtacaggta tttactaatg catcggctgg agtgtagtgt   660
tgtttacacg cctctgtgt gtgagttaaa tctcgagtcc ttttgaaggc ttgttgagaa   720
aaccagaatt ctgttgtaaa tattgtgagg tttctggttg ttttatggca tataatctga   780
cttttgatct tcagctttct ttaaagttca tattagtgac tttggtttcc atcttttctt   840
taatgagttg tatgtgactg aatatggaga agttgatgag gctttctagt ttccatgcta   900
gaattgctca aaagaagtt tgaattttac ttgagtttac caaacaagca tttgacaaaa   960
aaaaaaaaaa aaaaaaaaa a                                              981
```

<210> SEQ ID NO 30
<211> LENGTH: 47
<212> TYPE: PRT
<213> ORGANISM: Citrullus lanatus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 30

```
Asp Cys Ser Xaa Cys Leu Thr Gln Phe Glu Pro Ala Ser Glu Ile Asn
1               5                   10                  15

His Leu Ser Xaa Gly His Leu Phe His Thr Glu Cys Leu Glu Lys Xaa
            20                  25                  30

Leu Asp Tyr Trp Asn Ile Thr Cys Pro Leu Cys Arg Thr Pro Leu
        35                  40                  45
```

<210> SEQ ID NO 31
<211> LENGTH: 88

```
<212> TYPE: PRT
<213> ORGANISM: Citrullus lanatus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid

<400> SEQUENCE: 31

Xaa Gly Ser Xaa Trp Xaa Tyr Leu Glu Met Xaa Arg Asn Arg Tyr Pro
1               5                   10                  15

Arg Xaa Arg Phe Asp Lys Leu Gln Gly Ser Glu Xaa Arg Glu His Asp
            20                  25                  30

Cys Ser Xaa Cys Leu Thr Gln Phe Glu Pro Ala Ser Glu Ile Asn His
        35                  40                  45

Leu Ser Xaa Gly His Leu Phe His Thr Glu Cys Leu Glu Lys Xaa Leu
    50                  55                  60

Asp Tyr Trp Asn Ile Thr Cys Pro Leu Cys Arg Thr Pro Leu Met Xaa
65                  70                  75                  80

Glu Glu Glu Lys Ser Xaa Phe Trp
                85

<210> SEQ ID NO 32
<211> LENGTH: 143
<212> TYPE: DNA
<213> ORGANISM: Citrullus lanatus
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (60)..(60)
```

<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 32
gactgctcgg nctgtttaac tcaatttgaa cctgcatctg agataaatca cttatcttgn    60
ggtcatcttt ttcacacaga atgcttggag aagnggctag attactggaa catcacatgt   120
cctctttgca gaactcctct aat                                           143

<210> SEQ ID NO 33
<211> LENGTH: 537
<212> TYPE: DNA
<213> ORGANISM: Citrullus lanatus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t -continued

```
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (396)..(397)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (426)..(427)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t

<400> SEQUENCE: 33
ttntggctcc ncttggagnt acctcgagat gnttcgaaac cgatatccaa ggancngatt      60
tgataaatta cagggctcag aatgncgnga acatgactgc tcggnctgtt taactcaatt    120
tgaacctgca tctgagataa atcacttatc ttgnggtcat cttttcaca cagaatgctt     180 ggagaagngg ctagattact ggaacatcac atgtcctctt tgcagaactc ctctaatgnc   240
cgaagaagag aaatcgngct tttggtgagc gtagaatcta gttngggaa actcatgtac    300 agcatactct taaagataat tgtgaaagcg tttcctacct ttggcacgta tgacatttga    360
agnttgatgn gtctgacagg ncttagaggc caaagnnttg ncactgtaaa tacatgttta    420
tgaagnncta tgcntttggc ttgtgccttt agctttgagt taangcactg ttactncact    480
ttctttgtac atggaattgg ctgagtatgc acaaagntat tcaaattctg tttgttt      537

<210> SEQ ID NO 34
<211> LENGTH: 156
<212> TYPE: PRT
<213> ORGANISM: Hevea brasiliensis

<400> SEQUENCE: 34

Met Cys Leu Ser Asn Leu Pro Ala Ser Ser Glu Gly Val Ile Cys Val
1               5                  10                  15

Val Val Met Asn Thr Ala Leu Ser Ile Ser Ile Phe Lys Gly Ile Val
            20                  25                  30

Arg Ser Val Leu His Ile Val Asp Asn Arg Leu Ala Pro Phe Ser Ser
        35                  40                  45

Ser Ser Ser Ser Ile Leu Phe Pro Asp Tyr Ser Asp Thr Glu Ser Phe
    50                  55                  60

Glu Phe Pro Leu His Ser Ser Asp Asp Cys Val Arg Glu Leu Arg Ser
65                  70                  75                  80

Arg Arg Pro Ala Lys Arg Phe Asp Ala Val Ser Ser Cys Lys Gln Pro
                85                  90                  95
```

```
        Gln His Asp Cys Pro Val Cys Leu Ile Gln Phe Lys Pro Asp Ser Glu
                    100                 105                 110

Ile Asn Cys Leu Ser Cys Gly His Val Phe His Lys Ala Cys Leu Glu
                    115                 120                 125

Lys Trp Leu Asp Tyr Arg Lys Val Thr Cys Pro Leu Cys Lys Ser Pro
            130                 135                 140

Val Met Pro Glu Glu Glu Asp Thr Ser Ser Ser Trp
        145                 150                 155

<210> SEQ ID NO 35
<211> LENGTH: 580
<212> TYPE: DNA
<213> ORGANISM: Hevea brasiliensis
<220> FEATURE:
<221> NAME/KEY: misc_feature
<222> LOCATION: (535)..(535)
<223> OTHER INFORMATION: n is a, c, g, or t

<400> SEQUENCE: 35
tcttcccttc tacttccaca actgtcaatt gatctaagaa aatgtgtctc tcaaatcttc     60
cagcctcatc tgaaggagta atctgtgtgg ttgtgatgaa cactgcctta tcaatctcca    120
ttttcaaagg gatagtccgg tcggtccttc acattgttga caaccgctta gcacccttct    180
cctcatcatc atcttcaatc ctctttccag attacagtga caccgaatca tttgaatttc    240
ctttacattc atcagacgat tgcgttaggg agctccgaag caggaggcct gcaaaacgat    300
ttgatgcagt gtctagctgt aaacagcctc aacatgactg cccagtttgc ttgattcaat    360
tcaagccaga ctcggagata aattgcttat cctgtggcca tgtttttcat aaggcgtgct    420
tggagaagtg gttggattat cggaaagtta cttgtccgct ttgcaagtct cctgtgatgc    480
ctgaagaaga ggatacatct agctcttggt aagcatatac cagaagtttg ctcgncttag    540
taaatgttca cgtgcagcgt gttgagtcca cttggtgttc                         580

<210> SEQ ID NO 36
<211> LENGTH: 47
<212> TYPE: PRT
<213> ORGANISM: Hevea brasiliensis

<400> SEQUENCE: 36

Asp Cys Pro Val Cys Leu Ile Gln Phe Lys Pro Asp Ser Glu Ile Asn
1               5                   10                  15

Cys Leu Ser Cys Gly His Val Phe His Lys Ala Cys Leu Glu Lys Trp
            20                  25                  30

Leu Asp Tyr Arg Lys Val Thr Cys Pro Leu Cys Lys Ser Pro Val
        35                  40                  45

<210> SEQ ID NO 37
<211> LENGTH: 142
<212> TYPE: DNA
<213> ORGANISM: Hevea brasiliensis

<400> SEQUENCE: 37
gactgcccag tttgcttgat tcaattcaag ccagactcgg agataaattg cttatcctgt     60
ggccatgttt ttcataaggc gtgcttggag aagtggttgg attatcggaa agttacttgt    120
ccgctttgca agtctcctgt ga                                             142

<210> SEQ ID NO 38
<211> LENGTH: 499
<212> TYPE: DNA
```

<213> ORGANISM: Hevea brasiliensis
<220> FEATURE:
<221> NAME/KEY: misc_feature
<222> LOCATION: (494)..(494)
<223> OTHER INFORMATION: n is a, c, g, or t

<400> SEQUENCE: 38

```
atgtgtctct caaatcttcc agcctcatct gaaggagtaa tctgtgtggt tgtgatgaac      60
actgccttat caatctccat tttcaaaggg atagtccggt cggtccttca cattgttgac     120
aaccgcttag caccctcctc ctcatcatca tcttcaatcc tctttccaga ttacagtgac     180
accgaatcat ttgaatttcc tttacattca tcagacgatt gcgttaggga gctccgaagc     240
aggaggcctg caaaacgatt tgatgcagtg tctagctgta aacagcctca acatgactgc     300
ccagtttgct tgattcaatt caagccagac tcggagataa attgcttatc ctgtggccat     360
gtttttcata aggcgtgctt ggagaagtgg ttggattatc ggaaagttac ttgtccgctt     420
tgcaagtctc ctgtgatgcc tgaagaagag gatacatcta gctcttggta agcatatacc     480
agaagtttgc tcgncttag                                                   499
```

<210> SEQ ID NO 39
<211> LENGTH: 47
<212> TYPE: PRT
<213> ORGANISM: Vitis vinifera

<400> SEQUENCE: 39

```
Asp Cys Ala Val Cys Leu Thr Arg Phe Glu Pro Asp Ser Glu Ile Asn
1               5                   10                  15

His Leu Pro Cys Gly His Phe Phe Ser Gln Gly Leu Leu Gly Glu Val
            20                  25                  30

Ala Gly Leu Leu Glu His His Leu Pro Ser Val Gln Asp Ser Leu
        35                  40                  45
```

<210> SEQ ID NO 40
<211> LENGTH: 177
<212> TYPE: PRT
<213> ORGANISM: Vitis vinifera

<400> SEQUENCE: 40

```
Met Gly Leu Ser Ser Leu Pro Ala Pro Ser Glu Gly Val Leu Cys Val
1               5                   10                  15

Leu Leu Val Asn Thr Ala Leu Ser Ile Ser Ile Phe Lys Gly Ile Val
            20                  25                  30

Arg Ala Ile Leu His Val Ile Gly Ile His Leu Ser Ala Thr Pro Ser
        35                  40                  45

Ser Ser Asp Ser Pro Glu Pro Thr Ser Glu Pro Phe Glu Phe Arg Arg
    50                  55                  60

Asn Pro Ser Glu Thr Cys Met Glu Glu Phe Arg Ser Arg Asn Pro Ala
65                  70                  75                  80

Ile Arg Phe Asp Thr Val Cys Ser Cys Lys Arg Pro Glu His Asp Cys
                85                  90                  95

Ala Val Cys Leu Thr Arg Phe Glu Pro Asp Ser Glu Ile Asn His Leu
            100                 105                 110

Pro Cys Gly His Phe Phe Ser Gln Gly Leu Leu Gly Glu Val Ala Gly
        115                 120                 125

Leu Leu Glu His His Leu Pro Ser Val Gln Asp Ser Leu Asn Ala Gly
    130                 135                 140

Arg Gly Asn Ile Leu Leu Leu Val Ser Asn Ile Trp Glu Asn Asp Lys
```

| | 145 | | | 150 | | | 155 | | | 160 | |
|---|---|---|---|---|---|---|---|---|---|---|---|
Leu Arg Lys Tyr Ser Asn Ile Thr Val Gln Leu Met Tyr Arg Cys Phe
              165                 170                 175

Thr

<210> SEQ ID NO 41
<211> LENGTH: 141
<212> TYPE: DNA
<213> ORGANISM: Vitis vinifera

<400> SEQUENCE: 41

```
gactgtgcgg tttgcttgac tcgatttgaa ccagactctg agataaatca cctgccttgt    60
ggccattttt tttcacaagg tttgcttgga gaagtggctg gactattgga acatcacctg   120
ccctctgtgc aggactccct t                                              141
```

<210> SEQ ID NO 42
<211> LENGTH: 533
<212> TYPE: DNA
<213> ORGANISM: Vitis vinifera

<400> SEQUENCE: 42

```
atgggactat cgagtctccc agccccatct gaaggagtac tgtgtgtgct tctggtgaac    60
acagctctct ccatctccat cttcaagggc atagtccggg ccatcctcca tgtcattgga   120
attcacctct ccgcaacccc atcctcctcc gactcccctg aacccacctc agagcccttt   180
gagtttaggc ggaacccatc tgagacctgc atggaggaat caggagcag gaacccagca    240
atcaggtttg acacagtgtg ctcctgcaag cgccctgaac atgactgtgc ggtttgcttg   300
actcgatttg aaccagactc tgagataaat cacctgcctt gtggccattt ttttcacaa   360
ggtttgcttg gagaagtggc tggactattg gaacatcacc tgccctctgt gcaggactcc   420
cttaatgccg aagaggaaa catcttgctt tggtaagca atatctggga gaatgacaag    480
ttgaggaaat attcaaatat cactgtacag cttatgtata ggtgttttac atg          533
```

<210> SEQ ID NO 43
<211> LENGTH: 862
<212> TYPE: DNA
<213> ORGANISM: Vitis vinifera

<400> SEQUENCE: 43

```
acttctgctg tcaattccac atcattggga tcccatgaat ttctatgctg ctgctgcttc    60
ttctccttcc tgatcactcc aacgccccca tcatctttctc aagctcaacc ctatcagacc   120
ctccttctcc gcaaatctaa atcccaaaac tccaatttgg agcagcatgg gactatcgag   180
tctcccagcc ccatctgaag gagtactgtg tgtgcttctg gtgaacacag ctctctccat   240
ctccatcttc aagggcatag tccgggccat cctccatgtc attggaattc acctctccgc   300
aaccccatcc tcctccgact cccctgaacc cacctcagag cccttgagt ttaggcggaa   360
cccatctgag acctgcatgg aggaattcag gagcaggaac ccagcaatca ggtttgacac   420
agtgtgctcc tgcaagcgcc ctgaacatga ctgtgcggtt tgcttgactc gatttgaacc   480
agactctgag ataaatcacc tgccttgtgg ccattttttt tcacaaggtt tgcttggaga   540
agtggctgga ctattggaac atcacctgcc ctctgtgcag gactccctta atgccggaag   600
aggaaacatc ttgcttttgg taagcaatat ctgggagaat gacaagttga ggaaatattc   660
aaatatcact gtacagctta tgtataggtg ttttacatga atacatcagc taggtgtatc   720
```

```
tttattcat atgttagtta tatgctccag ttttatgcct ttatgtgaag aatctatatg    780
atatcagggt cacatatccc atgtctatat atgtatatat atatatattg tacatgttgt    840
gaggtttctg atgttttggc ac                                            862
```

```
<210> SEQ ID NO 44
<211> LENGTH: 48
<212> TYPE: PRT
<213> ORGANISM: Medicago truncatula

<400> SEQUENCE: 44
```

Asp Cys Ser Val Cys Leu Thr Gln Phe Glu Pro Glu Ser Glu Ile Asn
1               5                   10                  15

Tyr Cys Ile Ser Cys Gly His Val Phe His Lys Val Cys Leu Glu Lys
            20                  25                  30

Trp Leu Asp Tyr Trp Asn Ile Thr Cys Pro Leu Cys Arg Ser Pro Leu
        35                  40                  45

```
<210> SEQ ID NO 45
<211> LENGTH: 155
<212> TYPE: PRT
<213> ORGANISM: Medicago truncatula

<400> SEQUENCE: 45
```

Met Gly Leu Ser Ser Leu Pro Ala Gln Ser Glu Gly Val Leu Cys Ile
1               5                   10                  15

Ile Leu Val Asn Thr Ala Met Ser Ile Ser Ile Phe Lys Gly Ile Ile
            20                  25                  30

Arg Thr Ile Leu His Ile Val Gly Ile Ile Ala Ser Pro Ser Ser Ser
        35                  40                  45

Pro Ser Gln Asp Tyr Ile Pro Gln Asn Ile Pro Glu Ser Tyr Glu Ile
50                  55                  60

His Leu Ser Pro Ser Asp Asp Phe Val Glu Glu Phe Arg Ser Arg Thr
65                  70                  75                  80

Pro Thr Leu Arg Phe Asp Ser Val Cys Asn Ser Cys Lys Glu Pro Glu
                85                  90                  95

His Asp Cys Ser Val Cys Leu Thr Gln Phe Glu Pro Glu Ser Glu Ile
            100                 105                 110

Asn Tyr Cys Ile Ser Cys Gly His Val Phe His Lys Val Cys Leu Glu
        115                 120                 125

Lys Trp Leu Asp Tyr Trp Asn Ile Thr Cys Pro Leu Cys Arg Ser Pro
    130                 135                 140

Leu Ile Pro Glu Asp Asp Ala Ser Cys Leu Trp
145                 150                 155

```
<210> SEQ ID NO 46
<211> LENGTH: 129
<212> TYPE: DNA
<213> ORGANISM: Medicago truncatula

<400> SEQUENCE: 46
gattgctcag tgtgtctcac tcaatttgaa cctgaatcag agataaacta ttgcatatca    60
tgtggccatg ttttcataa agtgtgtttg gagaagtggt tggattattg gaacattaca   120
tgtccactt                                                           129
```

```
<210> SEQ ID NO 47
<211> LENGTH: 464
<212> TYPE: DNA
```

<213> ORGANISM: Medicago truncatula

<400> SEQUENCE: 47

| | | | | | |
|---|---|---|---|---|---|
| atgggcctat | caagtcttcc | agcacaatct | gaaggagtgt | tatgcatcat | tctagtaaac | 60 |
| actgccatgt | caatatccat | attcaaaggc | attataagga | ctatcctgca | cattgttggt | 120 |
| atcattgctt | caccatcttc | ctctccttcc | caagactaca | ttcctcaaaa | catacctgag | 180 |
| tcatatgaaa | tccatctaag | tccttcagat | gatttcgttg | aagagttcag | aagcagaaca | 240 |
| ccaacactta | ggtttgatag | tgtgtgtaat | agctgcaaag | aacctgaaca | tgattgctca | 300 |
| gtgtgtctca | ctcaatttga | acctgaatca | gagataaact | attgcatatc | atgtggccat | 360 |
| gttttcata | aagtgtgttt | ggagaagtgg | ttggattatt | ggaacattac | atgtccactt | 420 |
| gtaggagtcc | tttaattcct | gaagatgatg | catcttgctt | atgg | | 464 |

<210> SEQ ID NO 48
<211> LENGTH: 134
<212> TYPE: PRT
<213> ORGANISM: Gossypium sp.

<400> SEQUENCE: 48

Met Gly Leu Ser Gly Leu Pro Ala Pro Ser Glu Gly Val Leu Cys Val
1               5                   10                  15

Phe Gln Ser Ile Leu His Ile Val Gly Ile Ala Ser Ser Ser Pro Ser
            20                  25                  30

Ser Asp Ser Val Glu Asn Pro Ser Glu Ser Phe Glu Phe Thr Pro Thr
        35                  40                  45

Thr Cys Asp Ser Tyr Met Glu Glu Phe Arg Asn Arg Thr Pro Ala Met
    50                  55                  60

Arg Phe Asp Ala Ile Cys Ser Cys Lys Gln Pro Glu Tyr Glu Cys Ser
65                  70                  75                  80

Val Cys Leu Thr Arg Phe Glu Pro Glu Ser Glu Val Asn Arg Leu Thr
                85                  90                  95

Cys Gly His Leu Phe His Lys Val Cys Leu Glu Lys Trp Leu Asp Tyr
            100                 105                 110

Gln Lys Val Thr Cys Pro Asp Cys Arg Thr Pro Leu Leu His Glu Gln
        115                 120                 125

Glu Ala Ser Cys Ile Trp
    130

<210> SEQ ID NO 49
<211> LENGTH: 47
<212> TYPE: PRT
<213> ORGANISM: Gossypium sp.

<400> SEQUENCE: 49

Glu Cys Ser Val Cys Leu Thr Arg Phe Glu Pro Glu Ser Glu Val Asn
1               5                   10                  15

Arg Leu Thr Cys Gly His Leu Phe His Lys Val Cys Leu Glu Lys Trp
            20                  25                  30

Leu Asp Tyr Gln Lys Val Thr Cys Pro Asp Cys Arg Thr Pro Leu
        35                  40                  45

<210> SEQ ID NO 50
<211> LENGTH: 143
<212> TYPE: DNA
<213> ORGANISM: Gossypium sp.

<400> SEQUENCE: 50

```
gaatgttcgg tttgcctaac tcgatttgag ccggaatcgg aggttaatcg cttgacctgc    60
ggccatctct ttcacaaggt gtgcttggaa aagtggttgg attatcagaa ggttacatgc   120
ccggattgcc ggacgcctct gct                                           143
```

```
<210> SEQ ID NO 51
<211> LENGTH: 404
<212> TYPE: DNA
<213> ORGANISM: Gossypium sp.

<400> SEQUENCE: 51
```

```
atgggtctct caggtctccc agcaccatca gaaggagtgc tatgtgtatt ccaatcaatc    60
cttcacattg tcggtattgc gtcttcatcg ccatcctcgg attctgtcga aaatccctcg   120
gaatcattcg aattcacccc tacaacttgt gatagttaca tggaagagtt ccggaataga   180
accccagcga tgaggtttga tgctatatgt agctgcaagc aacctgagta tgaatgttcg   240
gtttgcctaa ctcgatttga gccggaatcg gaggttaatc gcttgacctg cggccatctc   300
tttcacaagg tgtgcttgga aaagtggttg gattatcaga aggttacatg cccggattgc   360
cggacgcctc tgctgcatga acaagaggct tcctgcattt ggtg                   404
```

```
<210> SEQ ID NO 52
<211> LENGTH: 43
<212> TYPE: PRT
<213> ORGANISM: Pinus taeda

<400> SEQUENCE: 52
```

```
Val Cys Ala Val Cys Leu Ser Arg Met Glu Glu Glu Asp Glu Met Arg
 1               5                  10                  15

Glu Leu Cys Asn Cys Phe His Val Phe His Arg Asn Cys Leu Glu Lys
            20                  25                  30

Trp Leu His Gln Arg Gln Thr Thr Cys Pro Leu
        35                  40
```

```
<210> SEQ ID NO 53
<211> LENGTH: 172
<212> TYPE: PRT
<213> ORGANISM: Pinus taeda

<400> SEQUENCE: 53
```

```
Met Gly Phe Leu Val Ile Pro Ser Leu Leu Leu His Ala Ala Val Leu
 1               5                  10                  15

Val Ala Cys Ile Lys Asn Ala Ile Thr Trp Ala Leu Gln Leu Val Gly
            20                  25                  30

Leu Ala Glu Ile Leu Glu Pro Glu Thr Ser Ala Ala Phe Ser Arg Gln
        35                  40                  45

Glu Thr Asp Cys Asn Pro Ser Ala Gln Asp Glu Ile Ile Arg Glu Trp
    50                  55                  60

Leu Leu Pro Val Thr Thr Phe Gly Glu Phe Val Gln Arg Phe Gln Gly
65                  70                  75                  80

Gly Val Ala Asp Asp Val Cys Ala Val Cys Leu Ser Arg Met Glu
                85                  90                  95

Glu Glu Asp Glu Met Arg Glu Leu Cys Asn Cys Phe His Val Phe His
            100                 105                 110

Arg Asn Cys Leu Glu Lys Trp Leu His Gln Arg Gln Thr Thr Cys Pro
        115                 120                 125

Leu Cys Arg Cys Cys Leu Leu Pro Glu Pro Glu Met Glu Lys Ala Asp
```

```
            130                 135                 140
Thr Met Ala Pro Gln Ser Asn Gln Ser Trp Leu Val Asp Ser Ile Ser
145                 150                 155                 160

Phe Leu Phe Ser Gln Asp Leu Ala Gly His Thr Leu
                165                 170
```

<210> SEQ ID NO 54
<211> LENGTH: 129
<212> TYPE: DNA
<213> ORGANISM: Pinus taeda

<400> SEQUENCE: 54

```
gtgtgtgctg tgtgtttgag caggatggag gaggaagatg agatgagaga attgtgtaat    60
tgctttcatg tatttcacag gaattgtttg gagaagtggc tccatcaacg tcagacgacg   120
tgccctctc                                                           129
```

<210> SEQ ID NO 55
<211> LENGTH: 518
<212> TYPE: DNA
<213> ORGANISM: Pinus taeda

<400> SEQUENCE: 55

```
atggggttcc tcgtcattcc tagcctgctg ctgcacgccg cagtttttggt agcgtgcata    60
aagaacgcca tcacgtgggc tctccagctt gttgggttgg ccgagatttt ggaacccgag   120
acctccgccg cctttttcacg gcaagaaacc gactgtaatc catccgcgca ggacgaaata   180
atacgagaat ggctgctgcc cgttactacg tttggcgagt tgtgcaaag atttcagggg    240
ggagttgcag acgatgatgt gtgtgctgtg tgtttgagca ggatggagga ggaagatgag   300
atgagagaat tgtgtaattg ctttcatgta tttcacagga attgtttgga gaagtggctc   360
catcaacgtc agacgacgtg ccctctctgc agatgctgtc tcctgccgga accggaaatg   420
gaaaaggcag atacgatggc ccctcagagt aaccagtcat ggcttgtgga cagtatctcg   480
ttttttatttt ctcaagattt agcaggtcac accttgta                          518
```

<210> SEQ ID NO 56
<211> LENGTH: 1005
<212> TYPE: DNA
<213> ORGANISM: Pinus taeda
<220> FEATURE:
<221> NAME/KEY: misc_feature
<222> LOCATION: (951)..(952)
<223> OTHER INFORMATION: n is a, c, g, or t
<220> FEATURE:
<221> NAME/KEY: misc_feature
<222> LOCATION: (988)..(989)
<223> OTHER INFORMATION: n is a, c, g, or t
<220> FEATURE:
<221> NAME/KEY: misc_feature
<222> LOCATION: (1004)..(1004)
<223> OTHER INFORMATION: n is a, c, g, or t

<400> SEQUENCE: 56

```
gctccctctc attgttgcta atgattcctt tccgcttccc ctcctcttcc gtccattcgt    60
atgggtagat tcttgctcac ctgagccgtt caaattctgg tgcttaggat tccttttctg   120
cctttccgtg cgagagtcgt ttcagacaac agcgggggat ggtgttcggt cgtgggcctt   180
tcaggctggc tggatcccat ctgggtcgtt tcaattccca tctgattttt atacccacaa   240
actggatttg acctttcaat ccctcaggct tgactgtgtc ttcttctgtt ctctatttat   300
tcatctccca gaccgttctt cacagcattg gaggtccagg gttcgactct cttccttcgc   360
```

-continued

```
tcctcatggg gttcctcgtc attcctagcc tgctgctgca cgccgcagtt ttggtagcgt    420
gcataaagaa cgccatcacg tgggctctcc agcttgttgg gttggccgag attttggaac    480
ccgagacctc cgccgccttt tcacggcaag aaaccgactg taatccatcc gcgcaggacg    540
aaataatacg agaatggctg ctgcccgtta ctacgtttgg cgagtttgtg caaagatttc    600
aggggggagt tgcagacgat gatgtgtgtg ctgtgtgttt gagcaggatg gaggaggaag    660
atgagatgag agaattgtgt aattgctttc atgtatttca caggaattgt ttggagaagt    720
ggctccatca acgtcagacg acgtgccctc tctgcagatg ctgtctcctg ccggaaccgg    780
aaatggaaaa ggcagatacg atggcccctc agagtaacca gtcatggctt gtggacagta    840
tctcgttttt attttctcaa gatttagcag gtcacacctt gtaacgtgtg gaggagaatt    900
gaatcatttg cttgcgttgc agctatgggt tggagtaaaa aactaacacc nntaggatat    960
cttcttgact gtaatgttac gggctttnna tgtaacgtta ccgnt                  1005
```

```
<210> SEQ ID NO 57
<211> LENGTH: 42
<212> TYPE: PRT
<213> ORGANISM: Pinus taeda

<400> SEQUENCE: 57
```

Glu Cys Ala Val Cys Leu Cys Lys Phe Glu Glu Gly Val Glu Ile Arg
1               5                   10                  15

Gln Leu Pro Cys Cys His Leu Phe His Arg Ser Cys Leu Asp Lys Trp
            20                  25                  30

Leu Asp His Gln Gln Ile Thr Cys Pro Leu
        35                  40

```
<210> SEQ ID NO 58
<211> LENGTH: 189
<212> TYPE: PRT
<213> ORGANISM: Pinus taeda

<400> SEQUENCE: 58
```

Met Gly Leu Ser Ser Phe Pro Thr Thr Val Ser Glu Gly Val Leu Pro
1               5                   10                  15

Ile Leu Ile Val Asn Thr Ala Leu Ser Phe Ala Ile Ile Lys Asp Ile
            20                  25                  30

Leu Arg Ser Phe Leu Gln Ile Val Gly Leu Thr Thr Gly Asn Glu Pro
        35                  40                  45

Asp Phe Asn Asp Pro Ser Trp Pro Tyr Pro Ser Glu Asn Ser Pro Ala
    50                  55                  60

Thr Ser Thr Asp His Ser Glu Val Gln Phe Val Ala Glu Glu Ile Arg
65                  70                  75                  80

Gln Ser Leu Pro Ile Lys Lys Phe Gln Ser Cys Ser Asp Gly Ser Val
                85                  90                  95

Gly Ser Asp Asn Thr His Val Glu Cys Ala Val Cys Leu Cys Lys Phe
            100                 105                 110

Glu Glu Gly Val Glu Ile Arg Gln Leu Pro Cys Cys His Leu Phe His
        115                 120                 125

Arg Ser Cys Leu Asp Lys Trp Leu Asp His Gln Gln Ile Thr Cys Pro
    130                 135                 140

Leu Cys Arg Ser Cys Leu Ile Ser Glu Glu Ala Ala Lys Asn Ile Arg
145                 150                 155                 160

Leu Arg Glu Gln Glu Leu Thr Asp Glu Leu Val Phe Trp Cys Ser Ser

```
                    165                 170                 175
Phe Gln Asp Ala Ala Tyr His Pro Thr Trp Ile Glu Ser
                180                 185

<210> SEQ ID NO 59
<211> LENGTH: 126
<212> TYPE: DNA
<213> ORGANISM: Pinus taeda

<400> SEQUENCE: 59
gagtgtgcag tctgcttatg caaatttgaa gaaggggttg agattagaca gctgccttgc      60
tgccaccttt ttcacagatc ttgtcttgat aaatggctgg accatcagca gatcacatgt     120
cccttg                                                                126

<210> SEQ ID NO 60
<211> LENGTH: 569
<212> TYPE: DNA
<213> ORGANISM: Pinus taeda

<400> SEQUENCE: 60
atgggtctct caagctttcc caccaccgtc tctgaaggag tcctgccaat tctgattgtg      60
aatactgctc tgtcgtttgc cattatcaag acatcctga ggtctttttct tcagatcgta     120 ggccttacca caggcaatga acctgacttt aacgatccat catggcctta cccatctgag     180
aatagccctg caaccagtac tgaccattcc gaggtgcagt tcgttgcaga ggaaataagg     240
cagagcctac ccatcaaaaa gttccaatct tgtagtgatg ggtctgttgg tagtgacaat     300
acccatgttg agtgtgcagt ctgcttatgc aaatttgaag aaggggttga gattagacag     360
ctgccttgct gccacctttt tcacagatct tgtcttgata aatggctgga ccatcagcag     420
atcacatgtc ccttgtgtag atcatgtctg atatcagaag aagcagccaa gaatatcagg     480
ctcagggaac aggagcttac agatgaattg gtattctggt gttcatcctt ccaagatgcg     540
gcttatcatc ctacatggat tgaaagtta                                       569

<210> SEQ ID NO 61
<211> LENGTH: 1211
<212> TYPE: DNA
<213> ORGANISM: Pinus taeda

<400> SEQUENCE: 61
aaggtgttca tttttctcac atctttcttt gttcatgcag atcttgttcg ttgtgccttc      60
tgtgactgaa aattctcatg ggtctctcaa gctttcccac caccgtctct gaaggagtcc     120
tgccaattct gattgtgaat actgctctgt cgtttgccat tatcaaggac atcctgaggt     180
cttttcttca gatcgtaggc cttaccacag gcaatgaacc tgactttaac gatccatcat     240
ggccttaccc atctgagaat agccctgcaa ccagtactga ccattccgag gtgcagttcg     300
ttgcagagga aataaggcag agcctaccca tcaaaaagtt ccaatcttgt agtgatgggt     360
ctgttggtag tgacaatacc catgttgagt gtgcagtctg cttatgcaaa tttgaagaag     420
gggttgagat tagacagctg ccttgctgcc accttttttca gatcttgtct tgataaatt      480 ggctggacca tcagcagatc acatgtccct tgtgtagatc atgtctgata tcagaagaag     540
cagccaagaa tatcaggctc agggaacagg agcttacaga tgaattggta ttctggtgtt     600
catccttcca agatgcggct tatcatccta catggattga agttagaat ttcttggatc       660 ctggtttgat ggattcttcg acacttgaac cagtcatctg ggtctataa ttggagattc       720
```

```
tgtaatttttt ttttttgtaa ataatcttta ggaaagttgc ttgtttctac aggatgcttt      780
gttgtttctc ctgttgaaag caatcctgtt ttctgaagat tatgtagtca atacttcttc      840
tgtatatagc aggaaagcct atatgtagag aagacctaga acttagaatc tgttcttttc      900
agtacttgag gttttctagg gtggcctgag aaggtctgga atgatctgtg tgggatctga      960
gatctaccga tcagccaaga aaaggaaaa aaaatcgtgt gccctgtctg ttagtggatg      1020
gcatacacac cattacaaaa actttgtttt gaagatatca ttttgcagtc cccatgggat      1080
tggctgagca gtgaagtcgg gtgatttccg ctctgccatc tatggctgtt ttgtggggat      1140
gtctgtaata actttgtatt actctctatt tgaacatgga atttgatttt tttgatgagt      1200
taggcaaaga a                                                          1211
```

<210> SEQ ID NO 62
<211> LENGTH: 43
<212> TYPE: PRT
<213> ORGANISM: Nicotiana tabacum
<220> FEATURE:
<221> NAME/KEY: misc_feature
<222> LOCATION: (29)..(29)
<223> OTHER INFORMATION: Xaa can be any naturally occurring amino acid

<400> SEQUENCE: 62

```
Glu Cys Pro Val Cys Pro Gly Ser Ile Ser Thr Met Met Lys Asn Arg
1               5                   10                  15

Leu Val Ser Val Ala His Val Phe His Lys Leu Cys Xaa Glu Lys Trp
            20                  25                  30

Ile Lys Asn Trp Asn Val Thr Cys Pro His Leu
        35                  40
```

<210> SEQ ID NO 63
<211> LENGTH: 135
<212> TYPE: DNA
<213> ORGANISM: Nicotiana tabacum
<220> FEATURE:
<221> NAME/KEY: misc_feature
<222> LOCATION: (91)..(91)
<223> OTHER INFORMATION: n is a, c, g, or t

<400> SEQUENCE: 63

```
gaatgcccgg tatgccctgg cagtatttca accatgatgt agaaatagaa ccgcctcgtc       60
agtgtggccc atgttttca taagctctgt ntcgagaaat ggatcaagaa ttggaatgtc      120
acctgtcctc atctg                                                      135
```

<210> SEQ ID NO 64
<211> LENGTH: 82
<212> TYPE: PRT
<213> ORGANISM: Nicotiana tabacum
<220> FEATURE:
<221> NAME/KEY: misc_feature
<222> LOCATION: (70)..(70)
<223> OTHER INFORMATION: Xaa can be any naturally occurring amino acid

<400> SEQUENCE: 64

```
Leu Lys Ser Pro Gly Thr Arg Leu Asn Val Val Gly Ser Pro Ser Gly
1               5                   10                  15

Ser Tyr Met Glu Asp Phe Arg Ser Arg Thr Pro Ala Val Ser Leu Phe
            20                  25                  30

Asn Val Tyr Ile Ile Thr Leu Arg Gln Glu Cys Pro Val Cys Pro Gly
        35                  40                  45

Ser Ile Ser Thr Met Met Lys Asn Arg Leu Val Ser Val Ala His Val
```

-continued

```
               50                  55                  60
Phe His Lys Leu Cys Xaa Glu Lys Trp Ile Lys Asn Trp Asn Val Thr
65                  70                  75                  80

Cys Pro
```

<210> SEQ ID NO 65
<211> LENGTH: 391
<212> TYPE: DNA
<213> ORGANISM: Nicotiana tabacum
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t

<400> SEQUENCE: 65

```
ggttgaacac agccatatct atctctgttg tcaaggagat antttggtct attcttcatg      60
tgatnggcat ccacttggca tcttcggaag aatattctga ttgaagtccc ctgggacccg     120
tttgaatgtc gtggggagcc cctcgggttc atatatggag gacttccgaa gccgaactcc     180
tgcagtatcg ttatgattca atgtgtacat ctgaatcacc ctgcgacaag aatgcccggt     240
atgccctggc agtatttcaa ccatgatgta gaaatagaac cgcctcgtca gtgtggccca     300
tgttttcat aagctctgtn tcgagaaatg gatcaagaat tggaatgtca cctgtcctca     360
tctgtcagga agttacatta tgcctcaaga a                                   391
```

<210> SEQ ID NO 66
<211> LENGTH: 391
<212> TYPE: DNA
<213> ORGANISM: Nicotiana tabacum
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t

<400> SEQUENCE: 66

```
ttcttgaggc ataatgtaac ttcctgacag atgaggacag gtgacattcc aattcttgat      60
ccatttctcg anacagagct tatgaaaaac atgggccaca ctgacgaggc ggttctattt     120
ctacatcatg gttgaaatac tgccagggca taccgggcat tcttgtcgca gggtgattca     180
gatgtacaca ttgaatcata cgatactgc aggagttcgg cttcggaagt cctccatata     240
tgaacccgag gggctcccca cgacattcaa acgggtccca ggggacttca atcagaatat     300
tcttccgaag atgccaagtg gatgccnatc acatgaagaa tagaccaaan tatctccttg     360
acaacagaga tagatatggc tgtgttcaac c                                   391
```

<210> SEQ ID NO 67
<211> LENGTH: 168
<212> TYPE: PRT

<213> ORGANISM: Pinus glabra

<400> SEQUENCE: 67

Asn Thr Ala Leu Ser Phe Ala Ile Ile Lys Asp Ile Leu Arg Ser Phe
1               5                   10                  15
Leu Gln Ile Val Gly Leu Thr Thr Gly Thr Glu Pro Asp Phe Ile Asp
            20                  25                  30
Pro Ser Trp Pro Tyr Pro Pro Glu Asn Thr Pro Ala Val Ser Thr Gly
        35                  40                  45
His Ser Glu Ala Gln Phe Ile Ala Glu Glu Ile Arg Gln Ser Leu Pro
    50                  55                  60
Ile Lys Arg Phe Gln Ser Phe Thr Asp Gly Phe Val Gly Ser Asp Asn
65                  70                  75                  80
Ser His Val Glu Cys Ala Val Cys Leu Ser Lys Phe Glu Glu Gly Val
                85                  90                  95
Glu Ile Arg Gln Leu Thr Cys Cys His Leu Phe His Arg Pro Cys Leu
            100                 105                 110
Asp Trp Leu Asp His Gln Gln Ile Thr Cys Pro Leu Cys Arg Ser Cys
        115                 120                 125
Leu Ile Ser Glu Glu Ala Ala Lys Asn Ile Arg Leu Arg Glu Gln Glu
    130                 135                 140
Leu Thr Asp Glu Ser Val Phe Trp Cys Ser Ser Phe Gln Glu Ala Ala
145                 150                 155                 160
Tyr His His Thr Trp Ile Glu Ser
                165

<210> SEQ ID NO 68
<211> LENGTH: 47
<212> TYPE: PRT
<213> ORGANISM: Pinus glabra

<400> SEQUENCE: 68

Glu Cys Ala Val Cys Leu Ser Lys Phe Glu Gly Val Glu Ile Arg
1               5                   10                  15
Gln Leu Thr Cys Cys His Leu Phe His Arg Pro Cys Leu Asp Lys Trp
            20                  25                  30
Leu Asp His Gln Gln Ile Thr Cys Pro Leu Cys Arg Ser Cys Leu
        35                  40                  45

<210> SEQ ID NO 69
<211> LENGTH: 509
<212> TYPE: DNA
<213> ORGANISM: Pinus glabra

<400> SEQUENCE: 69
aatactgctc tgtcttttgc cattatcaag gacatcctga ggtcttttct tcagattgta      60
ggccttacca caggcactga acctgatttt atcgacccat catggcctta cccacctgaa     120
aatacccctg cagtcagtac tggccattcc gaagcgcagt tcattgcaga ggaaatcagg     180
cagagcctac ccatcaaaag gttccaatct tttactgatg ggtttgttgg tagtgacaat     240
agccatgttg agtgtgcagt ctgtttatcc aaatttgagg aaggggttga gatcagacag     300
ctgacttgct gccacctttt tcacagacct tgccttgata aatggctgga ccatcagcag     360
atcacctgtc ccttgtgtag atcatgtctg atatccgaag aagcagccaa gaatatcagg     420
ctcagggaac aggagcttac agatgaatcg gtattttggt gttcatcctt ccaagaagct     480
gcttatcatc atacatggat tgaaagtta                                       509

<210> SEQ ID NO 70
<211> LENGTH: 132
<212> TYPE: PRT
<213> ORGANISM: Triphysaria versicolor

<400> SEQUENCE: 70

```
Met Phe Cys Ile Tyr Ala Glu Ser His Leu Gly Thr Leu Thr Phe Ile
1               5                   10                  15

Phe Tyr Thr Cys Ile Trp Ile Pro Phe Gln Thr Thr Leu Thr Ile
            20                  25                  30

Leu Arg His Phe Thr Cys Phe Ile Tyr Gln Thr Lys Asn Ile Asn Leu
        35                  40                  45

Gly Ser Asn Val Arg Glu Val Asp Leu Arg Val Ser His Phe Arg Asp
    50                  55                  60

Leu Glu Ser Lys Ser Lys Asn Lys Gly Glu Gly Ile Ile Asp Asn Glu
65                  70                  75                  80

Glu Asn Glu Glu Leu Cys Ser Ile Cys Leu Met Val Phe Glu Glu Lys
                85                  90                  95

Asp Ser Val Asn Lys Leu Pro Arg Cys Arg His Thr Phe His Thr Glu
            100                 105                 110

Cys Leu Lys Lys Trp Leu Asp Arg Cys Gln Ile Thr Cys Pro Leu Cys
        115                 120                 125

Arg Ser Leu Val
        130
```

<210> SEQ ID NO 71
<211> LENGTH: 45
<212> TYPE: PRT
<213> ORGANISM: Triphysaria versicolor

<400> SEQUENCE: 71

```
Cys Ser Ile Cys Leu Met Val Phe Glu Glu Lys Asp Ser Val Asn Lys
1               5                   10                  15

Leu Pro Arg Cys Arg His Thr Phe His Thr Glu Cys Leu Lys Lys Trp
            20                  25                  30

Leu Asp Arg Cys Gln Ile Thr Cys Pro Leu Cys Arg Ser
        35                  40                  45
```

<210> SEQ ID NO 72
<211> LENGTH: 398
<212> TYPE: DNA
<213> ORGANISM: Triphysaria versicolor

<400> SEQUENCE: 72

```
tgttttgcat atatgcagaa tcccatttag gcacattaac cttcatcttc tacacatgca    60
tatggatccc atttttccaa caactctaa caattctcag acacttcacc tgttttattt    120
atcaaaccaa aaacatcaac ttaggatcta atgttcgcga ggtggatctt cgggtctcac    180
attttcgtga tttggaaagc aaaagcaaaa acaaaggaga gggcattata gataatgaag    240
aaaacgaaga actctgctcg atttgcttga tggtattcga ggaaaaagat tcagtgaaca    300
aactgccaag atgcaggcac acatttcaca ccgagtgcct gaaaaaatgg cttgatagat    360
gccaaattac ctgcccattg tgtcggtctt tggtgtag                            398
```

<210> SEQ ID NO 73
<211> LENGTH: 47
<212> TYPE: PRT

<210> SEQ ID NO 73
<211> LENGTH: 48
<212> TYPE: PRT
<213> ORGANISM: Lotus japonicus

<400> SEQUENCE: 73

```
Glu Cys Ser Val Cys Leu Thr Lys Phe Glu Pro Glu Ser Glu Ile Asn
1               5                  10                  15
Cys Leu Pro Cys Gly His Leu Phe His Lys Ala Cys Leu Glu Lys Trp
            20                  25                  30
Leu Asp Tyr Trp Asn Ile Thr Cys Pro Leu Cys Arg Thr Pro Leu
        35                  40                  45
```

<210> SEQ ID NO 74
<211> LENGTH: 73
<212> TYPE: PRT
<213> ORGANISM: Lotus japonicus

<400> SEQUENCE: 74

```
Leu Arg Phe Glu Ser Val Cys Ser Cys Lys Gln Gln Pro Glu His
1               5                  10                  15
Glu Cys Ser Val Cys Leu Thr Lys Phe Glu Pro Glu Ser Glu Ile Asn
            20                  25                  30
Cys Leu Pro Cys Gly His Leu Phe His Lys Ala Cys Leu Glu Lys Trp
        35                  40                  45
Leu Asp Tyr Trp Asn Ile Thr Cys Pro Leu Cys Arg Thr Pro Leu Met
    50                  55                  60
Pro Glu Asp Asp Ala Ser Cys Phe Trp
65                  70
```

<210> SEQ ID NO 75
<211> LENGTH: 141
<212> TYPE: DNA
<213> ORGANISM: Lotus japonicus

<400> SEQUENCE: 75

```
gagtgttcag tgtgtctcac taaatttgaa ccagaatcag agataaactg tttaccttgt      60
ggccatctct tccataaagc atgcttggag aaatggttgg actattggaa cattacgtgc     120
ccactttgca ggactcccct a                                               141
```

<210> SEQ ID NO 76
<211> LENGTH: 219
<212> TYPE: DNA
<213> ORGANISM: Lotus japonicus

<400> SEQUENCE: 76

```
cttaggtttg agagtgtgtg tagcagttgc aaacaacaac ctgaacatga gtgttcagtg      60
tgtctcacta aatttgaacc agaatcagag ataaactgtt taccttgtgg ccatctcttc     120
cataaagcat gcttggagaa atggttggac tattggaaca ttacgtgccc actttgcagg     180
actcccttaa tgcctgaaga tgatgcatct tgcttttgg                            219
```

<210> SEQ ID NO 77
<211> LENGTH: 488
<212> TYPE: DNA
<213> ORGANISM: Lotus japonicus

<400> SEQUENCE: 77

```
aacatgaaat cctctcactt gaatcccacg tgtatgctac aatgtctact taccagaatc      60
aaacacaact aaccaaccag aaattatatc caccaggtac agagaaacta agaacaaaac     120
cctctacaag ctctacatca taaagagcaa aaggttaaat tgactctata agtcagctcc     180
```

```
atgagaacat caaaattgtc acaaatatgt acaccctaca ctgtacatta aactctctta      240
ttctatttag catgatcact cattgcttac caaaagcaag atgcatcatc ttcaggcatt      300
aagggagtcc tgcaaagtgg gcacgtaatg ttccaatagt ccaaccattt ctccaagcat      360
gctttatgga agagatggcc acaaggtaaa cagtttatct ctgattctgg ttcaaattta      420
gtgagacaca ctgaacactc atgttcaggt tgttgtttgc aactgctaca cacactctca      480
aacctaag                                                              488
```

<210> SEQ ID NO 78
<211> LENGTH: 40
<212> TYPE: PRT
<213> ORGANISM: Helianthus annuus

<400> SEQUENCE: 78

```
Lys Ile Cys Leu Val Glu Phe Lys Pro Asp Ala Glu Ile Asn His Leu
1               5                   10                  15
Ser Cys Gly His Val Phe His Thr Cys Cys Leu Glu Lys Trp Leu Lys
            20                  25                  30
Tyr Trp Asn Ile Thr Cys Pro Leu
        35                  40
```

<210> SEQ ID NO 79
<211> LENGTH: 58
<212> TYPE: PRT
<213> ORGANISM: Helianthus annuus

<400> SEQUENCE: 79

```
Lys Ile Cys Leu Val Glu Phe Lys Pro Asp Ala Glu Ile Asn His Leu
1               5                   10                  15
Ser Cys Gly His Val Phe His Thr Cys Cys Leu Glu Lys Trp Leu Lys
            20                  25                  30
Tyr Trp Asn Ile Thr Cys Pro Leu Cys Arg Asn His Met Met Gly Gly
        35                  40                  45
Asn Gln Val Glu Glu Asn Met Cys Pro Met
    50                  55
```

<210> SEQ ID NO 80
<211> LENGTH: 152
<212> TYPE: DNA
<213> ORGANISM: Helianthus annuus

<400> SEQUENCE: 80

```
ttcgagcggc cgcccgggca ggtcaagaat aaaaaatttg tttggttgag tttaaaccgg       60
agcggagatt aatcaccttt cttgtggaca tgtgttccat acatgttgcc ttgagaaatg      120
gttgaagtat tggaacatta cttgtcctct tt                                    152
```

<210> SEQ ID NO 81
<211> LENGTH: 344
<212> TYPE: DNA
<213> ORGANISM: Helianthus annuus

<400> SEQUENCE: 81

```
actcagctat gctccagcgt tgggcatcaa agagggtcg acctgcaggc gttccaaaat        60
actagtgatt agcgtggtcg cggccgaggt acactaacac attatctcac ccttaacaca     120
tgatgagcta accactcaca ttgggcacat gttttcttcc acttgattac cacccatcat     180
atggttccta caaagaggac aagtaatgtt ccaatacttc aaccatttct caaggcaaca     240
```

```
tgtatggaac acatgtccac aagaaaggtg attaatctcc gcatccggtt taaactcaac    300
caaacaaatt ttttattctt gacctgcccg ggcggccgct cgaa                     344
```

<210> SEQ ID NO 82
<211> LENGTH: 164
<212> TYPE: PRT
<213> ORGANISM: Triticum aestivum
<220> FEATURE:
<221> NAME/KEY: misc_feature
<222> LOCATION: (144)..(145)
<223> OTHER INFORMATION: Xaa can be any naturally occurring amino acid

<400> SEQUENCE: 82

```
Met Gly Ile Ser Ser Met Pro Ala Pro Lys Glu Ser Leu Leu Ile Tyr
 1               5                  10                  15

Leu Leu Tyr His Ala Val Val Ser Ile Ala Ala Leu Ala Gly Leu Leu
                20                  25                  30

Arg Ala Ala Leu Val Phe Leu Gly Leu Pro Ala Pro Ser Leu Leu
        35                  40                  45

Ala Gly Glu Asp Ala Asp Gly Ala Asp Gln Leu Thr Ala Ala Thr Pro
    50                  55                  60

Ala Gly Pro Ser Leu Ala Glu Arg Phe Arg Ser Arg Phe Arg Pro Ala
65                  70                  75                  80

Arg Phe Gly Arg Arg Gly Ala Ala Ala Ser Ala Thr Pro Asp Cys
                85                  90                  95

Arg Val Cys Leu Val Arg Phe Glu Ala Asp Ala Val Val Asn Arg Leu
               100                 105                 110

Pro Cys Gly His Leu Phe His Arg Ala Cys Leu Glu Thr Trp Leu Asp
           115                 120                 125

Tyr Asp His Ala Thr Cys Pro Leu Cys Arg Ser Arg Leu Leu Pro Xaa
       130                 135                 140

Xaa Gly Phe Gly Gly Asp Glu Ser Trp Ser Cys Ala Gly Pro Thr Leu
145                 150                 155                 160

Thr Gly Trp Ile
```

<210> SEQ ID NO 83
<211> LENGTH: 47
<212> TYPE: PRT
<213> ORGANISM: Triticum aestivum

<400> SEQUENCE: 83

```
Asp Cys Arg Val Cys Leu Val Arg Phe Glu Ala Asp Ala Val Val Asn
 1               5                  10                  15

Arg Leu Pro Cys Gly His Leu Phe His Arg Ala Cys Leu Glu Thr Trp
                20                  25                  30

Leu Asp Tyr Asp His Ala Thr Cys Pro Leu Cys Arg Ser Arg Leu
        35                  40                  45
```

<210> SEQ ID NO 84
<211> LENGTH: 141
<212> TYPE: DNA
<213> ORGANISM: Triticum aestivum

<400> SEQUENCE: 84

```
gactgccgcg tctgcctggt gcggttcgag gccgacgccg tggtgaaccg cctcccctgc    60
ggccacctct ccaccgcgc ctgcctcgag acctggctgg actacgacca cgccacctgc   120
ccgctctgcc gctcccgcct t                                             141
```

<210> SEQ ID NO 85
<211> LENGTH: 494
<212> TYPE: DNA
<213> ORGANISM: Triticum aestivum
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t

<400> SEQUENCE: 85

```
atgggcatct ccagcatgcc ggcgcccaag gagagcctcc tgatctacct gctctaccac      60
gccgtcgtct cgatcgccgc cctggcgggc ctcctccgcg ccgcgctcgt cttcctcggc     120
ctccccgcgc cgccctcgct gctggccggc gaggacgccg acggcgccga ccagctcacg     180
gcggccaccc cggcgggccc cagcctggcg gagcggttca ggagcaggtt ccgccccgcg     240
cggttcggcc ggagaagggg cgcggcggcg tcggcgacac ccgactgccg cgtctgcctg     300
gtgcggttcg aggccgacgc cgtggtgaac cgcctcccct gcggccacct cttccaccgc     360
gcctgcctcg agacctggct ggactacgac cacgccacct gcccgctctg ccgctcccgc     420
cttcttccgg ncgncggctt cggcggcgac gagtcgtggt cgtgcgccgg gcccaccctg     480
acgggctgga ttta                                                       494
```

<210> SEQ ID NO 86
<211> LENGTH: 184
<212> TYPE: PRT
<213> ORGANISM: Solanum tuberosum

<400> SEQUENCE: 86

```
Met Gly Leu Ser Gln Tyr Pro Thr Pro Ala Asp Ala Gly Val Leu Gly
1               5                   10                  15

Val Ile Leu Val Asn Thr Ala Ile Ser Ile Ser Ile Lys Glu Ile
            20                  25                  30

Leu Arg Ser Ile Leu Arg Val Ile Gly Ile Arg Ile Ala Ser Trp Glu
        35                  40                  45

Asp Tyr Ser Val Glu Gly Pro Leu Asp Ser Leu Glu Cys Arg Gly Ser
    50                  55                  60

Pro Pro Glu Ser Tyr Met Glu Glu Phe Arg Asn Arg Thr Pro Ala Phe
65                  70                  75                  80

Cys Tyr Asp Ser Leu Cys Ile Ser Asn His Pro Glu Gln Glu Cys Ser
                85                  90                  95

Val Cys Leu Thr Lys Phe Glu Pro Asp Ala Gly Val Asn Ser Leu Ser
            100                 105                 110

Cys Gly His Val Phe His Lys Leu Cys Leu Glu Lys Trp Leu Arg Tyr
        115                 120                 125

Trp His Val Thr Cys Pro Leu Cys Arg Asn Tyr Leu Met Ser Gln Gln
    130                 135                 140

Glu Arg Met Ile Arg Val Arg Cys Glu Ile Lys Arg Phe Thr Val Pro
145                 150                 155                 160

Leu His Pro Phe Asp Asp Val Ile Ile Tyr Ser Leu Val Val Tyr Arg
                165                 170                 175

Pro Ser Met Trp Met Leu Asp Leu
            180
```

<210> SEQ ID NO 87
<211> LENGTH: 47
<212> TYPE: PRT
<213> ORGANISM: Solanum tuberosum

<400> SEQUENCE: 87

Glu Cys Ser Val Cys Leu Thr Lys Phe Glu Pro Asp Ala Gly Val Asn
1               5                   10                  15

Ser Leu Ser Cys Gly His Val Phe His Lys Leu Cys Leu Glu Lys Trp
            20                  25                  30

Leu Arg Tyr Trp His Val Thr Cys Pro Leu Cys Arg Asn Tyr Leu
        35                  40                  45

<210> SEQ ID NO 88
<211> LENGTH: 141
<212> TYPE: DNA
<213> ORGANISM: Solanum tuberosum

<400> SEQUENCE: 88
gaatgctctg tgtgcctgac aaaattcgag cctgatgcag gggtaaacag tctctcatgc      60
ggtcacgttt tccataagct gtgtctagag aagtggctca ggtattggca tgtaacttgt     120
cctctttgca gaaattactt g                                                141

<210> SEQ ID NO 89
<211> LENGTH: 554
<212> TYPE: DNA
<213> ORGANISM: Solanum tuberosum

<400> SEQUENCE: 89
atgggcctct cacaatatcc aactccagca gatgcaggag tacttggtgt gattctagta      60
aacacagcca tatccatctc cattatcaag gagatactcc gatcgatcct tcgtgtgatt     120
ggcatccgta tcgcatcatg gaagactat tctgttgaag gacccttgga ctcacttgaa     180
tgccgtggaa gcccaccaga gtcatacatg gaggagttca gaaaccgaac acctgcattt    240
tgttatgact cgctatgtat ctctaaccac cctgaacaag aatgctctgt gtgcctgaca    300
aaattcgagc ctgatgcagg ggtaaacagt ctctcatgcg gtcacgtttt ccataagctg    360
tgtctagaga gtggctcag gtattggcat gtaacttgtc ctctttgcag aaattacttg    420
atgtctcaac aagagaggat gatacgtgtc cgatgtgaga ttaaacgttt tacggtgcca    480
cttcatccat ttgatgatgt tatcatttac agcttagtag tgtacaggcc gagtatgtgg    540
atgcttgatc tttg                                                      554

<210> SEQ ID NO 90
<211> LENGTH: 47
<212> TYPE: PRT
<213> ORGANISM: Capsicum annuum

<400> SEQUENCE: 90

Glu Cys Ser Val Cys Leu Thr Lys Phe Glu Pro Asp Ala Gly Val Asn
1               5                   10                  15

Ser Leu Ser Cys Gly His Val Phe His Lys Leu Cys Leu Glu Lys Trp
            20                  25                  30

Leu Thr Tyr Trp His Val Thr Cys Pro Leu Cys Arg Asn His Leu
        35                  40                  45

<210> SEQ ID NO 91
<211> LENGTH: 183

```
<212> TYPE: DNA
<213> ORGANISM: Capsicum annuum

<400> SEQUENCE: 91
gaatgccgtg gaagcccacc agagtcatac atggaggagt tcagaagccg aacacctgca      60
tttcgttatg actcgctatg catctctaac caccctcat gtggtcatgt tttccataag     120
ctgtgtctag agaagtggct cacgtattgg catgtaactt gtcctctttg cagaaatcac     180
ttg                                                                    183

<210> SEQ ID NO 92
<211> LENGTH: 149
<212> TYPE: PRT
<213> ORGANISM: Capsicum annuum

<400> SEQUENCE: 92

Met Gly Leu Ser Gln Tyr Pro Thr Pro Ala Asp Ala Gly Val Leu Gly
1               5                   10                  15

Val Ile Leu Val Asn Thr Ala Ile Ser Ile Ser Ile Val Lys Glu Ile
            20                  25                  30

Leu Arg Ser Ile Leu Arg Leu Ile Gly Ile Arg Ile Ala Ser Trp Glu
        35                  40                  45

Asp Tyr Ser Ile Glu Gly Ser Ser Asp Ser Leu Glu Cys Arg Gly Ser
    50                  55                  60

Pro Pro Glu Ser Tyr Met Glu Glu Phe Arg Ser Arg Thr Pro Ala Phe
65                  70                  75                  80

Arg Tyr Asp Ser Leu Cys Ile Ser Asn His Pro Glu Gln Glu Cys Ser
                85                  90                  95

Val Cys Leu Thr Lys Phe Glu Pro Asp Ala Gly Val Asn Ser Leu Ser
            100                 105                 110

Cys Gly His Val Phe His Lys Leu Cys Leu Glu Lys Trp Leu Thr Tyr
        115                 120                 125

Trp His Val Thr Cys Pro Leu Cys Arg Asn His Leu Met Pro Gln Gln
    130                 135                 140

Glu Gln Asp Asp Thr
145

<210> SEQ ID NO 93
<211> LENGTH: 509
<212> TYPE: DNA
<213> ORGANISM: Capsicum annuum

<400> SEQUENCE: 93
atgggcctct cacaatatcc aactccagca gatgcaggag tactaggtgt gattctagta      60
aacacagcca tatccatatc cattgtcaag gagatactac gatcgattct tcgcctgata     120
ggcatccgta tcgcatcatg ggaagactat tctattgaag ctcctcaga ctcacttgaa      180
tgccgtggaa gccccaccaga gtcatacatg gaggagttca gaagccgaac acctgcattt    240
cgttatgact cgctatgcat ctctaaccac cctgaacaag aatgttctgt gtgcctaaca     300
aaatttgagc ctgatgcagg ggtaaacagt ctcgaacaag aatgttctgt gtgcctaaca     360
aaatttgagc ctgatgcagg ggtaaacagt ctctcatgtg gtcatgtttt ccataagctg     420
tgtctagaga agtggctcac gtattggcat gtaacttgtc ctctttgcag aaatcacttg     480
atgcctcaac aagaacagga cgatacgtg                                        509

<210> SEQ ID NO 94
```

```
<211> LENGTH: 598
<212> TYPE: DNA
<213> ORGANISM: Capsicum annuum

<400> SEQUENCE: 94 gtccctctt acaaaaataa aaataaagta ctacagaaaa ttgctacaaa aaagtctcaa      60
gttttcatat tattagatcc ggtatattga gctcttccag aaggttttga agaaagaatc     120
atcatttcaa cactaggttc cgatccgtta tgggcctctc acaatatcca actccagcag     180
atgcaggagt actaggtgtg attctagtaa acacagccat atccatatcc attgtcaagg     240
agatactacg atcgattctt cgcctgatag gcatccgtat cgcatcatgg gaagactatt     300
ctattgaagg ctcctcagac tcacttgaat gccgtggaag cccaccagag tcatacatgg     360
aggagttcag aagccgaaca cctgcatttc gttatgactc gctatgcatc tctaaccacc     420
ctgaacaaga atgttctgtg tgcctaacaa aatttgagcc tgatgcaggg gtaaacagtc     480
tctcatgtgg tcatgttttc cataagctgt gtctagagaa gtggctcacg tattggcatg     540
taacttgtcc tctttgcaga aatcacttga tgcctcaaca agaacaggac gatacgtg       598

<210> SEQ ID NO 95
<211> LENGTH: 152
<212> TYPE: PRT
<213> ORGANISM: Glycine max

<400> SEQUENCE: 95

Met Gly Leu Ser Ser Leu Pro Ala Pro Ser Glu Gly Val Leu Cys Val
1               5                   10                  15

Leu Leu Val Asn Thr Ala Leu Ser Ile Ser Ile Phe Lys Gly Ile Val
            20                  25                  30

Arg Thr Ile Leu Gln Ile Val Gly Ile Arg Val Ser Ser Leu Ser Pro
        35                  40                  45

Ser Pro Asp Ile Ser Arg Asn Pro Pro Glu Pro Leu Glu Phe Asn Leu
    50                  55                  60

Ser Pro Ser Glu Gly Phe Ile Glu Glu Phe Arg Ser Arg Thr Pro Thr
65                  70                  75                  80

Leu Arg Phe Gly Ser Met Cys Gly Ser Lys Gln Pro Gln His Glu Cys
                85                  90                  95

Cys Cys Val Cys Leu Thr Lys Phe Glu Pro Glu Ser Glu Ile Asn Cys
            100                 105                 110

Leu Ser Cys Gly His Ile Phe His Lys Val Cys Met Glu Lys Trp Leu
        115                 120                 125

Asp Tyr Trp Asn Ile Thr Cys Pro Leu Cys Arg Thr Ser Leu Met Pro
    130                 135                 140

Glu Asp Asp Ala Ser Cys Phe Trp
145                 150

<210> SEQ ID NO 96
<211> LENGTH: 48
<212> TYPE: PRT
<213> ORGANISM: Glycine max

<400> SEQUENCE: 96

Glu Cys Cys Cys Val Cys Leu Thr Lys Phe Glu Pro Glu Ser Glu Ile
1               5                   10                  15

Asn Cys Leu Ser Cys Gly His Ile Phe His Lys Val Cys Met Glu Lys
            20                  25                  30

Trp Leu Asp Tyr Trp Asn Ile Thr Cys Pro Leu Cys Arg Thr Ser Leu
```

```
              35                  40                  45
```

<210> SEQ ID NO 97
<211> LENGTH: 144
<212> TYPE: DNA
<213> ORGANISM: Glycine max

<400> SEQUENCE: 97

```
gaatgttgtt gtgtgtgtct cacaaagttt gaaccagaat ctgagataaa ctgtttatca      60
tgtggccata ttttcacaa agtgtgcatg gagaagtggt tggactattg aacattaca      120 tgcccacttt gcaggacttc cttg                                              144
```

<210> SEQ ID NO 98
<211> LENGTH: 458
<212> TYPE: DNA
<213> ORGANISM: Glycine max

<400> SEQUENCE: 98

```
atgggcctgt caagtctccc agcaccatct gaaggagtgt tatgtgtgct tcttgtaaac      60
actgccttgt ctatatccat attcaaaggc attgttagga caattctaca aattgtcggt     120
atccgcgttt cgtcgttgtc tccttcacca gacatctccc gaaacccacc tgagccatta     180
gaattcaacc tcagcccctc ggagggtttc attgaagagt tcagaagcag acaccaaca     240 cttaggtttg gcagcatgtg tggcagtaaa caacctcaac atgaatgttg ttgtgtgtgt     300
ctcacaaagt ttgaaccaga atctgagata aactgtttat catgtggcca tatttttcac     360
aaagtgtgca tggagaagtg gttggactat tggaacatta catgcccact ttgcaggact     420
tccttgatgc ctgaagatga tgcatcttgc ttttggta                              458
```

<210> SEQ ID NO 99
<211> LENGTH: 155
<212> TYPE: PRT
<213> ORGANISM: Glycine max

<400> SEQUENCE: 99

```
Met Gly Leu Ser Ser Leu Pro Ala Pro Ser Glu Gly Val Leu Cys Val
1               5                   10                  15

Leu Leu Val Asn Thr Val Leu Ser Ile Ser Ile Phe Lys Gly Ile Val
            20                  25                  30

Arg Thr Ile Leu His Ile Val Gly Ile His Leu Ser Ser Ser Ser Ser
        35                  40                  45

Thr Ser Pro Ser Pro Asp Pro Ser Leu Thr Ala Pro Glu Ser Phe
    50                  55                  60

Glu Phe His Leu Ser Pro Ser Glu Ser Tyr Ile Glu Glu Phe Arg Ser
65                  70                  75                  80

Arg Thr Pro Thr Leu Arg Phe Asp Ser Val Cys Cys Lys Gln Pro
                85                  90                  95

Glu His Asp Cys Ser Val Cys Leu Thr Gln Phe Glu Pro Glu Ser Glu
            100                 105                 110

Ile Asn Arg Leu Ser Cys Gly His Leu Phe His Lys Val Cys Leu Glu
        115                 120                 125

Lys Trp Leu Asp Tyr Trp Asn Ile Thr Cys Pro Leu Cys Arg Thr Pro
    130                 135                 140

Leu Met Pro Glu Asp Asp Thr Pro Cys Phe Gln
145                 150                 155
```

-continued

<210> SEQ ID NO 100
<211> LENGTH: 47
<212> TYPE: PRT
<213> ORGANISM: Glycine max

<400> SEQUENCE: 100

Asp Cys Ser Val Cys Leu Thr Gln Phe Glu Pro Glu Ser Glu Ile Asn
1               5                   10                  15

Arg Leu Ser Cys Gly His Leu Phe His Lys Val Cys Leu Glu Lys Trp
            20                  25                  30

Leu Asp Tyr Trp Asn Ile Thr Cys Pro Leu Cys Arg Thr Pro Leu
        35                  40                  45

<210> SEQ ID NO 101
<211> LENGTH: 143
<212> TYPE: DNA
<213> ORGANISM: Glycine max

<400> SEQUENCE: 101
gactgctctg tatgcctcac tcagtttgaa ccggaatcgg agataaaccg cttatcgtgc      60
ggccatctct tccacaaagt gtgcttagag aagtggctgg actactggaa cattacatgc     120
cctctttgca ggactccctt gat                                             143

<210> SEQ ID NO 102
<211> LENGTH: 467
<212> TYPE: DNA
<213> ORGANISM: Glycine max

<400> SEQUENCE: 102
atgggccttt caagtctccc agcaccatct gaaggagtat tatgtgtcct tctggtgaac      60
actgtattgt caatttcaat attcaaaggc attgttagga caatcctaca cattgttggc     120
atccatcttt catcatcatc ctccacttca ccctcttcac cagatccctc gctaaccgca     180
cctgagtcat ttgaattcca tcttagtccc tctgagagtt acattgaaga gttcagaagc     240
cggacgccaa cacttcggtt cgacagtgtg tgctgctgta acaacctgag catgactgc      300 tctgtatgcc tcactcagtt tgaaccggaa tcggagataa accgcttatc gtgcggccat     360
ctcttccaca aagtgtgctt agagaagtgg ctggactact ggaacattac atgccctctt     420
tgcaggactc ccttgatgcc tgaagatgac acccttgct ttcagta                    467

<210> SEQ ID NO 103
<211> LENGTH: 152
<212> TYPE: PRT
<213> ORGANISM: Lactuca sativa

<400> SEQUENCE: 103

Met Gly Leu Ser Pro Tyr Ser Asn Pro Ser Asp Ala Gly Val Leu Cys
1               5                   10                  15

Val Ile Leu Val Asn Thr Ala Met Ser Ile Ser Ile Met Lys Glu Ile
            20                  25                  30

Val Cys Ser Ile Leu His Val Val Gly Leu Arg Val Ala Ser Ser Pro
        35                  40                  45

Ser Ser Ser Asn Gln Gly Ser Pro Glu Ala Ser Glu Arg Arg Gly Ser
    50                  55                  60

Pro Ser Glu Thr Tyr Met Glu Glu Phe Arg Ser Arg Thr Pro Ser Leu
65                  70                  75                  80

Arg Tyr Ile Ser Leu Arg Arg Pro Thr Lys Gln Glu Cys Ser Val Cys
                85                  90                  95

```
Leu Thr Glu Phe Lys Pro Asp Ser Glu Ile Asn Lys Leu Ser Cys Gly
            100                 105                 110

His Val Phe His Lys Ser Cys Leu Glu Lys Trp Leu Lys Cys Trp Asn
        115                 120                 125

Ile Thr Cys Pro Leu Cys Arg Asn His Met Met Ile Ser Lys Glu Met
    130                 135                 140

Glu Glu Asn Asn Thr Cys Pro Met
145                 150

<210> SEQ ID NO 104
<211> LENGTH: 47
<212> TYPE: PRT
<213> ORGANISM: Lactuca sativa

<400> SEQUENCE: 104

Glu Cys Ser Val Cys Leu Thr Glu Phe Lys Pro Asp Ser Glu Ile Asn
1               5                   10                  15

Lys Leu Ser Cys Gly His Val Phe His Lys Ser Cys Leu Glu Lys Trp
            20                  25                  30

Leu Lys Cys Trp Asn Ile Thr Cys Pro Leu Cys Arg Asn His Met
        35                  40                  45

<210> SEQ ID NO 105
<211> LENGTH: 143
<212> TYPE: DNA
<213> ORGANISM: Lactuca sativa

<400> SEQUENCE: 105
gaatgctccg tttgcttaac ggagtttaaa ccagattcag agataaataa gctttcgtgt    60
gggcatgttt ttcataaatc ctgccttgaa aaatggctaa aatgctggaa cattacttgc   120
cctctctgta gaaaccacat gat                                          143

<210> SEQ ID NO 106
<211> LENGTH: 458
<212> TYPE: DNA
<213> ORGANISM: Lactuca sativa

<400> SEQUENCE: 106
atggggctct cgccatactc aaacccatcg gatgcaggag tgttgtgcgt aattctggtt    60
aacacagcta tgtcgatatc aatcatgaag gaaatagttt gttcgattct tcatgtggtg   120
gggttacgtg tagcgtcatc accgtcatca tccaatcaag gctcgccgga agcttctgag   180
cgccggggaa gtccgtcgga cacgtacatg gaggagttca aagccggac gccgtcgctc    240 cgttacatct ccctccgtcg tcccaccaaa caagaatgct ccgtttgctt aacggagttt   300
aaaccagatt cagagataaa taagctttcg tgtgggcatg ttttcataa atcctgcctt   360 gaaaaatggc taaaatgctg gaacattact tgccctctct gtagaaacca catgatgatt   420
tctaaagaaa tggaagaaaa caacacttgc ccgatgtg                          458

<210> SEQ ID NO 107
<211> LENGTH: 152
<212> TYPE: PRT
<213> ORGANISM: Lycopersicon esculentum

<400> SEQUENCE: 107

Met Gly Leu Ser Gln Tyr Pro Thr Pro Ala Asp Ala Gly Val Leu Gly
1               5                   10                  15
```

Val Ile Leu Val Asn Thr Ala Ile Ser Ile Ile Lys Glu Ile
              20                  25                  30

Leu Arg Ser Ile Leu Arg Val Ile Gly Ile Arg Ile Ala Ser Trp Glu
            35                  40                  45

Asp Tyr Ser Ile Glu Gly Pro Leu Asp Ser Leu Glu Cys Arg Gly Ser
        50                  55                  60

Pro Pro Glu Ser Tyr Met Glu Glu Phe Arg Ser Arg Thr Pro Ala Phe
65                  70                  75                  80

Arg Tyr Asp Ser Leu Arg Ile Ser Asn His Pro Glu Gln Glu Cys Ser
                85                  90                  95

Val Cys Leu Thr Lys Phe Glu Pro Asp Ala Gly Val Asn Ser Leu Ser
            100                 105                 110

Cys Gly His Val Phe His Lys Leu Cys Leu Glu Lys Trp Leu Arg Tyr
        115                 120                 125

Trp His Val Thr Cys Pro Leu Cys Arg Asn Tyr Leu Met Pro Gln Gln
    130                 135                 140

Glu Glu Asp Asp Thr Cys Pro Met
145                 150

<210> SEQ ID NO 108
<211> LENGTH: 47
<212> TYPE: PRT
<213> ORGANISM: Lycopersicon esculentum

<400> SEQUENCE: 108

Glu Cys Ser Val Cys Leu Thr Lys Phe Glu Pro Asp Ala Gly Val Asn
1               5                   10                  15

Ser Leu Ser Cys Gly His Val Phe His Lys Leu Cys Leu Glu Lys Trp
            20                  25                  30

Leu Arg Tyr Trp His Val Thr Cys Pro Leu Cys Arg Asn Tyr Leu
        35                  40                  45

<210> SEQ ID NO 109
<211> LENGTH: 141
<212> TYPE: DNA
<213> ORGANISM: Lycopersicon esculentum

<400> SEQUENCE: 109
gaatgctctg tgtgcctgac aaaatttgag cctgatgcag gggtaaacag cctctcatgt       60
ggtcatgttt tccataagct gtgtctagag aagtggctca ggtattggca tgtaacttgt      120
cctctttgta gaaattactt g                                                141

<210> SEQ ID NO 110
<211> LENGTH: 458
<212> TYPE: DNA
<213> ORGANISM: Lycopersicon esculentum

<400> SEQUENCE: 110
atgggcctct cacaatatcc aactccagca gatgcaggag tactcggtgt aattctagta       60
aacacagcca tatccatctc cattatcaag gagatactcc gttcgatcct tcgtgtgatt      120
ggcatccgta tcgcatcatg gaagactat tctattgaag gacccttgga ctcacttgaa       180
tgccgtggaa gcccaccaga atcatacatg gaggagttca agccgaac gcctgcattt        240 cgttatgact cgctacgtat ctctaaccac cctgaacaag aatgctctgt gtgcctgaca      300
aaatttgagc tgatgcaggg gtaaacagc ctctcatgtg gtcatgtttt ccataagctg       360
tgtctagaga agtggctcag gtattggcat gtaacttgtc ctctttgtag aaattacttg      420

```
atgcctcaac aagaagagga cgatacatgt ccaatgtg                              458
```

<210> SEQ ID NO 111
<211> LENGTH: 44
<212> TYPE: PRT
<213> ORGANISM: Sorghum bicolor

<400> SEQUENCE: 111

```
Asp Cys Arg Val Cys Leu Val Arg Phe Glu Pro Glu Ser Val Val Asn
1               5                   10                  15

Arg Leu Pro Cys Gly His Leu Phe His Arg Ala Cys Leu Glu Thr Trp
            20                  25                  30

Leu Asp Tyr Asp His Ala Thr Cys Pro Leu Cys Arg
        35                  40
```

<210> SEQ ID NO 112
<211> LENGTH: 143
<212> TYPE: DNA
<213> ORGANISM: Sorghum bicolor

<400> SEQUENCE: 112

```
gactgccgcg tgtgcctggt gcggttcgag ccggagtcgg tggtcaaccg gctcccctgc     60
ggccacctct tccaccgcgc atgcctcgag acctggctcg actacgacca cgccacctgc    120
ccgctctgcc gccaccgcct cct                                            143
```

<210> SEQ ID NO 113
<211> LENGTH: 149
<212> TYPE: PRT
<213> ORGANISM: Sorghum bicolor

<400> SEQUENCE: 113

```
Met Gly Ile Ser Ser Met Pro Ala Pro Lys Asp Ser Leu Leu Gly Phe
1               5                   10                  15

Val Leu Tyr Asn Ala Ala Ala Ser Val Ala Ile Leu Ser Gly Leu Val
            20                  25                  30

Arg Ala Ala Leu Leu Phe Leu Gly Val Ala Ala Ala Pro Ser Ser Ser
        35                  40                  45

Pro Trp Glu Ala Pro Glu Glu Glu Arg Arg Gln Gln Gln Gln Gly Ala
    50                  55                  60

Val Arg Val Thr Pro Val Gly Pro Thr Leu Ala Asp Arg Phe Arg Ser
65                  70                  75                  80

Arg Phe Arg Pro Ser Arg Phe Gly Arg Arg Gly Cys Gly Gly Ser
                85                  90                  95

Gly Asp Cys Arg Val Cys Leu Val Arg Phe Glu Pro Glu Ser Val Val
            100                 105                 110

Asn Arg Leu Pro Cys Gly His Leu Phe His Arg Ala Cys Leu Glu Thr
        115                 120                 125

Trp Leu Asp Tyr Asp His Ala Thr Cys Pro Leu Cys Arg His Arg Leu
    130                 135                 140

Leu Pro Pro Ala Ala
145
```

<210> SEQ ID NO 114
<211> LENGTH: 447
<212> TYPE: DNA
<213> ORGANISM: Sorghum bicolor

<400> SEQUENCE: 114

```
atgggcatct cgagcatgcc ggcgcccaag gacagcctgc tggggttcgt gctgtacaac      60
gcggcggcgt ccgtcgcgat cctgtcgggt ctggtgcgcg ccgcgctgct cttcctgggc     120
gtggcggcgg cgccgtcgtc gtccccgtgg gaagcgccgg aggaggagcg gcggcagcag     180 cagcagggggg cggtgagggt cacgcccgtg gggcccaccc tcgcggaccg gttccggagc    240
aggttccgtc cgtcgcgctt cgggcggcgc cgcggctgcg gcggttcggg ggactgccgc     300
gtgtgcctgg tgcggttcga gcggagtcg gtggtcaacc ggctcccctg cggccacctc      360
ttccaccgcg catgcctcga gacctggctc gactacgacc acgccacctg cccgctctgc     420
cgccaccgcc tcctgccccc cgccgca                                        447
```

<210> SEQ ID NO 115  
<211> LENGTH: 44  
<212> TYPE: PRT  
<213> ORGANISM: Zea mays

<400> SEQUENCE: 115

```
Asp Cys Arg Val Cys Leu Val Arg Phe Glu Thr Glu Ser Val Val Gln
  1               5                  10                  15

Arg Leu Pro Cys Gly His Leu Phe His Arg Ala Cys Leu Glu Thr Trp
             20                  25                  30

Ile Asp Tyr Asp His Ala Thr Cys Pro Leu Cys Arg
         35                  40
```

<210> SEQ ID NO 116  
<211> LENGTH: 148  
<212> TYPE: DNA  
<213> ORGANISM: Zea mays

<400> SEQUENCE: 116

```
gcggggactg ccgcgtgtgc ctggtgcggt tcgagacgga gtcggtggtg cagcggctcc      60
cctgcggcca cctcttccac cgcgcatgcc tcgagacctg gatcgactac gaccacgcca    120
cctgcccgct gtgccgccac cgcctcct                                       148
```

<210> SEQ ID NO 117  
<211> LENGTH: 235  
<212> TYPE: PRT  
<213> ORGANISM: Zea mays

<400> SEQUENCE: 117

```
Met Gly Ile Ser Ser Met Pro Ala Pro Glu Asp Ser Leu Gly Phe
  1               5                  10                  15

Val Leu Tyr Asn Thr Ala Ala Ser Val Ala Ile Leu Ala Gly Leu Val
             20                  25                  30

Arg Ala Ala Leu Leu Phe Leu Gly Leu Ala Ala Ala Ala Glu Asp Glu
         35                  40                  45

Glu Pro Arg Gln Gln Ala Glu Ala Val Thr Val Thr Ala Val Gly Pro
     50                  55                  60

Ser Leu Ala Asp Arg Phe Arg Ser Arg Phe Arg Pro Ser Arg Tyr Gly
 65                  70                  75                  80

Arg Arg Arg Gly Gly Asp Cys Arg Val Cys Leu Val Arg Phe Glu Thr
                 85                  90                  95

Glu Ser Val Val Gln Arg Leu Pro Cys Gly His Leu Phe His Arg Ala
            100                 105                 110

Cys Leu Glu Thr Trp Ile Asp Tyr Asp His Ala Thr Cys Pro Leu Cys
        115                 120                 125
```

Arg His Arg Leu Leu Pro Pro Ala Ala Ala Asp Glu Val Ala Pro
130                 135                 140

Asp Cys Leu Ile Ser Ala Leu Gly Ile Glu Ser Arg Arg Ser Thr Leu
145                 150                 155                 160

His Leu Ala Ala Ala Val Ser Leu Tyr Arg Phe Phe Ser Phe Pro
                165                 170                 175

Phe Cys Ser Gly Glu Arg Glu Asp Arg Thr Glu Ile Glu Gly Arg Lys
                180                 185                 190

Trp Trp Gln Gln Ser Cys Ser Pro Phe Val Ser Lys Lys Lys Asn Tyr
                195                 200                 205

Ile Leu Tyr Thr Asp Leu Ser Lys Thr Gln Asn Cys Leu Trp Ala Cys
210                 215                 220

Ala Gly Val Asp Ala Lys Thr Thr Ile Leu Leu
225                 230                 235

<210> SEQ ID NO 118
<211> LENGTH: 534
<212> TYPE: DNA
<213> ORGANISM: Zea mays

<400> SEQUENCE: 118
gggcatctcg agcatgccgg cgcccgagga cagcctgctg ggttcgtgc tgtacaacac    60
ggcggcgtcg gtggcgatcc tggcggggct ggtgcgcgcc gcgctgctgt tcctgggcct   120
ggcggcggcg gcggaggacg aggagccgcg gcagcaggcg gaggccgtga cggtcacggc   180
cgtggggccc agcctcgcgg accggttccg gagcaggttc cggccgtcgc gctacgggcg   240
gcgccggggc ggggactgcc gcgtgtgcct ggtgcggttc gagacggagt cggtggtgca   300
gcggctcccc tgcggccacc tcttccaccg cgcatgcctc gagacctgga tcgactacga   360
ccacgccacc tgcccgctgt gccgccaccg cctcctgccc ccgccgctg ccgccgacga   420
ggtgccccgg attgcctgat tagcgcccta ggaattgaga gtaggcgtag cactctgcac   480
ctcgcagcag cagtgtctct gtacaggttt ttttttttctt ttccttttg ttcg         534

<210> SEQ ID NO 119
<211> LENGTH: 167
<212> TYPE: PRT
<213> ORGANISM: Oryza sativa

<400> SEQUENCE: 119

Met Gly Ile Ser Ser Met Pro Ala Pro Lys Asp Ser Val Val Ala Tyr
1               5                   10                  15

Leu Leu Tyr Asn Thr Ala Val Ser Ile Ala Ile Leu Ala Asp Met Val
                20                  25                  30

Arg Ala Ala Leu Val Phe Leu Gly Leu Pro Val Pro Pro Ser Ala Trp
            35                  40                  45

Glu Asp Gly Asp Asp Gln Leu Ala Ala Ile Ala Ala Ala Ala Ala
        50                  55                  60

Ala Ala Ala Ala Gly Gly Pro Ser Leu Ala Asp Arg Phe Arg Ser
65                  70                  75                  80

Arg Phe Arg Pro Ala Arg Phe Gly Arg Arg Gly Gly Gly Ala Gly
                85                  90                  95

Ala Ala Asp Cys Arg Val Cys Leu Ala Arg Phe Glu Pro Glu Ser Val
                100                 105                 110

Val Asn Arg Leu Pro Cys Gly His Leu Phe His Arg Ala Cys Leu Glu
            115                 120                 125

```
Lys Trp Leu Asp Tyr Asp His Ala Thr Cys Pro Leu Cys Arg His Arg
    130                 135                 140
Leu Leu Pro Ala Thr Thr Glu Ser Pro Ser Pro Ala Thr Ala
145                 150                 155                 160
Thr Pro His Phe Ala Arg Ile
            165

<210> SEQ ID NO 120
<211> LENGTH: 47
<212> TYPE: PRT
<213> ORGANISM: Oryza sativa

<400> SEQUENCE: 120

Asp Cys Arg Val Cys Leu Ala Arg Phe Glu Pro Glu Ser Val Val Asn
1               5                   10                  15
Arg Leu Pro Cys Gly His Leu Phe His Arg Ala Cys Leu Glu Lys Trp
            20                  25                  30
Leu Asp Tyr Asp His Ala Thr Cys Pro Leu Cys Arg His Arg Leu
        35                  40                  45

<210> SEQ ID NO 121
<211> LENGTH: 142
<212> TYPE: DNA
<213> ORGANISM: Oryza sativa

<400> SEQUENCE: 121
gactgccgcg tctgcctcgc gcggttcgag ccggagtcgg tggtgaaccg cctcccctgc      60
ggccacctct tccaccgcgc ctgcctcgag aagtggctcg actacgacca cgccacctgc     120
ccgctctgcc gccaccgcct cc                                              142

<210> SEQ ID NO 122
<211> LENGTH: 699
<212> TYPE: DNA
<213> ORGANISM: Oryza sativa

<400> SEQUENCE: 122
gtaccatctc ccgtgtcctc ctcccacctc gctccccgt aaaacccgaa attacaatca       60
ggtcctcggc ggacgccacc cccaaatctg aaaccctcgc cgccgccgcc gccgcgcgat     120
cccccccgga attccatcgg atcggccccc gcctctccgg cgagatgggc atctcgagca     180
tgccggcgcc caaggacagc gtggtggcgt acctgctgta caacacggcg gtgtcgatcg     240
ccatcctggc ggacatggtg cgggcggcgc tggtgttcct cggcctcccc gtgccgccct     300
cggcgtggga ggacggcgac gaccagctgg cggcgatcgc ggcggccgcc gcggccgcgg     360
ccgcggcggc gggggccccg agcctggcgg acaggttccg gagcaggttc aggcggcga     420 ggttcgggcg gcggcgaggc gggggcgcgg gcgcggccga ctgccgcgtc tgcctcgcgc     480
ggttcgagcc ggagtcggtg gtgaaccgcc tccctgcgg ccacctcttc accgcgcct     540 gcctcgagaa gtggctcgac tacgaccacg ccacctgccc gctctgccgc caccgcctcc     600
tccccgccac caccgagtcc ccctcgccgt cgccggcgac ggcgaccccc catttcgccc     660
ggatttagag agatctcccc ccttcaatcc gccactggg                            699

<210> SEQ ID NO 123
<211> LENGTH: 532
<212> TYPE: DNA
<213> ORGANISM: Oryza sativa
```

<400> SEQUENCE: 123

```
atgggcatct cgagcatgcc ggcgcccaag acagcgtgg tggcgtacct gctgtacaac        60
acggcggtgt cgatcgccat cctggcggac atggtgcggg cggcgctggt gttcctcggc       120
ctccccgtgc cgccctcggc gtgggaggac ggcgacgacc agctggcggc gatcgcggcg       180
gccgccgcgg ccgcggccgc ggcggcgggg ggcccgagcc tggcggacag gttccggagc       240
aggttcaggc cggcgaggtt cgggcggcgg cgaggcgggg gcgcgggcgc ggccgactgc       300
cgcgtctgcc tcgcgcggtt cgagccggag tcggtggtga accgcctccc ctgcggccac       360
ctcttccacc gcgcctgcct cgagaagtgg ctcgactacg accacgccac ctgcccgctc       420
tgccgccacc gcctcctccc cgccaccacc gagtccccct cgccgtcgcc ggcgacggat       480
ttagagagat ctccccccctt caatccggcg accccccatt cgcccggat tt              532
```

<210> SEQ ID NO 124
<211> LENGTH: 42
<212> TYPE: PRT
<213> ORGANISM: Zea mays

<400> SEQUENCE: 124

```
Asp Cys Ser Val Cys Leu Ala Gly Phe Glu Ala Glu Ala Val Val Asn
1               5                   10                  15
Arg Leu Pro Cys Gly His Leu Phe His Arg Ala Cys Leu Glu Thr Trp
                20                  25                  30
Leu Arg Tyr Glu Arg Ala Thr Cys Pro Leu
            35                  40
```

<210> SEQ ID NO 125
<211> LENGTH: 63
<212> TYPE: PRT
<213> ORGANISM: Zea mays

<400> SEQUENCE: 125

```
Asp Cys Ser Val Cys Leu Ala Gly Phe Glu Ala Glu Ala Val Val Asn
1               5                   10                  15
Arg Leu Pro Cys Gly His Leu Phe His Arg Ala Cys Leu Glu Thr Trp
                20                  25                  30
Leu Arg Tyr Glu Arg Ala Thr Cys Pro Leu Cys Arg Ala His Val Pro
            35                  40                  45
Leu Pro Ala Asp Glu Thr Pro Val Leu Arg Tyr Pro Glu Leu Glu
        50                  55                  60
```

<210> SEQ ID NO 126
<211> LENGTH: 133
<212> TYPE: DNA
<213> ORGANISM: Zea mays

<400> SEQUENCE: 126

```
gactgcagcg tgtgcctggc cgggttcgag gcggaggccg tggtgaaccg gctcccctgc        60
ggccacctct ccaccgcgc ctgcctcgag acctggctcc ggtacgagcg cgccacgtgc       120
ccgctctgcc gcg                                                          133
```

<210> SEQ ID NO 127
<211> LENGTH: 209
<212> TYPE: DNA
<213> ORGANISM: Zea mays

<400> SEQUENCE: 127

```
cggccgcggg cgacgacgac tgcagcgtgt gcctggccgg gttcgaggcg gaggccgtgg      60
tgaaccggct ccctgcggc cacctcttcc accgcgcctg cctcgagacc tggctccggt    120
acgagcgcgc cacgtgcccg ctctgccgcg cccacgtgcc cctccccgcc gacgagacgc    180
cggtgctccg ctacccggag ctcgagtga                                      209
```

<210> SEQ ID NO 128
<211> LENGTH: 520
<212> TYPE: DNA
<213> ORGANISM: Zea mays

<400> SEQUENCE: 128

```
acgacgactg cagcgtgtgc ctggccgggt tcgaggcgga ggccgtggtg aaccggctcc     60
cctgcggcca cctcttccac cgcgcctgcc tcgagacctg gctccggtac gagcgcgcca    120
cgtgcccgct ctgccgcgcc cacgtgcccc tccccgccga cgagacgccg gtgctccgct    180
acccggagct cgagtgatcc gggcctcggc cgtcgcgcgc tcggctgtg tgctgcaagc    240 tccgtgtggc cttccgtgtg cgcgtagcaa aggaaaaaaa ggagtatagg agcggtagta    300
gtagagttgc tgttgctttc cctttctcgt tttgtgtttt gcggttgccc ccatgctctt    360
gttgtttccg cgctgtcgct gtagcgtgta aatactccgg ttcgcccttg cagcagaga    420 gtagtagagt gctcccgtgg ctgggccgat ggtgtagcac cttttacgag ctcagctcgt    480
gtgtgtacat ttgcatgctt tcaattccaa tttcccgaga                          520
```

<210> SEQ ID NO 129
<211> LENGTH: 163
<212> TYPE: PRT
<213> ORGANISM: Hordeum vulgare

<400> SEQUENCE: 129

Met Gly Ile Ser Ser Met Pro Ala Pro Lys Glu Ser Leu Leu Ile Tyr
1               5                   10                  15

Leu Leu Tyr His Ala Val Val Ser Ile Ala Ala Leu Ala Gly Leu Leu
            20                  25                  30

Arg Ala Ala Leu Ala Phe Leu Gly Leu Pro Thr Pro Pro Ser Leu Leu
        35                  40                  45

Ala Gly Glu Asp Ala Asp Gly Gly Asp Gln Leu Thr Ala Ala Thr Pro
    50                  55                  60

Ala Gly Pro Ser Leu Ala Glu Arg Phe Arg Ser Arg Phe Arg Pro Ala
65                  70                  75                  80

Arg Phe Gly Arg Arg Gly Ala Ala Ala Pro Asp Cys Arg Val
            85                  90                  95

Cys Leu Val Arg Phe Glu Ala Asp Ala Val Val Asn Arg Leu Pro Cys
                100                 105                 110

Gly His Met Phe His Arg Ala Cys Leu Glu Thr Trp Leu Asp Tyr Asp
            115                 120                 125

His Ala Thr Cys Pro Leu Cys Arg Ser Arg Leu Leu Pro Ala Val Ala
        130                 135                 140

Ala Ala Ala Asp Glu Ser Ser Arg Ser Pro Ala Pro Ser Leu Thr
145                 150                 155                 160

Ala Trp Met

<210> SEQ ID NO 130
<211> LENGTH: 47
<212> TYPE: PRT
<213> ORGANISM: Hordeum vulgare

<400> SEQUENCE: 130

Asp Cys Arg Val Cys Leu Val Arg Phe Glu Ala Asp Ala Val Val Asn
1               5                   10                  15

Arg Leu Pro Cys Gly His Met Phe His Arg Ala Cys Leu Glu Thr Trp
            20                  25                  30

Leu Asp Tyr Asp His Ala Thr Cys Pro Leu Cys Arg Ser Arg Leu
        35                  40                  45

<210> SEQ ID NO 131
<211> LENGTH: 141
<212> TYPE: DNA
<213> ORGANISM: Hordeum vulgare

<400> SEQUENCE: 131
gactgccgcg tgtgcctggt gcggttcgag gcggacgccg tggtgaaccg cctcccctgc    60
ggccacatgt tccaccgcgc ctgcctcgag acctggctcg actacgacca cgccacctgc   120
ccgctctgcc gctcccgcct c                                             141

<210> SEQ ID NO 132
<211> LENGTH: 491
<212> TYPE: DNA
<213> ORGANISM: Hordeum vulgare

<400> SEQUENCE: 132
atgggcatct ccagcatgcc ggcgcccaag gagagcctcc tgatctacct gctctaccac    60
gcggtcgtct cgatcgccgc cctggcgggg ctcctccgcg ccgcgctcgc cttcctcggc   120
ctgcccacgc cgccgtcgct gctggccggg gaggacgcgg atggcggcga ccagctcacg   180
gcggccaccc cggccggccc cagcctggcc gagaggttca ggagcaggtt ccgcccggcg   240
cgctttggcc ggaggcgggg cgcggcggcg gcgcctgact gccgcgtgtg cctggtgcgg   300
ttcgaggcgg acgccgtggt gaaccgcctc ccctgcggcc acatgttcca ccgcgcctgc   360
ctcgagacct ggctcgacta cgaccacgcc acctgcccgc tctgccgctc ccgcctcctc   420
ccggcggtag ccgctgccgc cgacgagtcg tcgcggtcgc cgccggcccc cagcctgacg   480
gcgtggatgt a                                                       491

<210> SEQ ID NO 133
<211> LENGTH: 1001
<212> TYPE: DNA
<213> ORGANISM: Hordeum vulgare

<400> SEQUENCE: 133
cggcacgagg caccaccata gaagctcaga gcaggcagcc cctgaaagaa ggcgaaaatt    60
gcagacgggt ccagggatcg atccccaaca ccggccgccg cgatgggcat ctccagcatg   120
ccggcgccca aggagagcct cctgatctac ctgctctacc acgcggtcgt ctcgatcgcc   180
gccctggcgg ggctcctccg cgccgcgctc gccttcctcg gcctgcccac gccgccgtcg   240
ctgctggccg gggaggacgc ggatggcggc gaccagctca cggcggccac cccggccggc   300
cccagcctgg ccgagaggtt caggagcagg ttccgcccgg cgcgctttgg ccggaggcgg   360
ggcgcggcgg cggcgcctga ctgccgcgtg tgcctggtgc ggttcgaggc ggacgccgtg   420
gtgaaccgcc tcccctgcgg ccacatgttc caccgcgcct gcctcgagac ctggctcgac   480
tacgaccacg ccacctgccc gctctgccgc tcccgcctcc tcccggcggt agccgctgcc   540
gccgacgagt cgtcgcggtc gccgccggcc cccagcctga cggcgtggat gtagagacga   600

```
gacaagagaa gagagattcg ccccgtcgcc cccggctacg tgctagctcc gtgtgtggcc       660
tctccgtgtg cgcgtaggaa tttaggtcga tcctagcaaa gcagagaggg tgctcgttcc       720
ccttcgcatc cctccctcct tttttttttt gatttcgttt tctgtaggcc tcgtgccgtc       780
gctgtgccgt gtacatattt ttcagcagag agcgctccta cgggtgtagc gctttgtgtg       840
atgagagatt tgcgtgcagc ccttggcctt tttttttttac gagaaacgga aaattgatgc      900
gaagaggatt gtgtgttctt gcttgccctc tttcttggat ggctgcccct aacccgtctc       960
tccagatatt tatgaagaaa gttactctgc tgattttcct t                          1001

<210> SEQ ID NO 134
<211> LENGTH: 43
<212> TYPE: PRT
<213> ORGANISM: Sorghum bicolor

<400> SEQUENCE: 134

Glu Cys Cys Ile Cys Leu Ser Ala Tyr Asp Asp Gly Ala Glu Leu Arg
1               5                   10                  15

Glu Leu Pro Cys Gly His His Phe His Cys Thr Cys Ile Asp Lys Trp
            20                  25                  30

Leu His Ile Asn Ala Thr Cys Pro Leu Cys Lys
        35                  40

<210> SEQ ID NO 135
<211> LENGTH: 139
<212> TYPE: DNA
<213> ORGANISM: Sorghum bicolor

<400> SEQUENCE: 135
gagtgttgta tttgcctatc ggcttatgat gatggtgcag agttgcgcga actcccctgt        60
gggcaccatt tccactgcac ctgcatcgac aagtggcttc acatcaatgc aacatgcccc       120
ctgtgcaagt acaacattc                                                   139

<210> SEQ ID NO 136
<211> LENGTH: 268
<212> TYPE: PRT
<213> ORGANISM: Sorghum bicolor

<400> SEQUENCE: 136

Met Pro Leu Arg Thr Trp Val Ala Gly Tyr Ala Leu Gln Cys Val Val
1               5                   10                  15

His Met Val Cys Val Ala Ile Glu Tyr Arg Met Arg His Gly Gln Gly
            20                  25                  30

Gly Gly Ala Gly Ala Ala Pro Thr Asp Glu Glu Arg Gly Ser Asp Gly
        35                  40                  45

Ser Ser Ser Ser Ser Asp Asp Asp Arg Glu Phe Asp Arg His Gly
    50                  55                  60

Arg Arg Thr Asp Tyr Ala Ser Ile Ala Lys His Leu Glu Ser Ala Asn
65                  70                  75                  80

Thr Met Phe Ser Phe Ile Trp Trp Ile Ile Gly Phe Tyr Trp Ile Ser
                85                  90                  95

Ala Gly Gly Glu Glu Val Ile Arg Asp Ala Pro Gln Leu Tyr Trp Leu
            100                 105                 110

Cys Ile Val Phe Leu Ala Phe Asp Val Phe Phe Val Val Phe Cys Val
        115                 120                 125

Ala Leu Ala Cys Ile Ile Gly Ile Ala Val Cys Cys Cys Leu Pro Cys
```

```
                130                 135                 140
Ile Ile Ala Ile Leu Tyr Ala Val Ser Asp Gln Glu Gly Ala Ser Glu
145                 150                 155                 160

Asp Asp Ile Arg Gln Ile Pro Arg Tyr Lys Phe Arg Arg Thr Asp Glu
                165                 170                 175

Pro Glu Lys Gln Asp Val Asp Pro Met Gly Pro Phe Gly Gly Ile Met
                180                 185                 190

Thr Glu Cys Gly Thr Asn Gln Pro Ile Glu Lys Val Leu Ala Ala Glu
            195                 200                 205

Asp Ala Glu Cys Cys Ile Cys Leu Ser Ala Tyr Asp Asp Gly Ala Glu
            210                 215                 220

Leu Arg Glu Leu Pro Cys Gly His His Phe His Cys Thr Cys Ile Asp
225                 230                 235                 240

Lys Trp Leu His Ile Asn Ala Thr Cys Pro Leu Cys Lys Tyr Asn Ile
                245                 250                 255

Arg Lys Ser Ser Ser Ser Gly Ser Glu Glu Val
            260                 265

<210> SEQ ID NO 137
<211> LENGTH: 806
<212> TYPE: DNA
<213> ORGANISM: Sorghum bicolor

<400> SEQUENCE: 137
atgccgctcc ggacctgggt cgccggctac gccctgcagt gcgtcgtaca catggtctgc      60
gtcgcaatcg agtaccggat gccacggc cagggcggcg cgccggcgc cgcgcccact        120 gacgaggaaa ggggcagcga cggatcgtcc tcgtccagcg acgacgatga cagggagttc     180
gatcgccatg gtcgccgcac cgattacgcc agtattgcaa agcacttgga gtctgctaat     240
acaatgttct ccttcatatg gtggataatt ggattttatt ggatatctgc tgggggtgaa     300
gaggttatcc gggatgcacc tcaactttac tggctttgca tagtcttcct ggcatttgat     360
gtgttttttg ttgtattctg cgttgctctg gcttgtatca ttggtattgc tgtctgttgt     420
tgccttcctt gtatcatagc aattctctat gcagtatctg accaggaagg agcatctgaa     480
gatgacattc gtcaaatccc aagatacaaa tttcggcgga ccgacgagcc tgaaaagcaa     540
gatgttgacc ccatgggtcc ttttggtgga ataatgacag agtgcggcac caatcaacct     600
attgagaaag tgcttgcagc tgaggatgca gagtgttgta tttgcctatc ggcttatgat     660
gatggtgcag agttgcgcga actcccctgt gggcaccatt tccactgcac ctgcatcgac     720
aagtggcttc acatcaatgc aacatgcccc ctgtgcaagt acaacattcg gaaaagcagc     780
agtagcagtg gaagtgaaga gtttg                                            806

<210> SEQ ID NO 138
<211> LENGTH: 48
<212> TYPE: PRT
<213> ORGANISM: Oryza sativa

<400> SEQUENCE: 138

Asp Cys Ala Val Cys Ile Thr Glu Leu Ala Ala Gly Glu Ser Ala Arg
1               5                   10                  15

Val Leu Pro Arg Cys Gly His Gly Phe His Val Glu Cys Val Asp Met
                20                  25                  30

Trp Leu Arg Ser Asn Ser Thr Cys Pro Leu Cys Arg Cys Ala Val Ile
            35                  40                  45
```

<210> SEQ ID NO 139
<211> LENGTH: 143
<212> TYPE: DNA
<213> ORGANISM: Oryza sativa

<400> SEQUENCE: 139

```
gactgcgccg tctgcatcac ggagctcgcc gccggggagt ccgcccgcgt gctgccgcgg      60
tgcggccacg ggttccacgt cgagtgcgtc gacatgtggc tccggtcaaa ctccacctgc     120
ccgctctgcc gctgcgccgt cat                                             143
```

<210> SEQ ID NO 140
<211> LENGTH: 280
<212> TYPE: PRT
<213> ORGANISM: Oryza sativa

<400> SEQUENCE: 140

```
Met Ala Val Thr Gly Thr Ser Val Ala Ala Ala Thr Met Leu Ala
1               5                   10                  15

Ala Ala Ala Ala Ile Phe Ile Thr Phe Val Val Cys Phe Tyr Leu Phe
            20                  25                  30

Leu Cys Ala Lys Arg Tyr Arg Gly Ala Ala Pro Thr Ile Gly Gly Asp
        35                  40                  45

Ser Gly Gly Gly Gly Arg Gly Arg Ala Arg Phe Val Phe Gly Gly Pro
    50                  55                  60

Gly Asp Gly Gly Cys Gly Gly Arg Gly Leu Asp Glu Ala Ala Ile
65                  70                  75                  80

Ala Ala Leu Pro Thr Lys Val Val Ala Ala Ala Glu Gly Gly Asp
                85                  90                  95

Gly Gly Asp Pro Ala Ala Asp Cys Ala Val Cys Ile Thr Glu Leu Ala
            100                 105                 110

Ala Gly Glu Ser Ala Arg Val Leu Pro Arg Cys Gly His Gly Phe His
        115                 120                 125

Val Glu Cys Val Asp Met Trp Leu Arg Ser Asn Ser Thr Cys Pro Leu
    130                 135                 140

Cys Arg Cys Ala Val Ile Asp Glu Ala Leu Pro Pro Pro Ala Val
145                 150                 155                 160

Arg Pro Pro Glu Ala Asp Ala Glu Ser Pro Asn Phe Pro Thr Asn Val
                165                 170                 175

Leu Phe Phe Gly Ser Gln Asp Ala Val Arg Thr Gly Gly Ala Ala Ala
            180                 185                 190

Ala Thr Pro Pro Pro Pro Pro Ser Ser His His Gln Gln Pro
        195                 200                 205

Ala Phe Pro Pro Gln Pro Ser Ala Gly Pro Ile Ala Gly Val Ala Ala
    210                 215                 220

Val Val Glu Ala Ala Arg Ile Ala Ala Leu Arg Arg Leu Leu Gly Cys
225                 230                 235                 240

Gly Gly Ala Thr Pro Pro Pro Pro Ala Pro Ala Gln Gly Asp Arg
                245                 250                 255

Asp Val Glu Met Gly Leu Pro Gly Gly Glu Ser Ser Ala Ser Arg Pro
            260                 265                 270

Ala Thr Lys Pro Gln Pro Gly Ser
        275                 280
```

<210> SEQ ID NO 141
<211> LENGTH: 843

<212> TYPE: DNA
<213> ORGANISM: Oryza sativa

<400> SEQUENCE: 141

```
atggcggtga cggggacgtc ggtggcggcc gcggcgacga tgctggcggc ggcggcggcg      60
atcttcatca cgttcgtcgt gtgcttctac ctcttcctct cgccaagag gtaccgcggc      120
gccgcgccca cgatcggcgg cgacagcggt gggggaggga ggggacgcgc gcggttcgtg     180
ttcggggggcc ccggggacgg cgggtgcgga ggcgggaggg ggcttgacga ggcggccatc    240
gcggcgctgc cgacgaaggt ggtggcggcg gcggccgagg ggggcgacgg cggcgacccc     300
gcggcggact gcgccgtctg catcacggag ctcgccgccg gggagtccgc ccgcgtgctg     360
ccgcggtgcg gccacgggtt ccacgtcgag tgcgtcgaca tgtggctccg gtcaaactcc     420
acctgccccg tctgccgctg cgccgtcatc gacgaggcgc tgccgccgcc gcccgccgtg     480
cgcccgccgg aggctgacgc ggagtcgccc aacttcccca ccaacgtgct cttcttcggc     540
tcccaggacg ccgtcaggac aggcggcgcc gccgcggcaa cgccgccgcc gccgcctccg     600
tcgtcccatc atcagcagca accggccttc ccgccgcagc cgtcggcggg acccatcgcc     660
ggagtcgccg ccgtggtgga agcggcgagg atagcggccc tgcggcggct gctgggctgc    720
ggcggcgcga ctcccccgcc cccgccggcg ccggcgcagg cgaccgcga cgtggagatg     780
ggcctccccg gcggcgagag cagcgcgtcg cggccggcga cgaagccgca gccaggttct    840
tga                                                                    843
```

<210> SEQ ID NO 142
<211> LENGTH: 47
<212> TYPE: PRT
<213> ORGANISM: Zea mays

<400> SEQUENCE: 142

```
Glu Cys Ala Val Cys Leu Ser Glu Val Gly Ala Gly Glu Lys Val Arg
1               5                   10                  15

Thr Leu Pro Lys Cys Ser His Gly Phe His Val Glu Cys Ile Asp Met
            20                  25                  30

Trp Phe His Ser His Asp Thr Cys Pro Leu Cys Arg Ala Pro Val
        35                  40                  45
```

<210> SEQ ID NO 143
<211> LENGTH: 140
<212> TYPE: DNA
<213> ORGANISM: Zea mays

<400> SEQUENCE: 143

```
gagtgcgcgg tgtgcctgtc cgaggtgggc gccggcgaga aggtgcggac gctgcccaag      60
tgctcccacg ggttccacgt ggagtgcatc gacatgtggt tccattccca cgacacgtgc    120
cccctctgcc gcgcccccgt                                                 140
```

<210> SEQ ID NO 144
<211> LENGTH: 304
<212> TYPE: PRT
<213> ORGANISM: Zea mays

<400> SEQUENCE: 144

```
Met Phe Pro Ala Pro Gly Ser Ser Gly Gln Gln Gln Leu Ala Ile Ser
1               5                   10                  15

Asn Gly Val Leu Leu Ala Ala Val Ile Phe Leu Phe Met Val Val Val
            20                  25                  30
```

```
Phe Val Phe Leu Leu Tyr Leu Tyr Ala Lys Arg Tyr Leu Gly Ala Asn
         35                  40                  45

Pro Leu Leu Ala Pro Ser Ser Pro Ser Ser Arg Phe Leu Phe Val Ala
 50                  55                  60

Ala Ser Pro Leu Pro Gln Arg Gly Leu Pro Ala Ser Val Leu Gln Ser
 65                  70                  75                  80

Leu Pro Val Thr Val Tyr Gly Ser Pro Gly Gly Lys Asp Lys Asp Ala
                 85                  90                  95

Leu Glu Cys Ala Val Cys Leu Ser Glu Val Gly Ala Gly Glu Lys Val
                100                 105                 110

Arg Thr Leu Pro Lys Cys Ser His Gly Phe His Val Glu Cys Ile Asp
            115                 120                 125

Met Trp Phe His Ser His Asp Thr Cys Pro Leu Cys Arg Ala Pro Val
        130                 135                 140

Gly Asp Leu Asp Ala Leu Pro Arg Glu Glu Pro Ser Gly Ala Pro Leu
145                 150                 155                 160

Glu Leu Pro Val Phe Pro Thr Asn Val Leu Phe Trp Gly Thr His Asp
                165                 170                 175

Glu Val Thr Asn Ala Gly Leu Val Ala Pro Pro Arg Ala Ala Pro Ser
            180                 185                 190

Ala Ser Ser Ser Ala Ser Gly Arg Arg Lys Glu Asn Leu Val Ile Asp
        195                 200                 205

Ile Pro Thr Arg Ala Val Ala Thr Thr Thr Thr Pro Pro Pro Ala
    210                 215                 220

Asn Ser Pro Leu Pro Ala Ser Arg Met Pro Gly Ser Ala Asp Glu Met
225                 230                 235                 240

Arg Ser Pro Val Ser Ala Arg Leu Arg Ser Leu Arg Arg Leu Leu Ser
                245                 250                 255

Arg Gly Lys Gln Ala Met Val Gly Thr Ser Ser Ser Tyr Ser Pro Arg
            260                 265                 270

Asp Ile Glu Gln Gly Leu Ala Gly Gly Glu Ala Ala Ala Ala Ala Thr
        275                 280                 285

Ala Arg Pro Pro Lys Thr Pro Lys Thr Pro Pro Ser Ala His Ala His
    290                 295                 300

<210> SEQ ID NO 145
<211> LENGTH: 823
<212> TYPE: DNA
<213> ORGANISM: Zea mays

<400> SEQUENCE: 145
atgttcccgg ccccgggtag ctcggggcag cagcagctgg ccatcagcaa cggggtgctc      60
ctcgccgccg tcatcttcct cttcatggtc gtcgtcttcg tcttcctcct ctacctctac    120
gccaagcgct acctgggcgc gaacccgctg ctggcgccgt cgtcgccgtc ctcgcggttc    180
ctcttcgttg ccgcgtcccc gctcccgcag gcggcctgc  cgcctccgt cctgcaatcc    240 ctccccgtca ccgtctacgg ctcccccggc ggcaaggaca aggacgcgct ggagtgcgcg    300
gtgtgcctgt ccgaggtggg cgccggcgag aaggtgcgga cgctgcccaa gtgctcccac    360
gggttccacg tggagtgcat cgacatgtgg ttccattccc acgacacgtg cccccctctgc    420 cgcgccccg tgggcgacct cgacgcgctg ccgcgggagg agccctccgg cgcgccgctg    480
gagttgcccg tgttccccac caacgtcctg ttctggggca cccacgacga ggtcaccaac    540
gccgggctcg tcgcgccgcc gcgcgccgcc ccgtcggcca gctcctcggc ctccgggcgc    600
```

```
aggaaggaga acctggtcat cgacatcccg acgcgggccg tggccacgac cacgaccacg      660
ccgccgcccg ccaactcccc gctgccggcc agccggatgc ccgggagcgc cgacgagatg      720
cggtccccgg tgtccgccag gctgcggtcg ctgcgccggc tgctgagcag aggaaagcag      780
gccatggtcg gcacctcctc ctcctacagc ccgcgcgaca tcg                        823
```

```
<210> SEQ ID NO 146
<211> LENGTH: 258
<212> TYPE: PRT
<213> ORGANISM: Zea mays

<400> SEQUENCE: 146
```

| | | | | | | | | | | | | | | | |
|---|---|---|---|---|---|---|---|---|---|---|---|---|---|---|---|
| Met | Leu | Ala | Ala | Val | Ala | Ala | Val | Phe | Leu | Thr | Leu | Val | Leu | Cys | Phe |
| 1 | | | | 5 | | | | | 10 | | | | | 15 | |
| Tyr | Val | Phe | Leu | Cys | Ala | Lys | Arg | Tyr | Arg | Gly | Glu | Ala | Pro | Pro | His |
| | | | 20 | | | | | 25 | | | | | 30 | | |
| Ala | Val | Ala | Ala | Ala | Gly | Gly | Gly | Val | Arg | Ala | Trp | Leu | Arg | Val | |
| | | 35 | | | | | 40 | | | | | 45 | | | |
| Val | Phe | Gly | Val | Gly | Gly | Ala | Gly | Ala | His | Val | Gly | Gly | Thr | | |
| | 50 | | | | | 55 | | | | | 60 | | | | |
| Glu | Trp | Cys | Tyr | Asp | Gly | Gly | Leu | Asp | Asp | Lys | Ser | Met | Ala | Lys | Leu |
| 65 | | | | | 70 | | | | | 75 | | | | | 80 |
| Pro | Arg | Arg | Glu | Val | Gly | Arg | Gly | Asp | Glu | Ala | Ala | Asp | Cys | Ala | Val |
| | | | | 85 | | | | | 90 | | | | | 95 | |
| Cys | Ile | Thr | Glu | Leu | Ala | Pro | Gly | Glu | Thr | Ala | Arg | Val | Leu | Pro | Arg |
| | | | 100 | | | | | 105 | | | | | 110 | | |
| Cys | Gly | His | Ala | Phe | His | Val | Asp | Cys | Val | Asp | Met | Trp | Leu | Arg | Ser |
| | | 115 | | | | | 120 | | | | | 125 | | | |
| His | Ser | Thr | Cys | Pro | Leu | Cys | Arg | Cys | Pro | Ala | Val | Asp | Asp | Pro | Pro |
| | 130 | | | | | 135 | | | | | 140 | | | | |
| Val | Pro | Pro | Ala | Val | Pro | Thr | Pro | Glu | Ala | Asp | Pro | Glu | Ser | Pro | Asn |
| 145 | | | | | 150 | | | | | 155 | | | | | 160 |
| Phe | Pro | Thr | Asn | Val | Leu | Phe | Phe | Gly | Ser | Gln | Asp | Glu | Val | Ser | Thr |
| | | | | 165 | | | | | 170 | | | | | 175 | |
| Gly | Arg | Ser | Gln | Ser | Gln | Gln | His | Thr | Ala | Pro | Gln | Glu | Ala | Cys | Ala |
| | | | 180 | | | | | 185 | | | | | 190 | | |
| Gly | Leu | Arg | Arg | Leu | Ile | Gly | Cys | Gly | Gly | Ala | Pro | Pro | Thr | Gln | |
| | | 195 | | | | | 200 | | | | | 205 | | | |
| Pro | Cys | Asp | Cys | Glu | Gln | Arg | Arg | Cys | Arg | Arg | Glu | Glu | Glu | Asp | Asp |
| | 210 | | | | | 215 | | | | | 220 | | | | |
| Asp | Asp | Asp | Ala | Gly | Gly | Asp | Ile | Glu | Met | Gly | Leu | Ala | Ala | Gly | Ala |
| 225 | | | | | 230 | | | | | 235 | | | | | 240 |
| Gly | Thr | Gly | Glu | Ser | Ser | Ala | Ser | Arg | Pro | Val | Lys | Pro | Pro | Gln | Pro |
| | | | | 245 | | | | | 250 | | | | | 255 | |
| Gly | Ser | | | | | | | | | | | | | | |

```
<210> SEQ ID NO 147
<211> LENGTH: 49
<212> TYPE: PRT
<213> ORGANISM: Zea mays

<400> SEQUENCE: 147
```

| | | | | | | | | | | | | | | | |
|---|---|---|---|---|---|---|---|---|---|---|---|---|---|---|---|
| Asp | Cys | Ala | Val | Cys | Ile | Thr | Glu | Leu | Ala | Pro | Gly | Glu | Thr | Ala | Arg |
| 1 | | | | 5 | | | | | 10 | | | | | 15 | |
| Val | Leu | Pro | Arg | Cys | Gly | His | Ala | Phe | His | Val | Asp | Cys | Val | Asp | Met |

```
             20                  25                  30
Trp Leu Arg Ser His Ser Thr Cys Pro Leu Cys Arg Cys Pro Ala Val
         35                  40                  45
Asp

<210> SEQ ID NO 148
<211> LENGTH: 147
<212> TYPE: DNA
<213> ORGANISM: Zea mays

<400> SEQUENCE: 148
gactgcgccg tgtgcatcac ggagctggcg ccggggagga cggcgcgcgt gctgccgcgg      60
tgcgggcacg ccttccacgt ggactgcgtc gacatgtggc tccgctccca ctccacctgc     120
ccgctctgcc ggtgccccgc cgtggac                                         147

<210> SEQ ID NO 149
<211> LENGTH: 777
<212> TYPE: DNA
<213> ORGANISM: Zea mays

<400> SEQUENCE: 149
atgctggcgg ccgtggcggc ggtcttcctg accctggtgc tctgcttcta cgtcttcctc      60
tgcgccaagc ggtaccgcgg cgaggcgccc ccgcacgcgg tggccgccgc cggcggcggc     120
ggcgtcaggg cgtggctgcg cgtcgtgttc ggcgtcgggg gaggcgcagg cgcgcacgtc     180
ggcggcggca cggagtggtg ctacgacggc gggctcgacg acaagtcgat ggcgaagctg     240
ccccggcggg aggtgggcag gggcgacgag gcggcggact gcgccgtgtg catcacggag     300
ctggcgccgg gggagacggc gcgcgtgctg ccgcggtgcg ggcacgcctt ccacgtggac     360
tgcgtcgaca tgtggctccg ctcccactcc acctgcccgc tctgccggtg ccccgccgtg     420
gacgaccccg ccgtcccgcc cgccgtgccc acgcccgagg ccgacccgga gtccccgaac     480
ttccccacca acgtcctctt cttcggctcc aggacgagga tcagcaccgg ccgctcgcag     540
tcgcagcaac acacggcgcc gcaggaggcg tgcgccgggc tgcggaggct gatcgggtgt     600
ggcggcgcgc cgccgcccac gcagccttgc gactgcgagc agcgtcgctg tcgtcgggag     660
gaggaggacg acgacgacga cgcgggcggg gacatcgaga tgggcctcgc cgccggcgcc     720
ggcaccggcg agagcagcgc gtcgcggccg gtgaagccgc cgcagcccgg ttcgtga       777

<210> SEQ ID NO 150
<211> LENGTH: 279
<212> TYPE: PRT
<213> ORGANISM: Oryza sativa

<400> SEQUENCE: 150

Met Ala Val Thr Gly Thr Ser Val Ala Ala Ala Thr Met Leu Ala
1               5                   10                  15

Ala Ala Ala Ile Phe Ile Thr Phe Val Val Cys Phe Tyr Leu Phe
            20                  25                  30

Leu Cys Ala Lys Arg Tyr Arg Gly Ala Ala Pro Thr Ile Gly Gly Asp
        35                  40                  45

Ser Gly Gly Gly Gly Arg Gly Arg Ala Arg Phe Val Phe Gly Gly Pro
    50                  55                  60

Gly Asp Gly Gly Cys Gly Gly Gly Arg Gly Leu Asp Glu Ala Ala Ile
65                  70                  75                  80

Ala Ala Leu Pro Thr Lys Val Val Ala Ala Ala Ala Glu Gly Gly Asp
```

```
                    85                  90                  95
Gly Gly Asp Pro Ala Ala Asp Cys Ala Val Cys Ile Thr Glu Leu Ala
                100                 105                 110

Ala Gly Glu Ser Ala Arg Val Leu Pro Arg Cys Gly His Gly Phe His
            115                 120                 125

Val Glu Cys Val Asp Met Trp Leu Arg Ser Asn Ser Thr Cys Pro Leu
    130                 135                 140

Cys Arg Cys Ala Val Ile Asp Glu Ala Leu Pro Pro Pro Ala Val
145                 150                 155                 160

Arg Pro Pro Glu Ala Asp Ala Glu Ser Pro Asn Phe Pro Thr Asn Val
                165                 170                 175

Leu Phe Phe Gly Ser Gln Asp Ala Val Arg Thr Gly Gly Ala Ala Ala
            180                 185                 190

Ala Thr Pro Pro Pro Pro Pro Ser Ser His His Gln Gln Gln Pro
    195                 200                 205

Ala Phe Pro Pro Gln Pro Ser Ala Gly Pro Ile Ala Gly Val Ala Ala
                210                 215                 220

Val Val Glu Ala Ala Arg Ile Ala Ala Leu Arg Arg Leu Leu Gly Cys
225                 230                 235                 240

Gly Gly Ala Thr Pro Pro Pro Pro Ala Pro Ala Gln Gly Asp Arg
                245                 250                 255

Asp Val Glu Gly Leu Pro Gly Gly Glu Ser Ser Ala Ser Arg Pro Ala
                260                 265                 270

Thr Lys Pro Gln Pro Gly Ser
        275
```

<210> SEQ ID NO 151
<211> LENGTH: 48
<212> TYPE: PRT
<213> ORGANISM: Oryza sativa

<400> SEQUENCE: 151

```
Asp Cys Ala Val Cys Ile Thr Glu Leu Ala Ala Gly Glu Ser Ala Arg
1               5                   10                  15

Val Leu Pro Arg Cys Gly His Gly Phe His Val Glu Cys Val Asp Met
            20                  25                  30

Trp Leu Arg Ser Asn Ser Thr Cys Pro Leu Cys Arg Cys Ala Val Ile
        35                  40                  45
```

<210> SEQ ID NO 152
<211> LENGTH: 145
<212> TYPE: DNA
<213> ORGANISM: Oryza sativa

<400> SEQUENCE: 152

```
gactgcgccg tctgcatcac ggagctcgcc gccggggagt ccgcccgcgt gctgccgcgg    60
tgcggccacg gttccacgt cgagtgcgtc gacatgtggc tccggtcaaa ctccacctgc   120
ccgctctgcc gctgcgccgt catcg                                        145
```

<210> SEQ ID NO 153
<211> LENGTH: 843
<212> TYPE: DNA
<213> ORGANISM: Oryza sativa

<400> SEQUENCE: 153

```
atggcggtga cggggacgtc ggtggcggcc gcggcgacga tgctggcggc ggcggcggcg    60
```

```
atcttcatca cgttcgtcgt gtgcttctac ctcttcctct gcgccaagag gtaccgcggc    120
gccgcgccca cgatcggcgg cgacagcggt gggggaggga ggggacgcgc gcggttcgtg    180
ttcgggggcc ccggggacgg cgggtgcgga ggcgggaggg ggcttgacga ggcggccatc    240
gcggcgctgc cgacgaaggt ggtggcggcg gcggccgagg ggggcgacgg cggcgacccc    300
gcggcggact gcgccgtctg catcacggag ctcgccgccg gggagtccgc ccgcgtgctg    360
ccgcggtgcg gccacgggtt ccacgtcgag tgcgtcgaca tgtggctccg gtcaaactcc    420
acctgcccgc tctgccgctg cgccgtcatc gacgaggcgc tgccgccgcc gcccgccgtg    480
cgcccgccgg aggctgacgc ggagtcgccc aacttcccca ccaacgtgct cttcttcggc    540
tcccaggacg ccgtcaggac aggcggcgcc gccgcggcaa cgccgccgcc gccgcctccg    600
tcgtcccatc atcagcagca accggccttc ccgccgcagc cgtcggcggg acccatcgcc    660
ggagtcgccg ccgtggtgga agcggcgagg atagcggccc tgcggcggct gctgggctgc    720
ggcggcgcga ctcccccgcc cccgccggcg ccggcgcagg gcgaccgcga cgtggagatg    780
ggcctccccg gcggcgagag cagcgcgtcg cggccggcga cgaagccgca gccaggttct    840
tga                                                                  843
```

```
<210> SEQ ID NO 154
<211> LENGTH: 153
<212> TYPE: PRT
<213> ORGANISM: Populus sp.

<400> SEQUENCE: 154
```

```
Met Gly Leu Ser Ser Leu Pro Ala Pro Ser Glu Gly Val Leu Cys Val
1               5                   10                  15

Leu Leu Val Asn Thr Ala Leu Ser Ile Ser Ile Val Lys Gly Ile Val
            20                  25                  30

Arg Ser Ile Leu His Val Val Gly Ile Arg Leu Ser Pro Ser Ala Ser
        35                  40                  45

Leu Pro Ser Ser Asp Asn Ala Glu Asp Thr Arg Glu Ser Phe Glu Phe
    50                  55                  60

Arg Leu Ser Pro Pro Glu Asn Tyr Ile Glu Glu Phe Arg Ser Arg Met
65                  70                  75                  80

Pro Ser Ile Arg Phe Asn Thr Val Cys Ser Cys Lys Gln Pro Glu His
                85                  90                  95

Asp Cys Ser Val Cys Leu Thr Gln Phe Glu Pro Glu Ser Glu Ile Asn
            100                 105                 110

Ser Leu Ser Cys Gly His Ile Phe His Lys Met Cys Leu Glu Lys Trp
        115                 120                 125

Leu Asp Tyr Trp Asn Ile Thr Cys Pro Leu Cys Arg Thr Pro Leu Leu
    130                 135                 140

Pro Glu Glu Asp Ala Ser Cys Phe Trp
145                 150
```

```
<210> SEQ ID NO 155
<211> LENGTH: 47
<212> TYPE: PRT
<213> ORGANISM: Populus sp.

<400> SEQUENCE: 155
```

```
Asp Cys Ser Val Cys Leu Thr Gln Phe Glu Pro Glu Ser Glu Ile Asn
1               5                   10                  15

Ser Leu Ser Cys Gly His Ile Phe His Lys Met Cys Leu Glu Lys Trp
            20                  25                  30
```

Leu Asp Tyr Trp Asn Ile Thr Cys Pro Leu Cys Arg Thr Pro Leu
        35                  40                  45

<210> SEQ ID NO 156
<211> LENGTH: 143
<212> TYPE: DNA
<213> ORGANISM: Populus sp.

<400> SEQUENCE: 156
gactgctcgg tttgcttgac ccaatttgag ccagaatcgg agataaatag cctgtcatgt       60
ggccatatct ttcataaaat gtgcttggag aagtggttgg actattggaa cattacatgc      120
cctctttgca ggactccttt gct                                              143

<210> SEQ ID NO 157
<211> LENGTH: 461
<212> TYPE: DNA
<213> ORGANISM: Populus sp.

<400> SEQUENCE: 157
atgggtctat caagtctgcc agctccatct gaaggagtgc tatgtgtgct tttagtaaac       60
actgccttgt caatttccat tgtcaaaggg atagtccgtt caatccttca cgttgttggc      120
atccgtttgt caccatctgc ttcactccca tcgtcagata atgctgaaga caccagagag      180
tcgtttgaat tcgtttaag tcccccagag aattacattg aggagttccg aagcaggatg       240
ccatcaatcc gattcaacac ggtgtgcagc tgtaaacagc ctgaacatga ctgctcggtt      300
tgcttgaccc aatttgagcc agaatcggag ataaatagcc tgtcatgtgg ccatatcttt      360
cataaaatgt gcttggagaa gtggttggac tattggaaca ttacatgccc tctttgcagg      420
actcctttgc tgcctgaaga ggatgcatct tgcttttggt g                          461

<210> SEQ ID NO 158
<211> LENGTH: 1215
<212> TYPE: DNA
<213> ORGANISM: Populus sp.

<400> SEQUENCE: 158
gggcagccat cttcatctcc atcttctatg aaacaatccc atatgacatg tataaaagtt       60
ttgataatcc catgaatatg tcatgttttct aggctgctag catgttcttg atgcttatat     120
atttctttgc atagagacca agacaggaac ttcaaagctt ccctagtgtc actgttgtcg      180 gctccttta caggatttg ctattcatca cttcatcata gtcaaaaacc ctgtttatat        240
gccccaagat caagcaaaga aggaaacatc cggttttctc catttgcttc aactgtgatt      300
tatacaagca tccccccatt ggcttccata acttccattt gagcacactg tgaatcaaga     360
atctcttgtt agcttgagct tgcggaatc actgcaaaaa aaaaaccaag tcccacgaaa       420
cttcaatggg tctatcaagt ctgccagctc atctgaagg agtgctatgt gtgcttttag      480
taaacactgc cttgtcaatt tccattgtca aagggatagt ccgttcaatc cttcacgttg     540
ttggcatccg tttgtcacca tctgcttcac tcccatcgtc agataatgct gaagacacca    600
gagagtcgtt tgaatttcgt ttaagtcccc cagagaatta cattgaggag ttccgaagca    660
ggatgccatc aatccgattc aacacggtgt gcagctgtaa acagcctgaa catgactgct    720
cggtttgctt gacccaattt gagccagaat cggagataaa tagcctgtca tgtggccata    780
tctttcataa aatgtgcttg gagaagtggt tggactattg aacattaca tgccctcttt    840 gcaggactcc tttgctgcct gaagaggatg catcttgctt ttggtgagcg catactacca     900

```
tgtatgcttt gtcagaggaa ttctccttgt acagcgtgta catgtattta cgtgagtgca      960
tcgggcaggg catagtggtg tatactttgt gcttgagatc aagcatgatg tgctgatggg     1020
tccttgagag accaaaaatt ttattgtaca tattgtgaag aagtgatgtt taacctatct     1080
atcttgcttt gatctccacc ttttcttttt tccttgatct ttgcacacgt ttttactctt     1140
ctttaacaga ccagaaggat ggaatctaat gtatgggcaa gctaaactag aataaaaaaa     1200
ttcctccatg tttac                                                      1215
```

<210> SEQ ID NO 159
<211> LENGTH: 177
<212> TYPE: PRT
<213> ORGANISM: Populus sp.
<220> FEATURE:
<221> NAME/KEY: misc_feature
<222> LOCATION: (129)..(129)
<223> OTHER INFORMATION: Xaa can be any naturally occurring amino acid

<400> SEQUENCE: 159

```
Met Phe Ile Lys Tyr Leu Asn Leu Ile Ser Ala His Leu Arg Trp Ala
1               5                   10                  15

Phe Asn Phe Leu Cys Tyr Tyr Pro Phe Ser Phe Gln Glu His Glu Leu
            20                  25                  30

Phe Ala Val Thr Ala Ile Gly Glu Glu Leu Asn Thr Val Ile Asn Glu
        35                  40                  45

Ala Pro Ala Glu Cys Ala Val Cys Leu Ser Asp Val Gln Glu Gly Glu
    50                  55                  60

Glu Ile Arg Glu Leu Arg Cys Gly His Ile Phe His Arg Ala Cys Leu
65                  70                  75                  80

Tyr Arg Trp Leu Asp Phe Arg Gln Ser Thr Cys Pro Leu Cys Arg Gly
                85                  90                  95

Ser Leu Ala Pro Arg Arg Thr Leu Ile Leu Asp Gln His Arg Thr Glu
            100                 105                 110

Val Leu Thr Phe Lys Phe Cys Ser Phe Thr Ser Thr Asp Glu Arg Asp
        115                 120                 125

Xaa Met Val Ala Thr Met Asn Gln Val Phe Lys Ile Leu Val Pro Arg
    130                 135                 140

Gln Glu Lys Ala Gln Arg Ser Asn Tyr Leu Leu Pro Pro Pro Ser Glu
145                 150                 155                 160

Tyr His Gly Met Phe Val Asn Glu Leu Leu Leu Met Gln Thr Ser Gln
                165                 170                 175

Ala
```

<210> SEQ ID NO 160
<211> LENGTH: 47
<212> TYPE: PRT
<213> ORGANISM: Populus sp.

<400> SEQUENCE: 160

```
Glu Cys Ala Val Cys Leu Ser Asp Val Gln Glu Gly Glu Glu Ile Arg
1               5                   10                  15

Glu Leu Arg Cys Gly His Ile Phe His Arg Ala Cys Leu Tyr Arg Trp
            20                  25                  30

Leu Asp Phe Arg Gln Ser Thr Cys Pro Leu Cys Arg Gly Ser Leu
        35                  40                  45
```

<210> SEQ ID NO 161

<211> LENGTH: 158
<212> TYPE: DNA
<213> ORGANISM: Populus sp.

<400> SEQUENCE: 161

```
gaatgtgctg tgtgtctaag tgacgttcaa gaaggcgaag aaatcagaga gctgagatgt    60
gggcatatct ttcatagagc atgcttatac agatggcttg acttccggca atcgacttgc   120
ccactttgcc gaggaagtct tgctccccgg agaacatt                            158
```

<210> SEQ ID NO 162
<211> LENGTH: 530
<212> TYPE: DNA
<213> ORGANISM: Populus sp.
<220> FEATURE:
<221> NAME/KEY: misc_feature
<222> LOCATION: (524)..(524)
<223> OTHER INFORMATION: n is a, c, g, or t

<400> SEQUENCE: 162

```
atgtgctgtg tgtctaagtg acgttcaaga aggcgaagaa atcagagagc tgagatgtgg    60
gcatatcttt catagagcat gcttatacag atggcttgac ttccggcaat cgacttgccc   120
actttgccga ggaagtctta tgttcatcaa atacttaaat ctcattagtg cccatctcag   180
atgggcattt aatttcttgt gttactatcc gttcagcttc caagaacacg aattgtttgc   240
tgtgactgca attggtgaag aactaaacac ggtgatcaat gaagctcctg cggaatgtgc   300
tgtgtgtcta agtgacgttc aagaaggcga agaaatcaga gagctgagat gtgggcatat   360
cttttcataga gcatgcttat acagatggct tgacttccgg caatcgactt gcccactttg   420
ccgaggaagt cttgctcccc ggagaacatt gatccttgat cagcaccgaa cagaagtatt   480
gacgttcaag ttctgttctt tcacatccac cgatgaacgt gatnacatgg                530
```

<210> SEQ ID NO 163
<211> LENGTH: 534
<212> TYPE: DNA
<213> ORGANISM: Populus sp.
<220> FEATURE:
<221> NAME/KEY: misc_feature
<222> LOCATION: (385)..(385)
<223> OTHER INFORMATION: n is a, c, g, or t

<400> SEQUENCE: 163

```
atgttcatca aatacttaaa tctcattagt gcccatctca gatgggcatt taatttcttg    60
tgttactatc cgttcagctt ccaagaacac gaattgtttg ctgtgactgc aattggtgaa   120
gaactaaaca cggtgatcaa tgaagctcct gcggaatgtg ctgtgtgtct aagtgacgtt   180
caagaaggcg aagaaatcag agagctgaga tgtgggcata tctttcatag agcatgctta   240
tacagatggc ttgacttccg gcaatcgact tgcccacttt gccgaggaag tcttgctccc   300
cggagaacat tgatccttga tcagcaccga acagaagtat tgacgttcaa gttctgttct   360
ttcacatcca ccgatgaacg tgatnacatg gtggctacga tgaatcaagt cttcaagatt   420
ttagtacctc gtcaggagaa agcacaacgg agtaactacc ttctcccccc tccttcagaa   480
tatcatggca tgttcgttaa cgagttgcta ttgatgcaaa cttctcaagc atga          534
```

<210> SEQ ID NO 164
<211> LENGTH: 839
<212> TYPE: DNA
<213> ORGANISM: Populus sp.

<400> SEQUENCE: 164

```
ctccttgttc atctctccca actccttttc tagctcattt ttgttttgc gacaaaatta      60
acctctaaac tcaaccaatc atgttcatca aatacttaaa tctcattagt gcccatctca     120
gatgggcatt taatttcttg tgttactatc cgttcagctt ccaagaacac gaattgtttg     180
ctgtgactgc aattggtgaa gaactaaaca cggtgatcaa tgaagctcct gcggaatgtg     240
ctgtgtgtct aagtgacgtt caagaaggcg aagaaatcag agagctgaga tgtgggcata     300
tctttcatag agcatgctta tacagatggc ttgacttccg gcaatcgact tgcccacttt     360
gccgaggaag tcttgctccc cggagaacat tgatccttga tcagcaccga acagaagtat     420
tgacgttcaa gttctgttct ttcacatcca ccgatgaacg tgatacatgg tggctacgat     480
gaatcaagtc ttcaagattt tagtacctcg tcaggagaaa gcacaacgga gtaactacct     540
tctccccct ccttcagaat atcatggcat gttcgttaac gagttgctat tgatgcaaac     600
ttctcaagca tgaagtgatc gttaattcct gagcatgtga cagactaatt aagctgaagg     660
ttcattgtta gaataaacg ttttttttc cttcctatat tgcatcatct gctaatttac     720
ctgaaagggt gaagccatct ccctctcgga atctctaata acagtcctgc aatgccatgc     780
atgttgtctc ttagccatgc ttgtaataaa cttgatgttt ggtaagtgtt gttttagtt     839
```

<210> SEQ ID NO 165
<211> LENGTH: 48
<212> TYPE: PRT
<213> ORGANISM: Medicago truncatula

<400> SEQUENCE: 165

```
Asp Cys Ser Val Cys Leu Thr Gln Phe Glu Pro Glu Ser Glu Ile Asn
1               5                   10                  15

Tyr Cys Ile Ser Cys Gly His Val Phe His Lys Val Cys Leu Glu Lys
            20                  25                  30

Trp Leu Asp Tyr Trp Asn Ile Thr Cys Pro Leu Cys Arg Ser Pro Leu
        35                  40                  45
```

<210> SEQ ID NO 166
<211> LENGTH: 155
<212> TYPE: PRT
<213> ORGANISM: Medicago truncatula

<400> SEQUENCE: 166

```
Met Gly Leu Ser Ser Leu Pro Ala Gln Ser Glu Gly Val Leu Cys Ile
1               5                   10                  15

Ile Leu Val Asn Thr Ala Met Ser Ile Ser Phe Lys Gly Ile Ile
            20                  25                  30

Arg Thr Ile Leu His Ile Val Gly Ile Ala Ser Pro Ser Ser
        35                  40                  45

Pro Ser Gln Asp Tyr Ile Pro Gln Asn Ile Pro Glu Ser Tyr Glu Ile
    50                  55                  60

His Leu Ser Pro Ser Asp Asp Phe Val Glu Phe Arg Ser Arg Thr
65                  70                  75                  80

Pro Thr Leu Arg Phe Asp Ser Val Cys Asn Ser Cys Lys Glu Pro Glu
                85                  90                  95

His Asp Cys Ser Val Cys Leu Thr Gln Phe Glu Pro Glu Ser Glu Ile
            100                 105                 110

Asn Tyr Cys Ile Ser Cys Gly His Val Phe His Lys Val Cys Leu Glu
        115                 120                 125

Lys Trp Leu Asp Tyr Trp Asn Ile Thr Cys Pro Leu Cys Arg Ser Pro
```

```
                130                 135                 140
Leu Ile Pro Glu Asp Asp Ala Ser Cys Leu Trp
145                 150                 155
```

<210> SEQ ID NO 167
<211> LENGTH: 129
<212> TYPE: DNA
<213> ORGANISM: Medicago truncatula

<400> SEQUENCE: 167

| | | |
|---|---|---|
| gattgctcag tgtgtctcac tcaatttgaa cctgaatcag agataaacta ttgcatatca | 60 |
| tgtggccatg tttttcataa agtgtgtttg gagaagtggt tggattattg gaacattaca | 120 |
| tgtccactt | 129 |

<210> SEQ ID NO 168
<211> LENGTH: 467
<212> TYPE: DNA
<213> ORGANISM: Medicago truncatula

<400> SEQUENCE: 168

| | |
|---|---|
| atgggcctat caagtcttcc agcacaatct gaaggagtgt tatgcatcat tctagtaaac | 60 |
| actgccatgt caatatccat attcaaaggc attataagga ctatcctgca cattgttggt | 120 |
| atcattgctt caccatcttc ctctccttcc caagactaca ttcctcaaaa catacctgag | 180 |
| tcatatgaaa tccatctaag tccttcagat gatttcgttg aagagttcag aagcagaaca | 240 |
| ccaacactta ggtttgatag tgtgtgtaat agctgcaaag aacctgaaca tgattgctca | 300 |
| gtgtgtctca ctcaatttga acctgaatca gagataaact attgcatatc atgtggccat | 360 |
| gtttttcata agtgtgtttt ggagaagtgg ttggattatt ggaacattac atgtccactt | 420 |
| tgtaggagtc ctttaattcc tgaagatgat gcatcttgct tatggta | 467 |

<210> SEQ ID NO 169
<211> LENGTH: 911
<212> TYPE: DNA
<213> ORGANISM: Medicago truncatula
<220> FEATURE:
<221> NAME/KEY: misc_feature
<222> LOCATION: (795)..(795)
<223> OTHER INFORMATION: n is a, c, g, or t

<400> SEQUENCE: 169

| | |
|---|---|
| gcaccaggag aaaaacacaa tatcaaaaac tcacttcttg taacaaaaac aacctcttca | 60 |
| caaattgttc ttgttgaccc acatcacaaa tcctcaaatc ctttatctgt aaactattaa | 120 |
| caagatcaaa atagtttcca ttgataaatt ctgcttcaaa atacacattg catcataaag | 180 |
| tgtatcacaa atttgttcat caaaatgggc ctatcaagtc ttccagcaca atctgaagga | 240 |
| gtgttatgca tcattctagt aaacactgcc atgtcaatat ccatattcaa aggcattata | 300 |
| aggactatcc tgcacattgt tggtatcatt gcttccacat cttcctctcc ttcccaagac | 360 |
| tacattcctc aaaacatacc tgagtcatat gaaatccatc taagtccttc agatgatttc | 420 |
| gttgaagagt tcagaagcag aacaccaaca cttaggtttg atagtgtgtg taatagctgc | 480 |
| aaagaacctg aacatgattg ctcagtgtgt ctcactcaat ttgaacctga atcagagata | 540 |
| aactattgca tatcatgtgg ccatgttttt cataaagtgt gtttggagaa gtggttggat | 600 |
| tattggaaca ttcatgtcc actttgtagg agtcctttaa ttcctgaaga tgatgcatct | 660 |
| tgcttatggt aagagcaatg attgaagcat gcacaaaata tctaatggag aggttacttc | 720 |

```
atgtacagta tatagtgtgt acaaatatcc ctgtgacagt tttgatgtac ctatctatgt    780
atctgacttt ttctnttagt cttcttagtg cttttgcctt ttatgatgta gagttagtgg    840
agggttttgt ttaccttgtt ttttttcctt ttctgtatca tatgtttgcc acatatgaga    900
ttagggatat a                                                         911
```

```
<210> SEQ ID NO 170
<211> LENGTH: 42
<212> TYPE: PRT
<213> ORGANISM: Saccharum officinarum

<400> SEQUENCE: 170
```

Asp Cys Arg Val Cys Leu Val Arg Phe Glu Pro Glu Ser Val Val Asn
1               5                   10                  15

Arg Leu Pro Cys Gly His Leu Phe His Arg Ala Cys Leu Glu Thr Trp
            20                  25                  30

Leu Asp Tyr Asp His Ala Thr Cys Pro Leu
        35                  40

```
<210> SEQ ID NO 171
<211> LENGTH: 126
<212> TYPE: DNA
<213> ORGANISM: Saccharum officinarum

<400> SEQUENCE: 171
gactgccgcg tgtgcctggt gcggttcgag ccggagtcgg tggtgaaccg gctcccctgc    60
ggtcacctct ccaccgcgc ctgcctcgag acctggctcg actacgacca cgccacctgc   120
ccgctc                                                              126
```

```
<210> SEQ ID NO 172
<211> LENGTH: 75
<212> TYPE: PRT
<213> ORGANISM: Saccharum officinarum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 172
```

Gly Ala Gly Gly Gly Gly Xaa Asp Cys Arg Val Cys Leu Val Arg Phe
1               5                   10                  15

Glu Pro Glu Ser Val Val Asn Arg Leu Pro Cys Gly His Leu Phe His
            20                  25                  30

Arg Ala Cys Leu Glu Thr Trp Leu Asp Tyr Asp His Ala Thr Cys Pro
        35                  40                  45

Leu Cys Arg His Arg Leu Leu Pro Pro Ala Ala Asp Asp Glu Leu Ser
    50                  55                  60

Lys Thr Ile Ala Ala Pro Arg Leu Val Arg Phe
65                  70                  75

```
<210> SEQ ID NO 173
<211> LENGTH: 225
<212> TYPE: DNA
<213> ORGANISM: Saccharum officinarum
<220> FEATURE:
<221> NAME/KEY: misc_feature
<222> LOCATION: (19)..(19)
<223> OTHER INFORMATION: n is a, c, g, or t

<400> SEQUENCE: 173
ggcgcgggag ggggaggtnc cgactgccgc gtgtgcctgg tgcggttcga gccggagtcg    60
```

```
gtggtgaacc ggctcccctg cggtcacctc ttccaccgcg cctgcctcga gacctggctc    120
gactacgacc acgccacctg cccgctctgt cgccaccgcc tcctccctcc cgccgcagac    180
gacgagctct caaagaccat cgcggcgccc cgcctcgtcc ggttc                    225

<210> SEQ ID NO 174
<211> LENGTH: 494
<212> TYPE: DNA
<213> ORGANISM: Saccharum officinarum
<220> FEATURE:
<221> NAME/KEY: misc_feature
<222> LOCATION: (476)..(476)
<223> OTHER INFORMATION: n is a, c, g, or t

<400> SEQUENCE: 174
agccaacagt gtttttcagc cggctttaaa cgagccaaag cctgtacaca gacactgctg     60
cgaggtgcag agtgctccta cgcctacatc atcagagcac tccgccagta tttacagtac    120
agcaccaaac acgagcaacc aagacgagag agagagatga acaaaaacga agaaaaggaa    180
aggtactagt cctaatcgag agctaatcag gtaattggag cctcttaatt cctaagcagg    240
actggagttt ggagatccgt ctgtctctag aaccggacga ggcggggcgc cgcgatggtc    300
tttgagagct cgtcgtctgc ggcgggaggg aggaggcggt ggcgacagag cgggcaggtg    360
gcgtggtcgt agtcgagcca ggtctcgagg caggcgcggt ggaagaggtg accgcagggg    420
agccggttca ccaccgactc cggctcgaac cgcaccaggc acacgcggca gtcggnacct    480
ccccctcccg cgcc                                                      494

<210> SEQ ID NO 175
<211> LENGTH: 494
<212> TYPE: DNA
<213> ORGANISM: Saccharum officinarum
<220> FEATURE:
<221> NAME/KEY: misc_feature
<222> LOCATION: (476)..(476)
<223> OTHER INFORMATION: n is a, c, g, or t

<400> SEQUENCE: 175
agccaacagt gtttttcagc cggctttaaa cgagccaaag cctgtacaca gacactgctg     60
cgaggtgcag agtgctccta cgcctacatc atcagagcac tccgccagta tttacagtac    120
agcaccaaac acgagcaacc aagacgagag agagagatga acaaaaacga agaaaaggaa    180
aggtactagt cctaatcgag agctaatcag gtaattggag cctcttaatt cctaagcagg    240
actggagttt ggagatccgt ctgtctctag aaccggacga ggcggggcgc cgcgatggtc    300
tttgagagct cgtcgtctgc ggcgggaggg aggaggcggt ggcgacagag cgggcaggtg    360
gcgtggtcgt agtcgagcca ggtctcgagg caggcgcggt ggaagaggtg accgcagggg    420
agccggttca ccaccgactc cggctcgaac cgcaccaggc acacgcggca gtcggnacct    480
ccccctcccg cgcc                                                      494

<210> SEQ ID NO 176
<211> LENGTH: 49
<212> TYPE: PRT
<213> ORGANISM: Saccharum officinarum

<400> SEQUENCE: 176

Asp Cys Ser Val Cys Leu Ser Gly Phe Val Ala Lys Ala Val Val Asn
1               5                   10                  15

Arg Leu Pro Cys Gly His Leu Phe His Arg Ala Cys Leu Glu Thr Trp
```

```
                  20                  25                  30

Leu Arg Tyr Glu Arg Ala Thr Cys Pro Leu Cys Arg Ala Asn Val Pro
            35                  40                  45

Leu

<210> SEQ ID NO 177
<211> LENGTH: 149
<212> TYPE: DNA
<213> ORGANISM: Saccharum officinarum

<400> SEQUENCE: 177
gactgcagcg tgtgcctgtc cgggttcgtg gcgaaggccg tggtgaaccg cctcccctgc    60
ggccacctct tccaccgcgc ctgcctcgag acctggctcc ggtacgagcg cgccacgtgc   120
ccgctctgcc gcgccaacgt gcccctccc                                     149

<210> SEQ ID NO 178
<211> LENGTH: 163
<212> TYPE: PRT
<213> ORGANISM: Saccharum officinarum

<400> SEQUENCE: 178

Met Gly Ile Ser Ser Met Pro Glu Pro Arg Asp Ser Leu Leu Trp Tyr
1               5                   10                  15

Leu Val Tyr Asn Thr Val Ile Ser Ile Thr Ala Leu Ala Gly Leu Val
            20                  25                  30

Arg Lys Ala Leu Val Phe Leu Asp Leu Gln Ala Pro Ala Leu Pro Val
        35                  40                  45

Gly Gly Asp Asp Ala Ala Gly Gly Arg Leu Val Ala Ser Gly Pro Gly
    50                  55                  60

Leu Arg Leu Cys Leu Ala Asp Arg Phe Leu Arg Ala Phe Arg Pro Ala
65                  70                  75                  80

Leu Tyr Gly Val Leu Val Ser Thr Ser Thr Thr Cys Ser Ala Ala Asp
                85                  90                  95

Ala Asp Gly Asp Asp Cys Ser Val Cys Leu Ser Gly Phe Val Ala Lys
            100                 105                 110

Ala Val Val Asn Arg Leu Pro Cys Gly His Leu Phe His Arg Ala Cys
        115                 120                 125

Leu Glu Thr Trp Leu Arg Tyr Glu Arg Ala Thr Cys Pro Leu Cys Arg
    130                 135                 140

Ala Asn Val Pro Leu Pro Pro Glu Glu Thr Pro Val Leu Arg Tyr Pro
145                 150                 155                 160

Glu Phe Glu

<210> SEQ ID NO 179
<211> LENGTH: 489
<212> TYPE: DNA
<213> ORGANISM: Saccharum officinarum

<400> SEQUENCE: 179
ggggatctcg agcatgccgg agccacggga cagcctgctg tggtacctgg tgtacaacac    60
ggtgatctcg atcacggcgc tggcggggct ggtgcgcaag gcgctggtgt tcctggacct   120
ccaggccccc gcgctgccag tcggcgggga cgacgccgcc gggggccgcc tcgtggcgtc   180
ggggcccggc ctgcgcctgt gcctggcgga ccggttcctg agggcgttcc ggccggcgct   240
gtacggggtg ctggtgtcga cgtcgacgac gtgcagcgcg gcggacgcgg acggcgacga   300
```

```
ctgcagcgtg tgcctgtccg ggttcgtggc gaaggccgtg gtgaaccgcc tcccctgcgg        360
ccacctcttc caccgcgcct gcctcgagac ctggctccgg tacgagcgcg ccacgtgccc        420
gctctgccgc gccaacgtgc ccctcccgcc cgaagagacg cccgtgctcc gctacccgga        480
gttcgagtg                                                                489
```

<210> SEQ ID NO 180
<211> LENGTH: 43
<212> TYPE: PRT
<213> ORGANISM: Medicago truncatula

<400> SEQUENCE: 180

```
Asp Cys Ser Val Cys Leu Thr Gln Phe Glu Pro Glu Ser Glu Ile Asn
1               5                   10                  15

Tyr Cys Ile Ser Cys Gly His Val Phe His Lys Val Cys Leu Glu Lys
            20                  25                  30

Trp Leu Asp Tyr Trp Asn Ile Thr Cys Pro Leu
        35                  40
```

<210> SEQ ID NO 181
<211> LENGTH: 155
<212> TYPE: PRT
<213> ORGANISM: Medicago truncatula

<400> SEQUENCE: 181

```
Met Gly Leu Ser Ser Leu Pro Ala Gln Ser Glu Gly Val Leu Cys Ile
1               5                   10                  15

Ile Leu Val Asn Thr Ala Met Ser Ile Ser Phe Lys Gly Ile Ile
            20                  25                  30

Arg Thr Ile Leu His Ile Val Gly Ile Ala Ser Pro Ser Ser Ser
        35                  40                  45

Pro Ser Gln Asp Tyr Ile Pro Gln Asn Ile Pro Glu Ser Tyr Glu Ile
    50                  55                  60

His Leu Ser Pro Ser Asp Asp Phe Val Glu Glu Phe Arg Ser Arg Thr
65                  70                  75                  80

Pro Thr Leu Arg Phe Asp Ser Val Cys Asn Ser Cys Lys Glu Pro Glu
                85                  90                  95

His Asp Cys Ser Val Cys Leu Thr Gln Phe Glu Pro Glu Ser Glu Ile
            100                 105                 110

Asn Tyr Cys Ile Ser Cys Gly His Val Phe His Lys Val Cys Leu Glu
        115                 120                 125

Lys Trp Leu Asp Tyr Trp Asn Ile Thr Cys Pro Leu Cys Arg Ser Pro
    130                 135                 140

Leu Ile Pro Glu Asp Asp Ala Ser Cys Leu Trp
145                 150                 155
```

<210> SEQ ID NO 182
<211> LENGTH: 144
<212> TYPE: DNA
<213> ORGANISM: Medicago truncatula

<400> SEQUENCE: 182

```
gattgctcag tgtgtctcac tcaatttgaa cctgaatcag agataaacta ttgcatatca         60
tgtggccatg ttttcataa agtgtgtttg gagaagtggt tggattattg aacattaca         120 tgtccacttt gtaggagtcc ttta                                               144
```

<210> SEQ ID NO 183

<211> LENGTH: 465
<212> TYPE: DNA
<213> ORGANISM: Medicago truncatula

<400> SEQUENCE: 183

```
atgggcctat caagtcttcc agcacaatct gaaggagtgt tatgcatcat tctagtaaac    60
actgccatgt caatatccat attcaaaggc attataagga ctatcctgca cattgttggt   120
atcattgctt caccatcttc ctctccttcc caagactaca ttcctcaaaa catacctgag   180
tcatatgaaa tccatctaag tccttcagat gatttcgttg aagagttcag aagcagaaca   240
ccaacactta ggtttgatag tgtgtgtaat agctgcaaag aacctgaaca tgattgctca   300
gtgtgtctca ctcaatttga acctgaatca gagataaact attgcatatc atgtggccat   360
gttttcata aagtgtgttt ggagaagtgg ttggattatt ggaacattac atgtccactt   420
tgtaggagtc ctttaattcc tgaagatgat gcatcttgct tatgg                   465
```

<210> SEQ ID NO 184
<211> LENGTH: 91
<212> TYPE: PRT
<213> ORGANISM: Cucumis melo

<400> SEQUENCE: 184

```
Cys Ala Val Cys Leu Asn Glu Phe Glu Asp Asp Glu Thr Leu Arg Leu
1               5                   10                  15
Ile Pro Lys Cys Asp His Val Phe His Pro Glu Cys Ile Asp Ala Trp
                20                  25                  30
Leu Ala Ser His Ser Thr Cys Pro Val Cys Arg Ala Asn Glu Cys Ala
            35                  40                  45
Val Cys Leu Asn Glu Phe Glu Asp Asp Glu Thr Leu Arg Leu Ile Pro
        50                  55                  60
Lys Cys Asp His Val Phe His Pro Glu Cys Ile Asp Ala Trp Leu Ala
65                  70                  75                  80
Ser His Ser Thr Cys Pro Val Cys Arg Ala Asn
                85                  90
```

<210> SEQ ID NO 185
<211> LENGTH: 129
<212> TYPE: DNA
<213> ORGANISM: Cucumis melo

<400> SEQUENCE: 185

```
gaatgcgctg tttgtttgaa tgaatttgaa gatgatgaaa cgctgcgttt aatccctaaa    60
tgtgatcatg tgtttcaccc tgaatgtatt gatgcttggt tggcttctca ctctacttgc   120
cctgtttgt                                                           129
```

<210> SEQ ID NO 186
<211> LENGTH: 379
<212> TYPE: PRT
<213> ORGANISM: Cucumis melo

<400> SEQUENCE: 186

```
Met Pro Ser Leu Thr Ala Pro His Gly Leu Pro Leu Phe Leu Phe Leu
1               5                   10                  15
Leu Leu Phe Leu Phe Ser Ser Val Ser Ala Gln Phe Gln Pro Ala Pro
                20                  25                  30
Asp Pro Arg Ser Asp Pro Tyr Gln Tyr Arg Leu Ser Gly Ser Met Ala
            35                  40                  45
```

Val Ile Ile Val Ile Leu Ile Ala Ala Leu Phe Phe Met Ala Phe Phe
 50                  55                  60

Ser Val Tyr Ile Arg His Cys Asn Asp Ser Pro Ser Asn Thr Val Arg
 65                  70                  75                  80

Pro Ile Thr Ala Ala Gly Arg Ser Arg Ala Thr Arg Gly Leu
                 85                  90                  95

Asp Pro Ala Val Ile Glu Thr Phe Pro Thr Leu Ile Tyr Ser Asp Val
                100                 105                 110

Lys Glu His Lys Ile Gly Lys Ser Ala Leu Glu Cys Ala Val Cys Leu
                115                 120                 125

Asn Glu Phe Glu Asp Asp Glu Thr Leu Arg Leu Ile Pro Lys Cys Asp
130                 135                 140

His Val Phe His Pro Glu Cys Ile Asp Ala Trp Leu Ala Ser His Ser
145                 150                 155                 160

Thr Cys Pro Val Cys Arg Ala Asn Leu Ser Pro Gln Pro Thr Asp Ser
                165                 170                 175

Val His Arg Ala Asp Asp Ser Asn Ala Val Val Asn Ser Asp Thr Asp
                180                 185                 190

Gly Gly Asp Ile Glu Ala Gln Ser Asn Asp Val Val Ser Glu Thr Thr
                195                 200                 205

Ala Pro Pro Thr Val Gln Ile Gln Thr Glu Ser Glu Leu Ser Thr Thr
210                 215                 220

Thr Ser Asn Lys Ala Leu Asn Arg Thr Arg Thr Arg Gly Ser Arg Ser
225                 230                 235                 240

Asn Arg Leu Arg Trp Leu Phe Pro Arg Ser His Ser Thr Gly His Ser
                245                 250                 255

Leu Val Gln Pro Gly Glu Asp Thr Glu Arg Phe Thr Leu Arg Leu Pro
                260                 265                 270

Val Glu Ile Arg Lys Gln Val Val Asn Arg Lys Leu His Arg Ala Thr
                275                 280                 285

Ser Met Val Val Leu Ala Arg Gln Ser Ser Ser Met Arg Gly Tyr Arg
                290                 295                 300

Phe Gly Ser Gly Glu Gly Ser Ser Arg Gly Lys Tyr Tyr Arg Arg Leu
305                 310                 315                 320

Glu Arg Leu Asp Arg Thr Ser Lys Ser Asp Arg Trp Val Leu Ser Met
                325                 330                 335

Thr Pro Pro Phe Phe Thr Arg Met Ser Ser Met Lys Thr Pro Arg Gly
                340                 345                 350

Gly Ser Asn Arg Ala Glu Pro Gly Ser Gly Arg Glu Leu Gly Gln Gly
                355                 360                 365

Asn Thr Ala Val Asp Ser Ser Arg Leu Pro Val
                370                 375

<210> SEQ ID NO 187
<211> LENGTH: 1140
<212> TYPE: DNA
<213> ORGANISM: Cucumis melo

<400> SEQUENCE: 187
atgccctctc tcaccgcccc ccatggcctt ccctcttcc tcttcctcct cctcttcctc    60
ttctcctccg tctccgccca gttccagccc gcccccgacc ccagatcaga cccttaccag   120
taccgcctca gcggttccat ggccgtcatc atcgtcatcc tcatcgccgc tctcttcttc   180
atggctttct tctccgtcta catccgtcac tgcaacgatt caccatccaa caccgtccgc   240

-continued

```
cctatcaccg ccgccgccgg ccgctcccgt cgcgcaaccc gcggtctcga tccggcggta    300
attgaaacgt ttccgactct gatttactcc gatgtgaaag agcataaaat tggtaaaagt    360
gccctagaat gcgctgtttg tttgaatgaa tttgaagatg atgaaacgct gcgtttaatc    420
cctaaatgtg atcatgtgtt tcaccctgaa tgtattgatg cttggttggc ttctcactct    480
acttgccctg tttgtcgagc taatttgtct ccccaaccca ctgactccgt ccaccgagct    540
gacgattcca acgctgtcgt taactccgat accgacggag gtgatattga agctcagtcc    600
aacgacgttg tttcagagac gacggctcca cctacggttc agatacaaac ggaatcagag    660
ctcagtacga cgacaagtaa caaggcgttg aatcggacac gtacgcgggg atcccgatcc    720
aatagattgc ggtggctatt tccccggtct cactcgaccg gccactcctt ggttcagcct    780
ggggaagaca ctgagcggtt tactctccgg ttgccagtgg agataaggaa acaagtggtg    840
aaccggaagc tgcaccgggc gactagtatg gtggttctgg cgaggcagag cagttcgatg    900 agggggatacc gatttggttc aggtgaaggg agtagtcgag ggaagtatta ccggaggctt    960
gagcggttgg acagaacatc gaagtcggac cggtgggtgt tgtcaatgac accgccgttt   1020
tttacgcgta tgtcgtcgat gaagactccg cgtggaggga gtaaccgtgc tgaacccggt   1080
tcgggccgag aacttggaca ggggaatacc gcggtcgatt caagtaggct tccggtctga   1140
```

<210> SEQ ID NO 188
<211> LENGTH: 47
<212> TYPE: PRT
<213> ORGANISM: Medicago sativa

<400> SEQUENCE: 188

```
Glu Cys Ala Val Cys Leu Met Glu Phe Glu Asp Thr Glu Thr Leu Arg
1               5                   10                  15

Leu Ile Pro Lys Cys Asp His Val Phe His Pro Glu Cys Ile Asp Glu
            20                  25                  30

Trp Leu Ser Ser His Thr Thr Cys Pro Val Cys Arg Ala Asn Leu
        35                  40                  45
```

<210> SEQ ID NO 189
<211> LENGTH: 361
<212> TYPE: PRT
<213> ORGANISM: Medicago sativa

<400> SEQUENCE: 189

```
Met Lys Lys Asp Pro Thr Asn Leu Phe Ile Leu Phe Gly Ile Leu Leu
1               5                   10                  15

Leu Ser Ile Thr Lys Thr Gln Ser Gln Ala Thr Asn Asp Asn Pro Thr
            20                  25                  30

Asn Pro Asn Phe Asn Gln Glu Phe Asn Pro Ser Phe Ala Ile Ile Ile
        35                  40                  45

Val Ile Leu Val Ala Ala Leu Phe Leu Met Gly Phe Ser Ile Tyr
    50                  55                  60

Ile Arg Arg Cys Ser Asp Ser Pro Ser Asn Asn Leu Leu Leu Pro
65                  70                  75                  80

Ile Thr Asn Gly Arg Arg Ala Val Ala Arg Gly Leu Asp Pro Ser Val
                85                  90                  95

Ile Glu Thr Phe Pro Ile Leu Glu Tyr Ser Glu Val Lys Ile His Lys
            100                 105                 110

Ile Gly Lys Asp Val Leu Glu Cys Ala Val Cys Leu Met Glu Phe Glu
        115                 120                 125
```

```
Asp Thr Glu Thr Leu Arg Leu Ile Pro Lys Cys Asp His Val Phe His
    130                 135                 140

Pro Glu Cys Ile Asp Glu Trp Leu Ser Ser His Thr Thr Cys Pro Val
145                 150                 155                 160

Cys Arg Ala Asn Leu Val Pro Gln Pro Gly Asp Ser Val His Gly Val
                165                 170                 175

Pro Glu Ser Gln Gln Gln Asp Val Glu Ala Gln Asn Asp Ala Val Gln
            180                 185                 190

Leu Pro Thr Glu Ser Asp Ser Val Leu Leu Ala Pro Glu Val Ile Ser
        195                 200                 205

Leu Asn Lys Thr Leu Asn Arg Asn Arg Thr Arg Gly Ser Gln Ser Asn
210                 215                 220

Arg Pro Arg Arg Phe Pro Arg Ser His Ser Thr Gly His Ser Leu Ile
225                 230                 235                 240

Gln Pro Gly Glu Asn Thr Asp Arg Phe Thr Leu Lys Leu Pro Asn Lys
                245                 250                 255

Val Arg Lys Gln Ile Met Ser Arg Gln Leu Arg Ala Arg Ser Leu
            260                 265                 270

Ile Thr Leu Pro Arg Glu Ser Ser Arg His Gly Tyr Arg Thr Gly
        275                 280                 285

Gly Glu Gly Ser Asn Arg Gly Lys Ser Leu Arg Leu Asp Leu Ser
290                 295                 300

Phe Lys Ser Asp Arg Trp Ile Phe Asn Arg Ala Pro Ser Phe Leu Ala
305                 310                 315                 320

Arg Ala Leu Ser Phe Arg Ser Pro Lys Pro Lys Val Asn Asn Ser Asp
                325                 330                 335

Asp Asp Glu Gly Thr Ser Ser Ala Ala Ala Pro Ile Met Pro Ser Ser
            340                 345                 350

Ala Val Asp Ser Ala Arg Pro Gln Ile
        355                 360

<210> SEQ ID NO 190
<211> LENGTH: 141
<212> TYPE: DNA
<213> ORGANISM: Medicago sativa

<400> SEQUENCE: 190
gagtgtgccg tttgtttaat ggaattcgaa gatactgaaa cgctgcgttt gattccaaag    60
tgtgatcatg tttttcaccc tgagtgtatt gacgagtggt tatcttctca cacaacgtgt   120
cccgtttgtc gcgcgaatct c                                              141

<210> SEQ ID NO 191
<211> LENGTH: 1086
<212> TYPE: DNA
<213> ORGANISM: Medicago sativa

<400> SEQUENCE: 191
atgaagaaag atccaaccaa tttattcatc ctctttggaa tccttcttct ctcaatcaca    60
aaaacccaat cccaagctac taacgataac cccacaaatc caaatttcaa ccaagaattt   120
aacccttcct tcgctataat catagtcatt ttagtagctg ctctttttct catgggcttt   180
ttctccatct acatccgtcg ctgctccgat tcaccttcct ccaacaacct ccttctcccc   240
atcaccaacg gccgtagagc ggtggcgcgt ggactcgatc catcagtaat cgaaactttc   300
ccgattcttg aatactccga agtcaagatc cataagatcg gaaagatgt tcttgagtgt   360
```

```
gccgtttgtt taatggaatt cgaagatact gaaacgctgc gtttgattcc aaagtgtgat    420
catgtttttc accctgagtg tattgacgag tggttatctt ctcacacaac gtgtcccgtt    480
tgtcgcgcga atctcgttcc acaacctggt gactcagttc acggcgttcc tgagtcacag    540
caacaagacg ttgaagctca aaacgacgcg gttcaattac cgacggaatc tgactcagta    600
ttacttgctc cagaagtgat ttcgttgaat aaaacactga accggaaccg tacgcgtgga    660
tctcaatcaa accggccgcg tcgttttcca cggtctcact cgaccggaca ttctttaatc    720
caaccgggtg aaaacacgga ccggttcact ttgaaactgc ctaataaggt taggaaacag    780
ataatgagcc ggcaattgca acgagcgaga agtttgatta cgttaccaag agaaagtagc    840
tcaagacatg gctaccgaac cggaggtgaa ggaagtaata gaggaaaaag tttgaggcgg    900
ttggacctga gttttaaatc agaccggtgg atatttaata gagcaccgtc gtttttagca    960
agggcattgt cgtttaggtc tccaaagcca aaagtcaata atagcgatga tgatgaagga   1020
acttcttctg cagctgctcc tatcatgcca tcctctgctg ttgactctgc acgccctcag   1080
atttga                                                              1086

<210> SEQ ID NO 192
<211> LENGTH: 45
<212> TYPE: PRT
<213> ORGANISM: Medicago sativa

<400> SEQUENCE: 192

Asp Cys Ala Val Cys Leu Ser Lys Phe Glu Gln Asn Asp Leu Leu Arg
1               5                   10                  15

Leu Leu Pro Leu Cys Cys His Ala Phe His Thr Glu Cys Ile Asp Ala
            20                  25                  30

Trp Leu Ala Ser Asn Gln Thr Cys Pro Leu Cys Arg Ser
        35                  40                  45

<210> SEQ ID NO 193
<211> LENGTH: 126
<212> TYPE: DNA
<213> ORGANISM: Medicago sativa

<400> SEQUENCE: 193
gactgcgccg tttgcttatc aaagttcgag caaaacgatc tcctccgtct tcttcctctc     60
tgctgtcacg catttcacac cgaatgcatt gacgcgtggt tagcttcaaa tcaaacctgt    120
ccgtta                                                               126

<210> SEQ ID NO 194
<211> LENGTH: 295
<212> TYPE: PRT
<213> ORGANISM: Medicago sativa

<400> SEQUENCE: 194

Met Gly Asn Thr Asn Ser Ser His Asn Leu Leu Ile Thr Val Thr Val
1               5                   10                  15

Phe Ala Val Thr Val Thr Val Phe Phe Ile Leu Tyr Phe Ile Leu Arg
            20                  25                  30

Arg Arg Arg Phe Ser Pro Ser Ser Ser Thr Val Arg Val Ser Pro
        35                  40                  45

Val Thr Pro Thr Ser Ser Thr Ser Ser Val Val Asp Ser Leu Pro
    50                  55                  60

Ile Phe Thr Phe Ser Ser Ile Lys Arg Arg Ser Ser Thr Val Val Ser
65                  70                  75                  80
```

```
Gly Asp Cys Ala Val Cys Leu Ser Lys Phe Glu Gln Asn Asp Leu Leu
                85                  90                  95

Arg Leu Leu Pro Leu Cys Cys His Ala Phe His Thr Glu Cys Ile Asp
            100                 105                 110

Ala Trp Leu Ala Ser Asn Gln Thr Cys Pro Leu Cys Arg Ser Ser Val
        115                 120                 125

Phe Val Ser Glu Ser Glu Ile Met Lys Ile Phe Arg Ser Ser Ser Thr
    130                 135                 140

Ser Ser Gly Asn Asn Ser Phe Arg Leu Glu Ile Gly Asn Ile Ser His
145                 150                 155                 160

Arg Arg Glu Ala Thr Ala Thr Asp Asn Asn Asn Asn Asn Asn Asn Val
                165                 170                 175

Ala Gly Glu Thr Asp Arg Arg Thr Tyr Ser Val Gly Ala Phe Asp Tyr
            180                 185                 190

Phe Val Asp Glu Glu Ala Glu Ile Pro Val Gly Asn Thr Asn Arg Arg
        195                 200                 205

Ile Phe Ser Gly Glu Lys Asp Asp Ala Ala Val Leu Ser Val Glu Val
    210                 215                 220

Glu Thr Pro Val Asp Ser Gln Ala Ser Leu Ile Gly Glu Gly Asn Trp
225                 230                 235                 240

Leu Lys Asp Tyr Val Asp Gly Leu Thr Arg Val Met Ser Phe Arg Gly
                245                 250                 255

Ser Gly Ser Ser Arg Arg Asn Asp Val Val Ala Gly Val Gly Asp Phe
            260                 265                 270

Asp Val Glu Ala Asn Gly Asn Gly Phe Gly Glu Ile Ser Glu Met
        275                 280                 285

Phe Arg Trp Ile Ser Gly Val
    290                 295

<210> SEQ ID NO 195
<211> LENGTH: 898
<212> TYPE: DNA
<213> ORGANISM: Medicago sativa

<400> SEQUENCE: 195
```

| | | | | | |
|---|---|---|---|---|---|
| atgggaaaca | caaattcctc | acacaacctt | ctcataaccg | taaccgtttt | cgccgttacc | 60 |
| gtcaccgttt | tcttcattct | ctacttcatc | ctccgtcgtc | gtcgtttctc | tccgtcatcc | 120 |
| tcctccactg | ttagagtttc | tccggtgacg | cctacttcat | caacctcatc | ttccgtcgtt | 180 |
| gattctcttc | cgattttcac | tttctcctcc | atcaaacgcc | gttcctccac | cgtcgtctcc | 240 |
| ggcgactgcg | ccgtttgctt | atcaaagttc | gagcaaaacg | atctcctccg | tcttcttcct | 300 |
| ctctgctgtc | acgcatttca | caccgaatgc | attgacgcgt | ggttagcttc | aaatcaaacc | 360 |
| tgtccgttat | gtcgatcatc | ggtattcgta | tcggaatcgg | agattatgaa | gattttccgt | 420 |
| tcatcatcca | cttcttccgg | taacaacagc | ttccgtttag | ataggtaa | catcagccac | 480 |
| cgccgtgaag | caaccgcaac | tgacaataac | aataacaata | caatgtcgc | cggagaaact | 540 |
| gaccggagga | catactccgt | cggcgcgttc | gattatttcg | tcgacgagga | agctgagatt | 600 |
| ccggttggaa | acactaatcg | gagaatattt | tccggtgaaa | aggacgatgc | ggcggtgctt | 660 |
| tcggtggagg | tggagactcc | ggtggattct | caggcgagtt | tgatcggtga | aggtaactgg | 720 |
| ttgaaggatt | acgttgatgg | tttaacaaga | gtgatgtcgt | ttcgaggttc | tggaagtagt | 780 |
| agaagaaacg | acgtcgtagc | tggtgttgga | gattttgatg | ttgaagctaa | tggtaatgga | 840 | tttggtgaag agattagtga gatgtttagg tggatttcag gggtttaaat gggaatat            898

<210> SEQ ID NO 196
<211> LENGTH: 53
<212> TYPE: PRT
<213> ORGANISM: Oryza sativa

<400> SEQUENCE: 196

Glu Cys Ala Val Cys Leu Asp Glu Phe Ala Ala Gly Asp Val Leu Ala
1               5                   10                  15

His Leu Pro Cys Gly His Arg Phe His Trp Ala Cys Ala Leu Pro Trp
            20                  25                  30

Leu Glu Ala Gly Ala Ala Pro Arg Ser Cys Pro Phe Cys Arg Ala Ala
        35                  40                  45

Val Asp Thr Pro Pro
    50

<210> SEQ ID NO 197
<211> LENGTH: 149
<212> TYPE: DNA
<213> ORGANISM: Oryza sativa

<400> SEQUENCE: 197
gagtgcgccg tgtgcctgga cgagttcgcc gccggcgacg tcctggccca tctcccctgc     60
ggccaccgct ccactgggc ctgcgcgctc ccctggctcg aggccggcgc cgcccctcgc    120
tcctgcccat tctgccgcgc cgccgtcga                                      149

<210> SEQ ID NO 198
<211> LENGTH: 268
<212> TYPE: PRT
<213> ORGANISM: Oryza sativa

<400> SEQUENCE: 198

Met Glu Glu Arg Tyr Ser Tyr His Pro Leu Leu Leu Leu His Leu
1               5                   10                  15

Leu Pro Gln Met Ala Ala Asp His Ala Ala Phe Pro Ala Leu Ala Arg
            20                  25                  30

Phe Leu Ala Arg Lys Arg Thr Arg Thr Ala Ile Ala Met Val Ile Met
        35                  40                  45

Ala Ala Met Leu Pro Gly Val Glu Cys Ala Arg Arg Arg Leu Arg
    50                  55                  60

Gln Gly Gly Gly Ala Gly Ala Asp Ala Ala Ala Gly Gly Gly Thr
65                  70                  75                  80

Arg Arg Ser Ser Phe Cys Val His Ala Ala Gly His Gly Gly Gln
                85                  90                  95

Thr Cys Gly Gly Ala Ala Ala Asn His Ser Gly Lys Gln Arg Ser Ser
            100                 105                 110

Val Met Glu Leu Ile His Gly Trp Ser Leu Asp Ser Asn Ala Arg Glu
        115                 120                 125

Ala Lys Glu Arg Leu Asp Gln Lys Leu Arg Ser Gln Arg Glu Ser Val
    130                 135                 140

Ile Lys Arg His His Ser Thr Gly Ser Ile Lys Leu Asn Arg Gly Ala
145                 150                 155                 160

Thr Gly Gly Gly Gly Gly Gly Arg Ser Thr Ala Thr Ala Ala Met
                165                 170                 175

Gly Val Gln Arg Glu Val Tyr Ser Arg Lys Gly Val Met Arg Arg Leu
            180                 185                 190

Met Arg Trp Ser Arg Leu Arg Trp Asp Ala Ala Glu Gln Ala Glu Cys
            195                 200                 205

Ala Val Cys Leu Asp Glu Phe Ala Ala Gly Asp Val Leu Ala His Leu
        210                 215                 220

Pro Cys Gly His Arg Phe His Trp Ala Cys Ala Leu Pro Trp Leu Glu
225                 230                 235                 240

Ala Gly Ala Ala Pro Arg Ser Cys Pro Phe Cys Arg Ala Ala Val Asp
                245                 250                 255

Thr Pro Pro Pro Pro Pro Pro Ala Cys Ser Ser
                260                 265

<210> SEQ ID NO 199
<211> LENGTH: 807
<212> TYPE: DNA
<213> ORGANISM: Oryza sativa

<400> SEQUENCE: 199
atggaggagc gctactcgta ccacccgctg cttctcctcc tccaccttct cccacaaatg     60
gccgccgacc atgctgcttt ccccgccctc gctagatttc ttgcccgcaa gcgcactcgc    120
actgcgattg cgatggtgat catggcggcg atgctgcccg gggtggagtg cgcgcggcgg    180
cggcggctcc ggcagggagg gggagctggg gcggatgcgg cggcggctgg cggaggtacg    240
aggcggtcgt cgttctgcgt gcacgcggcc gggcatggtg gtggtcagac atgtggcggc    300
gccgccgcga atcattccgg caagcagagg agtagtgtga tggagctcat ccatgggtgg    360
tcgctggaca gcaatgcccg ggaggcgaag gagcggctgg accagaagct gaggagccag    420
agggaatccg tcatcaagag gcatcacagc acgggaagca tcaagctgaa cagaggcgcc    480
accggcggcg gcgaggggg cgggagatcg acggcgacgg cggcgatggg ggtgcagagg    540
gaggtgtact cgaggaaagg ggtgatgcgg cggctgatgc ggtggagccg gctgcggtgg    600
gacgcggcgg agcaggcgga gtgcgccgtg tgcctggacg agttcgccgc cggcgacgtc    660
ctggcccatc tccctgcgg ccaccgcttc cactgggcct gcgcgctccc ctggctcgag    720
gccggcgccg ccctcgctc ctgcccattc tgccgcgccg ccgtcgacac gccgccgccg    780
ccgccgccgc cggcgtgctc gtcctag                                       807

<210> SEQ ID NO 200
<211> LENGTH: 47
<212> TYPE: PRT
<213> ORGANISM: Beta vulgaris

<400> SEQUENCE: 200

Glu Glu Cys Ala Val Cys Leu Asp Glu Phe Lys Val Gly Glu Asn Leu
1               5                   10                  15

Val Asn Leu Pro Cys Ala His Arg Phe His Ser Arg Cys Leu Val Pro
            20                  25                  30

Trp Leu His Thr Asn Ala Gln Cys Pro Cys Cys Arg Thr Ser Ile
        35                  40                  45

<210> SEQ ID NO 201
<211> LENGTH: 138
<212> TYPE: DNA
<213> ORGANISM: Beta vulgaris

<400> SEQUENCE: 201
tgtgcagttt gtttggatga atttaaggtg ggtgaaaatc tggtgaattt accttgtgct     60
cattgtagat ttcattccag gtgtttggtg ccttggcttc acaccaatgc ccaatgccct    120
tgctgcagga cctccatc    138

<210> SEQ ID NO 202
<211> LENGTH: 186
<212> TYPE: PRT
<213> ORGANISM: Beta vulgaris

<400> SEQUENCE: 202

Met Ala Gly Met Leu Pro Gly Val Glu Ala Ala Arg Arg Arg Arg Phe
1               5                   10                  15

His Gln Ser Ser Gly Thr Asn Gly Asn Gly Ala Ser Pro Ser Ser Arg
            20                  25                  30

Arg Ser Ser Phe Ser Leu Phe Ser Pro Asn Ser Ser Thr Ser Phe Leu
        35                  40                  45

Ser His Ser Ala Asn Arg Thr Tyr His Asp Asp Glu Lys Leu Gly Gln
    50                  55                  60

Leu Ala Arg Gln Ala Lys Glu Arg Leu His Glu Lys Leu Arg Ala Gln
65                  70                  75                  80

Thr Lys Ser Leu Ile Arg Asn Asn Ser Asp Leu Ser Glu Glu Arg Val
                85                  90                  95

Asn Gly Arg Ser Arg Val Asn Thr Arg Tyr Glu Leu Lys Thr Glu Val
            100                 105                 110

Phe Gly Ser Lys Lys Asn Gly Gly Ala Lys Arg Leu Ile Gly Trp Ala
        115                 120                 125

Lys Leu Gly Trp Lys Ser Gly Glu Gln Glu Cys Ala Val Cys Leu
130                 135                 140

Asp Glu Phe Lys Val Gly Glu Asn Leu Val Asn Leu Pro Cys Ala His
145                 150                 155                 160

Arg Phe His Ser Arg Cys Leu Val Pro Trp Leu His Thr Asn Ala Gln
                165                 170                 175

Cys Pro Cys Cys Arg Thr Ser Ile Phe Ser
            180                 185

<210> SEQ ID NO 203
<211> LENGTH: 49
<212> TYPE: PRT
<213> ORGANISM: Beta vulgaris

<400> SEQUENCE: 203

Glu Ser Cys Ala Val Cys Leu His Glu Tyr Glu Ser Asp Asp Glu Val
1               5                   10                  15

Arg Arg Met Arg Asn Cys Arg His Met Phe His Arg Cys Cys Val Asp
            20                  25                  30

Arg Trp Ile Asp His Asp Arg Lys Thr Cys Pro Leu Cys Arg Lys Pro
        35                  40                  45

Leu

<210> SEQ ID NO 204
<211> LENGTH: 147
<212> TYPE: DNA
<213> ORGANISM: Beta vulgaris

<400> SEQUENCE: 204
gagagctgcg cggtgtgcct gcacgagtac gagagcgacg acgaggtgcg gaggatgaga    60
aactgccgcc acatgttcca ccggtgctgc gtggaccgat ggatcgacca cgatcgaaag   120
acgtgcccgt tgtgtaggaa gccgctg 147

<210> SEQ ID NO 205
<211> LENGTH: 174
<212> TYPE: PRT
<213> ORGANISM: Beta vulgaris

<400> SEQUENCE: 205

Met Gly Phe Pro Ala Gly Tyr Thr Glu Val Leu Leu Pro Lys Leu Phe
1               5                   10                  15

Leu Thr Ala Leu Ser Leu Leu Gly Phe Leu Arg Lys Ser Val Leu Ser
            20                  25                  30

Leu Leu Arg Leu Gly Leu Ala Ser Leu Ile Glu Pro Ala Ser Pro
        35                  40                  45

Leu Glu His Asp His Pro Glu Pro Gly Pro Ala Leu Ser Glu Ser Ser
    50                  55                  60

Ala Ala Ala Leu Ile Arg Glu Met Leu Pro Ala Val Thr Tyr Ala Glu
65                  70                  75                  80

Ala Ile Ala Ala Gly Pro Asp Glu Pro Gly Pro Ala Glu Ser Cys Ala
                85                  90                  95

Val Cys Leu His Glu Tyr Glu Ser Asp Asp Glu Val Arg Arg Met Arg
            100                 105                 110

Asn Cys Arg His Met Phe His Arg Cys Cys Val Asp Arg Trp Ile Asp
        115                 120                 125

His Asp Arg Lys Thr Cys Pro Leu Cys Arg Lys Pro Leu Val Pro His
    130                 135                 140

Glu Leu Gln Glu Asp Phe Asn Glu Lys Leu Trp Ala Ala Ser Gly Ile
145                 150                 155                 160

Pro Asp Phe Tyr Ser Glu Tyr Ser Pro Ile Thr Asn Phe Leu
                165                 170

<210> SEQ ID NO 206
<211> LENGTH: 522
<212> TYPE: DNA
<213> ORGANISM: Beta vulgaris

<400> SEQUENCE: 206
atggggtttc cagcaggata cacggaggtg ctcctcccca aactattcct gacagctctc      60
tccctcctcg gcttcctccg caagtccgtc tctcccctcc tccgcctcct cggcctcgcc     120
tccttaatcg agcccgcctc ccccctcgag cacgaccatc ccgagcccgg cccggccctc     180
tcggaatcct ccgcagcagc cctcatccgg gagatgctcc ccgccgtcac ctacgccgag     240
gcaatcgccg ccgggcccga cgagcccggc ccggcggaga gctgcgcggt gtgcctgcac     300
gagtacgaga gcgacgacga ggtgcggagg atgagaaact gccgccacat gttccaccgg     360
tgctgcgtgg accgatggat cgaccacgat cgaaagacgt gcccgttgtg taggaagccg     420
ctggtgccgc atgagttgca ggaggatttc aatgagaagc tttgggctgc ttctgggata     480
cctgattttt attctgaata ttctcctata actaatttct ta                       522

<210> SEQ ID NO 207
<211> LENGTH: 161
<212> TYPE: PRT
<213> ORGANISM: Beta vulgaris

<400> SEQUENCE: 207

Met Gly Phe Pro Ala Gly Tyr Thr Glu Val Leu Leu Pro Lys Leu Phe
1               5                   10                  15

```
Leu Thr Ala Leu Ser Leu Leu Gly Phe Leu Arg Lys Ser Val Leu Ser
            20                  25                  30

Leu Leu Arg Leu Leu Gly Leu Ala Ser Leu Ile Glu Pro Ala Ser Pro
        35                  40                  45

Leu Glu His Asp His Pro Glu Pro Gly Pro Ala Leu Ser Glu Ser Ser
    50                  55                  60

Ala Ala Ala Leu Ile Arg Glu Met Leu Pro Ala Val Thr Tyr Ala Glu
65                  70                  75                  80

Ala Ile Ala Ala Gly Pro Asp Glu Pro Gly Pro Ala Glu Ser Cys Ala
                85                  90                  95

Val Cys Leu His Glu Tyr Glu Ser Asp Asp Glu Val Arg Arg Met Arg
                100                 105                 110

Asn Cys Arg His Met Phe His Arg Cys Cys Val Asp Arg Trp Ile Asp
            115                 120                 125

His Asp Arg Lys Thr Cys Pro Leu Cys Arg Lys Pro Leu Val Pro His
        130                 135                 140

Glu Leu Gln Glu Asp Phe Asn Glu Lys Leu Trp Ala Ala Ser Trp Asp
145                 150                 155                 160

Thr
```

<210> SEQ ID NO 208
<211> LENGTH: 411
<212> TYPE: DNA
<213> ORGANISM: Beta vulgaris
<220> FEATURE:
<221> NAME/KEY: misc_feature
<222> LOCATION: (323)..(323)
<223> OTHER INFORMATION: n is a, c, g, or t

<400> SEQUENCE: 208

```
atggggtttc cagcaggata cacggaggtg ctcctcccca aactattcct gacagctctc    60
tccctcctcg gcttcctccg caagtccgtc tctcccctcc tccgcctcct cggcctcgcc   120
tccttaatcg agcccgcctc ccccctcgag cacgaccatc ccgagcccgg cccggccctc   180
tcggaatcct ccgcagcagc cctcatccgg gagatgctcc ccgccgtcac ctacgccgag   240
gcaatcgccg ccgggcccga cgagcccggc ccggcggaga gctgcgcggt gtgcctgcac   300
gagtacgaga cgacgacgcga ggntgcggag gatgagaaac tgccgccaca tgttccaccg   360
gtgctgcgtg gaccgatgga tcgaccacga tcgaaagacg tgcccgttgt g            411
```

<210> SEQ ID NO 209
<211> LENGTH: 487
<212> TYPE: DNA
<213> ORGANISM: Beta vulgaris
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t

<400> SEQUENCE: 209

```
tcaggtatcc cangaagcag cccaaagctt ctcattgaaa tcctcctgca actcatgcgg    60
caccagcggc ttcctacaca acgggcacgt ctttcgatcg tggtcgatcc atcggtccac   120
gcagcaccgt tggaacatgt ggcggcagtt tctcatcctc cgcanccctcg tcgtcgctct   180 cgtactcgtg caggcacacc gcgcagctct ccgccgggcc gggctcgtcg ggcccggcgg   240
```

```
cgattgcctc ggcgtaggtg acggcgggga gcatctcccg gatgagggct gctgcggagg      300
attccgagag ggccgggccg ggctcgggat ggtcgtgctc gagggggggag gcgggctcga      360 ttaaggaggc gaggccgagg aggcggagga gggagaggac ggacttgcgg aggaagccga      420
ggagggagag agctgtcagg aatagtttgg ggaggagcac ctccgtgtat cctgctggaa      480
accccat                                                                487
```

<210> SEQ ID NO 210
<211> LENGTH: 775
<212> TYPE: DNA
<213> ORGANISM: Beta vulgaris

<400> SEQUENCE: 210

```
atacctaac taactagct cgaaaagatc tcggattcaa gacctaattt ttaagttcaa       60
aaactaccta aaaattccga cctaataagt tagccaatag aaagaaagaa aaactgctat      120
ttactcattt ttttttctt cttcttgaaa actataagaa attagttata ggagaatatt      180
cagaataaaa atcaggtatc ccagaagcag cccaaagctt ctcattgaaa tcctcctgca      240
actcatgcgg caccagcggc ttcctacaca acgggcacgt ctttcgatcg tggtcgatcc      300
atcggtccac gcagcaccgg tggaacatgt ggcggcagtt tctcatcctc cgcacctcgt      360
cgtcgctctc gtactcgtgc aggcacaccg cgcagctctc cgccgggccg ggctcgtcgg      420
gcccggcggc gattgcctcg cgtaggtga cggcggggag catctcccgg atgagggctg      480
ctgcggagga ttccgagagg gccggccgg gctcgggatg gtcgtgctcg agggggggagg      540 cgggctcgat taaggaggcg aggccgagga ggcggaggag ggagaggacg gacttgcgga      600
ggaagccgag gagggagaga gctgtcagga atagtttggg gaggagcacc tccgtgtatc      660
ctgctggaaa ccccattttt tagattttgg agggagggat tgttttggtt gtcttgtaga      720
tgtgtgtgtt tttattttc tttccaagg gggatagaga ttagagagat aggag             775
```

<210> SEQ ID NO 211
<211> LENGTH: 45
<212> TYPE: PRT
<213> ORGANISM: Mesembryanthemum crystallinum

<400> SEQUENCE: 211

Glu Cys Cys Val Cys Leu Cys Lys Phe Gly Glu Glu Glu Val Ser
1               5                   10                  15

Glu Leu Ser Cys Lys His Phe Phe His Lys Lys Cys Leu Asp Lys Trp
            20                  25                  30

Phe Asp Asn His His Ser Thr Cys Pro Leu Cys Arg Ser
        35                  40                  45

<210> SEQ ID NO 212
<211> LENGTH: 135
<212> TYPE: DNA
<213> ORGANISM: Mesembryanthemum crystallinum

<400> SEQUENCE: 212

```
gagtgctgtg tttgtttgtg taaatttggg gaagaagaag aggtgagtga attgtcttgt       60
aagcatttct tccacaagaa gtgcttggat aagtggtttg ataaccatca cagtacttgc      120
ccactttgca gatcc                                                       135
```

<210> SEQ ID NO 213
<211> LENGTH: 153

```
<212> TYPE: PRT
<213> ORGANISM: Mesembryanthemum crystallinum

<400> SEQUENCE: 213

Gly Leu Ser Asn Phe Pro Ser Ala Ala Glu Gly Val Leu Pro Val Leu
1               5                   10                  15

Val Met Asn Thr Val Met Ser Val Ala Ile Leu Lys Asn Leu Leu Lys
                20                  25                  30

Ser Phe Leu Glu Leu Met Gly Ala Ala Trp Ile Ser Ser Asn Phe
        35                  40                  45

Glu Glu Asp Pro Thr Ser Val Thr Gly Ala Glu Phe Tyr Pro Pro Asn
    50                  55                  60

Ser Ser Ser Arg Arg Arg Asn Met Arg Gly Ile Arg Ile Thr Gln Phe
65              70                  75                  80

Lys Tyr Leu Cys Val Arg Glu Arg Lys Ser Lys Ser Thr Asn Phe Ala
                85                  90                  95

Leu Gly Gly Ala Gly Gly Arg Thr Ala Val Glu Cys Cys Val Cys Leu
                100                 105                 110

Cys Lys Phe Gly Glu Glu Glu Val Ser Glu Leu Ser Cys Lys His
            115                 120                 125

Phe Phe His Lys Lys Cys Leu Asp Lys Trp Phe Asp Asn His His Ser
    130                 135                 140

Thr Cys Pro Leu Cys Arg Ser Ile His
145                 150

<210> SEQ ID NO 214
<211> LENGTH: 674
<212> TYPE: DNA
<213> ORGANISM: Mesembryanthemum crystallinum

<400> SEQUENCE: 214
ggattgtcaa attttcctag tgcagctgaa ggtgtgctac cagttctagt gatgaacaca      60
gtaatgtcag tagcaatatt gaagaacttg ttgaagtcat tcttggaatt gatgggagca     120
gctgcttgga tttcaagcaa ttttgaagaa gacccaacat cagtaacagg agctgaattt     180
tacccaccaa acagttcctc taggaggagg aacatgaggg ggattagaat cacacagttc     240
aagtatttgt gtgttagaga gagaaaatca aaatctacca attttgccct tggaggtgca     300
ggaggaagaa cagcagtgga gtgctgtgtt tgtttgtgta aatttgggga agaagaagag     360
gtgagtgaat tgtcttgtaa gcatttcttc cacaagaagt gcttggataa gtggtttgat     420
aaccatcaca gtacttgccc actttgcaga tccatccatt gatcatttca tgcctaaata     480
tcttacaaaa tttccatctg agggttcaga tttcaggcta caaattaggg ttttatctt     540 cttttgggac cttttggtgg ttggggaaga tgagtacact tttttttttt tttttttcc     600 ttttcttttc ttttgtgata ctgtcttttt gaggagtctt tcatctcctt tttttttttt     660
tagtttttta tttt                                                       674

<210> SEQ ID NO 215
<211> LENGTH: 44
<212> TYPE: PRT
<213> ORGANISM: Medicago truncatula

<400> SEQUENCE: 215

Asp Cys Ser Val Cys Leu Ser Glu Phe Glu Glu Gly Glu Lys Val Arg
1               5                   10                  15

Arg Leu Lys Cys Lys His Thr Phe His Lys Asp Cys Leu Asp Lys Trp
```

```
                     20                  25                  30

Leu Gln Asp Tyr Phe Ala Thr Cys Pro Leu Cys Arg
        35                  40

<210> SEQ ID NO 216
<211> LENGTH: 140
<212> TYPE: DNA
<213> ORGANISM: Medicago truncatula

<400> SEQUENCE: 216
gattgtagcg tgtgcttatc agaattcgaa gaaggagaga aggttcgggg ttgaaatgca        60
aacacacatt tcataaggat tgtttggata aatggttgca agattatttt gctacatgtc       120
cactttgtag ggaacaagtt                                                   140

<210> SEQ ID NO 217
<211> LENGTH: 157
<212> TYPE: PRT
<213> ORGANISM: Medicago truncatula

<400> SEQUENCE: 217

Met Thr Val Asp Ile Ser Asn Val Phe Gln Lys Leu Cys Asn Lys Ile
1               5                   10                  15

Ala Ile Leu Leu Ile Phe Val Leu Val Glu Leu Ile Ile Phe Ile Trp
            20                  25                  30

Lys Leu Thr Ser Asp Thr Gln Ser Ile Thr Thr Arg Gln Tyr Ile Lys
        35                  40                  45

Phe Ile Glu Glu Lys Asn Pro Thr Ile Arg Tyr Asn Lys Lys Leu Asn
    50                  55                  60

Ser His Gly Asp Cys Ser Val Cys Leu Ser Glu Phe Glu Glu Gly Glu
65                  70                  75                  80

Lys Val Arg Arg Leu Lys Cys Lys His Thr Phe His Lys Asp Cys Leu
                85                  90                  95

Asp Lys Trp Leu Gln Asp Tyr Phe Ala Thr Cys Pro Leu Cys Arg Glu
            100                 105                 110

Gln Val Leu Pro Asp Asn Val Val Leu Lys His Arg Gln Gln Arg Asn
        115                 120                 125

Gln Gln Ser Asn Ile Glu Gly Asn Asp Glu Asn Leu Pro Tyr Val Leu
    130                 135                 140

Phe Leu Leu Arg Gly Gly Asn Asn Ser His Leu Arg Arg
145                 150                 155

<210> SEQ ID NO 218
<211> LENGTH: 474
<212> TYPE: DNA
<213> ORGANISM: Medicago truncatula

<400> SEQUENCE: 218
atgacagttg atatctccaa cgtcttccaa aaactttgca caaaattgc  aatcttacta        60 atattcgtgt tagtagaact tatcatcttc atttggaaac taacatcaga tacacaatca       120
atcacaactc gccaatacat aaaattcatc gaagaaaaga accctactat tcgttacaac       180
aaaaagttga attcacacgg ggattgtagc gtgtgcttat cagaattcga agaaggagag       240
aaggttcgga ggttgaaatg caaacacaca tttcataagg attgtttgga taatggttg        300 caagattatt ttgctacatg tccactttgt agggaacaag ttttaccaga taatgttgtg       360
ttaaaacatc gtcagcaacg aaatcaacag agtaatattg aggggaatga tgaaaatctt       420
```

```
ccctatgtgt tgttcttgtt acgtggtggt aataacagtc acttgcgtag atag        474
```

```
<210> SEQ ID NO 219
<211> LENGTH: 47
<212> TYPE: PRT
<213> ORGANISM: Citrullus lanatus
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 219

Asp Cys Ser Xaa Cys Leu Thr Gln Phe Glu Pro Ala Ser Glu Ile Asn
1               5                   10                  15

His Leu Ser Xaa Gly His Leu Phe His Thr Glu Cys Leu Glu Lys Xaa
            20                  25                  30

Leu Asp Tyr Trp Asn Ile Thr Cys Pro Leu Cys Arg Thr Pro Leu
        35                  40                  45

<210> SEQ ID NO 220
<211> LENGTH: 88
<212> TYPE: PRT
<213> ORGANISM: Citrullus lanatus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (80)..(80)
<223> OTHER INFORMATION: Xaa can be any naturally occurring amino acid
<220> FEATURE:
<221> NAME/KEY: misc_feature
<222> LOCATION: (86)..(86)
```

-continued

<223> OTHER INFORMATION: Xaa can be any naturally occurring amino acid

<400> SEQUENCE: 220

Xaa Gly Ser Xaa Trp Xaa Tyr Leu Glu Met Xaa Arg Asn Arg Tyr Pro
1               5                   10                  15

Arg Xaa Arg Phe Asp Lys Leu Gln Gly Ser Glu Xaa Arg Glu His Asp
            20                  25                  30

Cys Ser Xaa Cys Leu Thr Gln Phe Glu Pro Ala Ser Glu Ile Asn His
        35                  40                  45

Leu Ser Xaa Gly His Leu Phe His Thr Glu Cys Leu Glu Lys Xaa Leu
    50                  55                  60

Asp Tyr Trp Asn Ile Thr Cys Pro Leu Cys Arg Thr Pro Leu Met Xaa
65                  70                  75                  80

Glu Glu Glu Lys Ser Xaa Phe Trp
                85

<210> SEQ ID NO 221
<211> LENGTH: 141
<212> TYPE: DNA
<213> ORGANISM: Citrullus lanatus
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (60)..(60)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t

<400> SEQUENCE: 221
gactgctcgg nctgtttaac tcaatttgaa cctgcatctg agataaatca cttatcttgn    60
ggtcatcttt ttcacacaga atgcttggag aagnggctag attactggaa catcacatgt   120
cctctttgca gaactcctct a                                              141

<210> SEQ ID NO 222
<211> LENGTH: 537
<212> TYPE: DNA
<213> ORGANISM: Citrullus lanatus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature

```
<222> LOCATION: (88)..(88)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (396)..(397)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (426)..(427)
<223> OTHER INFORMATION: n is a, c, g, or t
<220> FEATURE:
<221> NAME/KEY: misc_feature
<222> LOCATION: (434)..(434)
<223> OTHER INFORMATION: n is a, c, g, or t
<220> FEATURE:
<221> NAME/KEY: misc_feature
<222> LOCATION: (464)..(464)
<223> OTHER INFORMATION: n is a, c, g, or t
<220> FEATURE:
<221> NAME/KEY: misc_feature
<222> LOCATION: (476)..(476)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t

<400> SEQUENCE: 222
ttntggctcc ncttggagnt acctcgagat gnttcgaaac cgatatccaa gganccgatt      60
tgataaatta cagggctcag aatgncgnga acatgactgc tcggnctgtt taactcaatt    120
tgaacctgca tctgagataa atcacttatc ttgnggtcat cttttttcaca cagaatgctt    180 ggagaagngg ctagattact ggaacatcac atgtcctctt tgcagaactc ctctaatgnc    240
cgaagaagag aaatcgngct tttggtgagc gtagaatcta gttngggaa actcatgtac     300
```

```
agcatactct taaagataat tgtgaaagcg tttcctacct ttggcacgta tgacatttga    360
agnttgatgn gtctgacagg ncttagaggc caaagnnttg ncactgtaaa tacatgttta    420
tgaagnncta tgcntttggc ttgtgccttt agctttgagt taangcactg ttactncact    480
ttctttgtac atggaattgg ctgagtatgc acaaagntat tcaaattctg tttgttt      537
```

<210> SEQ ID NO 223  
<211> LENGTH: 49  
<212> TYPE: PRT  
<213> ORGANISM: Capsicum annuum

<400> SEQUENCE: 223

```
Cys Ile Val Cys Met Glu Gly Phe Gln Arg Gly His Val Asp Gly His
1               5                   10                  15

Gly Ile Lys Val Pro Cys Gly His Val Phe His Ala Asn Cys Leu Thr
            20                  25                  30

Lys Trp Leu Ser Ile Cys Asn Ser Cys Pro Leu Cys Arg Phe Lys Phe
        35                  40                  45

Ile
```

<210> SEQ ID NO 224  
<211> LENGTH: 150  
<212> TYPE: DNA  
<213> ORGANISM: Capsicum annuum

<400> SEQUENCE: 224

```
ctttgtatag tatgtatgga aggttttcaa agaggtcatg ttgatggtca tggcataaaa    60
gtcccttgtg gtcatgtttt tcatgcaaat tgtcttacca aatggctctc catttgtaat   120
tcttgtcctc tttgccgttt taaattcatc                                    150
```

<210> SEQ ID NO 225  
<211> LENGTH: 480  
<212> TYPE: DNA  
<213> ORGANISM: Capsicum annuum

<400> SEQUENCE: 225

```
aaaccaaatt catggtattt ggttgttgt ccaaccccctc acccacgtag tgtagcacaa    60
ggtttgaatt tttttcatc tatatatatt caactatata tctaatcaac catcacaaat   120
tacatatttt cattctacat ggataaagat ttcgatctag atttagcatt aacggtgatc   180
ggaatttcag gcggtgacac gactgagcca tcgcggtgtt caacgcgtta cgatgatcac   240
gatgagagta gtcaagttca attattgcct atggttaatt gtgaaaatgg ctttgtata    300 gtatgtatgg aaggttttca agaggtcat gttgatggtc atggcataaa agtcccttgt   360
ggtcatgttt tcatgcaaa ttgtcttacc aaatggctct ccatttgtaa ttcttgtcct   420
ctttgccgtt ttaaattcat cggaaacagt ctctctacct ttacgagata ggagtaaggt   480
```

<210> SEQ ID NO 226  
<211> LENGTH: 47  
<212> TYPE: PRT  
<213> ORGANISM: Allium cepa

<400> SEQUENCE: 226

```
Asp Cys Ala Val Cys Leu Ser Glu Phe Ser Gln Asp Asp Lys Leu Arg
1               5                   10                  15

Leu Leu Pro Ile Cys Gly His Ala Phe His Ile Asn Cys Ile Glu Thr
            20                  25                  30
```

```
Trp Leu Leu Phe Tyr Ser Thr Cys Pro Leu Cys Arg Gly Ala Leu
            35                  40                  45
```

<210> SEQ ID NO 227
<211> LENGTH: 143
<212> TYPE: DNA
<213> ORGANISM: Allium cepa

<400> SEQUENCE: 227

```
gattgtgcag tttgcttatc cgagttctct caagatgata agcttcgtct tcttccaata    60
tgtggtcatg catttcatat caattgtata gaaacttggc ttcttttcta ttccacgtgc   120
cctctatgta gaggagctct cta                                           143
```

<210> SEQ ID NO 228
<211> LENGTH: 195
<212> TYPE: PRT
<213> ORGANISM: Allium cepa

<400> SEQUENCE: 228

```
Ile Val Phe Arg Thr Ser Lys Met Met Leu Lys Thr Ala Phe Phe Ser
1               5                   10                  15

Ser Lys Ser Tyr Arg Val Leu Ser Gln Ile Gly Lys Asp Ser Leu Pro
            20                  25                  30

Leu Gln Thr Ser Gln Ser Pro Pro Ala Gln Pro Ser Ser Asn Thr Thr
        35                  40                  45

Arg Ile Ser Pro Ala Val Leu Phe Ile Ile Ile Leu Ala Val Ile
    50                  55                  60

Phe Phe Ile Ser Gly Leu Leu His Leu Leu Val Arg Phe Leu Ile Arg
65                  70                  75                  80

Lys Asn Pro Ser Ser Ser Pro Gln Ser Asn Gly His Asn Gln Glu
                85                  90                  95

Asn Ser Asn Ser Asp Ala Leu Gln Arg Gln Leu Gln Gln Leu Phe His
            100                 105                 110

Leu His Asp Ser Gly Leu Asp Gln Ala Phe Ile Asp Ala Leu Pro Val
        115                 120                 125

Phe Leu Tyr Lys Glu Ile Val Gly Ser Lys Pro Phe Asp Cys Ala
    130                 135                 140

Val Cys Leu Ser Glu Phe Ser Gln Asp Lys Leu Arg Leu Pro
145                 150                 155                 160

Ile Cys Gly His Ala Phe His Ile Asn Cys Ile Glu Thr Trp Leu Leu
                165                 170                 175

Phe Tyr Ser Thr Cys Pro Leu Cys Arg Gly Ala Leu Tyr Val Gln Gly
            180                 185                 190

Arg Pro Ser
        195
```

<210> SEQ ID NO 229
<211> LENGTH: 925
<212> TYPE: DNA
<213> ORGANISM: Allium cepa

<400> SEQUENCE: 229

```
ggtgacctat agaacagttt gtactaaaaa gcaggctggt accggtccgg aattcccggg    60
attcaaattt caatattgat gaacgcccat cttctcagtt gagctggaaa catttgattt   120
aagagctcaa ccatcttcac aaatcatcag ttttaatcaa acaaagtttg attttgagc   180 tgtattgagc tcttctacag tagaaagttt gaatttagc ctcctcatgc tttcaaatga    240
```

```
attgttttc gtacgagcaa gatgatgtta aaaacagcct tttctcgtc aaaatcatat      300 cgggttttat cccaaatcgg aaaggattca cttccattgc aaacatctca gtctccaccg      360
gctcaacctt catcaaatac taccagaata agtccagctg tgcttttcat catcataatt      420
ctagcagtaa tatttttat atctggttta cttcatcttt tggttagatt tctaataaga      480
aagaatccat cttcgtcctc tccacaatcc aatggccaca atcaagaaaa ctcaaattct      540
gatgcgttac aaagacaact tcaacaattg tttcatctcc acgattctgg actcgatcaa      600
gctttcattg atgccttacc cgtgtttctc tataaagaga ttgtcgggtc gaaagagccc      660
tttgattgtg cagtttgctt atccgagttc tctcaagatg ataagcttcg tcttcttcca      720
atatgtggtc atgcatttca tatcaattgt atagaaactt ggcttctttt ctattccacg      780
tgccctctat gtagaggagc tctctatgtt caagggcgtc ccagttgaaa tccaatgtac      840
gagtttgatg aagagatggg actggaagga gggcgatttg gaaatacgga gactgggaag      900
agattggtgt gagaagagaa tattc                                            925
```

<210> SEQ ID NO 230
<211> LENGTH: 47
<212> TYPE: PRT
<213> ORGANISM: Cucumis melo

<400> SEQUENCE: 230

Glu Cys Ala Val Cys Leu Asn Glu Phe Glu Asp Asp Glu Thr Leu Arg
1               5                   10                  15

Leu Ile Pro Lys Cys Asp His Val Phe His Pro Glu Cys Ile Asp Ala
            20                  25                  30

Trp Leu Ala Ser His Ser Thr Cys Pro Val Cys Arg Ala Asn Leu
        35                  40                  45

<210> SEQ ID NO 231
<211> LENGTH: 150
<212> TYPE: DNA
<213> ORGANISM: Cucumis melo

<400> SEQUENCE: 231

```
gaatgcgctg tttgtttgaa tgaatttgaa gatgatgaaa cgctgcgttt aatccctaaa      60
tgtgatcatg tgtttcaccc tgaatgtatt gatgcttggt tggcttctca ctctacttgc     120
cctgtttgtc gagctaattt gtctccccaa                                       150
```

<210> SEQ ID NO 232
<211> LENGTH: 379
<212> TYPE: PRT
<213> ORGANISM: Cucumis melo

<400> SEQUENCE: 232

Met Pro Ser Leu Thr Ala Pro His Gly Leu Pro Leu Phe Leu Phe Leu
1               5                   10                  15

Leu Leu Phe Leu Phe Ser Ser Val Ser Ala Gln Phe Gln Pro Ala Pro
            20                  25                  30

Asp Pro Arg Ser Asp Pro Tyr Gln Tyr Arg Leu Ser Gly Ser Met Ala
        35                  40                  45

Val Ile Ile Val Ile Leu Ile Ala Ala Leu Phe Phe Met Ala Phe Phe
    50                  55                  60

Ser Val Tyr Ile Arg His Cys Asn Asp Ser Pro Ser Asn Thr Val Arg
65                  70                  75                  80

```
Pro Ile Thr Ala Ala Ala Gly Arg Ser Arg Arg Ala Thr Arg Gly Leu
                85                  90                  95
Asp Pro Ala Val Ile Glu Thr Phe Pro Thr Leu Ile Tyr Ser Asp Val
            100                 105                 110
Lys Glu His Lys Ile Gly Lys Ser Ala Leu Glu Cys Ala Val Cys Leu
        115                 120                 125
Asn Glu Phe Glu Asp Asp Glu Thr Leu Arg Leu Ile Pro Lys Cys Asp
    130                 135                 140
His Val Phe His Pro Glu Cys Ile Asp Ala Trp Leu Ala Ser His Ser
145                 150                 155                 160
Thr Cys Pro Val Cys Arg Ala Asn Leu Ser Pro Gln Pro Thr Asp Ser
                165                 170                 175
Val His Arg Ala Asp Asp Ser Asn Ala Val Val Asn Ser Asp Thr Asp
            180                 185                 190
Gly Gly Asp Ile Glu Ala Gln Ser Asn Asp Val Val Ser Glu Thr Thr
        195                 200                 205
Ala Pro Pro Thr Val Gln Ile Gln Thr Glu Ser Glu Leu Ser Thr Thr
    210                 215                 220
Thr Ser Asn Lys Ala Leu Asn Arg Thr Arg Thr Arg Gly Ser Arg Ser
225                 230                 235                 240
Asn Arg Leu Arg Trp Leu Phe Pro Arg Ser His Ser Thr Gly His Ser
                245                 250                 255
Leu Val Gln Pro Gly Glu Asp Thr Glu Arg Phe Thr Leu Arg Leu Pro
            260                 265                 270
Val Glu Ile Arg Lys Gln Val Val Asn Arg Lys Leu His Arg Ala Thr
        275                 280                 285
Ser Met Val Val Leu Ala Arg Gln Ser Ser Ser Met Arg Gly Tyr Arg
    290                 295                 300
Phe Gly Ser Gly Glu Gly Ser Ser Arg Gly Lys Tyr Tyr Arg Arg Leu
305                 310                 315                 320
Glu Arg Leu Asp Arg Thr Ser Lys Ser Asp Arg Trp Val Leu Ser Met
                325                 330                 335
Thr Pro Pro Phe Phe Thr Arg Met Ser Ser Met Lys Thr Pro Arg Gly
            340                 345                 350
Gly Ser Asn Arg Ala Glu Pro Gly Ser Gly Arg Glu Leu Gly Gln Gly
        355                 360                 365
Asn Thr Ala Val Asp Ser Ser Arg Leu Pro Val
    370                 375

<210> SEQ ID NO 233
<211> LENGTH: 1140
<212> TYPE: DNA
<213> ORGANISM: Cucumis melo

<400> SEQUENCE: 233
atgccctctc tcaccgcccc ccatggcctt ccctcttcc tcttcctcct cctcttcctc      60
ttctcctccg tctccgccca gttccagccc gcccccgacc ccagatcaga cccttaccag    120
taccgcctca gcggttccat ggccgtcatc atcgtcatcc tcatcgccgc tctcttcttc    180
atggctttct tctccgtcta catccgtcac tgcaacgatt caccatccaa caccgtccgc    240
cctatcaccg ccgccgcgg ccgctcccgt cgcgcaaccc gcggtctcga tccggcggta    300
attgaaacgt ttccgactct gatttactcc gatgtgaaag agcataaaat tggtaaaagt    360
gccctagaat gcgctgtttg tttgaatgaa tttgaagatg atgaaacgct gcgtttaatc    420
```

```
cctaaatgtg atcatgtgtt tcaccctgaa tgtattgatg cttggttggc ttctcactct      480
acttgccctg tttgtcgagc taatttgtct ccccaaccca ctgactccgt ccaccgagct      540
gacgattcca acgctgtcgt taactccgat accgacggag gtgatattga agctcagtcc      600
aacgacgttg tttcagagac gacggctcca cctacggttc agatacaaac ggaatcagag      660
ctcagtacga cgacaagtaa caaggcgttg aatcggacac gtacacgggg atcccgatcc      720
aatagattgc ggtggctatt tccccggtct cactcgaccg gccactcctt ggttcagcct      780
ggggaagaca ctgagcggtt tactctccgg ttgccagtgg agataaggaa acaagtggtg      840
aaccggaagc tgcaccgggc gactagtatg gtggttctgg cgaggcagag cagttcgatg      900
aggggatacc gatttggttc aggtgaaggg agtagtcgag ggaagtatta ccggaggctt      960
gagcggttgg acagaacatc gaagtcggac cggtgggtgt tgtcaatgac accgccgttt     1020
tttacgcgta tgtcgtcgat gaagactccg cgtggaggga gtaaccgtgc tgaacccggt     1080
tcgggccgag aacttggaca ggggaatacc gcggtcgatt caagtaggct tccggtctga     1140

<210> SEQ ID NO 234
<211> LENGTH: 42
<212> TYPE: PRT
<213> ORGANISM: Cucumis melo

<400> SEQUENCE: 234

Glu Cys Ala Val Cys Leu Asn Glu Phe Glu Asp Asp Glu Thr Leu Arg
1               5                   10                  15

Leu Ile Pro Lys Cys Asp His Val Phe His Pro Glu Cys Ile Asp Ala
            20                  25                  30

Trp Leu Ala Ser His Ser Thr Cys Pro Val
        35                  40

<210> SEQ ID NO 235
<211> LENGTH: 150
<212> TYPE: DNA
<213> ORGANISM: Cucumis melo

<400> SEQUENCE: 235
gaatgcgctg tttgtttgaa tgaatttgaa gatgatgaaa cgctgcgttt aatccctaaa       60
tgtgatcatg tgtttcaccc tgaatgtatt gatgcttggt tggcttctca ctctacttgc      120
cctgtttgtc gagctaattt gtctccccaa                                       150

<210> SEQ ID NO 236
<211> LENGTH: 379
<212> TYPE: PRT
<213> ORGANISM: Cucumis melo

<400> SEQUENCE: 236

Met Pro Ser Leu Thr Ala Pro His Gly Leu Pro Leu Phe Leu Phe Leu
1               5                   10                  15

Leu Leu Phe Leu Phe Ser Ser Val Ser Ala Gln Phe Gln Pro Ala Pro
            20                  25                  30

Asp Pro Arg Ser Asp Pro Tyr Gln Tyr Arg Leu Ser Gly Ser Met Ala
        35                  40                  45

Val Ile Ile Val Ile Leu Ile Ala Ala Leu Phe Met Ala Phe Phe
    50                  55                  60

Ser Val Tyr Ile Arg His Cys Asn Asp Ser Pro Ser Asn Thr Val Arg
65                  70                  75                  80

Pro Ile Thr Ala Ala Ala Gly Arg Ser Arg Arg Ala Thr Arg Gly Leu
```

```
                        85                  90                  95
Asp Pro Ala Val Ile Glu Thr Phe Pro Thr Leu Ile Tyr Ser Asp Val
                100                 105                 110
Lys Glu His Lys Ile Gly Lys Ser Ala Leu Glu Cys Ala Val Cys Leu
            115                 120                 125
Asn Glu Phe Glu Asp Asp Glu Thr Leu Arg Leu Ile Pro Lys Cys Asp
        130                 135                 140
His Val Phe His Pro Glu Cys Ile Asp Ala Trp Leu Ala Ser His Ser
145                 150                 155                 160
Thr Cys Pro Val Cys Arg Ala Asn Leu Ser Pro Gln Pro Thr Asp Ser
                165                 170                 175
Val His Arg Ala Asp Asp Ser Asn Ala Val Val Asn Ser Asp Thr Asp
            180                 185                 190
Gly Gly Asp Ile Glu Ala Gln Ser Asn Asp Val Val Ser Glu Thr Thr
        195                 200                 205
Ala Pro Pro Thr Val Gln Ile Gln Thr Glu Ser Glu Leu Ser Thr Thr
    210                 215                 220
Thr Ser Asn Lys Ala Leu Asn Arg Thr Arg Thr Arg Gly Ser Arg Ser
225                 230                 235                 240
Asn Arg Leu Arg Trp Leu Phe Pro Arg Ser His Ser Thr Gly His Ser
                245                 250                 255
Leu Val Gln Pro Gly Glu Asp Thr Glu Arg Phe Thr Leu Arg Leu Pro
            260                 265                 270
Val Glu Ile Arg Lys Gln Val Val Asn Arg Lys Leu His Arg Ala Thr
        275                 280                 285
Ser Met Val Val Leu Ala Arg Gln Ser Ser Met Arg Gly Tyr Arg
    290                 295                 300
Phe Gly Ser Gly Glu Gly Ser Ser Arg Gly Lys Tyr Tyr Arg Arg Leu
305                 310                 315                 320
Glu Arg Leu Asp Arg Thr Ser Lys Ser Asp Arg Trp Val Leu Ser Met
                325                 330                 335
Thr Pro Pro Phe Phe Thr Arg Met Ser Ser Met Lys Thr Pro Arg Gly
            340                 345                 350
Gly Ser Asn Arg Ala Glu Pro Gly Ser Gly Arg Glu Leu Gly Gln Gly
        355                 360                 365
Asn Thr Ala Val Asp Ser Ser Arg Leu Pro Val
    370                 375

<210> SEQ ID NO 237
<211> LENGTH: 1137
<212> TYPE: DNA
<213> ORGANISM: Cucumis melo

<400> SEQUENCE: 237
atgccctctc tcaccgcccc ccatggcctt cccctcttcc tcttcctcct cctcttcctc      60
ttctcctccg tctccgccca gttccagccc gccccgacc ccagatcaga cccttaccag     120
taccgcctca gcggttccat ggccgtcatc atcgtcatcc tcatcgccgc tctcttcttc     180
atggctttct tctccgtcta catccgtcac tgcaacgatt caccatccaa caccgtccgc     240
cctatcaccg ccgccgccgg ccgctcccgt cgcgcaaccc gcggtctcga tccggcggta     300
attgaaacgt ttccgactct gatttactcc gatgtgaaag agcataaaat tggtaaaagt     360
gccctagaat gcgctgtttg tttgaatgaa tttgaagatg atgaaacgct gcgtttaatc     420
cctaaatgtg atcatgtgtt tcaccctgaa tgtattgatg cttggttggc ttctcactct     480
```

```
acttgccctg tttgtcgagc taatttgtct ccccaaccca ctgactccgt ccaccgagct    540
gacgattcca acgctgtcgt taactccgat accgacggag gtgatattga agctcagtcc    600
aacgacgttg tttcagagac gacggctcca cctacggttc agatacaaac ggaatcagag    660
ctcagtacga cgacaagtaa caaggcgttg aatcggacac gtacacgggg atcccgatcc    720
aatagattgc ggtggctatt tccccggtct cactcgaccg gccactcctt ggttcagcct    780
ggggaagaca ctgagcggtt tactctccgg ttgccagtgg agataaggaa acaagtggtg    840
aaccggaagc tgcaccgggc gactagtatg gtggttctgg cgaggcagag cagttcgatg    900
aggggatacc gatttggttc aggtgaaggg agtagtcgag ggaagtatta ccggaggctt    960
gagcggttgg acagaacatc gaagtcggac cggtgggtgt tgtcaatgac accgccgttt   1020
tttacgcgta tgtcgtcgat gaagactccg cgtggaggga gtaaccgtgc tgaacccggt   1080
tcgggccgag aacttggaca ggggaatacc gcggtcgatt caagtaggct tccggtc      1137
```

<210> SEQ ID NO 238
<211> LENGTH: 42
<212> TYPE: PRT
<213> ORGANISM: Capsicum annuum

<400> SEQUENCE: 238

```
Glu Cys Ser Val Cys Leu Thr Lys Phe Glu Pro Asp Ala Gly Val Asn
1               5                   10                  15

Ser Leu Ser Cys Gly His Val Phe His Lys Leu Cys Leu Glu Lys Trp
            20                  25                  30

Leu Thr Tyr Trp His Val Thr Cys Pro Leu
        35                  40
```

<210> SEQ ID NO 239
<211> LENGTH: 162
<212> TYPE: PRT
<213> ORGANISM: Capsicum annuum

<400> SEQUENCE: 239

```
Arg Lys Asn His His Phe Asn Thr Arg Phe Arg Ser Val Met Gly Leu
1               5                   10                  15

Ser Gln Tyr Pro Thr Pro Ala Asp Ala Gly Val Leu Gly Val Ile Leu
            20                  25                  30

Val Asn Thr Ala Ile Ser Ile Ser Ile Val Lys Glu Ile Leu Arg Ser
        35                  40                  45

Ile Leu Arg Leu Ile Gly Ile Arg Ile Ala Ser Trp Glu Asp Tyr Ser
    50                  55                  60

Ile Glu Gly Ser Ser Asp Ser Leu Glu Cys Arg Gly Ser Pro Pro Glu
65                  70                  75                  80

Ser Tyr Met Glu Glu Phe Arg Ser Arg Thr Pro Ala Phe Arg Tyr Asp
                85                  90                  95

Ser Leu Cys Ile Ser Asn His Pro Glu Gln Cys Ser Val Cys Leu
            100                 105                 110

Thr Lys Phe Glu Pro Asp Ala Gly Val Asn Ser Leu Ser Cys Gly His
        115                 120                 125

Val Phe His Lys Leu Cys Leu Glu Lys Trp Leu Thr Tyr Trp His Val
    130                 135                 140

Thr Cys Pro Leu Cys Arg Asn His Leu Met Pro Gln Gln Glu Gln Asp
145                 150                 155                 160

Asp Thr
```

<210> SEQ ID NO 240
<211> LENGTH: 33
<212> TYPE: PRT
<213> ORGANISM: Capsicum annuum

<400> SEQUENCE: 240

Gly Val Leu Gly Val Ile Leu Val Asn Thr Ala Ile Ser Ile Ser Ile
1               5                   10                  15

Val Lys Glu Ile Leu Arg Ser Ile Leu Arg Leu Ile Gly Ile Arg Ile
            20                  25                  30

Ala

<210> SEQ ID NO 241
<211> LENGTH: 126
<212> TYPE: DNA
<213> ORGANISM: Capsicum annuum

<400> SEQUENCE: 241
gaatgttctg tgtgcctaac aaaatttgag cctgatgcag gggtaaacag tctctcatgt      60
ggtcatgttt tccataagct gtgtctagag aagtggctca cgtattggca tgtaacttgt     120
cctctt                                                                126

<210> SEQ ID NO 242
<211> LENGTH: 548
<212> TYPE: DNA
<213> ORGANISM: Capsicum annuum

<400> SEQUENCE: 242
agaaagaatc atcatttcaa cactaggttc cgatccgtta tgggcctctc acaatatcca      60
actccagcag atgcaggagt actaggtgtg attctagtaa acacagccat atccatatcc     120
attgtcaagg agatactacg atcgattctt cgcctgatag gcatccgtat cgcatcatgg     180
gaagactatt ctatactacg atcgattctt cgcctgatag gcatccgtat cgcatcatgg     240
gaagactatt ctattgaagg ctcctcagac tcacttgaat gccgtggaag cccaccagag     300
tcatacatgg aggagttcag aagccgaaca cctgcatttc gttatgactc gctatgcatc     360
tctaaccacc tgaacaaga tgttctgtg tgcctaacaa atttgagcc tgatgcaggg       420 gtaaacagtc tctcatgtgg tcatgttttc cataagctgt gtctagagaa gtggctcacg     480
tattggcatg taacttgtcc tctttgcaga atcacttga tgcctcaaca gaacaggac      540 gatacgtg                                                              548

<210> SEQ ID NO 243
<211> LENGTH: 598
<212> TYPE: DNA
<213> ORGANISM: Capsicum annuum

<400> SEQUENCE: 243
gtcccctctt acaaaaataa aaataaagta ctacagaaaa ttgctacaaa aaagtctcaa      60
gttttcatat tattagatcc ggtatattga gctcttccag aaggttttga agaaagaatc     120
atcatttcaa cactaggttc cgatccgtta tgggcctctc acaatatcca actccagcag     180
atgcaggagt actaggtgtg attctagtaa acacagccat atccatatcc attgtcaagg     240
agatactacg atcgattctt cgcctgatag gcatccgtat cgcatcatgg gaagactatt     300
ctattgaagg ctcctcagac tcacttgaat gccgtggaag cccaccagag tcatacatgg     360

-continued

```
aggagttcag aagccgaaca cctgcatttc gttatgactc gctatgcatc tctaaccacc    420
ctgaacaaga atgttctgtg tgcctaacaa aatttgagcc tgatgcaggg gtaaacagtc    480
tctcatgtgg tcatgttttc cataagctgt gtctagagaa gtggctcacg tattggcatg    540
taacttgtcc tctttgcaga aatcacttga tgcctcaaca agaacaggac gatacgtg     598
```

<210> SEQ ID NO 244
<211> LENGTH: 293
<212> TYPE: PRT
<213> ORGANISM: Populus alba x Populus tremula

<400> SEQUENCE: 244

```
Met Asp Pro Asp Ser Arg Asp Pro Pro Ile Glu Tyr Arg Glu Gly Tyr
1               5                   10                  15

Ala Leu Ser Gly Lys Ile Met Leu Ser Ala Ile Leu Ile Leu Phe Phe
            20                  25                  30

Val Ile Ile Val Met Val Leu Leu His Leu Tyr Ala Arg Trp Tyr Leu
        35                  40                  45

Thr Arg Ala Arg Gln Arg Gln Val Arg Val Arg Asn Arg Thr
    50                  55                  60

His Leu Val Phe Tyr Val Asp Ser Pro Gln Asn Pro Asn Asn Val Thr
65                  70                  75                  80

Ser His Val Thr Arg Gly Leu Glu Glu Thr Val Lys Asn Ser Leu Pro
                85                  90                  95

Val Phe Val Tyr Pro Arg Lys Thr His Gln Asp Ser Ile Glu Cys Ala
            100                 105                 110

Val Cys Leu Ser Glu Phe Glu Glu Asn Glu Arg Gly Arg Val Leu Pro
        115                 120                 125

Lys Cys Asn His Ser Phe His Thr Glu Cys Ile Asp Met Trp Phe His
    130                 135                 140

Ser His Ser Thr Cys Pro Leu Cys Arg Ser Pro Val Glu Pro Val Ala
145                 150                 155                 160

Glu Asn Pro Val Pro Glu Gly Ser Asn Phe Gly Ile Ser Glu Ala Gly
                165                 170                 175

Ser Gly Leu Cys Thr Ser Cys Gln His Glu Glu Asp His Leu Gly Ser
            180                 185                 190

Ala Ser Thr Ser Ser Phe Asn Gly Gly Arg Lys Pro Val Gly Leu Ile
        195                 200                 205

Gly Val Thr Ile Asp Val Pro Arg Arg Asn Gly Asn Phe Glu Asp Glu
    210                 215                 220

Ser Asn Thr Glu Ser Pro Ser Ala Ser His Ser Phe Arg Ser Pro Met
225                 230                 235                 240

Ser Arg Met Leu Ser Phe Lys Arg Met Leu Ser Arg Glu Arg Arg Gly
                245                 250                 255

Thr Val Ser Pro Thr Val Ala Asn Ser Val Ser Cys Gly Gly Gly Ser
            260                 265                 270

Gly Thr Thr Glu Phe Asp Ile Glu Gln Gly Arg Asp Glu Ser Met Pro
        275                 280                 285

Gln Gln Thr Arg Cys
    290
```

<210> SEQ ID NO 245
<211> LENGTH: 47
<212> TYPE: PRT
<213> ORGANISM: Populus alba x Populus tremula -continued

<400> SEQUENCE: 245

Glu Cys Ala Val Cys Leu Ser Glu Phe Glu Glu Asn Glu Arg Gly Arg
1               5                   10                  15

Val Leu Pro Lys Cys Asn His Ser Phe His Thr Glu Cys Ile Asp Met
            20                  25                  30

Trp Phe His Ser His Ser Thr Cys Pro Leu Cys Arg Ser Pro Val
        35                  40                  45

<210> SEQ ID NO 246
<211> LENGTH: 142
<212> TYPE: DNA
<213> ORGANISM: Populus alba x Populus tremula

<400> SEQUENCE: 246
gagtgtgcgg tttgtttatc cgaattcgaa gagaacgaaa ggggtcgggt cttgcccaag    60
tgtaaccaca gtttccacac cgagtgcatc gatatgtggt tcattctca ctccacttgc   120
cctctttgtc gctctccggt tg                                            142

<210> SEQ ID NO 247
<211> LENGTH: 987
<212> TYPE: DNA
<213> ORGANISM: Populus alba x Populus tremula

<400> SEQUENCE: 247
tgctaaacca aacccattat ccttctcttt ctcttaagca cacaagaatc aaaattggtc    60
catttattca agaaatggac ccagactcga gagatccacc aattgaatac agagaaggct   120
atgcattaag tggcaagata atgcttagtg ctattcttat tctcttcttt gttatcattg   180
taatggttct ctccacctt tacgctcgtt ggtacctcac tcgtgcacgc cagcgccaag    240
tccgccgtgt ccgcaaccgc cgtacccatc ttgtcttcta cgtcgactcc ccccaaaacc   300
ccaacaatgt cacctctcat gtcacgcgtg gccttgaaga gactgtcaaa aattctcttc   360
ctgttttgt atatccaaga aaacccacc aagattcgat tgagtgtgcg gtttgtttat    420
ccgaattcga agagaacgaa aggggtcggg tcttgcccaa gtgtaaccac agtttccaca   480
ccgagtgcat cgatatgtgg tttcattctc actccacttg ccctctttgt cgctctccgg   540
ttgagccggt ggcggaaaac cccgttccag aaggttcaaa tttcgggatt cagaagcag    600
gttcgggtct gtgtacctcg tgccagcacg aggaggatca tttgggatcg gcttctacgt   660
cgtcgtttaa tggtggaagg aaacctgttg ggcttattgg tgtgaccata gacgtgccaa   720
ggagaaatgg gaatttcgag gacgagtcaa ataccgagtc accatcagcg agtcactcct   780
ttagatcgcc aatgagtcgg atgttgtcgt ttaagaggat gctaagtagg gaaagaagag   840
gtactgtgtc tccaaccgtg gctaactcag tgagctgcgg tggtgggtca gggacgaccg   900
agtttgatat tgagcaaggg agggatgagt cgatgcctca gcaaactcgg tgttaaaata   960
agaggtggca attcttgacc cggttag                                       987

<210> SEQ ID NO 248
<211> LENGTH: 233
<212> TYPE: PRT
<213> ORGANISM: Populus alba x Populus tremula

<400> SEQUENCE: 248

Met Glu Phe Glu Lys Tyr Phe Thr Gln Gly Trp Lys Ser Val Ser Ser
1               5                   10                  15

Ala Ala Ser Asp Ser Glu Asn Pro Ser Gly Cys Phe Asp Cys Asn Ile

```
        20                  25                  30
Cys Phe Asp Phe Ala His Glu Pro Val Val Thr Leu Cys Gly His Leu
        35                  40                  45

Tyr Cys Trp Pro Cys Ile Tyr Lys Trp Leu His Val Gln Ser Ala Ser
 50                  55                  60

Leu Ala Ser Asp Glu His Pro Gln Cys Pro Val Cys Lys Ala Asp Ile
 65                  70                  75                  80

Ser His Thr Thr Met Val Pro Leu Tyr Gly Arg Gly Gln Gly Ser Thr
                 85                  90                  95

Glu Ala Glu Gly Lys Thr Pro Tyr Arg Gly Met Ile Ile Pro Pro Arg
            100                 105                 110

Pro Ser Ala Cys Gly Ala Gln Gly Val Val Ser Asn Thr Ser Asn Thr
            115                 120                 125

Gly Gln Arg Leu Pro Tyr Arg Asn Pro Tyr Arg Asn His Asn Tyr Asn
        130                 135                 140

Ala Asn Pro Tyr Gly Ser Phe Glu Glu Ala Ser Pro Ser Pro Leu Leu
145                 150                 155                 160

Asn Leu Gly Asp Pro Ala Met Thr Gly Leu Gln Gln Pro Ala Val Gly
                165                 170                 175

Met Phe Arg Glu Met Val Tyr Ala Arg Val Phe Gly Pro Phe Pro Asn
            180                 185                 190

Ser Tyr His Leu Met Gly Thr Gly Ser Pro Arg Leu Arg Arg His Glu
        195                 200                 205

Leu Met Ala Asp Lys Ser Leu Asn Arg Ile Ser Ile Phe Leu Phe Cys
210                 215                 220

Cys Phe Leu Leu Cys Leu Ile Val Phe
225                 230

<210> SEQ ID NO 249
<211> LENGTH: 52
<212> TYPE: PRT
<213> ORGANISM: Populus alba x Populus tremula

<400> SEQUENCE: 249

Asp Cys Asn Ile Cys Phe Asp Phe Ala His Glu Pro Val Val Thr Leu
 1                   5                  10                  15

Cys Gly His Leu Tyr Cys Trp Pro Cys Ile Tyr Lys Trp Leu His Val
                20                  25                  30

Gln Ser Ala Ser Leu Ala Ser Asp Glu His Pro Gln Cys Pro Val Cys
            35                  40                  45

Lys Ala Asp Ile
 50

<210> SEQ ID NO 250
<211> LENGTH: 156
<212> TYPE: DNA
<213> ORGANISM: Populus alba x Populus tremula

<400> SEQUENCE: 250
gactgtaata tctgttttga ctttgcacat gagccagtag tcaccctctg tggccacctc      60
tactgctggc cctgcatcta caagtggctc cacgtccaga gcgcctcgct tgcctccgat     120
gagcacccgc aatgcccagt ttgcaaggct gatata                               156

<210> SEQ ID NO 251
<211> LENGTH: 1003
<212> TYPE: DNA
```

<213> ORGANISM: Populus x canescens

<400> SEQUENCE: 251

```
acgcggggggg tccccttcgt ggaaatctct gtgtctctct gttatctgca aaatctccat    60
taaagcttcc tcgaatcctc ttattttaat caagccaaag aacactctgt tattttgcct   120
ttaactttcc ttcagagtta agaagaacg tgggaatcca tggaatttga aaatatttt    180
acccagggat ggaaatcagt ttcaagtgcg catctgact cggaaaatcc cagtggttgt    240
ttcgactgta atatctgttt tgactttgca catgagccag tagtcaccct ctgtggccac    300
ctctactgct ggccctgcat ctacaagtgg ctccacgtcc agagcgcctc gcttgcctcc    360
gatgagcacc cgcaatgccc agtttgcaag gctgatatat ctcacaccac catggttccc    420
ctgtatggcc gtggccaagg ctcaaccgaa gctgaaggca agacaccata caggggcatg    480
atcattcctc ctagaccatc agcttgtggt gctcaaggtg tggtgtcaaa cacatctaat    540
accggccagc ggcttccata tcgtaatcct taccggaacc ataactataa tgctaatcca    600
tacggcagtt tcgaagaggc ttccccatca cccttgctta atcttggaga ccctgcaatg    660
accggtttgc agcaaccagc tgttgggatg ttcagagaga tggtgtatgc gagggttttc    720
gggccctttc caaactcgta tcacttaatg ggtactggta gccctaggct gagaaggcat    780
gagctgatgg cagacaagtc attgaataga atctccattt ttctcttttg ttgctttctt    840
ttatgcctca ttgtatttg aaatatgaa ctaggttagt ctccattgtt cacctcgata    900
gttagtttgt aaagggcaat ggatccgagt ttatgaaata tccatggatc acttatattt    960
atatatatat gatttgatct tcatattttg ctggaaaaaa aaa                    1003
```

<210> SEQ ID NO 252
<211> LENGTH: 48
<212> TYPE: PRT
<213> ORGANISM: Arabidopsis thaliana

<400> SEQUENCE: 252

```
Asn Cys Ala Val Cys Leu Tyr Glu Phe Glu Gly Glu Gln Glu Ile Arg
1               5                   10                  15

Trp Leu Arg Asn Cys Arg His Ile Phe His Arg Ser Cys Leu Asp Arg
            20                  25                  30

Trp Met Asp His Asp Gln Lys Thr Cys Pro Leu Cys Arg Thr Pro Phe
        35                  40                  45
```

<210> SEQ ID NO 253
<211> LENGTH: 144
<212> TYPE: DNA
<213> ORGANISM: Arabidopsis thaliana

<400> SEQUENCE: 253

```
aactgcgccg tttgtctata cgaattcgaa ggagaacaag agatccggtg gctgagaaat    60
tgcagacata tatttcaccg gagctgtctt gaccgttgga tggatcatga tcagaagacg   120
tgtccacttt gtagaacacc gttt                                          144
```

<210> SEQ ID NO 254
<211> LENGTH: 170
<212> TYPE: PRT
<213> ORGANISM: Arabidopsis thaliana

<400> SEQUENCE: 254

```
Met Gly Phe Pro Val Gly Tyr Thr Glu Val Phe Leu Pro Lys Leu Phe
1               5                   10                  15
```

```
Val Gln Thr Leu Ser Ile Leu Gly Phe Ile Arg Thr Ile Val Phe Ser
             20                  25                  30

Ile Phe Arg Phe Leu Gly Leu Ser Asp Phe Leu Glu Met Asp Gln Thr
         35                  40                  45

Trp Pro Asp Tyr Thr Ser Tyr Pro Thr Arg Ile Pro Glu Thr Arg Ser
 50                  55                  60

Pro Phe Ser Ala Leu Leu Ile Arg Glu Ile Leu Pro Val Ile Lys Phe
 65                  70                  75                  80

Glu Glu Leu Thr Asn Ser Gly Glu Asp Leu Pro Glu Asn Cys Ala Val
                 85                  90                  95

Cys Leu Tyr Glu Phe Glu Gly Gln Glu Ile Arg Trp Leu Arg Asn
            100                 105                 110

Cys Arg His Ile Phe His Arg Ser Cys Leu Asp Arg Trp Met Asp His
            115                 120                 125

Asp Gln Lys Thr Cys Pro Leu Cys Arg Thr Pro Phe Val Pro Asp Glu
            130                 135                 140

Met Gln Glu Glu Phe Asn Gln Arg Leu Trp Ala Ala Ser Gly Val His
145                 150                 155                 160

Asp Phe His Cys Pro Val Thr Glu Leu Leu
            165                 170
```

<210> SEQ ID NO 255
<211> LENGTH: 513
<212> TYPE: DNA
<213> ORGANISM: Arabidopsis thaliana

<400> SEQUENCE: 255

```
atgggctttc ccgtaggtta cacagaggtt ttcttaccga agcttttcgt acaaacgctt      60
tcgattctcg gattcatcag aaccatcgtc ttctctatct tccgcttctt gggtctctca     120
gattttctcg aaatggatca aacctggccc gattacacat cgtacccgac ccgaataccc     180
gaaacccgct caccttttctc cgcactccta attagagaga tcctaccggt atcaaattc     240
gaagagttaa cgaattccgg cgaagatcta ccggaaaact gcgccgttg tctatacgaa      300
ttcgaaggag aacaagagat ccggtggctg agaaattgca gacatatatt tcaccggagc     360
tgtcttgacc gttggatgga tcatgatcag aagacgtgtc cactttgtag aacaccgttt     420
gttccagatg agatgcaaga agagtttaat caacggctat gggctgcttc tggtgttcat     480
gattttcact gtcccgtgac cgaattatta tag                                  513
```

<210> SEQ ID NO 256
<211> LENGTH: 146
<212> TYPE: DNA
<213> ORGANISM: Arabidopsis thaliana

<400> SEQUENCE: 256

```
aactgcgccg tttgtctata cgaattcgaa ggagaacaag agatccggtg gctgagaaat      60
tgcagacata tatttcaccg gagctgtctt gaccgttgga tggatcatga tcagaagacg     120
tgtccacttt gtagaacacc gtttgt                                          146
```

<210> SEQ ID NO 257
<211> LENGTH: 723
<212> TYPE: DNA
<213> ORGANISM: Arabidopsis thaliana

<400> SEQUENCE: 257

```
taaaaaccct agctttctcc atgggctttc ccgtaggtta cacagaggtt ttcttaccga      60
agcttttcgt acaaacgctt tcgattctcg gattcatcag aaccatcgtc ttctctatct     120
tccgcttctt gggtctctca gattttctcg aaatggatca aacctggccc gattacacat     180
cgtacccgac ccgaataccc gaaaccgct caccttctc cgcactccta attagagaga      240
tcctaccggt tatcaaattc gaagagttaa cgaattccgg cgaagatcta ccggaaaact     300
gcgccgtttg tctatacgaa ttcgaaggag aacaagagat ccggtggctg agaaattgca     360
gacatatatt tcaccggagc tgtcttgacc gttggatgga tcatgatcag aagacgtgtc     420
cactttgtag aacaccgttt gttccagatg agatgcaaga agagttaat caacggctat      480
gggctgcttc tggtgttcat gatttcact gtcccgtgac cgaattatta tagaagaagc      540
cacgcttttc tatcttttc tgtgtccctt atgttctttt tgttttgac tttcaccct        600
ctactttga tgttgctttt ttcacccctc ttactgacat ttagacttgc cacgctttta     660
tgtgtgtata tactccttac atatgaatga gagatgagca ataaatatta ccgagacagg    720
aaa                                                                    723
```

<210> SEQ ID NO 258
<211> LENGTH: 48
<212> TYPE: PRT
<213> ORGANISM: Arabidopsis thaliana

<400> SEQUENCE: 258

```
Asp Cys Val Val Cys Leu Ser Lys Leu Lys Glu Gly Glu Glu Val Arg
 1               5                  10                  15

Lys Leu Glu Cys Arg His Val Phe His Lys Cys Leu Glu Gly Trp
            20                  25                  30

Leu His Gln Phe Asn Phe Thr Cys Pro Leu Cys Arg Ser Ala Leu Val
        35                  40                  45
```

<210> SEQ ID NO 259
<211> LENGTH: 154
<212> TYPE: PRT
<213> ORGANISM: Arabidopsis thaliana

<400> SEQUENCE: 259

```
Met Gly Leu Gln Gly Gln Leu Ser Asp Val Ser Ser Asp Ser Ile Pro
 1               5                  10                  15

Leu Met Leu Leu Ser Leu Leu Ala Val Phe Ile Asn His Leu Arg Ser
            20                  25                  30

Phe Leu Leu Arg Leu Thr Ser Lys Ser Asn Pro Asn Leu Pro Val Asp
        35                  40                  45

Asp Val Ser Ile Ala Ser Gly Leu Ala Asn Ile Val Leu Ala Asp
    50                  55                  60

Gln Leu Ser Leu Asn Arg Leu Phe Ser Tyr Arg Cys Gly Asp Gly
 65                  70                  75                  80

Gly Gly Gly Ser Asp Cys Val Val Cys Leu Ser Lys Leu Lys Glu Gly
                85                  90                  95

Glu Glu Val Arg Lys Leu Glu Cys Arg His Val Phe His Lys Cys Leu
            100                 105                 110

Glu Gly Trp Leu His Gln Phe Asn Phe Thr Cys Pro Leu Cys Arg Ser
        115                 120                 125

Ala Leu Val Ser Asp Asp Cys Val Ser Lys Thr Gln Arg Ser Val Gly
    130                 135                 140

Arg Asp Leu Ile Ser Cys Phe Ser Leu His
145                 150
```

145          150

<210> SEQ ID NO 260
<211> LENGTH: 142
<212> TYPE: DNA
<213> ORGANISM: Arabidopsis thaliana

<400> SEQUENCE: 260

```
tgtgttgtgt gtttgtcgaa gttaaaggaa ggtgaagagg tgaggaagct ggaatgtcga      60
cacgtgttcc acaagaagtg tttggaagga tggcttcatc aattcaattt cacttgtcct     120
ctttgtagat ctgctttggt tt                                               142
```

<210> SEQ ID NO 261
<211> LENGTH: 468
<212> TYPE: DNA
<213> ORGANISM: Arabidopsis thaliana

<400> SEQUENCE: 261

```
atggggctac aaggtcagct aagtgacgtc tcttccgatt caatccctct tatgctcctc      60
tctctcctcg ccgtcttcat caaccatctc cgatctttcc cctccgtct cacctctaaa     120 tcaaatccta atccccccgt agacgatgtc tctatagcat cgggactagc caacataatc     180
gttctcgccg atcagcttag tttgaatcgg ttattctcgt accggtgcgg tgacggaggt     240
ggtggcggct ccgattgtgt tgtgtgtttg tcgaagttaa aggaaggtga agaggtgagg     300
aagctggaat gtcgacacgt gttccacaag aagtgtttgg aaggatggct tcatcaattc     360
aatttcactt gtcctctttg tagatctgct ttggttccg atgattgcgt ctctaaaacg     420
cagcgtagcg ttgggaggga tttgatctcg tgtttctctc tccactga                 468
```

<210> SEQ ID NO 262
<211> LENGTH: 781
<212> TYPE: DNA
<213> ORGANISM: Arabidopsis thaliana

<400> SEQUENCE: 262

```
gaagaagaag aaagatgggg ctacaaggtc agctaagtga cgtctcttcc gattcaatcc      60
ctcttatgct cctctctctc ctcgccgtct tcatcaacca tctccgatct ttcctcctcc     120
gtctcacctc taaatcaaat cctaatctcc ccgtagacga tgtctctata gcatcgggac     180
tagccaacat aatcgttctc gccgatcagc ttagtttgaa tcggttattc tcgtaccggt     240
gcggtgacgg aggtggtggc ggctccgatt gtgttgtgtg tttgtcgaag ttaaaggaag     300
gtgaagaggt gaggaagctg gaatgtcgac acgtgttcca caagaagtgt tggaaggat     360 ggcttcatca attcaatttc acttgtcctc tttgtagatc tgctttggtt tccgatgatt     420
gcgtctctaa aacgcagcgt agcgttggga gggatttgat ctcgtgtttc tctctccact     480
gagtaaaaga tcggaagatg aagaagatcc gatggtatct gagagatcta cggtggctgg     540
ctggttcggt ttgaccacgc gcgtgcgccc cttctttct cggatttttt ttgaggtctc     600
tttcttctgt gagaggagaa ccttttgttt gtttggtttt ttttttttact tttcgatttg     660 gaatatgtaa attttgaata tacaaatttt caccgtttgt atcttgttg ttccttgctg     720 ttgagtatat ataaatggag aagatatcaa ttccagtata aaaaaaaaaa aaaaaaaaa     780 a                                                                       781
```

<210> SEQ ID NO 263
<211> LENGTH: 47

<212> TYPE: PRT
<213> ORGANISM: Arabidopsis thaliana

<400> SEQUENCE: 263

Cys Ile Val Cys Leu Ser Lys Leu Lys Thr Gly Glu Glu Val Arg Lys
1               5                   10                  15

Leu Asp Cys Arg His Val Phe His Lys Gln Cys Leu Glu Gly Trp Leu
            20                  25                  30

Gln His Leu Asn Phe Asn Cys Pro Leu Cys Arg Ser Pro Leu Leu
        35                  40                  45

<210> SEQ ID NO 264
<211> LENGTH: 141
<212> TYPE: DNA
<213> ORGANISM: Arabidopsis thaliana

<400> SEQUENCE: 264
tgcatcgtgt gtctgtctaa actcaagacc ggagaagaag tgaggaagct agattgcaga      60
cacgtcttcc ataagcagtg tttggaaggc tggcttcaac atctcaactt caattgcccg     120
ctctgtagat ctccattgct a                                               141

<210> SEQ ID NO 265
<211> LENGTH: 147
<212> TYPE: PRT
<213> ORGANISM: Arabidopsis thaliana

<400> SEQUENCE: 265

Met Gly Leu Gln Gly Gln Leu Ser Asp Val Ser Ser Asp Ser Ile Pro
1               5                   10                  15

Leu Met Leu Leu Ala Leu Leu Ala Thr Phe Phe Arg His Val Arg Ser
            20                  25                  30

Leu Leu Leu Phe Pro Ser Ser Ala Pro Val Val Val Thr Ser Asn
        35                  40                  45

Leu Ser Val Leu Ala Asp Gln Leu Asn Leu Asn Arg Leu Phe Ser Tyr
50                  55                  60

Arg Tyr Ser Asp Asn Ala Ala Ser Asp Cys Ile Val Cys Leu Ser Lys
65                  70                  75                  80

Leu Lys Thr Gly Glu Glu Val Arg Lys Leu Asp Cys Arg His Val Phe
                85                  90                  95

His Lys Gln Cys Leu Glu Gly Trp Leu Gln His Leu Asn Phe Asn Cys
            100                 105                 110

Pro Leu Cys Arg Ser Pro Leu Leu Pro His His Gln Gly His Gly
        115                 120                 125

Ser Asp Ala Ser Ile Ser Ala Phe Pro Leu Arg Ser Thr Ser Thr Ala
    130                 135                 140

Ser Ser His
145

<210> SEQ ID NO 266
<211> LENGTH: 443
<212> TYPE: DNA
<213> ORGANISM: Arabidopsis thaliana

<400> SEQUENCE: 266
atgggactac aaggtcagct ctccgacgtg tcatcagatt cgatcccact gatgctactg      60
gctctcctcg caactttctt cagacacgtc cggtctcttc tcctcttccc ttcttctgcc     120
cccgttgttg ttgttactcc aaacctcagc gtcctcgccg accagctcaa cctaaatcgc     180

```
ctcttctcgt accgctactc cgacaacgca gcctctgact gcatcgtgtg tctgtctaaa      240
ctcaagaccg gagaagaagt gaggaagctg attgcagaca cgtcttccat aagcagtgtt      300
tggaaggctg gcttcaacat ctcaacttca attgcccgct ctgtagatct ccattgctac      360
ctcatcatca tcagggacat ggcagtgatg cgtcgatctc agccttccct cttcgctcta      420
cctctactgc atcatctcat tga                                              443
```

<210> SEQ ID NO 267
<211> LENGTH: 47
<212> TYPE: PRT
<213> ORGANISM: Arabidopsis thaliana

<400> SEQUENCE: 267

Asp Cys Ala Val Cys Leu Ser Lys Phe Glu Pro Glu Asp Gln Leu Arg
1               5                   10                  15

Leu Leu Pro Leu Cys Cys His Ala Phe His Ala Asp Cys Ile Asp Ile
                20                  25                  30

Trp Leu Val Ser Asn Gln Thr Cys Pro Leu Cys Arg Ser Pro Leu
            35                  40                  45

<210> SEQ ID NO 268
<211> LENGTH: 334
<212> TYPE: PRT
<213> ORGANISM: Arabidopsis thaliana

<400> SEQUENCE: 268

Met Glu Ser Leu Ile Asn Pro Ser His Gly Gly Gly Asn Tyr Asp Ser
1               5                   10                  15

His Ser Ser Ser Leu Asp Ser Leu Lys Pro Ser Val Leu Val Ile Ile
                20                  25                  30

Leu Ile Leu Leu Met Thr Leu Leu Ile Ser Val Ser Ile Cys Phe Leu
            35                  40                  45

Leu Arg Cys Leu Asn Arg Cys Ser His Arg Ser Val Leu Pro Leu Ser
        50                  55                  60

Ser Ser Ser Ser Val Ala Thr Val Thr Ser Asp Ser Arg Arg Phe Ser
65                  70                  75                  80

Gly His Arg Val Ser Pro Glu Thr Glu Arg Ser Ser Val Leu Asp Ser
                85                  90                  95

Leu Pro Ile Phe Lys Phe Ser Ser Val Thr Arg Arg Ser Ser Ser Met
                100                 105                 110

Asn Ser Gly Asp Cys Ala Val Cys Leu Ser Lys Phe Glu Pro Glu Asp
            115                 120                 125

Gln Leu Arg Leu Leu Pro Leu Cys Cys His Ala Phe His Ala Asp Cys
        130                 135                 140

Ile Asp Ile Trp Leu Val Ser Asn Gln Thr Cys Pro Leu Cys Arg Ser
145                 150                 155                 160

Pro Leu Phe Ala Ser Glu Ser Asp Leu Met Lys Ser Leu Ala Val Val
                165                 170                 175

Gly Ser Asn Asn Gly Gly Gly Glu Asn Ser Phe Arg Leu Glu Ile Gly
                180                 185                 190

Ser Ile Ser Arg Arg Arg Gln Thr Pro Ile Pro Glu Ser Val Glu Gln
            195                 200                 205

His Arg Thr Tyr Ser Ile Gly Ser Phe Asp Tyr Ile Val Asp Asp Val
        210                 215                 220

Asp Ser Glu Ile Ser Glu Ser Asn Phe Asn Arg Gly Lys Gln Glu Asp

```
                225                 230                 235                 240
Ala Thr Thr Thr Thr Ala Thr Ala Thr Ala Val Thr Thr Asn Pro Thr
                    245                 250                 255

Ser Phe Glu Ala Ser Leu Ala Ala Asp Ile Gly Asn Asp Gly Ser Arg
                260                 265                 270

Ser Trp Leu Lys Asp Tyr Val Asp Arg Leu Ser Arg Gly Ile Ser Ser
            275                 280                 285

Arg Ala Met Ser Phe Arg Ser Ser Gly Arg Phe Phe Thr Gly Ser Ser
        290                 295                 300

Arg Arg Ser Glu Glu Leu Thr Val Met Asp Leu Glu Ala Asn His Ala
305                 310                 315                 320

Gly Glu Glu Ile Ser Glu Leu Phe Arg Trp Leu Ser Gly Val
                325                 330

<210> SEQ ID NO 269
<211> LENGTH: 21
<212> TYPE: PRT
<213> ORGANISM: Arabidopsis thaliana

<400> SEQUENCE: 269

Val Leu Val Ile Ile Leu Ile Leu Leu Met Thr Leu Leu Ile Ser Val
1               5                   10                  15

Ser Ile Cys Phe Leu
            20

<210> SEQ ID NO 270
<211> LENGTH: 1005
<212> TYPE: DNA
<213> ORGANISM: Arabidopsis thaliana

<400> SEQUENCE: 270
atggaatctc tcatcaatcc cagccatggc ggaggaaact acgattctca ctcttcttct     60
ctcgatagtc tcaaaccaag cgtactagtc atcattctca ttctcctcat gactcttctc    120
atctccgttt ccatttgctt cctcctccgc tgtctcaatc gctgtagcca ccgctccgtt    180
ctccctcttt catcttcctc ttccgtcgca accgtaactt ccgattcccg acgattctct    240
ggacatcgag tctctcccga aacagaacgg tcctccgtgc ttgattcgct tccgattttc    300
aaattctcct ccgtcactcg ccgatctagc tccatgaatt ccggagattg cgccgttttgt    360
ttgtcgaaat cgaaccgga ggatcagctc cgtcttcttc ctctctgttg tcacgctttt    420
cacgccgatt gtatcgatat ctggctagtc tctaaccaga cttgtcctct ctgtcgctct    480
cctctcttcg cttcagaatc tgatctcatg aagtctctcg ccgtcgtcgg ctcaaacaac    540
ggcggaggag aaaacagctt ccgtctcgaa atcggatcca tcagccgtcg tcgtcaaaca    600
ccgattccag aatccgttga gcagcatcga acttactcaa tcggttcgtt cgattacata    660
gtagacgacg tagattcaga aatctcagag tcaaatttca accgtggaaa acaggaagac    720
gcgactacaa caactgccac agcaacggcg gttacgacta tccgacgtc gtttgaagct    780
agtttagcgg cggatatagg taacgatggt tctagaagct ggctcaagga ttacgttgac    840
agactctcac gaggtatatc gtcgcgtgca atgtcgttta aagctctgg tagattttttt    900
actgggagta gtcgtcggag tgaggaattg acggtgatgg atttagaagc gaatcatgcc    960
ggagaagaga taagtgagct tttccggtgg ctctcagggg tgtga              1005

<210> SEQ ID NO 271
<211> LENGTH: 90
```

```
<212> TYPE: PRT
<213> ORGANISM: Arabidopsis thaliana

<400> SEQUENCE: 271

Cys Ser Val Cys Leu Ser Glu Phe Glu Glu Asp Glu Gly Arg Leu
1               5                   10                  15

Leu Pro Lys Cys Gly His Ser Phe His Val Asp Cys Ile Asp Thr Trp
            20                  25                  30

Phe Arg Ser Arg Ser Thr Cys Pro Leu Cys Arg Glu Cys Ser Val Cys
            35                  40                  45

Leu Ser Glu Phe Glu Glu Asp Glu Gly Arg Leu Leu Pro Lys Cys
        50                  55                  60

Gly His Ser Phe His Val Asp Cys Ile Asp Thr Trp Phe Arg Ser Arg
65              70                  75                  80

Ser Thr Cys Pro Leu Cys Arg Ala Pro Val
                85                  90

<210> SEQ ID NO 272
<211> LENGTH: 227
<212> TYPE: PRT
<213> ORGANISM: Arabidopsis thaliana

<400> SEQUENCE: 272

Met Gly Ile Gly Glu Glu Ser Thr Lys Pro Ile Trp Gly Ser Val Ser
1               5                   10                  15

His Thr Ser Ser Gly Tyr Ala Leu Asn Gly Lys Ile Met Leu Ser Ser
            20                  25                  30

Val Ile Val Leu Phe Val Ala Val Ile Met Ile Leu Cys Phe His Ser
            35                  40                  45

Tyr Ala Arg Trp Leu Phe Arg Arg His Asn Arg Ile Arg Arg Arg
        50                  55                  60

Ile Arg Ser His Leu Arg Thr Leu Ser Ala Ser Pro Arg Asp Gln Ala
65              70                  75                  80

Leu Asp Gln Ala Val Leu Asp Lys Ile Pro Ile Phe Val Tyr Ser Ser
            85                  90                  95

Lys Asn Pro Pro Pro Glu Glu Lys Glu Cys Ser Val Cys Leu
            100                 105                 110

Ser Glu Phe Glu Glu Asp Glu Gly Arg Leu Leu Pro Lys Cys Gly
            115                 120                 125

His Ser Phe His Val Asp Cys Ile Asp Thr Trp Phe Arg Ser Arg Ser
    130                 135                 140

Thr Cys Pro Leu Cys Arg Ala Pro Val Gln Pro Phe Gln Val Ile
145                 150                 155                 160

Glu Thr Gly Ser Ser Ser Ser Ser Pro Leu Thr Phe Pro Thr Glu
                165                 170                 175

Gly Cys Glu Arg Glu Pro Ile Asp Leu Ala Gly Ile Ile Val Asp Ile
            180                 185                 190

Ser Arg Glu Val Glu Phe Glu Gly Ser Asn Pro Gly Leu Pro Ile Glu
            195                 200                 205

Asn Gly Ser Lys Phe Pro Gly Ser Arg Val Leu Ser Leu Lys Arg Leu
            210                 215                 220

Trp Ser Ile
225

<210> SEQ ID NO 273
<211> LENGTH: 21
```

```
<212> TYPE: PRT
<213> ORGANISM: Arabidopsis thaliana

<400> SEQUENCE: 273

Ile Met Leu Ser Ser Val Ile Val Leu Phe Val Ala Val Ile Met Ile
1               5                   10                  15

Leu Cys Phe His Ser
            20

<210> SEQ ID NO 274
<211> LENGTH: 684
<212> TYPE: DNA
<213> ORGANISM: Arabidopsis thaliana

<400> SEQUENCE: 274
atgggaatcg gtgaagaaag cacaaagcct atttggggga gcgtgagcca cacgtcttca       60
ggctacgctc tcaacggcaa atcatgctc tcctccgtga tcgttctatt cgtcgccgtt      120
attatgatcc tctgcttcca cagctacgcc cgttggttat ccgtcgtca caaccgtcgc      180 attcgccgcc gtattcgttc tcacctccgc actctctccg cctcaccccg agaccaagct      240
ctcgaccagg ctgttctcga caagattccg atcttcgttt actcctccaa gaatccacca      300
ccaccagaag agaaggagga gtgctccgtc tgcttgtcgg agttcgagga agaagacgaa      360
ggccgtcttc ttcctaaatg tggccactct tttcacgtcg actgcatcga tacttggttc      420
cgttccagat ccacttgccc gctttgcaga gctccggttc aaccccgtt tcaggtcatt      480 gaaaccggtt cttcttcttc ttcttcgccg ttgacattc cgacggaggg ttgcgagaga      540
gaaccgattg acctcgccgg tatcattgtg gatatttcca gagaagttga atttgaaggc      600
tcaaatccgg gtctacccat cgaaaacgga tcaaagtttc cgggtagtcg ggttttgtct      660
ttaaaaaggc tatggagcat ctga                                             684

<210> SEQ ID NO 275
<211> LENGTH: 359
<212> TYPE: PRT
<213> ORGANISM: Arabidopsis thaliana

<400> SEQUENCE: 275

Met Ser Ser Tyr Ser Ser Asp Ser Thr Ala Ala Arg Asp Gln His Ala
1               5                   10                  15

Pro Leu Leu Arg Pro Arg His Asp Gly Ser Phe Ser Ser Ser Ser
            20                  25                  30

Ser Ala Arg Pro Thr Ala Leu Ala Val Leu Leu Gly Arg Ile Thr Gly
        35                  40                  45

His Arg Ala Pro Ser Met Leu Val Arg Glu Thr Ala Ala Arg Ala Leu
    50                  55                  60

Glu Glu Arg Arg Ile Asp Trp Gly Tyr Ser Lys Pro Val Val Ala Ala
65                  70                  75                  80

Asp Ile Leu Trp Asn Ala Ala Leu Val Leu Ala Ser Ala Val Met Leu
                85                  90                  95

Val Gly Thr Val Glu Glu Arg Pro Asn Glu Pro Ile Arg Val Trp Ile
            100                 105                 110

Cys Val Tyr Gly Leu Gln Cys Leu Phe His Val Leu Val Trp Ser
            115                 120                 125

Glu Tyr Trp Arg Arg Asn Ser Thr Arg Arg Ala Arg Asp Leu Glu Ser
        130                 135                 140

Tyr Asp His Glu Asp Tyr Asn Ile Glu Tyr Asp Tyr Glu Gln Asp Ser
```

```
                145                 150                 155                 160
Asp Asp Asn Ser Thr Thr Tyr Ser Phe Val Lys Arg Cys Glu Ser Ile
                    165                 170                 175

Asn Thr Val Ile Ser Phe Ile Trp Trp Ile Gly Phe Tyr Trp Val
                180                 185                 190

Val Glu Gly Gly Asp Lys Leu Leu Gly Glu Ala Pro Asn Leu Tyr Trp
            195                 200                 205

Leu Ser Val Ile Phe Leu Ala Ile Asp Val Phe Phe Ala Val Phe Cys
        210                 215                 220

Val Val Leu Ala Cys Leu Val Gly Ile Ala Leu Cys Cys Cys Leu Pro
225                 230                 235                 240

Cys Ile Ile Ala Leu Leu Tyr Ala Val Ala Gly Thr Glu Gly Val Ser
                245                 250                 255

Glu Ala Glu Leu Gly Val Leu Pro Leu Tyr Lys Phe Lys Ala Phe His
                260                 265                 270

Ser Asn Glu Lys Asn Ile Thr Gly Pro Gly Lys Met Val Pro Ile Pro
            275                 280                 285

Ile Asn Gly Leu Cys Leu Ala Thr Glu Arg Thr Leu Leu Ala Glu Asp
        290                 295                 300

Ala Asp Cys Cys Ile Cys Leu Ser Ser Tyr Glu Asp Gly Ala Glu Leu
305                 310                 315                 320

His Ala Leu Pro Cys Asn His Phe His Ser Thr Cys Ile Val Lys
                325                 330                 335

Trp Leu Lys Met Arg Ala Thr Cys Pro Leu Cys Lys Tyr Asn Ile Leu
                340                 345                 350

Lys Gly Thr Thr Asp Gln Ser
        355
```

```
<210> SEQ ID NO 276
<211> LENGTH: 47
<212> TYPE: PRT
<213> ORGANISM: Arabidopsis thaliana

<400> SEQUENCE: 276

Asp Cys Cys Ile Cys Leu Ser Ser Tyr Glu Asp Gly Ala Glu Leu His
1               5                   10                  15

Ala Leu Pro Cys Asn His His Phe His Ser Thr Cys Ile Val Lys Trp
            20                  25                  30

Leu Lys Met Arg Ala Thr Cys Pro Leu Cys Lys Tyr Asn Ile Leu
        35                  40                  45

<210> SEQ ID NO 277
<211> LENGTH: 141
<212> TYPE: DNA
<213> ORGANISM: Arabidopsis thaliana

<400> SEQUENCE: 277
gattgttgca tatgtctgag ttcatatgag gatggcgcag agcttcatgc tcttccttgt    60
aaccaccatt tcattcgac ttgtattgtg aaatggctta agatgagagc aacatgccct   120
ctttgcaaat acaacattct t                                            141

<210> SEQ ID NO 278
<211> LENGTH: 2042
<212> TYPE: DNA
<213> ORGANISM: Arabidopsis thaliana

<400> SEQUENCE: 278
```

```
gaagaatctc aattctcttc gttactaatg tcatcgtatt cttcagattc cacggcggcg    60
cgtgatcaac atgcgcctct actccgtcca cgacacgacg gctcttttc ttcttcttct   120
tcatcagcca gacctacagc tctcgccgtt ctattaggac ggatcaccgg ccaccgagca   180
ccgtcgatgc tggttagaga aacagcggcg cgtgctctcg aggagagacg aatcgattgg   240
ggttactcga agcctgtagt tgctgctgat atactatgga acgctgcttt agttcttgcg   300
tcagcggtta tgcttgtcgg taccgttgaa gaaagaccta atgaaccgat tagggtttgg   360
atctgtgtgt atgggttaca gtgtttgttc catgtggttt tggtttggtc tgagtattgg   420
agaagaaact caactcgtag agctagggat ttggagtctt atgatcatga agattacaac   480
attgagtatg attatgaaca agacagtgat gacaattcaa caacttacag ttttgtgaag   540
agatgtgagt cgataaacac agtgatatca ttcatatggt ggataattgg attctactgg   600
gttgttgaag tggtgataa gcttttagga gaagctccta atctttactg ttatcggtg    660
attttcctgg cgattgacgt cttctttgct gttttctgtg ttgttttggc ttgccttgtt   720
ggaatagctc tttgttgctg tcttccttgc ataattgctc ttctttatgc cgttgctgga   780
acggaaggtc tatcggaggc ggagctcggt gttcttccct tgtacaaatt taaggctttc   840
catagcaatg agaagaacat tactggacct ggtaaaatgg ttcctatacc gatcaatggc   900
ttatgcttag caactgaaag aacactgctt gctgaggatg cggattgttg catatgtctg   960
agttcatatg aggatggcgc agagcttcat gctcttcctt gtaaccacca tttcattcg   1020
acttgtattg tgaaatggct taagatgaga gcaacatgcc ctctttgcaa atacaacatt   1080
cttaaaggaa ccactgatca atcttgaaga caaaactcaa ccaaccagag ggaataagat   1140
tctgcacata tagaaacaga ttccatttcc tcaattaaaa agcttctgta tatatttatt   1200
tacataacta tcaaagtcat gtgtcttttg ttaaaagcat ccatttaaa tgtaaaagat    1260
cacactttac aaatgccctt ttctatattt gcccatattt gagaatacag ctgatgctca   1320
tagtcatagc tcaaatcata agaaagttca cgaacagttc acttcattgc cacactgttt   1380
gctgcaatcc gcatcactta ctgctgttac aagcccccct ctctgcatat caagaagcaa   1440
atccgaagca gcggccatgt ttccctcctt ttcataagct ctaatcaaga gatcaaaaac   1500
agccgaatca ggacttattc cgctattcaa catttcatcg aaaacttgtc ttgcctcaac   1560
catcaaaccc ttgctagcta gcccgtaaat caatgtagta taggctaaca aatcaagcaa   1620
aagaccttcc tgaaccattc tggtttttaa cttaaacgca tccaccaaat tcccttgctt   1680
acacaaacca gctatccaag aagtgtacat gaacttatct ggaacaagtc cagcctctga   1740
gattttacta aacaatctct caacttctat aaagtctcct tctttgcaca agcatcaat   1800
aagcacagtg tacataacat cattagcttt ctctatacag aaataaacta tagcttcatg   1860
aaagcctctc tcaattaatt tgtggtacat gttaaccgca gccttcatgc gtccggattt   1920
aaaatatgca ttcatcattg tagtaaaaat caccatatca ggaactaaat cacttttctc   1980
catatcttct acaatctcag ttgcctcctt tagtttacca ttaccacaaa ggcctgatat   2040
ga                                                                 2042
```

<210> SEQ ID NO 279
<211> LENGTH: 2028
<212> TYPE: DNA
<213> ORGANISM: Arabidopsis thaliana

<400> SEQUENCE: 279

-continued

| | |
|---|---|
| atggaagaga tttcgacgga tccggttgtt ccagcggtga aacctgaccc gagaacatct | 60 |
| tcagttggtg aaggtgctaa tcgtcatgaa aatgacgacg gaggaagcgg cggttctgag | 120 |
| attggagcac cggatctgga taaagacttg ctttgtccga tttgtatgca gattattaaa | 180 |
| gatgctttcc tcacggcttg tggtcatagt ttctgctata tgtgtatcat cacacatctt | 240 |
| aggaacaaga gtgattgtcc ctgttgtagc aacacctca ccaataatca gctttaccct | 300 |
| aatttcttgc tcgataagct attgaagaaa acttcagctc ggcatgtgtc aaaaactgca | 360 |
| tcgcccttgg atcagtttcg ggaagcacta caaagggggtt gtgatgtgtc aattaaggag | 420 |
| gttgataatc ttctgacact tcttgcggaa aggaagagaa aaatggaaca ggaagaagct | 480 |
| gagaggaaca tgcagatact tttggacttt ttgcattgtc taaggaagca aaaagttgat | 540 |
| gaactaaatg aggtgcaaac tgatctccag tatattaaag aagatataaa tgccgttgag | 600 |
| agacatagaa tagatttata ccgagctagg gacagatatt ctgtaaagtt gcggatgctc | 660 |
| ggagatgatc caagcacaag aaatgcatgg ccacatgaga agaaccagat tggtttcaac | 720 |
| tccaattctc tcagcataag aggaggaaat tttgtaggca attatcaaaa caaaaaggta | 780 |
| gaggggaagg cacaaggaag ctctcatggg ctaccaaaga aggatgcgct gagtgggtca | 840 |
| gattcgcaaa gtttgaatca gtcaactgtc tcaattgcta gaaagaaacg gattcatgct | 900 |
| cagttcaatg atttacaaga atgttacctc caaaagcggc gtcagttggc agaccaacca | 960 |
| aatagtaaac aagaaaatga taagagtgta gtacggaggg aaggctatag caacggcctt | 1020 |
| gcagattttc aatctgtgtt gactaccttc actcgctaca gtcgtctaag agttatagca | 1080 |
| gaaatccggc atggggatat atttcattca gccaacattg tatcaagcat agagtttgat | 1140 |
| cgtgatgatg agctgtttgc cactgctggt gtttctagat gtataaaggt ttttgacttc | 1200 |
| tcttcgtttg taaatgaacc agcagatatg cagtgtccga ttgtggagat gtcaactcgg | 1260 |
| tctaaactta gttgcttgag ttggaataag catgaaaaaa atcacatagc aagcagtgat | 1320 |
| tatgaaggaa tagtaacagt gtgggatgta actactaggc agagtcggat ggagtatgaa | 1380 |
| gagcacgaaa acgtgcctg gagtgttgac ttttcacgaa cagaaccatc aatgcttgta | 1440 |
| tctggtagtg acgactgcaa ggttaaagtt tggtgcacga ggcaggaagc aagtgtgatt | 1500 |
| aatattgata tgaaagcaaa catatgttgt gtcaagtaca atcctggctc aagcaactac | 1560 |
| attgcggtcg gatcagctga tcatcacatc cattattacg atctaagaaa cataagccaa | 1620 |
| ccacttcatg tcttcagtgg acacaagaaa gcagtttcct atgttaaatt tttgtccaac | 1680 |
| aacgagctcg cttctgcgtc cacagatagc acactacgct tatgggatgt caaagacaac | 1740 |
| ttgccagttc gaacattcag aggacatact aacgagaaga actttgtggg tctcacagtg | 1800 |
| aacagcgagt atctcgcctg tggaagcgag acaaacgaag tatatgtata tcacaaggaa | 1860 |
| atcacgagac ccgtgacatc gcacagattt ggatcgccag acatggacga tgcagaggaa | 1920 |
| gaggcaggtt cctactttat tagtgcggtt tgctggaaga gtgatagtcc cacgatgttg | 1980 |
| actgcgaata gtcaaggaac catcaaagtt ctggtactcg ctgcgtga | 2028 |

<210> SEQ ID NO 280
<211> LENGTH: 675
<212> TYPE: PRT
<213> ORGANISM: Arabidopsis thaliana

<400> SEQUENCE: 280

Met Glu Glu Ile Ser Thr Asp Pro Val Val Pro Ala Val Lys Pro Asp
1               5                   10                  15

-continued

```
Pro Arg Thr Ser Ser Val Gly Glu Gly Ala Asn Arg His Glu Asn Asp
                20                  25                  30
Asp Gly Gly Ser Gly Ser Glu Ile Gly Ala Pro Asp Leu Asp Lys
        35                  40                  45
Asp Leu Leu Cys Pro Ile Cys Met Gln Ile Ile Lys Asp Ala Phe Leu
    50                  55                  60
Thr Ala Cys Gly His Ser Phe Cys Tyr Met Cys Ile Ile Thr His Leu
65                  70                  75                  80
Arg Asn Lys Ser Asp Cys Pro Cys Ser Gln His Leu Thr Asn Asn
                85                  90                  95
Gln Leu Tyr Pro Asn Phe Leu Leu Asp Lys Leu Leu Lys Thr Ser
                100                 105                 110
Ala Arg His Val Ser Lys Thr Ala Ser Pro Leu Asp Gln Phe Arg Glu
        115                 120                 125
Ala Leu Gln Arg Gly Cys Asp Val Ser Ile Lys Glu Val Asp Asn Leu
    130                 135                 140
Leu Thr Leu Leu Ala Glu Arg Lys Arg Lys Met Glu Gln Glu Glu Ala
145                 150                 155                 160
Glu Arg Asn Met Gln Ile Leu Leu Asp Phe Leu His Cys Leu Arg Lys
                165                 170                 175
Gln Lys Val Asp Glu Leu Asn Glu Val Gln Thr Asp Leu Gln Tyr Ile
            180                 185                 190
Lys Glu Asp Ile Asn Ala Val Glu Arg His Arg Ile Asp Leu Tyr Arg
        195                 200                 205
Ala Arg Asp Arg Tyr Ser Val Lys Leu Arg Met Leu Gly Asp Pro
    210                 215                 220
Ser Thr Arg Asn Ala Trp Pro His Glu Lys Asn Gln Ile Gly Phe Asn
225                 230                 235                 240
Ser Asn Ser Leu Ser Ile Arg Gly Gly Asn Phe Val Gly Asn Tyr Gln
                245                 250                 255
Asn Lys Lys Val Glu Gly Lys Ala Gln Gly Ser Ser His Gly Leu Pro
            260                 265                 270
Lys Lys Asp Ala Leu Ser Gly Ser Asp Ser Gln Ser Leu Asn Gln Ser
        275                 280                 285
Thr Val Ser Met Ala Arg Lys Lys Arg Ile His Ala Gln Phe Asn Asp
    290                 295                 300
Leu Gln Glu Cys Tyr Leu Gln Lys Arg Arg Gln Leu Ala Asp Gln Pro
305                 310                 315                 320
Asn Ser Lys Gln Glu Asn Asp Lys Ser Val Val Arg Arg Glu Gly Tyr
                325                 330                 335
Ser Asn Gly Leu Ala Asp Phe Gln Ser Val Leu Thr Thr Phe Thr Arg
            340                 345                 350
Tyr Ser Arg Leu Arg Val Ile Ala Glu Ile Arg His Gly Asp Ile Phe
        355                 360                 365
His Ser Ala Asn Ile Val Ser Ser Ile Glu Phe Asp Arg Asp Asp Glu
    370                 375                 380
Leu Phe Ala Thr Ala Gly Val Ser Arg Cys Ile Lys Val Phe Asp Phe
385                 390                 395                 400
Ser Ser Val Val Asn Glu Pro Ala Asp Met Gln Cys Pro Ile Val Glu
                405                 410                 415
Met Ser Thr Arg Ser Lys Leu Ser Cys Leu Ser Trp Asn Lys His Glu
            420                 425                 430
Lys Asn His Ile Ala Ser Ser Asp Tyr Glu Gly Ile Val Thr Val Trp
```

```
                435                 440                 445
Asp Val Thr Thr Arg Gln Ser Leu Met Glu Tyr Glu His Glu Lys
    450                 455                 460
Arg Ala Trp Ser Val Asp Phe Ser Arg Thr Glu Pro Ser Met Leu Val
465                 470                 475                 480
Ser Gly Ser Asp Asp Cys Lys Val Lys Val Trp Cys Thr Arg Gln Glu
                485                 490                 495
Ala Ser Val Ile Asn Ile Asp Met Lys Ala Asn Ile Cys Cys Val Lys
                500                 505                 510
Tyr Asn Pro Gly Ser Ser Asn Tyr Ile Ala Val Gly Ser Ala Asp His
                515                 520                 525
His Ile His Tyr Tyr Asp Leu Arg Asn Ile Ser Gln Pro Leu His Val
    530                 535                 540
Phe Ser Gly His Lys Lys Ala Val Ser Tyr Val Lys Phe Leu Ser Asn
545                 550                 555                 560
Asn Glu Leu Ala Ser Ala Ser Thr Asp Ser Thr Leu Arg Leu Trp Asp
                565                 570                 575
Val Lys Asp Asn Leu Pro Val Arg Thr Phe Arg Gly His Thr Asn Glu
                580                 585                 590
Lys Asn Phe Val Gly Leu Thr Val Asn Ser Glu Tyr Leu Ala Cys Gly
                595                 600                 605
Ser Glu Thr Asn Glu Val Tyr Val Tyr His Lys Glu Ile Thr Arg Pro
    610                 615                 620
Val Thr Ser His Arg Phe Gly Ser Pro Asp Met Asp Asp Ala Glu Glu
625                 630                 635                 640
Glu Ala Gly Ser Tyr Phe Ile Ser Ala Val Cys Trp Lys Ser Asp Ser
                645                 650                 655
Pro Thr Met Leu Thr Ala Asn Ser Gln Gly Thr Ile Lys Val Leu Val
                660                 665                 670
Leu Ala Ala
    675

<210> SEQ ID NO 281
<211> LENGTH: 39
<212> TYPE: PRT
<213> ORGANISM: Arabidopsis thaliana

<400> SEQUENCE: 281

Cys Pro Ile Cys Met Gln Ile Ile Lys Asp Ala Phe Leu Thr Ala Cys
1               5                   10                  15

Gly His Ser Phe Cys Tyr Met Cys Ile Ile Thr His Leu Arg Asn Lys
                20                  25                  30

Ser Asp Cys Pro Cys Cys Ser
        35

<210> SEQ ID NO 282
<211> LENGTH: 203
<212> TYPE: PRT
<213> ORGANISM: Arabidopsis thaliana

<400> SEQUENCE: 282

Met Gly Leu Gln Gly Gln Leu Ser Asp Val Ser Ser Asp Ser Ile Pro
1               5                   10                  15

Leu Met Leu Leu Ser Leu Leu Ala Val Phe Ile Asn His Leu Arg Ser
                20                  25                  30

Phe Leu Leu Arg Leu Thr Ser Lys Ser Asn Pro Asn Leu Pro Val Asp
```

```
                35                  40                  45
Asp Val Ser Ile Ala Ser Gly Leu Ala Asn Ile Ile Val Leu Ala Asp
         50                  55                  60

Gln Leu Ser Leu Asn Arg Leu Phe Ser Tyr Arg Cys Gly Asp Gly Gly
 65                  70                  75                  80

Gly Gly Gly Ser Asp Cys Val Val Cys Leu Ser Lys Leu Lys Glu Gly
                 85                  90                  95

Glu Glu Val Arg Lys Leu Glu Cys Arg His Val Phe His Lys Lys Cys
            100                 105                 110

Leu Glu Gly Trp Leu His Gln Phe Asn Phe Thr Cys Pro Leu Cys Arg
        115                 120                 125

Ser Ala Leu Val Ser Asp Asp Cys Val Ser Lys Thr Gln Arg Ser Val
    130                 135                 140

Gly Arg Asp Leu Ile Ser Cys Phe Ser Leu His Asp Cys Val Val Cys
145                 150                 155                 160

Leu Ser Lys Leu Lys Glu Gly Glu Val Arg Lys Leu Glu Cys Arg
                165                 170                 175

His Val Phe His Lys Lys Cys Leu Glu Gly Trp Leu His Gln Phe Asn
            180                 185                 190

Phe Thr Cys Pro Leu Cys Arg Ser Ala Leu Val
        195                 200

<210> SEQ ID NO 283
<211> LENGTH: 47
<212> TYPE: PRT
<213> ORGANISM: Arabidopsis thaliana

<400> SEQUENCE: 283

Asp Cys Val Val Cys Leu Ser Lys Leu Lys Glu Gly Glu Glu Val Arg
 1               5                  10                  15

Lys Leu Glu Cys Arg His Val Phe His Lys Lys Cys Leu Glu Gly Trp
            20                  25                  30

Leu His Gln Phe Asn Phe Thr Cys Pro Leu Cys Arg Ser Ala Leu
        35                  40                  45

<210> SEQ ID NO 284
<211> LENGTH: 141
<212> TYPE: DNA
<213> ORGANISM: Arabidopsis thaliana

<400> SEQUENCE: 284
gattgtgttg tgtgtttgtc gaagttaaag gaaggtgaag aggtgaggaa gctggaatgt      60
cgacacgtgt tccacaagaa gtgtttggaa ggatggcttc atcaattcaa tttcacttgt     120
cctctttgta gatctgcttt g                                               141

<210> SEQ ID NO 285
<211> LENGTH: 468
<212> TYPE: DNA
<213> ORGANISM: Arabidopsis thaliana

<400> SEQUENCE: 285
atggggctac aaggtcagct aagtgacgtc tcttccgatt caatccctct tatgctcctc      60
tctctcctcg ccgtcttcat caaccatctc cgatctttcc tcctccgtct cacctctaaa    120
tcaaatccta atctccccgt agacgatgtc tctatagcat cgggactagc caacataatc    180
gttctcgccg atcagcttag tttgaatcgg ttattctcgt accggtgcgg tgacggaggt    240
```

```
ggtggcggct ccgattgtgt tgtgtgtttg tcgaagttaa aggaaggtga agaggtgagg      300
aagctggaat gtcgacacgt gttccacaag aagtgtttgg aaggatggct tcatcaattc      360
aatttcactt gtcctctttg tagatctgct ttggtttccg atgattgcgt ctctaaaacg      420
cagcgtagcg ttgggaggga tttgatctcg tgtttctctc tccactga                  468
```

<210> SEQ ID NO 286
<211> LENGTH: 47
<212> TYPE: PRT
<213> ORGANISM: Arabidopsis thaliana

<400> SEQUENCE: 286

```
Asp Cys Val Val Cys Leu Ser Lys Leu Lys Glu Gly Glu Glu Val Arg
1               5                   10                  15

Lys Leu Glu Cys Arg His Val Phe His Lys Lys Cys Leu Glu Gly Trp
            20                  25                  30

Leu His Gln Phe Asn Phe Thr Cys Pro Leu Cys Arg Ser Ala Leu
        35                  40                  45
```

<210> SEQ ID NO 287
<211> LENGTH: 141
<212> TYPE: DNA
<213> ORGANISM: Arabidopsis thaliana

<400> SEQUENCE: 287

```
gattgtgttg tgtgtttgtc gaagttaaag gaaggtgaag aggtgaggaa gctggaatgt      60
cgacacgtgt tccacaagaa gtgtttggaa ggatggcttc atcaattcaa tttcacttgt     120
cctctttgta gatctgcttt g                                               141
```

<210> SEQ ID NO 288
<211> LENGTH: 150
<212> TYPE: PRT
<213> ORGANISM: Gossypium sp.

<400> SEQUENCE: 288

```
Met Gly Leu Ser Ser Leu Pro Ser Pro Ser Glu Gly Val Leu Cys Ile
1               5                   10                  15

Leu Leu Val Asn Thr Ala Leu Ser Ile Ser Ile Val Lys Gly Ile Ile
            20                  25                  30

Arg Ser Ile Leu His Val Val Gly Val His Leu Pro Pro Pro Ser Ser
        35                  40                  45

Asp Tyr Thr Glu Asn Leu Ser Glu Ser Phe Asp Phe His Leu Asn Thr
    50                  55                  60

Pro Glu Ser Tyr Ile Glu Glu Phe Arg Ser Arg Thr Pro Thr Ile His
65                  70                  75                  80

Phe Gly Ala Val Leu Cys Ser Cys Lys Arg Pro Gln His Asp Cys Gln
                85                  90                  95

Val Cys Leu Thr Gln Phe Glu Pro Lys Ser Glu Ile Asn His Leu Ser
            100                 105                 110

Cys Gly His Leu Phe His Lys Val Cys Leu Glu Lys Trp Leu Asp Tyr
        115                 120                 125

Trp Asn Ile Thr Cys Pro Leu Cys Arg Thr Pro Leu Leu Pro Glu Glu
    130                 135                 140

Glu Ala Ser Cys Phe Trp
145                 150
```

<210> SEQ ID NO 289

<211> LENGTH: 47
<212> TYPE: PRT
<213> ORGANISM: Gossypium sp.

<400> SEQUENCE: 289

Asp Cys Gln Val Cys Leu Thr Gln Phe Glu Pro Lys Ser Glu Ile Asn
1               5                   10                  15

His Leu Ser Cys Gly His Leu Phe His Lys Val Cys Leu Glu Lys Trp
            20                  25                  30

Leu Asp Tyr Trp Asn Ile Thr Cys Pro Leu Cys Arg Thr Pro Leu
        35                  40                  45

<210> SEQ ID NO 290
<211> LENGTH: 141
<212> TYPE: DNA
<213> ORGANISM: Gossypium sp.

<400> SEQUENCE: 290
gactgtcagg tttgtctgac tcagtttgag ccaaaatccg agattaacca cttgtcgtgt    60
ggccatctct ttcacaaggt gtgtttggaa aaatggttgg attattggaa tattacatgc   120
cctctttgca ggactccctt g                                             141

<210> SEQ ID NO 291
<211> LENGTH: 450
<212> TYPE: DNA
<213> ORGANISM: Gossypium sp.

<400> SEQUENCE: 291
gggtctctca agtcttccat ctccatcaga aggagtgtta tgtatactct tggtaaacac    60
agctttatct atatctatag ttaaaggcat aatccgatcg atccttcacg ttgtcggtgt   120
ccatctccca ccaccatcat cggattacac tgaaaatctc tcggaatcat tcgatttcca   180
ccttaatact cctgaaagtt acatcgagga attccggagt aggacccaa caattcattt    240 cggtgctgtt ttatgtagct gcaaacggcc tcagcacgac tgtcaggttt gtctgactca   300
gtttgagcca aaatccgaga ttaaccactt gtcgtgtggc catctctttc acaaggtgtg   360
tttgaaaaaa tggttggatt attggaatat tacatgccct ctttgcagga ctcccttgtt   420
gcctgaagaa gaagcttctt gcttttggta                                    450

<210> SEQ ID NO 292
<211> LENGTH: 65
<212> TYPE: PRT
<213> ORGANISM: Lotus japonicus

<400> SEQUENCE: 292

Met Gly Leu Ser Ser Leu Pro Ala Pro Ser Glu Gly Val Leu Cys Val
1               5                   10                  15

Leu Leu Val Asn Thr Val Met Ser Ile Ser Ile Phe Lys Gly Ile Val
            20                  25                  30

Arg Thr Ile Leu His Ile Val Gly Ile His Leu Ser Ser Pro Asp Ala
        35                  40                  45

Ser Gln Asn Pro Pro Glu Ser Phe Glu Val His Leu Ser Pro Ser Glu
    50                  55                  60

Ser
65

<210> SEQ ID NO 293
<211> LENGTH: 196

<212> TYPE: DNA
<213> ORGANISM: Lotus japonicus

<400> SEQUENCE: 293

```
atgggtctct caagtctccc agcaccatct gaaggagtgt tatgtgtgct tcttgtgaac    60
actgtgatgt ccatttccat attcaaaggc attgtcagaa caattctaca cattgttggt   120
atccatcttt cttcaccaga tgcctcccaa aacccacctg aatcatttga agtccatctc   180
agccctctg agagtt                                                    196
```

<210> SEQ ID NO 294
<211> LENGTH: 152
<212> TYPE: PRT
<213> ORGANISM: Solanum tuberosum

<400> SEQUENCE: 294

```
Met Gly Leu Ser Gln Tyr Pro Thr Pro Ala Asp Ala Gly Val Leu Cys
1               5                   10                  15
Val Ile Leu Val Asn Thr Ala Ile Ser Ile Ser Ile Val Lys Glu Met
            20                  25                  30
Val Arg Ser Ile Leu His Val Ile Gly Ile His Ile Ala Ser Trp Asp
        35                  40                  45
Asp Tyr Ser Ile Glu Gly Ser Leu Glu Ser Phe Glu Cys Arg Arg Ser
    50                  55                  60
Pro Ser Glu Ser Tyr Met Glu Glu Phe Arg Ser His Thr Pro Ala Ile
65                  70                  75                  80
Arg Tyr Asp Ser Ile Cys Ile Ser Asn His Ala Glu Lys Glu Cys Ser
                85                  90                  95
Val Cys Leu Thr Asp Phe Glu Pro Asp Ala Glu Ile Asn His Leu Ser
            100                 105                 110
Cys Gly His Val Phe His Lys His Cys Leu Glu Lys Trp Leu Lys Tyr
        115                 120                 125
Trp Asn Val Thr Cys Pro Leu Cys Arg Asn Tyr Met Met Ser Gln Glu
    130                 135                 140
Gly Glu Glu Asp Thr Cys Pro Met
145                 150
```

<210> SEQ ID NO 295
<211> LENGTH: 44
<212> TYPE: PRT
<213> ORGANISM: Solanum tuberosum

<400> SEQUENCE: 295

```
Glu Cys Ser Val Cys Leu Thr Asp Phe Glu Pro Asp Ala Glu Ile Asn
1               5                   10                  15
His Leu Ser Cys Gly His Val Phe His Lys His Cys Leu Glu Lys Trp
            20                  25                  30
Leu Lys Tyr Trp Asn Val Thr Cys Pro Leu Cys Arg
        35                  40
```

<210> SEQ ID NO 296
<211> LENGTH: 138
<212> TYPE: DNA
<213> ORGANISM: Solanum tuberosum

<400> SEQUENCE: 296

```
gagtgctccg tctgcctgac ggattttgag cctgatgcag agataaacca tctctcatgt    60
ggccatgttt tccacaagca ttgtttagag aagtggctca agtactggaa tgtaacttgt   120
```

```
ccactttgca ggaattac                                                              138

<210> SEQ ID NO 297
<211> LENGTH: 456
<212> TYPE: DNA
<213> ORGANISM: Solanum tuberosum

<400> SEQUENCE: 297
gggcctctca cagtatccaa ctccagcaga tgcaggagtg ctctgtgtta ttctagtgaa       60
cacagccata tccatctcca ttgtcaagga gatggtccga tcgatccttc atgtgattgg      120
catccatatt gcatcatggg acgattattc cattgaaggc tccttggagt cgtttgaatg      180
tcgcagaagc ccatcagagt catatatgga ggaattcaga agccataccc ctgcaattcg      240
ttatgattca atctgtatct ctaaccatgc tgagaaagag tgctccgtct gcctgacgga      300
ttttgagcct gatgcagaga taaaccatct ctcatgtggc catgttttcc acaagcattg      360
tttagagaag tggctcaagt actggaatgt aacttgtcca ctttgcagga attacatgat      420
gtctcaagaa ggcgaagaag atacttgtcc tatgtg                                456

<210> SEQ ID NO 298
<211> LENGTH: 152
<212> TYPE: PRT
<213> ORGANISM: Lycopersicon esculentum

<400> SEQUENCE: 298

Met Gly Leu Ser Gln Tyr Pro Thr Pro Ala Asp Ala Gly Val Leu Cys
1               5                   10                  15

Val Ile Leu Val Asn Thr Ala Ile Ser Ile Ser Ile Val Lys Glu Met
            20                  25                  30

Val Arg Ser Ile Leu His Val Ile Gly Ile His Ile Ala Ser Trp Asp
        35                  40                  45

Asp Tyr Ser Ile Glu Gly Ser Leu Asp Ser Phe Glu Cys Arg Arg Ser
    50                  55                  60

Pro Ser Glu Ser Tyr Met Glu Glu Phe Arg Ser His Thr Pro Ala Ile
65                  70                  75                  80

Arg Tyr Asp Ser Ile Cys Ile Ser Asn His Ala Glu Lys Glu Cys Ser
                85                  90                  95

Val Cys Leu Thr Asp Phe Glu Pro Asp Ala Gln Ile Asn His Leu Ser
            100                 105                 110

Cys Gly His Val Phe His Lys His Cys Leu Glu Lys Trp Leu Lys Tyr
        115                 120                 125

Trp Asn Val Thr Cys Pro Leu Cys Arg Asn Tyr Met Met Ser Gln Glu
    130                 135                 140

Gly Glu Glu Asp Thr Cys Pro Met
145                 150

<210> SEQ ID NO 299
<211> LENGTH: 46
<212> TYPE: PRT
<213> ORGANISM: Lycopersicon esculentum

<400> SEQUENCE: 299

Glu Cys Ser Val Cys Leu Thr Asp Phe Glu Pro Asp Ala Gln Ile Asn
1               5                   10                  15

His Leu Ser Cys Gly His Val Phe His Lys His Cys Leu Glu Lys Trp
            20                  25                  30
```

Leu Lys Tyr Trp Asn Val Thr Cys Pro Leu Cys Arg Asn Tyr
         35                  40                  45

<210> SEQ ID NO 300
<211> LENGTH: 138
<212> TYPE: DNA
<213> ORGANISM: Lycopersicon esculentum

<400> SEQUENCE: 300
gagtgctcag tctgcctgac ggattttgag cctgacgcac agataaacca tctctcatgt    60
ggccatgttt tccacaagca ttgcttagag aagtggctca agtactggaa tgtaacttgt   120
ccactttgca ggaattac                                                 138

<210> SEQ ID NO 301
<211> LENGTH: 456
<212> TYPE: DNA
<213> ORGANISM: Lycopersicon esculentum

<400> SEQUENCE: 301
gggactctca cagtatccaa ctccagcaga tgcaggagtg ctctgtgtta ttctagtgaa    60
cacagccata tccatctcca ttgtcaagga gatggtccga tcgatccttc atgtgattgg   120
catccacatt gcatcatggg acgattattc catcgaaggc tccttggact cgtttgaatg   180
tcgcagaagc ccatcagagt catatatgga ggaattcaga agccataccc ctgcaattcg   240
ttatgattcc atctgtatct ctaaccacgc tgagaaagag tgctcagtct gcctgacgga   300
ttttgagcct gacgcacaga taaaccatct ctcatgtggc catgttttcc acaagcattg   360
cttagagaag tggctcaagt actggaatgt aacttgtcca ctttgcagga attacatgat   420
gtctcaagaa ggcgaagaag atacttgtcc tatgtg                              456

<210> SEQ ID NO 302
<211> LENGTH: 152
<212> TYPE: PRT
<213> ORGANISM: Glycine max

<400> SEQUENCE: 302

Met Gly Leu Ser Ser Leu Pro Ala Pro Ser Glu Gly Val Leu Cys Val
1               5                   10                  15

Leu Leu Val Asn Thr Ala Leu Ser Ile Ser Ile Phe Lys Gly Ile Val
            20                  25                  30

Arg Thr Ile Leu Gln Ile Val Gly Ile Arg Val Ser Ser Leu Ser Pro
        35                  40                  45

Ser Pro Asp Ile Ser Arg Asn Pro Pro Glu Pro Leu Glu Phe Asn Leu
    50                  55                  60

Ser Pro Ser Glu Gly Phe Ile Glu Glu Phe Arg Ser Arg Thr Pro Thr
65                  70                  75                  80

Leu Arg Phe Gly Ser Met Cys Gly Ser Lys Gln Pro Gln His Glu Cys
                85                  90                  95

Cys Cys Val Cys Leu Thr Lys Phe Glu Pro Glu Ser Glu Ile Asn Cys
            100                 105                 110

Leu Ser Cys Gly His Ile Phe His Lys Val Cys Met Glu Lys Trp Leu
        115                 120                 125

Asp Tyr Trp Asn Ile Thr Cys Pro Leu Cys Arg Thr Ser Leu Met Pro
    130                 135                 140

Glu Asp Asp Ala Ser Cys Phe Trp
145                 150

<210> SEQ ID NO 303
<211> LENGTH: 47
<212> TYPE: PRT
<213> ORGANISM: Glycine max

<400> SEQUENCE: 303

Glu Cys Cys Cys Val Cys Leu Thr Lys Phe Glu Pro Glu Ser Glu Ile
1               5                   10                  15

Asn Cys Leu Ser Cys Gly His Ile Phe His Lys Val Cys Met Glu Lys
            20                  25                  30

Trp Leu Asp Tyr Trp Asn Ile Thr Cys Pro Leu Cys Arg Thr Ser
        35                  40                  45

<210> SEQ ID NO 304
<211> LENGTH: 138
<212> TYPE: DNA
<213> ORGANISM: Glycine max

<400> SEQUENCE: 304
gagtgctcag tctgcctgac ggattttgag cctgacgcac agataaacca tctctcatgt      60
ggccatgttt tccacaagca ttgcttagag aagtggctca agtactggaa tgtaacttgt    120
ccactttgca ggaattac                                                  138

<210> SEQ ID NO 305
<211> LENGTH: 456
<212> TYPE: DNA
<213> ORGANISM: Glycine max

<400> SEQUENCE: 305
gggcctgtca gtctcccag caccatctga aggagtgtta tgtgtgcttc ttgtaaacac       60
tgccttgtct atatccatat tcaaaggcat tgttaggaca attctacaaa ttgtcggtat    120
ccgcgtttcg tcgttgtctc cttcaccaga catctcccga aacccacctg agccattaga    180
attcaacctc agcccctcgg agggtttcat tgaagagttc agaagcagga caccaacact    240
taggtttggc agcatgtgtg gcagtaaaca acctcaacat gaatgttgtt gtgtgtgtct    300
cacaaagttt gaaccagaat ctgagataaa ctgtttatca tgtggccata tttttcacaa    360
agtgtgcatg gagaagtggt tggactattg gaacattaca tgcccacttt gcaggacttc    420
cttgatgcct gaagatgatg catcttgctt ttggta                              456

<210> SEQ ID NO 306

<400> SEQUENCE: 306

000

<210> SEQ ID NO 307

<400> SEQUENCE: 307

000

<210> SEQ ID NO 308

<400> SEQUENCE: 308

000

<210> SEQ ID NO 309

```
<400> SEQUENCE: 309

000

<210> SEQ ID NO 310

<400> SEQUENCE: 310

000

<210> SEQ ID NO 311

<400> SEQUENCE: 311

000

<210> SEQ ID NO 312

<400> SEQUENCE: 312

000

<210> SEQ ID NO 313

<400> SEQUENCE: 313

000

<210> SEQ ID NO 314

<400> SEQUENCE: 314

000

<210> SEQ ID NO 315

<400> SEQUENCE: 315

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320
```

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

-continued

<210> SEQ ID NO 332
<400> SEQUENCE: 332
000

<210> SEQ ID NO 333
<400> SEQUENCE: 333
000

<210> SEQ ID NO 334
<400> SEQUENCE: 334
000

<210> SEQ ID NO 335
<400> SEQUENCE: 335
000

<210> SEQ ID NO 336
<400> SEQUENCE: 336
000

<210> SEQ ID NO 337
<400> SEQUENCE: 337
000

<210> SEQ ID NO 338
<400> SEQUENCE: 338
000

<210> SEQ ID NO 339
<400> SEQUENCE: 339
000

<210> SEQ ID NO 340
<400> SEQUENCE: 340
000

<210> SEQ ID NO 341
<400> SEQUENCE: 341
000

<210> SEQ ID NO 342
<400> SEQUENCE: 342
000

<210> SEQ ID NO 343

```
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
000

<210> SEQ ID NO 350
<400> SEQUENCE: 350
000

<210> SEQ ID NO 351
<400> SEQUENCE: 351
000

<210> SEQ ID NO 352
<400> SEQUENCE: 352
000

<210> SEQ ID NO 353
<400> SEQUENCE: 353
000

<210> SEQ ID NO 354
<400> SEQUENCE: 354
```

000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<211> LENGTH: 47
<212> TYPE: PRT
<213> ORGANISM: Brassica napus

<400> SEQUENCE: 365

Glu Cys Ser Val Cys Leu Ser Asn Phe Glu Glu Asp Ser Glu Ile Asn
1               5                   10                  15

Lys Leu Lys Cys Gly His Leu Phe His Lys Thr Cys Leu Glu Lys Trp
            20                  25                  30

Ile Asp Tyr Trp Asn Ile Thr Cys Pro Leu Cys Arg Thr Pro Leu
        35                  40                  45

<210> SEQ ID NO 366
<211> LENGTH: 162
<212> TYPE: PRT
<213> ORGANISM: Brassica napus

<400> SEQUENCE: 366

Lys Met Gly Leu Ser Ser Leu Pro Gly Pro Ser Glu Gly Met Leu Cys
1               5                   10                  15

Val Ile Leu Val Asn Thr Ala Leu Ser Ile Ser Ile Phe Lys Gly Ile
            20                  25                  30

Leu Arg Ser Val Leu Gln Leu Ile Gly Ile Arg Leu Cys Pro Ser Ser
        35                  40                  45

Ala Ala Ala Ala Ala Ala Ser Ser Glu Asn Gln Thr Ser Glu Thr
    50                  55                  60

Phe Asp Phe Arg Val Cys Gln Pro Glu Ser Phe Leu Glu Glu Phe Arg
65              70                  75                  80

Asn Arg Thr Pro Thr Val Lys Phe Glu Ser Leu Cys Lys Cys Lys Lys
                85                  90                  95

Gln Ala Asp Asn Glu Cys Ser Val Cys Leu Ser Asn Phe Glu Glu Asp
            100                 105                 110

Ser Glu Ile Asn Lys Leu Lys Cys Gly His Leu Phe His Lys Thr Cys
        115                 120                 125

Leu Glu Lys Trp Ile Asp Tyr Trp Asn Ile Thr Cys Pro Leu Cys Arg
    130                 135                 140

Thr Pro Leu Val Val Val Ala Ala Asp Asp Gln Leu Val Ser Ser Asn
145                 150                 155                 160

Val Trp

<210> SEQ ID NO 367
<211> LENGTH: 840
<212> TYPE: DNA
<213> ORGANISM: Brassica napus

<400> SEQUENCE: 367
acatctctct gagaagaaca aagatctgat cggcttccga gaattacata ccttttgaaa      60
catccaaaag agttgaaaga tgggtctatc aagccttcct ggtccatcag aaggaatgct     120
atgcgtgata ttagttaaca cagcattgtc aatctccatc ttcaaaggca ttctcaggtc     180
agtgcttcag ctaataggaa tccgtctctg tccttcttca gcagcagcag cagcagctgc     240
atcttcagag aatcaaactt cagagacttt tgatttccgg gtctgccagc ctgagagttt     300
ccttgaggaa ttcaggaaca ggaccccccac agtgaagttt gagagcttgt gcaagtgcaa     360
gaaacaggcg acaacgagt gttctgtatg cctgtcgaat ttcgaagagg attcagagat     420
caacaagcta aaatgtggcc atttgtttca caaacatgc ttggagaaat ggatagacta     480
ctggaacatc acttgcccac tctgtaggac tcctcttgtt gttgtcgcag cagacgacca     540
gctggtttcc tctaatgttt ggtgactact tttctttgta tagagttttc ctggggttg     600

```
ggtgtgtctg ttgttgtgta cagctactac tacttttttac tctgaaatta ggctgcgtca    660
cggttgattc tttatcagat tcagaccgga gatgggagta ttctgttgtg catatttgt      720 gagctgttta tgtatgtagt agacccatgt gtaatggaag ctcttgtttg aacatagtct    780
tgatgaatct atctatgtgt gtattaagag ctcaggcttt gtcccaaaaa aaaaaaaaca    840
```

```
<210> SEQ ID NO 368
<211> LENGTH: 47
<212> TYPE: PRT
<213> ORGANISM: Brassica napus

<400> SEQUENCE: 368
```

Glu Cys Ser Val Cys Leu Ser Lys Phe Glu Glu Asp Ser Glu Ile Asn
1               5                   10                  15

Lys Ala Lys Cys Gly His Leu Phe His Lys Thr Cys Leu Glu Lys Trp
            20                  25                  30

Ile Asp Tyr Trp Asn Ile Thr Cys Pro Leu Cys Arg Thr Pro Leu
        35                  40                  45

```
<210> SEQ ID NO 369
<211> LENGTH: 161
<212> TYPE: PRT
<213> ORGANISM: Brassica napus

<400> SEQUENCE: 369
```

Lys Met Gly Leu Ser Ser Leu Pro Gly Pro Ser Glu Gly Met Leu Cys
1               5                   10                  15

Val Ile Leu Val Asn Thr Ala Leu Ser Ile Ser Ile Phe Lys Gly Ile
            20                  25                  30

Leu Arg Ser Val Leu Gln Leu Ile Gly Ile Arg Leu Ser Pro Ser Ser
        35                  40                  45

Ala Ala Ala Ala Ala Ser Ser Glu Asn Gln Thr Ser Asp Ser Phe
    50                  55                  60

Asp Phe Arg Val Cys Gln Pro Glu Ser Phe Leu Glu Glu Phe Arg Asn
65                  70                  75                  80

Arg Thr Pro Thr Val Lys Phe Glu Ser Leu Cys Lys Cys Lys Lys Gln
                85                  90                  95

Ala Asp Asn Glu Cys Ser Val Cys Leu Ser Lys Phe Glu Glu Asp Ser
            100                 105                 110

Glu Ile Asn Lys Ala Lys Cys Gly His Leu Phe His Lys Thr Cys Leu
        115                 120                 125

Glu Lys Trp Ile Asp Tyr Trp Asn Ile Thr Cys Pro Leu Cys Arg Thr
    130                 135                 140

Pro Leu Val Val Val Ala Ala Asp Asp Gln Leu Val Ser Ile Met Phe
145                 150                 155                 160

Gly

```
<210> SEQ ID NO 370
<211> LENGTH: 682
<212> TYPE: DNA
<213> ORGANISM: Brassica napus

<400> SEQUENCE: 370
gatccatctc tcacttctca gattcccatc actattttca acagaaactc aaaactttat    60
aataaagatt caatctttcg tttaattggt gatcatcgcc tctcatactt gtctccagat    120
cacatctctc tgagaagaac aaagatctga tcggcttccg agaattacat attgtttgaa    180
```

```
acatccaaaa gagttgaaag atgggtctat caagccttcc tggtccatca gaaggaatgc    240
tatgcgtgat attagttaac acagcattgt caatctccat cttcaaaggc attctcaggt    300
cagtgcttca gctaatagga atccgcctct ctccttcttc agcagcagca gcagctgcat    360
cttcagagaa tcaaacttca gattcttttg atttccgggt ctgccagcct gagagtttcc    420
ttgaggaatt caggaacagg acccccacag tgaagtttga gagcttgtgc aagtgcaaga    480
aacaggcgga caacgagtgt tctgtatgcc tgtcgaaatt cgaagaggat tcagagatca    540
acaaggctaa atgtggccat ttgtttcaca aacatgctt ggagaaatgg atagactact     600
ggaacatcac ttgcccactc tgtaggactc ctcttgttgt tgtcgcagca gacgaccagc    660
tggtttctat aatgtttggt ga                                             682
```

<210> SEQ ID NO 371
<211> LENGTH: 49
<212> TYPE: PRT
<213> ORGANISM: Brassica oleracea

<400> SEQUENCE: 371

```
Glu Cys Ser Val Cys Leu Ser Lys Phe Glu Glu Asp Ser Glu Ile Asn
1               5                   10                  15

Lys Leu Lys Cys Gly His Leu Phe His Lys Thr Cys Leu Glu Lys Trp
            20                  25                  30

Ile Asp Tyr Trp Asn Ile Thr Cys Pro Leu Cys Arg Thr Pro Leu Val
        35                  40                  45

Val
```

<210> SEQ ID NO 372
<211> LENGTH: 148
<212> TYPE: PRT
<213> ORGANISM: Brassica oleracea

<400> SEQUENCE: 372

```
Lys Met Gly Leu Ser Ser Leu Pro Gly Pro Ser Glu Gly Met Leu Cys
1               5                   10                  15

Val Ile Leu Val Asn Thr Ala Leu Ser Ile Ser Ile Phe Lys Gly Ile
            20                  25                  30

Leu Arg Ser Val Leu Gln Leu Ile Gly Ile Arg Leu Ser Pro Ser Ser
        35                  40                  45

Ala Ala Ala Ala Ala Ala Ser Ser Glu Asn Gln Thr Ser Asp Ser Phe
    50                  55                  60

Asp Phe Arg Val Cys Gln Pro Glu Ser Phe Leu Glu Glu Phe Arg Asn
65                  70                  75                  80

Arg Thr Pro Thr Val Lys Phe Glu Ser Leu Cys Lys Cys Lys Lys Gln
                85                  90                  95

Ala Asp Asn Glu Cys Ser Val Cys Leu Ser Lys Phe Glu Glu Asp Ser
            100                 105                 110

Glu Ile Asn Lys Leu Lys Cys Gly His Leu Phe His Lys Thr Cys Leu
        115                 120                 125

Glu Lys Trp Ile Asp Tyr Trp Asn Ile Thr Cys Pro Leu Cys Arg Thr
    130                 135                 140

Pro Leu Val Val
145
```

<210> SEQ ID NO 373
<211> LENGTH: 627
<212> TYPE: DNA

<213> ORGANISM: Brassica oleracea

<400> SEQUENCE: 373

```
tcccatcact attttcaaca gaaactcaaa actttataat aaagattcaa tctttcgttt      60
aattggtgat catcgcctct catacttgtc tccagatcac atctctctga aagaacaaa     120
gatctgatcg gcttccgaga attacatatt gtttgaaaca tccaaaagag ttgaaagatg    180
ggtctatcaa gccttcctgg tccatcagaa ggaatgctat gcgtgatatt agttaacaca    240
gcattgtcaa tctccatctt caaaggcatt ctcaggtcag tgcttcagct aataggaatc    300
cgcctctctc cttcttcagc agcagcagca gctgcatctt cagagaatca aacttcagat    360
tcttttgatt tccgggtctg ccagcctgag agtttccttg aggaattcag gaacaggacc    420
cccacagtga agtttgagag cttgtgcaag tgcaagaaac aggcggacaa cgagtgttct    480
gtatgcctgt cgaaattcga agaggattca gagatcaaca agctaaaatg tggccatttg    540
tttcacaaaa catgcttgga gaatggata gactactgga acatcacttg cccactctgt     600
aggactcctc ttgttgttgt cgcagca                                        627
```

<210> SEQ ID NO 374
<211> LENGTH: 66
<212> TYPE: PRT
<213> ORGANISM: Brassica rapa

<400> SEQUENCE: 374

Lys Met Gly Leu Ser Ser Leu Pro Gly Pro Ser Glu Gly Met Leu Cys
1               5                   10                  15

Ile Ile Leu Val Asn Ala Ala Leu Ser Ile Ser Met Phe Lys Gly Ile
            20                  25                  30

Val Arg Ser Val Leu His Leu Val Gly Ile Arg Leu Ser Pro Ser Ser
        35                  40                  45

Val Ala Ser Ser Glu Ile Gln Leu Arg Asp Phe Arg Phe Pro Asp Leu
    50                  55                  60

Pro Ala
65

<210> SEQ ID NO 375
<211> LENGTH: 468
<212> TYPE: DNA
<213> ORGANISM: Brassica rapa
<220> FEATURE:
<221> NAME/KEY: misc_feature
<222> LOCATION: (69)..(69)
<223> OTHER INFORMATION: n is a, c, g, or t

<400> SEQUENCE: 375

```
cccacgcgtc cgcacttttc agattctccg aaacaccaca cactaccttt caccagagga      60
aaacacacnc aaagggtatt aaggaaaatt atatctttca atcagtgacc atcatcgcct    120
ttcatacttt gactccagat cacatcccct tgagaagaac aaagatataa agacaaatta    180
catatagttc gaaacatcta aagagttgaa agatgggtct atcgagtctt cctggtccat    240
cagaaggaat gctatgcatt atattagtca acgcagcatt atcaatctcc atgttcaaag    300
gcattgtcag atcagtgctt cacctagtag gaatccgtct ctctccttct tcagtagcat    360
cttcagagat tcaacttcga gactttcgat ttccggatct gccagcctga gagtttcttg    420
agaatcagga cagactccac gctaagtcga gagttgtgca aaacagag                 468
```

<210> SEQ ID NO 376

```
<211> LENGTH: 415
<212> TYPE: DNA
<213> ORGANISM: Cauliflower mosaic virus

<400> SEQUENCE: 376
aacatggtgg agcacgacac tctcgtctac tccaagaata tcaaagatac agtctcagaa      60
gaccaaaggg ctattgagac ttttcaacaa agggtaatat cgggaaacct cctcggattc     120
cattgcccag ctatctgtca cttcatcaaa aggacagtag aaaaggaagg tggcacctac     180
aaatgccatc attgcgataa aggaaaggct atcgttcaag atgcctctgc cgacagtggt     240
cccaaagatg acccccacc cacgaggagc atcgtggaaa agaagacgt tccaaccacg        300 tcttcaaagc aagtggattg atgtgatatc tccactgacg taagggatga cgcacaatcc     360
cactatcctt cgcaagaccc ttcctctata taaggaagtt catttcattt ggaga          415

<210> SEQ ID NO 377
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (25)..(26)
<223> OTHER INFORMATION: Xaa can be any naturally occurring amino acid

<400> SEQUENCE: 377

Cys Xaa Xaa His Xaa Xaa Xaa Xaa Xaa Xaa Cys Xaa Xaa Xaa Xaa
1               5                   10                  15

Xaa Xaa Xaa Cys Xaa Xaa Cys His Xaa Xaa His
            20                  25

<210> SEQ ID NO 378
<211> LENGTH: 334
<212> TYPE: PRT
<213> ORGANISM: Arabidopsis thaliana

<400> SEQUENCE: 378

Met Ser Asp Ala Pro Ser Ser Pro Asp Ala Thr Ala Ser His Trp
1               5                   10                  15

Cys Tyr His Cys Asn Lys Arg Val Val Glu Thr Leu Asp Asp Phe
                20                  25                  30

Val Val Cys Cys Glu Cys Asn Lys Gly Phe Val Glu Ser Ile Gln Pro
            35                  40                  45

Thr Pro Ala Ala Tyr Ser Ser Pro Ala Pro Gln Pro Leu Ser Pro
        50                  55                  60

Asp Leu Asn Val Glu Asp Ser Ser Ile Gly Ser His Phe Leu Gln Met
65                  70                  75                  80
```

```
Leu Arg Leu Leu Ala His Ala Pro Ser Gln Arg Ser Pro Pro Arg His
                85                  90                  95

Leu Asp Val Leu Ser Tyr Glu Asp Asp Phe Phe Arg Leu Glu Leu Asn
            100                 105                 110

Ser Arg Asn Glu Ile Asp Asp Asp Glu Asp Glu Asp Glu Asp Asp Gly
        115                 120                 125

Asp Glu Glu Glu Asp Glu Glu Glu Asn Leu Thr Val Asn Asp Glu
    130                 135                 140

Glu Asp Glu Glu Asp Asp Leu Arg Arg Arg Asn Arg Phe Pro Leu Thr
145                 150                 155                 160

Thr Thr Gln Ser Arg Thr Gly Arg Asn Arg Ile Leu Asp Trp Ala Glu
                165                 170                 175

Ile Leu Met Gly Ile Glu Asp Asn Ser Ile Glu Phe Arg Met Glu Ser
            180                 185                 190

Asp Arg Tyr Ala Gly Asn Pro Ala Asp Tyr Ile Asp Asp Ala Ala Gly
        195                 200                 205

Tyr Glu Ala Leu Leu Gln Asn Leu Ala Glu Gly Asp Gly Gly Gly
    210                 215                 220

Gly Gly Arg Arg Gly Ala Pro Pro Ala Ala Lys Ser Ala Ile Glu Ala
225                 230                 235                 240

Leu Glu Thr Phe Glu Val Ser Ser Glu Gly Glu Met Val Met Val
                245                 250                 255

Cys Ala Val Cys Lys Asp Gly Met Val Met Gly Glu Thr Gly Lys Lys
            260                 265                 270

Leu Pro Cys Gly His Cys Tyr His Gly Asp Cys Ile Val Pro Trp Leu
        275                 280                 285

Gly Thr Arg Asn Ser Cys Pro Val Cys Arg Phe Gln Leu Glu Thr Asp
    290                 295                 300

Asp Ala Glu Tyr Glu Glu Glu Arg Lys Lys Arg Thr Ser Thr Val Ser
305                 310                 315                 320

Asp Ser Ala Ala Ala Ser Ser Ser Ser Thr Ser Arg Tyr
                325                 330

<210> SEQ ID NO 379
<211> LENGTH: 1555
<212> TYPE: DNA
<213> ORGANISM: Arabidopsis thaliana

<400> SEQUENCE: 379
acagagagac cttttctttt tattttctcc atcctcttaa tcggcttatc ggatccgaat      60
ccggacccga aagcctgaaa acccgacgat taattgcacg atgtccgatg ctccgtcgtc     120
ttccccggat gccacggcgt cgcactggtg ctatcactgc aacaaacgcg tcgtcgttga     180
aaccttagat gactttgtcg tgtgctgcga atgtaacaaa ggtttcgtcg agtcaattca     240
accgactccc gccgcttatt catcgccggc gccaccgcag ccactttccc cagatctgaa     300
tgtagaagac tccagtattg gctcgcattt cctccagatg ctccgcttgt tagcccacgc     360
gccttctcag cgttcaccac cacgacacct tgatgtttta tcttacgaag atgatttctt     420
caggttggag ctcaatagta gaaacgaaat cgacgatgac gaagacgaag atgaagatga     480
tggagatgaa gaagaagagg atgaggaaga gaatttaacc gtcaacgacg aagaagacga     540
agaagatgat ctgaggagga gaaatcgttt tcctctcacg acgacgcagt cgagaaccgg     600
aagaaacaga attctcgatt gggctgagat tttgatggga atcgaagaca attcgattga     660
gttccgtatg gaatcagatc gatacgcagg aaatccggct gattacatag acgatgcagc     720
```

```
cggatacgaa gctttgctac agaatttagc agaaggagat ggtggtggtg gcggaggaag    780
gagaggcgca ccaccggctg cgaaatcggc aatagaggca ttggagactt tcgaggttag    840
ttcttcggag ggagagatgg ttatggtttg tgctgtgtgt aaagatggaa tggtgatggg    900
agaaactggt aagaagttac cgtgtggaca ttgttaccac ggagattgta ttgtgccatg    960
gttaggaaca aggaactctt gtcctgtctg tagattccag cttgagactg atgatgctga   1020
atatgaggaa gagaggaaaa aaagaacttc taccgtgtca gattctgctg ctgcttcttc   1080
ttcttcttca acttctcgtt actgaagtgg aggaaatgcc cccatttgtt gttacttttg   1140
ttgttactct ttctctttag attaatcttt gcttagtctc tcaacactat ttggttggtt   1200
gcatgttgca tcaaagaagc gagaaaacag agaacaaaaa aaaaaatcc ggctccaaaa    1260 agacaattgt tatttgtaag tgtgttgtat ctttggccta aacaatccca tagtggtttc   1320
tttgattctc agttgttcat aaagtttgcc gaaacaaaaa ggttcctggg tttaggagaa   1380
acggttacag gacttcgtga gccttcccga agtacctgtt tatgaacggg gactgcacag   1440
agaccaacaa acttatatca gattttggca ataatattca gagttccatt gacaaactaa   1500
gttggatttg ttttgtacct tctcaattcc tgcagtgtgg ggtgtgtctg gtgaa         1555
```

<210> SEQ ID NO 380
<211> LENGTH: 380
<212> TYPE: PRT
<213> ORGANISM: Arabidopsis thaliana

<400> SEQUENCE: 380

```
Met Thr Phe Arg Ser Leu Leu Gln Glu Met Arg Ser Arg Pro His Arg
1               5                   10                  15

Val Val His Ala Ala Ala Ser Thr Ala Asn Ser Ser Asp Pro Phe Ser
            20                  25                  30

Trp Ser Glu Leu Pro Glu Glu Leu Leu Arg Glu Ile Leu Ile Arg Val
        35                  40                  45

Glu Thr Val Asp Gly Gly Asp Trp Pro Ser Arg Arg Asn Val Val Ala
    50                  55                  60

Cys Ala Gly Val Cys Arg Ser Trp Arg Ile Leu Thr Lys Glu Ile Val
65                  70                  75                  80

Ala Val Pro Glu Phe Ser Ser Lys Leu Thr Phe Pro Ile Ser Leu Lys
                85                  90                  95

Gln Ser Gly Pro Arg Asp Ser Leu Val Gln Cys Phe Ile Lys Arg Asn
            100                 105                 110

Arg Asn Thr Gln Ser Tyr His Leu Tyr Leu Gly Leu Thr Thr Ser Leu
        115                 120                 125

Thr Asp Asn Gly Lys Phe Leu Leu Ala Ala Ser Lys Leu Lys Arg Ala
    130                 135                 140

Thr Cys Thr Asp Tyr Ile Ile Ser Leu Arg Ser Asp Asp Ile Ser Lys
145                 150                 155                 160

Arg Ser Asn Ala Tyr Leu Gly Arg Met Arg Ser Asn Phe Leu Gly Thr
                165                 170                 175

Lys Phe Thr Val Phe Asp Gly Ser Gln Thr Gly Ala Ala Lys Met Gln
            180                 185                 190

Lys Ser Arg Ser Ser Asn Phe Ile Lys Val Ser Pro Arg Val Pro Gln
        195                 200                 205

Gly Ser Tyr Pro Ile Ala His Ile Ser Tyr Glu Leu Asn Val Leu Gly
    210                 215                 220
```

```
Ser Arg Gly Pro Arg Arg Met Arg Cys Ile Met Asp Thr Ile Pro Met
225                 230                 235                 240

Ser Ile Val Glu Ser Arg Gly Val Val Ala Ser Thr Ser Ile Ser Ser
            245                 250                 255

Phe Ser Ser Arg Ser Ser Pro Val Phe Arg Ser His Ser Lys Pro Leu
        260                 265                 270

Arg Ser Asn Ser Ala Ser Cys Ser Asp Ser Gly Asn Asn Leu Gly Asp
    275                 280                 285

Pro Pro Leu Val Leu Ser Asn Lys Ala Pro Arg Trp His Glu Gln Leu
290                 295                 300

Arg Cys Trp Cys Leu Asn Phe His Gly Arg Val Thr Val Ala Ser Val
305                 310                 315                 320

Lys Asn Phe Gln Leu Val Ala Val Ser Asp Cys Glu Ala Gly Gln Thr
                325                 330                 335

Ser Glu Arg Ile Ile Leu Gln Phe Gly Lys Val Gly Lys Asp Met Phe
            340                 345                 350

Thr Met Asp Tyr Gly Tyr Pro Ile Ser Ala Phe Gln Ala Phe Ala Ile
            355                 360                 365

Cys Leu Ser Ser Phe Glu Thr Arg Ile Ala Cys Glu
    370                 375                 380

<210> SEQ ID NO 381
<211> LENGTH: 1596
<212> TYPE: DNA
<213> ORGANISM: Arabidopsis thaliana

<400> SEQUENCE: 381
atccttatcc tatcagcgaa taatagaaga aaaagtacaa attctctaat aaagcggtaa      60
aagcgtttaa gaagatgaag aagaaaaagg aaacgcctcc aaatcaccat tattgtccga     120
atcttcttcg cgtctctcac caacaccact tctcctacct tcttcttcac accaaatgat     180
tctctcgtat aatattcatc aaacccagat catgttttca tcatcaatca tctcttaaac     240
tcctctatag atctcaccgc atgacgttcc gaagtttact ccaggaaatg cggtctaggc     300
cacaccgtgt agttcacgcc gccgcctcaa ccgctaatag ttcagaccct ttcagctggt     360
cggagctccc ggaggagctg cttagagaaa tcctgattag ggttgagact gttgacggcg     420
gcgattggcc gtcgcggcga aacgtggtgg cttgtgccgg cgtttgtcgt agctggagga     480
ttctcaccaa ggagattgta gctgttcctg aattctcctc taaattgact ttccctatct     540
ccctcaagca gtctggtcca agagattctc tagttcaatg ctttataaaa cgtaatcgaa     600
atactcaatc gtatcatctc tatctcggat taactacctc tttgacggat aacgggaagt     660
ttcttcttgc tgcttctaag ctgaagcgcg caacttgcac tgattacatc atctctttgc     720
gttcagacga tatctcaaag agaagcaacg cgtatcttgg gagaatgaga tcgaacttcc     780
ttggaacaaa attcacggtc tttgatggta gtcagaccgg agcagcgaag atgcagaaga     840
gccgctcttc taatttcatc aaagtttcac ctagagttcc tcaggaagt tacccccatcg      900 ctcacatttc atacgagtta aacgtcttag gctctcgggg accgagaaga atgcgttgca     960
tcatggatac aatacctatg agcatcgtgg agtcgcgagg agtagtagct tcaacatcca    1020
taagctcttt ttccagtcgg tcatcaccag tctttaggtc tcactcaaaa ccattgcgca    1080
gtaatagtgc atcatgtagc gactcaggca acaacctggg agatccacca ttggtgctga    1140
gcaacaaagc tccacggtgg catgagcagt tacgttgctg tgtgcttaaat ttccatggtc    1200 gagtcacagt ggcttcggtt aagaactttc agcttgtggc agttagtgac tgtgaagcag    1260
```

```
ggcagacatc tgagaggatc atactccagt ttgggaaagt tgggaaggac atgtttacca   1320
tggattatgg atatccgatt tctgcgtttc aagcgtttgc tatctgcctg agcagttttg   1380
aaaccagaat tgcctgtgaa taatgaagag actaacctta aatcacctcc gtgtgctcgt   1440
tgttgtggtc tgtagatggt gtagtacttg tccaaaatct caggaacgtt aatagctttc   1500
tctggattct ttctgacaat tcaaatctat ctgttgtatt tatttgtctt tcatgcaaag   1560
aagcgtacca gaaataggct acgattacgt tttttt                             1596
```

<210> SEQ ID NO 382
<211> LENGTH: 599
<212> TYPE: PRT
<213> ORGANISM: Arabidopsis thaliana

<400> SEQUENCE: 382

```
Met Ala Ser Phe Thr Ala Thr Ala Ala Val Ser Gly Arg Trp Leu Gly
1               5                   10                  15

Gly Asn His Thr Gln Pro Pro Leu Ser Ser Gln Ser Ser Asp Leu
            20                  25                  30

Ser Tyr Cys Ser Ser Leu Pro Met Ala Ser Arg Val Thr Arg Lys Leu
        35                  40                  45

Asn Val Ser Ser Ala Leu His Thr Pro Pro Ala Leu His Phe Pro Lys
    50                  55                  60

Gln Ser Ser Asn Ser Pro Ala Ile Val Val Lys Pro Lys Ala Lys Glu
65                  70                  75                  80

Ser Asn Thr Lys Gln Met Asn Leu Phe Gln Arg Ala Ala Ala Ala
                85                  90                  95

Leu Asp Ala Ala Glu Gly Phe Leu Val Ser His Glu Lys Leu His Pro
            100                 105                 110

Leu Pro Lys Thr Ala Asp Pro Ser Val Gln Ile Ala Gly Asn Phe Ala
        115                 120                 125

Pro Val Asn Glu Gln Pro Val Arg Arg Asn Leu Pro Val Val Gly Lys
    130                 135                 140

Leu Pro Asp Ser Ile Lys Gly Val Tyr Val Arg Asn Gly Ala Asn Pro
145                 150                 155                 160

Leu His Glu Pro Val Thr Gly His His Phe Phe Asp Gly Asp Gly Met
                165                 170                 175

Val His Ala Val Lys Phe Glu His Gly Ser Ala Ser Tyr Ala Cys Arg
            180                 185                 190

Phe Thr Gln Thr Asn Arg Phe Val Gln Glu Arg Gln Leu Gly Arg Pro
        195                 200                 205

Val Phe Pro Lys Ala Ile Gly Glu Leu His Gly His Thr Gly Ile Ala
    210                 215                 220

Arg Leu Met Leu Phe Tyr Ala Arg Ala Ala Ala Gly Ile Val Asp Pro
225                 230                 235                 240

Ala His Gly Thr Gly Val Ala Asn Ala Gly Leu Val Tyr Phe Asn Gly
                245                 250                 255

Arg Leu Leu Ala Met Ser Glu Asp Asp Leu Pro Tyr Gln Val Gln Ile
            260                 265                 270

Thr Pro Asn Gly Asp Leu Lys Thr Val Gly Arg Phe Asp Phe Asp Gly
        275                 280                 285

Gln Leu Glu Ser Thr Met Ile Ala His Pro Lys Val Asp Pro Glu Ser
    290                 295                 300

Gly Glu Leu Phe Ala Leu Ser Tyr Asp Val Val Ser Lys Pro Tyr Leu
```

```
305                 310                 315                 320
Lys Tyr Phe Arg Phe Ser Pro Asp Gly Thr Lys Ser Pro Asp Val Glu
                325                 330                 335
Ile Gln Leu Asp Gln Pro Thr Met Met His Asp Phe Ala Ile Thr Glu
                340                 345                 350
Asn Phe Val Val Pro Asp Gln Gln Val Val Phe Lys Leu Pro Glu
                355                 360                 365
Met Ile Leu Gly Gly Ser Pro Val Val Tyr Asp Lys Asn Lys Val Ala
        370                 375                 380
Arg Phe Gly Ile Leu Asp Lys Tyr Ala Glu Asp Ser Ser Asn Ile Lys
385                 390                 395                 400
Trp Ile Asp Ala Pro Asp Cys Phe Cys Phe His Leu Trp Asn Ala Trp
                405                 410                 415
Glu Glu Pro Glu Thr Asp Glu Val Val Val Ile Gly Ser Cys Met Thr
                420                 425                 430
Pro Pro Asp Ser Ile Phe Asn Glu Ser Asp Glu Asn Leu Lys Ser Val
                435                 440                 445
Leu Ser Glu Ile Arg Leu Asn Leu Lys Thr Gly Glu Ser Thr Arg Arg
        450                 455                 460
Pro Ile Ile Ser Asn Glu Asp Gln Gln Val Asn Leu Glu Ala Gly Met
465                 470                 475                 480
Val Asn Arg Asn Met Leu Gly Arg Lys Thr Lys Phe Ala Tyr Leu Ala
                485                 490                 495
Leu Ala Glu Pro Trp Pro Lys Val Ser Gly Phe Ala Lys Val Asp Leu
                500                 505                 510
Thr Thr Gly Glu Val Lys Lys His Leu Tyr Gly Asp Asn Arg Tyr Gly
                515                 520                 525
Gly Glu Pro Leu Phe Leu Pro Gly Glu Gly Glu Glu Asp Glu Gly
        530                 535                 540
Tyr Ile Leu Cys Phe Val His Asp Glu Lys Thr Trp Lys Ser Glu Leu
545                 550                 555                 560
Gln Ile Val Asn Ala Val Ser Leu Glu Val Glu Ala Thr Val Lys Leu
                565                 570                 575
Pro Ser Arg Val Pro Tyr Gly Phe His Gly Thr Phe Ile Gly Ala Asp
                580                 585                 590
Asp Leu Ala Lys Gln Val Val
        595

<210> SEQ ID NO 383
<211> LENGTH: 2331
<212> TYPE: DNA
<213> ORGANISM: Arabidopsis thaliana

<400> SEQUENCE: 383
aaaccaactc tctcttctct cttctctcct ctcttctaca agaagaaaaa aaacagagcc      60
tttacacatc tcaaaatcga acttacttta accaccaaat actgattgaa cacacttgaa     120
aaatggcttc tttcacggca acggctgcgg tttctgggag atggcttggt ggcaatcata     180
ctcagccgcc attatcgtct tctcaaagct ccgacttgag ttattgtagc tccttaccta     240
tggccagtcg tgtcacacgt aagctcaatg tttcatctgc gcttcacact cctccagctc     300
ttcatttccc taagcaatca tcaaactctc ccgccattgt tgttaagccc aaagccaaag     360
aatccaacac taaacagatg aatttgttcc agagagcggc ggcggcagcg ttggacgcgg     420
cggagggttt ccttgtcagc cacgagaagc tacacccgct tcctaaaacg gctgatccta     480
```

```
gtgttcagat cgccggaaat tttgctccgg tgaatgaaca gcccgtccgg cgtaatcttc    540
cggtggtcgg aaaacttccc gattccatca aggagtgta tgtgcgcaac ggagctaacc    600
cacttcacga gccggtgaca ggtcaccact tcttcgacgg agacggtatg gttcacgccg    660
tcaaattcga acacgttca gctagctacg cttgccggtt tactcagact aaccggtttg    720
ttcaggaacg tcaattgggt cgaccggttt tccccaaagc catcggtgag cttcacggcc    780
acaccggtat tgcccgactc atgctattct acgccagagc tgcagccggt atagtcgacc    840
cggcacacgg aaccggtgta gctaacgccg gtttggtcta tttcaatggc cggttattgg    900
ctatgtcgga ggatgattta ccttaccaag ttcagatcac tcccaatgga gatttaaaaa    960
ccgttggtcg gttcgatttt gatggacaat tagaatccac aatgattgcc caccccgaaag   1020 tcgacccgga atccggtgaa ctcttcgctt aagctacga cgtcgtttca aagccttacc    1080
taaaatactt ccgattctca ccggacggaa ctaaatcacc ggacgtcgag attcagcttg    1140
atcagccaac gatgatgcac gatttcgcga ttacagagaa cttcgtcgtc gtacctgacc    1200
agcaagtcgt tttcaagctg ccggagatga tcctcggtgg gtctccggtg gtttacgaca    1260
agaacaaggt cgcaagattc gggattttag acaaatacgc cgaagattca tcgaacatta    1320
agtggattga tgctccagat tgcttctgct tccatctctg gaacgcttgg gaagagccag    1380
aaacagatga agtcgtcgtg atagggtcct gtatgactcc accagactca attttcaacg    1440
agtctgacga gaatctcaag agtgtcctgt ctgaaatccg cctgaatctc aaaaccggtg    1500
aatcaactcg ccgtccgatc atctccaacg aagatcaaca agtcaacctc gaagcaggga    1560
tggtcaacag aaacatgctc ggccgtaaaa ccaaattcgc ttacttggct ttagccgagc    1620
cgtggcctaa agtctcagga ttcgctaaag ttgatctcac tactggagaa gttaagaaac    1680
atctttacgg cgataaccgt tacggaggag agcctctgtt tctccccgga gaaggaggag    1740
aggaagacga aggatacatc ctctgttcg ttcacgacga gaagacatgg aaatcggagt    1800
tacagatagt taacgccgtt agcttagagg ttgaagcaac ggttaaactt ccgtcaaggg    1860
ttccgtacgg atttcacggt acattcatcg gagccgatga tttggcgaag caggtcgtgt    1920
gagttcttat gtgtaaatac gcacaaaata catatacgtg atgaagaagc ttctagaagg    1980
aaaagagaga gcgagattta ccagtgggat gctctgcata tacgtccccg gaatctgctc    2040
ctctgttttt ttttttttg ctctgtttct tgtttgttgt ttcttttggg gtgcggtttg    2100
ctagttccct ttttttggg gtcaatctag aaatctgaaa gattttgagg accagcttg    2160 tagcttttgg gctgtagggt agcctagccg ttcgagctca gctggtttct gttattcttt    2220
cacttattgt tcatcgtaat gagaagtata taaaatatta aacaacaaag atatgtttgt    2280 atatgtcat gaattaagga acatttttttt ttccgaaaaa aaaaaaaaaa a            2331
```

<210> SEQ ID NO 384
<211> LENGTH: 552
<212> TYPE: DNA
<213> ORGANISM: Pinus taeda
<220> FEATURE:
<221> NAME/KEY: misc_feature
<222> LOCATION: (387)..(391)
<223> OTHER INFORMATION: n is a, c, g, or t
<220> FEATURE:
<221> NAME/KEY: misc_feature
<222> LOCATION: (394)..(401)
<223> OTHER INFORMATION: n is a, c, g, or t
<220> FEATURE:
<221> NAME/KEY: misc_feature
<222> LOCATION: (403)..(403)

<223> OTHER INFORMATION: n is a, c, g, or t
<220> FEATURE:
<221> NAME/KEY: misc_feature
<222> LOCATION: (415)..(418)
<223> OTHER INFORMATION: n is a, c, g, or t
<220> FEATURE:
<221> NAME/KEY: misc_feature
<222> LOCATION: (544)..(545)
<223> OTHER INFORMATION: n is a, c, g, or t

<400> SEQUENCE: 384

```
acgatttcga caagcagctc aactcgtcca tgatagcgca cccgaagatc gatcccgaga    60
ccaaggagtt cttcgctctg agctacgata tcatcaagaa gcctatctc aagtacttca    120
tggtccgccc cgatggaact aagagccccg atgtcacaat ttcgctgaag gagcctacaa   180
tgatgcatga tttcgccata acaaagaatt atgtcgtcgt tcctgatcag caagttgttt   240
tccggctcca agaaatgatc agaggcggtt ctccagttat tcacaacaaa gaaaaagtcc   300
cgcgcttcgg gcttctgccc aaatatgctt ctgacgagag tgagctgaaa tggatcgagg   360
tcccggattg cttctgcttt catctcnnnn ncgnnnnnnn nanaagagaa gacgnnnntg   420
tcgtcatcgg ctcctgtatg accccgccgg acgccatttt caacgaatct gacagcgcgc   480
tgcggagtgt tctgtcggaa attcggctca atctcaaaac cggcttgtcc accagacgcg   540
agannacgcc ga                                                      552
```

<210> SEQ ID NO 385
<211> LENGTH: 710
<212> TYPE: PRT
<213> ORGANISM: Arabidopsis thaliana

<400> SEQUENCE: 385

```
Met Asp Gln Thr Glu Glu Pro Pro Leu Asn Thr His Gln Gln His Pro
1               5                   10                  15

Glu Glu Val Glu His His Glu Asn Gly Ala Thr Lys Met Phe Arg Lys
            20                  25                  30

Val Lys Ala Arg Ala Lys Lys Phe Lys Asn Ser Leu Thr Lys His Gly
        35                  40                  45

Gln Ser Asn Glu His Glu Gln Asp His Asp Leu Val Glu Glu Asp Asp
    50                  55                  60

Asp Asp Asp Glu Leu Glu Pro Glu Val Ile Asp Ala Pro Gly Val Thr
65                  70                  75                  80

Gly Lys Pro Arg Glu Thr Asn Val Pro Ala Ser Glu Glu Ile Ile Pro
                85                  90                  95

Pro Gly Thr Lys Val Phe Pro Val Val Ser Ser Asp Tyr Thr Lys Pro
            100                 105                 110

Thr Glu Ser Val Pro Val Gln Glu Ala Ser Tyr Gly His Asp Ala Pro
        115                 120                 125

Ala His Ser Val Arg Thr Thr Phe Thr Ser Asp Lys Glu Glu Lys Arg
    130                 135                 140

Asp Val Pro Ile His His Pro Leu Ser Glu Leu Ser Asp Arg Glu Glu
145                 150                 155                 160

Ser Arg Glu Thr His His Glu Ser Leu Asn Thr Pro Val Ser Leu Leu
                165                 170                 175

Ser Gly Thr Glu Asp Val Thr Ser Thr Phe Ala Pro Ser Gly Asp Asp
            180                 185                 190

Glu Tyr Leu Asp Gly Gln Arg Lys Val Asn Val Glu Thr Pro Ile Thr
        195                 200                 205
```

```
Leu Glu Glu Ser Ala Val Ser Asp Tyr Leu Ser Gly Val Ser Asn
    210                 215                 220
Tyr Gln Ser Lys Val Thr Asp Pro Thr Lys Glu Thr Gly Gly Val
225                 230                 235                 240
Pro Glu Ile Ala Glu Ser Phe Gly Asn Met Glu Val Thr Asp Glu Ser
                245                 250                     255
Pro Asp Gln Lys Pro Gly Gln Phe Glu Arg Asp Leu Ser Thr Arg Ser
                260                 265                 270
Lys Glu Phe Lys Glu Phe Asp Gln Asp Phe Asp Ser Val Leu Gly Lys
            275                 280                 285
Asp Ser Pro Ala Lys Phe Pro Gly Glu Ser Gly Val Val Phe Pro Val
    290                 295                 300
Gly Phe Gly Asp Glu Ser Gly Ala Glu Leu Glu Lys Asp Phe Pro Thr
305                 310                 315                 320
Arg Ser His Asp Phe Asp Met Lys Thr Glu Thr Gly Met Asp Thr Asn
                325                 330                 335
Ser Pro Ser Arg Ser His Glu Phe Asp Leu Lys Thr Glu Ser Gly Asn
            340                 345                 350
Asp Lys Asn Ser Pro Met Gly Phe Gly Ser Glu Ser Gly Ala Glu Leu
            355                 360                 365
Glu Lys Glu Phe Asp Gln Lys Asn Asp Ser Gly Arg Asn Glu Tyr Ser
    370                 375                 380
Pro Glu Ser Asp Gly Gly Leu Gly Ala Pro Leu Gly Gly Asn Phe Pro
385                 390                 395                 400
Val Arg Ser His Glu Leu Asp Leu Lys Asn Glu Ser Asp Ile Asp Lys
                405                 410                 415
Asp Val Pro Thr Gly Phe Asp Gly Glu Pro Asp Phe Leu Ala Lys Gly
                420                 425                 430
Arg Pro Gly Tyr Gly Glu Ala Ser Glu Glu Asp Lys Phe Pro Ala Arg
            435                 440                 445
Ser Asp Asp Val Glu Val Glu Thr Glu Leu Gly Arg Asp Pro Lys Thr
    450                 455                 460
Glu Thr Leu Asp Gln Phe Ser Pro Glu Leu Ser His Pro Lys Glu Arg
465                 470                 475                 480
Asp Glu Phe Lys Glu Ser Arg Asp Asp Phe Glu Glu Thr Arg Asp Glu
                485                 490                 495
Lys Thr Glu Glu Pro Lys Gln Ser Thr Tyr Thr Glu Lys Phe Ala Ser
                500                 505                 510
Met Leu Gly Tyr Ser Gly Glu Ile Pro Val Gly Asp Gln Thr Gln Val
            515                 520                 525
Ala Gly Thr Val Asp Glu Lys Leu Thr Pro Val Asn Glu Lys Asp Gln
    530                 535                 540
Glu Thr Glu Ser Ala Val Thr Thr Lys Leu Pro Ile Ser Gly Gly Gly
545                 550                 555                 560
Ser Gly Val Glu Glu Gln Arg Gly Glu Asp Lys Ser Val Ser Gly Arg
                565                 570                 575
Asp Tyr Val Ala Glu Lys Leu Thr Thr Glu Glu Asp Lys Ala Phe
                580                 585                 590
Ser Asp Met Val Ala Glu Lys Leu Gln Ile Gly Gly Glu Glu Lys
            595                 600                 605
Lys Glu Thr Thr Thr Lys Glu Val Glu Lys Ile Ser Thr Glu Lys Ala
    610                 615                 620
Ala Ser Glu Glu Gly Glu Ala Val Glu Glu Val Lys Gly Gly Gly
```

```
                625                 630                 635                 640
            Gly Met Val Gly Arg Ile Lys Gly Trp Phe Gly Gly Ala Thr Asp
                            645                 650                 655
            Glu Val Lys Pro Glu Ser Pro His Ser Val Glu Glu Ala Pro Lys Ser
                        660                 665                 670
            Ser Gly Trp Phe Gly Gly Ala Thr Glu Glu Val Lys Pro Lys Ser
                    675                 680                 685
            Pro His Ser Val Glu Glu Ser Pro Gln Ser Leu Gly Ser Thr Val Val
                    690                 695                 700
            Pro Val Gln Lys Glu Leu
            705                 710

<210> SEQ ID NO 386
<211> LENGTH: 2500
<212> TYPE: DNA
<213> ORGANISM: Arabidopsis thaliana

<400> SEQUENCE: 386
acaaatatgc aaactagaaa acaatcatca ggaataaagg gtttgattac ttctattgga      60
aagaaaaaaa tctttggaaa atggatcaaa cagaggaacc accactcaac acacaccagc     120
agcacccaga agaagttgaa catcatgaga atggtgcgac taagatgttt aggaaagtaa     180
aggctagagc taagaagttc aagaacagtc tcactaaaca tggacaaagc aatgagcatg     240
agcaagatca tgatttggtt gaagaagatg atgatgatga cgagctagaa cctgaagtga     300
tcgatgcacc aggcgtaaca ggtaaaccta gagaaactaa tgttccagca tcggaggaaa     360
ttattccacc agggacaaag gtgtttcctg tcgtgtcttc cgattacacc aaacccactg     420
aatctgtacc agtacaagag gcctcttacg gacacgatgc accggctcat tctgtaagga     480
cgacgtttac atcggacaag gaagagaaaa gagatgtacc gattcatcat cctctgtccg     540
aattgtcaga cagagaagag agtagagaga ctcatcatga gtcattgaac actccggtct     600
ctctgctttc tggaacagag gatgtaacga gtacgtttgc tccaagtggt gatgatgaat     660
atcttgatgg tcaacggaag gtcaacgtcg agaccccgat aacgttggag gaagagtcgg     720
ctgtttcaga ctatcttagt ggtgtatcta attatcagtc caaagttact gatcccacca     780
aagaagaaac tggaggagta ccggagattg ctgagtcttt tggtaatatg gaagtgactg     840
atgagtctcc tgatcagaag ccaggacaat ttgaaagaga cttgtcgacg agaagcaaag     900
aattcaaaga gtttgatcag gactttgact ctgttctcgg taaggattcg ccggcgaaat     960
ttccaggtga atcaggagtt gttttcccgg tgggctttgg tgacgagtca ggagctgagc    1020
tggaaaaaga ttttccgacg agaagtcatg attttgatat gaagactgaa actggaatgg    1080
acacgaattc tccatcaaga agccatgaat ttgatctgaa gactgaatct ggaaacgaca    1140
agaattctcc gatgggcttt ggtagtgaat caggagctga gctggaaaaa gaatttgatc    1200
agaagaacga ttctggaaga aacgagtatt cgccggaatc tgacggcggt ttaggagctc    1260
cgttgggagg aaattttccg gtgagaagtc atgagttgga tctgaagaac gaatctgata    1320
tcgacaagga tgtgccgacg ggatttgacg agaaccagat ttttctggcg aagggaagac    1380
ctggatacgg tgaggcatca gaagaggata aatttccggc gagaagtgat gatgtggaag    1440
tagagactga gctgggaaga gacccaaaga cggagactct tgatcaattc tcaccggaac    1500
tttctcatcc taaagaaaga gatgagttta aggagtccag agatgatttt gaggagacga    1560
gagatgagaa aacagaggag ccaaaacaga gcacttacac agagaagttt gcttcaatgc    1620
```

```
taggttactc cggagaaatt ccggtgggag atcaaactca agtggcggga actgttgatg    1680
agaagttgac tccggtcaat gagaaggatc aagaaacaga gtctgccgtg acgacgaagt    1740
tacctatctc cggaggtgga agtggagtag aggagcaacg aggggaagat aaaagtgtgt    1800
cgggtagaga ttatgtggcg gagaaactga caactgaaga agaagacaaa gccttttctg    1860
atatggttgc cgagaaactt cagattggag agaagaagaa gaagaaggaa acgacgacaa    1920
aggaagtgga agatctctct accgagaagg cagcatcgga ggagggtgag gcggtggaag    1980
aggaagtgaa aggaggagga ggaatggttg ggaggattaa aggatggttc ggtggtggtg    2040
cgactgatga ggtgaagcca gaatcgccac attctgttga agaggctcca aaatcatctg    2100
gctggtttgg tggtggtgcg acggaggagg tgaagccaaa atcgcctcat tccgttgaag    2160
agtctccaca atcacttggc tccactgttg ttccggtgca gaaggagctt taagaatatg    2220
agaactgaga ttttcaagtt tcactttgga tgtttatgtg tgttttgttt gacgtctttg    2280
atgtattatg gtataattcc ttgtttgtgt gaaaaaagga catttggtta ataaattgtt    2340
cggctttgga ttaagaagtt cctccatacc agctactagg tctaaagtgg gtaaaatcat    2400
tggatttatt cccttcaaag ttcttagaat tattcacagg attttacatt atgagctagt    2460
agtgtgactt gttgaggtgt tgtctctatc gttaaagttc                          2500
```

<210> SEQ ID NO 387
<211> LENGTH: 363
<212> TYPE: PRT
<213> ORGANISM: Arabidopsis thaliana

<400> SEQUENCE: 387

```
Met Asp Lys Tyr Glu Leu Val Lys Asp Ile Gly Ala Gly Asn Phe Gly
1               5                   10                  15

Val Ala Arg Leu Met Lys Val Lys Asn Ser Lys Glu Leu Val Ala Met
            20                  25                  30

Lys Tyr Ile Glu Arg Gly Pro Lys Ile Asp Glu Asn Val Ala Arg Glu
        35                  40                  45

Ile Ile Asn His Arg Ser Leu Arg His Pro Asn Ile Ile Arg Phe Lys
    50                  55                  60

Glu Val Val Leu Thr Pro Thr His Leu Ala Ile Ala Met Glu Tyr Ala
65                  70                  75                  80

Ala Gly Gly Glu Leu Phe Glu Arg Ile Cys Ser Ala Gly Arg Phe Ser
                85                  90                  95

Glu Asp Glu Ala Arg Tyr Phe Phe Gln Gln Leu Ile Ser Gly Val Ser
            100                 105                 110

Tyr Cys His Ala Met Gln Ile Cys His Arg Asp Leu Lys Leu Glu Asn
        115                 120                 125

Thr Leu Leu Asp Gly Ser Pro Ala Pro Arg Leu Lys Ile Cys Asp Phe
    130                 135                 140

Gly Tyr Ser Lys Ser Ser Leu Leu His Ser Arg Pro Lys Ser Thr Val
145                 150                 155                 160

Gly Thr Pro Ala Tyr Ile Ala Pro Glu Val Leu Ser Arg Arg Glu Tyr
                165                 170                 175

Asp Gly Lys Met Ala Asp Val Trp Ser Cys Gly Val Thr Leu Tyr Val
            180                 185                 190

Met Leu Val Gly Ala Tyr Pro Phe Glu Asp Gln Glu Asp Pro Lys Asn
        195                 200                 205

Phe Arg Lys Thr Ile Gln Lys Ile Met Ala Val Gln Tyr Lys Ile Pro
    210                 215                 220
```

Asp Tyr Val His Ile Ser Gln Asp Cys Lys Asn Leu Leu Ser Arg Ile
225                 230                 235                 240

Phe Val Ala Asn Ser Leu Lys Arg Ile Thr Ile Ala Glu Ile Lys Lys
            245                 250                 255

His Ser Trp Phe Leu Lys Asn Leu Pro Arg Glu Leu Thr Glu Thr Ala
        260                 265                 270

Gln Ala Ala Tyr Phe Lys Lys Glu Asn Pro Thr Phe Ser Leu Gln Thr
    275                 280                 285

Val Glu Glu Ile Met Lys Ile Val Ala Asp Ala Lys Thr Pro Pro Pro
290                 295                 300

Val Ser Arg Ser Ile Gly Gly Phe Gly Trp Gly Gly Asn Gly Asp Ala
305                 310                 315                 320

Asp Gly Lys Glu Glu Asp Ala Glu Asp Val Glu Glu Glu Glu Glu
            325                 330                 335

Val Glu Glu Glu Glu Asp Asp Glu Asp Glu Tyr Asp Lys Thr Val Lys
            340                 345                 350

Glu Val His Ala Ser Gly Glu Val Arg Ile Ser
        355                 360

<210> SEQ ID NO 388
<211> LENGTH: 1752
<212> TYPE: DNA
<213> ORGANISM: Arabidopsis thaliana

<400> SEQUENCE: 388

```
ggagtttgtt taggcagggg agattcttct tcattctcat cattatttct ctattaattt      60
caccccaaaa aagaaaaaag aaaaattcca acaagaaaaa aaaagaaaaa agaaagttga     120
ttcttcgctt aggcttgaaa tctctccaat ccaaatctca aattaacctt ccatcgtcat     180
ctctttccct ttttttttcc cactttcttt gcgaatcgcg agatctcgga atcgcatcct     240
tgattttggg atactgtttt ttttttttttt aatcttgttt cattttcacg tgaaattctt     300
agctgctaga actggacttg aatttcaacg agaattttgg agattttttt tttgtttggg     360
ttttccttt ctgttttgtg tgtttggaat tagggttgtc gagcgagaat ggacaagtac     420
gagctggtga agacatagg tgctgggaat tttggagttg ccaggctcat gaaggtcaaa     480
aactctaagg aacttgttgc catgaagtac atcgagcgtg gtcctaagat tgatgagaat     540
gtggcaagag agatcattaa tcacagatca cttcgccatc cgaatataat ccggttcaag     600
gaggtggtgt tgactccaac ccatcttgcc attgccatgg aatatgctgc tggtggtgaa     660
ctattcgagc gtatatgcag tgctggaaga tttagtgagg atgaggcgag atatttcttc     720
cagcagctta tatcaggtgt tagctattgc catgctatgc aaatatgcca tagagatctg     780
aagctcgaga atacgctctt ggatggaagt cctgctccac gtctgaaaat ctgtgatttt     840
ggttattcca agtcctctct gctgcactct aggcccaaat caacagttgg aactccagca     900
tatattgcac ctgaggtcct ttctcgaaga gaatatgatg caagatggc tgatgtatgg     960
tcttgtggtg tgactctttta tgtcatgctg gttggagcat acccatttga agaccaggaa    1020
gaccccaaga acttcaggaa aacaatacaa aaaataatgg ctgtccagta caagatcccg    1080
gactacgtcc atatctcaca ggattgtaaa aatctccttt cccgtatatt tgtcgccaat    1140
tcactcaaga ggatcaccat tgcagaaatc aagaaacatt catggttcct aaagaatttg    1200
ccaagggaac tcagagagac agctcaagct gcatatttca agaaagagaa cccaaccttc    1260
tcccttcaga ccgttgaaga gatcatgaag atagtggctg acgccaaaac accgcctcct    1320
```

-continued

```
gtttcccgat ccatcggagg ttttggctgg ggaggaaatg gggatgcaga tggaaaagag    1380
gaagatgcag aagacgtgga ggaggaagag gaggaggtgg aagaagagga agacgatgag    1440
gatgaatacg ataagactgt aaaggaagta cacgcaagtg gagaagtgag aataagttga    1500
tattttggtt tttggtctgt gtaagaaaga agtcgtcgtt ggtttgttga aactgaaaag    1560
tctctgttct cgtgtttgcc tttacaatgc tttggctaag gttttggttc tggttttgga    1620
gatttgtaaa atttgcagta taagatgaac aaacagagag gttgatgatg agaatgagtc    1680
ctttgctacg catggtacta tgaacattgt gacctccaat aaatatttt gtaaattaga    1740 ttttattttc cg                                                        1752
```

<210> SEQ ID NO 389
<211> LENGTH: 511
<212> TYPE: PRT
<213> ORGANISM: Arabidopsis thaliana

<400> SEQUENCE: 389

```
Met Asp Lys Tyr Glu Leu Val Lys Asp Ile Gly Ala Gly Asn Phe Gly
1               5                   10                  15

Val Ala Arg Leu Met Lys Val Lys Asn Ser Lys Glu Leu Val Ala Met
            20                  25                  30

Lys Tyr Ile Glu Arg Gly Pro Lys Ile Asp Glu Asn Val Ala Arg Glu
        35                  40                  45

Ile Ile Asn His Arg Ser Leu Arg His Pro Asn Ile Ile Arg Phe Lys
    50                  55                  60

Glu Val Val Leu Thr Pro Thr His Leu Ala Ile Ala Met Glu Tyr Ala
65                  70                  75                  80

Ala Gly Gly Glu Leu Phe Glu Arg Ile Cys Ser Ala Gly Arg Phe Ser
                85                  90                  95

Glu Asp Glu Ala Arg Tyr Phe Gln Gln Leu Ile Ser Gly Val Ser
            100                 105                 110

Tyr Cys His Ala Met Gln Ile Cys His Arg Asp Leu Lys Leu Glu Asn
        115                 120                 125

Thr Leu Leu Asp Gly Ser Pro Ala Pro Arg Leu Lys Ile Cys Asp Phe
    130                 135                 140

Gly Tyr Ser Lys Ser Ser Leu Leu His Ser Arg Pro Lys Ser Thr Val
145                 150                 155                 160

Gly Thr Pro Ala Tyr Ile Ala Pro Glu Val Leu Ser Arg Arg Glu Tyr
                165                 170                 175

Asp Gly Lys Met Ala Asp Val Trp Ser Cys Gly Val Thr Leu Tyr Val
            180                 185                 190

Met Leu Val Gly Ala Tyr Pro Phe Glu Asp Gln Glu Asp Pro Lys Asn
        195                 200                 205

Phe Arg Lys Thr Ile Gln Lys Ile Met Ala Val Gln Tyr Lys Ile Pro
    210                 215                 220

Asp Tyr Val His Ile Ser Gln Asp Cys Lys Asn Leu Leu Ser Arg Ile
225                 230                 235                 240

Phe Val Ala Asn Ser Leu Lys Arg Ile Thr Ile Ala Glu Ile Lys Lys
                245                 250                 255

His Ser Trp Phe Leu Lys Asn Leu Pro Arg Glu Leu Thr Glu Thr Ala
            260                 265                 270

Gln Ala Ala Tyr Phe Lys Lys Glu Asn Pro Thr Phe Ser Leu Gln Thr
        275                 280                 285
```

| | | | | | | | | | | | |
|---|---|---|---|---|---|---|---|---|---|---|---|
|Val|Glu|Glu|Ile|Met|Lys|Ile|Val|Ala|Asp|Ala|Lys|Thr|Pro|Pro|
|290| | | | |295| | | |300| | | | | |

Val Ser Arg Ser Ile Gly Gly Phe Gly Trp Gly Gly Asn Gly Asp Ala
305              310             315                 320

Asp Gly Lys Glu Glu Asp Ala Glu Asp Val Glu Glu Glu Glu Glu Glu
                325             330                 335

Val Glu Glu Glu Glu Asp Asp Glu Asp Glu Tyr Asp Lys Thr Val Lys
            340             345             350

Glu Val His Ala Ser Gly Glu Val Arg Ile Ser Met Ala Ser Lys Arg
            355             360             365

Ile Leu Lys Glu Leu Lys Asp Leu Gln Lys Asp Pro Pro Thr Ser Cys
370             375             380

Ser Ala Gly Pro Val Ala Glu Asp Met Phe His Trp Gln Ala Thr Ile
385             390             395                 400

Met Gly Pro Ala Glu Ser Pro Tyr Ser Gly Gly Val Phe Leu Val Thr
                405             410             415

Ile His Phe Pro Pro Asp Tyr Pro Phe Lys Pro Lys Val Ala Phe
            420             425             430

Arg Thr Lys Val Phe His Pro Asn Ile Asn Ser Asn Gly Ser Ile Cys
            435             440             445

Leu Asp Ile Leu Lys Glu Gln Trp Ser Pro Ala Leu Thr Ile Ser Lys
450             455             460

Val Leu Leu Ser Ile Cys Ser Leu Leu Thr Asp Pro Asn Pro Asp Asp
465             470             475             480

Pro Leu Val Pro Glu Ile Ala His Met Tyr Lys Thr Asp Arg Ala Lys
                485             490             495

Tyr Glu Ala Thr Ala Arg Asn Trp Thr Gln Lys Tyr Ala Met Gly
500             505             510

<210> SEQ ID NO 390
<211> LENGTH: 1773
<212> TYPE: DNA
<213> ORGANISM: Arabidopsis thaliana

<400> SEQUENCE: 390

```
ggagtttgtt taggcagggg agattcttct tcattctcat cattatttct ctattaattt    60
caccccaaaa aagaaaaaag aaaaattcca acaagaaaaa aaaagaaaaa agaaagttga   120
ttcttcgctt aggcttgaaa tctctccaat ccaaatctca aattaacctt ccatcgtcat   180
ctctttccct ttttttttcc cactttcttt gcgaatcgcg agatctcgga atcgcatcct   240
tgatttgggg atactgtttt tttttttttt aatcttgttt cattttcacg tgaaattctt   300
agctgctaga actggacttg aatttcaacg agaattttgg agatttttt tttgtttggg   360
ttttcctttt ctgttttgtg tgtttggaat tagggttgtc gagcgagaat ggacaagtac   420
gagctggtga agacatagg tgctgggaat tttggagttg ccaggctcat gaaggtcaaa   480
aactctaagg aacttgttgc catgaagtac atcgagcgtg gtcctaagat tgatgagaat   540
gtggcaagag agatcattaa tcacagatca cttcgccatc cgaatataat ccggttcaag   600
gaggtggtgt tgactccaac ccatcttgcc attgccatgg aatatgctgc tggtggtgaa   660
ctattcgagc gtatatgcag tgctggaaga tttagtgagg atgaggcgag atatttcttc   720
cagcagctta tatcaggtgt tagctattgc catgctatgc aaatatgcca tagagatctg   780
aagctcgaga atacgctctt ggatggaagt cctgctccac gtctgaaaat ctgtgatttt   840
ggttattcca gtcctctctct gctgcactct aggcccaaat caacagttgg aactccagca   900
```

```
tatattgcac ctgaggtcct ttctcgaaga gaatatgatg gcaagatggc tgatgtatgg    960
tcttgtggtg tgactcttta tgtcatgctg gttggagcat acccatttga agaccaggaa   1020
gaccccaaga acttcaggaa aacaatacaa aaaataatgg ctgtccagta caagatcccg   1080
gactacgtcc atatctcaca ggattgtaaa aatctccttt cccgtatatt tgtcgccaat   1140
tcactcaaga ggatcaccat tgcagaaatc aagaaacatt catggttcct aaagaatttg   1200
ccaagggaac tcacagagac agctcaagct gcatatttca agaaagagaa cccaaccttc   1260
tcccttcaga ccgttgaaga gatcatgaag atagtggctg acgccaaaac accgcctcct   1320
gtttcccgat ccatcggagg ttttggctgg ggaggaaatg gggatgcaga tggaaaagag   1380
gaagatgcag aagacgtgga ggaggaagag gaggaggtgg aagaagagga agacgatgag   1440
gatgaatacg ataagactgt aaaggaagta cacgcaagtg agaagtgag aataagttga    1500
tattttggtt tttggtctgt gtaagaaaga agtcgtcgtt ggtttgttga aactgaaaag   1560
tctctgttct cgtgtttgcc tttacaatgc tttggctaag gttttggttc tggttttgga   1620
gatttgtaaa atttgcagta aagatgaac aaacagagag gttgatgatg agaatgagtc    1680
ctttgctacg catggtacta tgaacattgt gacctccaat aaatattttt gtaaattaga   1740
ttttattttc cgaaaagatt catgtatttg att                                1773
```

<210> SEQ ID NO 391
<211> LENGTH: 380
<212> TYPE: PRT
<213> ORGANISM: Arabidopsis thaliana

<400> SEQUENCE: 391

```
Met Thr Phe Arg Ser Leu Leu Gln Glu Met Arg Ser Arg Pro His Arg
1               5                   10                  15
Val Val His Ala Ala Ser Thr Ala Asn Ser Ser Asp Pro Phe Ser
            20                  25                  30
Trp Ser Glu Leu Pro Glu Glu Leu Leu Arg Glu Ile Leu Ile Arg Val
        35                  40                  45
Glu Thr Val Asp Gly Gly Asp Trp Pro Ser Arg Asn Val Val Ala
    50                  55                  60
Cys Ala Gly Val Cys Arg Ser Trp Arg Ile Leu Thr Lys Glu Ile Val
65                  70                  75                  80
Ala Val Pro Glu Phe Ser Ser Lys Leu Thr Phe Pro Ile Ser Leu Lys
                85                  90                  95
Gln Ser Gly Pro Arg Asp Ser Leu Val Gln Cys Phe Ile Lys Arg Asn
            100                 105                 110
Arg Asn Thr Gln Ser Tyr His Leu Tyr Leu Gly Leu Thr Thr Ser Leu
        115                 120                 125
Thr Asp Asn Gly Lys Phe Leu Leu Ala Ala Ser Lys Leu Lys Arg Ala
    130                 135                 140
Thr Cys Thr Asp Tyr Ile Ile Ser Leu Arg Ser Asp Ile Ser Lys
145                 150                 155                 160
Arg Ser Asn Ala Tyr Leu Gly Arg Met Arg Ser Asn Phe Leu Gly Thr
                165                 170                 175
Lys Phe Thr Val Phe Asp Gly Ser Gln Thr Gly Ala Ala Lys Met Gln
            180                 185                 190
Lys Ser Arg Ser Ser Asn Phe Ile Lys Val Ser Pro Arg Val Pro Gln
        195                 200                 205
Gly Ser Tyr Pro Ile Ala His Ile Ser Tyr Glu Leu Asn Val Leu Gly
```

```
                   210                 215                 220
Ser Arg Gly Pro Arg Arg Met Arg Cys Ile Met Asp Thr Ile Pro Met
225                 230                 235                 240

Ser Ile Val Glu Ser Arg Gly Val Val Ala Ser Thr Ser Ile Ser Ser
                245                 250                 255

Phe Ser Ser Arg Ser Ser Pro Val Phe Arg Ser His Ser Lys Pro Leu
                260                 265                 270

Arg Ser Asn Ser Ala Ser Cys Ser Asp Ser Gly Asn Asn Leu Gly Asp
                275                 280                 285

Pro Pro Leu Val Leu Ser Asn Lys Ala Pro Arg Trp His Glu Gln Leu
        290                 295                 300

Arg Cys Trp Cys Leu Asn Phe His Gly Arg Val Thr Val Ala Ser Val
305                 310                 315                 320

Lys Asn Phe Gln Leu Val Ala Val Ser Asp Cys Glu Ala Gly Gln Thr
                325                 330                 335

Ser Glu Arg Ile Ile Leu Gln Phe Gly Lys Val Gly Lys Asp Met Phe
                340                 345                 350

Thr Met Asp Tyr Gly Tyr Pro Ile Ser Ala Phe Gln Ala Phe Ala Ile
                355                 360                 365

Cys Leu Ser Ser Phe Glu Thr Arg Ile Ala Cys Glu
        370                 375                 380

<210> SEQ ID NO 392
<211> LENGTH: 1596
<212> TYPE: DNA
<213> ORGANISM: Arabidopsis thaliana

<400> SEQUENCE: 392
atccttatcc tatcagcgaa taatagaaga aaaagtacaa attctctaat aaagcggtaa    60
aagcgtttaa gaagatgaag aagaaaaagg aaacgcctcc aaatcaccat tattgtccga   120
atcttcttcg cgtctctcac caacaccact tctcctacct tcttcttcac accaaatgat   180
tctctcgtat aatattcatc aaacccagat catgttttca tcatcaatca tctcttaaac   240
tcctctatag atctcaccgc atgacgttcc gaagtttact ccaggaaatg cggtctaggc   300
cacaccgtgt agttcacgcc gccgcctcaa ccgctaatag ttcagaccct ttcagctggt   360
cggagctccc ggaggagctg cttagagaaa tcctgattag ggttgagact gttgacggcg   420
gcgattggcc gtcgcggcga acgtggtgg cttgtgccgg cgtttgtcgt agctggagga   480
ttctcaccaa ggagattgta gctgttcctg aattctcctc taaattgact ttccctatct   540
ccctcaagca gtctggtcca agagattctc tagttcaatg ctttataaaa cgtaatcgaa   600
atactcaatc gtatcatctc tatctcggat taactacctc tttgacggat aacgggaagt   660
ttcttcttgc tgcttctaag ctgaagcgcg caacttgcac tgattacatc atctctttgc   720
gttcagacga tatctcaaag agaagcaacg cgtatcttgg gagaatgaga tcgaacttcc   780
ttggaacaaa attcacggtc tttgatggta gtcagaccgg agcagcgaag atgcagaaga   840
gccgctcttc taatttcatc aaagtttcac ctagagttcc tcagggaagt taccccatcg   900
ctcacatttc atacgagtta aacgtcttag gctctcgggg accgagaaga atgcgttgca   960
tcatggatac aataccctatg agcatcgtgg agtcgcgagg agtagtagct tcaacatcca  1020
taagctcttt ttccagtcgg tcatcaccag tctttaggtc tcactcaaaa ccattgcgca  1080
gtaatagtgc atcatgtagc gactcaggca acaacctggg agatccacca ttggtgctga  1140
gcaacaaagc tccacggtgg catgagcagt tacgttgctg gtgcttaaat ttccatggtc  1200
```

```
gagtcacagt ggcttcggtt aagaactttc agcttgtggc agttagtgac tgtgaagcag    1260
ggcagacatc tgagaggatc atactccagt ttgggaaagt tgggaaggac atgtttacca    1320
tggattatgg atatccgatt tctgcgtttc aagcgtttgc tatctgcctg agcagttttg    1380
aaaccagaat tgcctgtgaa taatgaagag actaaccta aatcacctcc gtgtgctcgt     1440
tgttgtggtc tgtagatggt gtagtacttg tccaaaatct caggaacgtt aatagctttc    1500
tctggattct ttctgacaat tcaaatctat ctgttgtatt tatttgtctt tcatgcaaag    1560
aagcgtacca gaaataggct acgattacgt tttttt                              1596
```

<210> SEQ ID NO 393
<211> LENGTH: 363
<212> TYPE: PRT
<213> ORGANISM: Arabidopsis thaliana

<400> SEQUENCE: 393

```
Met Asp Lys Tyr Glu Leu Val Lys Asp Ile Gly Ala Gly Asn Phe Gly
1               5                   10                  15

Val Ala Arg Leu Met Lys Val Lys Asn Ser Lys Glu Leu Val Ala Met
            20                  25                  30

Lys Tyr Ile Glu Arg Gly Pro Lys Ile Asp Glu Asn Val Ala Arg Glu
        35                  40                  45

Ile Ile Asn His Arg Ser Leu Arg His Pro Asn Ile Ile Arg Phe Lys
    50                  55                  60

Glu Val Val Leu Thr Pro Thr His Leu Ala Ile Ala Met Glu Tyr Ala
65                  70                  75                  80

Ala Gly Gly Glu Leu Phe Glu Arg Ile Cys Ser Ala Gly Arg Phe Ser
                85                  90                  95

Glu Asp Glu Ala Arg Tyr Phe Phe Gln Gln Leu Ile Ser Gly Val Ser
            100                 105                 110

Tyr Cys His Ala Met Gln Ile Cys His Arg Asp Leu Lys Leu Glu Asn
        115                 120                 125

Thr Leu Leu Asp Gly Ser Pro Ala Pro Arg Leu Lys Ile Cys Asp Phe
    130                 135                 140

Gly Tyr Ser Lys Ser Ser Leu Leu His Ser Arg Pro Lys Ser Thr Val
145                 150                 155                 160

Gly Thr Pro Ala Tyr Ile Ala Pro Glu Val Leu Ser Arg Arg Glu Tyr
                165                 170                 175

Asp Gly Lys Met Ala Asp Val Trp Ser Cys Gly Val Thr Leu Tyr Val
            180                 185                 190

Met Leu Val Gly Ala Tyr Pro Phe Glu Asp Gln Glu Asp Pro Lys Asn
        195                 200                 205

Phe Arg Lys Thr Ile Gln Lys Ile Met Ala Val Gln Tyr Lys Ile Pro
    210                 215                 220

Asp Tyr Val His Ile Ser Gln Asp Cys Lys Asn Leu Leu Ser Arg Ile
225                 230                 235                 240

Phe Val Ala Asn Ser Leu Lys Arg Ile Thr Ile Ala Glu Ile Lys Lys
                245                 250                 255

His Ser Trp Phe Leu Lys Asn Leu Pro Arg Glu Leu Thr Glu Thr Ala
            260                 265                 270

Gln Ala Ala Tyr Phe Lys Lys Glu Asn Pro Thr Phe Ser Leu Gln Thr
        275                 280                 285

Val Glu Glu Ile Met Lys Ile Val Ala Asp Ala Lys Thr Pro Pro Pro
    290                 295                 300
```

```
Val Ser Arg Ser Ile Gly Gly Phe Gly Trp Gly Asn Gly Asp Ala
305                 310                 315                 320

Asp Gly Lys Glu Glu Asp Ala Glu Asp Val Glu Glu Glu Glu Glu
            325                 330                 335

Val Glu Glu Glu Glu Asp Asp Glu Asp Glu Tyr Asp Lys Thr Val Lys
            340                 345                 350

Glu Val His Ala Ser Gly Glu Val Arg Ile Ser
        355                 360

<210> SEQ ID NO 394
<211> LENGTH: 1749
<212> TYPE: DNA
<213> ORGANISM: Arabidopsis thaliana

<400> SEQUENCE: 394
```

| | | | | | |
|---|---|---|---|---|---|
| gagtttgttt | aggcagggga | gattcttctt | cattctcatc | attatttctc | tattaatttc | 60 |
| accccaaaaa | agaaaaaaga | aaaattccaa | caagaaaaaa | aaaagaaaaa | gaaagttgat | 120 |
| tcttcgctta | ggcttgaaat | ctctccaatc | caaatctcaa | attaaccttc | catcgtcatc | 180 |
| tctttccctt | ttttttttccc | actttctttg | cgaatcgcga | gatctcggaa | tcgcatcctt | 240 |
| gattttggga | tactgttttt | tttttttta | atcttgtttc | attttcacgt | gaaattctta | 300 |
| gctgctagaa | ctggacttga | atttcaacga | gaattttgga | gatttttttt | ttgtttgggt | 360 |
| ttttcctttc | tgttttgtgt | gtttggaatt | agggttgtcg | agcgagaatg | gacaagtacg | 420 |
| agctggtgaa | agacataggt | gctgggaatt | ttggagttgc | caggctcatg | aaggtcaaaa | 480 |
| actctaagga | acttgttgcc | atgaagtaca | tcgagcgtgg | tcctaagatt | gatgagaatg | 540 |
| tggcaagaga | gatcattaat | cacagatcac | ttcgccatcc | gaatataatc | cggttcaagg | 600 |
| aggtggtgtt | gactccaacc | catcttgcca | tgccatggaa | atatgctgct | ggtggtgaac | 660 |
| tattcgagcg | tatatgcagt | gctggaagat | ttagtgagga | tgaggcgaga | tatttcttcc | 720 |
| agcagcttat | atcaggtgtt | agctattgcc | atgctatgca | aatatgccat | agagatctga | 780 |
| agctcgagaa | tacgctcttg | gatggaagtc | ctgctccacg | tctgaaaatc | tgtgattttg | 840 |
| gttattccaa | gtcctctctg | ctgcactcta | ggcccaaatc | aacagttgga | actccagcat | 900 |
| atattgcacc | tgaggtcctt | tctcgaagag | aatatgatgg | caagatggct | gatgtatggt | 960 |
| cttgtggtgt | gactctttat | gtcatgctgg | ttggagcata | cccatttgaa | gaccaggaag | 1020 |
| accccaagaa | cttcaggaaa | acaatacaaa | aaataatggc | tgtccagtac | aagatcccgg | 1080 |
| actacgtcca | tatctcacag | gattgtaaaa | atctcctttc | ccgtatattt | gtcgccaatt | 1140 |
| cactcaagag | gatcaccatt | gcagaaatca | agaaacattc | atggttccta | agaatttgc | 1200 |
| caagggaact | cacagagaca | gctcaagctg | catatttcaa | gaaagagaac | ccaaccttct | 1260 |
| cccttcagac | cgttgaagag | atcatgaaga | tagtggctga | cgccaaaaca | ccgcctcctg | 1320 |
| tttcccgatc | catcggaggt | tttggctggg | gaggaaatgg | ggatgcagat | ggaaaagagg | 1380 |
| aagatgcaga | agacgtggag | gaggaagagg | aggaggtgga | agaagaggaa | gacgatgagg | 1440 |
| atgaatacga | taagactgta | aaggaagtac | acgcaagtgg | agaagtgaga | ataagttgat | 1500 |
| attttggttt | ttggtctgtg | taagaaagaa | gtcgtcgttg | gtttgttgaa | actgaaaagt | 1560 |
| ctctgttctc | gtgtttgcct | ttacaatgct | ttggctaagg | ttttggttct | ggttttggag | 1620 |
| atttgtaaaa | tttgcagtat | aagatgaaca | aacagagagg | ttgatgatga | gaatgagtcc | 1680 |
| tttgctacgc | atggtactat | gaacattgtg | acctccaata | aatattttg | taaattagat | 1740 | tttattttc                                                         1749

<210> SEQ ID NO 395
<211> LENGTH: 148
<212> TYPE: PRT
<213> ORGANISM: Arabidopsis thaliana

<400> SEQUENCE: 395

Met Ala Ser Lys Arg Ile Leu Lys Glu Leu Lys Asp Leu Gln Lys Asp
1               5                   10                  15

Pro Pro Thr Ser Cys Ser Ala Gly Pro Val Ala Glu Asp Met Phe His
                20                  25                  30

Trp Gln Ala Thr Ile Met Gly Pro Ala Glu Ser Pro Tyr Ser Gly Gly
            35                  40                  45

Val Phe Leu Val Thr Ile His Phe Pro Pro Asp Tyr Pro Phe Lys Pro
    50                  55                  60

Pro Lys Val Ala Phe Arg Thr Lys Val Phe His Pro Asn Ile Asn Ser
65                  70                  75                  80

Asn Gly Ser Ile Cys Leu Asp Ile Leu Lys Glu Gln Trp Ser Pro Ala
                85                  90                  95

Leu Thr Ile Ser Lys Val Leu Leu Ser Ile Cys Ser Leu Leu Thr Asp
            100                 105                 110

Pro Asn Pro Asp Asp Pro Leu Val Pro Glu Ile Ala His Met Tyr Lys
        115                 120                 125

Thr Asp Arg Ala Lys Tyr Glu Ala Thr Ala Arg Asn Trp Thr Gln Lys
    130                 135                 140

Tyr Ala Met Gly
145

<210> SEQ ID NO 396
<211> LENGTH: 667
<212> TYPE: DNA
<213> ORGANISM: Arabidopsis thaliana

<400> SEQUENCE: 396
caatcatctg caggagtgaa tcgcaaaacc aaatttggag gattctttct gaggggtttc      60
tcagtgagaa atggcttcg aaacggatct tgaaggagct gaaggatctc cagaaagacc     120
ctccaacctc ctgcagtgca ggtccagttg ctgaagacat gtttcattgg caagctacaa     180
ttatgggtcc tgcagagagt ccgtattcag gcggtgtgtt tctcgttacc attcacttcc     240
ctccggacta tccattcaaa ccaccaaagg ttgcatttag gacgaaggtg tttcacccta     300
atatcaacag caacggaagc atttgccttg acattttgaa agaacaatgg agccctgccc     360
tcaccatttc caaggtgttg ctctcgatat gttcgctgtt aacagatcca atccagatg      420 acccttggt accagagatt gcacacatgt acaaaaccga cagagccaaa tacgaggcta     480
ctgcaagaaa ctggactcag aagtatgcca tgggctaaac aaagattcgt atgcttcagc     540
acctgtttat gttttcatgt ctgtttcttt cttcttcttg ttttaacttt aataaaaatg     600
tctaaaatat caacttttc gtctgtacta tatatgttta tgggttttat tatcatcatc     660
tttatct                                                               667

<210> SEQ ID NO 397
<211> LENGTH: 180
<212> TYPE: PRT
<213> ORGANISM: Arabidopsis thaliana

<400> SEQUENCE: 397

```
Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Gly Lys
    50                  55                  60

Lys Lys Phe Glu Thr Leu Ser Tyr Leu Pro Asp Leu Thr Asp Ser Glu
65              70                  75                  80

Leu Ala Lys Glu Val Asp Tyr Leu Ile Arg Asn Lys Trp Ile Pro Cys
            85                  90                  95

Val Glu Phe Glu Leu Glu His Gly Phe Val Tyr Arg Glu His Gly Asn
        100                 105                 110

Ser Pro Gly Tyr Tyr Asp Gly Arg Tyr Trp Thr Met Trp Lys Leu Pro
        115                 120                 125

Leu Phe Gly Cys Thr Asp Ser Ala Gln Val Leu Lys Glu Val Glu Glu
    130                 135                 140

Cys Lys Lys Glu Tyr Pro Asn Ala Phe Ile Arg Ile Ile Gly Phe Asp
145             150                 155                 160

Asn Thr Arg Gln Val Gln Cys Ile Ser Phe Ile Ala Tyr Lys Pro Pro
                165                 170                 175

Ser Phe Thr Gly
            180

<210> SEQ ID NO 398
<211> LENGTH: 871
<212> TYPE: DNA
<213> ORGANISM: Arabidopsis thaliana

<400> SEQUENCE: 398
tcagtcacac aaagagtaaa gaagaacaat ggcttcctct atgctctctt ccgctactat     60
ggttgcctct ccggctcagg ccactatggt cgctcctttc aacggactta agtcctccgc    120
tgccttccca gccacccgca aggctaacaa cgacattact ccatcacaa gcaacggcgg    180 aagagttaac tgcatgcagg tgtggcctcc gattggaaag aagaagtttg agactctctc    240
ttaccttcct gaccttaccg attccgaatt ggctaaggaa gttgactacc ttatccgcaa    300
caagtggatt ccttgtgttg aattcgacac ggatttgtgt accgtgagca cggtaactca    360
cccggatact atgatggacg gtactggaca atgtggaagc ttcccttgtt cggttgcacc    420
gactccgctc aagtgttgaa ggaagtggaa gagtgcaaga aggagtaccc caatgccttc    480
attaggatca tcggattcga caacacccgt caagtccagt gcatcagttt cattgcctac    540
aagccaccaa gcttcaccgg ttaatttccc tttgcttttg tgtaaacctc aaaactttat    600
cccccatctt tgattttatc ccttgttttt ctgcttttt cttctttctt gggttttaat    660
ttccggactt aacgtttgtt ttccggtttg cgagacatat tctatcggat tctcaactgt    720
ctgatgaaat aaatatgtaa tgttctataa gtctttcaat ttgatatgca tatcaacaaa    780
aagaaaatag acaatgcgg ctacaaatat gaaatttaca agtttaagaa ccatgagtcg    840
ctaaagaaat cattaagaaa attagtttca c                                   871

<210> SEQ ID NO 399
<211> LENGTH: 136
<212> TYPE: PRT
```

<213> ORGANISM: Arabidopsis thaliana

<400> SEQUENCE: 399

Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Gly Lys
    50                  55                  60

Lys Lys Phe Glu Thr Leu Ser Tyr Leu Pro Asp Leu Thr Asp Ser Glu
65                  70                  75                  80

Leu Ala Lys Glu Val Asp Tyr Leu Ile Arg Asn Lys Trp Ile Pro Cys
                85                  90                  95

Val Glu Phe Asp Thr Asp Leu Cys Thr Val Ser Thr Val Thr His Pro
            100                 105                 110

Asp Thr Met Met Asp Gly Thr Gly Gln Cys Gly Ser Phe Pro Cys Ser
        115                 120                 125

Val Ala Pro Thr Pro Leu Lys Cys
        130                 135

<210> SEQ ID NO 400
<211> LENGTH: 878
<212> TYPE: DNA
<213> ORGANISM: Arabidopsis thaliana

<400> SEQUENCE: 400
tcagtcacac aaagagtaaa gaagaacaat ggcttcctct atgctctctt ccgctactat     60
ggttgcctct ccggctcagg ccactatggt cgctcctttc aacggactta agtcctccgc    120
tgccttccca gccacccgca aggctaacaa cgacattact ccatcacaa gcaacggcgg     180
aagagttaac tgcatgcagg tgtggcctcc gattggaaag aagaagtttg agactctctc    240
ttaccttcct gaccttaccg attccgaatt ggctaaggaa gttgactacc ttatccgcaa    300
caagtggatt ccttgtgttg aattcgagtt ggagcacgga tttgtgtacc gtgagcacgg    360
taactcaccc ggatactatg atggacggta ctggacaatg tggaagcttc ccttgttcgg    420
ttgcaccgac tccgctcaag tgttgaagga agtggaagag tgcaagaagg agtaccccaa    480
tgccttcatt aggatcatcg gattcgacaa cacccgtcaa gtccagtgca tcagtttcat    540
tgcctacaag ccaccaagct tcaccggtta atttcccttt gcttttgtgt aaacctcaaa    600
actttatccc ccatctttga ttttatccct tgttttctg cttttttctt ctttcttggg    660
ttttaatttc cggacttaac gtttgttttc cggtttgcga dacatattct atcggattct    720
caactgtctg atgaaataaa tatgtaatgt tctataagtc tttcaatttg atatgcatat    780
caacaaaaag aaaataggac aatgcggcta caaatatgaa atttacaagt ttaagaacca    840
tgagtcgcta aagaaatcat taagaaaatt agtttcac                            878

<210> SEQ ID NO 401
<211> LENGTH: 118
<212> TYPE: PRT
<213> ORGANISM: Arabidopsis thaliana

<400> SEQUENCE: 401

Met Ala Thr Leu Asp Ser Asp Val Thr Met Ile Pro Ala Gly Glu Ala
1               5                   10                  15

```
Ser Ser Ser Val Ala Ser Ser Asn Lys Lys Ala Lys Arg Phe
            20              25              30

Glu Ile Lys Lys Trp Ser Ala Val Ala Leu Trp Ala Trp Asp Ile Val
        35              40              45

Val Asp Asn Cys Ala Ile Cys Arg Asn His Ile Met Asp Leu Cys Ile
 50              55              60

Glu Cys Gln Ala Asn Gln Ala Ser Ala Thr Ser Glu Glu Cys Thr Val
 65              70              75              80

Ala Trp Gly Val Cys Asn His Ala Phe His Phe His Cys Ile Ser Arg
                85              90              95

Trp Leu Lys Thr Arg Gln Val Cys Pro Leu Asp Asn Ser Glu Trp Glu
            100             105             110

Phe Gln Lys Tyr Gly His
        115

<210> SEQ ID NO 402
<211> LENGTH: 357
<212> TYPE: DNA
<213> ORGANISM: Arabidopsis thaliana

<400> SEQUENCE: 402
atggcgactc tagactccga cgttaccatg attcctgccg agaagcctc cagcagcgta      60 gccgcgtcgt cttccaacaa gaaagctaag cgattcgaaa ttaagaagtg gagcgccgtt     120
gctctctggg cttgggatat cgttgttgac aactgtgcga tctgcagaaa ccacatcatg     180
gatctttgta tcgagtgtca ggctaatcag gccagtgcca caagtgaaga gtgcactgta     240
gcttgggggg tttgcaatca cgccttccac tttcactgca tcagcagatg gctaaagact     300
cgtcaagttt gtccattgga taacagtgag tgggagtttc agaaatatgg tcactaa       357

<210> SEQ ID NO 403
<211> LENGTH: 115
<212> TYPE: PRT
<213> ORGANISM: Arabidopsis thaliana

<400> SEQUENCE: 403

Met Ala Ser Leu Asn Ser Asp Val Ile Met Gly Glu Ser Ser Ile
1               5              10              15

Ser Val Pro Ser Ser Ser Lys Asn Ser Lys Arg Phe Glu Leu Lys
            20              25              30

Lys Trp Ser Ala Val Ala Leu Trp Ala Trp Asp Ile Val Val Asp Asn
        35              40              45

Cys Ala Ile Cys Arg Asn His Ile Met Asp Leu Cys Ile Glu Cys Leu
 50              55              60

Ala Asn Gln Ala Ser Ala Thr Ser Glu Glu Cys Thr Val Ala Trp Gly
 65              70              75              80

Val Cys Asn His Ala Phe His Phe His Cys Ile Ser Arg Trp Leu Lys
                85              90              95

Thr Arg Gln Val Cys Pro Leu Asp Val Cys Glu Trp Glu Phe Gln Lys
            100             105             110

Tyr Gly His
        115

<210> SEQ ID NO 404
<211> LENGTH: 348
<212> TYPE: DNA
<213> ORGANISM: Arabidopsis thaliana
```

<400> SEQUENCE: 404

```
atggcttctc tcaactccga cgttatcatg ggtgaatcct cctccatctc cgtaccttca        60
tcttcgtcca agaactcgaa acgatttgaa ttaaagaagt ggagtgctgt cgctctctgg       120
gcttgggata tcgttgttga taactgcgca atttgtagga atcacatcat ggatctctgt       180
attgaatgtc tagctaatca agctagtgcc actagtgagg aatgcactgt tgcttggggg       240
gtttgcaacc acgcctttca cttccactgt atcagcagat ggctcaaaac tcgtcaagtg       300
tgtccactag atgtctgcga gtgggaattc cagaaatatg gtcactaa                    348
```

<210> SEQ ID NO 405
<211> LENGTH: 325
<212> TYPE: PRT
<213> ORGANISM: Oryza sativa

<400> SEQUENCE: 405

```
Met Val Arg Gly Val Glu Gln Gly Gly Pro Ala Met Asp Glu Ser Ser
1               5                   10                  15

Ser Ser Ser Ser Pro Ser Pro Val Ser Ala Pro Ala Gly Gln Ala Ala
            20                  25                  30

Met Thr Ala Gly Gly Ile Ala Thr Val Ala Ala Val Leu Ile Val Phe
        35                  40                  45

Ala Ala Leu Thr Leu Ala Phe Val Leu Leu Gln Cys Tyr Cys Asp Glu
    50                  55                  60

Arg Arg Arg Ala Val Thr Thr Thr Ser Thr Ser Gly Arg Gly Arg Arg
65                  70                  75                  80

Pro Arg Pro Arg Arg Ser Gly Ser Gly Gly Asp Gly Gly Thr Gly
                85                  90                  95

Gly Gly Val Asp Pro Glu Val Leu Arg Ser Leu Pro Val Thr Val Tyr
            100                 105                 110

Ser Arg Ser Thr Ala Ala Ala Ala Lys Glu Glu Glu Glu Glu Asp
        115                 120                 125

Asp Asp Gly Val Glu Cys Ala Val Cys Leu Ala Glu Leu Glu Asp Gly
    130                 135                 140

Glu Glu Ala Arg Phe Leu Pro Arg Cys Gly His Gly Phe His Ala Glu
145                 150                 155                 160

Cys Val Asp Met Trp Leu Gly Ser His Ser Thr Cys Pro Leu Cys Arg
                165                 170                 175

Leu Thr Val Val Val Pro Pro Pro Leu Pro Pro Val Pro Pro Glu
            180                 185                 190

Pro Pro Ala Ser Tyr Thr Val Ser Leu Pro Ala Ser Val Leu Leu Gly
        195                 200                 205

Leu Ser Asp His Gly Ala Gly Ala Val Thr Met Thr Ala Glu Gly Arg
    210                 215                 220

Ser Thr Leu Val Ile Glu Ile Pro Glu Ser Ala Ala Ser Thr Thr Pro
225                 230                 235                 240

Arg Asp Ala Ala Ala Arg Ser Ser Pro Ser Leu Ala Arg Leu Arg Ser
                245                 250                 255

Leu Arg Arg Leu Trp Ser Phe Gly Arg Gln Gly Ala Ala Gly Ser Thr
            260                 265                 270

Ser Ser Cys Ser Cys Ala Thr Gly Gly Asp Asn Asp Gly Asp Val
        275                 280                 285

Glu His Gly Val Ser Val Thr Val Ala Ile Arg Ala Val Glu Ala Ala
    290                 295                 300
```

Thr Pro Ala Arg Pro Pro Glu Ala Glu Ala Gly Ala Arg Thr Ala Ala
305                 310                 315                 320

Ala His Val Arg Asn
                325

<210> SEQ ID NO 406
<211> LENGTH: 1216
<212> TYPE: DNA
<213> ORGANISM: Oryza sativa

<400> SEQUENCE: 406

| | | | | | |
|---|---|---|---|---|---|
| gtcgattatt | atggtgcggg | gtgtcgagca | gggcggcccc | gccatggacg | agtcttcgtc | 60 |
| gtcgtcgtcg | ccgtcgccgg | tgtccgcgcc | tgcagggcag | gcagccatga | cggccggcgg | 120 |
| catcgccacc | gtggcggccg | tgctcatcgt | cttcgcggcg | ctcacgctcg | ccttcgtcct | 180 |
| gctccagtgc | tactgcgacg | agcggcgccg | cgccgtgacg | acgacgtcga | cgagcgggcg | 240 |
| cgggcggcgg | ccgcggccgc | ggcggcgctc | tgggagcggc | ggggacggtg | aacgggagg | 300 |
| aggggtcgac | ccggaggtgc | tccggtcgct | gccggtcacg | gtgtacagcc | gcagcacggc | 360 |
| ggcggcggcg | gcgaaggagg | aggaggagga | ggacgacgac | ggcgtcgagt | gcgcggtgtg | 420 |
| cctcgcggag | ctcgaggacg | gcgaggaggc | caggttcctc | ccccggtgcg | gccacggctt | 480 |
| ccacgccgag | tgcgtcgaca | tgtggctcgg | ctcccactcc | acctgcccgc | tctgccgcct | 540 |
| caccgtcgtc | gtgccgccgc | cgcctcttcc | tcccgtcccg | ccggagccgc | cggcgagcta | 600 |
| caccgtgagc | ctcccggcga | gcgtcctgct | cggcctgtcc | gaccatggcg | ccggcgcggt | 660 |
| gaccatgaca | gcggagggcc | gcagcacgct | ggtgatcgag | atccccgaat | ccgcggcttc | 720 |
| gacgaccccg | cgcgacgcgg | cggcgaggtc | gtcgccgagc | ttggcgcggc | tgaggtcact | 780 |
| gagaaggctc | tggagcttcg | gcggcaagg | ggcggcgggg | tcgacgtcgt | catgctcctg | 840 |
| cgccaccgga | ggagacaacg | acgacggcga | cgtcgagcac | ggtgtcagcg | tcaccgtcgc | 900 |
| catccgcgcc | gtggaggcgg | caacgccggc | acggccaccg | gaggccgagg | ccggtgcaag | 960 |
| aaccgccgcc | gcgcatgtcc | ggaattgacg | gcggcgaggt | cgtcaagtat | tataaggcga | 1020 |
| tctccctgta | catatcggta | gaaccgaact | ggaatcgcca | ttaattccta | cgattttaga | 1080 |
| aaatatcaat | ttcattttta | agattagaaa | catttaagta | gaaattattt | gttcatcagt | 1140 |
| caagtagcaa | agagaaatgt | atggatggca | gtgagaagca | tccctctccg | tatgttccaa | 1200 |
| aaaaaaaaaa | aaaaaa | | | | | 1216 |

<210> SEQ ID NO 407
<211> LENGTH: 249
<212> TYPE: PRT
<213> ORGANISM: Arabidopsis thaliana

<400> SEQUENCE: 407

Met Ala Leu Asp Gln Ser Phe Glu Asp Ala Ala Leu Leu Gly Glu Leu
1               5                   10                  15

Tyr Gly Glu Gly Ala Phe Cys Phe Lys Ser Lys Pro Glu Pro Ile
                20                  25                  30

Thr Val Ser Val Pro Ser Asp Asp Thr Asp Ser Asn Phe Asp Cys
            35                  40                  45

Asn Ile Cys Leu Asp Ser Val Gln Glu Pro Val Val Thr Leu Cys Gly
        50                  55                  60

His Leu Phe Cys Trp Pro Cys Ile His Lys Trp Leu Asp Val Gln Ser
65                  70                  75                  80

```
Phe Ser Thr Ser Asp Glu Tyr Gln Arg His Arg Gln Cys Pro Val Cys
                85                  90                  95

Lys Ser Lys Val Ser His Ser Thr Leu Val Pro Leu Tyr Gly Arg Gly
            100                 105                 110

Arg Cys Thr Thr Gln Glu Glu Gly Lys Asn Ser Val Pro Lys Arg Pro
        115                 120                 125

Val Gly Pro Val Tyr Arg Leu Glu Met Pro Asn Ser Pro Tyr Ala Ser
    130                 135                 140

Thr Asp Leu Arg Leu Ser Gln Arg Val His Phe Asn Ser Pro Gln Glu
145                 150                 155                 160

Gly Tyr Tyr Pro Val Ser Gly Val Met Ser Ser Asn Ser Leu Ser Tyr
                165                 170                 175

Ser Ala Val Leu Asp Pro Val Met Val Met Val Gly Glu Met Val Ala
                180                 185                 190

Thr Arg Leu Phe Gly Thr Arg Val Met Asp Arg Phe Ala Tyr Pro Asp
                195                 200                 205

Thr Tyr Asn Leu Ala Gly Thr Ser Gly Pro Arg Met Arg Arg Arg Ile
        210                 215                 220

Met Gln Ala Asp Lys Ser Leu Gly Arg Ile Phe Phe Phe Phe Met Cys
225                 230                 235                 240

Cys Val Val Leu Cys Leu Leu Leu Phe
                245

<210> SEQ ID NO 408
<211> LENGTH: 980
<212> TYPE: DNA
<213> ORGANISM: Arabidopsis thaliana

<400> SEQUENCE: 408
ctctcgtcga aagcaaaaca gtctcctttc tctatcttct gctcatatca gccattgaca      60
cagttgcttt gggtttccct caaacggcgc cgattgtctg gattttgacc actgatggcc     120
ttagatcaat cttttgaaga tgctgcttta cttggagaac tctatggaga aggtgcattt     180
tgtttcaaga gcaagaaacc tgaacccatt acagtctcgg ttccttctga tgatactgat     240
gattcgaatt ttgactgcaa tatttgctta gactcggtgc aagaacctgt tgtgactctc     300
tgtggtcacc tcttttgctg gccttgtatt cacaaatggc ttgatgtaca gagcttctca     360
acaagtgatg aataccaaag acatagacag tgtcctgttt gtaaatctaa agtttctcat     420
tctactttgg ttcctttgta tggtagaggc cgttgtacta ctcaggagga aggtaaaaac     480
agtgtgccta aaagacccgt aggaccggtt tatcggcttg aaatgccgaa ttcacccttat     540
gcaagtactg atctgcggtt atcacaacgg gttcatttca atagcccaca ggaaggttac     600
taccctgtct cagggtgtgat gagctcgaac agtttatcat actctgctgt tttggatccg     660
gtgatggtga tggttggaga aatggtagct acgaggttgt ttggaacacg agtgatggat     720
agatttgcgt atccggacac ttacaatctc gcagggacta gcgggccgag gatgagaagg     780
cggataatgc aggcagataa atcgctggga agaatcttct tcttctttat gtgttgtgtt     840
gttctgtgtc ttctccttgtt ttaggttttc atagctagct tggttctgct actgttcagt     900
ttcttcaggt gtaaggaaaa catagtcaaa gaaatgtaca tttgtgttgg aaacaaatca     960
aagttgctta atgttgaggg                                                 980

<210> SEQ ID NO 409
<211> LENGTH: 442
```

<212> TYPE: PRT
<213> ORGANISM: Arabidopsis thaliana

<400> SEQUENCE: 409

```
Met Val Thr Arg Glu Thr Lys Leu Thr Ser Glu Arg Val Glu Ser
1               5                   10                  15

Ser Met Ala Gln Ala Arg His Asn Gly Gly Gly Gly Glu Asn His
            20                  25                  30

Pro Phe Thr Ser Leu Gly Arg Gln Ser Ser Ile Tyr Ser Leu Thr Leu
        35                  40                  45

Asp Glu Phe Gln His Ala Leu Cys Glu Asn Gly Lys Asn Phe Gly Ser
    50                  55                  60

Met Asn Met Asp Glu Phe Leu Val Ser Ile Trp Asn Ala Glu Glu Asn
65                  70                  75                  80

Asn Asn Asn Gln Gln Gln Ala Ala Ala Ala Gly Ser His Ser Val
                85                  90                  95

Pro Ala Asn His Asn Gly Phe Asn Asn Asn Asn Asn Gly Gly Glu
            100                 105                 110

Gly Gly Val Gly Val Phe Ser Gly Gly Ser Arg Gly Asn Glu Asp Ala
            115                 120                 125

Asn Asn Lys Arg Gly Ile Ala Asn Glu Ser Ser Leu Pro Arg Gln Gly
    130                 135                 140

Ser Leu Thr Leu Pro Ala Pro Leu Cys Arg Lys Thr Val Asp Glu Val
145                 150                 155                 160

Trp Ser Glu Ile His Arg Gly Gly Ser Gly Asn Gly Gly Asp Ser
                165                 170                 175

Asn Gly Arg Ser Ser Ser Asn Gly Gln Asn Asn Ala Gln Asn Gly
            180                 185                 190

Gly Glu Thr Ala Ala Arg Gln Pro Thr Phe Gly Glu Met Thr Leu Glu
            195                 200                 205

Asp Phe Leu Val Lys Ala Gly Val Val Arg Glu His Pro Thr Asn Pro
    210                 215                 220

Lys Pro Asn Pro Asn Pro Asn Gln Asn Gln Asn Pro Ser Ser Val Ile
225                 230                 235                 240

Pro Ala Ala Ala Gln Gln Gln Leu Tyr Gly Val Phe Gln Gly Thr Gly
                245                 250                 255

Asp Pro Ser Phe Pro Gly Gln Ala Met Gly Val Gly Asp Pro Ser Gly
            260                 265                 270

Tyr Ala Lys Arg Thr Gly Gly Gly Tyr Gln Gln Ala Pro Pro Val
            275                 280                 285

Gln Ala Gly Val Cys Tyr Gly Gly Val Gly Phe Gly Ala Gly Gly
    290                 295                 300

Gln Gln Met Gly Met Val Gly Pro Leu Ser Pro Val Ser Ser Asp Gly
305                 310                 315                 320

Leu Gly His Gly Gln Val Asp Asn Ile Gly Gly Gln Tyr Gly Val Asp
                325                 330                 335

Met Gly Gly Leu Arg Gly Arg Lys Arg Val Val Asp Gly Pro Val Glu
            340                 345                 350

Lys Val Val Glu Arg Arg Gln Arg Arg Met Ile Lys Asn Arg Glu Ser
            355                 360                 365

Ala Ala Arg Ser Arg Ala Arg Lys Gln Ala Tyr Thr Val Glu Leu Glu
    370                 375                 380

Ala Glu Leu Asn Gln Leu Lys Glu Glu Asn Ala Gln Leu Lys His Ala
385                 390                 395                 400
```

Leu Ala Glu Leu Glu Arg Lys Arg Lys Gln Gln Tyr Phe Glu Ser Leu
            405                 410                 415

Lys Ser Arg Ala Gln Pro Lys Leu Pro Lys Ser Asn Gly Arg Leu Arg
            420                 425                 430

Thr Leu Met Arg Asn Pro Ser Cys Pro Leu
            435                 440

<210> SEQ ID NO 410
<211> LENGTH: 1694
<212> TYPE: DNA
<213> ORGANISM: Arabidopsis thaliana

<400> SEQUENCE: 410

| | | | | | |
|---|---|---|---|---|---|
| atctctctct | ttctcaaaac | ctttcagtca | aaattctccg | gcggctttta | aactatgtga | 60 |
| aggaggagaa | cctccataac | aagaagcgga | ttctctcagt | tttccggcgg | cggaggaaca | 120 |
| caaagccacc | ggttttaga | cacacagatt | tcattttcag | ttgttaaatg | gtaactagag | 180 |
| aaacgaagtt | gacgtcagag | cgagaagtag | agtcgtccat | ggcgcaagcg | agacataatg | 240 |
| gaggaggtgg | tggtgagaat | catccgttta | cttctttggg | aagacaatcc | tctatctact | 300 |
| cattgaccct | tgacgagttc | caacatgctt | tatgtgagaa | cggcaagaac | tttgggtcca | 360 |
| tgaacatgga | cgagtttctt | gtctctattt | ggaacgcaga | ggagaataat | aacaatcaac | 420 |
| aacaagcagc | agcagctgca | ggttcacatt | ctgttccggc | taatcacaat | ggtttcaaca | 480 |
| acaacaataa | caatggaggc | gagggtggtg | ttggtgtctt | tagtggtggt | tctagaggca | 540 |
| acgaagatgc | taacaataag | agagggatag | cgaacgagtc | tagtcttcct | cgacaaggct | 600 |
| ctttgacact | tccagctccg | ctttgtagga | agactgttga | tgaggtttgg | tctgagatac | 660 |
| atagaggtgg | tggtagcggt | aatggaggag | acagcaatgg | acgtagtagt | agtagtaatg | 720 |
| gacagaacaa | tgctcagaac | ggcggtgaga | ctgcggctag | acaaccgact | tttggagaga | 780 |
| tgacacttga | ggatttcttg | gtgaaggctg | gtgtggttag | agaacatccc | actaatccta | 840 |
| aacctaatcc | aaacccgaac | caaaaccaaa | acccgtctag | tgtaataccc | gcagctgcac | 900 |
| agcaacagct | ttatggtgtg | tttcaaggaa | ccggtgatcc | ttcattcccg | ggtcaagcta | 960 |
| tgggtgtggg | tgacccatca | ggttatgcta | aaaggacagg | aggaggaggg | tatcagcagg | 1020 |
| cgccaccagt | tcaggcaggt | gtttgctatg | gaggtggcgt | tgggtttgga | gcgggtggac | 1080 |
| agcaaatggg | aatggttgga | ccgttaagcc | cggtgtcttc | agatggatta | ggacatggac | 1140 |
| aagtggataa | cataggaggt | cagtatggag | tagatatggg | agggctaagg | ggaaggaaaa | 1200 |
| gagtagtgga | tggtccagtg | gagaaagtag | tggagagaag | acagaggagg | atgatcaaga | 1260 |
| accgcgagtc | tgctgctaga | tctagagcaa | gaaaacaagc | atatacagtg | gaattggaag | 1320 |
| ctgaacttaa | ccagttgaaa | gaagagaatg | cgcagctaaa | acatgcattg | gcggagttgg | 1380 |
| agaggaagag | gaagcaacag | tattttgaga | gtttgaagtc | aagggcacaa | ccgaaattgc | 1440 |
| cgaaatcgaa | cgggagattg | cggacattga | tgaggaaccc | gagttgtcca | ctctaaacaa | 1500 |
| acaataggaa | gatggagaag | aagtcggaga | cagaacgagg | gaaaaactga | tgattttcta | 1560 |
| cgttgttgtt | ttgtctttga | ggaatgaggt | tatagaatct | ttatactttg | atgttttctg | 1620 |
| tgttggtagg | aggaacacca | tctgatctgc | tttactagtg | ttccctgtga | acaaagaaag | 1680 |
| tgattctgtg | tttc | | | | | 1694 |

<210> SEQ ID NO 411
<211> LENGTH: 720

<212> TYPE: PRT
<213> ORGANISM: Arabidopsis thaliana

<400> SEQUENCE: 411

```
Met Lys Ser Leu His Val Ala Ala Asn Ala Gly Asp Leu Ala Glu Asp
1               5                   10                  15

Cys Gly Ile Leu Gly Gly Asp Ala Asp Thr Val Leu Met Asp Gly
            20                  25                  30

Ile Asp Glu Val Gly Arg Glu Ile Trp Leu Asp His Gly Gly Asp
        35                  40                  45

Asn Asn His Val His Gly His Gln Asp Asp Leu Ile Val His His
    50                  55                  60

Asp Pro Ser Ile Phe Tyr Gly Asp Leu Pro Thr Leu Pro Asp Phe Pro
65                  70                  75                  80

Cys Met Ser Ser Ser Ser Ser Ser Thr Ser Pro Ala Pro Val Asn
                85                  90                  95

Ala Ile Val Ser Ser Ala Ser Ser Ser Ala Ala Ser Ser Ser Thr
            100                 105                 110

Ser Ser Ala Ala Ser Trp Ala Ile Leu Arg Ser Asp Gly Glu Asp Pro
        115                 120                 125

Thr Pro Asn Gln Asn Gln Tyr Ala Ser Gly Asn Cys Asp Asp Ser Ser
130                 135                 140

Gly Ala Leu Gln Ser Thr Ala Ser Met Glu Ile Pro Leu Asp Ser Ser
145                 150                 155                 160

Gln Gly Phe Gly Cys Gly Glu Gly Gly Asp Cys Ile Asp Met Met
                165                 170                 175

Glu Thr Phe Gly Tyr Met Asp Leu Leu Asp Ser Asn Glu Phe Phe Asp
            180                 185                 190

Thr Ser Ala Ile Phe Ser Gln Asp Asp Thr Gln Asn Pro Asn Leu
        195                 200                 205

Met Asp Gln Thr Leu Glu Arg Gln Glu Asp Gln Val Val Pro Met
210                 215                 220

Met Glu Asn Asn Ser Gly Gly Asp Met Gln Met Met Asn Ser Ser Leu
225                 230                 235                 240

Glu Gln Asp Asp Asp Leu Ala Ala Val Phe Leu Glu Trp Leu Lys Asn
                245                 250                 255

Asn Lys Glu Thr Val Ser Ala Glu Asp Leu Arg Lys Val Lys Ile Lys
            260                 265                 270

Lys Ala Thr Ile Glu Ser Ala Ala Arg Arg Leu Gly Gly Gly Lys Glu
        275                 280                 285

Ala Met Lys Gln Leu Leu Lys Leu Ile Leu Glu Trp Val Gln Thr Asn
290                 295                 300

His Leu Gln Arg Arg Arg Thr Thr Thr Thr Thr Asn Leu Ser Tyr
305                 310                 315                 320

Gln Gln Ser Phe Gln Gln Asp Pro Phe Gln Asn Pro Asn Pro Asn Asn
                325                 330                 335

Asn Asn Leu Ile Pro Pro Ser Asp Gln Thr Cys Phe Ser Pro Ser Thr
            340                 345                 350

Trp Val Pro Pro Pro Gln Gln Gln Ala Phe Val Ser Asp Pro Gly
        355                 360                 365

Phe Gly Tyr Met Pro Ala Pro Asn Tyr Pro Gln Pro Glu Phe Leu
370                 375                 380

Pro Leu Leu Glu Ser Pro Pro Ser Trp Pro Pro Pro Gln Ser Gly
385                 390                 395                 400
```

```
Pro Met Pro His Gln Gln Phe Pro Met Pro Pro Thr Ser Gln Tyr Asn
            405                 410                 415

Gln Phe Gly Asp Pro Thr Gly Phe Asn Gly Tyr Asn Met Asn Pro Tyr
            420                 425                 430

Gln Tyr Pro Tyr Val Pro Ala Gly Gln Met Arg Asp Gln Arg Leu Leu
            435                 440                 445

Arg Leu Cys Ser Ser Ala Thr Lys Glu Ala Arg Lys Lys Arg Met Ala
            450                 455                 460

Arg Gln Arg Arg Phe Leu Ser His His His Arg His Asn Asn Asn Asn
465                 470                 475                 480

Asn Asn Asn Asn Asn Gln Gln Asn Gln Thr Gln Ile Gly Glu Thr
            485                 490                 495

Cys Ala Ala Val Ala Pro Gln Leu Asn Pro Val Ala Thr Thr Ala Thr
            500                 505                 510

Gly Gly Thr Trp Met Tyr Trp Pro Asn Val Pro Ala Val Pro Pro Gln
            515                 520                 525

Leu Pro Pro Val Met Glu Thr Gln Leu Pro Thr Met Asp Arg Ala Gly
            530                 535                 540

Ser Ala Ser Ala Met Pro Arg Gln Gln Val Val Pro Asp Arg Arg Gln
545                 550                 555                 560

Gly Trp Lys Pro Glu Lys Asn Leu Arg Phe Leu Leu Gln Lys Val Leu
            565                 570                 575

Lys Gln Ser Asp Val Gly Asn Leu Gly Arg Ile Val Leu Pro Lys Lys
            580                 585                 590

Glu Ala Glu Thr His Leu Pro Glu Leu Glu Ala Arg Asp Gly Ile Ser
            595                 600                 605

Leu Ala Met Glu Asp Ile Gly Thr Ser Arg Val Trp Asn Met Arg Tyr
            610                 615                 620

Arg Phe Trp Pro Asn Asn Lys Ser Arg Met Tyr Leu Leu Glu Asn Thr
625                 630                 635                 640

Gly Asp Phe Val Lys Thr Asn Gly Leu Gln Glu Gly Asp Phe Ile Val
            645                 650                 655

Ile Tyr Ser Asp Val Lys Cys Gly Lys Tyr Leu Ile Arg Gly Val Lys
            660                 665                 670

Val Arg Gln Pro Ser Gly Gln Lys Pro Glu Ala Pro Pro Ser Ser Ala
            675                 680                 685

Ala Thr Lys Arg Gln Asn Lys Ser Gln Arg Asn Ile Asn Asn Asn Ser
            690                 695                 700

Pro Ser Ala Asn Val Val Val Ala Ser Pro Thr Ser Gln Thr Val Lys
705                 710                 715                 720
```

<210> SEQ ID NO 412
<211> LENGTH: 2965
<212> TYPE: DNA
<213> ORGANISM: Arabidopsis thaliana

<400> SEQUENCE: 412

| | | | | | |
|---|---|---|---|---|---|
| gttggagtaa | acccaaacgg | ttttagatta | cttattagct | gttcatcagt | tcttcctctc | 60 |
| taaaagagta | aaacctaaac | atctctctct | gttctattag | aaccaagac | caatctttgt | 120 |
| gaacaaaaca | catctcgtat | acttcagatc | tagactcgaa | aattttagac | ctctttacaa | 180 |
| ttggtctttg | ttcatctgaa | gttggagaaa | atagttagct | taggtcggat | cttttcatat | 240 |
| gctttggatc | ctccttcgtc | tcttttgtat | aattttaacc | ttatcaagag | ttcttttga | 300 |

```
atctcaaaag attatatagt agtatagaag gtttatatgt atatgtatag ccagatagtt    360
tatgttgttt aaagattcga tgatagccaa gttgggttaa cttcttttt ccttgcctcc    420 ttactcacat acaaacccta tctgtccgta caaaatacta aaaccctaa cttttctctc    480 tccaccaatc tagtttattg tttcatttcc acttcaacga tgaaaagctt gcatgtggcg    540
gccaacgccg gagatctggc tgaggattgt ggaatactcg gtggagacgc tgatgatact    600
gttttgatgg atggaattga tgaagttggt agagagatct ggttagatga ccatggagga    660
gataataatc atgttcatgg tcatcaagat gatgatttga ttgttcatca tgacccttca    720
atcttctatg gagatctccc aacgcttcct gatttcccat gcatgtcgtc ttcatcatcg    780
tcttcaacat ctccagctcc tgtcaacgca atcgtctcct cagcctcttc ttcttcggca    840
gcttcttcct ccacttcctc agctgcttct tgggctatat tgagatcaga tggagaagat    900
ccgactccaa accaaaacca atacgcatca ggaaactgtg acgactcttc tggtgcattg    960
caatccacag cttccatgga gattccatta gacagcagtc aaggttttgg ttgcggcgaa   1020
ggcggtggtg attgcattga tatgatggag actttcgggt acatggatct acttgatagc   1080
aacgagttct ttgacacctc agctatattt agccaagacg acgacacgca aaaccctaac   1140 ttgatgacc aaacccttga gagacaagaa gaccaggtcg ttgttccgat gatggagaat   1200
aacagtggtg gagacatgca aatgatgaat tcttccttgg aacaggacga tgatctcgct   1260
gctgtgtttt tggagtggct aaagaacaac aaggagactg tgtcggctga ggatttgagg   1320
aaagtaaaga taaagaaagc tacgattgaa tcagcggcaa gaagactagg cggtggtaaa   1380
gaagcgatga agcagctttt aaagctgatt cttgaatggg tccaaactaa tcacttacaa   1440
agaagacgca ccaccaccac caccaccaac ctctcttatc aacaatcatt ccaacaagat   1500
ccatttcaaa accctaaccc taataacaac aacctaatcc caccgtccga ccaaacctgt   1560
ttctcacctt caacatgggt tcctccacca ccacaacaac aagcttttgt ctcggacccg   1620
ggttttggat acatgcctgc tccaaactat ccgccacagc cagagttcct tcctttactt   1680
gaatctccac cgtcatggcc accaccacca cagtctggtc ccatgccaca tcaacaattc   1740
cccatgccgc caacctcgca gtataatcaa tttggagatc caacaggttt caatggatac   1800
aacatgaatc cgtaccaata tccttatgtt cctgcaggac aaatgagaga tcagagatta   1860
ctccgtttgt gttcctcagc aactaaagag gcaagaaaga aacggatggc gagacagagg   1920
aggttcttgt ctcatcacca cagacataac aacaacaaca acaacaacaa caataatcag   1980
cagaaccaaa cccaaatcgg agaaacctgt gccgcggtgg ctccacaact taaccccgtg   2040
gccacaaccg ccacgggagg gacctggatg tattggccta atgtcccggc agtgccgcct   2100
caattaccgc cagtgatgga gactcagtta cctaccatgg accgagctgg ctcagcttct   2160
gctatgccac gtcagcaggt ggtaccagat cgccggcagg gatggaaacc agaaaagaat   2220
ttgcggtttc tcttgcagaa agtcttgaag caaagcgacg tgggtaacct cggaaggatc   2280
gttttgccaa aaaagaagc tgagacacac ttgccggagc tagaggcaag agacggcatc   2340
tctctggcca tggaagacat cggaacctct cgtgtttgga acatgcgcta caggttttgg   2400
cctaacaaca aaagcaggat gtatctcctc gagaacaccg gcgattttgt gaaaaccaat   2460
gggctccaag aaggtgattt catagtcata tactccgacg tcaaatgtgg caaatatttg   2520
atacgagggg ttaaagtaag acaaccgagc ggacaaaagc cggaggcccc accgtcgtca   2580
gcagctacga agagacaaaa caagtcgcaa aggaacataa acaataactc tccgtcggcg   2640
aatgtggtgg tcgcttcacc aacttctcaa actgttaaat gaaaaacaga gacaaaaaga   2700
```

-continued

```
aacaatataa atattattat gtaccaaata agaaagaggg caaaaggaaa aaatggcagc    2760
gtacccgagt gtgccacttc tcgtgcatgc atgggatctt gaagacaaat ggagggtcat    2820
gattaaagct gtttggtcgg ggtccggggtt tttactccat tttttgcttt ttcttgtcga    2880
gtcggttctt ttataactct ttactctttt taccttcagg atattgtaga gatgattaat    2940
tctggaaatg gtgtttgtgt tatat                                          2965
```

<210> SEQ ID NO 413
<211> LENGTH: 623
<212> TYPE: PRT
<213> ORGANISM: Arabidopsis thaliana

<400> SEQUENCE: 413

```
Met Thr Asp Tyr Arg Leu Gln Pro Thr Met Asn Leu Trp Thr Thr Asp
1               5                   10                  15

Asp Asn Ala Ser Met Met Glu Ala Phe Met Ser Ser Ser Asp Ile Ser
            20                  25                  30

Thr Leu Trp Pro Pro Ala Ser Thr Thr Thr Thr Ala Thr Thr Glu
        35                  40                  45

Thr Thr Pro Thr Pro Ala Met Glu Ile Pro Ala Gln Ala Gly Phe Asn
    50                  55                  60

Gln Glu Thr Leu Gln Gln Arg Leu Gln Ala Leu Ile Glu Gly Thr His
65                  70                  75                  80

Glu Gly Trp Thr Tyr Ala Ile Phe Trp Gln Pro Ser Tyr Asp Phe Ser
                85                  90                  95

Gly Ala Ser Val Leu Gly Trp Gly Asp Gly Tyr Tyr Lys Gly Glu Glu
            100                 105                 110

Asp Lys Ala Asn Pro Arg Arg Arg Ser Ser Ser Pro Pro Phe Ser Thr
        115                 120                 125

Pro Ala Asp Gln Glu Tyr Arg Lys Lys Val Leu Arg Glu Leu Asn Ser
    130                 135                 140

Leu Ile Ser Gly Gly Val Ala Pro Ser Asp Asp Ala Val Asp Glu Glu
145                 150                 155                 160

Val Thr Asp Thr Glu Trp Phe Phe Leu Val Ser Met Thr Gln Ser Phe
                165                 170                 175

Ala Cys Gly Ala Gly Leu Ala Gly Lys Ala Phe Ala Thr Gly Asn Ala
            180                 185                 190

Val Trp Val Ser Gly Ser Asp Gln Leu Ser Gly Ser Cys Glu Arg
        195                 200                 205

Ala Lys Gln Gly Gly Val Phe Gly Met His Thr Ile Ala Cys Ile Pro
    210                 215                 220

Ser Ala Asn Gly Val Val Glu Val Gly Ser Thr Glu Pro Ile Arg Gln
225                 230                 235                 240

Ser Ser Asp Leu Ile Asn Lys Val Arg Ile Leu Phe Asn Phe Asp Gly
                245                 250                 255

Gly Ala Gly Asp Leu Ser Gly Leu Asn Trp Asn Leu Asp Pro Asp Gln
            260                 265                 270

Gly Glu Asn Asp Pro Ser Met Trp Ile Asn Asp Pro Ile Gly Thr Pro
        275                 280                 285

Gly Ser Asn Glu Pro Gly Asn Gly Ala Pro Ser Ser Ser Gln Leu
    290                 295                 300

Phe Ser Lys Ser Ile Gln Phe Glu Asn Gly Ser Ser Thr Ile Thr
305                 310                 315                 320
```

```
Glu Asn Pro Asn Leu Asp Pro Thr Pro Ser Pro Val His Ser Gln Thr
                325                 330                 335
Gln Asn Pro Lys Phe Asn Asn Thr Phe Ser Arg Glu Leu Asn Phe Ser
            340                 345                 350
Thr Ser Ser Ser Thr Leu Val Lys Pro Arg Ser Gly Glu Ile Leu Asn
        355                 360                 365
Phe Gly Asp Glu Gly Lys Arg Ser Ser Gly Asn Pro Asp Pro Ser Ser
370                 375                 380
Tyr Ser Gly Gln Thr Gln Phe Glu Asn Lys Lys Arg Ser Met Val
385                 390                 395                 400
Leu Asn Glu Asp Lys Val Leu Ser Phe Asp Lys Thr Ala Gly Glu
                405                 410                 415
Ser Asp His Ser Asp Leu Glu Ala Ser Val Lys Glu Val Ala Val
            420                 425                 430
Glu Lys Arg Pro Lys Lys Arg Gly Arg Lys Pro Ala Asn Gly Arg Glu
        435                 440                 445
Glu Pro Leu Asn His Val Glu Ala Glu Arg Gln Arg Glu Lys Leu
450                 455                 460
Asn Gln Arg Phe Tyr Ala Leu Arg Ala Val Val Pro Asn Val Ser Lys
465                 470                 475                 480
Met Asp Lys Ala Ser Leu Leu Gly Asp Ala Ile Ala Tyr Ile Asn Glu
                485                 490                 495
Leu Lys Ser Lys Val Val Lys Thr Glu Ser Glu Lys Leu Gln Ile Lys
            500                 505                 510
Asn Gln Leu Glu Glu Val Lys Leu Glu Leu Ala Gly Arg Lys Ala Ser
        515                 520                 525
Ala Ser Gly Gly Asp Met Ser Ser Ser Cys Ser Ser Ile Lys Pro Val
530                 535                 540
Gly Met Glu Ile Glu Val Lys Ile Ile Gly Trp Asp Ala Met Ile Arg
545                 550                 555                 560
Val Glu Ser Ser Lys Arg Asn His Pro Ala Ala Arg Leu Met Ser Ala
                565                 570                 575
Leu Met Asp Leu Glu Leu Glu Val Asn His Ala Ser Met Ser Val Val
            580                 585                 590
Asn Asp Leu Met Ile Gln Gln Ala Thr Val Lys Met Gly Phe Arg Ile
        595                 600                 605
Tyr Thr Gln Glu Gln Leu Arg Ala Ser Leu Ile Ser Lys Ile Gly
610                 615                 620

<210> SEQ ID NO 414
<211> LENGTH: 2677
<212> TYPE: DNA
<213> ORGANISM: Arabidopsis thaliana

<400> SEQUENCE: 414
actttctcct atctctctct ctctcattaa aaacgtgttt ttttttaccg gtcaccggtt      60
tatggaatga ctgattaccg gctacaacca acgatgaatc tttggaccac cgtcgtcaac     120
gcttctatga tggaagcttt catgagctct tccgatatct caactttatg gcctccggcg     180
tcgacgacaa ccacgacggc gacgactgaa acaactccga cgccggcgat ggagattccg     240
gcacaggcgg gatttaatca agagactctt cagcaacgtt acaagctttt gattgaagga     300
acacacgaag gttggaccta cgctatattc tggcaaccgt cgtatgattt ctccggcgcc     360
tccgtgctcg gatggggaga tggttattac aaaggtgaag aagataaagc aaaccccgaga    420
```

```
cggagatcga gttcgccgcc gttttctact ccggcggatc aggagtacag gaaaaaagtg    480
ttgagagagc ttaactcgtt gatctccggt ggtgttgctc cgtcggatga cgctgttgat    540
gaggaggtga cggatacgga atggtttttc ttggtttcga tgacgcagag cttcgcttgc    600
ggtgcgggat tagctggtaa agcgtttgca acgggtaacg cggtttgggt ttccgggtca    660
gatcaattat ccgggtcggg ttgtgaacgg gctaagcaag gaggagtgtt tgggatgcat    720
actattgcgt gtattccttc ggcgaacgga gttgtggaag tcgggtcaac ggagccgatc    780
cgacagagtt cggaccttat taacaaggtt cgaattcttt tcaatttcga cggcggagct    840
ggagatttat cgggtcttaa ttggaatctt gacccggatc aaggtgagaa cgacccgtct    900
atgtggatta atgacccgat tggaacacct ggatctaacg aaccgggtaa cggagctcca    960
agttctagct cccagctttt ttcaaagtct attcagtttg agaacggtag ctcaagcaca   1020
ataaccgaaa acccgaatct ggatccgact ccgagtccgg ttcattctca gacccagaat   1080
ccgaaattca ataacacttt ctcccgagaa cttaattttt cgacgtcaag ttctacttta   1140
gtgaaaccaa gatccggcga gatattaaac ttcggcgatg aaggtaaacg aagctccgga   1200
aacccggatc caagttctta ttcgggtcaa acacaattcg aaaacaaaag aaagaggtcg   1260
atggttttga acgaagataa agttctatca ttcggagata aaaccgccgg agaatcagat   1320
cactccgatc tagaagcttc cgtcgtgaaa gaagtagcag tagagaaacg tccaaagaaa   1380
cgaggaagaa agccagcaaa cggtagagaa gagccactaa accacgtcga agcagagaga   1440
caaagacgcg agaaactaaa ccaaagattc tacgcgttac gagcggttgt accaaacgtt   1500
tcaaaaatgg ataaagcttc gttactcggt gacgcaatcg cttacatcaa cgagcttaaa   1560
tccaaagtag tcaaaacaga gtcagagaaa ctccaaatca gaaccagct cgaggaagtg   1620
aaactcgagc tcgccggaag aaaagcgagt gctagtggag gagatatgtc gtcttcgtgt   1680
tcttcgatta aaccggtggg gatggagatt gaagtgaaga taattggttg ggacgcaatg   1740
attagagttg aatctagtaa gaggaatcat ccggcggcga ggttgatgtc ggcgttgatg   1800
gatttggagt tggaagtgaa tcacgcgagt atgtcggtgg ttaacgattt gatgattcaa   1860
caagcgacgt tgaagatggg ttttaggatc tatacgcaag aacagctcag agcaagtttg   1920
atttcaaaaa tcggttaaaa gggtgtgttt tgggaagttt agaaagttat ggggtcaaat   1980
cataattaat tcgttttagt ggcttcagta attttgtaga ttttagtttt gtaagaaaaa   2040
aatcttaaaa tagagcgaca agtttcttct tttgctctat gtttgagtct gtatcgtttt   2100
attgttgtat ctcctcaatg agtaaacttg tatatattga tatgagcccg ggggaaaagg   2160
aatcagtttt tggtggaagt aattgatccg atctaggaaa aatgggagga ggtgatcatg   2220
gacatggagc agaaggaggc gatttcagag ccaaagtctg gagtatgact ggtgggccct   2280
aactgtaggc ccaaacattg gcgtcggaac accgccattg ctatgttcgg ccgttttcct   2340
tgtgtgcatc cccatcgcca agctatctgc taagcttgag caaaggccac acatgccagt   2400
acgcccaatt ccttcacaga tctggtgcaa gaactttgga accaaggacg attacgaaaa   2460
agagcattaa aagttttttt cttggtttgg agagaaccct ttaattggtc ttcttatttg   2520
cagacaatgt gagcataaaa aaagcgcaac tagctttgtc tatggatttc agagtactgt   2580
gaacataata atatgtcttt ttccttgcca tgtagaacaa caccatggaa tctttccaaa   2640
ttaagaaatt tcatgttttt ttccatatta aaaaaaa                           2677

<210> SEQ ID NO 415
<211> LENGTH: 273
```

<212> TYPE: PRT
<213> ORGANISM: Arabidopsis thaliana

<400> SEQUENCE: 415

Met Glu Asp Tyr Glu Arg Ile Asn Ser Asn Ser Pro Thr His Glu Glu
1               5                   10                  15

Asp Ser Asp Val Arg Lys Gly Pro Trp Thr Glu Glu Asp Ala Ile
            20                  25                  30

Leu Val Asn Phe Val Ser Ile His Gly Asp Ala Arg Trp Asn His Ile
                35                  40                  45

Ala Arg Ser Ser Gly Leu Lys Arg Thr Gly Lys Ser Cys Arg Leu Arg
        50                  55                  60

Trp Leu Asn Tyr Leu Arg Pro Asp Val Arg Arg Gly Asn Ile Thr Leu
65                  70                  75                  80

Glu Glu Gln Phe Met Ile Leu Lys Leu His Ser Leu Trp Gly Asn Arg
                85                  90                  95

Trp Ser Lys Ile Ala Gln Tyr Leu Pro Gly Arg Thr Asp Asn Glu Ile
            100                 105                 110

Lys Asn Tyr Trp Arg Thr Arg Val Gln Lys Gln Ala Lys His Leu Arg
        115                 120                 125

Cys Asp Val Asn Ser Asn Leu Phe Lys Glu Thr Met Arg Asn Val Trp
130                 135                 140

Met Pro Arg Leu Val Glu Arg Ile Asn Ala Gln Ser Leu Pro Thr Thr
145                 150                 155                 160

Cys Glu Gln Val Glu Ser Met Ile Thr Asp Pro Ser Gln Pro Val Asn
                165                 170                 175

Glu Pro Ser Pro Val Glu Pro Gly Phe Val Gln Phe Ser Gln Asn His
            180                 185                 190

His Gln Gln Phe Val Pro Ala Thr Glu Leu Ser Ala Thr Ser Ser Asn
        195                 200                 205

Ser Pro Ala Glu Thr Phe Ser Asp Val Arg Gly Gly Val Val Asn Gly
210                 215                 220

Ser Gly Tyr Asp Pro Ser Gly Gln Thr Gly Phe Gly Glu Phe Asn Asp
225                 230                 235                 240

Trp Gly Cys Val Gly Gly Asp Asn Met Trp Thr Asp Glu Glu Ser Phe
                245                 250                 255

Trp Phe Leu Gln Asp Gln Phe Cys Pro Asp Thr Thr Ser Tyr Ser Tyr
            260                 265                 270

Asn

<210> SEQ ID NO 416
<211> LENGTH: 2521
<212> TYPE: DNA
<213> ORGANISM: Arabidopsis thaliana

<400> SEQUENCE: 416
tcccaacgta cgataaaatt ttgtttgata aaactcacaa aagtttagta tatttctgta      60
aatatatgca tagaagtcat agtgattgac agaggaaaga cgtctctttg actactcttc     120
aatcgaaaac aaaatgtgct aaaatttcaa aagcaaagtc cctaaactcg cctaactcca     180
tttctcattt gactttgcct taaatgtcaa tagtcctatg ttatttagct acattcaaaa     240
ttgggaatta agaattattt tagactccat atacttagaa acgaatccgt attggaaact     300
aatttccatt tagtaatagt atttaagtat tattatgctt accgagtagc atgtagtagt     360
ttcttaatgt tagctaattt caaagcaaac gcgaatatta aatcgtgatt gcacacaaca     420

-continued

```
tgaagtgatt aataaatcat taatttcgcc catagtaatc actaaccaga gtaattttga      480
acaagactaa ggatgtacaa taacttacgt ctgcgatact gtgtgggaat aaatatagaa      540
actttatgaa atagaactct cttaccaaag aaagaaaaag caagagtgcg tgttactata      600
catctgaaca ggtcaaaggg tcaaaccttaa gtattttaaaa attacacaaa caattgacca    660
aatggagagc taattatgtt tagcataatt tactatatag ttgcaaaatt ccactttaga      720
aacaggataa aaaataaaa attgaacata acacttatgc cgtgttccag tcactcttca       780
acattctact cattttcaaa tatccttttt ataaatact acttttaaaa ttatttgatt       840
cttatgttcc ttcactatat atatataaat atcgcacatt gctttaatca cttcaaatct     900
aatccacaaa accattcaca ccatctcatc ttctttctct ctatctcttt tcctttcctc     960
atttaaagtt tctttataag aaatggaaga ttacgagcga ataaactcaa actctccaac    1020
acatgaagaa gattctgatg tacggaaagg tccatggacc gaggaagaag atgcaatcct    1080
agtcaacttc gtctctattc atggcgatgc tcgttggaac cacatcgctc gttcctctgg    1140
tatcatcaaa acatcaatct ctaaatatac atatacacaa aggctttata tatagataaa    1200
cttatatata ttttactcat atatgtgcag ggctaaagcg aactggtaag agttgtagat    1260
taagatggct taattactta cgtccagatg ttagaagagg caacatcact ctcgaagaac    1320
aatttatgat cctcaaactc cattctcttt ggggcaatag gtacacacta tatctcaa      1380
atgttaatat tttgctattc tatatgttac tagttaagta tgttattaat atatgtcttt    1440
tttttcaatt gaatatataa ggtggtcgaa gattgcgcaa tatctaccgg gaagaacaga    1500
taatgaaata aagaattatt ggagaactcg agtccaaaag caagccaaac acctaagatg    1560
cgatgttaac agtaatcttt tcaaggagac tatgagaaat gtttggatgc cgagattagt    1620
ggaacgaatc aacgcccaat cattacccac cacgtgtgaa caagtggagt caatgatcac    1680
cgacccaagt caaccagtta acgaaccgag tccggtcgag ccgggtttcg ttcaattcag    1740
ccagaatcat catcagcaat tcgtaccggc tacggaattg tcagcaacgt cttcgaattc    1800
tccggctgag acgttttcgg acgttcgagg tggggtggtg aacgggtcag gttatgatcc    1860
gtcgggtcaa acgggtttcg gagagttcaa cgattgggc tgtgttggtg gggacaacat    1920
gtggactgac gaggagagtt tttggttctt gcaggaccag ttctgccccg atacgacatc    1980
gtattcgtat aattaaggaa atatacgatt actatacgta acgaggaatt caattgcgtc    2040
acgtttggtg taatattcat tcgtgcgtga tgccaatttt agatacggcc ttggtatacg    2100
aatctttgac ttaattatta tcttttcttt tcctctcttg ttttaaaccc ctgattaaat    2160
taagatttga tcatcagacg aggatatttg tgattcactg atttgtgata ttgatatatg    2220
tgaattattt gatataacgt tttaaaaacc aacaaaaaaa aaaatcatt ccaaggaaaa     2280
gttcttaatt ttgatactcg aaaagagcgt agactgactc gaatcagttc atattttctt    2340
tggttcgttt tatttacgac aaaattcact aacaaaaatt aaaaaacgac aaaacgaaaa    2400
tatgactaaa tttattttt tgtcagttaa ccactgatta taggttgaaa ttgtcacaac     2460
acatgattta tcttgataga aatttagtag tccagaatgc tgcatggttg atcctaagaa    2520
a                                                                   2521
```

<210> SEQ ID NO 417
<211> LENGTH: 460
<212> TYPE: PRT
<213> ORGANISM: Arabidopsis thaliana

<400> SEQUENCE: 417

```
Met Leu Ser Ser Lys Val Val Gly Asp Ser His Gly Gln Asp Ser Ser
1               5                   10                  15

Tyr Phe Leu Gly Trp Gln Glu Tyr Glu Lys Asn Pro Phe His Glu Ser
            20                  25                  30

Phe Asn Thr Ser Gly Ile Val Gln Met Gly Leu Ala Glu Asn Gln Leu
        35                  40                  45

Ser Phe Asp Leu Ile Glu Lys Trp Leu Glu His Pro Glu Val Leu
    50                  55                  60

Gly Leu Lys Lys Asn Asp Glu Ser Val Phe Arg Gln Leu Ala Leu Phe
65                  70                  75                  80

Gln Asp Tyr His Gly Leu Pro Ala Phe Lys Asp Ala Met Ala Lys Phe
                85                  90                  95

Met Gly Lys Ile Arg Glu Asn Lys Val Lys Phe Asp Thr Asn Lys Met
            100                 105                 110

Val Leu Thr Ala Gly Ser Thr Ser Ala Asn Glu Thr Leu Met Phe Cys
        115                 120                 125

Leu Ala Asn Pro Gly Asp Ala Phe Leu Ile Pro Ala Pro Tyr Tyr Pro
    130                 135                 140

Gly Phe Asp Arg Asp Leu Lys Trp Arg Thr Gly Val Glu Ile Val Pro
145                 150                 155                 160

Ile His Cys Val Ser Ser Asn Gly Tyr Lys Ile Thr Glu Asp Ala Leu
                165                 170                 175

Glu Asp Ala Tyr Glu Arg Ala Leu Lys His Asn Leu Asn Val Lys Gly
            180                 185                 190

Val Leu Ile Thr Asn Pro Ser Asn Pro Leu Gly Thr Ser Thr Thr Arg
        195                 200                 205

Glu Glu Leu Asp Leu Leu Thr Phe Thr Ser Thr Lys Lys Ile His
    210                 215                 220

Met Val Ser Asp Glu Ile Tyr Ser Gly Thr Val Phe Asp Ser Pro Glu
225                 230                 235                 240

Phe Thr Ser Val Leu Glu Val Ala Lys Asp Lys Asn Met Gly Leu Asp
                245                 250                 255

Gly Lys Ile His Val Val Tyr Ser Leu Ser Lys Asp Leu Gly Leu Pro
            260                 265                 270

Gly Phe Arg Val Gly Leu Ile Tyr Ser Asn Asn Glu Lys Val Val Ser
        275                 280                 285

Ala Ala Thr Lys Met Ser Ser Phe Gly Leu Ile Ser Ser Gln Thr Gln
    290                 295                 300

His Leu Leu Ala Asn Leu Leu Ser Asp Glu Arg Phe Thr Thr Asn Tyr
305                 310                 315                 320

Leu Glu Glu Asn Lys Lys Arg Leu Arg Glu Arg Lys Asp Arg Leu Val
                325                 330                 335

Ser Gly Leu Lys Glu Ala Gly Ile Ser Cys Leu Lys Ser Asn Ala Gly
            340                 345                 350

Leu Phe Cys Trp Val Asp Leu Arg His Leu Leu Lys Ser Asn Thr Phe
        355                 360                 365

Glu Ala Glu His Ser Leu Trp Thr Lys Ile Val Cys Glu Val Gly Leu
    370                 375                 380

Asn Ile Ser Pro Gly Ser Ser Cys His Cys Asp Glu Pro Gly Trp Phe
385                 390                 395                 400

Arg Val Cys Phe Ala Asn Met Ser Asp Gln Thr Met Glu Val Ala Met
                405                 410                 415
```

```
Asp Arg Val Lys Gly Phe Val Asp Asn Asn Gly Gly Lys Gln Lys
            420                 425                 430

Arg Thr Met Trp Asp Thr Arg Arg Ser Leu Ile Asn Lys Trp Val
            435                 440                 445

Ser Lys Leu Ser Ser Val Thr Cys Glu Ser Glu Arg
            450                 455                 460

<210> SEQ ID NO 418
<211> LENGTH: 1383
<212> TYPE: DNA
<213> ORGANISM: Arabidopsis thaliana

<400> SEQUENCE: 418
atgttgtcaa gcaaagttgt tggcgactct catggacaag actcatccta cttccttgga      60
tggcaagaat acgagaagaa tcctttccac gagtcgttta acactagtgg gattgttcaa     120
atgggtcttg ctgaaaacca gctttctttt gacctaatag agaaatggct tgaagagcat     180
ccagaagtct tgggtttgaa gaaaaatgat gagtcggtgt ttagacaatt agctctgttc     240
caagattacc atggcttgcc agcttttcaag gatgccatgg cgaagttcat ggggaaaatc     300
agagagaaca aagtgaaatt cgatacgaac aagatggttc ttacagctgg atcaacctcg     360
gctaacgaga ctctaatgtt ctgtcttgct aatccaggag atgcctttct tatccctgca     420
ccttattatc cagggtttga tagagatctc aaatggagga caggagtaga gattgttcct     480
atccattgcg taagctcaaa tgggtacaag ataaccgagg atgcattaga agatgcctac     540
gaacgagctc tcaaacataa cctaaatgtt aaaggagttc tcataaccaa cccttcaaac     600
ccacttggaa cctctaccac ccgtgaagag cttgatcttc ttctgacctt cacatcaacc     660
aagaaaatcc atatggttag cgatgagatc tactcgggaa cggttttcga ctctcctgag     720
ttcaccagcg ttctagaagt ggctaaggac aagaacatgg gtttagatgg taaaatccat     780
gttgtttaca gcttgtccaa agatctaggc ctccccggat tcgtgttgg cttgatttac     840 tcaaacaatg agaaagtggt gtcagccgcg actaaaatgt cgagttttgg actcatttct     900
tcccaaactc aacatttgct agccaatttg ctgtctgatg aaagattcac gaccaactat     960
ttggaagaga caagaagag gctgagagag agaaaggata ggctggtttc gggtctaaag    1020
gaagcgggta tcagttgttt gaagagtaac gcaggtttgt tctgttgggt tgacttaaga    1080
cacctcttga atccaacac ttttgaggcc gagcattctt tatggacaaa gattgtgtgt    1140
gaagttggtc ttaacatctc tccaggctca tcgtgtcatt gcgatgaacc tggttggttt    1200 agagttttgtt tcgcgaatat gtcggaccaa acgatggagg ttgctatgga ccgtgttaaa    1260
ggttttgttg acaacaataa tggtggtaaa caaaagagaa ccatgtggga tacaaggaga    1320
agatctctta tcaacaaatg ggtctccaag ctttcctctg ttacttgtga atcagaacgt    1380
tga                                                                  1383

<210> SEQ ID NO 419
<211> LENGTH: 524
<212> TYPE: PRT
<213> ORGANISM: Arabidopsis thaliana

<400> SEQUENCE: 419

Met Gln Pro Pro Ala Ser Ala Gly Leu Phe Arg Ser Pro Glu Asn Leu
1               5                   10                  15

Pro Trp Pro Tyr Asn Tyr Met Asp Tyr Leu Val Ala Gly Phe Leu Val
            20                  25                  30
```

-continued

```
Leu Thr Ala Gly Ile Leu Leu Arg Pro Trp Leu Trp Leu Arg Leu Arg
         35                  40                  45

Asn Ser Lys Thr Lys Asp Gly Asp Glu Glu Asp Asn Glu Glu Lys
 50                  55                  60

Lys Lys Gly Met Ile Pro Asn Gly Ser Leu Gly Trp Pro Val Ile Gly
 65                  70                  75                  80

Glu Thr Leu Asn Phe Ile Ala Cys Gly Tyr Ser Ser Arg Pro Val Thr
                 85                  90                  95

Phe Met Asp Lys Arg Lys Ser Leu Tyr Gly Lys Val Phe Lys Thr Asn
                100                 105                 110

Ile Ile Gly Thr Pro Ile Ile Ser Thr Asp Ala Glu Val Asn Lys
                115                 120                 125

Val Val Leu Gln Asn His Gly Asn Thr Phe Val Pro Ala Tyr Pro Lys
130                 135                 140

Ser Ile Thr Glu Leu Leu Gly Glu Asn Ser Ile Leu Ser Ile Asn Gly
145                 150                 155                 160

Pro His Gln Lys Arg Leu His Thr Leu Ile Gly Ala Phe Leu Arg Ser
                165                 170                 175

Pro His Leu Lys Asp Arg Ile Thr Arg Asp Ile Glu Ala Ser Val Val
                180                 185                 190

Leu Thr Leu Ala Ser Trp Ala Gln Leu Pro Leu Val His Val Gln Asp
                195                 200                 205

Glu Ile Lys Lys Met Thr Phe Glu Ile Leu Val Lys Val Leu Met Ser
210                 215                 220

Thr Ser Pro Gly Glu Asp Met Asn Ile Leu Lys Leu Glu Phe Glu Glu
225                 230                 235                 240

Phe Ile Lys Gly Leu Ile Cys Ile Pro Ile Lys Phe Pro Gly Thr Arg
                245                 250                 255

Leu Tyr Lys Ser Leu Lys Ala Lys Glu Arg Leu Ile Lys Met Val Lys
                260                 265                 270

Lys Val Val Glu Glu Arg Gln Val Ala Met Thr Thr Thr Ser Pro Ala
                275                 280                 285

Asn Asp Val Val Asp Val Leu Leu Arg Asp Gly Gly Asp Ser Glu Lys
                290                 295                 300

Gln Ser Gln Pro Ser Asp Phe Val Ser Gly Lys Ile Val Glu Met Met
305                 310                 315                 320

Ile Pro Gly Glu Glu Thr Met Pro Thr Ala Met Thr Leu Ala Val Lys
                325                 330                 335

Phe Leu Ser Asp Asn Pro Val Ala Leu Ala Lys Leu Val Glu Glu Asn
                340                 345                 350

Met Glu Met Lys Arg Arg Lys Leu Glu Leu Gly Glu Glu Tyr Lys Trp
                355                 360                 365

Thr Asp Tyr Met Ser Leu Ser Phe Thr Gln Asn Val Ile Asn Glu Thr
                370                 375                 380

Leu Arg Met Ala Asn Ile Ile Asn Gly Val Trp Arg Lys Ala Leu Lys
385                 390                 395                 400

Asp Val Glu Ile Lys Gly Tyr Leu Ile Pro Lys Gly Trp Cys Val Leu
                405                 410                 415

Ala Ser Phe Ile Ser Val His Met Asp Glu Asp Ile Tyr Asp Asn Pro
                420                 425                 430

Tyr Gln Phe Asp Pro Trp Arg Trp Asp Arg Ile Asn Gly Ser Ala Asn
                435                 440                 445
```

-continued

```
Ser Ser Ile Cys Phe Thr Pro Phe Gly Gly Gln Arg Leu Cys Pro
    450                 455                 460
Gly Leu Glu Leu Ser Lys Leu Glu Ile Ser Ile Phe Leu His His Leu
465                 470                 475                 480
Val Thr Arg Tyr Ser Trp Thr Ala Glu Glu Asp Glu Ile Val Ser Phe
                485                 490                 495
Pro Thr Val Lys Met Lys Arg Arg Leu Pro Ile Arg Val Ala Thr Val
            500                 505                 510
Asp Asp Ser Ala Ser Pro Ile Ser Leu Glu Asp His
            515                 520
```

<210> SEQ ID NO 420
<211> LENGTH: 1999
<212> TYPE: DNA
<213> ORGANISM: Arabidopsis thaliana

<400> SEQUENCE: 420

```
attgagaaaa ccctttaaa attctctatc gatctcatca caaatttgc tatatccaca    60
attcatgtgc ttaggcatat agttattccc aagaaaccgg tttaactgtt tacgtatgca   120
acctccggca agcgcaggac ttttccggtc gccggaaaat ctcccttggc cttataatta   180
catggattat ttggtcgctg gtttcttggt tttgacggcc ggaatacttc tccgtccatg   240
gctctggtta cgtctacgaa actcgaaaac gaaagatgga gatgaagaag aagataatga   300
ggagaagaag aagggaatga ttccaaacgg aagcttaggc tggccggtga tcggagaaac   360
cctaaacttc atcgcttgtg gttattcttc tcggcctgtt accttcatgg acaaacgaaa   420
gtctttatac gggaaagtgt tcaaaacgaa cataataggg acaccaatca taatatcaac   480
cgatgcagag gtgaataaag tggtgctcca aaccatggg aacacatttg tccctgcata   540
ccctaaatca attacggaac tacttggaga aaactctatt ctcagcatca atggacctca   600
tcaaaaaagg cttcacacgc tcattggcgc gttcctcaga tctcctcacc tcaaagaccg   660
gatcactcga gacattgagg cctcggttgt tctcactttg gcgtcttggg ctcaacttcc   720
attggttcat gttcaggatg agatcaaaaa gatgacgttt gagatattag taaaagtgtt   780
gatgagcaca tctcctggtg aagatatgaa cattctcaaa cttgagttcg aagaattcat   840
caaaggtttg atttgtatcc caatcaaatt ccctggcact agactctaca aatccttaaa   900
ggcgaaagag aggttaataa agatggtaaa aaaggttgtg gaggagagac aagtggcgat   960
gacaacgacg tctccggcaa atgacgtggt ggacgtactt ctaagagacg tggtgattc   1020
agagaagcaa tctcaaccgt cagatttcgt cagcggaaag atcgtagaga tgatgatacc  1080
cggagaggaa acaatgccaa cggcgatgac cttggctgtc aaattcttaa gtgacaaccc  1140
cgtcgctcta gccaaactcg tggaggagaa tatgagatg aagaggcgta aattggaatt  1200
gggagaagaa tacaagtgga ccgattatat gtctctctct tttactcaaa atgtgataaa  1260
cgaaacgctt agaatggcta acattattaa cggggtgtgg aggaaagctc tcaaggatgt  1320
agaaattaaa ggttacttaa taccgaaagg atggtgtgta ttggcatcat tcatatcggt  1380
tcacatggat gaagacattt atgataatcc ctatcaattc gatccgtgga gatgggacag  1440
aattaatgga tcggcaaaca gcagtatttg cttcacaccc tttggtggtg ggcaaaggct  1500
atgtcctggt ttagagctgt cgaagctcga aatatccatc tttcttcacc accttgtaac  1560
ccggtacagt tggacggctg aggaagacga gatagtgtca tttccgactg tgaagatgaa  1620
gcggaggctc ccgatccgag tggctactgt agatgatagt gcttctccga tctcacttga  1680
```

-continued

```
agatcattaa tagatcattt caaagaacaa aactgtttgt gcaaagagga agcagagaag    1740
taaacaaatg atcttattaa caaatagtag agaagagaag caaacaagat tggtgggtaa    1800
gacagaaaga gccatacgta cagctagtga tggctcaaag atgagagatt ctaattataa    1860
ttttttttgt ttgtcatgtc aaattataag cgttggttag gttgtcccct tctcttttat    1920
ttatcgtacc aaacgcaagt tgagatatga ttccatatat atggatgata gatatgtata    1980
ttaatatata ccttcttct                                                1999

<210> SEQ ID NO 421
<211> LENGTH: 520
<212> TYPE: PRT
<213> ORGANISM: Arabidopsis thaliana

<400> SEQUENCE: 421

Met Glu Glu Glu Ser Ser Ser Trp Phe Ile Pro Lys Val Leu Val Leu
1               5                   10                  15

Ser Val Ile Leu Ser Leu Val Ile Val Lys Gly Met Ser Leu Leu Trp
            20                  25                  30

Trp Arg Pro Arg Lys Ile Glu Glu His Phe Ser Lys Gln Gly Ile Arg
        35                  40                  45

Gly Pro Pro Tyr His Phe Phe Ile Gly Asn Val Lys Glu Leu Val Gly
    50                  55                  60

Met Met Leu Lys Ala Ser Ser His Pro Met Pro Phe Ser His Asn Ile
65                  70                  75                  80

Leu Pro Arg Val Leu Ser Phe Tyr His His Trp Arg Lys Ile Tyr Gly
                85                  90                  95

Ala Thr Phe Leu Val Trp Phe Gly Pro Thr Phe Arg Leu Thr Val Ala
            100                 105                 110

Asp Pro Asp Leu Ile Arg Glu Ile Phe Ser Lys Ser Glu Phe Tyr Glu
        115                 120                 125

Lys Asn Glu Ala His Pro Leu Val Lys Gln Leu Glu Gly Asp Gly Leu
    130                 135                 140

Leu Ser Leu Lys Gly Glu Lys Trp Ala His His Arg Lys Ile Ile Ser
145                 150                 155                 160

Pro Thr Phe His Met Glu Asn Leu Lys Leu Leu Val Pro Val Val Leu
                165                 170                 175

Lys Ser Val Thr Asp Met Val Asp Lys Trp Ser Asp Lys Leu Ser Glu
            180                 185                 190

Asn Gly Glu Val Glu Val Asp Val Tyr Glu Trp Phe Gln Ile Leu Thr
        195                 200                 205

Glu Asp Val Ile Ser Arg Thr Ala Phe Gly Ser Ser Tyr Glu Asp Gly
    210                 215                 220

Arg Ala Val Phe Arg Leu Gln Ala Gln Gln Met Leu Leu Cys Ala Glu
225                 230                 235                 240

Ala Phe Gln Lys Val Phe Ile Pro Gly Tyr Arg Phe Phe Pro Thr Arg
                245                 250                 255

Gly Asn Leu Lys Ser Trp Lys Leu Asp Lys Glu Ile Arg Lys Ser Leu
            260                 265                 270

Leu Lys Leu Ile Glu Arg Arg Gln Asn Ala Ile Asp Gly Glu Gly
        275                 280                 285

Glu Glu Cys Lys Glu Pro Ala Ala Lys Asp Leu Leu Gly Leu Met Ile
    290                 295                 300

Gln Ala Lys Asn Val Thr Val Gln Asp Ile Val Glu Glu Cys Lys Ser
305                 310                 315                 320
```

```
Phe Phe Phe Ala Gly Lys Gln Thr Thr Ser Asn Leu Leu Thr Trp Thr
                325                 330                 335
Thr Ile Leu Leu Ser Met His Pro Glu Trp Gln Ala Lys Ala Arg Asp
            340                 345                 350
Glu Val Leu Arg Val Cys Gly Ser Arg Asp Val Pro Thr Lys Asp His
        355                 360                 365
Val Val Lys Leu Lys Thr Leu Ser Met Ile Leu Asn Glu Ser Leu Arg
    370                 375                 380
Leu Tyr Pro Pro Ile Val Ala Thr Ile Arg Arg Ala Lys Ser Asp Val
385                 390                 395                 400
Lys Leu Gly Gly Tyr Lys Ile Pro Cys Gly Thr Glu Leu Leu Ile Pro
                405                 410                 415
Ile Ile Ala Val His His Asp Gln Ala Ile Trp Gly Asn Asp Val Asn
            420                 425                 430
Glu Phe Asn Pro Ala Arg Phe Ala Asp Gly Val Pro Arg Ala Ala Lys
        435                 440                 445
His Pro Val Gly Phe Ile Pro Phe Gly Leu Gly Val Arg Thr Cys Ile
    450                 455                 460
Gly Gln Asn Leu Ala Ile Leu Gln Ala Lys Leu Thr Leu Ala Val Met
465                 470                 475                 480
Ile Gln Arg Phe Thr Phe His Leu Ala Pro Thr Tyr Gln His Ala Pro
                485                 490                 495
Thr Val Leu Met Leu Leu Tyr Pro Gln His Gly Ala Pro Ile Thr Phe
            500                 505                 510
Arg Arg Leu Thr Asn His Glu Asp
        515                 520

<210> SEQ ID NO 422
<211> LENGTH: 1563
<212> TYPE: DNA
<213> ORGANISM: Arabidopsis thaliana

<400> SEQUENCE: 422
atggaggaag aaagtagcag ctggttcatt ccaaaggttc ttgttctgtc tgtaatctta      60
agtcttgtaa tagtgaaggg tatgtctctg ttatggtgga gaccaagaaa gattgaagaa     120
catttctcta acaaggaatc gaggtcct ccttatcatt tcttcatcgg aaatgttaaa       180
gaacttgttg aatgatgct taaagcttct tctcatccta tgcctttctc tcacaatatt     240
cttcctagag ttctctcttt ttaccatcac tggagaaaaa tctacggtgc tcatttctg      300 gtttggttcg gtccaacttt ccggttaacg gtagccgatc ctgatttgat cagagagatc    360
ttctctaagt ctgagttcta cgagaagaat gaagctcacc ctttggttaa caacttgaa     420 ggcgatggac tacttagtct caaaggtgaa aaatgggctc atcatcgaaa atcattagc     480 cctactttc atatggagaa tcttaagttg cttgtaccag ttgtgttgaa gagtgtgact    540
gatatggtgg ataaatggtc cgataagtta tcagaaaacg gtgaagttga ggtagatgtc    600
tatgagtggt ttcagatttt gactgaagat gttattagta gaacagcttt tggaagtagc    660
tatgaagatg gtcgagcagt ttttcgactt caagctcaac aaatgcttct ttgtgctgaa    720
gcttttcaaa aagtcttcat tcctggctat agatttttc gacaagagg gaatttgaag     780 tcttggaagt tagacaagga gataaggaag tcgttgttga agctgataga gcggcggaga    840
caaaacgcta tagatggaga aggggaagaa tgtaaggagc cggcggcgaa ggatttgttg    900
ggattaatga ttcaggcaaa gaatgtgacg gttcaggaca ttgtggagga gtgtaaaagc    960
```

-continued

```
tttttcttcg ccgggaaaca gacaacttct aatctgctga cgtggacgac catcttgcta    1020
tccatgcacc cggagtggca ggccaaagca cgtgatgagg tcctcagggt ctgcggctca    1080
cgtgatgtcc ctaccaagga ccatgtcgtt aagcttaaaa cgttgagtat gatcttgaac    1140
gagtctttaa ggttgtatcc accaatagta gctacgattc gacgcgctaa atcggatgtg    1200
aagctaggag ggtacaaaat cccatgtggc acggagcttc taatcccaat catagcggtc    1260
catcatgacc aagccatttg gggtaatgac gtgaacgaat tcaatccagc tcggtttgcg    1320
gatggagtgc cgcgtgctgc caaacacccc gttggattca taccgtttgg cctcggagtt    1380
cgtacatgca ttggtcagaa tcttgctata cttcaggcca aattgacact cgctgtaatg    1440
atccaacgct tcacctttca cttggctcct acttatcagc atgcacctac cgtccttatg    1500
ttgctttatc ctcaacatgg tgcaccaatc accttccgga gattgaccaa tcatgaggat    1560
tga                                                                 1563
```

<210> SEQ ID NO 423
<211> LENGTH: 358
<212> TYPE: PRT
<213> ORGANISM: Arabidopsis thaliana

<400> SEQUENCE: 423

```
Met Pro Ala Met Leu Thr Asp Val Phe Arg Gly His Pro Ile His Leu
1               5                   10                  15

Pro His Ser His Ile Pro Asp Phe Thr Ser Leu Arg Glu Leu Pro Asp
            20                  25                  30

Ser Tyr Lys Trp Thr Pro Lys Asp Asp Leu Leu Phe Ser Ala Ala Pro
        35                  40                  45

Ser Pro Pro Ala Thr Gly Glu Asn Ile Pro Leu Ile Asp Leu Asp His
    50                  55                  60

Pro Asp Ala Thr Asn Gln Ile Gly His Ala Cys Arg Thr Trp Gly Ala
65                  70                  75                  80

Phe Gln Ile Ser Asn His Gly Val Pro Leu Gly Leu Leu Gln Asp Ile
                85                  90                  95

Glu Phe Leu Thr Gly Ser Leu Phe Gly Leu Pro Val Gly Arg Lys Leu
            100                 105                 110

Lys Ser Ala Arg Ser Glu Thr Gly Val Ser Gly Tyr Gly Val Ala Arg
        115                 120                 125

Ile Ala Ser Phe Phe Asn Lys Gln Met Trp Ser Glu Gly Phe Thr Ile
    130                 135                 140

Thr Gly Ser Pro Leu Asn Asp Phe Arg Lys Leu Trp Pro Gln His His
145                 150                 155                 160

Leu Asn Tyr Cys Asp Ile Val Glu Glu Tyr Glu Glu His Met Lys Lys
                165                 170                 175

Leu Ala Ser Lys Leu Met Trp Leu Ala Leu Asn Ser Leu Gly Val Ser
            180                 185                 190

Glu Glu Asp Ile Glu Trp Ala Ser Leu Ser Ser Asp Leu Asn Trp Ala
        195                 200                 205

Gln Ala Ala Leu Gln Leu Asn His Tyr Pro Val Cys Pro Glu Pro Asp
    210                 215                 220

Arg Ala Met Gly Leu Ala Ala His Thr Asp Ser Thr Leu Leu Thr Ile
225                 230                 235                 240

Leu Tyr Gln Asn Asn Thr Ala Gly Leu Gln Val Phe Arg Asp Asp Leu
                245                 250                 255
```

Gly Trp Val Thr Val Pro Pro Phe Pro Gly Ser Leu Val Asn Val
            260                 265                 270

Gly Asp Leu Phe His Ile Leu Ser Asn Gly Leu Phe Lys Ser Val Leu
        275                 280                 285

His Arg Ala Arg Val Asn Gln Thr Arg Ala Arg Leu Ser Val Ala Phe
    290                 295                 300

Leu Trp Gly Pro Gln Ser Asp Ile Lys Ile Ser Pro Val Pro Lys Leu
305                 310                 315                 320

Val Ser Pro Val Glu Ser Pro Leu Tyr Gln Ser Val Thr Trp Lys Glu
                325                 330                 335

Tyr Leu Arg Thr Lys Ala Thr His Phe Asn Lys Ala Leu Ser Met Ile
            340                 345                 350

Arg Asn His Arg Glu Glu
        355

<210> SEQ ID NO 424
<211> LENGTH: 1256
<212> TYPE: DNA
<213> ORGANISM: Arabidopsis thaliana

<400> SEQUENCE: 424

```
atcaccaaac accacacttc tcataagaaa aaaaacacaa acatctatca aatttacaaa      60
gttttaaaac taattaaaaa agagcaagat gcctgctatg ttaacagatg tgtttagagg     120
ccatcccatt cacctcccac actctcacat acctgacttc acatctctcc gggagctccc     180
ggattcttac aagtggaccc ctaaagacga tctcctcttc tccgctgctc cttctcctcc     240
ggccaccggt gaaaacatcc ctctcatcga cctcgaccac ccggacgcga ctaaccaaat     300
cggtcatgca tgtagaactt ggggtgcctt ccaaatctca aaccacgcg tgcctttggg      360
acttctccaa gacattgagt ttctcaccgg tagtctcttc gggctacctg tccaacgcaa     420
gcttaagtct gctcggtcgg agacaggtgt gtccggctac ggcgtcgctc gtatcgcatc     480
tttcttcaat aagcaaatgt ggtccgaagg tttcaccatc actggctcgc tctctcaacga    540
tttccgtaaa ctttggcccc aacatcacct caactactgc gatatcgttg aagagtacga     600
ggaacatatg aaaaagttgg catcgaaatt gatgtggtta gcactaaatt cacttggggt     660
cagcgaagaa gacattgaat gggccagtct cagttcagat ttaaactggg cccaagctgc     720
tctccagcta aatcactacc cggtttgtcc tgaaccggac cgagccatgg gtctagcagc     780
tcataccgac tccaccctcc taaccattct gtaccagaac aataccgccg gtctacaagt     840
atttcgcgat gatcttggtt gggtcaccgt gccaccgttt cctggctcgc tcgtggttaa     900
cgttggtgac ctcttccaca tcctatccaa tggattgttt aaaagcgtgt gcaccgcgc      960
tcgggttaac caaaccagag cccggttatc tgtagcattc ctttgggtc cgcaatctga     1020
tatcaagata tcacctgtac cgaagctggt tagtcccgtt gaatcgcctc tataccaatc    1080
ggtgacatgg aaaagtatc ttcgaacaaa agcaactcac ttcaacaaag ctctttcaat    1140
gattagaaat cacagagaag aatgattaga taataatagt tgtgatctac tagttagttt    1200
gattaataaa ttgttgtaaa tgatttcagc aatatgattt gtttgtcctc aatcat        1256
```

<210> SEQ ID NO 425
<211> LENGTH: 467
<212> TYPE: PRT
<213> ORGANISM: Arabidopsis thaliana

<400> SEQUENCE: 425

```
Met Asp Ile Ser Ala Leu Phe Leu Thr Leu Phe Ala Gly Ser Leu Phe
1               5                   10                  15

Leu Tyr Phe Leu Arg Cys Leu Ile Ser Gln Arg Arg Phe Gly Ser Ser
            20                  25                  30

Lys Leu Pro Leu Pro Pro Gly Thr Met Gly Trp Pro Tyr Val Gly Glu
            35                  40                  45

Thr Phe Gln Leu Tyr Ser Gln Asp Pro Asn Val Phe Phe Gln Ser Lys
    50                  55                  60

Gln Lys Arg Tyr Gly Ser Val Phe Lys Thr His Val Leu Gly Cys Pro
65                  70                  75                  80

Cys Val Met Ile Ser Ser Pro Glu Ala Ala Lys Phe Val Leu Val Thr
                85                  90                  95

Lys Ser His Leu Phe Lys Pro Thr Phe Pro Ala Ser Lys Glu Arg Met
                100                 105                 110

Leu Gly Lys Gln Ala Ile Phe Phe His Gln Gly Asp Tyr His Ala Lys
            115                 120                 125

Leu Arg Lys Leu Val Leu Arg Ala Phe Met Pro Glu Ser Ile Arg Asn
    130                 135                 140

Met Val Pro Asp Ile Glu Ser Ile Ala Gln Asp Ser Leu Arg Ser Trp
145                 150                 155                 160

Glu Gly Thr Met Ile Asn Thr Tyr Gln Glu Met Lys Thr Tyr Thr Phe
                165                 170                 175

Asn Val Ala Leu Leu Ser Ile Phe Gly Lys Asp Glu Val Leu Tyr Arg
            180                 185                 190

Glu Asp Leu Lys Arg Cys Tyr Tyr Ile Leu Glu Lys Gly Tyr Asn Ser
    195                 200                 205

Met Pro Val Asn Leu Pro Gly Thr Leu Phe His Lys Ser Met Lys Ala
210                 215                 220

Arg Lys Glu Leu Ser Gln Ile Leu Ala Arg Ile Leu Ser Glu Arg Arg
225                 230                 235                 240

Gln Asn Gly Ser Ser His Asn Asp Leu Leu Gly Ser Phe Met Gly Asp
                245                 250                 255

Lys Glu Glu Leu Thr Asp Glu Gln Ile Ala Asp Asn Ile Ile Gly Val
            260                 265                 270

Ile Phe Ala Ala Arg Asp Thr Thr Ala Ser Val Met Ser Trp Ile Leu
    275                 280                 285

Lys Tyr Leu Ala Glu Asn Pro Asn Val Leu Glu Ala Val Thr Glu Glu
290                 295                 300

Gln Met Ala Ile Arg Lys Asp Lys Glu Glu Gly Glu Ser Leu Thr Trp
305                 310                 315                 320

Gly Asp Thr Lys Lys Met Pro Leu Thr Ser Arg Val Ile Gln Glu Thr
                325                 330                 335

Leu Arg Val Ala Ser Ile Leu Ser Phe Thr Phe Arg Glu Ala Val Glu
            340                 345                 350

Asp Val Glu Tyr Glu Gly Tyr Leu Ile Pro Lys Gly Trp Lys Val Leu
    355                 360                 365

Pro Leu Phe Arg Asn Ile His His Ser Ala Asp Ile Phe Ser Asn Pro
370                 375                 380

Gly Lys Phe Asp Pro Ser Arg Phe Glu Val Ala Pro Lys Pro Asn Thr
385                 390                 395                 400

Phe Met Pro Phe Gly Asn Gly Thr His Ser Cys Pro Gly Asn Glu Leu
                405                 410                 415

Ala Lys Leu Glu Met Ser Ile Met Ile His His Leu Thr Thr Lys Tyr
```

|  |  | 420 |  |  | 425 |  |  | 430 |  |  |  |
|---|---|---|---|---|---|---|---|---|---|---|---|
| Ser | Trp | Ser | Ile | Val | Gly | Ala | Ser | Asp | Gly | Ile | Gln | Tyr | Gly | Pro | Phe |
|  |  |  | 435 |  |  |  |  | 440 |  |  |  |  | 445 |  |  |

Ala Leu Pro Gln Asn Gly Leu Pro Ile Val Leu Ala Arg Lys Pro Glu
　　450　　　　　　　455　　　　　　　460

Ile Glu Val
465

```
<210> SEQ ID NO 426
<211> LENGTH: 1989
<212> TYPE: DNA
<213> ORGANISM: Arabidopsis thaliana
<220> FEATURE:
<221> NAME/KEY: misc_feature
<222> LOCATION: (1867)..(1867)
<223> OTHER INFORMATION: n is a, c, g, or t

<400> SEQUENCE: 426
```

| | | | | |
|---|---|---|---|---|
| attacattaa | aactccaaaa | aattcatttt | tgttttcttt | tagagttcac aagttcttcg | 60 |
| ttgttcagct | actcccactg | tcataacacg | aagtgggttt | ttttctgatc aaagaacaaa | 120 |
| aacaaaaatg | gatatctccg | ccttgtttct | cactctcttc | gccggaagtc tcttccttta | 180 |
| ctttctccgg | tgtctaatct | ctcagcgccg | ctttggatct | ccaaactcc cactccctcc | 240 |
| gggaacaatg | ggttggcctt | acgtcggaga | aactttccag | ctttactctc aagaccctaa | 300 |
| tgtcttttc | caatcaaaac | agaaaaggta | tggatcggtg | tttaagactc atgtattggg | 360 |
| atgtccatgt | gtgatgatct | cgagtccaga | ggctgctaag | ttcgtgctgg tgacgaaatc | 420 |
| tcatctcttt | aaaccaactt | ttccggcgag | taaagagagg | atgttgggga acaagccat | 480 |
| cttcttccac | cagggtgatt | atcacgctaa | actcaggaag | cttgttcttc gtgcttttat | 540 |
| gcctgaatct | atcagaaaca | tggttcctga | tattgaatcc | atcgctcaag actctctccg | 600 |
| aagtgggag | ggaacaatga | tcaacactta | ccaagaaatg | aaaacataca ccttcaacgt | 660 |
| tgcgttgcta | tcgatcttcg | gaaaagacga | ggttttatac | agagaagatc taaaacgatg | 720 |
| ctactacatt | ctcgagaaag | gttacaattc | gatgccagtg | aatctccctg gaacactttt | 780 |
| ccacaaatca | atgaaagctc | ggaaggaact | ctcacagatc | ctcgctagaa tcttatcaga | 840 |
| gagaagacag | aacggttcct | cacacaacga | tcttctcgga | tcattcatgg agacaaaga | 900 |
| agagctaacc | gacgaacaga | tcgccgacaa | cataatcgga | gtaatcttcg ccgctagaga | 960 |
| cacgacggcg | agtgtgatgt | cgtggatcct | caagtaccta | gccgagaatc caacgttct | 1020 |
| agaagccgtt | actgaagaac | aaatggcaat | aaggaaagac | aaagaagaag agagtctct | 1080 |
| aacttgggga | gatacaaaga | agatgccatt | aacttcaaga | gttattcaag aaacattaag | 1140 |
| agtcgcttca | atcttatctt | tcacattcag | agaagctgtc | gaagatgtcg aatacgaagg | 1200 |
| atatttgata | cctaaaggat | ggaaagtgtt | acccctattc | agaaacattc atcatagtgc | 1260 |
| tgatattttt | tctaatccgg | ggaaatttga | tccatcaaga | ttcgaggtgg ctccaaaacc | 1320 |
| caatacgttc | atgccatttg | gcaatggaac | ccactcgtgt | cctggaaatg aattagccaa | 1380 |
| gcttgagatg | tctattatga | ttcatcatct | caccaccaag | tacagttggt caattgttgg | 1440 |
| agcgagcgac | gggattcagt | atgggccatt | cgcgcttccc | caaaacggac tgcccattgt | 1500 |
| gctggcccgg | aagccggaga | tcgaagtgta | gaatgacaga | attgccttta gcttttctat | 1560 |
| atttggaaag | aggagactag | agaagaagaa | taaataattc | tttctttctt tatcaagaaa | 1620 |
| aaaagataga | gatggaggaa | aacaggttca | agattttggt | agaaaatat tccccaaatg | 1680 |

```
ggatcaagga gaaaacacca agtgtacaaa aacttcaatt ttattttttct tgactttctt    1740 tagtttttt  tttttgagtt tttaatttta atttaagatg ggaaaagcta gtaattgaat     1800
ttaaaaaaac aggggaaaat gttagtacaa gtctctcatg tattttttt  ttgttttttcc    1860 tgaaaaatc  ttatggttat gttataacta tttcctcctg gattgagact tcccttgttt     1920
tttgaataaa ttttttttgt tataaaaaaa aaaaaaaaa aaaaaaaaa aaaaaaaaa        1980 aaaaaaaaa                                                             1989
```

<210> SEQ ID NO 427
<211> LENGTH: 482
<212> TYPE: PRT
<213> ORGANISM: Arabidopsis thaliana

<400> SEQUENCE: 427

```
Met Gln Ile Ser Ser Ser Ser Ser Asn Phe Phe Ser Leu Tyr
1               5                   10                  15

Ala Asp Glu Pro Ala Leu Ile Thr Leu Thr Ile Val Val Val Val
            20                  25                  30

Val Leu Leu Phe Lys Trp Trp Leu His Trp Lys Glu Gln Arg Leu Arg
        35                  40                  45

Leu Pro Pro Gly Ser Met Gly Leu Pro Tyr Ile Gly Glu Thr Leu Arg
    50                  55                  60

Leu Tyr Thr Glu Asn Pro Asn Ser Phe Phe Ala Thr Arg Gln Asn Lys
65                  70                  75                  80

Tyr Gly Asp Ile Phe Lys Thr His Ile Leu Gly Cys Pro Cys Val Met
                85                  90                  95

Ile Ser Ser Pro Glu Ala Ala Arg Met Val Leu Val Ser Lys Ala His
            100                 105                 110

Leu Phe Lys Pro Thr Tyr Pro Pro Ser Lys Glu Arg Met Ile Gly Pro
        115                 120                 125

Glu Ala Leu Phe Phe His Gln Gly Pro Tyr His Ser Thr Leu Lys Arg
    130                 135                 140

Leu Val Gln Ser Ser Phe Met Pro Ser Ala Leu Arg Pro Thr Val Ser
145                 150                 155                 160

His Ile Glu Leu Leu Val Leu Gln Thr Leu Ser Ser Trp Thr Ser Gln
                165                 170                 175

Lys Ser Ile Asn Thr Leu Glu Tyr Met Lys Arg Tyr Ala Phe Asp Val
            180                 185                 190

Ala Ile Met Ser Ala Phe Gly Asp Lys Glu Glu Pro Thr Thr Ile Asp
        195                 200                 205

Val Ile Lys Leu Leu Tyr Gln Arg Leu Glu Arg Gly Tyr Asn Ser Met
    210                 215                 220

Pro Leu Asp Leu Pro Gly Thr Leu Phe His Lys Ser Met Lys Ala Arg
225                 230                 235                 240

Ile Glu Leu Ser Glu Glu Leu Arg Lys Val Ile Glu Lys Arg Arg Glu
                245                 250                 255

Asn Gly Arg Glu Glu Gly Gly Leu Leu Gly Val Leu Leu Gly Ala Lys
            260                 265                 270

Asp Gln Lys Arg Asn Gly Leu Ser Asp Ser Gln Ile Ala Asp Asn Ile
        275                 280                 285

Ile Gly Val Ile Phe Ala Ala Thr Asp Thr Thr Ala Ser Val Leu Thr
    290                 295                 300

Trp Leu Leu Lys Tyr Leu His Asp His Pro Asn Leu Leu Gln Glu Val
305                 310                 315                 320
```

Ser Arg Glu Gln Phe Ser Ile Arg Gln Lys Ile Lys Glu Asn Arg
            325                 330                 335

Arg Ile Ser Trp Glu Asp Thr Arg Lys Met Pro Leu Thr Thr Arg Val
        340                 345                 350

Ile Gln Glu Thr Leu Arg Ala Ala Ser Val Leu Ser Phe Thr Phe Arg
            355                 360                 365

Glu Ala Val Gln Asp Val Glu Tyr Asp Gly Tyr Leu Ile Pro Lys Gly
        370                 375                 380

Trp Lys Val Leu Pro Leu Phe Arg Arg Ile His His Ser Ser Glu Phe
385                 390                 395                 400

Phe Pro Asp Pro Glu Lys Phe Asp Pro Ser Arg Phe Glu Val Ala Pro
                405                 410                 415

Lys Pro Tyr Thr Tyr Met Pro Phe Gly Asn Gly Val His Ser Cys Pro
            420                 425                 430

Gly Ser Glu Leu Ala Lys Leu Glu Met Leu Ile Leu Leu His His Leu
        435                 440                 445

Thr Thr Ser Phe Arg Trp Glu Val Ile Gly Asp Glu Glu Gly Ile Gln
    450                 455                 460

Tyr Gly Pro Phe Pro Val Pro Lys Lys Gly Leu Pro Ile Arg Val Thr
465                 470                 475                 480

Pro Ile

<210> SEQ ID NO 428
<211> LENGTH: 1449
<212> TYPE: DNA
<213> ORGANISM: Arabidopsis thaliana

<400> SEQUENCE: 428
atgcaaatct catcttcatc gtcttcaaat ttcttctctt ctctttatgc tgatgaaccg      60
gcactaatca cattaacaat tgttgtagta gtagtagtgt tactatttaa atggtggttg     120
cactggaaag agcaaagact acggctacct cctggctcca tggggttgcc ttacatcgga     180
gagacactcc gcctctacac agaaaatccc aattccttct tcgccactcg ccaaaacaag     240 tacgggata tattcaagac gcacatatta ggatgtccat gtgtgatgat aagtagtcca     300
gaggcggctc gaatggtgtt agtgagcaaa gctcacttgt tcaagccaac ttatcctcca     360
agcaaagagc gtatgattgg accagaggct cttttcttcc accaaggtcc ataccattct     420
acccttaagc ggctggtcca gtcttctttc atgccttctg ctctcagacc aaccgtctct     480
cacatcgagc tccttgtcct ccaaacccctt tcctcttgga cgtcccaaaa gtccatcaac     540
accctcgaat acatgaaacg atatgcattc gatgtggcga tcatgtcagc gttcggggac     600
aaagaggagc ccactacgat tgatgttatt aagcttctct atcaacgtct cgaaaggggt     660
tacaactcca tgcctctcga cctaccgggc acacttttttc ataagtccat gaaggcaaga     720
atagaattaa gcgaggaact aaggaaagta atagagaaga gaaagagaa tgggagagaa     780 gaaggaggac tattgggagt acttctggga gcaaaggatc aaaaacgcaa cggcttaagt     840
gattcacaga ttgctgacaa catcatcggt gttatattcg ccgccaccga caccaccgct     900
tctgtcttaa cttggcttct caagtactta cacgaccacc caatctcct caagaagtc     960 tccagggagc aattcagcat cgacagaaa ataaaaaag aaaaccgaag aatctcatgg    1020
gaagatacaa gaaaaatgcc actgaccact agggtgatac aagagacact aagagcagca    1080
agtgtactgt cctttacatt tagagaagca gtacaagacg tcgaatatga tggctacttg    1140

-continued

```
atcccaaagg gttggaaggt tcttcctctt tccggcgaa tccatcactc ctccgaattc    1200
ttccccgatc ctgaaaaatt cgatccttct agattcgagg tggcaccaaa accttacacg    1260
tacatgccat tcggaaatgg agtgcactca tgtccaggaa gtgagctggc taaacttgag    1320
atgcttatcc tccttcacca cctcactact tccttcagat gggaagtgat tggagatgaa    1380
gaaggtatac agtatggtcc tttccctgta cccaagaagg gtttaccaat aagagtaacc    1440
ccgatttaa                                                            1449
```

```
<210> SEQ ID NO 429
<211> LENGTH: 463
<212> TYPE: PRT
<213> ORGANISM: Arabidopsis thaliana

<400> SEQUENCE: 429
```

```
Met Asp Phe Ser Gly Leu Phe Leu Thr Leu Ser Ala Ala Ala Leu Phe
1               5                   10                  15

Leu Cys Leu Leu Arg Phe Ile Ala Gly Val Arg Arg Ser Ser Ser Thr
            20                  25                  30

Lys Leu Pro Leu Pro Pro Gly Thr Met Gly Tyr Pro Tyr Val Gly Glu
        35                  40                  45

Thr Phe Gln Leu Tyr Ser Gln Asp Pro Asn Val Phe Phe Ala Ala Lys
    50                  55                  60

Gln Arg Arg Tyr Gly Ser Val Phe Lys Thr His Val Leu Gly Cys Pro
65                  70                  75                  80

Cys Val Met Ile Ser Ser Pro Glu Ala Ala Lys Phe Val Leu Val Thr
                85                  90                  95

Lys Ser His Leu Phe Lys Pro Thr Phe Pro Ala Ser Lys Glu Arg Met
            100                 105                 110

Leu Gly Lys Gln Ala Ile Phe Phe His Gln Gly Asp Tyr His Ser Lys
        115                 120                 125

Leu Arg Lys Leu Val Leu Arg Ala Phe Met Pro Asp Ala Ile Arg Asn
    130                 135                 140

Met Val Pro His Ile Glu Ser Ile Ala Gln Glu Ser Leu Asn Ser Trp
145                 150                 155                 160

Asp Gly Thr Gln Leu Asn Thr Tyr Gln Glu Met Lys Thr Tyr Thr Phe
                165                 170                 175

Asn Val Ala Leu Ile Ser Ile Leu Gly Lys Asp Glu Val Tyr Tyr Arg
            180                 185                 190

Glu Asp Leu Lys Arg Cys Tyr Tyr Ile Leu Glu Lys Gly Tyr Asn Ser
        195                 200                 205

Met Pro Ile Asn Leu Pro Gly Thr Leu Phe His Lys Ala Met Lys Ala
    210                 215                 220

Arg Lys Glu Leu Ala Gln Ile Leu Ala Asn Ile Leu Ser Lys Arg Arg
225                 230                 235                 240

Gln Asn Pro Ser Ser His Thr Asp Leu Leu Gly Ser Phe Met Glu Asp
                245                 250                 255

Lys Ala Gly Leu Thr Asp Glu Gln Ile Ala Asp Asn Ile Ile Gly Val
            260                 265                 270

Ile Phe Ala Ala Arg Asp Thr Thr Ala Ser Val Leu Thr Trp Ile Leu
        275                 280                 285

Lys Tyr Leu Ala Asp Asn Pro Thr Val Leu Glu Ala Val Thr Glu Glu
    290                 295                 300

Gln Met Ala Ile Arg Lys Asp Lys Lys Glu Gly Glu Ser Leu Thr Trp
305                 310                 315                 320
```

Glu Asp Thr Lys Lys Met Pro Leu Thr Tyr Arg Val Ile Gln Glu Thr
                325                 330                 335

Leu Arg Ala Ala Thr Ile Leu Ser Phe Thr Phe Arg Glu Ala Val Glu
            340                 345                 350

Asp Val Glu Tyr Glu Gly Tyr Leu Ile Pro Lys Gly Trp Lys Val Leu
        355                 360                 365

Pro Leu Phe Arg Asn Ile His His Asn Ala Asp Ile Phe Ser Asp Pro
    370                 375                 380

Gly Lys Phe Asp Pro Ser Arg Phe Glu Val Ala Pro Lys Pro Asn Thr
385                 390                 395                 400

Phe Met Pro Phe Gly Ser Gly Ile His Ser Cys Pro Gly Asn Glu Leu
                405                 410                 415

Ala Lys Leu Glu Ile Ser Val Leu Ile His His Leu Thr Thr Lys Tyr
            420                 425                 430

Arg Trp Ser Ile Val Gly Pro Ser Asp Gly Ile Gln Tyr Gly Pro Phe
        435                 440                 445

Ala Leu Pro Gln Asn Gly Leu Pro Ile Ala Leu Glu Arg Lys Pro
    450                 455                 460

<210> SEQ ID NO 430
<211> LENGTH: 1814
<212> TYPE: DNA
<213> ORGANISM: Arabidopsis thaliana

<400> SEQUENCE: 430
caaaaaccaa tccattagag agagaactca caaaacatac ttcgaattcc cattgtttaa      60
aagacgaaga taatggattt ctccggtttg tttctcactc tctccgcggc ggctctgttt     120
ctctgtttac tccgatttat cgccggagtc cgccgtagct cctccacgaa actccctctt     180
cctccgggaa caatgggtta tccttacgtc ggcgaaacat ccaactttta ctcacaagac     240
cctaatgtgt tctttgcagc aaaacagaga agatacggat cggtgttcaa gactcatgta     300
ttgggatgtc catgtgtgat gatctcgagc cctgaagcag cgaaattcgt attggttaca     360
aagtctcatt tgtttaaacc gacttttccg gccagtaaag agaggatgct tggaaaacaa     420
gccatcttct tccatcaagg agattatcat ccaaacttta gaagcttgtg tttaagagct     480
ttcatgcctg atgcaatcag aaacatggtc cctcacattg aatcaattgc tcaagaatca     540
ctcaattctt gggatggaac tcaactcaac acttaccagg aaatgaaaac atacactttc     600
aatgttgcgt taatctcaat actcggcaaa gacgaagttt attaccgaga gatctaaaa      660 cgatgctact acattctaga gaaaggttac aattcgatgc cgattaatct tccaggaaca     720
ttattccaca aagccatgaa agctcgcaag gagctagctc aaatcctcgc taacatctta     780
tccaaaagaa gacaaaaccc atcatcacac acagatctcc tcggatcatt catggaagac     840
aaagcaggat taaccgacga acaaatcgcc gataacatca tcggagtaat cttcgccgca     900
agagacacga cggcgagtgt tctgacgtgg atcctcaagt acttagctga taatccaact     960
gttctagaag ctgtcactga gagcaaatg gcaataagga agataaaaa agaaggagag     1020 agtctcactt gggaagatac aaagaagatg ccattaactt atagagtaat ccaagagaca    1080
ttaagagctg ctacaatctt atctttcaca tttagagaag ctgtcgaaga tgtcgaatac    1140
gaaggatatt tgataccaaa gggatggaaa gtactgccac tattcagaaa tattcatcac    1200
aatgctgata tattttcgga tccggggaaa ttcgatccgt cgagattcga agttgcgccg    1260
aaaccgaata cattcatgcc ttttggtagt gggattcatt cttgtccagg caatgagtta    1320

```
gctaaacttg aaatctctgt tctaatccat catctcacca ctaagtacag atggtcaatc    1380
gtagggccta gcgatggaat tcagtatggg ccgttcgctc ttcctcagaa tggattgcct    1440
attgccttgg aacgaaaacc atagatgaat tacgagaata ccatttacct ttcttaaatt    1500
agaaagtgag gaattttttt tcttatttaa gaggaaaatc taattctttt ttataataga    1560
aatgaaaaga agtagaaga aaaaaatccc aagtgggacc ccccaagtgt atataagttt     1620
tagtttataa aatgtagaga attaaatttt cggagaaaaa agagaattag ttatataaat    1680
gttccatgtg tatgtaactt ggttcatgcc tctatatctt tattttttgta attttctcaa   1740 attgtaaatt cctttattac gaatgtaatg actgatggaa tgctcataga gaatttcaga   1800
aaaaaaaaaa aaaa                                                       1814
```

<210> SEQ ID NO 431
<211> LENGTH: 468
<212> TYPE: PRT
<213> ORGANISM: Arabidopsis thaliana

<400> SEQUENCE: 431

```
Met Ala Glu Ile Trp Phe Leu Val Val Pro Ile Leu Ile Leu Cys Leu
1               5                   10                  15

Leu Leu Val Arg Val Ile Val Ser Lys Lys Lys Asn Ser Arg Gly
            20                  25                  30

Lys Leu Pro Pro Gly Ser Met Gly Trp Pro Tyr Leu Gly Glu Thr Leu
        35                  40                  45

Gln Leu Tyr Ser Gln Asn Pro Asn Val Phe Phe Thr Ser Lys Gln Lys
    50                  55                  60

Arg Tyr Gly Glu Ile Phe Lys Thr Arg Ile Leu Gly Tyr Pro Cys Val
65                  70                  75                  80

Met Leu Ala Ser Pro Glu Ala Ala Arg Phe Val Leu Val Thr His Ala
                85                  90                  95

His Met Phe Lys Pro Thr Tyr Pro Arg Ser Lys Glu Lys Leu Ile Gly
            100                 105                 110

Pro Ser Ala Leu Phe Phe His Gln Gly Asp Tyr His Ser His Ile Arg
        115                 120                 125

Lys Leu Val Gln Ser Ser Phe Tyr Pro Glu Thr Ile Arg Lys Leu Ile
    130                 135                 140

Pro Asp Ile Glu His Ile Ala Leu Ser Ser Leu Gln Ser Trp Ala Asn
145                 150                 155                 160

Met Pro Ile Val Ser Thr Tyr Gln Glu Met Lys Lys Phe Ala Phe Asp
                165                 170                 175

Val Gly Ile Leu Ala Ile Phe Gly His Leu Glu Ser Ser Tyr Lys Glu
            180                 185                 190

Ile Leu Lys His Asn Tyr Asn Ile Val Asp Lys Gly Tyr Asn Ser Phe
        195                 200                 205

Pro Met Ser Leu Pro Gly Thr Ser Tyr His Lys Ala Leu Met Ala Arg
    210                 215                 220

Lys Gln Leu Lys Thr Ile Val Ser Glu Ile Ile Cys Glu Arg Arg Glu
225                 230                 235                 240

Lys Arg Ala Leu Gln Thr Asp Phe Leu Gly His Leu Leu Asn Phe Lys
                245                 250                 255

Asn Glu Lys Gly Arg Val Leu Thr Gln Glu Gln Ile Ala Asp Asn Ile
            260                 265                 270

Ile Gly Val Leu Phe Ala Ala Gln Asp Thr Thr Ala Ser Cys Leu Thr
```

```
                275                 280                 285
Trp Ile Leu Lys Tyr Leu His Asp Asp Gln Lys Leu Leu Glu Ala Val
    290                 295                 300
Lys Ala Glu Gln Lys Ala Ile Tyr Glu Glu Asn Ser Arg Glu Lys Lys
305                 310                 315                 320
Pro Leu Thr Trp Arg Gln Thr Arg Asn Met Pro Leu Thr His Lys Val
                325                 330                 335
Ile Val Glu Ser Leu Arg Met Ala Ser Ile Ile Ser Phe Thr Phe Arg
            340                 345                 350
Glu Ala Val Val Asp Val Glu Tyr Lys Gly Tyr Leu Ile Pro Lys Gly
            355                 360                 365
Trp Lys Val Met Pro Leu Phe Arg Asn Ile His His Asn Pro Lys Tyr
        370                 375                 380
Phe Ser Asn Pro Glu Val Phe Asp Pro Ser Arg Phe Glu Val Asn Pro
385                 390                 395                 400
Lys Pro Asn Thr Phe Met Pro Phe Gly Ser Gly Val His Ala Cys Pro
                405                 410                 415
Gly Asn Glu Leu Ala Lys Leu Gln Ile Leu Ile Phe Leu His His Leu
            420                 425                 430
Val Ser Asn Phe Arg Trp Glu Val Lys Gly Gly Glu Lys Gly Ile Gln
            435                 440                 445
Tyr Ser Pro Phe Pro Ile Pro Gln Asn Gly Leu Pro Ala Thr Phe Arg
    450                 455                 460
Arg His Ser Leu
465
```

<210> SEQ ID NO 432
<211> LENGTH: 1685
<212> TYPE: DNA
<213> ORGANISM: Arabidopsis thaliana

<400> SEQUENCE: 432

```
gtatgttttt gttccctatt atatcttcta gcttctttct tcctcttctt ccttaaaaat    60
tcatcctcca aaacattcta tcatcaacga aacatttcat attaaattaa ataataatcg   120
atggctgaaa tttggttctt ggttgtacca atcctcatct tatgcttgct tttggtaaga   180
gtgattgttt caagaagaa aaagaacagt agaggtaagc ttcctcctgg ttccatggga   240
tggccttact taggagagac tctacaactc tattcacaaa accccaatgt tttcttcacc   300
tccaagcaaa agagatatgg agagatattc aaaacccgaa tcctcggcta tccatgcgtg   360
atgttggcta gccctgaggc tgcgaggttt gtacttgtga ctcatgccca tatgttcaaa   420
ccaacttatc cgagaagcaa agagaagctg ataggaccct ctgcactctt tttccaccaa   480
ggagattatc attcccatat aaggaaactt gttcaatcct ctttctaccc tgaaaccatc   540
cgtaaactca tccctgatat cgagcacatt gcccttttctt ccttacaatc ttgggccaat   600
atgccgattg tctccaccta ccaggagatg aagaagttcg cctttgatgt gggtattcta   660
gccatatttg acatttgga gagttcttac aaagagatct tgaaacataa ctacaatatt   720
gtggacaaag ctacaactc tttccccatg agtctccccg aacatctta tcacaaagct   780
ctcatggcga gaaagcagct aaagacgata gtaagcgaga ttatatgcga agaagagag   840
aaaagggcct tgcaaacgga ctttcttggt catctactca acttcaagaa cgaaaaggt   900
cgtgtgctaa cccaagaaca gattgcagac aacatcatcg gagtcctttt cgccgcacag   960
gacacgacag ctagttgctt aacttggatt cttaagtact acatgatga tcagaaactt  1020
```

-continued

```
ctagaagctg ttaaggctga gcaaaaggct atatatgaag aaaacagtag agagaagaaa      1080
cctttaacat ggagacaaac gaggaatatg ccactgacac ataaggttat agttgaaagc      1140
ttgaggatgg caagcatcat atccttcaca ttcagagaag cagtggttga tgttgaatat      1200
aagggatatt tgatacctaa gggatggaaa gtgatgccac tgtttcggaa tattcatcac      1260
aatccgaaat attttttcaaa ccctgaggtt ttcgacccat ctagattcga ggtaaatccg      1320
aagccgaata cattcatgcc ttttggaagt ggagttcatg cttgtcccgg aacgaactc       1380 gccaagttac aaattcttat atttctccac catttagttt ccaatttccg atgggaagtg      1440
aagggaggag agaaaggaat acagtacagt ccatttccaa tacctcaaaa cggtcttccc      1500
gctacatttc gtcgacattc tctttagttc cttaaacctt tgtagtaatc tttgttgtag      1560
ttagccaaat ctaatccaaa ttcgatataa aaaatcccct ttctattttt ttttaaaatc      1620
attgttgtag tcttgagggg gtttaacatg taacaactat gatgaagtaa aatgtcgatt      1680
ccggt                                                                  1685
```

<210> SEQ ID NO 433
<211> LENGTH: 904
<212> TYPE: PRT
<213> ORGANISM: Homo sapiens

<400> SEQUENCE: 433

```
Met Ala Gly Asn Val Lys Lys Ser Ser Gly Ala Gly Gly Gly Thr Gly
1               5                   10                  15

Ser Gly Gly Ser Gly Ser Gly Gly Leu Ile Gly Leu Met Lys Asp Ala
            20                  25                  30

Phe Gln Pro His His His His His His Leu Ser Pro His Pro Pro
        35                  40                  45

Gly Thr Val Asp Lys Lys Met Val Glu Lys Cys Trp Lys Leu Met Asp
    50                  55                  60

Lys Val Val Arg Leu Cys Gln Asn Pro Lys Leu Ala Leu Lys Asn Ser
65                  70                  75                  80

Pro Pro Tyr Ile Leu Asp Leu Leu Pro Asp Thr Tyr Gln His Leu Arg
                85                  90                  95

Thr Ile Leu Ser Arg Tyr Glu Gly Lys Met Glu Thr Leu Gly Glu Asn
            100                 105                 110

Glu Tyr Phe Arg Val Phe Met Glu Asn Leu Met Lys Lys Thr Lys Gln
        115                 120                 125

Thr Ile Ser Leu Phe Lys Glu Gly Lys Glu Arg Met Tyr Glu Glu Asn
    130                 135                 140

Ser Gln Pro Arg Arg Asn Leu Thr Lys Leu Ser Leu Ile Phe Ser Met
145                 150                 155                 160

Leu Ala Glu Leu Lys Gly Ile Phe Pro Ser Gly Leu Phe Gln Gly Asp
                165                 170                 175

Thr Phe Arg Ile Thr Lys Ala Asp Ala Ala Glu Phe Trp Arg Lys Ala
            180                 185                 190

Phe Gly Glu Lys Thr Ile Val Pro Trp Lys Ser Phe Arg Gln Ala Leu
        195                 200                 205

His Glu Val His Pro Ile Ser Ser Gly Leu Glu Ala Met Ala Leu Lys
    210                 215                 220

Ser Thr Ile Asp Leu Thr Cys Asn Asp Tyr Ile Ser Val Phe Glu Phe
225                 230                 235                 240

Asp Ile Phe Thr Arg Leu Phe Gln Pro Trp Ser Ser Leu Leu Arg Asn
```

-continued

```
                245                 250                 255
Trp Asn Ser Leu Ala Val Thr His Pro Gly Tyr Met Ala Phe Leu Thr
            260                 265                 270

Tyr Asp Glu Val Lys Ala Arg Leu Gln Lys Phe Ile His Lys Pro Gly
        275                 280                 285

Ser Tyr Ile Phe Arg Leu Ser Cys Thr Arg Leu Gly Gln Trp Ala Ile
    290                 295                 300

Gly Tyr Val Thr Ala Asp Gly Asn Ile Leu Gln Thr Ile Pro His Asn
305                 310                 315                 320

Lys Pro Leu Phe Gln Ala Leu Ile Asp Gly Phe Arg Glu Gly Phe Tyr
                325                 330                 335

Leu Phe Pro Asp Gly Arg Asn Gln Asn Pro Asp Leu Thr Gly Leu Cys
            340                 345                 350

Glu Pro Thr Pro Gln Asp His Ile Lys Val Thr Gln Glu Gln Tyr Glu
        355                 360                 365

Leu Tyr Cys Glu Met Gly Ser Thr Phe Gln Leu Cys Lys Ile Cys Ala
    370                 375                 380

Glu Asn Asp Lys Asp Val Lys Ile Glu Pro Cys Gly His Leu Met Cys
385                 390                 395                 400

Thr Ser Cys Leu Thr Ser Trp Gln Glu Ser Glu Gly Gln Gly Cys Pro
                405                 410                 415

Phe Cys Arg Cys Glu Ile Lys Gly Thr Glu Pro Ile Val Val Asp Pro
            420                 425                 430

Phe Asp Pro Arg Gly Ser Gly Ser Leu Leu Arg Gln Gly Ala Glu Gly
        435                 440                 445

Ala Pro Ser Pro Asn Tyr Asp Asp Asp Asp Glu Arg Ala Asp Asp
    450                 455                 460

Thr Leu Phe Met Met Lys Glu Leu Ala Gly Ala Lys Val Glu Arg Pro
465                 470                 475                 480

Pro Ser Pro Phe Ser Met Ala Pro Gln Ala Ser Leu Pro Pro Val Pro
                485                 490                 495

Pro Arg Leu Asp Leu Leu Pro Gln Arg Val Cys Val Pro Ser Ser Ala
            500                 505                 510

Ser Ala Leu Gly Thr Ala Ser Lys Ala Ala Ser Gly Ser Leu His Lys
        515                 520                 525

Asp Lys Pro Leu Pro Val Pro Pro Thr Leu Arg Asp Leu Pro Pro Pro
    530                 535                 540

Pro Pro Pro Asp Arg Pro Tyr Ser Val Gly Ala Glu Ser Arg Pro Gln
545                 550                 555                 560

Arg Arg Pro Leu Pro Cys Thr Pro Gly Asp Cys Pro Ser Arg Asp Lys
                565                 570                 575

Leu Pro Pro Val Pro Ser Ser Arg Leu Gly Asp Ser Trp Leu Pro Arg
            580                 585                 590

Pro Ile Pro Lys Val Pro Val Ser Ala Pro Ser Ser Ser Asp Pro Trp
        595                 600                 605

Thr Gly Arg Glu Leu Thr Asn Arg His Ser Leu Pro Phe Ser Leu Pro
    610                 615                 620

Ser Gln Met Glu Pro Arg Pro Asp Val Pro Arg Leu Gly Ser Thr Phe
625                 630                 635                 640

Ser Leu Asp Thr Ser Met Ser Met Asn Ser Ser Pro Leu Val Gly Pro
                645                 650                 655

Glu Cys Asp His Pro Lys Ile Lys Pro Ser Ser Ser Ala Asn Ala Ile
            660                 665                 670
```

```
Tyr Ser Leu Ala Ala Arg Leu Pro Val Pro Lys Leu Pro Pro Gly Glu
        675                 680                 685

Gln Cys Glu Gly Glu Glu Asp Thr Glu Tyr Met Thr Pro Ser Ser Arg
    690                 695                 700

Pro Leu Arg Pro Leu Asp Thr Ser Gln Ser Ser Arg Ala Cys Asp Cys
705                 710                 715                 720

Asp Gln Gln Ile Asp Ser Cys Thr Tyr Glu Ala Met Tyr Asn Ile Gln
                725                 730                 735

Ser Gln Ala Pro Ser Ile Thr Glu Ser Ser Thr Phe Gly Glu Gly Asn
            740                 745                 750

Leu Ala Ala His Ala Asn Thr Gly Pro Glu Glu Ser Glu Asn Glu
        755                 760                 765

Asp Asp Gly Tyr Asp Val Pro Lys Pro Pro Val Pro Ala Val Leu Ala
    770                 775                 780

Arg Arg Thr Leu Ser Asp Ile Ser Asn Ala Ser Ser Ser Phe Gly Trp
785                 790                 795                 800

Leu Ser Leu Asp Gly Asp Pro Thr Thr Asn Val Thr Glu Gly Ser Gln
                805                 810                 815

Val Pro Glu Arg Pro Pro Lys Pro Phe Pro Arg Arg Ile Asn Ser Glu
            820                 825                 830

Arg Lys Ala Gly Ser Cys Gln Gln Gly Ser Gly Pro Ala Ala Ser Ala
        835                 840                 845

Ala Thr Ala Ser Pro Gln Leu Ser Ser Glu Ile Glu Asn Leu Met Ser
    850                 855                 860

Gln Gly Tyr Ser Tyr Gln Asp Ile Gln Lys Ala Leu Val Ile Ala Gln
865                 870                 875                 880

Asn Asn Ile Glu Met Ala Lys Asn Ile Leu Arg Glu Phe Val Ser Ile
                885                 890                 895

Ser Ser Pro Ala His Val Ala Thr
            900

<210> SEQ ID NO 434
<211> LENGTH: 3090
<212> TYPE: DNA
<213> ORGANISM: Homo sapiens

<400> SEQUENCE: 434
gaattccggg cccggatagc cggcggcggc ggcggcggcg gcggcggcgg cggccgggag      60
aggcccctcc ttcacgccct gcttctctcc ctcgctcgca gtcgagccga gccggcggac     120
ccgcctgggc tccgaccctg cccaggccat ggccggcaac gtgaagaaga gctctggggc     180
cggggggcgg cacgggctcc ggggctcggg ttcgggtggc ctgattgggc tcatgaagga     240
cgccttccag ccgcaccacc accaccacca ccacctcagc ccccaccgc cggggacggt     300 ggacaagaag atggtggaga gtgctggaa gctcatggac aaggtggtgc ggttgtgtca     360
gaacccaaag ctggcgctaa agaatagccc accttatatc ttagacctgc taccagatac     420
ctaccagcat ctccgtacta tcttgtcaag atatgagggg aagatggaga cacttggaga     480
aaatgagtat tttagggtgt ttatggagaa tttgatgaag aaaactaagc aaaccataag     540
cctcttcaag gagggaaaag aaagaatgta tgaggagaat tctcagccta ggcgaaacct     600
aaccaaactg tccctcatct tcagccacat gctggcagaa ctaaaaggaa tctttccaag     660
tggactcttt cagggagaca catttcggat tactaaagca gatgctgcgg aattttggag     720
aaaagctttt ggggaaaaga caatagtccc ttggaagagc tttcgacagg ctctacatga     780
```

```
agtgcatccc atcagttctg ggctggaggc catggctctg aaatccacta ttgatctgac      840
ctgcaatgat tatatttcgg tttttgaatt tgacatcttt acccgactct ttcagccctg      900
gtcctctttg ctcaggaatt ggaacagcct tgctgtaact catcctggct acatggcttt      960
tttgacgtat gacgaagtga aagctcggct ccagaaattc attcacaaac ctggcagtta     1020
tatcttccgg ctgagctgta ctcgtctggg tcagtgggct attgggtatg ttactgctga     1080
tgggaacatt ctccagacaa tccctcacaa taaacctctc ttccaagcac tgattgatgg     1140
cttcagggaa ggcttctatt tgtttcctga tggacgaaat cagaatcctg atctgactgg     1200
cttatgtgaa ccaactcccc aagaccatat caaagtgacc caggaacaat atgaattata     1260
ctgtgagatg ggctccacat tccaactatg taaaatatgt gctgaaaatg ataaggatgt     1320
aaagattgag ccctgtggac acctcatgtg cacatcctgt cttacatcct ggcaggaatc     1380
agaaggtcag ggctgtcctt tctgccgatg tgaaattaaa ggtactgaac ccatcgtggt     1440
agatccgttt gatcctagag ggagtggcag cctgttgagg caaggagcag agggagctcc     1500
ctccccaaat tatgatgatg atgatgatga acgagctgat gatactctct tcatgatgaa     1560
ggaattggct ggtgccaagg tggaacggcc gccttctcca ttctccatgg ccccacaagc     1620
ttcccttccc ccggtgccac cacgacttga ccttctgccg cagcgagtat gtgttccctc     1680
aagtgcttct gctcttggaa ctgcttctaa ggctgcttct ggctcccttc ataaagacaa     1740
accattgcca gtacctccca cacttcgaga tcttccacca ccaccgcctc cagaccggcc     1800
atattctgtt ggagcagaat cccgacctca aagacgcccc ttgccttgta caccaggcga     1860
ctgtccctcc agagacaaac tgcccccctgt ccctctagc cgccttggag actcatggct     1920
gccccggcca atccccaaag taccagtatc tgccccaagt tccagtgatc cctggacagg     1980
aagagaatta accaaccggc actcacttcc attttcattg ccctcacaaa tggagcccag     2040
accagatgtg cctaggctcg gaagcacgtt cagtctggat acctccatga gtatgaatag     2100
cagcccatta gtaggtccag agtgtgacca ccccaaaatc aaaccttcct catctgccaa     2160
tgccatttat tctctggctg ccagacctct tcctgtgcca aaactgccac ctggggagca     2220
atgtgagggt gaagaggaca cagagtacat gactccctct tccaggcctc tacggccttt     2280
ggatacatcc cagagttcac gagcatgtga ttgcgaccag cagattgata gctgtacgta     2340
tgaagcaatg tataatattc agtcccaggc gccatctatc accgagagca gcacctttgg     2400
tgaagggaat ttggccgcag cccatgccaa cactggtccc gaggagtcag aaaatgagga     2460
tgatgggtat gatgtcccaa agccacctgt gccggccgtg ctggcccgcc gaactctctc     2520
agatatctct aatgccagct cctcctttgg ctggttgtct ctggatggtg atcctacaac     2580
aaatgtcact gaaggttccc aagttcccga gaggcctcca aaaccattcc cgcggagaat     2640
caactctgaa cggaaagctg gcagctgtca gcaaggtagt ggtcctgccg cctctgctgc     2700
caccgcctca cctcagctct ccagtgagat cgagaacctc atgagtcagg gtactcccta     2760
ccaggacatc cagaaagctt tggtcattgc ccagaacaac atcgagatgg ccaaaaacat     2820
cctccgggaa tttgtttcca tttcttctcc tgcccatgta gctacctagc acaccatctc     2880
cctgctgcag gtttagagga ccagtgagtt gggagttatt actcaagtgg cacctagaag     2940
ggcaggagtt cctttggtga cttcacagtg aagtcttgcc ctctctgtgg gatatcacat     3000
cagtggttcc aagatttcaa agtggtgaaa tgaaaatgga gcagctagta tgttttatta     3060
ttttatgggt cttgagtgca tttgaaggtg                                       3090
```

<210> SEQ ID NO 435
<211> LENGTH: 379
<212> TYPE: PRT
<213> ORGANISM: Arabidopsis thaliana

<400> SEQUENCE: 435

Met Ser Thr Thr Gly Gln Ile Ile Arg Cys Lys Ala Ala Val Ala Trp
1               5                   10                  15

Glu Ala Gly Lys Pro Leu Val Ile Glu Val Glu Val Ala Pro Pro
            20                  25                  30

Gln Lys His Glu Val Arg Ile Lys Ile Leu Phe Thr Ser Leu Cys His
        35                  40                  45

Thr Asp Val Tyr Phe Trp Glu Ala Lys Gly Gln Thr Pro Leu Phe Pro
    50                  55                  60

Arg Ile Phe Gly His Glu Ala Gly Ile Val Glu Ser Val Gly Glu
65                  70                  75                  80

Gly Val Thr Asp Leu Gln Pro Gly Asp His Val Leu Pro Ile Phe Thr
                85                  90                  95

Gly Glu Cys Gly Glu Cys Arg His Cys His Ser Glu Glu Ser Asn Met
            100                 105                 110

Cys Asp Leu Leu Arg Ile Asn Thr Glu Arg Gly Gly Met Ile His Asp
        115                 120                 125

Gly Glu Ser Arg Phe Ser Ile Asn Gly Lys Pro Ile Tyr His Phe Leu
    130                 135                 140

Gly Thr Ser Thr Phe Ser Glu Tyr Thr Val Val His Ser Gly Gln Val
145                 150                 155                 160

Ala Lys Ile Asn Pro Asp Ala Pro Leu Asp Lys Val Cys Ile Val Ser
                165                 170                 175

Cys Gly Leu Ser Thr Gly Leu Gly Ala Thr Leu Asn Val Ala Lys Pro
            180                 185                 190

Lys Lys Gly Gln Ser Val Ala Ile Phe Gly Leu Gly Ala Val Gly Leu
        195                 200                 205

Gly Ala Ala Glu Gly Ala Arg Ile Ala Gly Ala Ser Arg Ile Ile Gly
    210                 215                 220

Val Asp Phe Asn Ser Lys Arg Phe Asp Gln Ala Lys Glu Phe Gly Val
225                 230                 235                 240

Thr Glu Cys Val Asn Pro Lys Asp His Asp Lys Pro Ile Gln Gln Val
                245                 250                 255

Ile Ala Glu Met Thr Asp Gly Gly Val Asp Arg Ser Val Glu Cys Thr
            260                 265                 270

Gly Ser Val Gln Ala Met Ile Gln Ala Phe Glu Cys Val His Asp Gly
        275                 280                 285

Trp Gly Val Ala Val Leu Val Gly Val Pro Ser Lys Asp Asp Ala Phe
    290                 295                 300

Lys Thr His Pro Met Asn Phe Leu Asn Glu Arg Thr Leu Lys Gly Thr
305                 310                 315                 320

Phe Phe Gly Asn Tyr Lys Pro Lys Thr Asp Ile Pro Gly Val Val Glu
                325                 330                 335

Lys Tyr Met Asn Lys Glu Leu Glu Leu Glu Lys Phe Ile Thr His Thr
            340                 345                 350

Val Pro Phe Ser Glu Ile Asn Lys Ala Phe Asp Tyr Met Leu Lys Gly
        355                 360                 365

Glu Ser Ile Arg Cys Ile Ile Thr Met Gly Ala
    370                 375

<210> SEQ ID NO 436
<211> LENGTH: 1399
<212> TYPE: DNA
<213> ORGANISM: Arabidopsis thaliana

<400> SEQUENCE: 436

```
tacatcacaa tcacacaaaa ctaacaaaag atcaaaagca agttcttcac tgttgataat      60
gtctaccacc ggacagatta ttcgatgcaa agctgctgtg gcatgggaag ccggaaagcc     120
actggtgatc gaggaagtgg aggttgctcc accgcagaaa cacgaagttc gtatcaagat     180
tctcttcact tctctctgtc acccgatgt ttacttctgg gaagctaagg gacaaacacc      240
gttgttcca cgtatcttcg gccatgaagc tggagggatt gttgagagtg ttggagaagg      300
agtgactgat cttcagccag agatcatgt gttgccgatc tttaccggag aatgtgggga     360
gtgtcgtcat tgccactcgg aggaatcaaa catgtgtgat cttctcagga tcaacaccga     420
gcgaggaggg atgattcacg atggtgaatc aagattctcc attaatggca aaccaattta     480
ccatttcctt gggacttcca cgttcagtga gtacacagtg gttcactctg gtcaggttgc     540
taagatcaat ccggatgctc ctcttgacaa ggtctgtatt gtcagttgtg gtttgtctac     600
tgggttagga gcaactttga atgtggctaa acccaagaaa ggtcaaagtg ttgccatttt     660
tggtcttggt gctgttggtt taggcgctgc agaaggtgct agaatcgctg gtgcttctag     720
gatcatcggt gttgatttta actctaaaag attcgaccaa gctaaggaat cggtgtgac     780
cgagtgtgtg aacccgaaag accatgcaa gccaattcaa caggtgatcg ctgagatgac     840
ggatggtggg gtggacagga gtgtggaatg caccggaagc gttcaggcca tgattcaagc     900
atttgaatgt gtccacgatg gctgggtgt tgcagtgctg gtgggtgtgc caagcaaaga     960
cgatgccttc aagactcatc cgatgaattt cttgaatgag aggactctta agggtacttt    1020
cttcgggaac tacaaaccca aaactgacat tcccggggtt gtggaaaagt acatgaacaa    1080
ggagctggag cttgagaaat tcatcactca cacagtgcca ttctcggaaa tcaacaaggc    1140
ctttgattac atgctgaagg gagagagtat tcgttgcatc atcaccatgg gtgcttgaag    1200
ccattctctc gcagatgatg ttcactttgt gttttacttc ctttatgcat tcacagcaat    1260
aaaagaaaga aatctccatc gcttttggtt ttcttctctg tcttaagtta gtcgttttcg    1320
tgtctaatct attacttatc attgtaatag actcttcttc tattgagatt tgaatataaa    1380
ctaaaacaca ttccattt                                                  1399
```

<210> SEQ ID NO 437
<211> LENGTH: 31
<212> TYPE: DNA
<213> ORGANISM: Arabidopsis thaliana

<400> SEQUENCE: 437

```
tttggatccg acaacatcat ttctaccgac a                                     31
```

<210> SEQ ID NO 438
<211> LENGTH: 33
<212> TYPE: DNA
<213> ORGANISM: Arabidopsis thaliana

<400> SEQUENCE: 438

```
ccctctagat agctgtacac aacaaacaca ctc                                   33
```

<210> SEQ ID NO 439

```
<211> LENGTH: 20
<212> TYPE: DNA
<213> ORGANISM: Arabidopsis thaliana

<400> SEQUENCE: 439
ttggaacatc acttgcccat                                              20

<210> SEQ ID NO 440
<211> LENGTH: 21
<212> TYPE: DNA
<213> ORGANISM: Arabidopsis thaliana

<400> SEQUENCE: 440
tgtgttcaaa caagagctcc a                                            21

<210> SEQ ID NO 441
<211> LENGTH: 20
<212> TYPE: DNA
<213> ORGANISM: Arabidopsis thaliana

<400> SEQUENCE: 441
aatcatactc agccgccatt                                              20

<210> SEQ ID NO 442
<211> LENGTH: 21
<212> TYPE: DNA
<213> ORGANISM: Arabidopsis thaliana

<400> SEQUENCE: 442
tttagttccg tccggtgaga a                                            21

<210> SEQ ID NO 443
<211> LENGTH: 21
<212> TYPE: DNA
<213> ORGANISM: Arabidopsis thaliana

<400> SEQUENCE: 443
tgcaaatctc atcttcatcg t                                            21

<210> SEQ ID NO 444
<211> LENGTH: 20
<212> TYPE: DNA
<213> ORGANISM: Arabidopsis thaliana

<400> SEQUENCE: 444
tgtcgaatgc tgaattgctc                                              20

<210> SEQ ID NO 445
<211> LENGTH: 25
<212> TYPE: DNA
<213> ORGANISM: Arabidopsis thaliana

<400> SEQUENCE: 445
gtggagaaga tctctaccga gaagg                                        25

<210> SEQ ID NO 446
<211> LENGTH: 25
<212> TYPE: DNA
<213> ORGANISM: Arabidopsis thaliana

<400> SEQUENCE: 446
catcaaagac gtcaaacaaa acaca                                        25
```

```
<210> SEQ ID NO 447
<211> LENGTH: 21
<212> TYPE: DNA
<213> ORGANISM: Arabidopsis thaliana

<400> SEQUENCE: 447
atgaagatta aggtcgtggc a                                              21

<210> SEQ ID NO 448
<211> LENGTH: 20
<212> TYPE: DNA
<213> ORGANISM: Arabidopsis thaliana

<400> SEQUENCE: 448
tccgagtttg aagaggctac                                                20

<210> SEQ ID NO 449
<211> LENGTH: 30
<212> TYPE: DNA
<213> ORGANISM: Arabidopsis thaliana

<400> SEQUENCE: 449
gggggaattc gagtcatttg atttccgggt                                     30

<210> SEQ ID NO 450
<211> LENGTH: 32
<212> TYPE: DNA
<213> ORGANISM: Arabidopsis thaliana

<400> SEQUENCE: 450
ggggctgcag tcaccaaaca ttagaagaaa gc                                  32

<210> SEQ ID NO 451
<211> LENGTH: 255
<212> TYPE: DNA
<213> ORGANISM: Arabidopsis thaliana

<400> SEQUENCE: 451
ttggaacatc acttgcccat tgtgtaggac tcctcttgtt gttgtgccag aagaccatca    60
gctttcttct aatgtttggt gactgctttt cactgtatag gttttttgtt tgagtgtgtt   120
tgttgtgtac agctactttt actatgaatt aggttgcatc gcggttgatt ctcgagcaga   180
tttaaaccgg ggatgggata atctgatgta catatatata tacccatgt gtatggagc    240 tcttgtttga acaca                                                    255

<210> SEQ ID NO 452
<211> LENGTH: 942
<212> TYPE: DNA
<213> ORGANISM: Arabidopsis thaliana

<400> SEQUENCE: 452
aatcatactc agccgccatt atcgtcttct caaagctccg acttgagtta ttgtagctcc    60
ttacctatgg ccagtcgtgt cacacgtaag ctcaatgttt catctgcgct tcacactcct   120
ccagctcttc atttccctaa gcaatcatca aactctcccg ccattgttgt taagcccaaa   180
gccaaagaat ccaacactaa acagatgaat tgttccaga gagcggcggc ggcagcgttg    240
gacgcggcgg agggtttcct tgtcagccac gagaagctac acccgcttcc taaaacggct   300
gatcctagtg ttcagatcgc cggaaatttt gctccggtga atgaacagcc cgtccggcgt   360
aatcttccgg tggtcggaaa acttcccgat tccatcaaag gagtgtatgt gcgcaacgga   420
```

```
gctaacccac ttcacgagcc ggtgacaggt caccacttct tcgacggaga cggtatggtt      480
cacgccgtca aattcgaaca cggttcagct agctacgctt gccggtttac tcagactaac      540
cggtttgttc aggaacgtca attgggtcga ccggttttcc ccaaagccat cggtgagctt      600 cacgccaca ccggtattgc ccgactcatg ctattctacg ccagagctgc agccggtata       660
gtcgacccgg cacacggaac cggtgtagct aacgccggtt tggtctattt caatggccgg      720
ttattggcta tgtcggagga tgatttacct taccaagttc agatcactcc caatggagat      780
ttaaaaaccg ttggtcggtt cgattttgat ggacaattag aatccacaat gattgcccac      840
ccgaaagtcg acccggaatc cggtgaactc ttcgctttaa gctacgacgt cgtttcaaag      900
ccttacctaa aatacttccg attctcaccg gacggaacta aa                         942

<210> SEQ ID NO 453
<211> LENGTH: 985
<212> TYPE: DNA
<213> ORGANISM: Arabidopsis thaliana

<400> SEQUENCE: 453
tgcaaatctc atcttcatcg tcttcaaatt tcttctcttc tctttatgct gatgaaccgg       60
cactaatcac attaacaatt gttgtagtag tagtagtgtt actatttaaa tggtggttgc      120
actggaaaga gcaaagacta cggctacctc ctggctccat ggggttgcct tacatcggag      180
agacactccg cctctacaca gaaaatccca attccttctt cgccactcgc caaacaagt       240 acggggatat attcaagacg cacatattag gatgtccatg tgtgatgata agtagtccag      300
aggcggctcg aatggtgtta gtgagcaaag ctcacttgtt caagccaact tatcctccaa      360
gcaaagagcg tatgattgga ccagaggctc ttttcttcca ccaaggtcca taccattcta      420
cccttaagcg gctggtccag tcttctttca tgccttctgc tctcagacca accgtctctc      480
acatcgagct ccttgtcctc caaacccttt cctcttggac gtcccaaaag tccatcaaca      540
ccctcgaata catgaaacga tatgcattcg atgtggcgat catgtcagcg ttcggggaca      600
aagaggagcc cactacgatt gatgttatta agcttctcta tcaacgtctc gaaagggggtt     660 acaactccat gcctctcgac ctaccgggca cactttttca taagtccatg aaggcaagaa      720
tagaattaag cgaggaacta aggaaagtaa tagagaagag aagagagaat gggagagaag      780
aaggaggact attgggagta cttctgggag caaaggatca aaaacgcaac ggcttaagtg      840
attcacagat tgctgacaac atcatcggtg ttatattcgc cgccaccgac accaccgctt      900
ctgtcttaac ttggcttctc aagtacttac acgaccaccc caatctcctc caagaagtct      960
ccagggagca attcagcatt cgaca                                           985

<210> SEQ ID NO 454
<211> LENGTH: 358
<212> TYPE: DNA
<213> ORGANISM: Arabidopsis thaliana

<400> SEQUENCE: 454
gtggagaaga tctctaccga gaaggcagca tcggaggagg gtgaggcggt ggaagaggaa       60
gtgaaaggag gaggaggaat ggttgggagg attaaaggat ggttcggtgg tggtgcgact      120
gatgaggtga agccagaatc gccacattct gttgaagagg ctccaaaatc atctggctgg      180
tttggtggtg gtgcgacgga ggaggtgaag ccaaaatcgc ctcattccgt tgaagagtct      240
ccacaatcac ttggctccac tgttgttccg gtgcagaagg agctttaaga atatgagaac      300
tgagattttc aagtttcact ttggatgttt atgtgtgttt tgtttgacgt ctttgatg        358
```

<210> SEQ ID NO 455
<211> LENGTH: 418
<212> TYPE: DNA
<213> ORGANISM: Arabidopsis thaliana

<400> SEQUENCE: 455

```
atgaagatta aggtcgtggc accacccgag aggaagtaca gtgtctggat tggtggttct    60
atccttgctt ccctcagcac tttccagcag atgtggatct ctaaggcaga gtatgatgaa   120
gcaggtccag gcattgtcca cagaaaatgc ttctaaacta aagagacatc gtttccatga   180
cgggatcaca tttctttcta tttctccaat ttgtttgttt caaattttt tcccctttgt   240
catttgtgca ctatgtgaga aactttccgg ttacagcgtt tggagagatg tctaaggagg   300
agcaggtttg aaaacccgct ctcgctctta cctgaggcac taatccgcgt ttcaaaactca   360
gcttcattct ctattcttgt ccatttgttt gtttgtttgt agcctcttca aactcgga    418
```

<210> SEQ ID NO 456
<211> LENGTH: 24
<212> TYPE: PRT
<213> ORGANISM: Arabidopsis thaliana

<400> SEQUENCE: 456

Ser Leu Ser Pro Ser Ser Ser Pro Ser Ser Val Thr Val Ser Ser
1               5                   10                  15

Glu Asn Ser Ser Thr Ser Glu Ser
            20

<210> SEQ ID NO 457
<211> LENGTH: 11
<212> TYPE: PRT
<213> ORGANISM: Oryza sativa

<400> SEQUENCE: 457

Ala Ala Ala Ala Ala Ala Ala Ala Ala Ala
1               5                   10

<210> SEQ ID NO 458
<211> LENGTH: 18
<212> TYPE: PRT
<213> ORGANISM: Zea mays

<400> SEQUENCE: 458

Ala Pro Ser Ser Pro Ser Ser Arg Phe Leu Phe Val Ala Ala Ser Pro
1               5                   10                  15

Leu Pro

<210> SEQ ID NO 459
<211> LENGTH: 9
<212> TYPE: PRT
<213> ORGANISM: Gossypium sp.

<400> SEQUENCE: 459

Ala Ser Ser Ser Pro Ser Ser Asp Ser
1               5

<210> SEQ ID NO 460
<211> LENGTH: 11
<212> TYPE: PRT
<213> ORGANISM: Poncirus trifoliata

<400> SEQUENCE: 460

```
Ser Ser Ser Thr Pro Tyr Ser Tyr Phe Ala Ser
1               5                   10

<210> SEQ ID NO 461
<211> LENGTH: 7
<212> TYPE: PRT
<213> ORGANISM: Glycine max

<400> SEQUENCE: 461

Ser Ser Leu Ser Pro Ser Pro
1               5

<210> SEQ ID NO 462
<211> LENGTH: 9
<212> TYPE: PRT
<213> ORGANISM: Populus sp.

<400> SEQUENCE: 462

Ser Pro Ser Ala Ser Leu Pro Ser Ser
1               5

<210> SEQ ID NO 463
<211> LENGTH: 5
<212> TYPE: PRT
<213> ORGANISM: Capsicum annuum

<400> SEQUENCE: 463

Ser Pro Pro Glu Ser
1               5

<210> SEQ ID NO 464
<211> LENGTH: 5
<212> TYPE: PRT
<213> ORGANISM: Arabidopsis thaliana

<400> SEQUENCE: 464

Ser Thr Ser Glu Ser
1               5

<210> SEQ ID NO 465
<211> LENGTH: 5
<212> TYPE: PRT
<213> ORGANISM: Thellungiella halophila

<400> SEQUENCE: 465

Ser Ser Pro Ser Ser
1               5

<210> SEQ ID NO 466
<211> LENGTH: 5
<212> TYPE: PRT
<213> ORGANISM: Zea mays

<400> SEQUENCE: 466

Ser Ser Ser Ala Ser
1               5

<210> SEQ ID NO 467
<211> LENGTH: 5
<212> TYPE: PRT
<213> ORGANISM: Cucumis melo

<400> SEQUENCE: 467

Ser Ser Val Ser Ala
```

<210> SEQ ID NO 468
<211> LENGTH: 4
<212> TYPE: PRT
<213> ORGANISM: Triticum aestivum

<400> SEQUENCE: 468

Ser Ser Met Pro
1

<210> SEQ ID NO 469
<211> LENGTH: 4
<212> TYPE: PRT
<213> ORGANISM: Arabidopsis thaliana

<400> SEQUENCE: 469

Ser Pro Ser Ser
1

<210> SEQ ID NO 470
<211> LENGTH: 4
<212> TYPE: PRT
<213> ORGANISM: Cucumis melo

<400> SEQUENCE: 470

Ser Pro Ser Asn
1

<210> SEQ ID NO 471
<211> LENGTH: 4
<212> TYPE: PRT
<213> ORGANISM: Medicago truncatula

<400> SEQUENCE: 471

Ser Pro Ser Asp
1

<210> SEQ ID NO 472
<211> LENGTH: 4
<212> TYPE: PRT
<213> ORGANISM: Fragaria x ananassa

<400> SEQUENCE: 472

Ser Ser Ser Gly
1

<210> SEQ ID NO 473
<211> LENGTH: 4
<212> TYPE: PRT
<213> ORGANISM: Poncirus trifoliata

<400> SEQUENCE: 473

Ser Ser Ser Thr
1

<210> SEQ ID NO 474
<211> LENGTH: 4
<212> TYPE: PRT
<213> ORGANISM: Thellungiella halophila

<400> SEQUENCE: 474

Ser Ser Ser Ser
1

```
<210> SEQ ID NO 475
<211> LENGTH: 4
<212> TYPE: PRT
<213> ORGANISM: Thellungiella halophila

<400> SEQUENCE: 475

Ser Ser Ser Pro
1

<210> SEQ ID NO 476
<211> LENGTH: 4
<212> TYPE: PRT
<213> ORGANISM: Zea mays

<400> SEQUENCE: 476

Ser Ser Ser Ala
1

<210> SEQ ID NO 477
<211> LENGTH: 4
<212> TYPE: PRT
<213> ORGANISM: Lactuca sativa

<400> SEQUENCE: 477

Ser Ser Ser Asn
1

<210> SEQ ID NO 478
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Residue can be Cysteine or Glycine.
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (12)..(13)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: MISC_FEATURE
<222> LOCATION: (19)..(19)
<223> OTHER INFORMATION: Residue can be Glycine or Glutamic acid.
<220> FEATURE:
<221> NAME/KEY: misc_feature
<222> LOCATION: (21)..(21)
<223> OTHER INFORMATION: Xaa can be any naturally occurring amino acid

<400> SEQUENCE: 478

Gly Xaa Xaa Xaa Xaa Xaa Xaa Xaa Asn Thr Ala Xaa Xaa Ile Ser Ile
1               5                   10                  15

Xaa Lys Xaa Ile Xaa
            20

<210> SEQ ID NO 479
```

```
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Residue can be Cysteine or Glycine.
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: MISC_FEATURE
<222> LOCATION: (12)..(12)
<223> OTHER INFORMATION: Residue can be any amino acid.
<220> FEATURE:
<221> NAME/KEY: MISC_FEATURE
<222> LOCATION: (14)..(14)
<223> OTHER INFORMATION: Residue can be Isoleucine or Valine.
<220> FEATURE:
<221> NAME/KEY: misc_feature
<222> LOCATION: (15)..(15)
<223> OTHER INFORMATION: Xaa can be any naturally occurring amino acid

<400> SEQUENCE: 479

Gly Xaa Xaa Xaa Xaa Xaa Xaa Xaa Asn Thr Ala Xaa Ser Xaa Xaa Ile
1               5                   10                  15

<210> SEQ ID NO 480
<211> LENGTH: 21
<212> TYPE: PRT
<213> ORGANISM: Arabidopsis thaliana

<400> SEQUENCE: 480

Gly Met Leu Cys Val Ile Leu Val Asn Thr Ala Leu Ser Ile Ser Ile
1               5                   10                  15

Val Lys Gly Ile Val
            20

<210> SEQ ID NO 481
<211> LENGTH: 21
<212> TYPE: PRT
<213> ORGANISM: Brassica napus

<400> SEQUENCE: 481

Gly Met Leu Cys Val Ile Leu Val Asn Thr Ala Leu Ser Ile Ser Ile
1               5                   10                  15

Phe Lys Gly Ile Leu
            20

<210> SEQ ID NO 482
<211> LENGTH: 21
<212> TYPE: PRT
<213> ORGANISM: Poncirus trifoliata

<400> SEQUENCE: 482

Gly Met Leu Cys Leu Ile Leu Met Asn Thr Ala Met Pro Ile Ser Ile
1               5                   10                  15

Val Lys Gly Ile Phe
            20

<210> SEQ ID NO 483
```

```
<211> LENGTH: 21
<212> TYPE: PRT
<213> ORGANISM: Hevea brasiliensis

<400> SEQUENCE: 483

Gly Val Ile Cys Val Val Met Asn Thr Ala Leu Ser Ile Ser Ile
1               5                   10                  15

Phe Lys Gly Ile Val
            20

<210> SEQ ID NO 484
<211> LENGTH: 15
<212> TYPE: PRT
<213> ORGANISM: Gossypium sp.

<400> SEQUENCE: 484

Gly Val Leu Cys Val Phe Gln Ser Ile Leu His Ile Val Gly Ile
1               5                   10                  15

<210> SEQ ID NO 485
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid

<400> SEQUENCE: 485

Asn Thr Ala Leu Ser Xaa Xaa Xaa Ile Xaa Xaa Xaa Xaa Ser Phe Leu
1               5                   10                  15

Gln Ile Val

<210> SEQ ID NO 486
<211> LENGTH: 21
<212> TYPE: PRT
<213> ORGANISM: Medicago truncatula
<220> FEATURE:
<221> NAME/KEY: misc_feature
<222> LOCATION: (21)..(21)
<223> OTHER INFORMATION: Xaa can be any naturally occurring amino acid

<400> SEQUENCE: 486

Gly Val Leu Cys Ile Ile Leu Val Asn Thr Ala Met Ser Ile Ser Ile
1               5                   10                  15

Phe Lys Gly Ile Xaa
            20

<210> SEQ ID NO 487
<211> LENGTH: 21
<212> TYPE: PRT
<213> ORGANISM: Solanum tuberosum

<400> SEQUENCE: 487

Gly Val Leu Gly Val Ile Leu Val Asn Thr Ala Ile Ser Ile Ser Ile
1               5                   10                  15

Ile Lys Glu Ile Leu
            20
```

```
<210> SEQ ID NO 488
<211> LENGTH: 21
<212> TYPE: PRT
<213> ORGANISM: Capsicum annuum

<400> SEQUENCE: 488

Gly Val Leu Gly Val Ile Leu Val Asn Thr Ala Ile Ser Ile Ser Ile
1               5                   10                  15

Val Lys Glu Ile Leu
            20

<210> SEQ ID NO 489
<211> LENGTH: 21
<212> TYPE: PRT
<213> ORGANISM: Lactuca sativa

<400> SEQUENCE: 489

Gly Val Leu Cys Val Ile Leu Val Asn Thr Ala Met Ser Ile Ser Ile
1               5                   10                  15

Met Lys Glu Ile Val
            20

<210> SEQ ID NO 490
<211> LENGTH: 22
<212> TYPE: PRT
<213> ORGANISM: Oryza sativa

<400> SEQUENCE: 490

Asp Ser Val Val Ala Tyr Leu Leu Tyr Asn Thr Ala Val Ser Ile Ala
1               5                   10                  15

Ile Leu Ala Asp Met Val
            20

<210> SEQ ID NO 491
<211> LENGTH: 21
<212> TYPE: PRT
<213> ORGANISM: Medicago truncatula

<400> SEQUENCE: 491

Gly Val Leu Cys Ile Ile Leu Val Asn Thr Ala Met Ser Ile Ser Ile
1               5                   10                  15

Phe Lys Gly Ile Ile
            20

<210> SEQ ID NO 492
<211> LENGTH: 21
<212> TYPE: PRT
<213> ORGANISM: Thellungiella halophila

<400> SEQUENCE: 492

Ser Leu Leu Gly Phe Val Leu Tyr Asn Thr Ala Ala Ser Val Ala Ile
1               5                   10                  15

Leu Ala Gly Leu Val
            20

<210> SEQ ID NO 493

<400> SEQUENCE: 493

000
```